US008932814B2

(12) United States Patent
Cong et al.

(10) Patent No.: US 8,932,814 B2
(45) Date of Patent: *Jan. 13, 2015

(54) CRISPR-CAS NICKASE SYSTEMS, METHODS AND COMPOSITIONS FOR SEQUENCE MANIPULATION IN EUKARYOTES

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Le Cong, Cambridge, MA (US); Feng Zhang, Cambridge, MA (US)

(73) Assignees: The Broad Institute Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,458

(22) Filed: Apr. 22, 2014

(65) Prior Publication Data
US 2014/0248702 A1 Sep. 4, 2014

Related U.S. Application Data

(63) Continuation of application No. 14/105,031, filed on Dec. 12, 2013.

(60) Provisional application No. 61/791,409, filed on Mar. 15, 2013, provisional application No. 61/748,427, filed on Jan. 2, 2013, provisional application No. 61/736,527, filed on Dec. 12, 2012, provisional application No. 61/802,174, filed on Mar. 15, 2013, provisional application No. 61/835,931, filed on Jun. 17, 2013.

(51) Int. Cl.
| | | |
|---|---|---|
| C12Q 1/68 | (2006.01) |
| C12N 15/85 | (2006.01) |
| C12N 9/14 | (2006.01) |
| C12N 9/22 | (2006.01) |
| C12N 9/52 | (2006.01) |
| C12N 15/00 | (2006.01) |
| C07H 21/02 | (2006.01) |
| C07H 21/04 | (2006.01) |
| A61K 38/43 | (2006.01) |
| A61K 38/46 | (2006.01) |
| A61K 38/47 | (2006.01) |

(52) U.S. Cl.
CPC ..................................... C12N 15/85 (2013.01)
USPC ........... 435/6.1; 435/6.13; 435/195; 435/199; 435/220; 435/320.1; 424/94.1; 424/94.6; 424/94.61; 536/22.1; 536/23.1; 536/23.7; 536/24.1

(58) Field of Classification Search
None
See application file for complete search history.

(56) References Cited

U.S. PATENT DOCUMENTS

| | | |
|---|---|---|
| 2010/0076057 A1 | 3/2010 | Sontheimer et al. |
| 2011/0189776 A1 | 8/2011 | Terns et al. |
| 2011/0223638 A1 | 9/2011 | Wiedenheft et al. |
| 2013/0130248 A1 | 5/2013 | Haurwitz et al. |

FOREIGN PATENT DOCUMENTS

| | | | | |
|---|---|---|---|---|
| WO | WO/2008/108989 | 9/2008 | | |
| WO | WO/2010/054108 | 5/2010 | | |
| WO | WO/2012/164565 | 12/2012 | | |
| WO | WO/2013/098244 | 7/2013 | | |
| WO | 2013/141680 * | 9/2013 | ............. | C12N 15/10 |
| WO | 2013/142578 * | 9/2013 | ............. | C12N 15/10 |
| WO | WO/2013176772 | 11/2013 | | |
| WO | WO 2014/065596 | 5/2014 | | |
| WO | 2014/099750 A2 * | 6/2014 | ............. | A61K 48/00 |
| WO | WO 2014/089290 | 6/2014 | | |
| WO | WO 2014/093479 | 6/2014 | | |
| WO | WO 2014/099744 | 6/2014 | | |
| WO | WO 2014/099750 | 6/2014 | | |

OTHER PUBLICATIONS

U.S. Appl. No. 61/613,373 (Mar. 20, 2012) 51 pages.*
U.S. Appl. No. 61/625,420 (Apr. 17, 2012) 51 pages.*
Al-Attar et al., Clustered Regularly Interspaced Short Palindromic Repeats (CRISPRs): The Hallmark of an Ingenious Antiviral Defense Mechanism In Prokaryotes, *Biol Chem.* (2011) vol. 392, Issue 4, pp. 277-289.
Carroll, A CRISPR Approach to Gene Targeting, Molecular Therapy (2012) vol. 20, No. 9, p. 1658-1660.
Gasiunas, et al., Cas9-crRNA Ribonucleoprotein Complex Mediates Specific DNA cleavage for Adaptive Immunity in Bacteria, PNAS USA (2012) vol. 109, No. 39, p. E2579-E2586.
Hale et al., Essential Features and Rational Design of CRISPR RNAs That Function With the Cas RAMP Module Complex to Cleave RNAs, *Molecular Cell*,(2012) vol. 45, Issue 3, 292-302.
Jinek et al, A Programmable Dual-RNA-Guided DNA Endonuclease In Adaptive Bacterial Immunity, Science (2012) vol. 337, p. 816-821.
Makarova et al., Evolution and Classification of the CRISPR-CAS Systems, Nature Reviews Microbiology (2011) vol. 9, No. 6, p. 467-477.
Erik Sontheimer, Project 7: Establishing RNA-Directed DNA Targeting in Eukaryotic Cells; Project dates: Nov. 16, 2011 to Dec. 31, 2012 (Feb. 4, 2012).

(Continued)

*Primary Examiner* — Anne Gussow
*Assistant Examiner* — Nancy J Leith
(74) *Attorney, Agent, or Firm* — Vedder Price PC; Thomas J. Kowalski; Deborah L. Lu

(57) ABSTRACT

The invention provides for systems, methods, and compositions for manipulation of sequences and/or activities of target sequences. Provided are vectors and vector systems, some of which encode one or more components of a CRISPR complex, as well as methods for the design and use of such vectors. Also provided are methods of directing CRISPR complex formation in eukaryotic cells and methods for selecting specific cells by introducing precise mutations utilizing the CRISPR/Cas system.

30 Claims, 116 Drawing Sheets

(56) References Cited

OTHER PUBLICATIONS

Wiedenheft, et al., RNA-Guided Genetic Silencing Systems in Bacteria and Archaea, Nature (2012) vol. 482, p. 331-338.
U.S. Appl. No. 61/738,355, filed Dec. 17, 2012, George M. Church.
U.S. Appl. No. 61/779,169, filed Mar. 13, 2013, Prashant Mali.
Le Cong, et al., Supplementary Material: Multiplex Genome Engineering Using CRISPR-Cas Systems, Science Express (Jan. 3, 2013).
U.S. Appl. No. 61/735,876, filed Dec. 11, 2012, Blake A. Wiedenheft.
U.S. Appl. No. 61/799,531, filed Mar. 15, 2013, Blake A. Wiedenheft.
Le Cong, et al., Multiplex Genome Engineering Using CRISPR-Cas Systems, Science (Feb. 2013) vol. 339, p. 819-823.
Le Cong, et al., Supplementary Material: Multiplex Genome Engineering Using CRISPR-Cas Systems, Science Express (Jul. 5, 2012).
Seung Woo Cho, et al., Targeted Genome Engineering in Human Cells With the Cas9 RNA-Guided Endonuclease, Nature Biotechnology (Mar. 2013) vol. 31, No. 3, p. 230-232.
Seung Woo Cho, et al., Supplementary Information: Targeted Genome Engineering in Human Cells With the Cas9 RNA-Guided Endonuclease, Nature Biotechnology (Mar. 2013) vol. 31, No. 3, p. 1-10.
U.S. Appl. No. 61/734,256, filed Dec. 6, 2012, Fuqiang Chen.
U.S. Appl. No. 61/758,624, filed Jan. 30, 2013, Fuqiang Chen.
U.S. Appl. No. 61/761,046, filed Feb. 5, 2013, Scott Knight.
U.S. Appl. No. 61/794,422, filed Mar. 15, 2013, Scott Knight.
Kirill A. Datsenko, et al., Molecular Memory of Prior Infections Activates the CRISPR/Cas Adaptive Bacterial Immunity System, Nature Communications, Jul. 10, 2012, DOI:10.1038/ncomms1937.
Ksenia Pougach, et al., Transcription, Processing and Function of CRISPR Cassettes in *Escherichia coli*, Mol. Microbiol, Sep. 2010, 77(6), p. 1367-1379.

\* cited by examiner

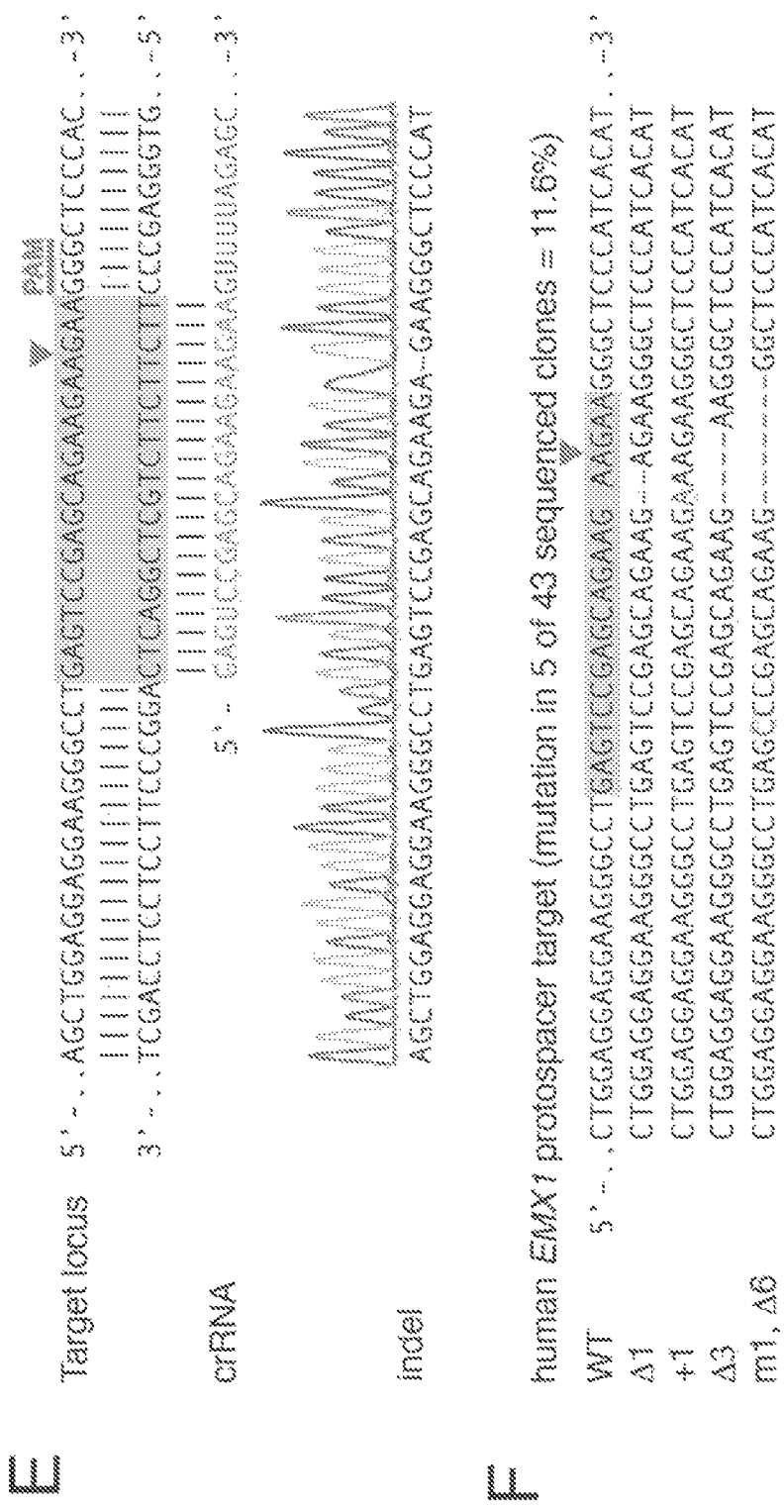
FIG. 2E.-F

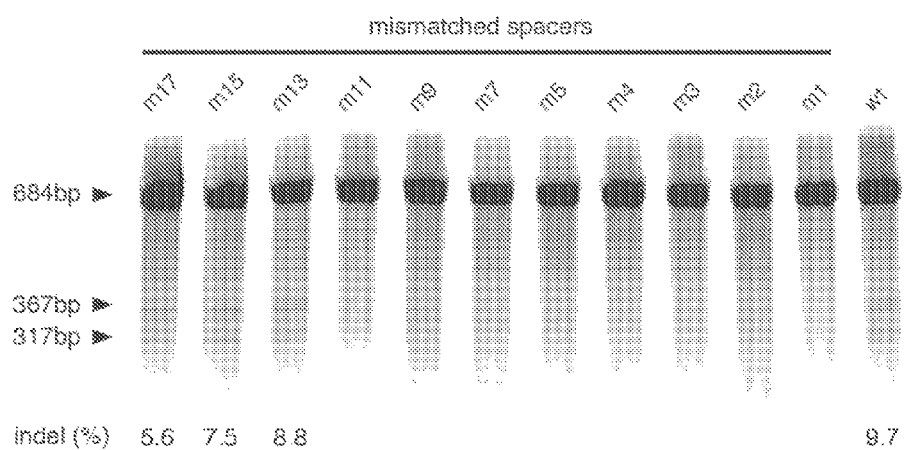
FIG. 4A-C

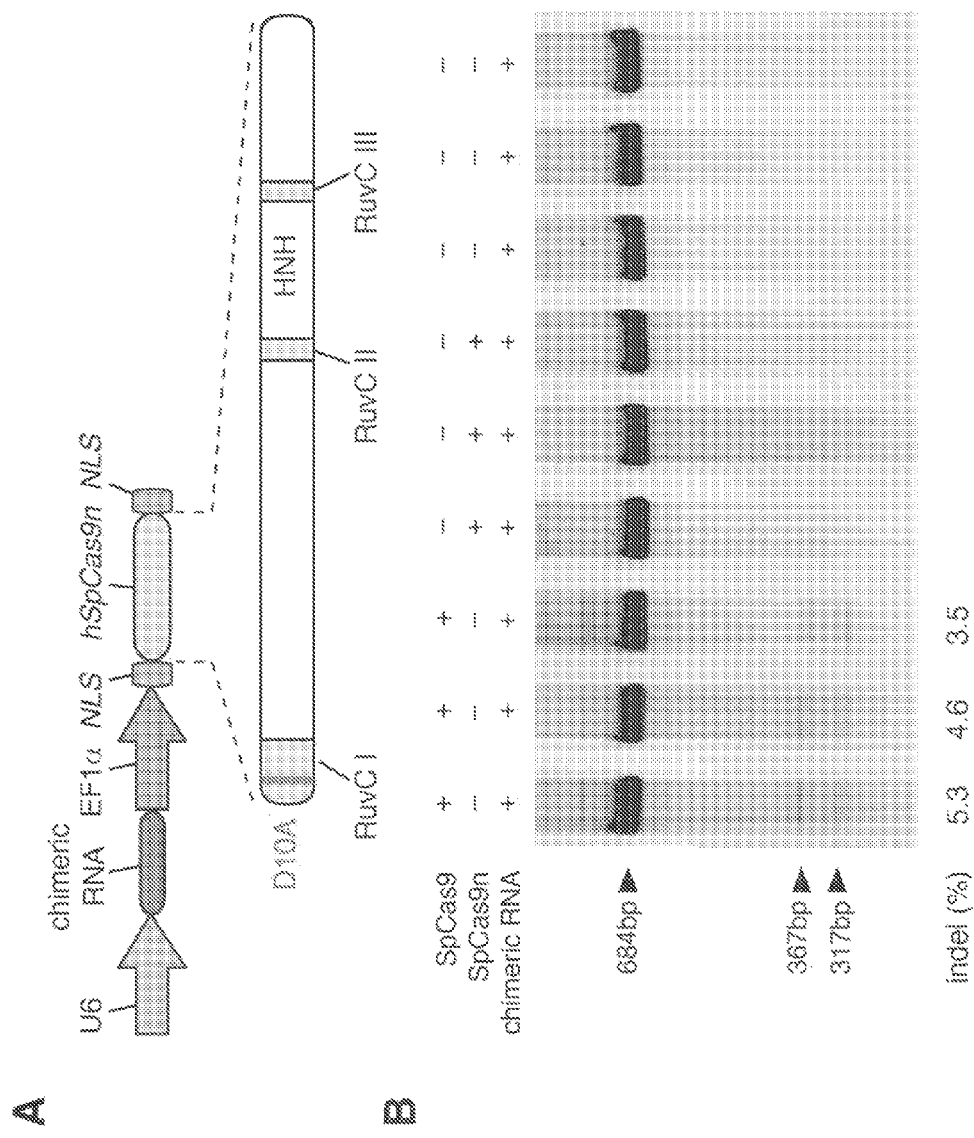
FIG. 5A-B

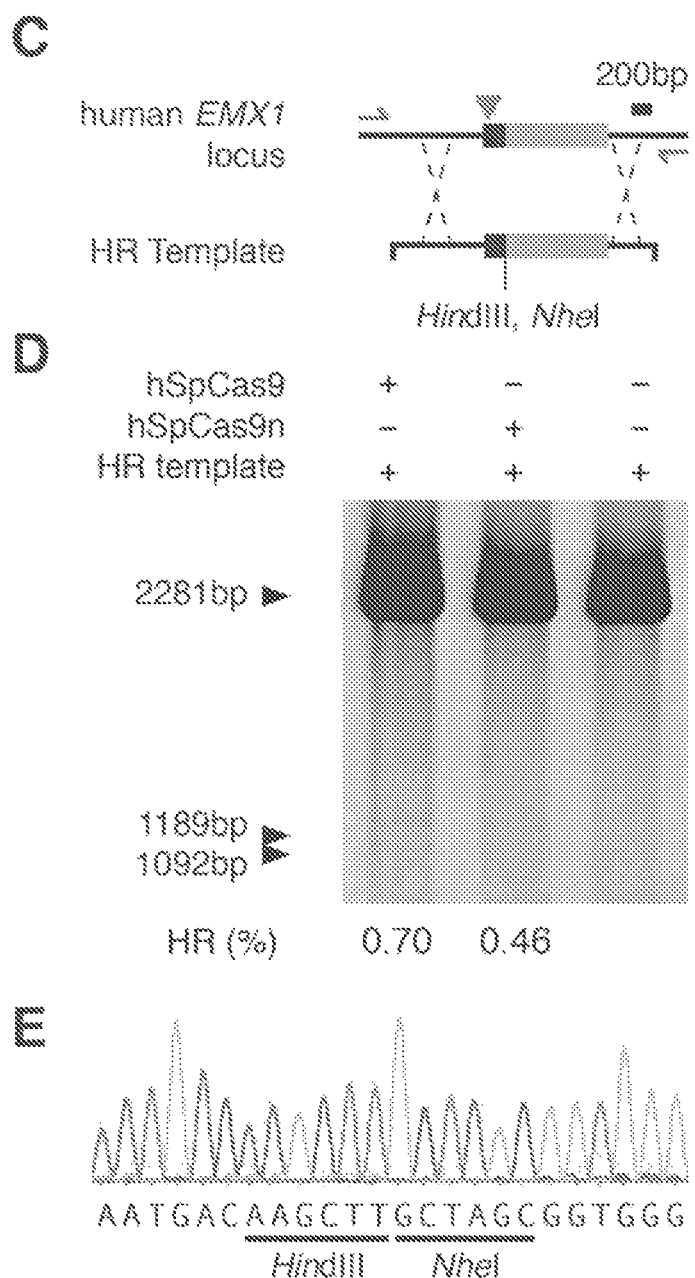
FIG. 5C-E

| Cas9 | target species | gene | protospacer ID | protospacer sequence (5' to 3') | PAM | strand | cell line tested | % indel (pre-crRNA + tracrRNA) | % indel (chimeric RNA) |
|---|---|---|---|---|---|---|---|---|---|
| S. pyogenes SF370 type II CRISPR | Homo sapiens | EMX1 | 1 | GGAAGGGCCTGAGTCCGAGCAGAAGAAGAA | GGG | + | 293FT | 2.0 ± 1.9 | 6.7 ± 0.82 |
| | | EMX1 | 2 | CATTGGAGGTGACATCGATGTCCTCCCCAT | TGG | − | 293FT | 2.1 ± 0.31 | N.D. |
| | | EMX1 | 3 | GGACATCGATGTCACCTCCAATGACTAGGG | TGG | + | 293FT | 14 ± 1.1 | N.D. |
| | | EMX1 | 4 | CATTCGATGTCACCTCCAATGACTAGGGTG | TGG | + | 293FT | 11 ± 1.7 | N.D. |
| | | EMX1 | 5 | TTCGTGGCAATGCGCCACCGGTTGATGTGA | TGG | − | 293FT | 4.3 ± 0.48 | 2.1 ± 0.51 |
| | | EMX1 | 6 | TGTGGCAATGCGCCACCGGTTGATGTGATG | GGG | − | 293FT | 4.0 ± 0.88 | 0.41 ± 0.25 |
| | | EMX1 | 7 | TCCAGCTTCTGCCGTTTGTACTTTGTCCTC | CGG | − | 293FT | 1.5 ± 0.12 | N.D. |
| | | EMX1 | 8 | GGAGGACAAAGTACAAACGGCAGAAGCTGG | AGG | − | 293FT | 7.8 ± 0.63 | 2.9 ± 1.2 |
| | | PVALB | 9 | AGGGCCCAGATTGGTCTTCAGGCCAGCAGC | AGG | + | 293FT | 2.1 ± 2.6 | 0.5 ± 0.32 |
| | | PVALB | 10 | ATGCAGAAGGTGGCCAAGGGCCTGAGATGG | TGG | + | 293FT | N.D. | N.D. |
| | | PVALB | 11 | GGTGGCGAGAGGGGCCAGGGCAGATGACGTTC | AGG | + | 293FT | N.D. | N.D. |
| | Mus musculus | Th | 12 | CAAGCACTGTACTAGTCCATTAGCTAATGCAT | AGG | − | Neuro2A | 27 ± 4.3 | 4.1 ± 2.2 |
| | | Th | 13 | AATCATAGGATACCACCACAGGTGCAG | GGG | + | Neuro2A | 4.8 ± 1.2 | N.D. |
| | | Th | 14 | ACACACATGGAAGCTTCTGGGCAGAA | AGG | − | Neuro2A | 11.3 ± 1.3 | N.D. |
| S. thermophilus LMD-9 CRISPR1 | Homo sapiens | EMX1 | 15 | GGAAGCAAGCTACTATAGAAACACAGAGA | GTACAAT | − | 293FT | 14 ± 0.88 | N.T. |
| | | EMX1 | 16 | AGAATGTAGAAGGAGTACAGAAAATTCAGCA | CTAAAAA | − | 293FT | 7.8 ± 0.77 | N.T. |

FIG. 6

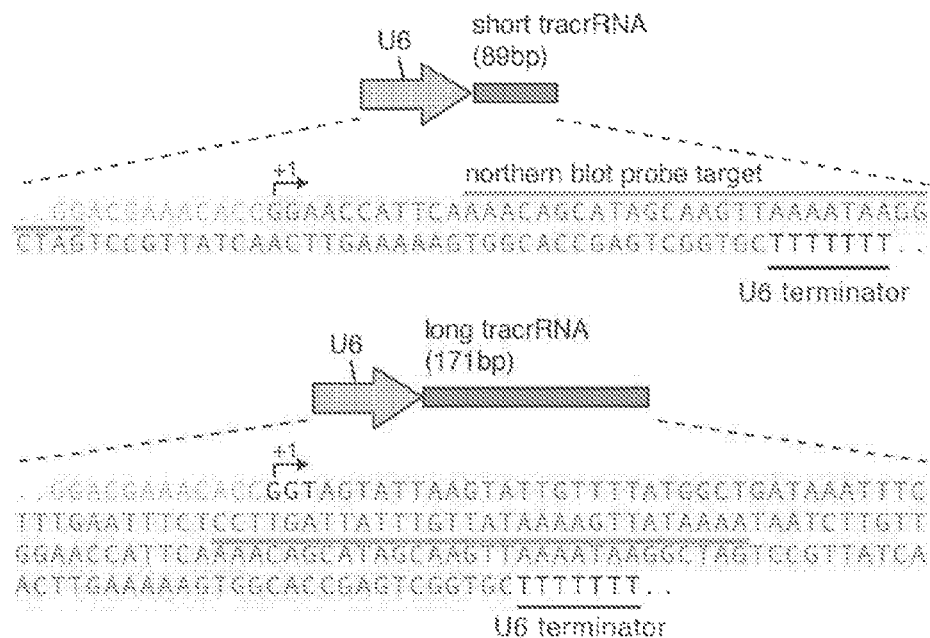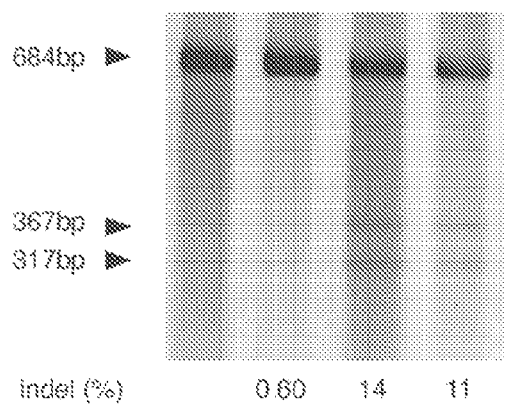
FIG. 7A-B

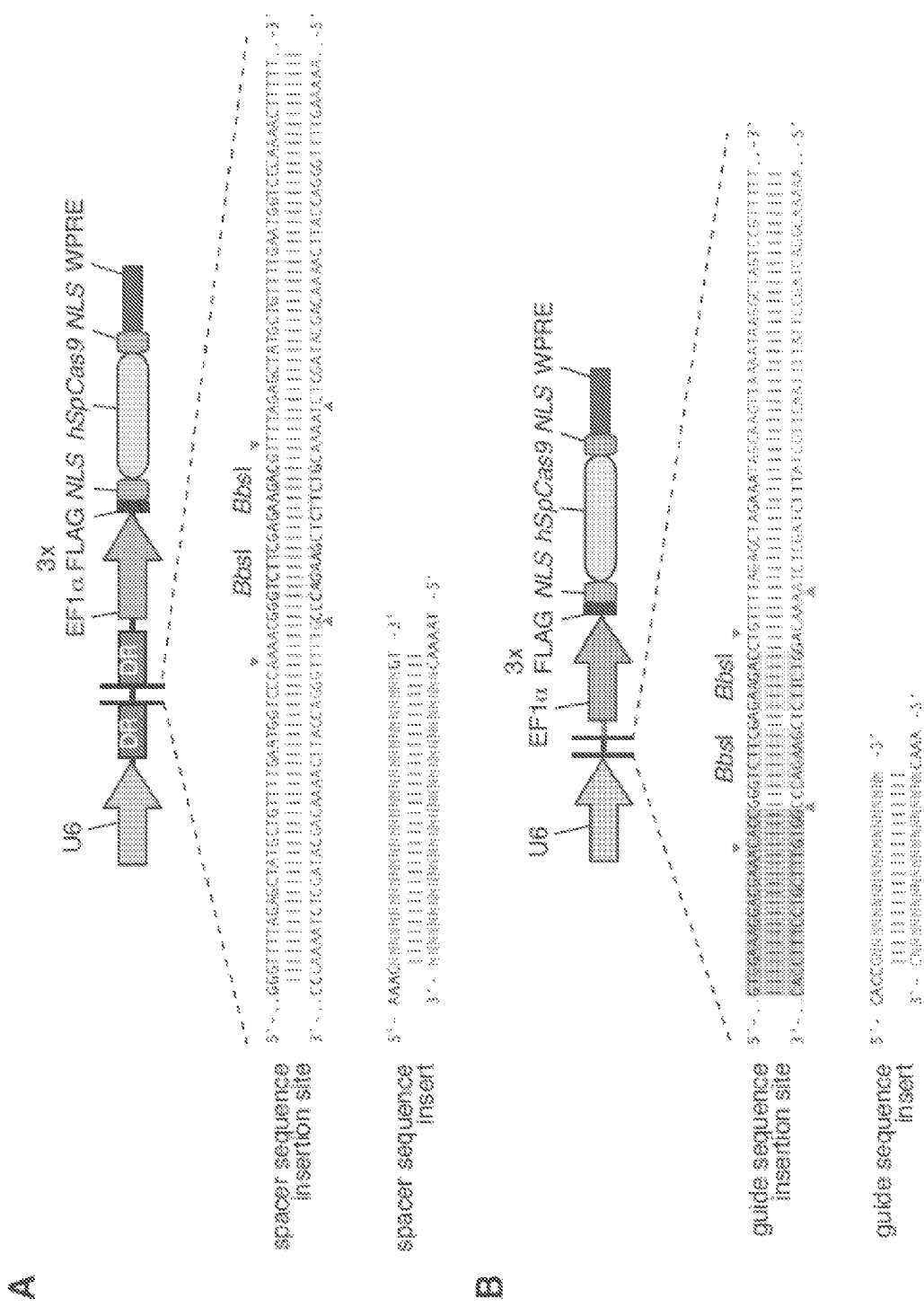
FIG. 9A-B

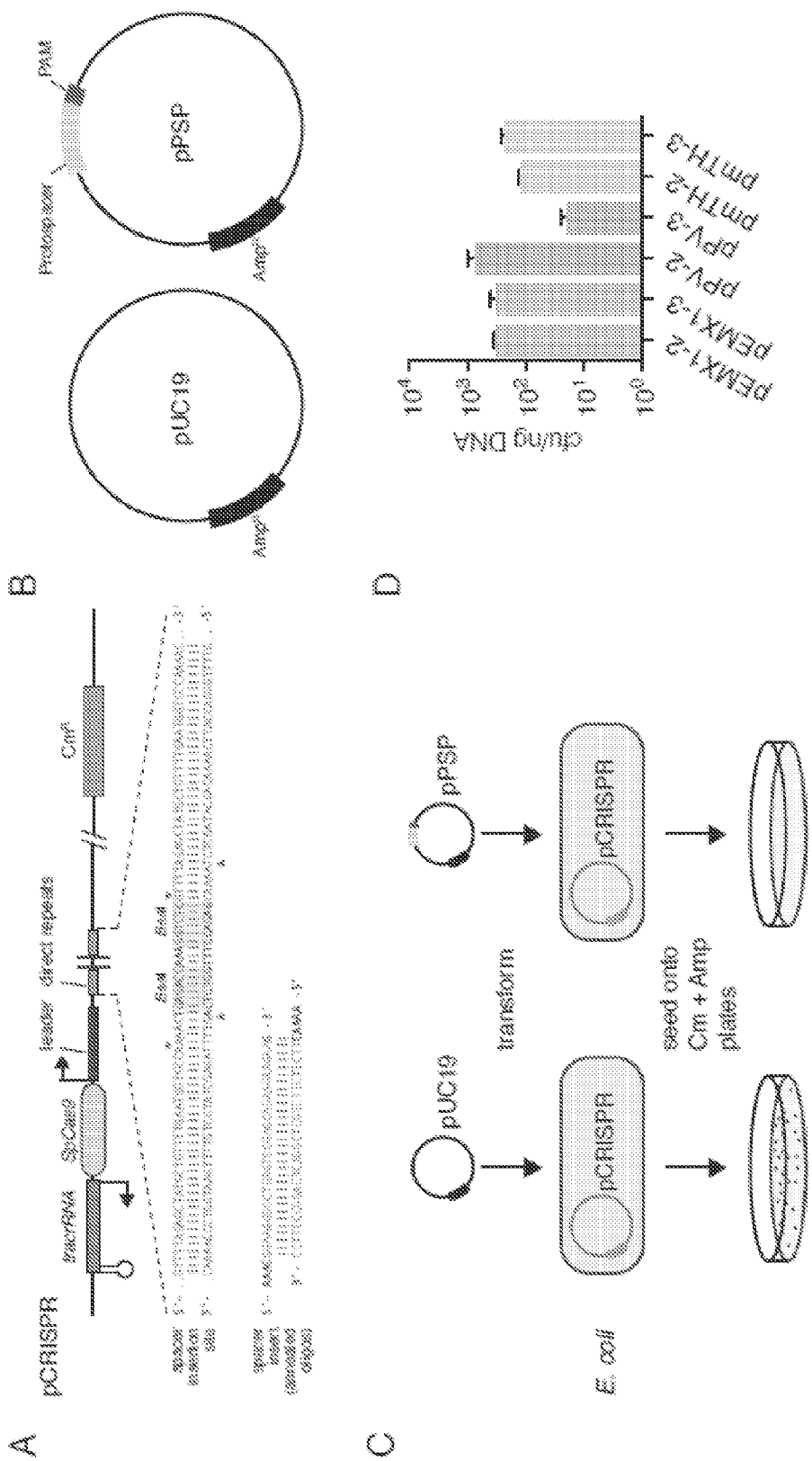
FIG. 10A-D

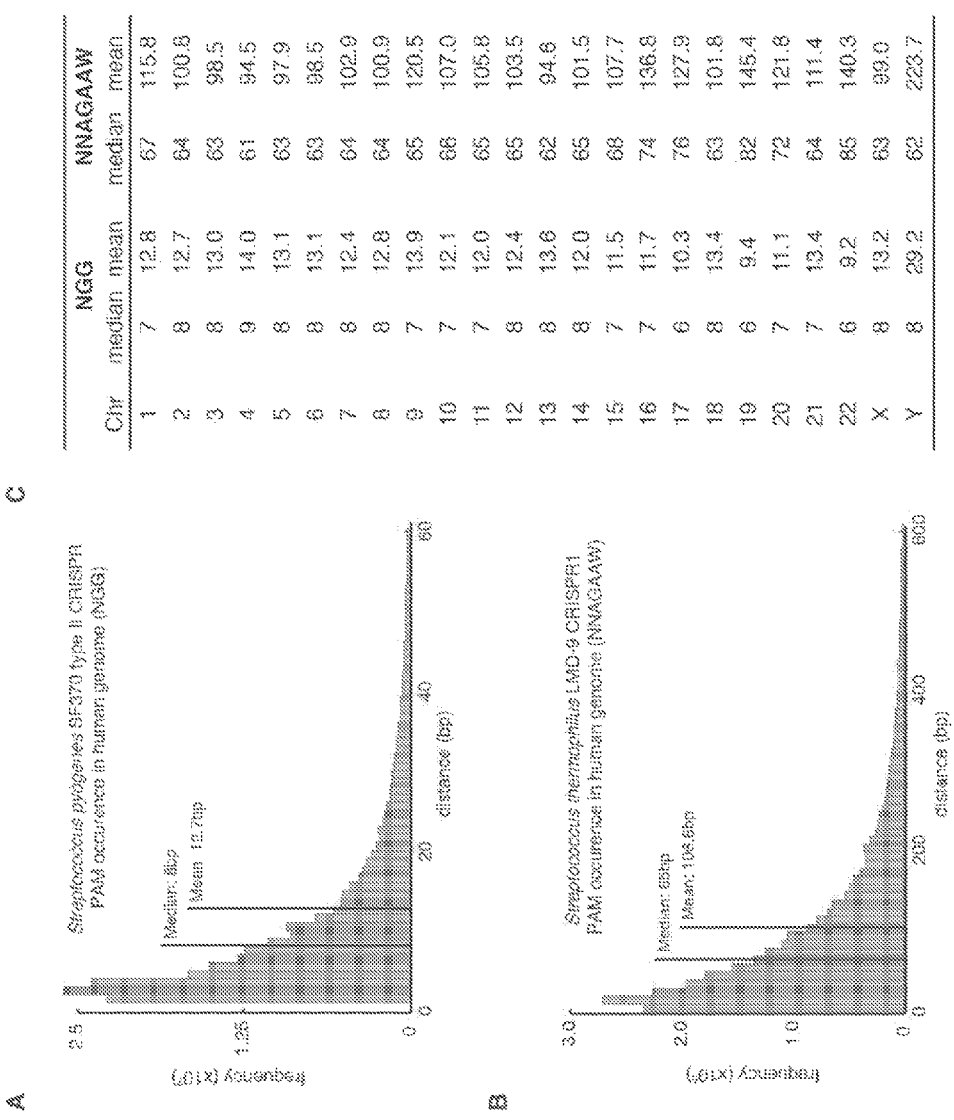
FIG. 11A-C

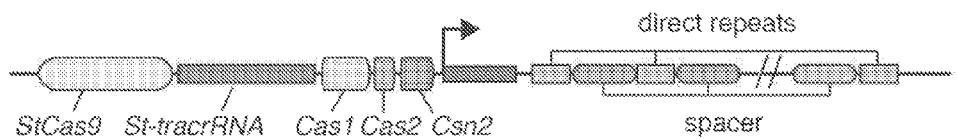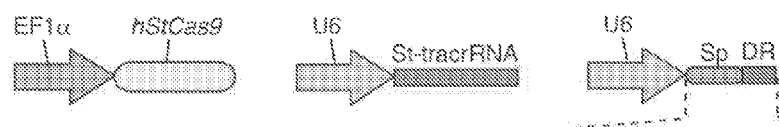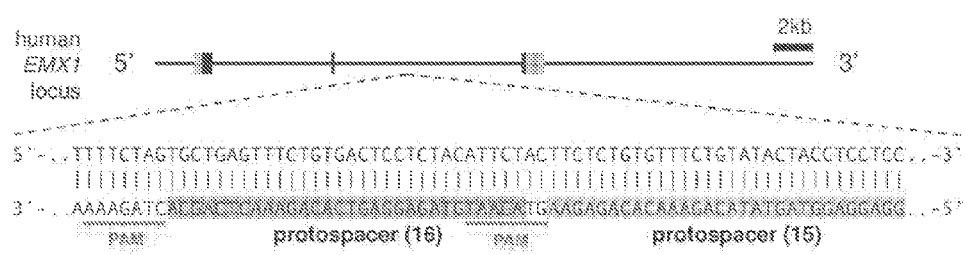
FIG. 12A-C

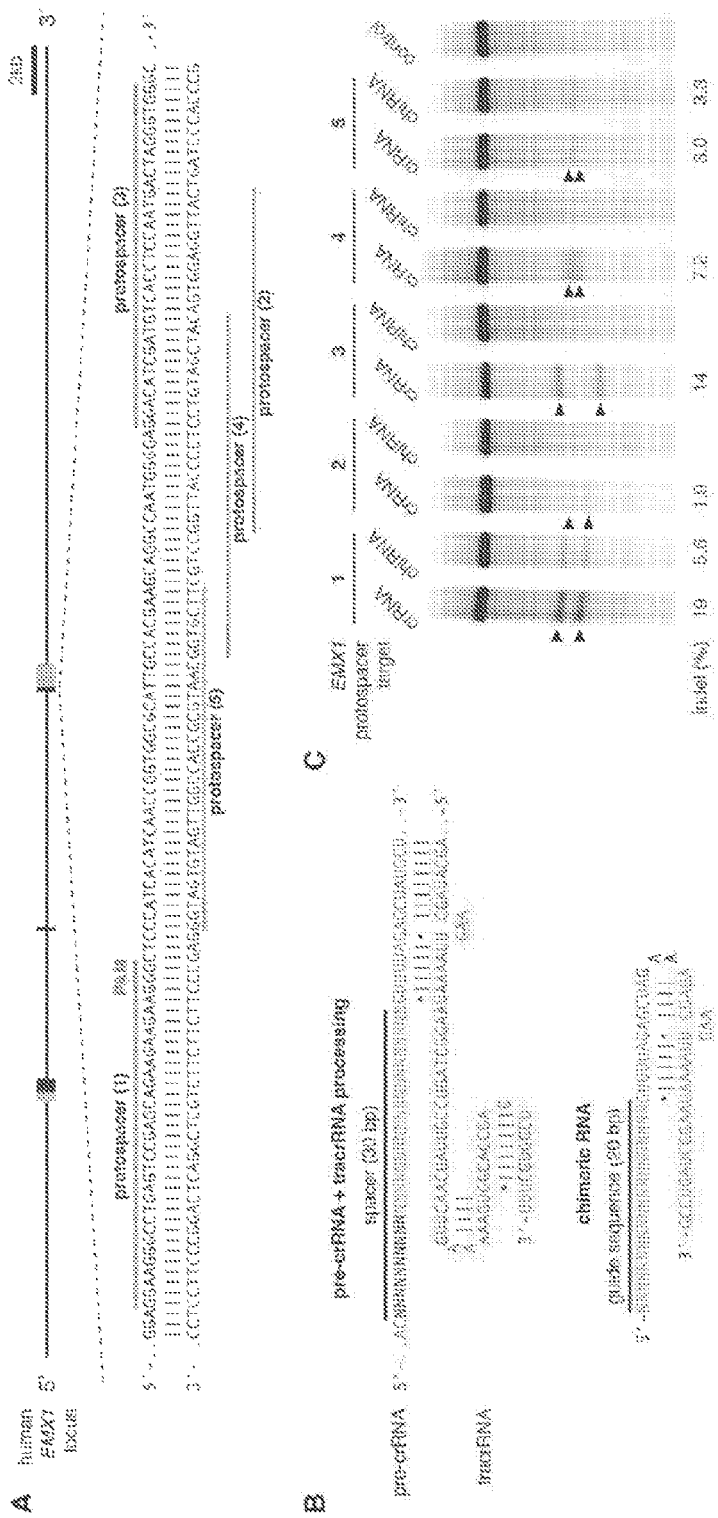
FIG. 13A-C

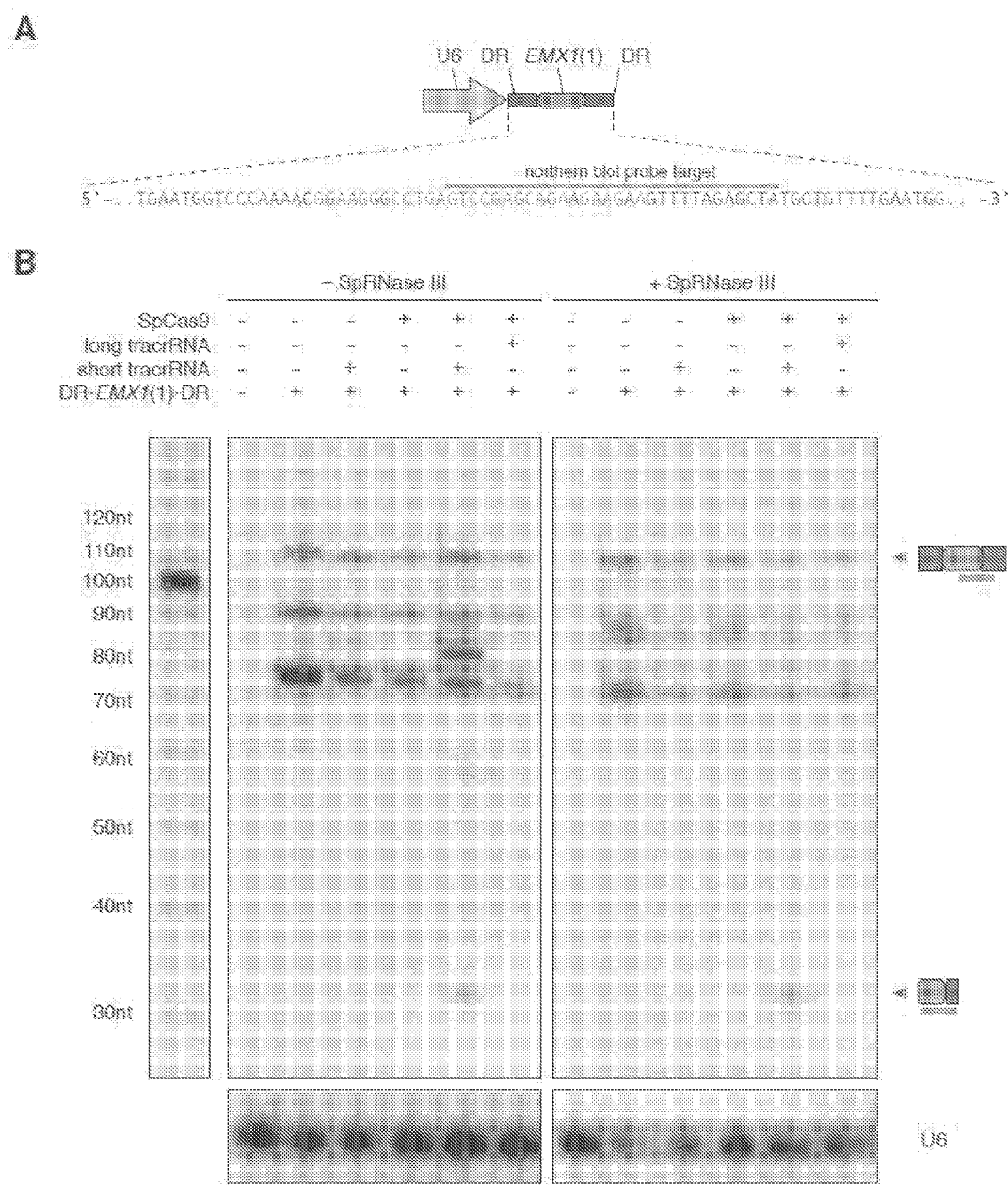
FIG. 14A-B

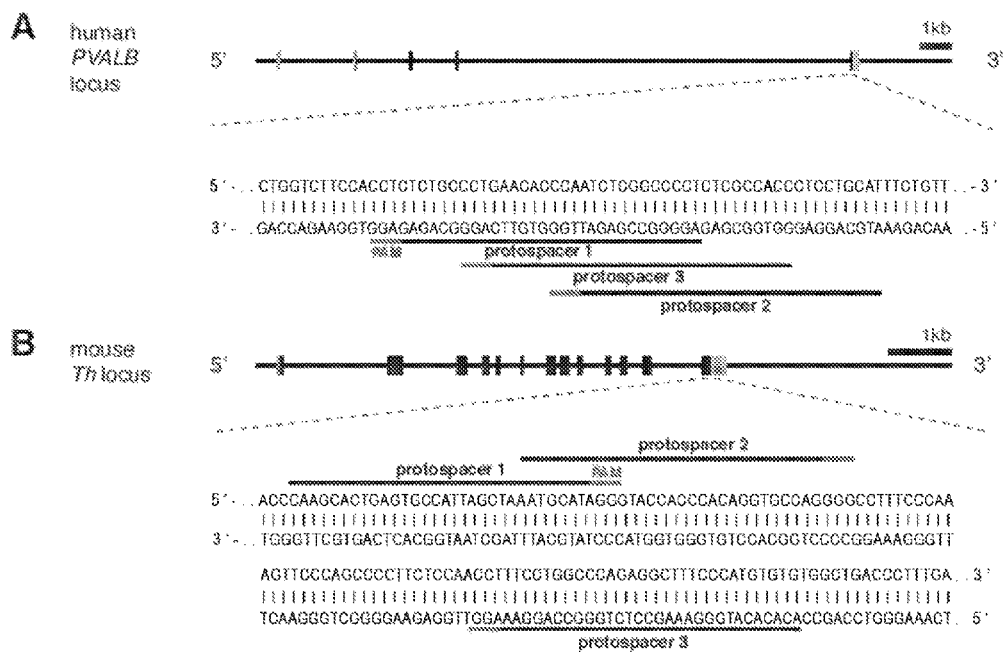
FIG. 15A-B

| Primer name | Assay | Genomic Target | Primer sequence |
|---|---|---|---|
| Sp-EMX1-F | SURVEYOR assay, sequencing | *EMX1* | AAAACCACCCTTCTCTCTGGC |
| Sp-EMX1-R | SURVEYOR assay, sequencing | *EMX1* | GGAGATTGGAGACACGGAGAG |
| Sp-PVALB-F | SURVEYOR assay, sequencing | *PVALB* | CTGGAAAGCCAATGCCTGAC |
| Sp-PVALB-R | SURVEYOR assay, sequencing | *PVALB* | GGCAGCAAACTCCTTGTCCT |
| Sp-Th-F | SURVEYOR assay, sequencing | *Th* | GTGCTTTGCAGAGGCCTACC |
| Sp-Th-R | SURVEYOR assay, sequencing | *Th* | CCTGGAGCGCATGCAGTAGT |
| St-EMX1-F | SURVEYOR assay, sequencing | *EMX1* | ACCTTCTGTGTTTCCACCATTC |
| St-EMX1-R | SURVEYOR assay, sequencing | *EMX1* | TTGGGGAGTGCACAGACTTC |
| Sp-EMX1-RFLP-F | RFLP, sequencing | *EMX1* | GGCTCCCTGGGTTCAAAGTA |
| Sp-EMX1-RFLP-R | RFLP, sequencing | *EMX1* | AGAGGGGTCTGGATGTCGTAA |
| Pb_EMX1_sp1 | Northern Blot Probe | Not applicable | TAGCTCTAAAACTTCTTCTTCTGCTCGGAC |
| Pb_tracrRNA | Northern Blot Probe | Not applicable | CTAGCCTTATTTTAACTTGCTATGCTGTTT |

FIG. 17

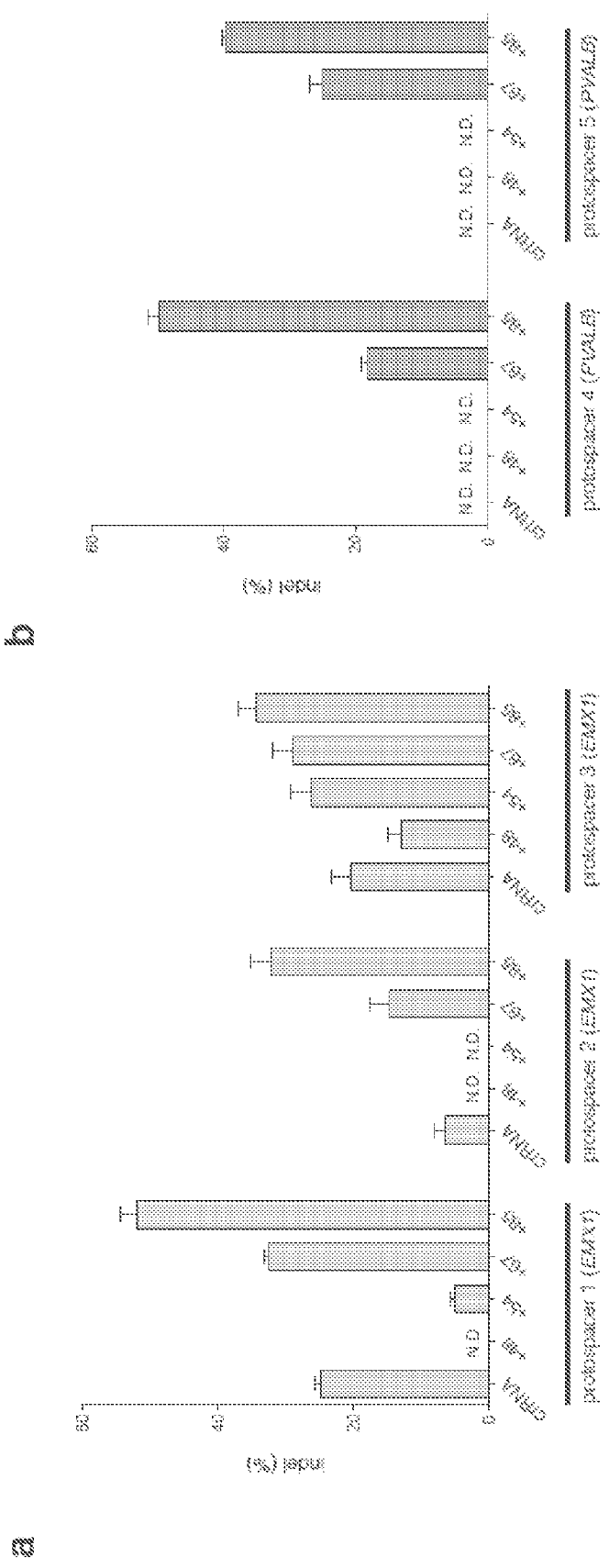
FIG. 19A-B

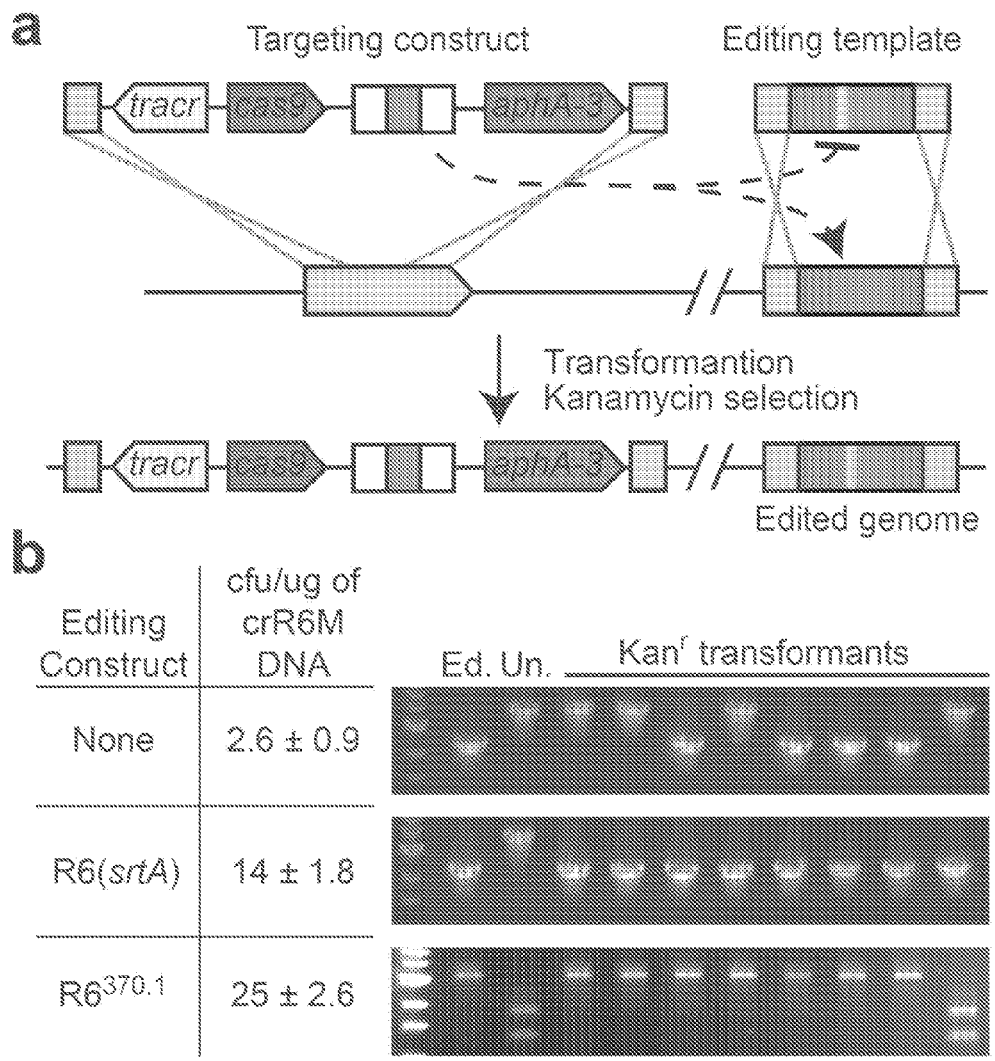
FIG. 23A-B

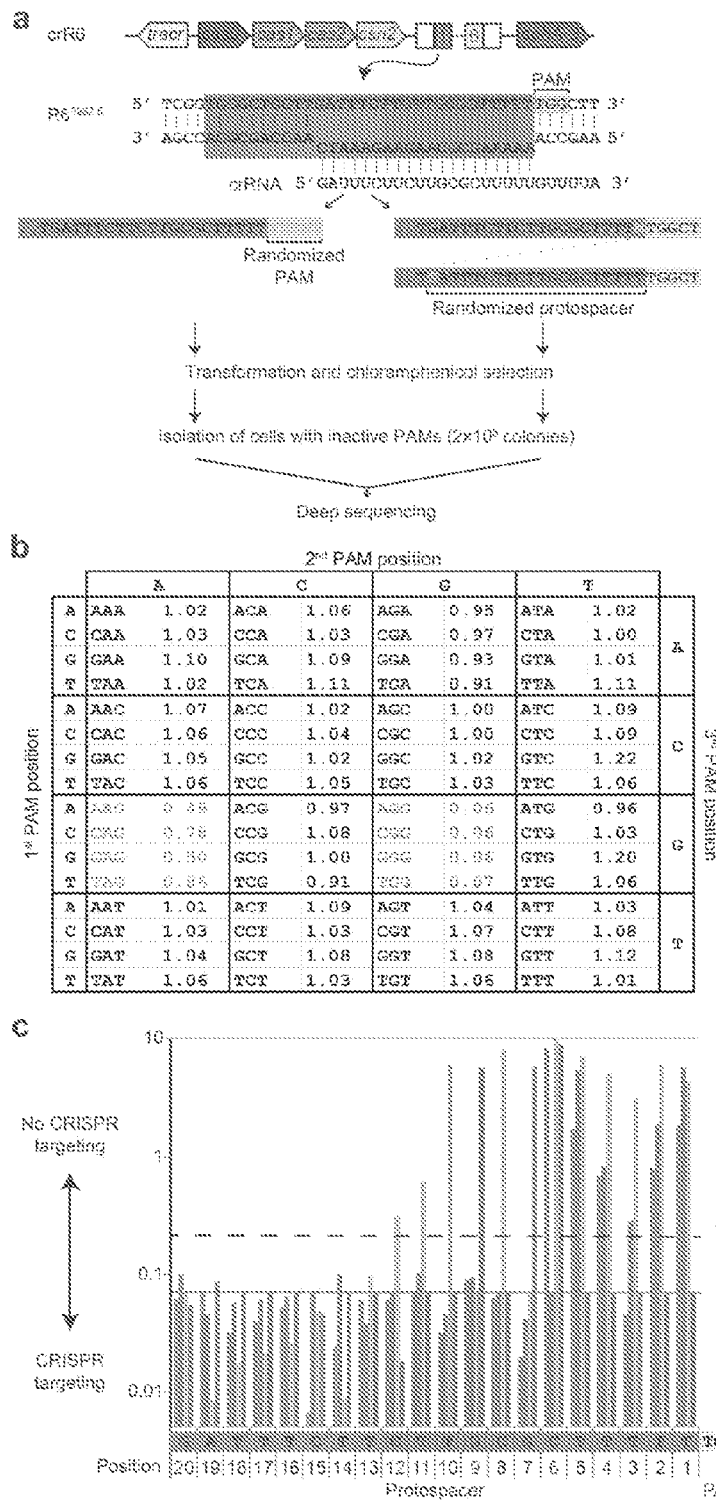
FIG. 24A-C

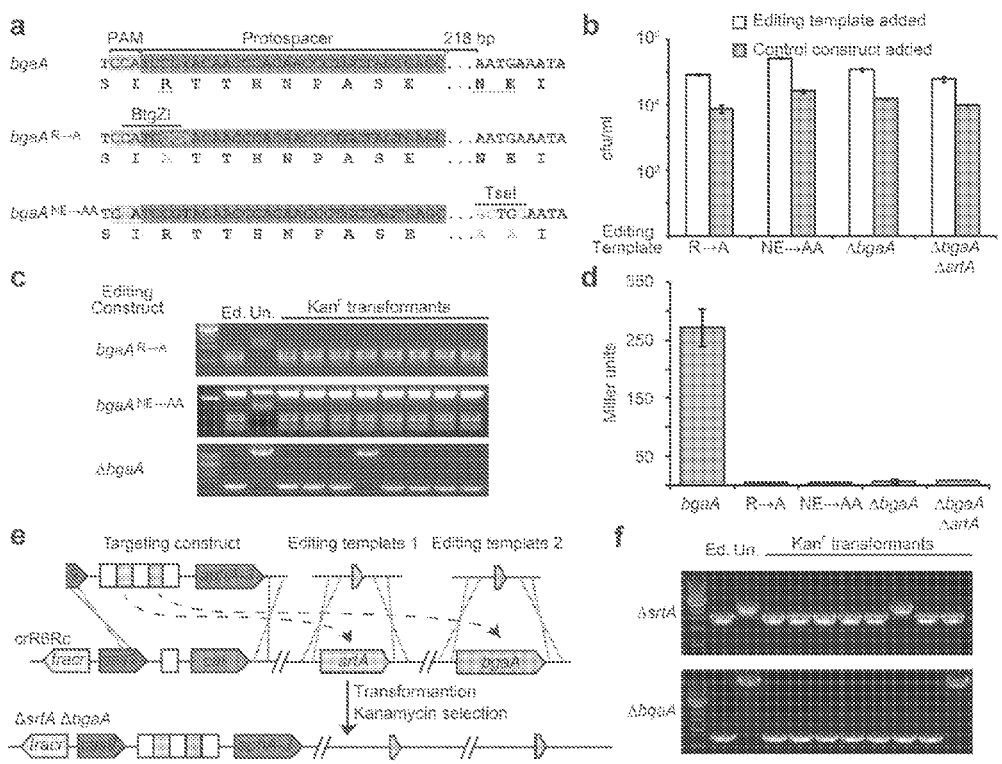
FIG. 25A-F

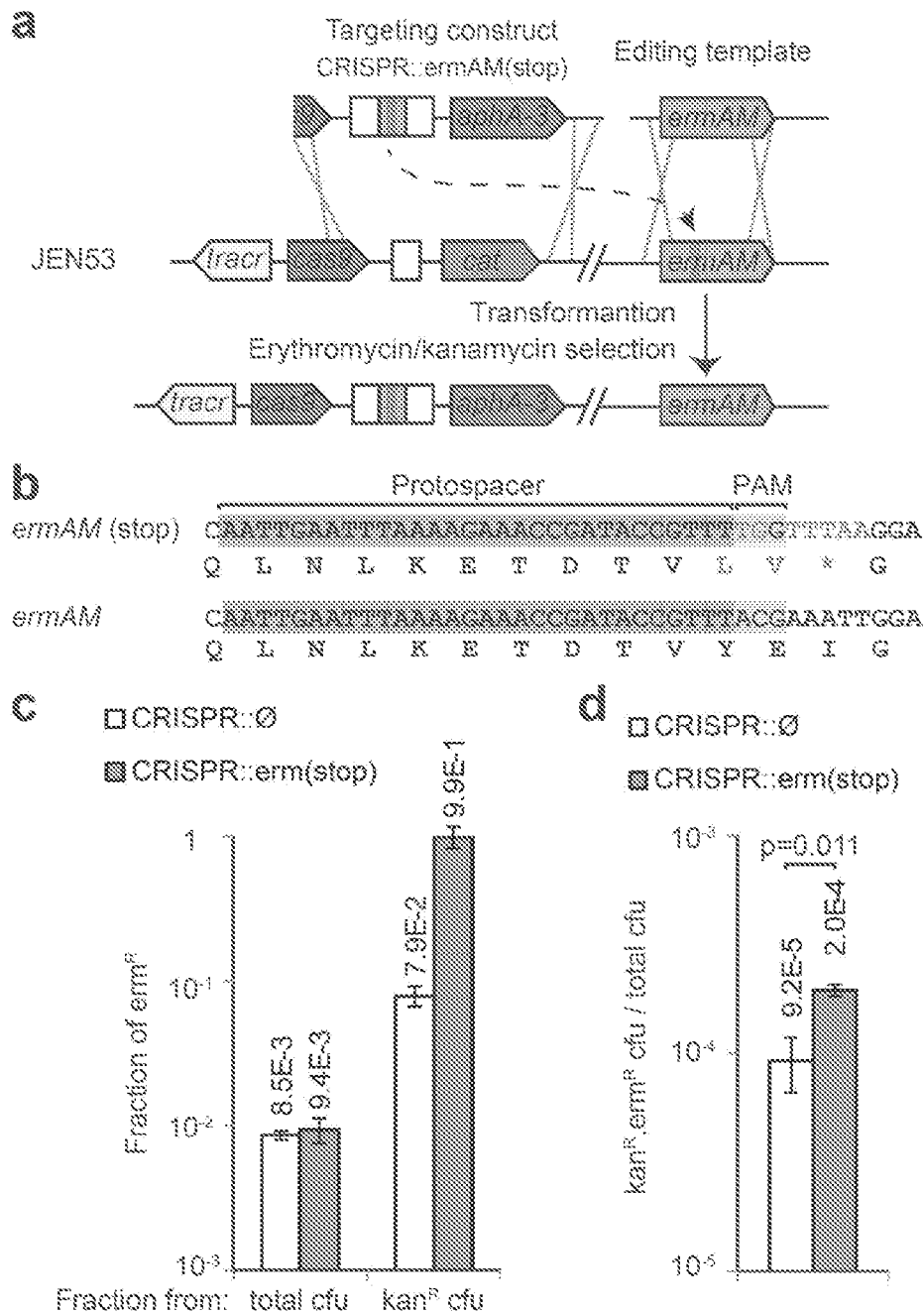
FIG. 26A-D

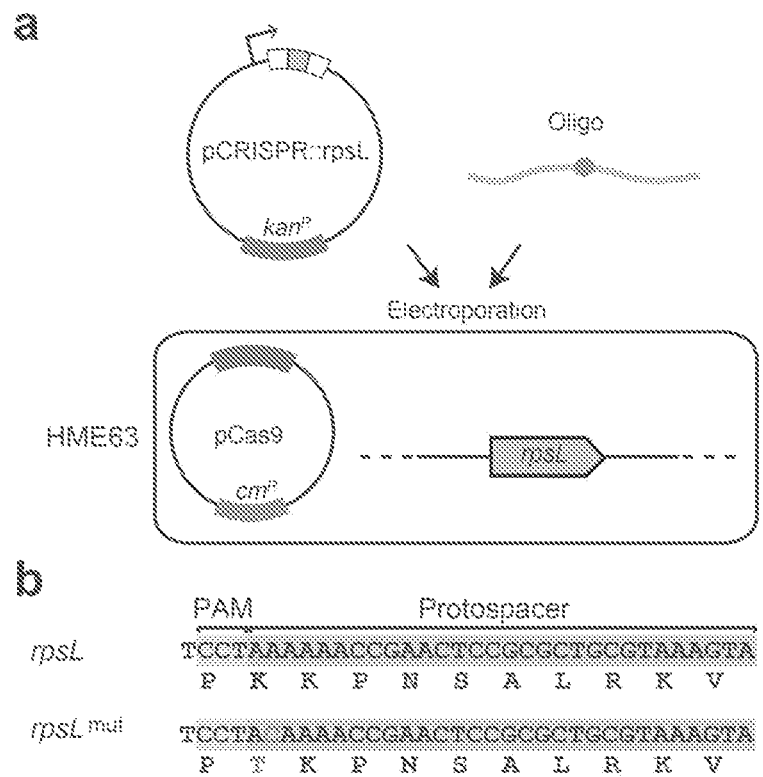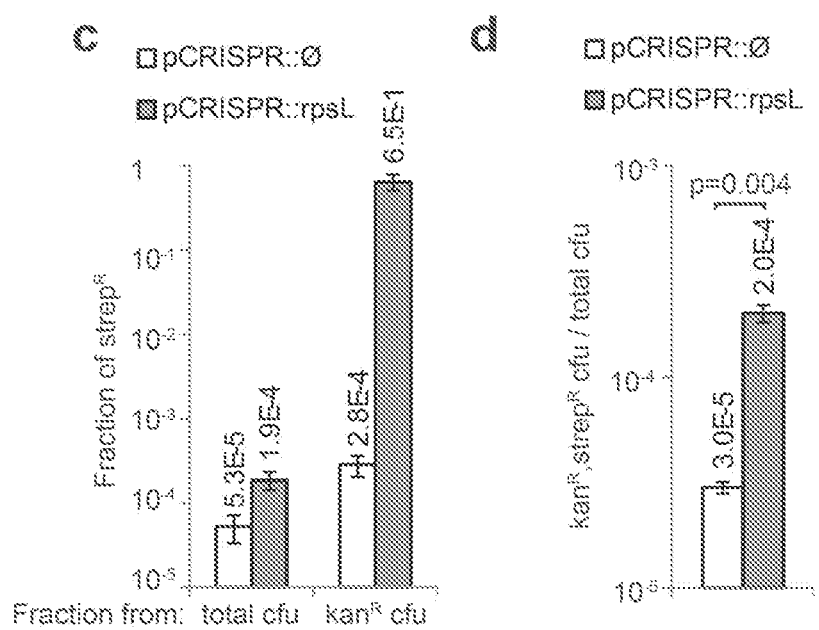
FIG. 27A-D

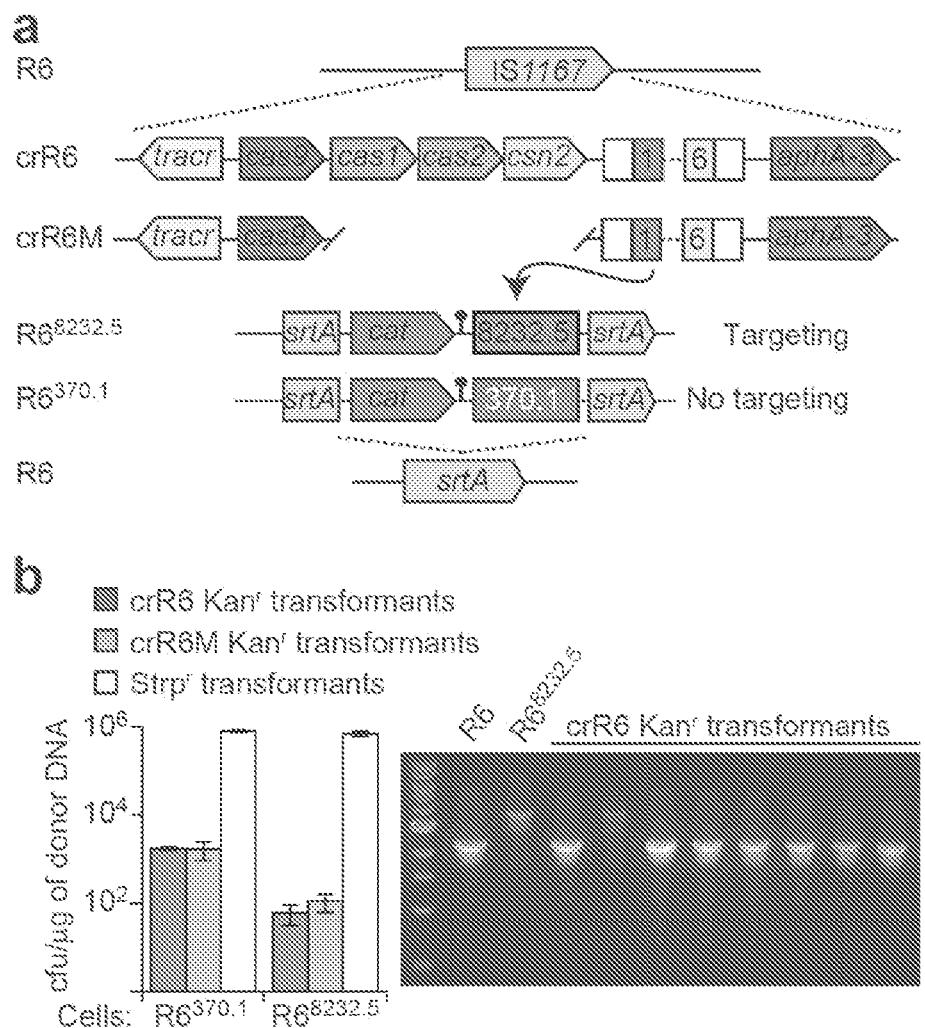
FIG. 28A-B

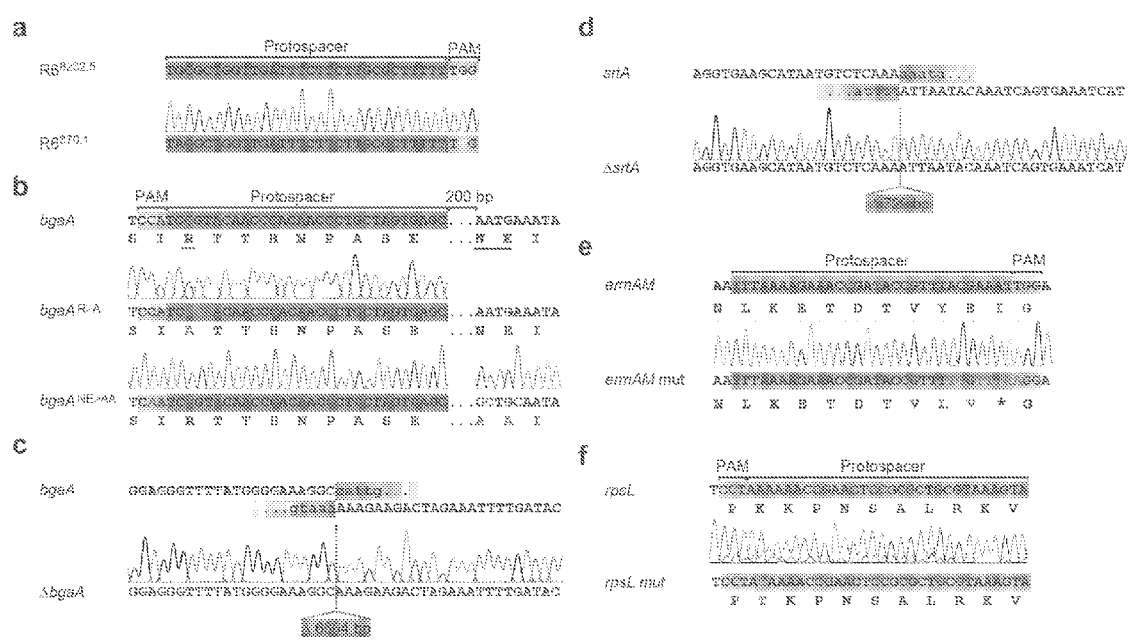
FIG. 29A-F

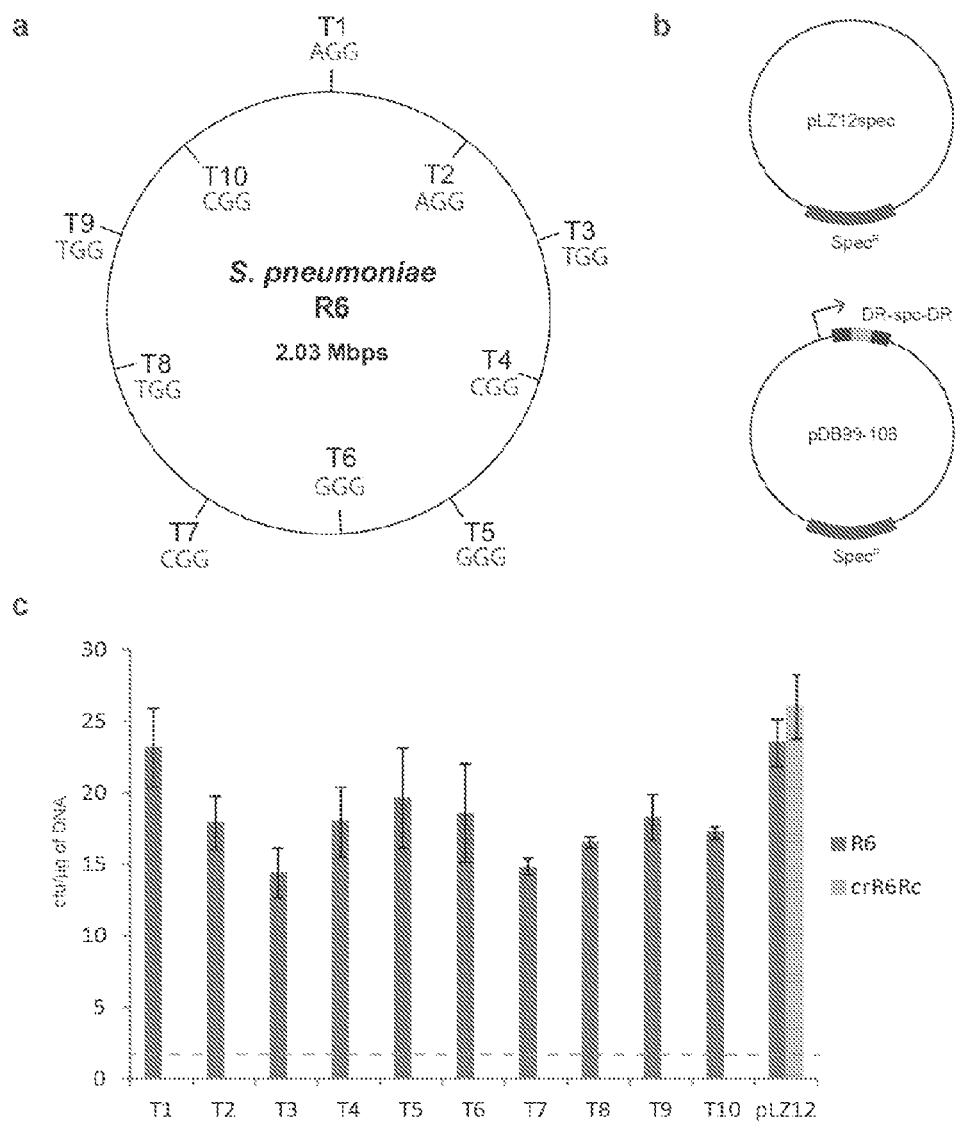
FIG. 30A-C

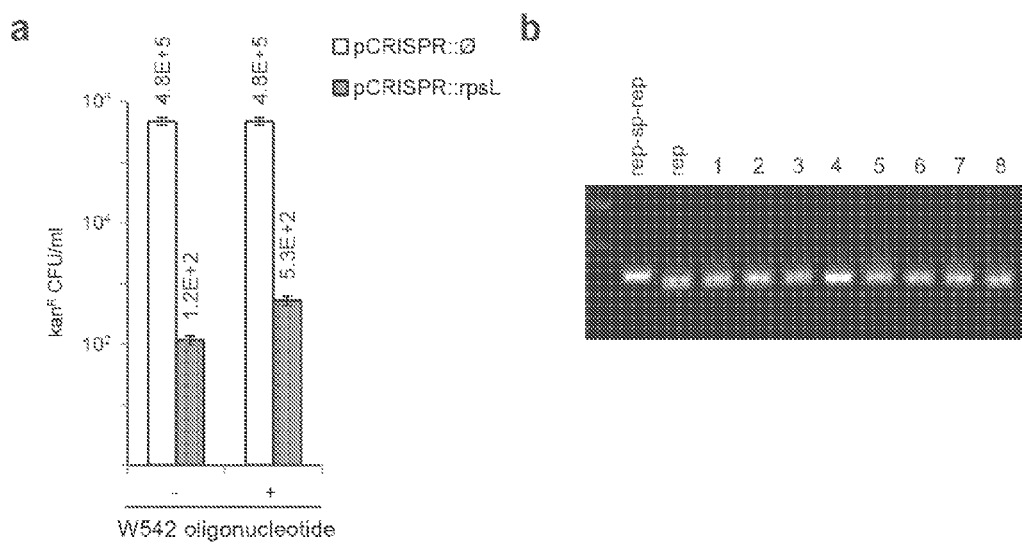
FIG. 38A-B hSpCas9

```
5'  CTGGAAGAGTCCTTCCTGGTGGAAGAGGATAAGAAGCACGAGCGGCACCCCATCTTCGGC
                                                                              360
            L  E  E  S  F  L  V  E  E  D  K  K  H  E  R  H  P  I  F  G
           101 102 103 104 105 106 107 108 109 110 111 112 113 114 115 116 117 118 119 120

5'  AACATCGTGGACGAGGTGGCCTACCACGAGAAGTACCCCACCATCTACCACCTGAGAAAG
                                                                              420
            N  I  V  D  E  V  A  Y  H  E  K  Y  P  T  I  Y  H  L  R  K
           121 122 123 124 125 126 127 128 129 130 131 132 133 134 135 136 137 138 139 140

5'  AAACTGGTGGACAGCACCGACAAGGCCGACCTGCGGCTGATCTATCTGGCCCTGGCCCAT
                                                                              480
            K  L  V  D  S  T  D  K  A  D  L  R  L  I  Y  L  A  L  A  H
           141 142 143 144 145 146 147 148 149 150 151 152 153 154 155 156 157 158 159 160

5'  ATGATCAAGTTCCGGGGCCACTTCCTGATCGAGGGCGACCTGAACCCCGACAATAGCGAC
                                                                              540
            M  I  K  F  R  G  H  F  L  I  E  G  D  L  N  P  D  N  S  D
           161 162 163 164 165 166 167 168 169 170 171 172 173 174 175 176 177 178 179 180

5'  GTGGACAAGCTGTTCATCCAGCTGGTGCAGACCTACAACCAGCTGTTCGAGGAAAACCCC
                                                                              600
            V  D  K  L  F  I  Q  L  V  Q  T  Y  N  Q  L  F  E  E  N  P
           181 182 183 184 185 186 187 188 189 190 191 192 193 194 195 196 197 198 199 200

5'  ATCAACGCCAGCGGCGTGGACGCCAAGGCCATCCTGTCTGCCAGACTGAGCAAGAGCAGA
                                                                              660
            I  N  A  S  G  V  D  A  K  A  I  L  S  A  R  L  S  K  S  R
           201 202 203 204 205 206 207 208 209 210 211 212 213 214 215 216 217 218 219 220
```

FIG. 41B hSpCas9

```
5' CGGCTGGAAAATCTGATCGCCCAGCTGCCCGGTGAGAAGAAGAATGGCCTGTTCGGCAAC
   ++++++++++++++++++++++++++++++++++++++++++++++++++++++++++++ 720
    R  L  E  N  L  I  A  Q  L  P  G  E  K  K  N  G  L  F  G  N
   221 222 223 224 225 226 227 228 229 230 231 232 233 234 235 236 237 238 239 240

5' CTGATTGCCCTGAGCCTGGGCCTGACCCCAAATTCAAGAGCAATTTCGATCTGGCCGAG
   ++++++++++++++++++++++++++++++++++++++++++++++++++++++++++++ 780
    L  I  A  L  S  L  G  L  T  P  N  F  K  S  N  F  D  L  A  E
   241 242 243 244 245 246 247 248 249 250 251 252 253 254 255 256 257 258 259 260

5' GATGCCAAACTGCAGCTGAGCAAGGACACCTACGACGACGACCTGGACAACCTGCTGGCC
   ++++++++++++++++++++++++++++++++++++++++++++++++++++++++++++ 840
    D  A  K  L  Q  L  S  K  D  T  Y  D  D  D  L  D  N  L  L  A
   261 262 263 264 265 266 267 268 269 270 271 272 273 274 275 276 277 278 279 280

5' CAGATCGGCGACCAGTACGCCGACCTGTTCCTGGCCGCTAAGAACCTGTCTGACGCCATC
   ++++++++++++++++++++++++++++++++++++++++++++++++++++++++++++ 900
    Q  I  G  D  Q  Y  A  D  L  F  L  A  A  K  N  L  S  D  A  I
   281 282 283 284 285 286 287 288 289 290 291 292 293 294 295 296 297 298 299 300

5' CTGCTGAGCGACATCCTGAGAGTGAACACCGAGATCACCAAGGCCCCCCTGAGCGCTTCT
   ++++++++++++++++++++++++++++++++++++++++++++++++++++++++++++ 960
    L  L  S  D  I  L  R  V  N  T  E  I  T  K  A  P  L  S  A  S
   301 302 303 304 305 306 307 308 309 310 311 312 313 314 315 316 317 318 319 320

5' ATGATCAAGAGATACGACGAGCACCACCAGGACCTGACCCTGCTGAAAGCTCTCGTGCGG
   ++++++++++++++++++++++++++++++++++++++++++++++++++++++++++++ 1020
    M  I  K  R  Y  D  E  H  H  Q  D  L  T  L  L  K  A  L  V  R
   321 322 323 324 325 326 327 328 329 330 331 332 333 334 335 336 337 338 339 340
```

FIG. 41C

FIG. 41D hSpCas9

```
5' AGATTCGCCTGGATGACCAGAAAGAGCGAGGAAACCATCACCCCCTGGAACTTCGAGGAA
   ++++++++++++++++++++++++++++++++++++++++++++++++++++++++++++  1440
     R  F  A  W  M  T  R  K  S  E  E  T  I  T  P  W  N  F  E  E
    461 462 463 464 465 466 467 468 469 470 471 472 473 474 475 476 477 478 479 480
```

```
5' GTGGTGGACAAGGGCGCTTCCGCCCAGAGCTTCATCGAGCGGATGACCAACTTCGATAAG
   ++++++++++++++++++++++++++++++++++++++++++++++++++++++++++++  1500
     V  V  D  K  G  A  S  A  Q  S  F  I  E  R  M  T  N  F  D  K
    481 482 483 484 485 486 487 488 489 490 491 492 493 494 495 496 497 498 499 500
```

```
5' AACCTGCCCAACGAGAAGGTGCTGCCCAAGCACAGCCTGCTGTACGAGTACTTCACCGTG
   ++++++++++++++++++++++++++++++++++++++++++++++++++++++++++++  1560
     N  L  P  N  E  K  V  L  P  K  H  S  L  L  Y  E  Y  F  T  V
    501 502 503 504 505 506 507 508 509 510 511 512 513 514 515 516 517 518 519 520
```

```
5' TATAACGAGCTGACCAAAGTGAAATACGTGACCGAGGGAATGAGAAAGCCCGCCTTCCTG
   ++++++++++++++++++++++++++++++++++++++++++++++++++++++++++++  1620
     Y  N  E  L  T  K  V  K  Y  V  T  E  G  M  R  K  P  A  F  L
    521 522 523 524 525 526 527 528 529 530 531 532 533 534 535 536 537 538 539 540
```

```
5' AGCGGCGAGCAGAAAAAGGCCATCGTGGACCTGCTGTTCAAGACCAACCGGAAAGTGACC
   ++++++++++++++++++++++++++++++++++++++++++++++++++++++++++++  1680
     S  G  E  Q  K  K  A  I  V  D  L  L  F  K  T  N  R  K  V  T
    541 542 543 544 545 546 547 548 549 550 551 552 553 554 555 556 557 558 559 560
```

```
5' GTGAAGCAGCTGAAAGAGGACTACTTCAAGAAAATCGAGTGCTTCGACTCCGTGGAAATC
   ++++++++++++++++++++++++++++++++++++++++++++++++++++++++++++  1740
     V  K  Q  L  K  E  D  Y  F  K  K  I  E  C  F  D  S  V  E  I
    561 562 563 564 565 566 567 568 569 570 571 572 573 574 575 576 577 578 579 580
```

FIG. 41E hSpCas9

```
5' GTGGAAAACACTCAGCTGCAGAACGAGAAGCTGTACCTGTATTACCTGCAGAATGGCCGG
   ++++++++++++++++++++++++++++++++++++++++++++++++++++++++++++ 2460
                              hSpCas9
    V  E  N  T  Q  L  Q  N  E  K  L  Y  L  Y  Y  L  Q  N  G  R
   801 802 803 804 805 806 807 808 809 810 811 812 813 814 815 816 817 818 819 820

5' GATATGTACGTGGACCAGGAACTGGACATCAACCGGCTGTCCGACTATGATGTGGACGCC
   ++++++++++++++++++++++++++++++++++++++++++++++++++++++++++++ 2520
                              hSpCas9
                                                          HNH
                                                           N
    D  M  Y  V  D  Q  E  L  D  I  N  R  L  S  D  Y  D  V  D  A
   821 822 823 824 825 826 827 828 829 830 831 832 833 834 835 836 837 838 839 840

5' ATCGTGCCTCAGAGCTTTCTGAAGGACGACTCCATCGACGCCAAGGTTCTGACTAGAAGC
   ++++++++++++++++++++++++++++++++++++++++++++++++++++++++++++ 2580
                              hSpCas9
                               HNH
                                N
    I  V  P  Q  S  F  L  K  D  D  S  I  D  A  K  V  L  T  R  S
   841 842 843 844 845 846 847 848 849 850 851 852 853 854 855 856 857 858 859 860

5' GACAAGGGCCGGGGCAAGAGCGACAACGTGCCCTCCGAAGAGGTCGTGAAGAAGATGAAG
   ++++++++++++++++++++++++++++++++++++++++++++++++++++++++++++ 2640
                              hSpCas9
         NHN
          N
    D  K  A  R  G  K  S  D  N  V  P  S  E  E  V  V  K  K  M  K
   861 862 863 864 865 866 867 868 869 870 871 872 873 874 875 876 877 878 879 880

5' AACTATTGGCGGCAGCTGCTGAACGCCAAGCTGATTACCCAGAGAAAGTTCGACAATCTG
   ++++++++++++++++++++++++++++++++++++++++++++++++++++++++++++ 2700
                              hSpCas9
    N  Y  W  R  Q  L  L  N  A  K  L  I  T  Q  R  K  F  D  N  L
   881 882 883 884 885 886 887 888 889 890 891 892 893 894 895 896 897 898 899 900
```

FIG. 41H hSpCas9

```
5'  ACCAAGGCCGAGAGAGGCGGCCTGAGCGAACTGGATAAGGCCGGCTTCATCAAGAGACAG       2760
              T  K  A  E  R  G  G  L  S  E  L  D  K  A  G  F  I  K  R  Q
             901 902 903 904 905 906 907 908 909 910 911 912 913 914 915 916 917 918 919 920

5'  CTGGTGGAAACCCGGCAGATCACAAAGCACGTGGCACAGATCCTGGACTCCCGGATGAAC       2820
              L  V  E  T  R  Q  I  T  K  H  V  A  Q  I  L  D  S  R  M  N
             921 922 923 924 925 926 927 928 929 930 931 932 933 934 935 936 937 938 939 940

5'  ACTAAGTACGACGAGAATGACAAGCTGATCCGGGAAGTGAAAGTGATCACCCTGAAGTCC       2880
              T  K  Y  D  E  N  D  K  L  I  R  E  V  K  V  I  T  L  K  S
             941 942 943 944 945 946 947 948 949 950 951 952 953 954 955 956 957 958 959 960

5'  AAGCTGGTGTCCGATTTCCGGAAGGATTTCCAGTTTTACAAAGTGCGCGAGATCAATAAC       2940
              K  L  V  S  D  F  R  K  D  F  Q  F  Y  K  V  R  E  I  N  N
             961 962 963 964 965 966 967 968 969 970 971 972 973 974 975 976 977 978 979 980

5'  TACCACCACGCCCACGACGCCTATCTGAACGCCGTCGTGGGAACCGCCCTGATCAAAAAG       3000
              Y  H  H  A  H  D  A  Y  L  N  A  V  V  G  T  A  L  I  K  K
             981 982 983 984 985 986 987 988 989 990 991 992 993 994 995 996 997 998 999 1000
```

FIG. 41I

FIG. 41J hSpCas9

```
5'  GCCAGAAAGAAGGACTGGGACCCTAAGAAGTACGGCGGCTTCGACAGCCCCACCGTGGCC
                                                                    3420
    A  R  K  K  D  W  D  P  K  K  Y  G  G  F  D  S  P  T  V  A
   1121 1122 1123 1124 1125 1126 1127 1128 1129 1130 1131 1132 1133 1134 1135 1136 1137 1138 1139 1140

5'  TATTCTGTGCTGGTGGTGGCCAAAGTGGAAAAGGGCAAGTCCAAGAAACTGAAGAGTGTG
                                                                    3480
    Y  S  V  L  V  V  A  K  V  E  K  G  K  S  K  K  L  K  S  V
   1141 1142 1143 1144 1145 1146 1147 1148 1149 1150 1151 1152 1153 1154 1155 1156 1157 1158 1159 1160

5'  AAAGAGCTGCTGGGGATCACCATCATGGAAAGAAGCAGCTTCGAGAAGAATCCCATCGAC
                                                                    3540
    K  E  L  L  G  I  T  I  M  E  R  S  S  F  E  K  N  P  I  D
   1161 1162 1163 1164 1165 1166 1167 1168 1169 1170 1171 1172 1173 1174 1175 1176 1177 1178 1179 1180

5'  TTCCTGGAAGCCAAGGGCTACAAAGAAGTGAAAAAGGACCTGATCATCAAGCTGCCTAAG
                                                                    3600
    F  L  E  A  K  G  Y  K  E  V  K  K  D  L  I  I  K  L  P  K
   1181 1182 1183 1184 1185 1186 1187 1188 1189 1190 1191 1192 1193 1194 1195 1196 1197 1198 1199 1200

5'  TACTCCCTGTTCGAGCTGGAAAACGGCCGGAAGAGAATGCTGGCCTCTGCCGGCGAACTG
                                                                    3660
    Y  S  L  F  E  L  E  N  G  R  K  R  M  L  A  S  A  G  E  L
   1201 1202 1203 1204 1205 1206 1207 1208 1209 1210 1211 1212 1213 1214 1215 1216 1217 1218 1219 1220

5'  CAGAAGGGAAACGAACTGGCCCTGCCCTCCAAATATGTGAACTTCCTGTACCTGGCCAGC
                                                                    3720
    Q  K  G  N  E  L  A  L  P  S  K  Y  V  N  F  L  Y  L  A  S
   1221 1222 1223 1224 1225 1226 1227 1228 1229 1230 1231 1232 1233 1234 1235 1236 1237 1238 1239 1240
```

FIG. 41K hSpCas9

```
5'  CACTATGAGAAGCTGAAGGGCTCCCCCGAGGATAATGAGCAGAAACAGCTGTTTGTGGAA  3780
        H  Y  E  K  L  K  G  S  P  E  D  N  E  Q  K  Q  L  F  V  E
       1241 1242 1243 1244 1245 1246 1247 1248 1249 1250 1251 1252 1253 1254 1255 1256 1257 1258 1259 1260

5'  CAGCACAAGCACTACCTGGACGAGATCATCGAGCAGATCAGCGAGTTCTCCAAGAGAGTG  3840
        Q  H  K  H  Y  L  D  E  I  I  E  Q  I  S  E  F  S  K  R  V
       1261 1262 1263 1264 1265 1266 1267 1268 1269 1270 1271 1272 1273 1274 1275 1276 1277 1278 1279 1280

5'  ATCCTGGCCGACGCTAATCTGGACAAAGTGCTGTCCGCCTACAACAAGCACCGGGATAAG  3900
        I  L  A  D  A  N  L  D  K  V  L  S  A  Y  N  K  H  R  D  K
       1281 1282 1283 1284 1285 1286 1287 1288 1289 1290 1291 1292 1293 1294 1295 1296 1297 1298 1299 1300

5'  CCCATCAGAGAGCAGGCCGAGAATATCATCCACCTGTTTACCCTGACCAATCTGGGAGCC  3960
        P  I  R  E  Q  A  E  N  I  I  H  L  F  T  L  T  N  L  G  A
       1301 1302 1303 1304 1305 1306 1307 1308 1309 1310 1311 1312 1313 1314 1315 1316 1317 1318 1319 1320

5'  CCTGCCGCCTTCAAGTACTTTGATACCACCATCGACCGGAAGAGGTACACCAGCACCAAA  4020
        P  A  A  F  K  Y  F  D  T  T  I  D  R  K  R  Y  T  S  T  K
       1321 1322 1323 1324 1325 1326 1327 1328 1329 1330 1331 1332 1333 1334 1335 1336 1337 1338 1339 1340

5'  GAGGTGCTGGACGCCACCCTGATCCACCAGAGCATCACCGGCCTGTACGAGACACGGATC  4080
        E  V  L  D  A  T  L  I  H  Q  S  I  T  G  L  Y  E  T  R  I
       1341 1342 1343 1344 1345 1346 1347 1348 1349 1350 1351 1352 1353 1354 1355 1356 1357 1358 1359 1360
```

FIG. 41L hSpCas9
5'   GACCTGTCTCAGCTGGGAGGCGAC

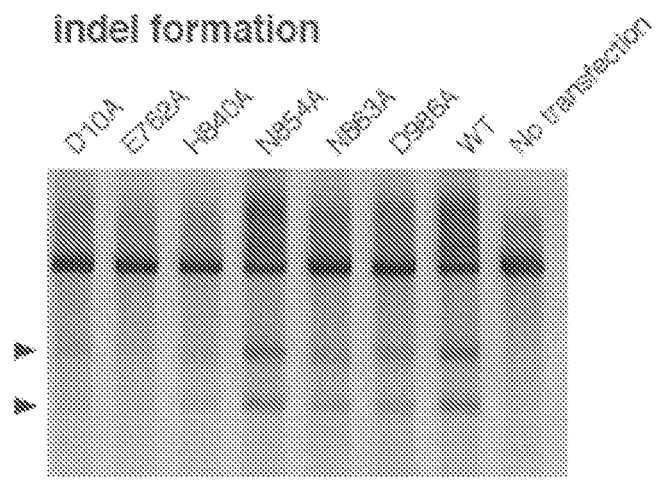
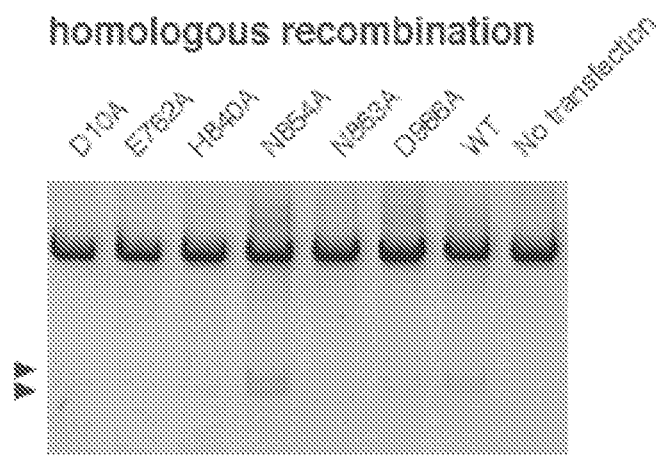
FIG. 47

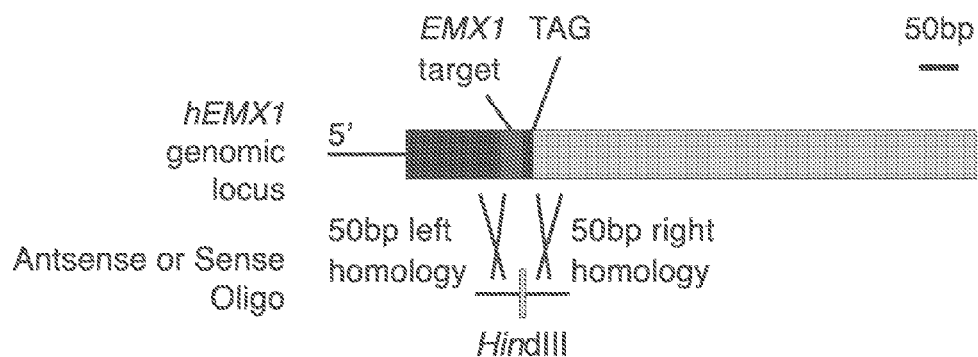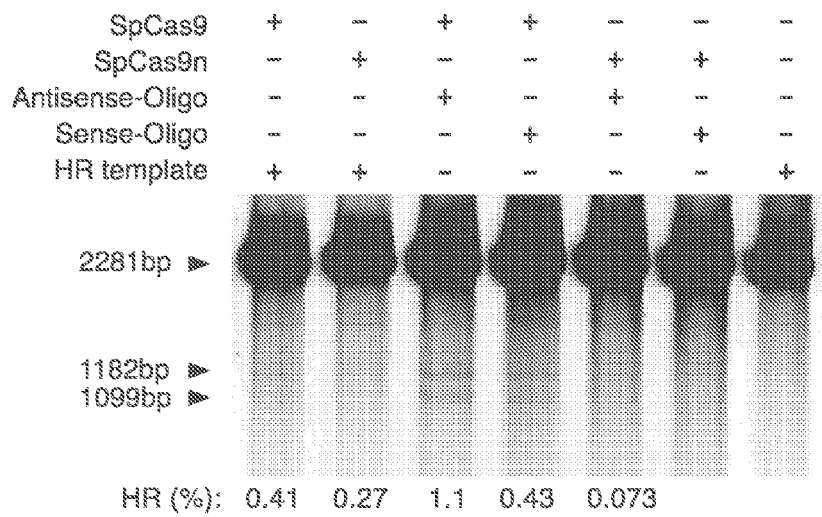
FIG. 48A-B

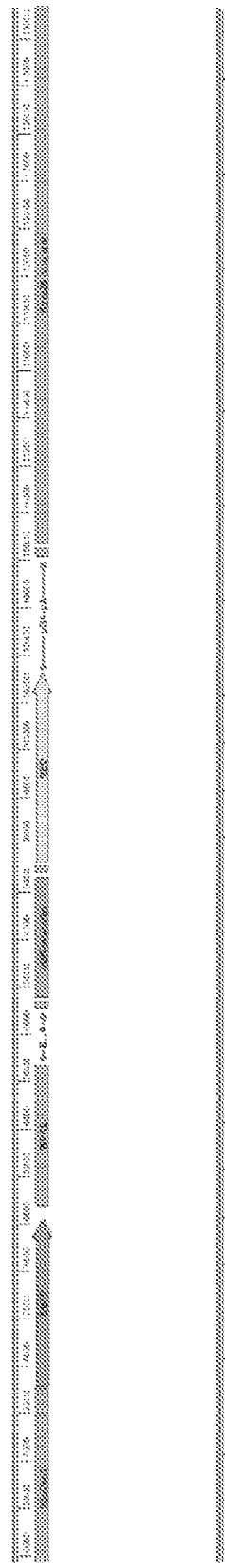
Constitutive Cas9, Rosa26 targeting vector map
FIG. 49B pCAG
ccgttaaacaattctgcaggaatctagttattaatagtaatcaattacggggtcattagttcatagcccatatatggagttccgcgttacataactt
acggtaaatggcccgcctggctgaccgcccaacgacccccgcccattgacgtcaataatgacgtatgttcccatagtaacgccaatagggga
ctttccattgacgtcaatgggtggagtatttacggtaaactgcccacttggcagtacatcaagtgtatcatatgccaagtacgccccctattgac
gtcaatgacggtaaatggcccgcctggcattatgcccagtacatgaccttatgggactttcctacttggcagtacatctacgtattagtcatcgc
tattaccatggtcgaggtgagccccacgttctgcttcactctccccatctcccccctccccacccccaatttgtatttatttatttttaattatttt
gtgcagcgatgggggcgggggggggggggggcgcgcgccaggcggggcggggcggggcgaggggcggggcggggcgaggc
ggagaggtgcggcggcagccaatcagagcggcgcgctccgaaagtttccttttatggcgaggcggcggcggcggcggccctataaaaa
gcgaagcgcgcggcgggcggaAGTCGCTGCGgcgtgccttcgcccgtgccccgctccgccgccgcctcgcgccgcccgcc
ccggctctgactgaccgcgttactcccacaggtgagcgggcgggacggcccttctcctccgggctgtaattagcgcttggtttaatgacggc
ttgtttcttttctgtggctgcgtgaaagccttgaggggctccggggagggccctttgtgcgggggagcggctcggggggtgcgtgcgtgtgt
gtgtgcgtgggggagcgccgcgtgcggctccgcgctgcccggcggctgtgagcgctgcgggcgcggcgcgggggctttgtgcgctccgc
agtgtgcgcgaggggagcgcggccgggggcggtgccccgcggtgcggggggggctgcgagggggaacaaaggctgcgtgcggggt
gtgtgcgtgggggggtgagcaggggggtgtgggcgcgtcggtcgaggctgcaaccccccctgcaccccctcccgagttgctgagcacg
gcccggcttcggtgtgcgggctccgtacgggcgtggcgcggggctcgccgtgccggcgggggggtggcggcaggtgggggtgcc
gggcggggcggggccgcctcggggccgggagagctcggggagggggcgcggcggccccggagcgccggcggctgtcgaggcg
cggcgagccgcagccattgcctttatggtaatcgtgcgagatggcgcagggacttcctttgtcccaaatctgtgcggagccgaaatctgg
gaggcgccgccgcacccctagcggggcgcggggcgaagcggttgcggcgccggcaggaaggaaatgggcggggagggccttcgt
gcgtcgccgcgccgccgtcccttctccctctccagcctcggggctgtccgcggggggacggctgccttcgggggggacgggcaggga
cggggttcggcttctggcgtgtgaccggcggctctagagcctctgctaaccatgttcatgccttcttctttttcctacagctcctgggcaacgtg
ctggttattgtgctgtctcatcatttggcaaa NLS-Cas9-NLS
ATGGACTATAAGGACCACGACGGAGACTACAAGGATCATGATATTGATTACAAAGA
CGATGACGATAAGATGGCCCCAAAGAAGAAGCGGAAGGTCGGTATCCACGGAGTCC
CAGCAGCCGACAAGAAGTACAGCATCGGCCTGGACATCGGCACCAACTCTGTGGGC
TGGGCCGTGATCACCGACGAGTACAAGGTGCCCAGCAAGAAATTCAAGGTGCTGGG
CAACACCGACCGGCACAGCATCAAGAAGAACCTGATCGGAGCCCTGCTGTTCGACA
GCGGCGAAACAGCCGAGGCCACCCGGCTGAAGAGAACCGCCAGAAGAAGATACAC
CAGACGGAAGAACCGGATCTGCTATCTGCAAGAGATCTTCAGCAACGAGATGGCCA
AGGTGGACGACAGCTTCTTCCACAGACTGGAAGAGTCCTTCCTGGTGGAAGAGGAT
AAGAAGCACGAGCGGCACCCCATCTTCGGCAACATCGTGGACGAGGTGGCCTACCA
CGAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGCC
ACTTCCTGATCGAGGGCGACCTGAACCCCGACAACAGCGACGTGGACAAGCTGTTC

FIG. 50A

```
ATCCAGCTGGTGCAGACCTACAACCAGCTGTTCGAGGAAAACCCCATCAACGCCAG
CGGCGTGGACGCCAAGGCCATCCTGTCTGCCAGACTGAGCAAGAGCAGACGGCTGG
AAAATCTGATCGCCCAGCTGCCCGGCGAGAAGAAGAATGGCCTGTTCGGaAACCTG
ATTGCCCTGAGCCTGGGCCTGACCCCAACTTCAAGAGCAACTTCGACCTGGCCGAG
GATGCCAAACTGCAGCTGAGCAAGGACACCTACGACGACGACCTGGACAACCTGCT
GGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCC
CTGAGCGCCTCTATGATCAAGAGATACGACGAGCACCACCAGGACCTGACCCTGCT
GAAAGCTCTCGTGCGGCAGCAGCTGCCTGAGAAGTACAAAGAGATTTTCTTCGACC
AGAGCAAGAACGGCTACGCCGGCTACATTGACGGCGGAGCCAGCCAGGAAGAGTTC
TACAAGTTCATCAAGCCCATCCTGGAAAAGATGGACGGCACCGAGGAACTGCTCGT
GAAGCTGAACAGAGAGGACCTGCTGCGGAAGCAGCGGACCTTCGACAACGGCAGC
ATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCG
CATCCCCTACTACGTGGGCCCTCTGGCCAGGGGAAACAGCAGATTCGCCTGGATGA
CCAGAAAGAGCGAGGAAACCATCACCCCCTGGAACTTCGAGGAAGTGGTGGACAA
GGGCGCTTCCGCCCAGAGCTTCATCGAGCGGATGACCAACTTCGATAAGAACCTGC
CCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCT
GAGCGGCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTTCGACTC
CGTGGAAATCTCCGGCGTGGAAGATCGGTTCAACGCCTCCCTGGGCACATACCACG
ATCTGCTGAAAATTATCAAGGACAAGGACTTCCTGGACAATGAGGAAAACGAGGAC
ATTCTGGAAGATATCGTGCTGACCCTGACACTGTTTGAGGACAGAGAGATGATCGA
GGAACGGCTGAAAACCTATGCCCACCTGTTCGACGACAAAGTGATGAAGCAGCTGA
AGCGGCGGAGATACACCGGCTGGGGCAGGCTGAGCCGGAAGCTGATCAACGGCATC
CGGGACAAGCAGTCCGGCAAGACAATCCTGGATTTCCTGAAGTCCGACGGCTTCGC
CAACAGAAACTTCATGCAGCTGATCCACGACGACAGCCTGACCTTTAAAGAGGACA
TCCAGAAAGCCCAGGTGTCCGGCCAGGGCGATAGCCTGCACGAGCACATTGCCAAT
CTGGCCGGCAGCCCCGCCATTAAGAAGGGCATCCTGCAGACAGTGAAGGTGGTGGA
CGAGCTCGTGAAAGTGATGGGCCGGCACAAGCCCGAGAACATCGTGATCGAAATGG
CCAGAGAGAACCAGACCACCCAGAAGGGACAGAAGAACAGCCGCGAGAGAATGAA
GCGGATCGAAGAGGGCATCAAAGAGCTGGGCAGCCAGATCCTGAAAGAACACCCC
GTGGAAAACACCCAGCTGCAGAACGAGAAGCTGTACCTGTACTACCTGCAGAATGG
GCGGGATATGTACGTGGACCAGGAACTGGACATCAACCGGCTGTCCGACTACGAT
```

FIG. 50B

GTGGACCATATCGTGCCTCAGAGCTTTCTGAAGGACGACTCCATCGACAACAAGGTG
CTGACCAGAAGCGACAAGAACCGGGGCAAGAGCGACAACGTGCCCTCCGAAGAGG
TCGTGAAGAAGATGAAGAACTACTGGCGGCAGCTGCTGAACGCCAAGCTGATTACC
CAGAGAAAGTTCGACAATCTGACCAAGGCCGAGAGAGGCGGCCTGAGCGAACTGG
ATAAGGCCGGCTTCATCAAGAGACAGCTGGTGGAAACCCGGCAGATCACAAAGCAC
GTGGCACAGATCCTGGACTCCCGGATGAACACTAAGTACGACGAGAATGACAAGCT
GATCCGGGAAGTGAAAGTGATCACCCTGAAGTCCAAGCTGGTGTCCGATTTCCGGA
AGGATTTCCAGTTTTACAAAGTGCGCGAGATCAACAACTACCACCACGCCCACGAC
GCCTACCTGAACGCCGTCGTGGGAACCGCCCTGATCAAAAAGTACCCTAAGCTGGA
AAGCGAGTTCGTGTACGGCGACTACAAGGTGTACGACGTGCGGAAGATGATCGCCA
AGAGCGAGCAGGAAATCGGCAAGGCTACCGCCAAGTACTTCTTCTACAGCAACATC
ATGAACTTTTTCAAGACCGAGATTACCCTGGCCAACGGCGAGATCCGGAAGCGGCC
TCTGATCGAGACAAACGGCGAAACCGGGGAGATCGTGTGGGATAAGGGCCGGGATT
TTGCCACCGTGCGGAAAGTGCTGAGCATGCCCCAAGTGAATATCGTGAAAAAGACC
GAGGTGCAGACAGGCGGCTTCAGCAAAGAGTCTATCCTGCCCAAGAGGAACAGCGA
TAAGCTGATCGCCAGAAAGAAGGACTGGGACCCTAAGAAGTACGGCGGCTTCGACA
GCCCCACCGTGGCCTATTCTGTGCTGGTGGTGGCCAAAGTGGAAAAGGGCAAGTCC
AAGAAACTGAAGAGTGTGAAAGAGCTGCTGGGGATCACCATCATGGAAAGAAGCA
GCTTCGAGAAGAATCCCATCGACTTTCTGGAAGCCAAGGGCTACAAAGAAGTGAAA
AAGGACCTGATCATCAAGCTGCCTAAGTACTCCCTGTTCGAGCTGGAAAACGGCCG
GAAGAGAATGCTGGCCTCTGCCGGCGAACTGCAGAAGGGAAACGAACTGGCCCTGC
CCTCCAAATATGTGAACTTCCTGTACCTGGCCAGCCACTATGAAGCTGAAGGGCT
CCCCCGAGGATAATGAGCAGAAACAGCTGTTTGTGGAACAGCACAAGCACTACCTG
GACGAGATCATCGAGCAGATCAGCGAGTTCTCCAAGAGAGTGATCCTGGCCGACGC
TAATCTGGACAAAGTGCTGTCCGCCTACAACAAGCACCGGGATAAGCCCATCAGAG
AGCAGGCCGAGAATATCATCCACCTGTTTACCCTGACCAATCTGGGAGCCCCTGCCG
CCTTCAAGTACTTTGACACCACCATCGACCGGAAGAGGTACACCAGCACCAAAGAG
GTGCTGGACGCCACCCTGATCCACCAGAGCATCACCGGCCTGTACGAGACACGGAT
CGACCTGTCTCAGCTGGGAGGCGACAAAAGGCCGGCGGCCACGAAAAAGGCCGGC
CAGGCAAAAAAGAAAAAG

P2A-EGFP
ggaagcggagccactaacttctccctgttgaaacaagcagggggatgtcgaagagaatcccgggccaGTGAGCAAGGGCGA
GGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTG
ACCCTGAAGTTCATCT

FIG. 50C

GCACCACCGGCAAGCTGCCCGTGCCCTGGCCCACCCTCGTGACCACCCTGACCTACG
GCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGG
AGTACAACTACAACAGCCACAACGTCTATATCATGGCCGACAAGCAGAAGAACGGC
ATCAAGGTGAACTTCAAGATCCGCCACAACATCGAGGACGGCAGCGTGCAGCTCGC
CGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGAT
CACATGGTCCTGCTGGAGTTCGTGACCGCCGCCGGGATCACTCTCGGCATGGACGAG
CTGTACAAG

WPRE
Cgataatcaacctctggattacaaaatttgtgaaagattgactggtattcttaactatgttgctccttttacgctatgtggatacgctgctttaatgc
cttgtatcatgctattgcttcccgtatggctttcattttctcctccttgtataaatcctggttgctgtctctttatgaggagttgtggcccgttgtcagg
caacgtggcgtggtgtgcactgtgtttgctgacgcaacccccactggttggggcattgccaccacctgtcagctcctttccgggactttcgctt
tccccctccctattgccacggcggaactcatcgccgcctgccttgcccgctgctggacaggggctcggctgttgggcactgacaattccgtg
gtgttgtcggggaaatcatcgtcctcctggctgctcgcctgtgttgccacctggattctgcgcgggacgtcctctgctacgtccctcggc
cctcaatccagcggaccttccttcccgcggcctgctgccggctctgcggcctcttccgcgtcttcgccttcgccctcagacgagtcggatctc
ccttgggccgcctccccgcatcg bGHpolyA
cgacCTCGACtgtgccttctagttgccagccatctgttgtttgcccctcccccgtgccttccttgaccctggaaggtgccactcccactgt
cctttcctaataaaatgaggaaattgcatcgcattgtctgagtaggtgtcattctattctggggggtggggtggggcaggacagcaaggggg
aggattgggaagacaatGgcaggcatg loxP-SV40polyAx3-loxP
ataacttcgtataatgtatgctatacgaagttattcgcgatgaataaatgaaagcttgcagatctgcgactctagaggatctgcgactctagagg
atcataatcagccataccacatttgtagaggttttacttgctttaaaaaacctcccacacctccccctgaacctgaaacataaaatgaatgcaa
ttgttgttgttaacttgtttattgcagcttataatggttacaaataaagcaatagcatcacaaatttcacaaataaagcatttttttcactgcattctagt
tgtggtttgtccaaactcatcaatgtatcttatcatgtctggatctgcgactctagaggatcataatcagccataccacatttgtagaggtttactt
gctttaaaaaacctcccacacctccccctgaacctgaaacataaaatgaatgcaattgttgttgttaacttgtttattgcagcttataatggttaca
aataaagcaatagcatcacaaatttcacaaataaagcatttttttcactgcattctagttgtggtttgtccaaactcatcaatgtatcttatcatgtct
ggatctgcgactctagaggatcataatcagccataccacatttgtagaggttttacttgctttaaaaaacctcccacacctccccctgaacctga
aacataaaatgaatgcaattgttgttgttaacttgtttattgcagcttataatggttacaaata

FIG. 50D aagcaatagcatcacaaaatttcacaaataaaagcattttttcactgcattctagttgtgggttgtccaaactcatcaatgtatcttatcatgtctggat
cccatcaagctgatccggaacccttaatataacttcgtataatgtatgctatacgaagttat Rosa26 short homology arm
caggccctccgagcgtggtggagccgttctgtgagacagccgggtacgagtcgtgacgctggaagggggcaagcgggtggtggcagg
aatgcggtccgccctgcagcaaccggaggggggaggggagaagggagcggaaaaagtctccaccggacgcggccatggctcggggggg
gggggcagcggaggaGcgcttcggccgacgtctcgtcgctgattggcttCttttcctcccgccgtgtgtgaaaacacaaatggcgtgtt
ttggttggcgtaaggcgcctgtcagttaacggcagccggagtgcgcagccgccggcagcctcgctctgcccactgggtggggcgggag
gtaggtggggtgaggcgagctgGacgtgcgggcgcgtcggcctctggcggagcggggaggggagtgagggtcagcgaaagta
gctcgcgcgcgagcggccgcccaccctcccttcctctgggggagtcgtttacccgccgccggccgggcctcgtcgtctgattggctctc
gggcccagaaaactggcccttgccattggctcgtgttcgtgcaagttgagtccatccgccggccagcggggacggcgaggaggcgctc
caggtccggccctccctcgggccccgcgccgcagagtctggccgcgcgcccctgcgcaacgtggcaggaagcgcgcgctgggggc
ggggacgggcagtagggctgagcgactgcggagcggagtgcaagcacgttccgactgagttgcctcaagaggggcgtgctgagccag
acctccatcgcgcactccggggagtggaggggaaggagcgaggggctcagtggctgtttggaggcaggaagcacttgctctcccaaagt
cgctctgagttgttatcagtaagggggagctgcagtggagtaggcgggggagaaggccgcaccctctccggagggggggaggggagtgttgc
aataccttctggggagttctctgctgcctcctggcttctgaggaccgccctgggcctgggagaatccttccccctcttccctcgtgatctgcaa
ctccagtctttctag Rosa26 long homology arm
agatgggcgggagtctctgggcaggcttaaaggctaacctggtgtgtgggcgttgtcctgcaggtgtaattgaacaggtgtaaaattggag
ggacaagacttcccacagattttcggttttgtcggaagttttttaataggggcaaataaggaaatgtggaggataggtagtcatctgggggttt
atgcagcaaaactacaggttattattgctgtgatccgcctcggagtatttccatcgaggtagattaaagacatgctcaccgagtttatactct
ccttgctGAGATCCTTACTACAGTATGAAATTACAGTGTCGCGAGTTAGACTATGTAAGC
AGAATTTTAATCATttttaaagagcccagtacttcatatccattctccgctcctctgcagccttatcaaaggtaTtttagaaca
ctcatttttagcccatttcatttattatactggctatccaaccctagacagagcattggcatttccttcctgatcttagaagtctgatgactca
tgaaccagacagattagttacatacaccacaaatgaggctgtagctggggcctcaacactgcagtctttataactccttagtacacttttg
ttgatccttgccttgatccttaattcagtgtctatcacctctccgtcaggtggtgtccacattgggcctattctcagtccaggagtttaca
acaatgatgtattgagaatccaacctaaagcttaactttccactcccatgaatgcctctctccttttctccattTATAAACTGAGCT
ATTAACCATTAATGGTTTCCAGGTGGATGTCTCCTCCCCCAATATTACCTGATGTATC
TTACATATTGCCAGGCTGATATTTTAAGACATTAAAAGGTATATTTCATTATTGAGCC
ACATGGTATTGATTACTGCTtactaaaattttgtcatlgtacacatcgtaaaaggtggttcctttggaatgcaaagttcaggt
gtttgttgtcttcctgacctaaggtcttgtgagcttgtattttttctatttaagcagtgctttctcttggactggcttgactcatggcattctacacgtta
ttgctggtctaaatgtgatttgccaagcttcttcaggacctataatttgcttgactgtagccaaacacaagtaaaatgattaagcaacaaatgt
attgtgaagctggttttagttgtgtgtgttgtgtgtgcttgtgctctataataatactatccaggtggctggagaggtggctcggagttcaagag
cacagactgctcttccagaagtc

FIG. 50E ctgagttcaattcccagcaaccacatggtggctacaaccatctgtaatgggatctgatgccctcttctggtgtgtctgaagaccacaagtgta
ttcacattaaataaataaaTCCTCCTTCTTCTTCTTTTTTTTTTTTTtAAAGAGAATACTGTCTCCAG
TAGAAtTTACTGAAGTAATGAAATACTTTGTGTTTGTTCCAATATGGTAGCCAATAAT
CAAATtACTCTTTaAGCACTGGAAATGTtACCAAGGAACTAaTTTTtATTTgAAGTGTaA
CTGTGGACAGAGGAGCCATAACTGCAGACTTGTGGATACAGAAGACCAATGCAGA
CtTAATGTCTTTTCTCTTACACTAAGCAATAAAGAAATAAAAATTGAACTTCTAGTA
TCCTATTTGTTtAAACTGCTAGCTTTACtTAACTTTTGTGCTTCATCTATACAAAGCTG
AAAGCTAAGTCTGCAGCCATTACTAAACATGAAAGCAAGTAATGATAATTTTGGATT
TCAAAAATGTAGGGCCAGAGTTTAGCCAGCCAGTGGTGGTGCTTGCCTTTATGCCtTT
AATCCCAGCACTCTGGAGGCAGAGACAGGCAGATCTCTGAGTTTGAGCCCAGCCTG
GtCTACACATCAAGTTCTATCTAGGATAGCCAGGAATACACACAGAAACCCTGTTGG
GGAGGGGGCTCTGAGATTTCATAAAATTATAATTGAAGCATTCCCTAATGAGCCAC
TATGGATGTGGCTAAATCCGTCTACCTTTCTGATGAGATTTGGGTATTATTTTTCTG
TCTCTGCTGTTGGTTGGGTCTTTGACACTGTGGGCTTTCTTAAAGCCTCCTTCCTGC
CATGTGGTCTCTTGTTTGCTACTAACTTCCCATGGCTTAAATGGCATGGCTTTTTGCC
TTCTAAGGGCAGCTGCtGAGATTTGCAGCCTGATTCCAGGGTGGGGTTGGGAAATC
TTTCAAACACTAAAATTGTCCTTTAAtTTTTTTTTAAAAAATGGGTTATATAATAAA
CCTCATAAAATAGTTATGAGGAGTGAGGTGGACTAATATTAAaTGAGTCCCTCCCCT
ATAAAAGAGCTATTAAGGCTTTTTGTCTTATACTtAACTTTTTTTTAAATGTGGTATC
TTTAGAACCAAGGGTCTTAGAGTTTTAGTATACAGAAACTGTTGCATCGCTTAATCA
GATTTTCTAGTTTCAAATCCAGAGAATCCAAATTCTTCACAGCCAAAGTCAAATTAA
GAATTCTGACTTTtAATGTTAaTTTGCtTACTGTGAATATaAAAATGATAGCTTTTCCT
GAGGCAGGGTCTCACTATGTATCTCTGCCTGATCTGCAACAAGATATGTAGACTAAA
GTTCTGCCTGCTTTTGTCTCCTGAATACTAAGGTTAAAATGTAGTAATACTTTTGGAA
CTTGCAGGTCAGATTCTTTTATAGGGACACACTAAGGGAGCTTGGGTGATAGTTGG
TAAAtgtgttaagtgatgaaaactgaattattatcaccgcaacctactttttaaaaaaaaaagccaggcctgttagagcatgctTaaggg
atcctaggacttgctgagcacacaAGAGTAGtTACTTGGCAGGCTCCTGGTGAGAGCATATTTCAA
AAAACAAGGCAGACAACCAAGAAACTACAGTtAAGGTTACCTGTCTTTaAACCATCT
GCATATACACAGGGATATTAAAATATTCCAAATAATATTTCATTCAAGTTTTCCCCC
ATCAAATTGGGACATGGATTTCTCCGGTGAATAGGCAGAGTTGGAAACTAAACAAA
TGTTGGTTTTGTGATTTGTGAAATTGTTTCAAGTGATAGTTAAAGCCCATGAGATAC
AGAACAAAGCTGCTATTTCGAGGTCTCTTGGTTtATACTCAGAAGCACTTCTTTGGGT
TTCCCTGCACTATCCTGATCATGTGCTAGGCCTACCTTAGGCTGATTGTTGTTCAAAT
aAACTTAAGTTTCCTGTCAGGTGATGTCATATGATTTCATATATCAAGGCAAAACATG
TTATATATGTTAAACATTTGTACTTAATGTGAAAGTTAGGTCTTTGTGGGTT

FIG. 50F

```
TGATTTTtAAfTTTCAAAACCTGAGCTAAATAAGTCATTTTtACATGTCTTACATTTGGT
GgAATTGTATaATTGTGGTTTGCAGGCAAGACTCTCTGACCTAGTAACCCTaCCTATA
GAGCACTTTGCTGGGTCACAAGTCTAGGAGTCAAGCATTTCACCTTGAAGTTGAGAC
GTTTTGTTAGTGTATACTAGTTtATATGTTGGAGGACATGTTTATCCAGAAGATATTC
AGGACTATTTTGACTGGGCTAAGGAATTGATTCTGATTAGCACTGTTAGTGAGCAT
TGAGTGGCCTTTAGGCTTGAATTggagtcactgtatatctcaaataatgctggcctttttaaaagccttgttcttatca
ccctgttttctacataattttgttcaaagaaatacttgttggaTCTCCTTTTGACAACAATAGCATGTTTTCAAG
CCATATTTTTTTCCTTTTTTTTTTTTTTTTGGTTTTTCGAGACAGGGTTTCTCTGTAT
AGCCCTGGCTGTCCTGGAACTCACTTTGTAGACCAGGCTGGCCTCGAACTCAGAAAT
CCGCCTGCCTCTGCCTCCTGAGTGCCGGGATTAAAGGCGTGCACCACCACGCCTGGC
TAAGTTGGATATTTTGTtATATAACTATAACCAATACTAACTCCACTGGGTGGATTTT
TAATTCAGTCAGTAGTCTTAAGTGGTCTTTATTGGCCCTTcATTAAAATCTACTGTTC
ACTCTAACAGAGGCTGTTGGtACTAGTGGCACtAAGCAACTTCCTACGGATATACTA
GCAGAtTAAGGGTCAGGGATAGAAACTAGTCTAGCGTTTTGTATACCTACCAGCTTtA
TACTACCTTGTTCTGATAGAAATATTTcAGGACATCTAGCTT
``` pPGK-Neo-pPGK-polyA aattctaccgggtaggggaggcgctttcccaaggcagtctggagcatgcgctttagcagcccgctggcacttggcgctacacaagtgg
cctctggcctcgcacacattccacatccaccggtaggcgccaaccggctccgttcttggatggcccttcgcgccaccttctactcctcccct
agtcaggaagttccccccgccccgcagctcgcgtcgtgcaggacgtgacaaatggaagtagcacgtctcactagtctcgtgcagatgga
cagcaccgctgagcaatggaagcgggtaggccttttggggcagcggccaatagcagcttgctccttcgctttctgggctcagaggctggg
aagggtggatccgggcggagctcaggggcgggctcagggcgggggcggcgcccgaaggtcctccggaggcccggcattctgc
acgcttcaaaagcgcacgtctgccgcgctgttctcctcttcctcatctccggggccttcgaccctgcaatcgccgctagcgaagttcctattctct
agaaagtataggaacttcgccaccatgggatcggccattgaacaagatggattgcacgcaggttctccggccgcttgggtggagaggctat
tcggctatgactgggcacaacagacaatcggctgctctgatgccgccgtgttccggctgtcagcgcaggggcgcccggttcttttttgtcaag
accgacctgtccggtgccctgaatgaactgcaggacgaggcagcgcggctatcgtggctggccacgacgggcgttccttgcgcagctgt
gctcgacgttgtcactgaagcgggaagggactggctgctattgggcgaagtgccggggcaggatctcctgtcatctcaccttgctcctgcc
gagaaagtatccatcatggctgatgcaatgcggcggctgcatacgcttgatccggctacctgcccattcgaccaccaagcgaaacatcgca
tcgagcgagcacgtactcggatggaagccggtcttgtcgatcaggatgatctggacgaagagcatcaggggctcgcgccagccgaactg
ttcgccaggctcaaggcgcgcatgcccgacggcgatgatctcgtcgtgacccatggcgatgcctgcttgccgaatatcatggtggaaaatg
gccgcttttctggattcatcgactgtggccggctgggtgtggcggaccgctatcaggacatagcgttggctacccgtgatattgctgaagag
cttggcggcgaatgggctgaccgcttcctcgtgctttacggtatcgccgctcccgattcgcagcgcatcgccttctatcgccttcttgacgagt
tcttctgagggggatccgctgtaagtctgcagaaattgatgatctattaaacaataaagatgtccacataaaatggaagttttcctgtcatactttgtt
aagaagggtgagaacagagtacctacatttgaatggaaggattggagctacgggggtgggggtgggattagataaatgcctgct
ctttactgaaggctcttactattgctttatgataatgtttcatagttg

FIG. 50G gatatcataattaaacaagcaaaaccaaattaagggccagctcattcctcccactcatgatctatagatctatagatctctcgtgggatcattgt
ttttctcttgattcccacttgtggttctaagtactgtggtttccaaatgtgtcagtttcatagcctgaagaacgagatcagcagcctctgttccaca
tacacttcattctcagtattgttttgccaagttctaattccatcagaaagc pPGK-DTA
TACCGGGTAGGGGAGGCGCTTTTCCcAAGGCAGTCTGgAGCATGCGCtTAGCAGCCC
CGCTgGGCACTTGGCGCTACACAAGTGGCCTCTGGCCTCGCACACATTCCACATCCA
CCGGTAGGCGCCAACCGGCTCCGTTCTTTGGTGGCCCCTTCGCGCCACCTTCTACTCC
TCCCCTAGTCAGGAAGTTCCCCCCCGCCCCGCAGCTCGCGTCGTGcAGGACGTGACA
AATGGAAGTAGCACGTCTCACTAGTCTCGTgCAGATGGACAGCACCGCTGAGCAATG
GAAGCGGGTAGGCCTTTGGGGCAGCGGCCAATAGCAGCTTTGCTCCTTCGCTTTCTG
GGCTCAGAGGCTGGGAAGGGGTGGGTCCGGGGGCGGGCTCAGGGGCGGGCTCAGG
GGCGGGGCGGGCGCCCGAAGGTCCTCCGGAGGCCCCGGCATTCTGCACGCTTCAAAA
GCGCACGTCTGCCGCGCTGTTCTCCTCTTCCTCATCTCCGGGCCTTTCGACCTGCAGG
TCCTCGCCATggatcctgatgatgttgttGatcttctaaAtctttgtGatggaaaactttcttcgtaccacgggactaaacctggtt
atgtagattccattcaaaaaggtatacaaaagccaaaatctggtacacaaggaaattatgacgatgattggaaagggtttatagtaccgacaa
taaatacgacgctgcgggatactctgtagataatgaaaaccccgctctctggaaaagctggaggcgtggtcaaagtgacgtatccaggactg
acgaaggttctcgcactaaaagtggataatgccgaaactattaagaaagagttaggtttaagtctcactgaaccgttgatggagcaagtcgga
acggaagagtttatcaaaaggttcggtgatggtgcttcgcgtgtagtgctcagccttcccttcgctgagggagttctagcgtgaatatattaa
taactgggaacaggcgaaagcgttaagcgtagaacttgagattaatttttgaaacccgtggaaaacgtggccaagatgcgatgtatgagtata
tggctcaagcctgtgcaggaaatcgtgtcaggcgatctctttgtgaaggaaccttacttctgtggtgtgacataatggacaaactacctacag
agattaaagctctaaggtaaatataaaatttttaagtgtataatgtgttaaactactgattctaattgttgtgtattttagattccaacctatggaact
gatgaatgggagcagtggtggaatgcagatcctagagctcgctgatcagcctcgactgtgccttctagttgccagccatctgttgttgccctt
ccccgtgccttccttgaccctggaaggtgccactcccactgtcctttcctaataaaatgaggaaattgcatcgcattgtctgagtaggtgtcat
tctattctggggggtggggtggggcaggacagcaagggggaggattgggaagacaatagcaggcatg

FIG. 50H

|  |  | Average | StDev |
|---|---|---|---|
| pCAG-loxp(pA)loxp-NLS-hSpCas9-NLS-2A-GFP | Clone 1 | 32.1 | 7.1 |
|  | Clone 2 | 27.3 | 3.5 |
|  | Clone 3 | 35.9 | 1.4 |
|  | Clone 4 | 39.0 | 4.7 |
| pCAG-NLS-hSpCas9-NLS-2A-GFP | Clone 1 | 26.9 | 1.3 |
|  | Clone 2 | 33.1 | 2.7 |

FIG. 63A-C gRNA sequences for Chd8 targeting:

Chd8.1 - agctgttttactggtcggct
Chd8.2 - aatggatacacctggtcgaa
Chd8.3 - caatggatacacctggtcga

FIG. NLS1

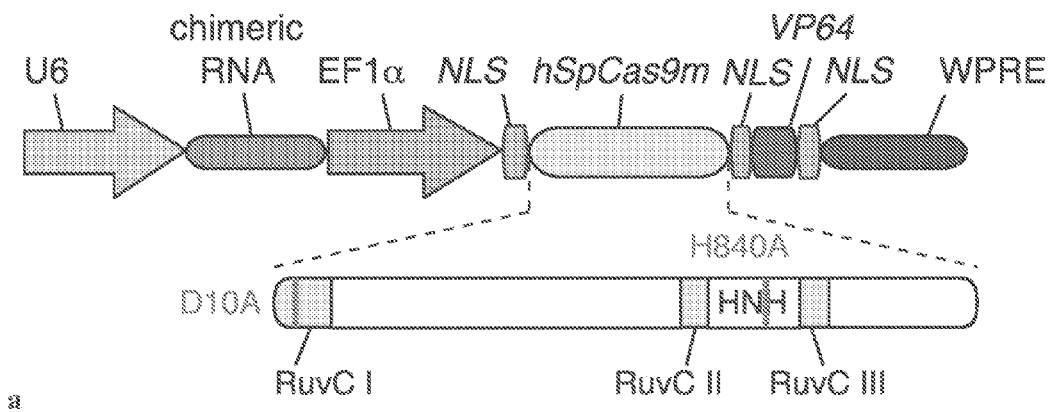
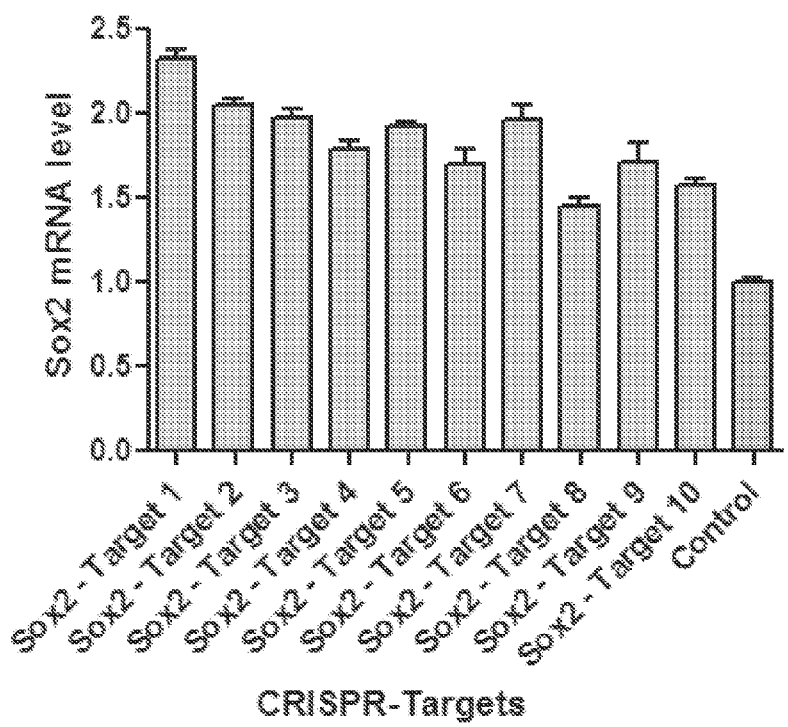
FIG. 69A-B

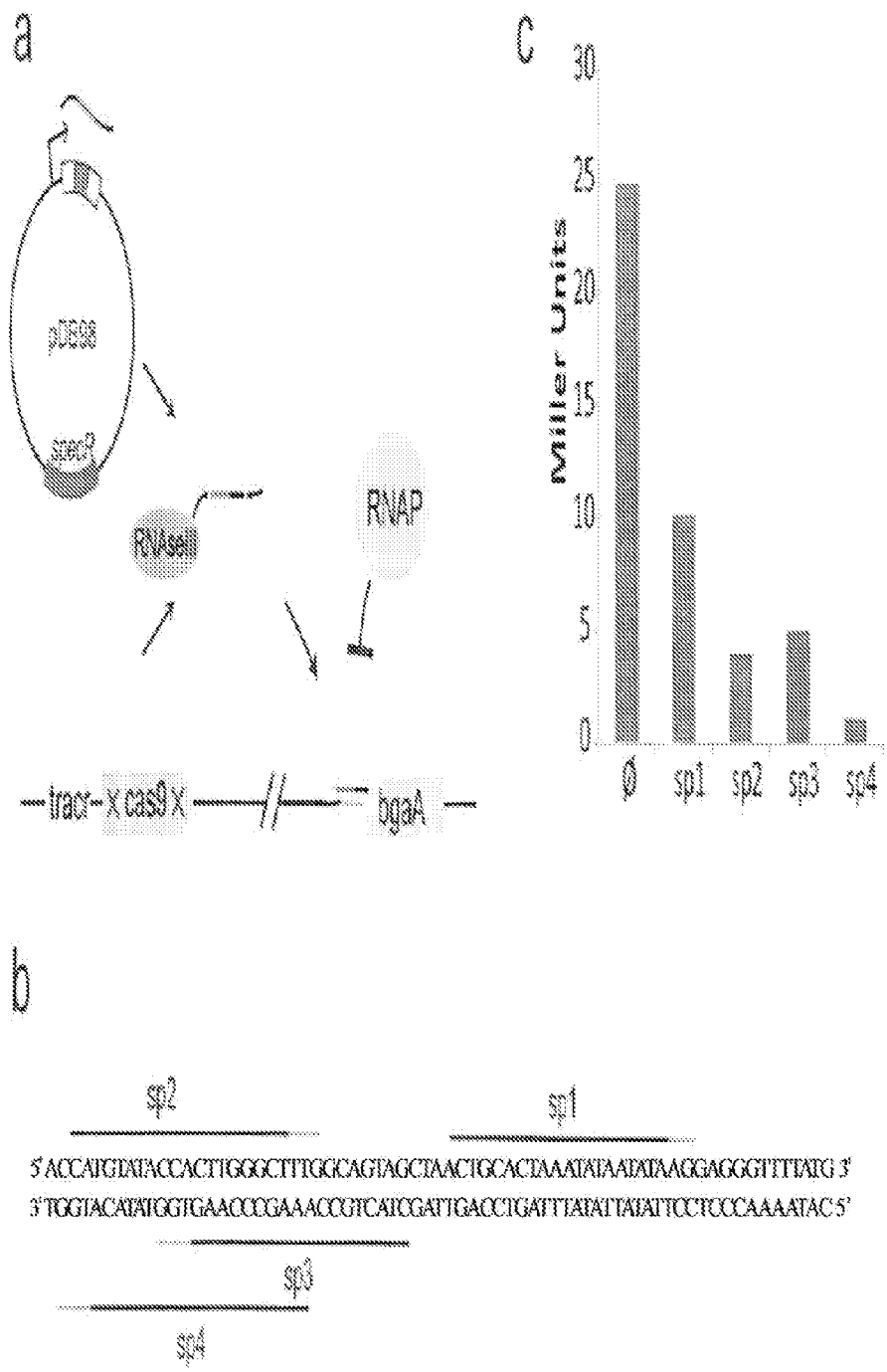
FIG. 73A-C

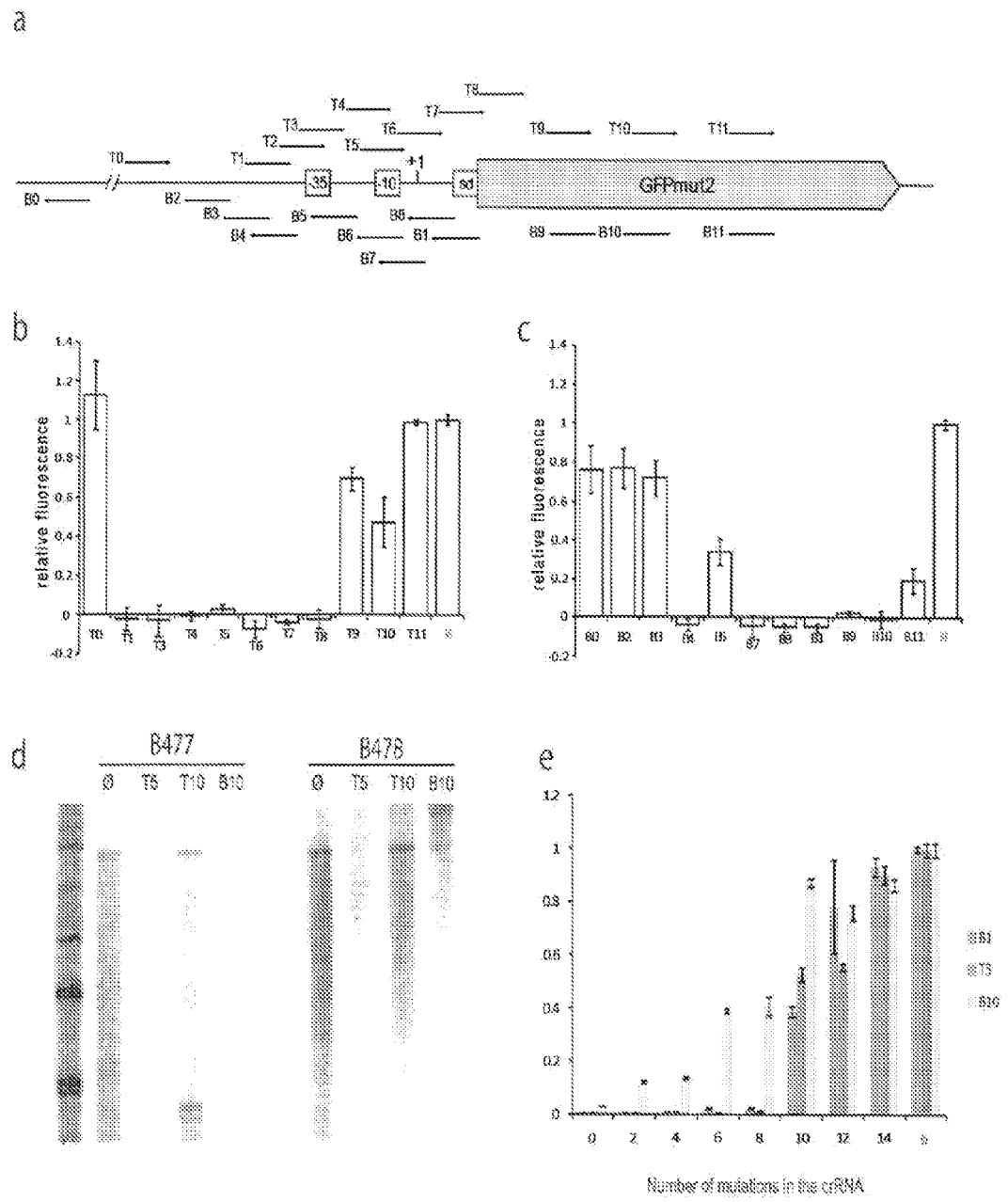
FIG. 74A-E

SEQUENCE LISTING

```
<160> NUMBER OF SEQ ID NOS: 531

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Unknown
<220> FEATURE:
<223> OTHER INFORMATION: Description of Unknown:
```

C-myc NLS sequence

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 7
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens

<400> SEQUENCE: 9

```
Pro Gln Pro Lys Lys Lys Pro Leu
1               5

<210> SEQ ID NO 10
<211> LENGTH: 12
<212> TYPE: PRT
<213> ORGANISM: Mus musculus

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Hepatitus delta virus

<400> SEQUENCE: 13

Arg Lys Leu Lys Lys Lys Ile Lys Lys Leu
1               5                   10

<210> SEQ ID NO 14
<211> LENGTH: 10
<212> TYPE: PRT
<213> ORGANISM: Mus musculus

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Homo sapiens
```

```
<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 17
nnnnnnnnnn nnnnnnnnnn nnagaaw                                          27

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 18
nnnnnnnnnn nnnnagaaw                                                   19

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 19
nnnnnnnnnn nnnnnnnnnn nnagaaw                                          27

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 20
nnnnnnnnnn nnnagaaw                                                    18

<210> SEQ ID NO 21
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 21
nnnnnnnnnn nnnnnnnnnn gttttgtac tctcaagatt tagaaataaa tcttgcagaa        60
gctacaaaga taaggcttca tgccgaaatc aacaccctgt cattttatgg cagggtgttt     120
tcgttattta atttttt                                                    137

<210> SEQ ID NO 22
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 22
nnnnnnnnnn nnnnnnnnnn gttttgtac tctcagaaat gcagaagcta caaagataag        60
gcttcatgcc gaaatcaaca ccctgtcatt ttatggcagg gtgttttcgt tatttaattt     120
ttt                                                                   123

<210> SEQ ID NO 23
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 23
nnnnnnnnnn nnnnnnnnnn gttttgtac tctcagaaat gcagaagcta caaagataag        60
gcttcatgcc gaaatcaaca ccctgtcatt ttatggcagg gtgtttttt                 110

<210> SEQ ID NO 24
<211> LENGTH: 102
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 24
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 25
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 25
nnnnnnnnnn nnnnnnnnnn gttttagagc tagaaatagc aagttaaaat aaggctagtc    60
cgttatcaac ttgaaaaagt gtttttt                                       88

<210> SEQ ID NO 26
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 26
nnnnnnnnnn nnnnnnnnnn gttttagagc tagaaatagc aagttaaaat aaggctagtc    60
cgttatcatt tttttt                                                   76

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gttttagagc ta                                                       12

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tagcaagtta aaataaggct agtccgtttt t                                  31

<210> SEQ ID NO 29
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, t, g, unknown or other

<400> SEQUENCE: 29
nnnnnnnnnn nnnnnnnnnn nnagaaw                                              27

<210> SEQ ID NO 30
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
guuuuagagc ua                                                              12

<210> SEQ ID NO 31
<211> LENGTH: 33
<212> TYPE: DNA
<213> ORGANISM: Homo sapiens

<400> SEQUENCE: 31
ggacatcgat gtcacctcca atgactaggg tgg                                       33

<210> SEQ ID NO 32
<211> LENGTH: 33
<212> TYPE: DNA
<213> ORGANISM: Homo sapiens

<400> SEQUENCE: 32
cattggaggt gacatcgatg tcctccccat tgg                                       33

<210> SEQ ID NO 33
<211> LENGTH: 33
<212> TYPE: DNA
<213> ORGANISM: Homo sapiens

<400> SEQUENCE: 33
ggaagggcct gagtccgagc agaagaagaa ggg                                       33

<210> SEQ ID NO 34
<211> LENGTH: 33
<212> TYPE: DNA
<213> ORGANISM: Homo sapiens

<400> SEQUENCE: 34
ggtggcgaga ggggccgaga ttgggtgttc agg                                       33

<210> SEQ ID NO 35
<211> LENGTH: 33
<212> TYPE: DNA
<213> ORGANISM: Homo sapiens

<400> SEQUENCE: 35
atgcaggagg gtggcgagag gggccgagat tgg                                       33
```

```
<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaaaccaccc ttctctctgg c                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggagattgga gacacggaga g                                              21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctggaaagcc aatgcctgac                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggcagcaaac tccttgtcct                                                20

<210> SEQ ID NO 40
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gagggcctat ttcccatgat tccttcatat ttgcatatac gatacaaggc tgttagagag    60
ataattggaa ttaatttgac tgtaaacaca agatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg gaaccattca aaacagcata gcaagttaaa ataaggctag tccgttatca    300
acttgaaaaa gtggcaccga gtcggtgctt ttttt                               335

<210> SEQ ID NO 41
<211> LENGTH: 423
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 41
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg gtagtattaa gtattgtttt atggctgata aatttctttg aatttctcct     300
tgattatttg ttataaaagt tataaaataa tcttgttgga accattcaaa acagcatagc     360
aagttaaaat aaggctagtc cgttatcaac ttgaaaaagt ggcaccgagt cggtgctttt     420
ttt                                                                   423

<210> SEQ ID NO 42
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg ggttttagag ctatgctgtt ttgaatggtc ccaaaacggg tcttcgagaa     300
gacgttttag agctatgctg ttttgaatgg tcccaaaac                            339

<210> SEQ ID NO 43
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg gtcttcgag aagacctgtt ttagagctag aaatagcaag ttaaaataag     300
gctagtccg                                                             309

<210> SEQ ID NO 44
<211> LENGTH: 1648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20              25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
            165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
            245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
        290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
            325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
            405                 410                 415

Pro Ile Leu Glu Lys Met Asp Gly Thr Glu Glu Leu Leu Val Lys Leu
```

-continued

```
                420                 425                 430
Asn Arg Glu Asp Leu Leu Arg Lys Gln Arg Thr Phe Asp Asn Gly Ser
            435                 440                 445
Ile Pro His Gln Ile His Leu Gly Glu Leu His Ala Ile Leu Arg Arg
450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
515                 520                 525
Ser Phe Ile Glu Arg Met Thr Asn Phe Asp Lys Asn Leu Pro Asn Glu
530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
            580                 585                 590
Lys Thr Asn Arg Lys Val Thr Val Lys Gln Leu Lys Glu Asp Tyr Phe
        595                 600                 605
Lys Lys Ile Glu Cys Phe Asp Ser Val Glu Ile Ser Gly Val Glu Asp
    610                 615                 620
Arg Phe Asn Ala Ser Leu Gly Thr Tyr His Asp Leu Leu Lys Ile Ile
625                 630                 635                 640
Lys Asp Lys Asp Phe Leu Asp Asn Glu Glu Asn Glu Asp Ile Leu Glu
                645                 650                 655
Asp Ile Val Leu Thr Leu Thr Leu Phe Glu Asp Arg Glu Met Ile Glu
            660                 665                 670
Glu Arg Leu Lys Thr Tyr Ala His Leu Phe Asp Asp Lys Val Met Lys
        675                 680                 685
Gln Leu Lys Arg Arg Arg Tyr Thr Gly Trp Gly Arg Leu Ser Arg Lys
    690                 695                 700
Leu Ile Asn Gly Ile Arg Asp Lys Gln Ser Gly Lys Thr Ile Leu Asp
705                 710                 715                 720
Phe Leu Lys Ser Asp Gly Phe Ala Asn Arg Asn Phe Met Gln Leu Ile
                725                 730                 735
His Asp Asp Ser Leu Thr Phe Lys Glu Asp Ile Gln Lys Ala Gln Val
            740                 745                 750
Ser Gly Gln Gly Asp Ser Leu His Glu His Ile Ala Asn Leu Ala Gly
        755                 760                 765
Ser Pro Ala Ile Lys Lys Gly Ile Leu Gln Thr Val Lys Val Val Asp
    770                 775                 780
Glu Leu Val Lys Val Met Gly Arg His Lys Pro Glu Asn Ile Val Ile
785                 790                 795                 800
Glu Met Ala Arg Glu Asn Gln Thr Thr Gln Lys Gly Gln Lys Asn Ser
                805                 810                 815
Arg Glu Arg Met Lys Arg Ile Glu Glu Gly Ile Lys Glu Leu Gly Ser
            820                 825                 830
Gln Ile Leu Lys Glu His Pro Val Glu Asn Thr Gln Leu Gln Asn Glu
        835                 840                 845
```

```
Lys Leu Tyr Leu Tyr Leu Gln Asn Gly Arg Asp Met Tyr Val Asp
    850                 855                 860

Gln Glu Leu Asp Ile Asn Arg Leu Ser Asp Tyr Val Asp His Ile
865                 870                 875                 880

Val Pro Gln Ser Phe Leu Lys Asp Asp Ser Ile Asp Asn Lys Val Leu
                    885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
                980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245
```

```
Arg Lys Arg Met Leu Ala Ser Ala Gly Glu Leu Gln Lys Gly Asn
1250                1255                1260

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Ala Ala Val Ser Lys
1400                1405                1410

Gly Glu Glu Leu Phe Thr Gly Val Val Pro Ile Leu Val Glu Leu
1415                1420                1425

Asp Gly Asp Val Asn Gly His Lys Phe Ser Val Ser Gly Glu Gly
1430                1435                1440

Glu Gly Asp Ala Thr Tyr Gly Lys Leu Thr Leu Lys Phe Ile Cys
1445                1450                1455

Thr Thr Gly Lys Leu Pro Val Pro Trp Pro Thr Leu Val Thr Thr
1460                1465                1470

Leu Thr Tyr Gly Val Gln Cys Phe Ser Arg Tyr Pro Asp His Met
1475                1480                1485

Lys Gln His Asp Phe Phe Lys Ser Ala Met Pro Glu Gly Tyr Val
1490                1495                1500

Gln Glu Arg Thr Ile Phe Phe Lys Asp Asp Gly Asn Tyr Lys Thr
1505                1510                1515

Arg Ala Glu Val Lys Phe Glu Gly Asp Thr Leu Val Asn Arg Ile
1520                1525                1530

Glu Leu Lys Gly Ile Asp Phe Lys Glu Asp Gly Asn Ile Leu Gly
1535                1540                1545

His Lys Leu Glu Tyr Asn Tyr Asn Ser His Asn Val Tyr Ile Met
1550                1555                1560

Ala Asp Lys Gln Lys Asn Gly Ile Lys Val Asn Phe Lys Ile Arg
1565                1570                1575

His Asn Ile Glu Asp Gly Ser Val Gln Leu Ala Asp His Tyr Gln
1580                1585                1590

Gln Asn Thr Pro Ile Gly Asp Gly Pro Val Leu Leu Pro Asp Asn
1595                1600                1605

His Tyr Leu Ser Thr Gln Ser Ala Leu Ser Lys Asp Pro Asn Glu
1610                1615                1620

Lys Arg Asp His Met Val Leu Leu Glu Phe Val Thr Ala Ala Gly
1625                1630                1635

Ile Thr Leu Gly Met Asp Glu Leu Tyr Lys
```

```
                                  1640            1645

<210> SEQ ID NO 45
<211> LENGTH: 1625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

```
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
```

```
                770             775             780
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185
```

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ala Ala Ala Val Ser Lys Gly Glu Glu Leu Phe Thr Gly Val Val
    1370                1375                1380

Pro Ile Leu Val Glu Leu Asp Gly Asp Val Asn Gly His Lys Phe
    1385                1390                1395

Ser Val Ser Gly Glu Gly Glu Gly Asp Ala Thr Tyr Gly Lys Leu
    1400                1405                1410

Thr Leu Lys Phe Ile Cys Thr Thr Gly Lys Leu Pro Val Pro Trp
    1415                1420                1425

Pro Thr Leu Val Thr Thr Leu Thr Tyr Gly Val Gln Cys Phe Ser
    1430                1435                1440

Arg Tyr Pro Asp His Met Lys Gln His Asp Phe Phe Lys Ser Ala
    1445                1450                1455

Met Pro Glu Gly Tyr Val Gln Glu Arg Thr Ile Phe Phe Lys Asp
    1460                1465                1470

Asp Gly Asn Tyr Lys Thr Arg Ala Glu Val Lys Phe Glu Gly Asp
    1475                1480                1485

Thr Leu Val Asn Arg Ile Glu Leu Lys Gly Ile Asp Phe Lys Glu
    1490                1495                1500

Asp Gly Asn Ile Leu Gly His Lys Leu Glu Tyr Asn Tyr Asn Ser
    1505                1510                1515

His Asn Val Tyr Ile Met Ala Asp Lys Gln Lys Asn Gly Ile Lys
    1520                1525                1530

Val Asn Phe Lys Ile Arg His Asn Ile Glu Asp Gly Ser Val Gln
    1535                1540                1545

Leu Ala Asp His Tyr Gln Gln Asn Thr Pro Ile Gly Asp Gly Pro
    1550                1555                1560

Val Leu Leu Pro Asp Asn His Tyr Leu Ser Thr Gln Ser Ala Leu
    1565                1570                1575
```

```
Ser Lys Asp Pro Asn Glu Lys Arg Asp His Met Val Leu Leu Glu
    1580                1585                1590

Phe Val Thr Ala Ala Gly Ile Thr Leu Gly Met Asp Glu Leu Tyr
1595                1600                1605

Lys Lys Arg Pro Ala Ala Thr Lys Lys Ala Gly Gln Ala Lys Lys
1610                1615                1620

Lys Lys
1625

<210> SEQ ID NO 46
<211> LENGTH: 1664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
290                 295                 300
```

```
Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
        370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
        595                 600                 605

Lys Lys Ile Glu Cys Phe Asp Ser Val Glu Ile Ser Gly Val Glu Asp
    610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
        675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720
```

```
Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
            770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
                835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
                915                 920                 925

Lys Leu Ile Thr Gln Arg Lys Phe Asp Asn Leu Thr Lys Ala Glu Arg
                930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
                980                 985                 990

Lys Val Ile Thr Leu Lys Ser Lys Leu Val Ser Asp Phe Arg Lys Asp
                995                 1000                1005

Phe Gln Phe Tyr Lys Val Arg Glu Ile Asn Asn Tyr His His Ala
            1010                1015                1020

His Asp Ala Tyr Leu Asn Ala Val Val Gly Thr Ala Leu Ile Lys
            1025                1030                1035

Lys Tyr Pro Lys Leu Glu Ser Glu Phe Val Tyr Gly Asp Tyr Lys
            1040                1045                1050

Val Tyr Asp Val Arg Lys Met Ile Ala Lys Ser Glu Gln Glu Ile
            1055                1060                1065

Gly Lys Ala Thr Ala Lys Tyr Phe Phe Tyr Ser Asn Ile Met Asn
            1070                1075                1080

Phe Phe Lys Thr Glu Ile Thr Leu Ala Asn Gly Glu Ile Arg Lys
            1085                1090                1095

Arg Pro Leu Ile Glu Thr Asn Gly Glu Thr Gly Glu Ile Val Trp
            1100                1105                1110

Asp Lys Gly Arg Asp Phe Ala Thr Val Arg Lys Val Leu Ser Met
            1115                1120                1125

Pro Gln Val Asn Ile Val Lys Lys Thr Glu Val Gln Thr Gly Gly
```

```
                1130                1135               1140
Phe Ser Lys Glu Ser Ile Leu Pro Lys Arg Asn Ser Asp Lys Leu
    1145                1150               1155
Ile Ala Arg Lys Lys Asp Trp Asp Pro Lys Lys Tyr Gly Gly Phe
    1160                1165               1170
Asp Ser Pro Thr Val Ala Tyr Ser Val Leu Val Val Ala Lys Val
    1175                1180               1185
Glu Lys Gly Lys Ser Lys Lys Leu Lys Ser Val Lys Glu Leu Leu
    1190                1195               1200
Gly Ile Thr Ile Met Glu Arg Ser Ser Phe Glu Lys Asn Pro Ile
    1205                1210               1215
Asp Phe Leu Glu Ala Lys Gly Tyr Lys Glu Val Lys Lys Asp Leu
    1220                1225               1230
Ile Ile Lys Leu Pro Lys Tyr Ser Leu Phe Glu Leu Glu Asn Gly
    1235                1240               1245
Arg Lys Arg Met Leu Ala Ser Ala Gly Glu Leu Gln Lys Gly Asn
    1250                1255               1260
Glu Leu Ala Leu Pro Ser Lys Tyr Val Asn Phe Leu Tyr Leu Ala
    1265                1270               1275
Ser His Tyr Glu Lys Leu Lys Gly Ser Pro Glu Asp Asn Glu Gln
    1280                1285               1290
Lys Gln Leu Phe Val Glu Gln His Lys His Tyr Leu Asp Glu Ile
    1295                1300               1305
Ile Glu Gln Ile Ser Glu Phe Ser Lys Arg Val Ile Leu Ala Asp
    1310                1315               1320
Ala Asn Leu Asp Lys Val Leu Ser Ala Tyr Asn Lys His Arg Asp
    1325                1330               1335
Lys Pro Ile Arg Glu Gln Ala Glu Asn Ile Ile His Leu Phe Thr
    1340                1345               1350
Leu Thr Asn Leu Gly Ala Pro Ala Ala Phe Lys Tyr Phe Asp Thr
    1355                1360               1365
Thr Ile Asp Arg Lys Arg Tyr Thr Ser Thr Lys Glu Val Leu Asp
    1370                1375               1380
Ala Thr Leu Ile His Gln Ser Ile Thr Gly Leu Tyr Glu Thr Arg
    1385                1390               1395
Ile Asp Leu Ser Gln Leu Gly Gly Asp Ala Ala Ala Val Ser Lys
    1400                1405               1410
Gly Glu Glu Leu Phe Thr Gly Val Val Pro Ile Leu Val Glu Leu
    1415                1420               1425
Asp Gly Asp Val Asn Gly His Lys Phe Ser Val Ser Gly Glu Gly
    1430                1435               1440
Glu Gly Asp Ala Thr Tyr Gly Lys Leu Thr Leu Lys Phe Ile Cys
    1445                1450               1455
Thr Thr Gly Lys Leu Pro Val Pro Trp Pro Thr Leu Val Thr Thr
    1460                1465               1470
Leu Thr Tyr Gly Val Gln Cys Phe Ser Arg Tyr Pro Asp His Met
    1475                1480               1485
Lys Gln His Asp Phe Phe Lys Ser Ala Met Pro Glu Gly Tyr Val
    1490                1495               1500
Gln Glu Arg Thr Ile Phe Phe Lys Asp Asp Gly Asn Tyr Lys Thr
    1505                1510               1515
Arg Ala Glu Val Lys Phe Glu Gly Asp Thr Leu Val Asn Arg Ile
    1520                1525               1530
```

```
Glu Leu Lys Gly Ile Asp Phe Lys Glu Asp Gly Asn Ile Leu Gly
    1535                1540                1545

His Lys Leu Glu Tyr Asn Tyr Asn Ser His Asn Val Tyr Ile Met
    1550                1555                1560

Ala Asp Lys Gln Lys Asn Gly Ile Lys Val Asn Phe Lys Ile Arg
    1565                1570                1575

His Asn Ile Glu Asp Gly Ser Val Gln Leu Ala Asp His Tyr Gln
    1580                1585                1590

Gln Asn Thr Pro Ile Gly Asp Gly Pro Val Leu Leu Pro Asp Asn
    1595                1600                1605

His Tyr Leu Ser Thr Gln Ser Ala Leu Ser Lys Asp Pro Asn Glu
    1610                1615                1620

Lys Arg Asp His Met Val Leu Leu Glu Phe Val Thr Ala Ala Gly
    1625                1630                1635

Ile Thr Leu Gly Met Asp Glu Leu Tyr Lys Lys Arg Pro Ala Ala
    1640                1645                1650

Thr Lys Lys Ala Gly Gln Ala Lys Lys Lys Lys
    1655                1660
```

<210> SEQ ID NO 47
<211> LENGTH: 1423
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Ile His Gly Val Pro Ala Ala Asp Lys Lys Tyr Ser Ile Gly Leu
                35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
                100                 105                 110

Arg Arg Lys Asn Arg Ile Cys Tyr Leu Gln Glu Ile Phe Ser Asn Glu
                115                 120                 125

Met Ala Lys Val Asp Asp Ser Phe Phe His Arg Leu Glu Glu Ser Phe
                130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
                180                 185                 190

Ile Tyr Leu Ala Leu Ala His Met Ile Lys Phe Arg Gly His Phe Leu
                195                 200                 205

Ile Glu Gly Asp Leu Asn Pro Asp Asn Ser Asp Val Asp Lys Leu Phe
```

-continued

```
                210                 215                 220
Ile Gln Leu Val Gln Thr Tyr Asn Gln Leu Phe Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
                260                 265                 270

Lys Asn Gly Leu Phe Gly Asn Leu Ile Ala Leu Ser Leu Gly Leu Thr
                275                 280                 285

Pro Asn Phe Lys Ser Asn Phe Asp Leu Ala Glu Asp Ala Lys Leu Gln
                290                 295                 300

Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
                340                 345                 350

Lys Ala Pro Leu Ser Ala Ser Met Ile Lys Arg Tyr Asp Glu His His
                355                 360                 365

Gln Asp Leu Thr Leu Leu Lys Ala Leu Val Arg Gln Gln Leu Pro Glu
                370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
                435                 440                 445

Ile Pro His Gln Ile His Leu Gly Glu Leu His Ala Ile Leu Arg Arg
                450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
                515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
                610                 615                 620

Arg Phe Asn Ala Ser Leu Gly Thr Tyr His Asp Leu Leu Lys Ile Ile
625                 630                 635                 640
```

-continued

Lys Asp Lys Asp Phe Leu Asp Asn Glu Glu Asn Glu Asp Ile Leu Glu
            645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Lys Val Met Lys
        675                 680                 685

Gln Leu Lys Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
            725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
        755                 760                 765

Ser Pro Ala Ile Lys Lys Gly Ile Leu Gln Thr Val Lys Val Val Asp
    770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
        835                 840                 845

Lys Leu Tyr Leu Tyr Tyr Leu Gln Asn Gly Arg Asp Met Tyr Val Asp
    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
            965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
1055                1060                1065

Gly Lys Ala Thr Ala Lys Tyr Phe Phe Tyr Ser Asn Ile Met Asn
1070                1075                1080

Phe Phe Lys Thr Glu Ile Thr Leu Ala Asn Gly Glu Ile Arg Lys
1085                1090                1095

Arg Pro Leu Ile Glu Thr Asn Gly Glu Thr Gly Glu Ile Val Trp
1100                1105                1110

Asp Lys Gly Arg Asp Phe Ala Thr Val Arg Lys Val Leu Ser Met
1115                1120                1125

Pro Gln Val Asn Ile Val Lys Lys Thr Glu Val Gln Thr Gly Gly
1130                1135                1140

Phe Ser Lys Glu Ser Ile Leu Pro Lys Arg Asn Ser Asp Lys Leu
1145                1150                1155

Ile Ala Arg Lys Lys Asp Trp Asp Pro Lys Lys Tyr Gly Gly Phe
1160                1165                1170

Asp Ser Pro Thr Val Ala Tyr Ser Val Leu Val Val Ala Lys Val
1175                1180                1185

Glu Lys Gly Lys Ser Lys Lys Leu Lys Ser Val Lys Glu Leu Leu
1190                1195                1200

Gly Ile Thr Ile Met Glu Arg Ser Ser Phe Glu Lys Asn Pro Ile
1205                1210                1215

Asp Phe Leu Glu Ala Lys Gly Tyr Lys Glu Val Lys Lys Asp Leu
1220                1225                1230

Ile Ile Lys Leu Pro Lys Tyr Ser Leu Phe Glu Leu Glu Asn Gly
1235                1240                1245

Arg Lys Arg Met Leu Ala Ser Ala Gly Glu Leu Gln Lys Gly Asn
1250                1255                1260

Glu Leu Ala Leu Pro Ser Lys Tyr Val Asn Phe Leu Tyr Leu Ala
1265                1270                1275

Ser His Tyr Glu Lys Leu Lys Gly Ser Pro Glu Asp Asn Glu Gln
1280                1285                1290

Lys Gln Leu Phe Val Glu Gln His Lys His Tyr Leu Asp Glu Ile
1295                1300                1305

Ile Glu Gln Ile Ser Glu Phe Ser Lys Arg Val Ile Leu Ala Asp
1310                1315                1320

Ala Asn Leu Asp Lys Val Leu Ser Ala Tyr Asn Lys His Arg Asp
1325                1330                1335

Lys Pro Ile Arg Glu Gln Ala Glu Asn Ile Ile His Leu Phe Thr
1340                1345                1350

Leu Thr Asn Leu Gly Ala Pro Ala Ala Phe Lys Tyr Phe Asp Thr
1355                1360                1365

Thr Ile Asp Arg Lys Arg Tyr Thr Ser Thr Lys Glu Val Leu Asp
1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Lys
1415                1420

<210> SEQ ID NO 48
<211> LENGTH: 483
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 48

```
Met Phe Leu Phe Leu Ser Leu Thr Ser Phe Leu Ser Ser Ser Arg Thr
1               5                   10                  15

Leu Val Ser Lys Gly Glu Glu Asp Asn Met Ala Ile Ile Lys Glu Phe
            20                  25                  30

Met Arg Phe Lys Val His Met Glu Gly Ser Val Asn Gly His Glu Phe
        35                  40                  45

Glu Ile Glu Gly Glu Gly Glu Gly Arg Pro Tyr Glu Gly Thr Gln Thr
    50                  55                  60

Ala Lys Leu Lys Val Thr Lys Gly Gly Pro Leu Pro Phe Ala Trp Asp
65                  70                  75                  80

Ile Leu Ser Pro Gln Phe Met Tyr Gly Ser Lys Ala Tyr Val Lys His
                85                  90                  95

Pro Ala Asp Ile Pro Asp Tyr Leu Lys Leu Ser Phe Pro Glu Gly Phe
            100                 105                 110

Lys Trp Glu Arg Val Met Asn Phe Glu Asp Gly Gly Val Val Thr Val
        115                 120                 125

Thr Gln Asp Ser Ser Leu Gln Asp Gly Glu Phe Ile Tyr Lys Val Lys
130                 135                 140

Leu Arg Gly Thr Asn Phe Pro Ser Asp Gly Pro Val Met Gln Lys Lys
145                 150                 155                 160

Thr Met Gly Trp Glu Ala Ser Ser Glu Arg Met Tyr Pro Glu Asp Gly
                165                 170                 175

Ala Leu Lys Gly Glu Ile Lys Gln Arg Leu Lys Leu Lys Asp Gly Gly
            180                 185                 190

His Tyr Asp Ala Glu Val Lys Thr Thr Tyr Lys Ala Lys Lys Pro Val
        195                 200                 205

Gln Leu Pro Gly Ala Tyr Asn Val Asn Ile Lys Leu Asp Ile Thr Ser
    210                 215                 220

His Asn Glu Asp Tyr Thr Ile Val Glu Gln Tyr Glu Arg Ala Glu Gly
225                 230                 235                 240

Arg His Ser Thr Gly Gly Met Asp Glu Leu Tyr Lys Gly Ser Lys Gln
                245                 250                 255

Leu Glu Glu Leu Leu Ser Thr Ser Phe Asp Ile Gln Phe Asn Asp Leu
            260                 265                 270

Thr Leu Leu Glu Thr Ala Phe Thr His Thr Ser Tyr Ala Asn Glu His
        275                 280                 285

Arg Leu Leu Asn Val Ser His Asn Glu Arg Leu Glu Phe Leu Gly Asp
    290                 295                 300

Ala Val Leu Gln Leu Ile Ile Ser Glu Tyr Leu Phe Ala Lys Tyr Pro
305                 310                 315                 320

Lys Lys Thr Glu Gly Asp Met Ser Lys Leu Arg Ser Met Ile Val Arg
                325                 330                 335

Glu Glu Ser Leu Ala Gly Phe Ser Arg Phe Cys Ser Phe Asp Ala Tyr
            340                 345                 350

Ile Lys Leu Gly Lys Gly Glu Glu Lys Ser Gly Gly Arg Arg Arg Asp
        355                 360                 365

Thr Ile Leu Gly Asp Leu Phe Glu Ala Phe Leu Gly Ala Leu Leu Leu
    370                 375                 380
```

-continued

Asp Lys Gly Ile Asp Ala Val Arg Arg Phe Leu Lys Gln Val Met Ile
385                 390                 395                 400

Pro Gln Val Glu Lys Gly Asn Phe Glu Arg Val Lys Asp Tyr Lys Thr
            405                 410                 415

Cys Leu Gln Glu Phe Leu Gln Thr Lys Gly Asp Val Ala Ile Asp Tyr
            420                 425                 430

Gln Val Ile Ser Glu Lys Gly Pro Ala His Ala Lys Gln Phe Glu Val
            435                 440                 445

Ser Ile Val Val Asn Gly Ala Val Leu Ser Lys Gly Leu Gly Lys Ser
            450                 455                 460

Lys Lys Leu Ala Glu Gln Asp Ala Ala Lys Asn Ala Leu Ala Gln Leu
465                 470                 475                 480

Ser Glu Val

<210> SEQ ID NO 49
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Lys Gln Leu Glu Glu Leu Ser Thr Ser Phe Asp Ile Gln Phe
1               5                   10                  15

Asn Asp Leu Thr Leu Leu Glu Thr Ala Phe Thr His Thr Ser Tyr Ala
            20                  25                  30

Asn Glu His Arg Leu Leu Asn Val Ser His Asn Glu Arg Leu Glu Phe
            35                  40                  45

Leu Gly Asp Ala Val Leu Gln Leu Ile Ile Ser Glu Tyr Leu Phe Ala
            50                  55                  60

Lys Tyr Pro Lys Lys Thr Glu Gly Asp Met Ser Lys Leu Arg Ser Met
65                  70                  75                  80

Ile Val Arg Glu Glu Ser Leu Ala Gly Phe Ser Arg Phe Cys Ser Phe
                85                  90                  95

Asp Ala Tyr Ile Lys Leu Gly Lys Gly Glu Lys Ser Gly Gly Arg
            100                 105                 110

Arg Arg Asp Thr Ile Leu Gly Asp Leu Phe Glu Ala Phe Leu Gly Ala
            115                 120                 125

Leu Leu Leu Asp Lys Gly Ile Asp Ala Val Arg Arg Phe Leu Lys Gln
            130                 135                 140

Val Met Ile Pro Gln Val Glu Lys Gly Asn Phe Glu Arg Val Lys Asp
145                 150                 155                 160

Tyr Lys Thr Cys Leu Gln Glu Phe Leu Gln Thr Lys Gly Asp Val Ala
                165                 170                 175

Ile Asp Tyr Gln Val Ile Ser Glu Lys Gly Pro Ala His Ala Lys Gln
            180                 185                 190

Phe Glu Val Ser Ile Val Val Asn Gly Ala Val Leu Ser Lys Gly Leu
            195                 200                 205

Gly Lys Ser Lys Lys Leu Ala Glu Gln Asp Ala Ala Lys Asn Ala Leu
            210                 215                 220

Ala Gln Leu Ser Glu Val Gly Ser Val Ser Lys Gly Glu Glu Asp Asn
225                 230                 235                 240

Met Ala Ile Ile Lys Glu Phe Met Arg Phe Lys Val His Met Glu Gly
                245                 250                 255

Ser Val Asn Gly His Glu Phe Glu Ile Glu Gly Gly Glu Gly Arg
             260                 265                 270

Pro Tyr Glu Gly Thr Gln Thr Ala Lys Leu Lys Val Thr Lys Gly Gly
         275                 280                 285

Pro Leu Pro Phe Ala Trp Asp Ile Leu Ser Pro Gln Phe Met Tyr Gly
     290                 295                 300

Ser Lys Ala Tyr Val Lys His Pro Ala Asp Ile Pro Asp Tyr Leu Lys
305                 310                 315                 320

Leu Ser Phe Pro Glu Gly Phe Lys Trp Glu Arg Val Met Asn Phe Glu
                 325                 330                 335

Asp Gly Gly Val Val Thr Val Thr Gln Asp Ser Ser Leu Gln Asp Gly
             340                 345                 350

Glu Phe Ile Tyr Lys Val Lys Leu Arg Gly Thr Asn Phe Pro Ser Asp
         355                 360                 365

Gly Pro Val Met Gln Lys Lys Thr Met Gly Trp Glu Ala Ser Ser Glu
     370                 375                 380

Arg Met Tyr Pro Glu Asp Gly Ala Leu Lys Gly Glu Ile Lys Gln Arg
385                 390                 395                 400

Leu Lys Leu Lys Asp Gly Gly His Tyr Asp Ala Glu Val Lys Thr Thr
                 405                 410                 415

Tyr Lys Ala Lys Lys Pro Val Gln Leu Pro Gly Ala Tyr Asn Val Asn
             420                 425                 430

Ile Lys Leu Asp Ile Thr Ser His Asn Glu Asp Tyr Thr Ile Val Glu
         435                 440                 445

Gln Tyr Glu Arg Ala Glu Gly Arg His Ser Thr Gly Gly Met Asp Glu
     450                 455                 460

Leu Tyr Lys Lys Arg Pro Ala Ala Thr Lys Lys Ala Gly Gln Ala Lys
465                 470                 475                 480

Lys Lys Lys

<210> SEQ ID NO 50
<211> LENGTH: 1423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
             20                  25                  30

Gly Ile His Gly Val Pro Ala Ala Asp Lys Lys Tyr Ser Ile Gly Leu
         35                  40                  45

Ala Ile Gly Thr Asn Ser Val Gly Trp Ala Val Ile Thr Asp Glu Tyr
     50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                 85                  90                  95

Thr Ala Glu Ala Thr Arg Leu Lys Arg Thr Ala Arg Arg Arg Tyr Thr
             100                 105                 110

Arg Arg Lys Asn Arg Ile Cys Tyr Leu Gln Glu Ile Phe Ser Asn Glu
         115                 120                 125

```
Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
```

```
             545                 550                 555                 560
        Asn Glu Leu Thr Lys Val Lys Tyr Val Thr Glu Gly Met Arg Lys Pro
                        565                 570                 575
        Ala Phe Leu Ser Gly Glu Gln Lys Lys Ala Ile Val Asp Leu Leu Phe
                        580                 585                 590
        Lys Thr Asn Arg Lys Val Thr Val Lys Gln Leu Lys Glu Asp Tyr Phe
                        595                 600                 605
        Lys Lys Ile Glu Cys Phe Asp Ser Val Glu Ile Ser Gly Val Glu Asp
                        610                 615                 620
        Arg Phe Asn Ala Ser Leu Gly Thr Tyr His Asp Leu Leu Lys Ile Ile
        625                 630                 635                 640
        Lys Asp Lys Asp Phe Leu Asp Asn Glu Glu Asn Glu Asp Ile Leu Glu
                        645                 650                 655
        Asp Ile Val Leu Thr Leu Thr Leu Phe Glu Asp Arg Glu Met Ile Glu
                        660                 665                 670
        Glu Arg Leu Lys Thr Tyr Ala His Leu Phe Asp Asp Lys Val Met Lys
                        675                 680                 685
        Gln Leu Lys Arg Arg Arg Tyr Thr Gly Trp Gly Arg Leu Ser Arg Lys
                        690                 695                 700
        Leu Ile Asn Gly Ile Arg Asp Lys Gln Ser Gly Lys Thr Ile Leu Asp
        705                 710                 715                 720
        Phe Leu Lys Ser Asp Gly Phe Ala Asn Arg Asn Phe Met Gln Leu Ile
                        725                 730                 735
        His Asp Asp Ser Leu Thr Phe Lys Glu Asp Ile Gln Lys Ala Gln Val
                        740                 745                 750
        Ser Gly Gln Gly Asp Ser Leu His Glu His Ile Ala Asn Leu Ala Gly
                        755                 760                 765
        Ser Pro Ala Ile Lys Lys Gly Ile Leu Gln Thr Val Lys Val Val Asp
                        770                 775                 780
        Glu Leu Val Lys Val Met Gly Arg His Lys Pro Glu Asn Ile Val Ile
        785                 790                 795                 800
        Glu Met Ala Arg Glu Asn Gln Thr Thr Gln Lys Gly Gln Lys Asn Ser
                        805                 810                 815
        Arg Glu Arg Met Lys Arg Ile Glu Glu Gly Ile Lys Glu Leu Gly Ser
                        820                 825                 830
        Gln Ile Leu Lys Glu His Pro Val Glu Asn Thr Gln Leu Gln Asn Glu
                        835                 840                 845
        Lys Leu Tyr Leu Tyr Tyr Leu Gln Asn Gly Arg Asp Met Tyr Val Asp
                        850                 855                 860
        Gln Glu Leu Asp Ile Asn Arg Leu Ser Asp Tyr Asp Val Asp His Ile
        865                 870                 875                 880
        Val Pro Gln Ser Phe Leu Lys Asp Asp Ser Ile Asp Asn Lys Val Leu
                        885                 890                 895
        Thr Arg Ser Asp Lys Asn Arg Gly Lys Ser Asp Asn Val Pro Ser Glu
                        900                 905                 910
        Glu Val Val Lys Lys Met Lys Asn Tyr Trp Arg Gln Leu Leu Asn Ala
                        915                 920                 925
        Lys Leu Ile Thr Gln Arg Lys Phe Asp Asn Leu Thr Lys Ala Glu Arg
                        930                 935                 940
        Gly Gly Leu Ser Glu Leu Asp Lys Ala Gly Phe Ile Lys Arg Gln Leu
        945                 950                 955                 960
        Val Glu Thr Arg Gln Ile Thr Lys His Val Ala Gln Ile Leu Asp Ser
                        965                 970                 975
```

```
Arg Met Asn Thr Lys Tyr Asp Glu Asn Asp Lys Leu Ile Arg Glu Val
            980                 985                 990

Lys Val Ile Thr Leu Lys Ser Lys  Leu Val Ser Asp Phe  Arg Lys Asp
            995                 1000                1005

Phe Gln Phe Tyr Lys Val Arg  Glu Ile Asn Asn Tyr  His His Ala
        1010                1015                1020

His Asp Ala Tyr Leu Asn Ala  Val Val Gly Thr Ala  Leu Ile Lys
        1025                1030                1035

Lys Tyr Pro Lys Leu Glu Ser  Glu Phe Val Tyr Gly  Asp Tyr Lys
        1040                1045                1050

Val Tyr Asp Val Arg Lys Met  Ile Ala Lys Ser Glu  Gln Glu Ile
        1055                1060                1065

Gly Lys Ala Thr Ala Lys Tyr  Phe Phe Tyr Ser Asn  Ile Met Asn
        1070                1075                1080

Phe Phe Lys Thr Glu Ile Thr  Leu Ala Asn Gly Glu  Ile Arg Lys
        1085                1090                1095

Arg Pro Leu Ile Glu Thr Asn  Gly Glu Thr Gly Glu  Ile Val Trp
        1100                1105                1110

Asp Lys Gly Arg Asp Phe Ala  Thr Val Arg Lys Val  Leu Ser Met
        1115                1120                1125

Pro Gln Val Asn Ile Val Lys  Lys Thr Glu Val Gln  Thr Gly Gly
        1130                1135                1140

Phe Ser Lys Glu Ser Ile Leu  Pro Lys Arg Asn Ser  Asp Lys Leu
        1145                1150                1155

Ile Ala Arg Lys Lys Asp Trp  Asp Pro Lys Lys Tyr  Gly Gly Phe
        1160                1165                1170

Asp Ser Pro Thr Val Ala Tyr  Ser Val Leu Val Val  Ala Lys Val
        1175                1180                1185

Glu Lys Gly Lys Ser Lys Lys  Leu Lys Ser Val Lys  Glu Leu Leu
        1190                1195                1200

Gly Ile Thr Ile Met Glu Arg  Ser Ser Phe Glu Lys  Asn Pro Ile
        1205                1210                1215

Asp Phe Leu Glu Ala Lys Gly  Tyr Lys Glu Val Lys  Lys Asp Leu
        1220                1225                1230

Ile Ile Lys Leu Pro Lys Tyr  Ser Leu Phe Glu Leu  Glu Asn Gly
        1235                1240                1245

Arg Lys Arg Met Leu Ala Ser  Ala Gly Glu Leu Gln  Lys Gly Asn
        1250                1255                1260

Glu Leu Ala Leu Pro Ser Lys  Tyr Val Asn Phe Leu  Tyr Leu Ala
        1265                1270                1275

Ser His Tyr Glu Lys Leu Lys  Gly Ser Pro Glu Asp  Asn Glu Gln
        1280                1285                1290

Lys Gln Leu Phe Val Glu Gln  His Lys His Tyr Leu  Asp Glu Ile
        1295                1300                1305

Ile Glu Gln Ile Ser Glu Phe  Ser Lys Arg Val Ile  Leu Ala Asp
        1310                1315                1320

Ala Asn Leu Asp Lys Val Leu  Ser Ala Tyr Asn Lys  His Arg Asp
        1325                1330                1335

Lys Pro Ile Arg Glu Gln Ala  Glu Asn Ile Ile His  Leu Phe Thr
        1340                1345                1350

Leu Thr Asn Leu Gly Ala Pro  Ala Ala Phe Lys Tyr  Phe Asp Thr
        1355                1360                1365
```

| | | | | | | | | | | |
|---|---|---|---|---|---|---|---|---|---|---|
| Thr | Ile | Asp | Arg | Lys | Arg | Tyr | Thr | Ser | Thr | Lys | Glu | Val | Leu | Asp |
| 1370 | | | | | 1375 | | | | | 1380 | | | | |
| Ala | Thr | Leu | Ile | His | Gln | Ser | Ile | Thr | Gly | Leu | Tyr | Glu | Thr | Arg |
| 1385 | | | | | 1390 | | | | | 1395 | | | | |
| Ile | Asp | Leu | Ser | Gln | Leu | Gly | Gly | Asp | Lys | Arg | Pro | Ala | Ala | Thr |
| 1400 | | | | | 1405 | | | | | 1410 | | | | |
| Lys | Lys | Ala | Gly | Gln | Ala | Lys | Lys | Lys | | | | | | |
| 1415 | | | | | 1420 | | | | | | | | | |

<210> SEQ ID NO 51
<211> LENGTH: 2012
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | | | | | |
|---|---|---|---|---|---|
| gaatgctgcc | ctcagacccg | cttcctccct | gtccttgtct | gtccaaggag | aatgaggtct | 60 |
| cactggtgga | tttcggacta | ccctgaggag | ctggcacctg | agggacaagg | cccccacct | 120 |
| gcccagctcc | agcctctgat | gaggggtggg | agagagctac | atgaggttgc | taagaaagcc | 180 |
| tcccctgaag | gagaccacac | agtgtgtgag | gttggagtct | ctagcagcgg | gttctgtgcc | 240 |
| cccagggata | gtctggctgt | ccaggcactg | ctcttgatat | aaacaccacc | tcctagttat | 300 |
| gaaaccatgc | ccattctgcc | tctctgtatg | gaaaagagca | tggggctggc | ccgtggggtg | 360 |
| gtgtccactt | taggccctgt | gggagatcat | gggaacccac | gcagtgggtc | ataggctctc | 420 |
| tcatttacta | ctcacatcca | ctctgtgaag | aagcgattat | gatctctcct | ctagaaactc | 480 |
| gtagagtccc | atgtctgccg | gcttccagag | cctgcactcc | tccaccttgg | cttggctttg | 540 |
| ctggggctag | aggagctagg | atgcacagca | gctctgtgac | cctttgtttg | agaggaacag | 600 |
| gaaaaccacc | cttctctctg | gcccactgtg | tcctcttcct | gccctgccat | ccccttctgt | 660 |
| gaatgttaga | cccatgggag | cagctggtca | gaggggaccc | cggcctgggg | ccctaaccc | 720 |
| tatgtagcct | cagtcttccc | atcaggctct | cagctcagcc | tgagtgttga | ggccccagtg | 780 |
| gctgctctgg | gggcctcctg | agtttctcat | ctgtgcccct | ccctccctgg | cccaggtgaa | 840 |
| ggtgtggttc | cagaaccgga | ggacaaagta | caaacggcag | aagctggagg | aggaagggcc | 900 |
| tgagtccgag | cagaagaaga | agggctccca | tcacatcaac | cggtggcgca | ttgccacgaa | 960 |
| gcaggccaat | ggggaggaca | tcgatgtcac | ctccaatgac | aagcttgcta | gcggtgggca | 1020 |
| accacaaacc | cacgagggca | gagtgctgct | tgctgctggc | caggcccctg | cgtgggccca | 1080 |
| agctggactc | tggccactcc | ctggccaggc | tttggggagg | cctggagtca | tggccccaca | 1140 |
| gggcttgaag | cccggggccg | ccattgacag | agggacaagc | aatgggctgg | ctgaggcctg | 1200 |
| ggaccacttg | gccttctcct | cggagagcct | gcctgcctgg | gcgggcccgc | cgccaccgc | 1260 |
| agcctcccag | ctgctctccg | tgtctccaat | ctccctttttg | ttttgatgca | tttctgtttt | 1320 |
| aatttatttt | ccaggcacca | ctgtagttta | gtgatcccca | gtgtccccct | tcctatggg | 1380 |
| aataataaaa | gtctctctct | taatgacacg | ggcatccagc | tccagcccca | gagcctgggg | 1440 |
| tggtagattc | cggctctgag | ggccagtggg | ggctggtaga | gcaaacgcgt | tcagggcctg | 1500 |
| ggagcctggg | gtgggtact | ggtggagggg | gtcaaggta | attcattaac | tcctctcttt | 1560 |
| tgttggggga | ccctggtctc | tacctccagc | tccacagcag | gagaaacagg | ctagacatag | 1620 |
| ggaagggcca | tcctgtatct | tgagggagga | caggcccagg | tctttcttaa | cgtattgaga | 1680 |

```
ggtgggaatc aggcccaggt agttcaatgg gagagggaga gtgcttccct ctgcctagag    1740
actctggtgg cttctccagt tgaggagaaa ccagaggaaa ggggaggatt ggggtctggg    1800
ggagggaaca ccattcacaa aggctgacgg ttccagtccg aagtcgtggg cccaccagga    1860
tgctcacctg tccttggaga accgctgggc aggttgagac tgcagagaca gggcttaagg    1920
ctgagcctgc aaccagtccc cagtgactca gggcctcctc agcccaagaa agagcaacgt    1980
gccagggccc gctgagctct tgtgttcacc tg                                  2012
```

<210> SEQ ID NO 52
<211> LENGTH: 1153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Lys Arg Pro Ala Ala Thr Lys Lys Ala Gly Gln Ala Lys Lys Lys
1               5                   10                  15

Lys Ser Asp Leu Val Leu Gly Leu Asp Ile Gly Ile Gly Ser Val Gly
                20                  25                  30

Val Gly Ile Leu Asn Lys Val Thr Gly Glu Ile Ile His Lys Asn Ser
            35                  40                  45

Arg Ile Phe Pro Ala Ala Gln Ala Glu Asn Asn Leu Val Arg Arg Thr
        50                  55                  60

Asn Arg Gln Gly Arg Arg Leu Ala Arg Arg Lys His Arg Arg Val
65                  70                  75                  80

Arg Leu Asn Arg Leu Phe Glu Glu Ser Gly Leu Ile Thr Asp Phe Thr
                85                  90                  95

Lys Ile Ser Ile Asn Leu Asn Pro Tyr Gln Leu Arg Val Lys Gly Leu
            100                 105                 110

Thr Asp Glu Leu Ser Asn Glu Glu Leu Phe Ile Ala Leu Lys Asn Met
        115                 120                 125

Val Lys His Arg Gly Ile Ser Tyr Leu Asp Asp Ala Ser Asp Asp Gly
    130                 135                 140

Asn Ser Ser Val Gly Asp Tyr Ala Gln Ile Val Lys Glu Asn Ser Lys
145                 150                 155                 160

Gln Leu Glu Thr Lys Thr Pro Gly Gln Ile Gln Leu Glu Arg Tyr Gln
                165                 170                 175

Thr Tyr Gly Gln Leu Arg Gly Asp Phe Thr Val Glu Lys Asp Gly Lys
            180                 185                 190

Lys His Arg Leu Ile Asn Val Phe Pro Thr Ser Ala Tyr Arg Ser Glu
        195                 200                 205

Ala Leu Arg Ile Leu Gln Thr Gln Gln Glu Phe Asn Pro Gln Ile Thr
    210                 215                 220

Asp Glu Phe Ile Asn Arg Tyr Leu Glu Ile Leu Thr Gly Lys Arg Lys
225                 230                 235                 240

Tyr Tyr His Gly Pro Gly Asn Glu Lys Ser Arg Thr Asp Tyr Gly Arg
                245                 250                 255

Tyr Arg Thr Ser Gly Glu Thr Leu Asp Asn Ile Phe Gly Ile Leu Ile
            260                 265                 270

Gly Lys Cys Thr Phe Tyr Pro Asp Glu Phe Arg Ala Ala Lys Ala Ser
        275                 280                 285

Tyr Thr Ala Gln Glu Phe Asn Leu Leu Asn Asp Leu Asn Asn Leu Thr
    290                 295                 300
```

```
Val Pro Thr Glu Thr Lys Lys Leu Ser Lys Glu Gln Lys Asn Gln Ile
305                 310                 315                 320

Ile Asn Tyr Val Lys Asn Glu Lys Ala Met Gly Pro Ala Lys Leu Phe
            325                 330                 335

Lys Tyr Ile Ala Lys Leu Leu Ser Cys Asp Val Ala Asp Ile Lys Gly
            340                 345                 350

Tyr Arg Ile Asp Lys Ser Gly Lys Ala Glu Ile His Thr Phe Glu Ala
            355                 360                 365

Tyr Arg Lys Met Lys Thr Leu Glu Thr Leu Asp Ile Glu Gln Met Asp
370                 375                 380

Arg Glu Thr Leu Asp Lys Leu Ala Tyr Val Leu Thr Leu Asn Thr Glu
385                 390                 395                 400

Arg Glu Gly Ile Gln Glu Ala Leu Glu His Glu Phe Ala Asp Gly Ser
                405                 410                 415

Phe Ser Gln Lys Gln Val Asp Glu Leu Val Gln Phe Arg Lys Ala Asn
            420                 425                 430

Ser Ser Ile Phe Gly Lys Gly Trp His Asn Phe Ser Val Lys Leu Met
            435                 440                 445

Met Glu Leu Ile Pro Glu Leu Tyr Glu Thr Ser Glu Glu Gln Met Thr
450                 455                 460

Ile Leu Thr Arg Leu Gly Lys Gln Lys Thr Thr Ser Ser Asn Lys
465                 470                 475                 480

Thr Lys Tyr Ile Asp Glu Lys Leu Leu Thr Glu Ile Tyr Asn Pro
                485                 490                 495

Val Val Ala Lys Ser Val Arg Gln Ala Ile Lys Ile Val Asn Ala Ala
                500                 505                 510

Ile Lys Glu Tyr Gly Asp Phe Asp Asn Ile Val Ile Glu Met Ala Arg
            515                 520                 525

Glu Thr Asn Glu Asp Asp Glu Lys Lys Ala Ile Gln Lys Ile Gln Lys
            530                 535                 540

Ala Asn Lys Asp Glu Lys Asp Ala Ala Met Leu Lys Ala Ala Asn Gln
545                 550                 555                 560

Tyr Asn Gly Lys Ala Glu Leu Pro His Ser Val Phe His Gly His Lys
                565                 570                 575

Gln Leu Ala Thr Lys Ile Arg Leu Trp His Gln Gln Gly Glu Arg Cys
            580                 585                 590

Leu Tyr Thr Gly Lys Thr Ile Ser Ile His Asp Leu Ile Asn Asn Ser
        595                 600                 605

Asn Gln Phe Glu Val Asp His Ile Leu Pro Leu Ser Ile Thr Phe Asp
            610                 615                 620

Asp Ser Leu Ala Asn Lys Val Leu Val Tyr Ala Thr Ala Asn Gln Glu
625                 630                 635                 640

Lys Gly Gln Arg Thr Pro Tyr Gln Ala Leu Asp Ser Met Asp Asp Ala
                645                 650                 655

Trp Ser Phe Arg Glu Leu Lys Ala Phe Val Arg Glu Ser Lys Thr Leu
            660                 665                 670

Ser Asn Lys Lys Lys Glu Tyr Leu Leu Thr Glu Glu Asp Ile Ser Lys
            675                 680                 685

Phe Asp Val Arg Lys Lys Phe Ile Glu Arg Asn Leu Val Asp Thr Arg
            690                 695                 700

Tyr Ala Ser Arg Val Val Leu Asn Ala Leu Gln Glu His Phe Arg Ala
705                 710                 715                 720
```

-continued

His Lys Ile Asp Thr Lys Val Ser Val Val Arg Gly Gln Phe Thr Ser
            725                 730                 735

Gln Leu Arg Arg His Trp Gly Ile Glu Lys Thr Arg Asp Thr Tyr His
        740                 745                 750

His His Ala Val Asp Ala Leu Ile Ile Ala Ala Ser Ser Gln Leu Asn
    755                 760                 765

Leu Trp Lys Lys Gln Lys Asn Thr Leu Val Ser Tyr Ser Glu Asp Gln
770                 775                 780

Leu Leu Asp Ile Glu Thr Gly Glu Leu Ile Ser Asp Asp Glu Tyr Lys
785                 790                 795                 800

Glu Ser Val Phe Lys Ala Pro Tyr Gln His Phe Val Asp Thr Leu Lys
                805                 810                 815

Ser Lys Glu Phe Glu Asp Ser Ile Leu Phe Ser Tyr Gln Val Asp Ser
            820                 825                 830

Lys Phe Asn Arg Lys Ile Ser Asp Ala Thr Ile Tyr Ala Thr Arg Gln
        835                 840                 845

Ala Lys Val Gly Lys Asp Lys Ala Asp Glu Thr Tyr Val Leu Gly Lys
    850                 855                 860

Ile Lys Asp Ile Tyr Thr Gln Asp Gly Tyr Asp Ala Phe Met Lys Ile
865                 870                 875                 880

Tyr Lys Lys Asp Lys Ser Lys Phe Leu Met Tyr Arg His Asp Pro Gln
                885                 890                 895

Thr Phe Glu Lys Val Ile Glu Pro Ile Leu Glu Asn Tyr Pro Asn Lys
            900                 905                 910

Gln Ile Asn Glu Lys Gly Lys Glu Val Pro Cys Asn Pro Phe Leu Lys
        915                 920                 925

Tyr Lys Glu Glu His Gly Tyr Ile Arg Lys Tyr Ser Lys Lys Gly Asn
    930                 935                 940

Gly Pro Glu Ile Lys Ser Leu Lys Tyr Tyr Asp Ser Lys Leu Gly Asn
945                 950                 955                 960

His Ile Asp Ile Thr Pro Lys Asp Ser Asn Asn Lys Val Val Leu Gln
                965                 970                 975

Ser Val Ser Pro Trp Arg Ala Asp Val Tyr Phe Asn Lys Thr Thr Gly
            980                 985                 990

Lys Tyr Glu Ile Leu Gly Leu Lys Tyr Ala Asp Leu Gln Phe Glu Lys
        995                 1000                1005

Gly Thr Gly Thr Tyr Lys Ile Ser Gln Glu Lys Tyr Asn Asp Ile
        1010                1015                1020

Lys Lys Lys Glu Gly Val Asp Ser Asp Ser Glu Phe Lys Phe Thr
        1025                1030                1035

Leu Tyr Lys Asn Asp Leu Leu Leu Val Lys Asp Thr Glu Thr Lys
        1040                1045                1050

Glu Gln Gln Leu Phe Arg Phe Leu Ser Arg Thr Met Pro Lys Gln
        1055                1060                1065

Lys His Tyr Val Glu Leu Lys Pro Tyr Asp Lys Gln Lys Phe Glu
        1070                1075                1080

Gly Gly Glu Ala Leu Ile Lys Val Leu Gly Asn Val Ala Asn Ser
        1085                1090                1095

Gly Gln Cys Lys Lys Gly Leu Gly Lys Ser Asn Ile Ser Ile Tyr
        1100                1105                1110

Lys Val Arg Thr Asp Val Leu Gly Asn Gln His Ile Ile Lys Asn
        1115                1120                1125

Glu Gly Asp Lys Pro Lys Leu Asp Phe Lys Arg Pro Ala Ala Thr

```
                    1130              1135              1140
    Lys Lys  Ala Gly Gln Ala Lys  Lys Lys Lys
             1145              1150

<210> SEQ ID NO 53
<211> LENGTH: 340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg ttacttaaat cttgcagaag ctacaaagat aaggcttcat gccgaaatca    300
acaccctgtc attttatggc agggtgtttt cgttatttaa                          340

<210> SEQ ID NO 54
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (288)..(317)
<223> OTHER INFORMATION: a, c, t, g, unknown or other

<400> SEQUENCE: 54
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg ggttttagag ctatgctgtt ttgaatggtc ccaaaacnnn nnnnnnnnn    300 nnnnnnnnnn nnnnnngtt ttagagctat gctgttttga atggtcccaa aacttttttt    360

<210> SEQ ID NO 55
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (250)..(269)
<223> OTHER INFORMATION: a, c, t, g, unknown or other

<400> SEQUENCE: 55
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccn nnnnnnnnnn nnnnnnnnng ttttagagct agaaatagca agttaaaata    300
```

```
aggctagtcc gtttttttt                                              318

<210> SEQ ID NO 56
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (250)..(269)
<223> OTHER INFORMATION: a, c, t, g, unknown or other

<400> SEQUENCE: 56
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccn nnnnnnnnn nnnnnnnnng ttttagagct agaaatagca agttaaaata    300
aggctagtcc gttatcattt ttttt                                         325

<210> SEQ ID NO 57
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (250)..(269)
<223> OTHER INFORMATION: a, c, t, g, unknown or other

<400> SEQUENCE: 57
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccn nnnnnnnnn nnnnnnnnng ttttagagct agaaatagca agttaaaata    300
aggctagtcc gttatcaact tgaaaagtg ttttttt                             337

<210> SEQ ID NO 58
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (250)..(269)
<223> OTHER INFORMATION: a, c, t, g, unknown or other

<400> SEQUENCE: 58
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
```

```
cgaaacaccn nnnnnnnnnn nnnnnnnnng ttttagagct agaaatagca agttaaaata    300
aggctagtcc gttatcaact tgaaaaagtg gcaccgagtc ggtgcttttt tt            352

<210> SEQ ID NO 59
<211> LENGTH: 5101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtcgag gtgagcccca cgttctgctt cactctcccc atctcccccc cctccccacc    360
cccaattttg tatttattta ttttttaatt attttgtgca gcgatggggg cggggggggg    420 ggggggcgc gcgccaggcg gggcggggcg gggcgagggg cggggcgggg cgaggcggag    480
aggtgcggcg gcagccaatc agagcggcgc gctccgaaag tttccttta tggcgaggcg    540 gcggcggcgg cggccctata aaaagcgaag cgcgcggcgg gcgggagtcg ctgcgacgct    600
gccttcgccc cgtgccccgc tccgccgccg cctcgcgccg cccgccccgg ctctgactga    660
ccgcgttact cccacaggtg agcgggcggg acggcccttc tcctccgggc tgtaattagc    720
tgagcaagag gtaagggttt aagggatggt tggttggtgg ggtattaatg tttaattacc    780
tggagcacct gcctgaaatc actttttttc aggttggacc ggtgccacca tggactataa    840
ggaccacgac ggagactaca aggatcatga tattgattac aaagacgatg acgataagat    900
ggccccaaag aagaagcgga aggtcggtat ccacggagtc ccagcagccg acaagaagta    960
cagcatcggc ctggacatcg gcaccaactc tgtgggctgg gccgtgatca ccgacgagta    1020
caaggtgccc agcaagaaat tcaaggtgct gggcaacacc gaccggcaca gcatcaagaa    1080
gaacctgatc ggagccctgc tgttcgacag cggcgaaaca gccgaggcca cccggctgaa    1140
gagaaccgcc agaagaagat acaccagacg gaagaaccgg atctgctatc tgcaagagat    1200
cttcagcaac gagatggcca aggtggacga cagcttcttc cacagactgg aagagtcctt    1260
cctggtggaa gaggataaga agcacgagcg gcaccccatc ttcggcaaca tcgtggacga    1320
ggtggcctac cacgagaagt accccaccat ctaccacctg agaaagaaac tggtggacag    1380
caccgacaag gccgacctgc ggctgatcta tctggccctg gcccacatga tcaagttccg    1440
gggccacttc ctgatcgagg gcgacctgaa ccccgacaac agcgacgtgg acaagctgtt    1500
catccagctg gtgcagacct acaaccagct gttcgaggaa aacccatca acgccagcgg    1560 cgtggacgcc aaggccatcc tgtctgccag actgagcaag agcagacggc tggaaaatct    1620
gatcgcccag ctgcccggcg agaagaagaa tggcctgttc ggcaacctga ttgccctgag    1680
cctgggcctg acccccaact tcaagagcaa cttcgacctg gccgaggatg ccaaactgca    1740
gctgagcaag gacacctacg acgacgacct ggacaacctg ctggcccaga tcggcgacca    1800
gtacgccgac ctgtttctgg ccgccaagaa cctgtccgac gccatcctgc tgagcgacat    1860
cctgagagtg aacaccgaga tcaccaaggc ccccctgagc gcctctatga tcaagagata    1920
```

```
cgacgagcac caccaggacc tgaccctgct gaaagctctc gtgcggcagc agctgcctga   1980
gaagtacaaa gagattttct tcgaccagag caagaacggc tacgccggct acattgacgg   2040
cggagccagc caggaagagt tctacaagtt catcaagccc atcctggaaa agatggacgg   2100
caccgaggaa ctgctcgtga agctgaacag agaggacctg ctgcggaagc agcggacctt   2160
cgacaacggc agcatccccc accagatcca cctgggagag ctgcacgcca ttctgcggcg   2220
gcaggaagat ttttacccat tcctgaagga caaccgggaa aagatcgaga gatcctgac    2280 cttccgcatc ccctactacg tgggccctct ggccagggga acagcagat tcgcctggat    2340 gaccagaaag agcgaggaaa ccatcacccc ctggaacttc gaggaagtgg tggacaaggg   2400
cgcttccgcc cagagcttca tcgagcggat gaccaacttc gataagaacc tgcccaacga   2460
gaaggtgctg cccaagcaca gcctgctgta cgagtacttc accgtgtata cagagctgac   2520
caaagtgaaa tacgtgaccg agggaatgag aaagcccgcc ttcctgagcg gcgagcagaa   2580
aaaggccatc gtggacctgc tgttcaagac caaccggaaa gtgaccgtga agcagctgaa   2640
agaggactac ttcaagaaaa tcgagtgctt cgactccgtg gaaatctccg gcgtggaaga   2700
tcggttcaac gcctccctgg gcacatacca cgatctgctg aaaattatca aggacaagga   2760
cttcctggac aatgaggaaa acgaggacat tctggaagat atcgtgctga ccctgacact   2820
gtttgaggac agagagatga tcgaggaacg gctgaaaacc tatgcccacc tgttcgacga   2880
caaagtgatg aagcagctga gcggcggag atacaccggc tggggcaggc tgagccggaa    2940
gctgatcaac ggcatccggg acaagcagtc cggcaagaca atcctggatt tcctgaagtc   3000
cgacggcttc gccaacagaa acttcatgca gctgatccac gacgacagcc tgaccttta    3060 agaggacatc cagaaagccc aggtgtccgg ccagggcgat agcctgcacg agcacattgc   3120
caatctggcc ggcagccccg ccattaagaa gggcatcctg cagacagtga aggtggtgga   3180
cgagctcgtg aaagtgatgg gccggcacaa gcccgagaac atcgtgatcg aaatggccag   3240
agagaaccag accacccaga agggacagaa gaacagccgc gagagaatga agcggatcga   3300
agagggcatc aaagagctgg gcagccagat cctgaaagaa caccccgtgg aaaacaccca   3360
gctgcagaac gagaagctgt acctgtacta cctgcagaat gggcgggata tgtacgtgga   3420
ccaggaactg gacatcaacc ggctgtccga ctacgatgtg gaccatatcg tgcctcagag   3480
ctttctgaag gacgactcca tcgacaacaa ggtgctgacc agaagcgaca gaaccgggg    3540 caagagcgac aacgtgccct ccgaagaggt cgtgaagaag atgaagaact actggcggca   3600
gctgctgaac gccaagctga ttacccgag aaagttcgac aatctgacca aggccgagag   3660
aggcggcctg agcgaactgg ataaggccgg cttcatcaag agacagctgg tggaaacccg   3720
gcagatcaca aagcacgtgg cacagatcct ggactcccgg atgaacacta agtacgacga   3780
gaatgacaag ctgatccggg aagtgaaagt gatcacccctg aagtccaagc tggtgtccga   3840
tttccggaag gatttccagt tttacaaagt gcgcgagatc aacaactacc accacgccca   3900
cgacgcctac ctgaacgccg tcgtgggaac cgccctgatc aaaaagtacc ctaagctgga   3960
aagcgagttc gtgtacggcg actacaaggt gtacgacgtg cggaagatga tcgccaagag   4020
cgagcaggaa atcggcaagg ctaccgccaa gtacttcttc tacagcaaca tcatgaactt   4080
tttcaagacc gagattaccc tggccaacgg cgagatccgg aagcggcctc tgatcgagac   4140
aaacggcgaa accggggaga tcgtgtggga taagggccgg gattttgcca ccgtgcgaa    4200 agtgctgagc atgccccaag tgaatatcgt gaaaaagacc gaggtgcaga caggcggctt   4260
```

```
cagcaaagag tctatcctgc ccaagaggaa cagcgataag ctgatcgcca gaaagaagga    4320
ctgggaccct aagaagtacg gcggcttcga cagccccacc gtggcctatt ctgtgctggt    4380
ggtggccaaa gtggaaaagg gcaagtccaa gaaactgaag agtgtgaaag agctgctggg    4440
gatcaccatc atggaaagaa gcagcttcga gaagaatccc atcgactttc tggaagccaa    4500
gggctacaaa gaagtgaaaa aggacctgat catcaagctg cctaagtact ccctgttcga    4560
gctggaaaac ggccggaaga gaatgctggc ctctgccggc gaactgcaga agggaaacga    4620
actggccctg ccctccaaat atgtgaactt cctgtacctg gccagccact atgagaagct    4680
gaagggctcc cccgaggata tgagcagaa acagctgttt gtggaacagc acaagcacta    4740
cctggacgag atcatcgagc agatcagcga gttctccaag agagtgatcc tggccgacgc    4800
taatctggac aaagtgctgt ccgcctacaa caagcaccgg ataagccca tcagagagca    4860 ggccgagaat atcatccacc tgtttaccct gaccaatctg ggagcccctg ccgccttcaa    4920
gtactttgac accaccatcg accggaagag gtacaccagc accaaagagg tgctggacgc    4980
caccctgatc caccagagca tcaccggcct gtacgagaca cggatcgacc tgtctcagct    5040
gggaggcgac tttcttttc ttagcttgac cagctttctt agtagcagca ggacgcttta    5100
a                                                                    5101
```

<210> SEQ ID NO 60
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 60

```
nnnnnnnnnn nnnnnnnnnn gttattgtac tctcaagatt tagaaataaa tcttgcagaa    60
gctacaaaga taaggcttca tgccgaaatc aacaccctgt cattttatgg cagggtgttt    120
tcgttattta atttttt                                                   137
```

<210> SEQ ID NO 61
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 61

```
nnnnnnnnnn nnnnnnnnnn gttattgtac tctcagaaat gcagaagcta caaagataag    60
gcttcatgcc gaaatcaaca ccctgtcatt ttatggcagg gtgttttcgt tatttaattt    120
ttt                                                                  123
```

<210> SEQ ID NO 62
<211> LENGTH: 110
<212> TYPE: DNA
<213> ORGANISM: Artificial Sequence
<220> FEATURE:
<223> OTHER INFORMATION: Description of Artificial Sequence: Synthetic -continued

```
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 62
nnnnnnnnnn nnnnnnnnnn gttattgtac tctcagaaat gcagaagcta caaagataag      60
gcttcatgcc gaaatcaaca ccctgtcatt ttatggcagg gtgttttttt                110

<210> SEQ ID NO 63
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 63
nnnnnnnnnn nnnnnnnnnn gttattgtac tctcaagatt tagaaataaa tcttgcagaa      60
gctacaatga taaggcttca tgccgaaatc aacaccctgt cattttatgg cagggtgttt     120
tcgttattta atttttt                                                    137

<210> SEQ ID NO 64
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 64
nnnnnnnnnn nnnnnnnnnn gttattgtac tctcagaaat gcagaagcta caatgataag      60
gcttcatgcc gaaatcaaca ccctgtcatt ttatggcagg gtgttttcgt tatttaattt     120
ttt                                                                   123

<210> SEQ ID NO 65
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 65
nnnnnnnnnn nnnnnnnnnn gttattgtac tctcagaaat gcagaagcta caatgataag      60
gcttcatgcc gaaatcaaca ccctgtcatt ttatggcagg gtgttttttt                110

<210> SEQ ID NO 66
<211> LENGTH: 107
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 66
nnnnnnnnnn nnnnnnnnnn gttttagagc tgtggaaaca cagcgagtta aaataaggct      60
tagtccgtac tcaacttgaa aaggtggcac cgattcggtg ttttttt                  107

<210> SEQ ID NO 67
<211> LENGTH: 4263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgaaaaggc cggcggccac gaaaaaggcc ggccaggcaa aaagaaaaa gaccaagccc      60 tacagcatcg gcctggacat cggcaccaat agcgtgggct gggccgtgac caccgacaac   120
tacaaggtgc ccagcaagaa aatgaaggtg ctgggcaaca cctccaagaa gtacatcaag   180
aaaaacctgc tgggcgtgct gctgttcgac agcggcatta cagccgaggg cagacggctg   240
aagagaaccg ccagacggcg gtacacccgg cggagaaaca gaatcctgta tctgcaagag   300
atcttcagca ccgagatggc taccctggac gacgccttct ccagcggct ggacgacagc    360 ttcctggtgc ccgacgacaa gcgggacagc aagtacccca tcttcggcaa cctggtggaa   420
gagaaggcct accacgacga gttccccacc atctaccacc tgagaaagta cctggccgac   480
agcaccaaga aggccgacct gagactggtg tatctggccc tggcccacat gatcaagtac   540
cggggccact tcctgatcga gggcgagttc aacagcaaga caacgacat ccagaagaac    600 ttccaggact tcctggacac ctacaacgcc atcttcgaga gcgacctgtc cctggaaaac   660
agcaagcagc tggaagagat cgtgaaggac aagatcagca gctggaaaa gaaggaccgc    720 atcctgaagc tgttccccgg cgagaagaac agcggaatct tcagcgagtt tctgaagctg   780
atcgtgggca ccaggccga cttcagaaag tgcttcaacc tggacgagaa agccagcctg    840
cacttcagca agagagcta cgacgaggac ctggaacccc tgctgggata tatcggcgac    900
gactacagcg acgtgttcct gaaggccaag aagctgtacg acgctatcct gctgagcggc    960
ttcctgaccg tgaccgacaa cgagacagag gccccactga gcagcgccat gattaagcgg   1020
tacaacgagc acaaagagga tctggctctg ctgaaagagt acatccggaa catcagcctg   1080
aaaacctaca tgaggtgtt caaggacgac accaagaacg gctacgccgg ctacatcgac    1140
ggcaagacca ccaggaaga tttctatgtg tacctgaaga gctgctggc cgagttcgag     1200 ggggccgact actttctgga aaaaatcgac cgcgaggatt tcctgcggaa gcagcggacc   1260
ttcgacaacg gcagcatccc ctaccagatc catctgcagg aaatgcgggc catcctggac   1320
aagcaggcca gttctaccc attcctggcc aagaacaaag agcggatcga agatcctg      1380 accttccgca tcccttacta cgtgggcccc ctggccagag caacagcga ttttgcctgg    1440 tccatccgga agcgcaatga agatcacc ccctggaact tcgaggacgt gatcgacaaa     1500
gagtccagcg ccgaggcctt catcaaccgg atgaccagct cgacctgta cctgcccgag    1560 gaaaaggtgc tgcccaagca cagcctgctg tacgagacat tcaatgtgta taacgagctg    1620
accaaagtgc ggtttatcgc cgagtctatg cgggactacc agttcctgga ctccaagcag    1680
```

```
aaaaaggaca tcgtgcggct gtacttcaag gacaagcgga aagtgaccga taaggacatc    1740
atcgagtacc tgcacgccat ctacggctac gatggcatcg agctgaaggg catcgagaag    1800
cagttcaact ccagcctgag cacataccac gacctgctga acattatcaa cgacaaagaa    1860
tttctggacg actccagcaa cgaggccatc atcgaagaga tcatccacac cctgaccatc    1920
tttgaggacc gcgagatgat caagcagcgg ctgagcaagt tcgagaacat cttcgacaag    1980
agcgtgctga aaaagctgag cagacggcac tacaccggct ggggcaagct gagcgccaag    2040
ctgatcaacg gcatccggga cgagaagtcc ggcaacacaa tcctggacta cctgatcgac    2100
gacggcatca gcaaccggaa cttcatgcag ctgatccacg acgacgccct gagcttcaag    2160
aagaagatcc agaaggccca gatcatcggg gacgaggaca agggcaacat caaagaagtc    2220
gtgaagtccc tgcccggcag ccccgccatc aagaagggaa tcctgcagag catcaagatc    2280
gtggacgagc tcgtgaaagt gatgggcggc agaaagcccg agagcatcgt ggtggaaatg    2340
gctagagaga accagtacac caatcagggc aagagcaaca gccagcagag actgaagaga    2400
ctggaaaagt ccctgaaaga gctgggcagc aagattctga agagaatat ccctgccaag    2460 ctgtccaaga tcgacaacaa cgccctgcag aacgaccggc tgtacctgta ctacctgcag    2520
aatggcaagg acatgtatac aggcgacgac ctggatatcg accgcctgag caactacgac    2580
atcgaccata ttatccccca ggccttcctg aaagacaaca gcattgacaa caaagtgctg    2640
gtgtcctccg ccagcaaccg cggcaagtcc gatgatgtgc ccagcctgga agtcgtgaaa    2700
aagagaaaga ccttctggta tcagctgctg aaaagcaagc tgattagcca gaggaagttc    2760
gacaacctga ccaaggccga gagaggcggc ctgagccctg aagataaggc cggcttcatc    2820
cagagacagc tggtggaaac ccggcagatc accaagcacg tggccagact gctggatgag    2880
aagtttaaca acaagaagga cgagaacaac cgggccgtgc ggaccgtgaa gatcatcacc    2940
ctgaagtcca ccctggtgtc ccagttccgg aaggacttcg agctgtataa agtgcgcgag    3000
atcaatgact tcaccacgc ccacgacgcc tacctgaatg ccgtggtggc ttccgccctg    3060
ctgaagaagt accctaagct ggaacccgag ttcgtgtacg gcgactaccc caagtacaac    3120
tccttcagag agcggaagtc cgccaccgag aaggtgtact ctactccaa catcatgaat    3180 atctttaaga agtccatctc cctggccgat ggcagagtga tcgagcggcc cctgatcgaa    3240
gtgaacgaag agacaggcga gagcgtgtgg aacaaagaaa gcgacctggc caccgtgcgg    3300
cgggtgctga gttatcctca agtgaatgtc gtgaagaagg tggaagaaca gaaccacggc    3360
ctggatcggg gcaagcccaa gggcctgttc aacgccaacc tgtccagcaa gcctaagccc    3420
aactccaacg agaatctcgt gggggccaaa gagtacctgg accctaagaa gtacggcgga    3480
tacgccggca tctccaatag cttcaccgtg ctcgtgaagg gcaatcga aagggcgct    3540 aagaaaaga tcacaaacgt gctggaattt caggggatct ctatcctgga ccggatcaac    3600
taccggaagg ataagctgaa ctttctgctg gaaaaaggct acaaggacat tgagctgatt    3660
atcgagctgc ctaagtactc cctgttcgaa ctgagcgacg gctccagacg gatgctggcc    3720
tccatcctgt ccaccaacaa caagcggggc gagatccaca agggaaacca gatcttcctg    3780
agccagaaat ttgtgaaact gctgtaccac gccaagcgga tctccaacac catcaatgag    3840
aaccaccgga aatacgtgga aaaccacaag aaagagtttg aggaactgtt ctactacatc    3900
ctggagttca acgagaacta tgtgggagcc aagaagaacg gcaaactgct gaactccgcc    3960
ttccagagct ggcagaacca cagcatcgac gagctgtgca gctccttcat cggccctacc    4020
```

```
ggcagcgagc ggaagggact gtttgagctg acctccagag gctctgccgc cgactttgag    4080
ttcctgggag tgaagatccc ccggtacaga gactacaccc cctctagtct gctgaaggac    4140
gccaccctga tccaccagag cgtgaccggc ctgtacgaaa cccggatcga cctggctaag    4200
ctgggcgagg gaaagcgtcc tgctgctact aagaaagctg gtcaagctaa gaaaaagaaa    4260
taa                                                                  4263

<210> SEQ ID NO 68
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcctagcagg atttctgata ttactgtcac gttttagagc tatgctgttt tga           53

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtgacagtaa tatcagaaat cctgctagga gttttgggac cattcaaaac agc           53

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gggtttcaag tctttgtagc aagag                                          25

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gccaatgaac gggaacccct ggtc                                           24

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(4)
<223> OTHER INFORMATION: a, c, t, g, unknown or other

<400> SEQUENCE: 72
nnnngacgag gcaatggctg aaatc                                          25
```

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)..(4)
<223> OTHER INFORMATION: a, c, t, g, unknown or other

<400> SEQUENCE: 73
nnnnttattt ggctcatatt tgctg                                25

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ctttacacca atcgctgcaa cagac                                25

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
caaaatttct agtcttcttt gcctttcccc ataaaaccct cctta           45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
agggttttat ggggaaaggc aaagaagact agaaattttg atacc           45

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cttacggtgc ataaagtcaa tttcc                                25

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
tggctcgatt tcagccattg c                                           21

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: a, c, t, g, unknown or other

<400> SEQUENCE: 79
ctttgacgag gcaatggctg aaatcgagcc aanaaagcgc aag                   43

<210> SEQ ID NO 80
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(34)
<223> OTHER INFORMATION: a, c, t, g, unknown or other

<400> SEQUENCE: 80
ctttgacgag gcaatggctg aaatcgagcc aaanaagcgc aag                   43

<210> SEQ ID NO 81
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(35)
<223> OTHER INFORMATION: a, c, t, g, unknown or other

<400> SEQUENCE: 81
ctttgacgag gcaatggctg aaatcgagcc aaaanagcgc aag                   43

<210> SEQ ID NO 82
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(36)
<223> OTHER INFORMATION: a, c, t, g, unknown or other

<400> SEQUENCE: 82
ctttgacgag gcaatggctg aaatcgagcc aaaaangcgc aag                   43

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence: Synthetic
      primer -continued

```
<220> FEATURE:
<221> NAME/KEY: modified_base
<222> LOCATION: (37)..(37)
<223> OTHER INFORMATION: a, c, t, g, unknown or other

<400> SEQUENCE: 83
ctttgacgag gcaatggctg aaatcgagcc aaaaaancgc aag                43

<210> SEQ ID NO 84
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(38)
<223> OTHER INFORMATION: a, c, t, g, unknown or other

<400> SEQUENCE: 84
ctttgacgag gcaatggctg aaatcgagcc aaaaaagngc aag                43

<210> SEQ ID NO 85
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (39)..(39)
<223> OTHER INFORMATION: a, c, t, g, unknown or other

<400> SEQUENCE: 85
ctttgacgag gcaatggctg aaatcgagcc aaaaaagcnc aagaag             46

<210> SEQ ID NO 86
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (40)..(40)
<223> OTHER INFORMATION: a, c, t, g, unknown or other

<400> SEQUENCE: 86
ctttgacgag gcaatggctg aaatcgagcc aaaaaagcgn aagaag             46

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(41)
<223> OTHER INFORMATION: a, c, t, g, unknown or other

<400> SEQUENCE: 87
ctttgacgag gcaatggctg aaatcgagcc aaaaaagcgc nagaag             46

<210> SEQ ID NO 88
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88 gcgcttttt ggctcgattt cag                                             23

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: a, c, t, g, unknown or other

<400> SEQUENCE: 89
caatggctga aatcgagcca aaaaagcgca ngaagaaatc                          40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(32)
<223> OTHER INFORMATION: a, c, t, g, unknown or other

<400> SEQUENCE: 90
caatggctga aatcgagcca aaaaagcgca anaagaaatc                          40

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: a, c, t, g, unknown or other

<400> SEQUENCE: 91
caatggctga aatcgagcca aaaaagcgca agnagaaatc                          40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(34)
<223> OTHER INFORMATION: a, c, t, g, unknown or other

<400> SEQUENCE: 92
caatggctga aatcgagcca aaaaagcgca agangaaatc                          40
```

```
<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(35)
<223> OTHER INFORMATION: a, c, t, g, unknown or other

<400> SEQUENCE: 93
caatggctga aatcgagcca aaaaagcgca agaanaaatc                                40

<210> SEQ ID NO 94
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(36)
<223> OTHER INFORMATION: a, c, t, g, unknown or other

<400> SEQUENCE: 94
caatggctga aatcgagcca aaaaagcgca agaagnaatc aacc                          44

<210> SEQ ID NO 95
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (37)..(37)
<223> OTHER INFORMATION: a, c, t, g, unknown or other

<400> SEQUENCE: 95
caatggctga aatcgagcca aaaaagcgca agaaganatc aacc                          44

<210> SEQ ID NO 96
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(38)
<223> OTHER INFORMATION: a, c, t, g, unknown or other

<400> SEQUENCE: 96
caatggctga aatcgagcca aaaaagcgca agaagaantc aacc                          44

<210> SEQ ID NO 97
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (39)..(39)
```

<223> OTHER INFORMATION: a, c, t, g, unknown or other

<400> SEQUENCE: 97
caatggctga aatcgagcca aaaaagcgca agaagaaanc aacc                    44

<210> SEQ ID NO 98
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (40)..(40)
<223> OTHER INFORMATION: a, c, t, g, unknown or other

<400> SEQUENCE: 98
caatggctga aatcgagcca aaaaagcgca agaagaaatn aaccagc                 47

<210> SEQ ID NO 99
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(41)
<223> OTHER INFORMATION: a, c, t, g, unknown or other

<400> SEQUENCE: 99
caatggctga aatcgagcca aaaaagcgca agaagaaatc naccagc                 47

<210> SEQ ID NO 100
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gatcctccat ccgtacaacc cacaaccctg g                                  31

<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aattccaggg ttgtgggttg tacggatgga g                                  31

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
catggatcct atttcttaat aactaaaaat atgg                               34

```
<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
catgaattca actcaacaag tctcagtgtg ctg                                  33

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
aaacattttt tctccattta ggaaaaagga tgctg                                35

<210> SEQ ID NO 105
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
aaaacagcat ccttttcct aaatggagaa aaaat                                 35

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
aaaccttaaa tcagtcacaa atagcagcaa aattg                                35

<210> SEQ ID NO 107
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
aaaacaattt tgctgctatt tgtgactgat ttaag                                35

<210> SEQ ID NO 108
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108 aaactttca tcatacgacc aatctgcttt atttg                                 35
```

```
<210> SEQ ID NO 109
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aaaacaaata aagcagattg gtcgtatgat gaaaa                                  35

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aaactcgtcc agaagttatc gtaaaagaaa tcgag                                  35

<210> SEQ ID NO 111
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aaaactcgat ttcttttacg ataacttctg gacga                                  35

<210> SEQ ID NO 112
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
aaacaatctc tccaaggttt ccttaaaaat ctctg                                  35

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aaaacagaga tttttaagga aaccttggag agatt                                  35

<210> SEQ ID NO 114
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
aaacgccatc gtcaggaaga agctatgctt gagtg                                  35

<210> SEQ ID NO 115
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaaacactca agcatagctt cttcctgacg atggc                              35

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aaacatctct atacttattg aaatttcttt gtatg                              35

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
aaaacataca aagaaatttc aataagtata gagat                              35

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aaactagctg tgatagtccg caaaaccagc cttcg                              35

<210> SEQ ID NO 119
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aaaacgaagg ctggttttgc ggactatcac agcta                              35

<210> SEQ ID NO 120
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
aaacatcgga aggtcgagca agtaattatc ttttg                              35

<210> SEQ ID NO 121
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aaaacaaaag ataattactt gctcgacctt ccgat                             35

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
aaacaagatg gtatcgcaaa gtaagtgaca ataag                             35

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
aaaacttatt gtcacttact ttgcgatacc atctt                             35

<210> SEQ ID NO 124
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gagacctttg agcttccgag actggtctca gttttgggac cattcaaaac ag          52

<210> SEQ ID NO 125
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgagaccagt ctcggaagct caaaggtctc gttttagagc tatgctgttt tg          52

<210> SEQ ID NO 126
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126 aaactactttt acgcagcgcg gagttcggtt ttttg                            35

<210> SEQ ID NO 127
<211> LENGTH: 35
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 127
aaaacaaaaa accgaactcc gcgctgcgta aagta        35

<210> SEQ ID NO 128
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
atgccggtac tgccgggcct cttgcgggat tacgaaatca tcctg        45

<210> SEQ ID NO 129
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
gtgactggcg atgctgtcgg aatggacgat cacactactc ttctt        45

<210> SEQ ID NO 130
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
ttaagaaata atcttcatct aaaatatact tcagtcacct cctagctgac        50

<210> SEQ ID NO 131
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
attgatttga gtcagctagg aggtgactga agtatatttt agatgaag        48

<210> SEQ ID NO 132
<211> LENGTH: 85
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
gagacctttg agcttccgag actggtctca gttttgggac cattcaaaac agcatagctc        60
taaaacctcg tagactattt ttgtc        85

<210> SEQ ID NO 133
<211> LENGTH: 84

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gagaccagtc tcggaagctc aaaggtctcg ttttagagct atgctgtttt gaatggtccc    60
aaaacttcag cacactgaga cttg                                           84

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agtcatccca gcaacaaatg g                                              21

<210> SEQ ID NO 135
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgtggtaaat cggataacgt tccaagtgaa g                                   31

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgctcttctt cacaaacaag gg                                             22

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
aagccaaagt ttggcaccac c                                              21

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gtagcttatt cagtcctagt gg                                             22

<210> SEQ ID NO 139
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cgtttgttga actaatgggt gcaaattacg aatcttctcc tgacg            45

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cgtcaggaga agattcgtaa tttgcaccca ttagttcaac aaacg            45

<210> SEQ ID NO 141
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gatattatgg agcctatttt tgtgggtttt taggcataaa actatatg         48

<210> SEQ ID NO 142
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
catatagttt tatgcctaaa aacccacaaa aataggctcc ataatatc         48

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
attatttctt aataactaaa aatatgg                                27

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cgtgtacaat tgctagcgta cggc                                   24

<210> SEQ ID NO 145
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gcaccggtga tcactagtcc tagg                                            24

<210> SEQ ID NO 146
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cctaggacta gtgatcaccg gtgcaaatat gagccaaata aatatat                   47

<210> SEQ ID NO 147
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gccgtacgct agcaattgta cacgtttgtt gaactaatgg gtgc                      44

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttcaaatttt cccatttgat tctcc                                           25

<210> SEQ ID NO 149
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ccatattttt agttattaag aaataatacc agccatcagt cacctcc                   47

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
agacgattca atagacaata agg                                             23

<210> SEQ ID NO 151
<211> LENGTH: 45
<212> TYPE: DNA
```

<210> SEQ ID NO 151
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
gttttgggac cattcaaaac agcatagctc taaaacctcg tagac          45

<210> SEQ ID NO 152
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gctatgctgt tttgaatggt cccaaaacca ttattttaac acacgaggtg     50

<210> SEQ ID NO 153
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
gctatgctgt tttgaatggt cccaaaacgc acccattagt tcaacaaacg     50

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
aattcttttc ttcatcatcg gtc                                  23

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
aagaaagaat gaagattgtt catg                                 24

<210> SEQ ID NO 156
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
ggtactaatc aaaatagtga ggagg                                25

<210> SEQ ID NO 157
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 157
gtttttcaaa atctgcggtt gcg                                              23

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
aaaaattgaa aaatggtgg aaacac                                            26

<210> SEQ ID NO 159
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
atttcgtaaa cggtatcggt ttcttttaaa gttttgggac cattcaaaac agc             53

<210> SEQ ID NO 160
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tttaaaagaa accgataccg tttacgaaat gttttagagc tatgctgttt tga             53

<210> SEQ ID NO 161
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
aaacggtatc ggtttctttt aaattcaatt gttttgggac cattcaaaac agc             53

<210> SEQ ID NO 162
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
aattgaattt aaagaaacc gataccgttt gttttagagc tatgctgttt tga              53

<210> SEQ ID NO 163
<211> LENGTH: 39
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 163
gttccttaaa ccaaaacggt atcggtttct tttaaattc                                39

<210> SEQ ID NO 164
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gaaaccgata ccgttttggt ttaaggaaca ggtaaagggc atttaac                       47

<210> SEQ ID NO 165
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
cgatttcagc cattgcctcg tc                                                  22

<210> SEQ ID NO 166
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(33)
<223> OTHER INFORMATION: a, c, t, g, unknown or other

<400> SEQUENCE: 166
gcctttgacg aggcaatggc tgaaatcgnn nnnaaaaagc gcaagaagaa atcaac            56

<210> SEQ ID NO 167
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tccgtacaac ccacaaccct gctagtgagc gttttgggac cattcaaaac agc               53

<210> SEQ ID NO 168
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gctcactagc agggttgtgg gttgtacgga gttttagagc tatgctgttt tga               53

<210> SEQ ID NO 169
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ttgttgccac tcttccttct ttc                                          23

<210> SEQ ID NO 170
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
cagggttgtg ggttgttgcg atggagttaa ctcccatctc c                      41

<210> SEQ ID NO 171
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gggagttaac tccatcgcaa caacccacaa ccctgctagt g                      41

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gtggtatcta tcgtgatgtg ac                                           22

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ttaccgaaac ggaatttatc tgc                                          23

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
aaagctagag ttccgcaatt gg                                           22

<210> SEQ ID NO 175
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 175
gtgggttgta cggattgagt taactcccat ctccttc                              37

<210> SEQ ID NO 176
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gatgggagtt aactcaatcc gtacaaccca caaccctg                             38

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gcttcaccta ttgcagcacc aattgaccac atgaagatag                           40

<210> SEQ ID NO 178
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtggtcaatt ggtgctgcaa taggtgaagc taatggtgat g                         41

<210> SEQ ID NO 179
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ctgatttgta ttaattttga gacattatgc ttcaccttc                            39

<210> SEQ ID NO 180
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gcataatgtc tcaaaattaa tacaaatcag tgaaatcatg                           40

<210> SEQ ID NO 181
<211> LENGTH: 52
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 181
gttttgggac cattcaaaac agcatagctc taaaacgtga cagtaatatc ag      52

<210> SEQ ID NO 182
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gttttagagc tatgctgttt tgaatggtcc caaaacgctc actagcaggg ttg     53

<210> SEQ ID NO 183
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
atactttacg cagcgcggag ttcggttttg taggagtggt agtatataca cgagtacat    59

<210> SEQ ID NO 184
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gctcactagc agggttgtgg gttgtacgga tgg      33

<210> SEQ ID NO 185
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tcctagcagg atttctgata ttactgtcac tgg      33

<210> SEQ ID NO 186
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tttaaaagaa accgataccg tttacgaaat tgg      33

<210> SEQ ID NO 187
<211> LENGTH: 84
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 187
ggaaccattc ataacagcat agcaagttat aataaggcta gtccgttatc aacttgaaaa    60
agtggcaccg agtcggtgct tttt                                          84

<210> SEQ ID NO 188
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gttatagagc tatgctgtta tgaatggtcc caaaac                             36

<210> SEQ ID NO 189
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ggaaccattc aatacagcat agcaagttaa tataaggcta gtccgttatc aacttgaaaa    60
agtggcaccg agtcggtgct tttt                                          84

<210> SEQ ID NO 190
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gtattagagc tatgctgtat tgaatggtcc caaaac                             36

<210> SEQ ID NO 191
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 191
nnnnnnnnnn nnnnnnnnnn gttttagagc tagaaatagc aagttaaaat aaggctagtc    60
cgttatcaac ttgaaaaagt ggcaccgagt cggtgctttt ttt                     103

<210> SEQ ID NO 192
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base

```
<222> LOCATION: (1)..(20)
<223> OTHER INFORMATION: a, c, t, g, unknown or other

<400> SEQUENCE: 192
nnnnnnnnnn nnnnnnnnnn gtattagagc tagaaatagc aagttaatat aaggctagtc      60
cgttatcaac ttgaaaaagt ggcaccgagt cggtgctttt ttt                       103

<210> SEQ ID NO 193
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 193
nnnnnnnnnn nnnnnnnnnn gttttagagc tatgctgttt tggaaacaaa acagcatagc      60
aagttaaaat aaggctagtc cgttatcaac ttgaaaaagt ggcaccgagt cggtgctttt    120
ttt                                                                  123

<210> SEQ ID NO 194
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 194
nnnnnnnnnn nnnnnnnnnn gtattagagc tatgctgtat tggaaacaat acagcatagc      60
aagttaatat aaggctagtc cgttatcaac ttgaaaaagt ggcaccgagt cggtgctttt    120
ttt                                                                  123

<210> SEQ ID NO 195
<211> LENGTH: 20
<212> TYPE: DNA
<213> ORGANISM: Homo sapiens

<400> SEQUENCE: 195
gtcacctcca atgactaggg                                                 20

<210> SEQ ID NO 196
<211> LENGTH: 4203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
atggccccaa agaagaagcg gaaggtcggt atccacggag tcccagcagc cgacaagaag      60
tacagcatcg gcctggacat cggcaccaac tctgtgggct gggccgtgat caccgacgag    120
tacaaggtgc ccagcaagaa attcaaggtg ctgggcaaca ccgaccggca gagcatcaag    180
aagaacctga tcggagccct gctgttcgac agcggcgaaa cagccgaggc cacccggctg    240
```

```
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacctg aaccccgaca cagcgacgt ggacaagctg    600 ttcatccagc tggtgcagac ctacaaccag ctgttcgagg aaaacccat caacgccagc    660 ggcgtggacg ccaaggccat cctgtctgcc agactgagca gagcagacg gctggaaaat    720 ctgatcgccc agctgcccgg cgagaagaag aatggcctgt tcggaaacct gattgccctg    780
agcctgggcc tgaccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gccccctga gcgcctctat gatcaagaga   1020
tacgacgagc accaccagga cctgaccctg ctgaaagctc tcgtgcggca gcagctgcct   1080
gagaagtaca agagattttt cttcgaccag agcaagaacg gctacgccgg ctacattgac   1140
ggcggagcca gccaggaaga gttctacaag ttcatcaagc catcctgga aaagatggac   1200 ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag attttttaccc attcctgaag gacaaccggg aaaagatcga aagatcctg   1380 accttccgca tccctactgc cgtgggccct ctggccaggg gaaacagcag attcgcctgg   1440
atgaccagaa agagcgagga aaccatcacc ccctggaact cgaggaagt ggtggacaag   1500 ggcgcttccg cccagagctt catcgagcgg atgaccaact cgataagaa cctgcccaac   1560 gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga agtgaccgt gaagcagctg   1740 aaagaggact acttcaagaa aatcgagtgc ttcgactccg tggaaatctc cggcgtggaa   1800
gatcggttca acgcctccct gggcacatac acgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg ctggggcag gctgagccgg   2040 aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgccatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
```

```
agctttctga aggacgactc catcgacaac aaggtgctga ccagaagcga caagaaccgg    2640
ggcaagagcg acaacgtgcc ctccgaagag gtcgtgaaga agatgaagaa ctactggcgg    2700
cagctgctga acgccaagct gattacccag agaaagttcg acaatctgac caaggccgag    2760
agaggcggcc tgagcgaact ggataaggcc ggcttcatca agagacagct ggtggaaacc    2820
cggcagatca caaagcacgt ggcacagatc ctggactccc ggatgaacac taagtacgac    2880
gagaatgaca agctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgacgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180
tttttcaaga ccgagattac cctggccaac ggcgagatcc ggaagcggcc tctgatcgag    3240
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata agctgatcgc cagaaagaag    3420
gactgggacc ctaagaagta cggcggcttc gacagcccca ccgtggccta ttctgtgctg    3480
gtggtggcca agtgtgaaaa gggcaagtcc aagaaactga agagtgtgaa agagctgctg    3540
gggatcacca tcatggaaag aagcagcttc gagaagaatc ccatcgactt tctggaagcc    3600
aagggctaca aagaagtgaa aaaggacctg atcatcaagc tgcctaagta ctccctgttc    3660
gagctggaaa acggccggaa gagaatgctg gcctctgccg cgaactgca aagggaaac    3720 gaactggccc tgcccctcca atatgtgaac ttcctgtacc tggccagcca ctatgagaag    3780
ctgaagggct ccccgagga taatgagcag aaacagctgt tgtggaaca gcacaagcac    3840 tacctggacg agatcatcga gcagatcagc gagttctcca agagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140 ctggaggcg acaaaaggcc ggcggccacg aaaaaggccg ccaggcaaa aaagaaaaag    4200 taa                                                                 4203

<210> SEQ ID NO 197
<211> LENGTH: 4200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
atggccccaa agaagaagcg gaaggtcggt atccacggag tcccagcagc cgacaagaag      60
tacagcatcg gcctggacat cggcaccaac tctgtgggct gggccgtgat caccgacgag     120
tacaaggtgc ccagcaagaa attcaaggtg ctgggcaaca ccgaccggca cagcatcaag     180
aagaacctga tcggagccct gctgttcgac agcggcgaaa cagccgaggc cacccggctg     240
aagagaaccg ccagaagaag atacaccaga cggaagaacc ggatctgcta tctgcaagag     300
atcttcagca acgagatggc caaggtggac gacagcttct tccacagact ggaagagtcc     360
```

| | |
|---|---|
| ttcctggtgg aagaggataa gaagcacgag cggcacccca tcttcggcaa catcgtggac | 420 |
| gaggtggcct accacgagaa gtaccccacc atctaccacc tgagaaagaa actggtggac | 480 |
| agcaccgaca aggccgacct gcggctgatc tatctggccc tggcccacat gatcaagttc | 540 |
| cggggccact tcctgatcga gggcgacctg aaccccgaca cagcgacgt ggacaagctg | 600 |
| ttcatccagc tggtgcagac ctacaaccag ctgttcgagg aaaaccccat caacgccagc | 660 |
| ggcgtggacg ccaaggccat cctgtctgcc agactgagca gagcagacg gctgaaaat | 720 |
| ctgatcgccc agctgcccgg cgagaagaag aatggcctgt cggaaacct gattgccctg | 780 |
| agcctgggcc tgaccccaa cttcaagagc aacttcgacc tggccgagga tgccaaactg | 840 |
| cagctgagca aggacaccta cgacgacgac ctggacaacc tgctggccca gatcggcgac | 900 |
| cagtacgccg acctgtttct ggccgccaag aacctgtccg acgccatcct gctgagcgac | 960 |
| atcctgagag tgaacaccga gatcaccaag gcccccctga gcgcctctat gatcaagaga | 1020 |
| tacgacgagc accaccagga cctgaccctg ctgaaagctc tcgtgcggca gcagctgcct | 1080 |
| gagaagtaca agagattttt cttcgaccag agcaagaacg gctacgccgg ctacattgac | 1140 |
| ggcggagcca gccaggaaga gttctacaag ttcatcaagc ccatcctgga aaagatggac | 1200 |
| ggcaccgagg aactgctcgt gaagctgaac agagaggacc tgctgcgaa gcagcggacc | 1260 |
| ttcgacaacg gcagcatccc ccaccagatc cacctgggag agctgcacgc cattctgcgg | 1320 |
| cggcaggaag atttttaccc attcctgaag gacaaccggg aaaagatcga agatcctg | 1380 |
| accttccgca tcccctacta cgtgggccct ctggccaggg aaacagcag attcgcctgg | 1440 |
| atgaccagaa agagcgagga aaccatcacc ccctggaact tcgaggaagt ggtggacaag | 1500 |
| ggcgcttccg cccagagctt catcgagcgg atgaccaact tcgataagaa cctgcccaac | 1560 |
| gagaaggtgc tgcccaagca cagcctgctg tacgagtact tcaccgtgta taacgagctg | 1620 |
| accaaagtga aatacgtgac cgagggaatg agaaagcccg ccttcctgag cggcgagcag | 1680 |
| aaaaaggcca tcgtggacct gctgttcaag accaaccgga agtgaccgt gaagcagctg | 1740 |
| aaagaggact acttcaagaa aatcgagtgc ttcgactccg tggaaatctc cggcgtggaa | 1800 |
| gatcggttca acgcctccct gggcacatac cacgatctgc tgaaaattat caaggacaag | 1860 |
| gacttcctgg acaatgagga aaacgaggac attctggaag atatcgtgct gaccctgaca | 1920 |
| ctgtttgagg acagagagat gatcgaggaa cggctgaaaa cctatgccca cctgttcgac | 1980 |
| gacaaagtga tgaagcagct gaagcggcgg agatacaccg gctggggcag gctgagccgg | 2040 |
| aagctgatca acggcatccg ggacaagcag tccggcaaga caatcctgga tttcctgaag | 2100 |
| tccgacggct tcgccaacag aaacttcatg cagctgatcc acgacgacag cctgaccttt | 2160 |
| aaagaggaca tccagaaagc ccaggtgtcc ggccagggcg atagcctgca cgagcacatt | 2220 |
| gccaatctgg ccggcagccc cgccattaag aagggcatcc tgcagacagt gaaggtggtg | 2280 |
| gacgagctcg tgaaagtgat gggccggcac aagcccgaga acatcgtgat cgaaatggcc | 2340 |
| agagagaacc agaccaccca gaagggacag aagaacagcc gcgagagaat gaagcggatc | 2400 |
| gaagagggca tcaaagagct gggcagccag atcctgaaag aacaccccgt ggaaaacacc | 2460 |
| cagctgcaga acgagaagct gtacctgtac tacctgcaga atgggcggga tatgtacgtg | 2520 |
| gaccaggaac tggacatcaa ccggctgtcc gactacgatg tggaccatat cgtgcctcag | 2580 |
| agctttctga aggacgactc catcgacaac aaggtgctga ccagaagcga caagaaccgg | 2640 |
| ggcaagagca caacgtgcc ctccgaagag gtcgtgaaga gatgaagaa ctactggcgg | 2700 |
| cagctgctga acgccaagct gattacccag agaaagttcg acaatctgac caaggccgag | 2760 |

```
agaggcggcc tgagcgaact ggataaggcc ggcttcatca agagacagct ggtggaaacc    2820
cggcagatca caaagcacgt ggcacagatc ctggactccc ggatgaacac taagtacgac    2880
gagaatgaca agctgatccg ggaagtgaaa gtgatcaccc tgaagtccaa gctggtgtcc    2940
gatttccgga aggatttcca gttttacaaa gtgcgcgaga tcaacaacta ccaccacgcc    3000
cacgccgcct acctgaacgc cgtcgtggga accgccctga tcaaaaagta ccctaagctg    3060
gaaagcgagt tcgtgtacgg cgactacaag gtgtacgacg tgcggaagat gatcgccaag    3120
agcgagcagg aaatcggcaa ggctaccgcc aagtacttct tctacagcaa catcatgaac    3180
tttttcaaga ccgagattac cctggccaac ggcgagatcc ggaagcggcc tctgatcgag    3240
acaaacggcg aaaccgggga gatcgtgtgg gataagggcc gggattttgc caccgtgcgg    3300
aaagtgctga gcatgcccca agtgaatatc gtgaaaaaga ccgaggtgca gacaggcggc    3360
ttcagcaaag agtctatcct gcccaagagg aacagcgata agctgatcgc cagaaagaag    3420
gactgggacc ctaagaagta cggcggcttc gacagcccca ccgtggccta ttctgtgctg    3480
gtggtggcca agtggaaaaa gggcaagtcc aagaaactga gagtgtgaa agagctgctg    3540
gggatcacca tcatggaaag aagcagcttc gagaagaatc ccatcgactt tctggaagcc    3600
aagggctaca agaagtgaa aaaggacctg atcatcaagc tgcctaagta ctccctgttc    3660
gagctggaaa acggccggaa gagaatgctg gcctctgccg cgaactgca aagggaaac    3720
gaactggccc tgcctccaa atatgtgaac ttcctgtacc tggccagcca ctatgagaag    3780
ctgaagggct cccccgagga taatgagcag aaacagctgt ttgtggaaca gcacaagcac    3840
tacctggacg agatcatcga gcagatcagc gagttctcca gagagtgat cctggccgac    3900
gctaatctgg acaaagtgct gtccgcctac aacaagcacc gggataagcc catcagagag    3960
caggccgaga atatcatcca cctgtttacc ctgaccaatc tgggagcccc tgccgccttc    4020
aagtactttg acaccaccat cgaccggaag aggtacacca gcaccaaaga ggtgctggac    4080
gccaccctga tccaccagag catcaccggc ctgtacgaga cacggatcga cctgtctcag    4140
ctggaggcg acaaaaggcc ggcggccacg aaaaaggccg ccaggcaaa aaagaaaaag    4200
```

<210> SEQ ID NO 198
<211> LENGTH: 23
<212> TYPE: DNA
<213> ORGANISM: Homo sapiens

<400> SEQUENCE: 198
gacatcgatg tcctccccat tgg                                              23

<210> SEQ ID NO 199
<211> LENGTH: 23
<212> TYPE: DNA
<213> ORGANISM: Homo sapiens

<400> SEQUENCE: 199
gagtccgagc agaagaagaa ggg                                              23

<210> SEQ ID NO 200
<211> LENGTH: 23
<212> TYPE: DNA
<213> ORGANISM: Homo sapiens

<400> SEQUENCE: 200
gcgccaccgg ttgatgtgat ggg                                              23

```
<210> SEQ ID NO 201
<211> LENGTH: 23
<212> TYPE: DNA
<213> ORGANISM: Homo sapiens

<400> SEQUENCE: 201
ggggcacaga tgagaaactc agg                                          23

<210> SEQ ID NO 202
<211> LENGTH: 23
<212> TYPE: DNA
<213> ORGANISM: Homo sapiens

<400> SEQUENCE: 202
gtacaaacgg cagaagctgg agg                                          23

<210> SEQ ID NO 203
<211> LENGTH: 23
<212> TYPE: DNA
<213> ORGANISM: Homo sapiens

<400> SEQUENCE: 203
ggcagaagct ggaggaggaa ggg                                          23

<210> SEQ ID NO 204
<211> LENGTH: 23
<212> TYPE: DNA
<213> ORGANISM: Homo sapiens

<400> SEQUENCE: 204
ggagcccttc ttcttctgct cgg                                          23

<210> SEQ ID NO 205
<211> LENGTH: 23
<212> TYPE: DNA
<213> ORGANISM: Homo sapiens

<400> SEQUENCE: 205
gggcaaccac aaacccacga ggg                                          23

<210> SEQ ID NO 206
<211> LENGTH: 23
<212> TYPE: DNA
<213> ORGANISM: Homo sapiens

<400> SEQUENCE: 206
gctcccatca catcaaccgg tgg                                          23

<210> SEQ ID NO 207
<211> LENGTH: 23
<212> TYPE: DNA
<213> ORGANISM: Homo sapiens

<400> SEQUENCE: 207
gtggcgcatt gccacgaagc agg                                          23

<210> SEQ ID NO 208
<211> LENGTH: 23
<212> TYPE: DNA
<213> ORGANISM: Homo sapiens

<400> SEQUENCE: 208
ggcagagtgc tgcttgctgc tgg                                          23
```

<210> SEQ ID NO 209
<211> LENGTH: 23
<212> TYPE: DNA
<213> ORGANISM: Homo sapiens

<400> SEQUENCE: 209
gcccctgcgt gggcccaagc tgg                                              23

<210> SEQ ID NO 210
<211> LENGTH: 23
<212> TYPE: DNA
<213> ORGANISM: Homo sapiens

<400> SEQUENCE: 210
gagtggccag agtccagctt ggg                                              23

<210> SEQ ID NO 211
<211> LENGTH: 23
<212> TYPE: DNA
<213> ORGANISM: Homo sapiens

<400> SEQUENCE: 211
ggcctcccca aagcctggcc agg                                              23

<210> SEQ ID NO 212
<211> LENGTH: 23
<212> TYPE: DNA
<213> ORGANISM: Homo sapiens

<400> SEQUENCE: 212
ggggccgaga ttgggtgttc agg                                              23

<210> SEQ ID NO 213
<211> LENGTH: 23
<212> TYPE: DNA
<213> ORGANISM: Homo sapiens

<400> SEQUENCE: 213
gtggcgagag gggccgagat tgg                                              23

<210> SEQ ID NO 214
<211> LENGTH: 23
<212> TYPE: DNA
<213> ORGANISM: Homo sapiens

<400> SEQUENCE: 214
gagtgccgcc gaggcggggc ggg                                              23

<210> SEQ ID NO 215
<211> LENGTH: 23
<212> TYPE: DNA
<213> ORGANISM: Homo sapiens

<400> SEQUENCE: 215
ggagtgccgc cgaggcgggg cgg                                              23

<210> SEQ ID NO 216
<211> LENGTH: 23
<212> TYPE: DNA
<213> ORGANISM: Homo sapiens

<400> SEQUENCE: 216

```
ggagaggagt gccgccgagg cgg                                          23
```

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217

```
ccatcccctt ctgtgaatgt                                              20
```

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218

```
ggagattgga gacacggaga                                              20
```

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219

```
aagcaccgac tcggtgccac                                              20
```

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220

```
tcacctccaa tgactagggg                                              20
```

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221

```
caagttgata acggactagc ct                                           22
```

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222

```
agtccgagca gaagaagaag ttt                                          23
```

<210> SEQ ID NO 223
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
tttcaagttg ataacggact agcct                                          25

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
aaacagcaga ttcgcctgga                                                20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tcatccgctc gatgaagctc                                                20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
tccaaaatca agtggggcga                                                20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tgatgaccct tttggctccc                                                20

<210> SEQ ID NO 228
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
gaggaattct tttttgtty gaatatgttg gaggtttttt ggaag                     45

```
<210> SEQ ID NO 229
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gagaagctta aataaaaaac racaatactc aacccaacaa cc                          42

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
caggaaacag ctatgac                                                      17

<210> SEQ ID NO 231
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gcctctagag gtacctgagg gcctatttcc catgattcc                              39

<210> SEQ ID NO 232
<211> LENGTH: 133
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (92)..(111)
<223> OTHER INFORMATION: a, c, t, g, unknown or other

<400> SEQUENCE: 232
acctctagaa aaaagcacc gactcggtgc cacttttca agttgataac ggactagcct         60
tattttaact tgctatttct agctctaaaa cnnnnnnnnn nnnnnnnnnn nggtgtttcg       120
tcctttccac aag                                                         133

<210> SEQ ID NO 233
<211> LENGTH: 133
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (92)..(111)
<223> OTHER INFORMATION: a, c, t, g, unknown or other

<400> SEQUENCE: 233
acctctagaa aaaagcacc gactcggtgc cacttttca agttgataac ggactagcct         60
tatattaact tgctatttct agctctaata cnnnnnnnnn nnnnnnnnnn nggtgtttcg       120
```
tcctttccac aag                                                          133

<210> SEQ ID NO 234
<211> LENGTH: 153
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (112)..(131)
<223> OTHER INFORMATION: a, c, t, g, unknown or other

<400> SEQUENCE: 234
acctctagaa aaaagcacc gactcggtgc cacttttca agttgataac ggactagcct       60
tattttaact tgctatgctg ttttgtttcc aaaacagcat agctctaaaa cnnnnnnnnn    120
nnnnnnnnnn nggtgtttcg tcctttccac aag                                 153

<210> SEQ ID NO 235
<211> LENGTH: 153
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (112)..(131)
<223> OTHER INFORMATION: a, c, t, g, unknown or other

<400> SEQUENCE: 235
acctctagaa aaaagcacc gactcggtgc cacttttca agttgataac ggactagcct       60
tatattaact tgctatgctg tattgtttcc aatacagcat agctctaata cnnnnnnnnn    120
nnnnnnnnnn nggtgtttcg tcctttccac aag                                 153

<210> SEQ ID NO 236
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 236
aggccccagt ggctgctctn aa                                                22

<210> SEQ ID NO 237
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 237
acatcaaccg gtggcgcatn at                                                22

<210> SEQ ID NO 238
<211> LENGTH: 22
<212> TYPE: DNA
<213> ORGANISM: Homo sapiens
<220> FEATURE:
<221> NAME/KEY: modified_base

```
<222> LOCATION: (20)..(20)
<223> OTHER INFORMATION: a, c, t, g, unknown or other

<400> SEQUENCE: 238
aaggtgtggt tccagaaccn ac                                            22

<210> SEQ ID NO 239
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 239
ccatcacatc aaccggtggn ag                                            22

<210> SEQ ID NO 240
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 240
aaacggcaga agctggaggn ta                                            22

<210> SEQ ID NO 241
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 241
ggcagaagct ggaggaggan tt                                            22

<210> SEQ ID NO 242
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 242
ggtgtggttc cagaaccggn tc                                            22

<210> SEQ ID NO 243
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 243
aaccggagga caaagtacan tg                                            22

<210> SEQ ID NO 244
```

```
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 244
ttccagaacc ggaggacaan ca                                              22

<210> SEQ ID NO 245
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 245
gtgtggttcc agaaccggan ct                                              22

<210> SEQ ID NO 246
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 246
tccagaaccg gaggacaaan cc                                              22

<210> SEQ ID NO 247
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 247
cagaagctgg aggaggaagn cg                                              22

<210> SEQ ID NO 248
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 248
catcaaccgg tggcgcattn ga                                              22

<210> SEQ ID NO 249
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 249
```
gcagaagctg gaggaggaan gt                                              22

<210> SEQ ID NO 250
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 250
cctccctccc tggcccaggn gc                                              22

<210> SEQ ID NO 251
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 251
tcatctgtgc ccctccctcn aa                                              22

<210> SEQ ID NO 252
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 252
gggaggacat cgatgtcacn at                                              22

<210> SEQ ID NO 253
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 253
caaacggcag aagctggagn ac                                              22

<210> SEQ ID NO 254
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 254
gggtgggcaa ccacaaaccn ag                                              22

<210> SEQ ID NO 255
<211> LENGTH: 22
<212> TYPE: DNA
<213> ORGANISM: Homo sapiens
<220> FEATURE:

```
<221> NAME/KEY: modified_base
<222> LOCATION: (20)..(20)
<223> OTHER INFORMATION: a, c, t, g, unknown or other

<400> SEQUENCE: 255
ggtgggcaac cacaaacccn ta                                              22

<210> SEQ ID NO 256
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 256
ggctcccatc acatcaaccn tt                                              22

<210> SEQ ID NO 257
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 257
gaagggcctg agtccgagcn tc                                              22

<210> SEQ ID NO 258
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 258
caaccggtgg cgcattgccn tg                                              22

<210> SEQ ID NO 259
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 259
aggaggaagg gcctgagtcn ca                                              22

<210> SEQ ID NO 260
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 260
agctggagga ggaagggccn ct                                              22
```

```
<210> SEQ ID NO 261
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 261
gcattgccac gaagcaggcn cc                                                    22

<210> SEQ ID NO 262
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 262
attgccacga agcaggccan cg                                                    22

<210> SEQ ID NO 263
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 263
agaaccggag gacaaagtan ga                                                    22

<210> SEQ ID NO 264
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 264
tcaaccggtg gcgcattgcn gt                                                    22

<210> SEQ ID NO 265
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 265
gaagctggag gaggaagggn gc                                                    22

<210> SEQ ID NO 266
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266
```

```
ccaatgggga ggacatcgat gtcacctcca atgactaggg tgggcaacca caaacccacg    60
agggcagagt gctgcttgct gctggccagg cccctgcgtg gcccaagct ggactctggc    120 cac                                                                  123
```

<210> SEQ ID NO 267
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267

```
cgagcagaag aagaagggct cccatcacat caaccggtgg cgcattgcca cgaagcaggc    60
caatggggag acatcgatg tcacctccaa tgactagggg gggcaaccac aaacccacga    120
g                                                                    121
```

<210> SEQ ID NO 268
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 268

```
ggaggacaaa gtacaaacgg cagaagctgg aggaggaagg gcctgagtcc gagcagaaga    60
agaagggctc ccatcacatc aaccggtggc gcattgccac gaagcaggcc aatggggagg    120
acatcgat                                                             128
```

<210> SEQ ID NO 269
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

```
agaagctgga ggaggaaggg cctgagtccg agcagaagaa gaagggctcc catcacatca    60
accggtggcg cattgccacg aagcaggcca atggggagga catcgatgtc acctccaatg    120
actagggtgg                                                           130
```

<210> SEQ ID NO 270
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270

```
cctcagtctt cccatcaggc tctcagctca gcctgagtgt tgaggcccca gtggctgctc    60
tgggggcctc ctgagtttct catctgtgcc cctccctccc tggcccaggt gaaggtgtgg    120
ttcca                                                                125
```

<210> SEQ ID NO 271
<211> LENGTH: 129
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 271

```
tcatctgtgc ccctccctcc ctggcccagg tgaaggtgtg gttccagaac cggaggacaa    60
agtacaaacg gcagaagctg gaggaggaag ggcctgagtc cgagcagaag aagaagggct   120
cccatcaca                                                           129
```

<210> SEQ ID NO 272
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 272

```
ctccaatgac tagggtgggc aaccacaaac ccacgagggc agagtgctgc ttgctgctgg    60
ccaggcccct gcgtgggccc aagctggact ctggccactc cctggccagg ctttggggag   120
gcctggagt                                                           129
```

<210> SEQ ID NO 273
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 273

```
ctgcttgctg ctggccaggc ccctgcgtgg gcccaagctg gactctggcc actccctggc    60
caggctttgg ggaggcctgg agtcatggcc ccacagggct tgaagcccgg ggccgccatt   120
gacagag                                                             127
```

<210> SEQ ID NO 274
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 274

```
gaaattaata cgactcacta taggg                                          25
```

<210> SEQ ID NO 275
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 275

```
aaaaaagcac cgactcggtg ccacttttc aagttgataa cggactagcc ttattttaac    60
ttgctatttc tagctctaaa acaacgacga gcgtgacacc ccctatagt gagtcgtatt   120
aatttc                                                              126
```

<210> SEQ ID NO 276

```
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
aaaaaagcac cgactcggtg ccactttttc aagttgataa cggactagcc ttattttaac    60
ttgctatttc tagctctaaa acgcaacaat taatagactg gacctatagt gagtcgtatt   120
aatttc                                                              126

<210> SEQ ID NO 277
<211> LENGTH: 4677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
tctttcttgc gctatgacac ttccagcaaa aggtagggcg gctgcgaga cggcttcccg      60 gcgctgcatg caacaccgat gatgcttcga ccccccgaag ctccttcggg gctgcatggg   120
cgctccgatg ccgctccagg gcgagcgctg tttaaatagc caggccccg attgcaaaga   180 cattatagcg agctaccaaa gccatattca aacacctaga tcactaccac ttctacacag   240
gccactcgag cttgtgatcg cactccgcta aggggcgcc tcttcctctt cgtttcagtc    300
acaacccgca aacatgtacc catacgatgt tccagattac gcttcgccga agaaaaagcg   360
caaggtcgaa gcgtccgaca agaagtacag catcggcctg gacatcggca ccaactctgt   420
gggctgggcc gtgatcaccg acgagtacaa ggtgcccagc aagaaattca aggtgctggg   480
caacaccgac cggcacagca tcaagaagaa cctgatcgga gccctgctgt tcgacagcgg   540
cgaaacagcc gaggccaccc ggctgaagag aaccgccaga agaagataca ccagacggaa   600
gaaccggatc tgctatctgc aagagatctt cagcaacgag atggccaagg tggacgacag   660
cttcttccac agactggaag agtccttcct ggtggaagag gataagaagc acgagcggca   720
ccccatcttc ggcaacatcg tggacgaggt ggcctaccac gagaagtacc ccaccatcta   780
ccacctgaga aagaaactgg tggacagcac cgacaaggcc gacctgcggc tgatctatct   840
ggccctggcc cacatgatca agttccgggg ccacttcctg atcgagggcg acctgaaccc   900
cgacaacagc gacgtggaca gctgttcat ccagctggtg cagacctaca accagctgtt   960
cgaggaaaac cccatcaacg ccagcggcgt ggacgccaag gccatcctgt ctgccagact  1020
gagcaagagc agacggctgg aaaatctgat cgcccagctg cccggcgaga agaagaatgg  1080
cctgttcggc aacctgattg ccctgagcct gggcctgacc cccaacttca gagcaacttt  1140
cgacctggcc gaggatgcca aactgcagct gagcaaggac acctacgacg acgacctgga  1200
caacctgctg gcccagatcg cgaccagta cgccgacctg tttctggccg ccaagaacct  1260
gtccgacgcc atcctgctga gcgacatcct gagagtgaac accgagatca ccaaggcccc  1320
cctgagcgcg tctatgatca agagatacga cgagcaccac caggacctga ccctgctgaa  1380
agctctcgtg cggcagcagc tgcctgagaa gtacaaagag attttcttcg accagagcaa  1440
gaacggctac gccggctaca ttgacggcgg agccagccag gaagagttct acaagttcat  1500
caagcccatc ctggaaaaga tggacggcac cgaggaactg ctcgtgaagc tgaacagaga  1560
ggacctgctg cggaagcagc ggaccttcga caacggcagc atcccccacc agatccacct  1620
```

```
gggagagctg cacgccattc tgcggcggca ggaagatttt tacccattcc tgaaggacaa   1680
ccgggaaaag atcgagaaga tcctgacctt ccgcatcccc tactacgtgg ccctctggc    1740 caggggaaac agcagattcg cctggatgac cagaaagagc gaggaaacca tcacccctg    1800 gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg gaatgagaaa   1980
gccccgcctt ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca cataccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca gcagtccgg    2400 caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agcccggcca ttaagaaggg   2580
catcctgcag acagtgaagg tggtggacga gctcgtgaaa gtgatgggcc ggcacaagcc   2640
cgagaacatc gtgatcgaaa tggccagaga gaaccagacc acccgaagg acagaagaa    2700 cagccgcgag agaatgaagc ggatcgaaga gggcatcaaa gagctgggca gccagatcct   2760
gaaagaacac cccgtggaaa cacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccggatg aacactaagt acgacgagaa tgacaagctg atccgggaag tgaaagtgat   3240 cacccctgaag tccaagctgg tgtccgattt ccggaaggat ttccagtttt acaaagtgcg   3300
cgagatcaac aactaccacc acgcccacga cgcctacctg aacgccgtcg tgggaaccgc   3360
cctgatcaaa aagtacccta agctggaaag cgagttcgtg tacggcgact acaaggtgta   3420
cgacgtgcgc aagatgatcg ccaagagcga gcaggaaatc ggcaaggcta ccgccaagta   3480
cttcttctac agcaacatca tgaactttt caagaccgag attaccctgg ccaacggcga   3540
gatccggaag cggcctctga tcgagacaaa cggcgaaacc ggggagatcg tgtgggataa   3600
gggccgggat tttgccaccg tgcggaaagt gctgagcatg ccccaagtga atatcgtgaa   3660
aaagaccgag gtgcagacag gcggcttcag caaagagtct atcctgcccaa agaggaacag   3720 cgataagctg atcgccagaa agaaggactg ggaccctaag aagtacgccg gcttcgacag   3780
ccccaccgtg gcctattctg tgctggtggt ggccaaagtg gaaagggca agtccaagaa   3840 actgaagagt gtgaaagagc tgctggggat caccatcatg gaaagaagca gcttcgagaa   3900
gaatcccatc gactttctgg aagccaaggg ctacaaagaa gtgaaaaagg acctgatcat   3960
```

| | |
|---|---|
| caagctgcct aagtactccc tgttcgagct ggaaaacggc cggaagagaa tgctggcctc | 4020 |
| tgccggcgaa ctgcagaagg gaaacgaact ggccctgccc tccaaatatg tgaacttcct | 4080 |
| gtacctggcc agccactatg agaagctgaa gggctccccc gaggataatg agcagaaaca | 4140 |
| gctgtttgtg aacagcacac agcactacct ggacagagatc atcgagcaga tcagcgagtt | 4200 |
| ctccaagaga gtgatcctgg ccgacgctaa tctggacaaa gtgctgtccg cctacaacaa | 4260 |
| gcaccgggat aagcccatca gagagcaggc cgagaatatc atccacctgt ttaccctgac | 4320 |
| caatctggga gcccctgccg ccttcaagta ctttgacacc accatcgacc ggaagaggta | 4380 |
| caccagcacc aaagaggtgc tggacgccac cctgatccac cagagcatca ccggcctgta | 4440 |
| cgagacacgg atcgacctgt ctcagctggg aggcgacagc cccaagaaga agagaaaggt | 4500 |
| ggaggccagc taaggatccg gcaagactgg ccccgcttgg caacgcaaca gtgagcccct | 4560 |
| ccctagtgtg tttggggatg tgactatgta ttcgtgtgtt ggccaacggg tcaacccgaa | 4620 |
| cagattgata cccgccttgg catttcctgt cagaatgtaa cgtcagttga tggtact | 4677 |

<210> SEQ ID NO 278
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278

| | |
|---|---|
| tctttcttgc gctatgacac ttccagcaaa aggtagggcg ggctgcgaga cggcttcccg | 60 |
| gcgctgcatg caacaccgat gatgcttcga cccccccgaag ctccttcggg gctgcatggg | 120 |
| cgctccgatg ccgctccagg gcgagcgctg tttaaatagc caggccccg attgcaaaga | 180 |
| cattatagcg agctaccaaa gccatattca aacacctaga tcactaccac ttctacacag | 240 |
| gccactcgag cttgtgatcg cactccgcta aggggggcgcc tcttcctctt cgtttcagtc | 300 |
| acaacccgca aacatgccta agaagaagag gaaggttaac acgattaaca tcgctaagaa | 360 |
| cgacttctct gacatcgaac tggctgctat cccgttcaac actctggctg accattacgg | 420 |
| tgagcgttta gctcgcgaac agttggccct tgagcatgag tcttacgaga tgggtgaagc | 480 |
| acgcttccgc aagatgtttg agcgtcaact aaagctggt gaggttgcgg ataacgctgc | 540 |
| cgccaagcct ctcatcacta ccctactccc taagatgatt gcacgcatca acgactggtt | 600 |
| tgaggaagtg aaagctaagc gcggcaagcg cccgacagcc ttccagttcc tgcaagaaat | 660 |
| caagccggaa gccgtagcgt acatcaccat taagaccact ctggcttgcc taaccagtgc | 720 |
| tgacaataca accgttcagg ctgtagcaag cgcaatcggt cgggccattg aggacgaggc | 780 |
| tcgcttcggt cgtatccgtg accttgaagc taagcacttc aagaaaaacg ttgaggaaca | 840 |
| actcaacaag cgcgtagggc acgtctacaa gaaagcattt atgcaagttg tcgaggctga | 900 |
| catgctctct aagggtctac tcggtggcga ggcgtggtct tcgtggcata aggaagactc | 960 |
| tattcatgta ggagtacgct gcatcgagat gctcattgag tcaaccggaa tggttagctt | 1020 |
| acaccgccaa aatgctggcg tagtaggtca agactctgag actatcgaac tcgcacctga | 1080 |
| atacgctgag gctatcgcaa cccgtgcagg tgcgctggct ggcatctctc cgatgttcca | 1140 |
| accttgcgta gttcctccta agccgtggac tggcattact ggtggtggct attgggctaa | 1200 |
| cggtcgtcgt cctctggcgc tggtgcgtac tcacagtaag aaaagcactga tgcgctacga | 1260 |
| agacgtttac atgcctgagg tgtacaaagc gattaacatt gcgcaaaaca ccgcatggaa | 1320 |

```
aatcaacaag aaagtcctag cggtcgccaa cgtaatcacc aagtggaagc attgtccggt    1380
cgaggacatc cctgcgattg agcgtgaaga actcccgatg aaaccggaag acatcgacat    1440
gaatcctgag gctctcaccg cgtggaaacg tgctgccgct gctgtgtacc gcaaggacaa    1500
ggctcgcaag tctcgccgta tcagccttga gttcatgctt gagcaagcca ataagtttgc    1560
taaccataag gccatctggt tcccttacaa catggactgg cgcggtcgtg tttacgctgt    1620
gtcaatgttc aacccgcaag gtaacgatat gaccaaagga ctgcttacgc tggcgaaagg    1680
taaaccaatc ggtaaggaag ttactactg gctgaaaatc cacggtgcaa actgtgcggg    1740
tgtcgacaag gttccgttcc ctgagcgcat caagttcatt gaggaaaacc acgagaacat    1800
catggcttgc gctaagtctc cactggagaa cacttggtgg gctgagcaag attctccgtt    1860
ctgcttcctt gcgttctgct ttgagtacgc tggggtacag caccacggcc tgagctataa    1920
ctgctcccctt ccgctggcgt ttgacgggtc ttgctctggc atccagcact tctccgcgat    1980
gctccgagat gaggtaggtg gtcgcgcggt taacttgctt cctagtgaaa ccgttcagga    2040
catctacggg attgttgcta agaaagtcaa cgagattcta caagcagacg caatcaatgg    2100
gaccgataac gaagtagtta ccgtgaccga tgagaacact ggtgaaatct ctgaaaaagt    2160
caagctgggc actaaggcac tggctggtca atggctggct tacggtgtta ctcgcagtgt    2220
gactaagcgt tcagtcatga cgctggctta cgggtccaaa gagttcggct tccgtcaaca    2280
agtgctggaa gataccattc agccagctat tgattccggc aagggtctga tgttcactca    2340
gccgaatcag gctgctggat acatggctaa gctgatttgg gaatctgtga gcgtgacggt    2400
ggtagctgcg gttgaagcaa tgaactggct taagtctgct gctaagctgc tggctgctga    2460
ggtcaaagat aagaagactg gagagattct tcgcaagcgt tgcgctgtgc attgggtaac    2520
tcctgatggt ttccctgtgt ggcaggaata caagaagcct attcagacgc gcttgaacct    2580
gatgttcctc ggtcagttcc gcttacagcc taccattaac accaacaaag atagcgagat    2640
tgatgcacac aaacaggagt ctggtatcgc tcctaacttt gtacacagcc aagacggtag    2700
ccaccttcgt aagactgtag tgtgggcaca cgagaagtac ggaatcgaat cttttgcact    2760
gattcacgac tccttcggta cgattccggc tgacgctgcg aacctgttca agcagtgcg    2820
cgaaactatg gttgacacat atgagtcttg tgatgtactg gctgatttct acgaccagtt    2880
cgctgaccag ttgcacgagt ctcaattgga caaaatgcca gcacttccgg ctaaaggtaa    2940
cttgaacctc cgtgacatct tagagtcgga cttcgcgttc gcgtaaggat ccggcaagac    3000
tggcccccgct tggcaacgca acagtgagcc cctcccctagt gtgtttgggg atgtgactat    3060
gtattcgtgt gttggccaac gggtcaaccc gaacagattg atacccgcct tggcatttcc    3120
tgtcagaatg taacgtcagt tgatggtact                                     3150
```

<210> SEQ ID NO 279
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(42)
<223> OTHER INFORMATION: a, c, t, g, unknown or other

<400> SEQUENCE: 279
gaaattaata cgactcacta tannnnnnnn nnnnnnnnnn nngttttaga gctagaaata      60

```
gcaagttaaa ataaggctag tccgttatca acttgaaaaa gtggcaccga gtcggtgctt      120
ttttt                                                                  125

<210> SEQ ID NO 280
<211> LENGTH: 8452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
tgcggtattt cacaccgcat caggtggcac ttttcgggga aatgtgcgcg gaacccctat       60
ttgtttattt ttctaaatac attcaaatat gtatccgctc atgagattat caaaaaggat      120
cttcacctag atccttttaa attaaaaatg aagttttaaa tcaatctaaa gtatatatga      180
gtaaacttgg tctgacagtt accaatgctt aatcagtgag gcacctatct cagcgatctg      240
tctatttcgt tcatccatag ttgcctgact ccccgtcgtg tagataacta cgatacggga      300
gggcttacca tctggcccca gtgctgcaat gataccgcga cccacgctca ccggctcc        360 agatttatca gcaataaacc agccagccgg aagggccgag cgcagaagtg gtcctgcaac      420
tttatccgcc tccatccagt ctattaattg ttgccgggaa gctagagtaa gtagttcgcc      480
agttaatagt ttgcgcaacg ttgttgccat tgctacaggc atcgtggtgt cacgctcgtc      540
gtttggtatg gcttcattca gctccggttc ccaacgatca aggcgagtta catgatcccc      600
catgttgtgc aaaaaagcgg ttagctcctt cggtcctccg atcgttgtca gaagtaagtt      660
ggccgcagtg ttatcactca tggttatggc agcactgcat aattctctta ctgtcatgcc      720
atccgtaaga tgcttttctg tgactggtga gtactcaacc aagtcattct gagaatagtg      780
tatgcggcga ccgagttgct cttgcccggc gtcaatacgg gataataccg cgccacatag      840
cagaacttta aaagtgctca tcattggaaa acgttcttcg gggcgaaaac tctcaaggat      900
cttaccgctg ttgagatcca gttcgatgta acccactcgt gcacccaact gatcttcagc      960
atcttttact ttcaccagcg tttctgggtg agcaaaaaca ggaaggcaaa atgccgcaaa     1020
aaagggaata agggcgacac ggaaatgttg aatactcata ctcttccttt ttcaatatta     1080
ttgaagcatt tatcagggtt attgtctcat gaccaaaatc ccttaacgtg agttttcgtt     1140
ccactgagcg tcagaccccg tagaaaagat caaaggatct tcttgagatc ctttttttct     1200
gcgcgtaatc tgctgcttgc aaacaaaaaa accaccgcta ccagcggtgg tttgtttgcc     1260
ggatcaagag ctaccaactc tttttccgaa ggtaactggc ttcagcagag cgcagatacc     1320
aaatactgtt cttctagtgt agccgtagtt aggccaccac ttcaagaact ctgtagcacc     1380
gcctacatac ctcgctctgc taatcctgtt accagtggct gttgccagtg gcgataagtc     1440
gtgtcttacc gggttggact caagacgata gttaccggat aaggcgcagc ggtcgggctg     1500
aacggggggt tcgtgcacac agcccagctt ggagcgaacg acctacaccg aactgagata     1560
cctacagcgt gagctatgag aaagcgccac gcttcccgaa gggagaaagg cggacaggta     1620
tccggtaagc ggcagggtcg gaacaggaga gcgcacgagg gagcttccag ggggaaacgc     1680
ctggtatctt tatagtcctg tcgggtttcg ccacctctga cttgagcgtc gatttttgtg     1740
atgctcgtca ggggggcgga gcctatggaa aaacgccagc aacgcggcct ttttacggtt     1800
cctggccttt tgctggcctt ttgctcacat gttctttcct gcgttatccc ctgattctgt     1860
ggataaccgt attaccgcct ttgagtgagc tgataccgct cgccgcagcc gaacgaccga     1920
```

```
gcgcagcgag tcagtgagcg aggaagcggt cgctgaggct tgacatgatt ggtgcgtatg   1980
tttgtatgaa gctacaggac tgatttggcg ggctatgagg gcgggggaag ctctggaagg   2040
gccgcgatgg ggcgcgcggc gtccagaagg cgccatacgg cccgctggcg gcacccatcc   2100
ggtataaaag cccgcgaccc cgaacggtga cctccacttt cagcgacaaa cgagcactta   2160
tacatacgcg actattctgc cgctatacat aaccactcag ctagcttaag atcccatcaa   2220
gcttgcatgc cgggcgcgcc agaaggagcg cagccaaacc aggatgatgt ttgatggggt   2280
atttgagcac ttgcaaccct tatccggaag cccctggcc cacaaaggct aggcgccaat    2340
gcaagcagtt cgcatgcagc ccctggagcg gtgccctcct gataaaccgg caggggggcc   2400
tatgttcttt acttttttac aagagaagtc actcaacatc ttaaaatggc caggtgagtc   2460
gacgagcaag cccggcggat caggcagcgt gcttgcagat ttgacttgca acgcccgcat   2520
tgtgtcgacg aaggcttttg gctcctctgt cgctgtctca agcagcatct aaccctgcgt   2580 cgccgttttcc atttgcagga gattcgaggt accatgtacc catacgatgt tccagattac   2640
gcttcgccga agaaaaagcg caaggtcgaa gcgtccgaca gaagtacag catcggcctg     2700 gacatcggca ccaactctgt gggctgggcc gtgatcaccg acgagtacaa ggtgcccagc   2760
aagaaattca aggtgctggg caacaccgac cggcacagca tcaagaagaa cctgatcgga   2820
gccctgctgt tcgacagcgg cgaaacagcc gaggccaccc ggctgaagag aaccgccaga   2880
agaagataca ccagacggaa gaaccggatc tgctatctgc aagagatctt cagcaacgag   2940
atggccaagg tggacgacag cttcttccac agactggaag agtccttcct ggtggaagag   3000
gataagaagc acgagcggca ccccatcttc ggcaacatcg tggacgaggt ggcctaccac   3060
gagaagtacc ccaccatcta ccacctgaga aagaaactgg tggacagcac cgacaaggcc   3120
gacctgcggc tgatctatct ggccctggcc cacatgatca agttccgggg ccacttcctg   3180
atcgagggcg acctgaaccc cgacaacagc gacgtggaca gctgttcat ccagctggtg    3240 cagacctaca accagctgtt cgaggaaaac cccatcaacg ccagcggcgt ggacgccaag   3300
gccatcctgt ctgccagact gagcaagagc agacggctgg aaaatctgat cgcccagctg   3360
cccggcgaga agaagaatgg cctgttcggc aacctgattg ccctgagcct gggcctgacc   3420
cccaacttca gagcaacttc agacctggcc gaggatgcca aactgcagct gagcaaggac   3480
acctacgacg acgacctgga caacctgctg gcccagatcg cgaccagta cgccgacctg   3540 tttctggccg ccaagaacct gtccgacgcc atcctgctga gcgacatcct gagagtgaac   3600
accgagatca ccaaggcccc cctgagcgcc tctatgatca agagatacga cgagcaccac   3660
caggacctga cctgctgaa agctctcgtg cggcagcagc tgcctgagaa gtacaaagag    3720
attttcttcg accagagcaa gaacggctac gccggctaca ttgacggcgg agccagccag   3780
gaagagttct acaagttcat caagcccatc ctggaaaaga tggacggcac cgaggaactg   3840
ctcgtgaagc tgaacagaga ggacctgctg cggaagcagc ggaccttcga caacggcagc   3900
atcccccacc agatccacct gggagagctg cacgccattc tgcggcggca ggaagatttt   3960
tacccattcc tgaaggacaa ccgggaaaag atcgagaaga tcctgacctt ccgcatcccc   4020
tactacgtgg gccctctggc caggggaaac agcagattcg cctggatgac cagaaagagc   4080
gaggaaacca tcacccctg aacttcgag gaagtggtgg acaagggcgc ttccgcccag     4140
agcttcatcg agcggatgac caacttcgat aagaacctgc ccaacgagaa ggtgctgccc   4200
aagcacagcc tgctgtacga gtacttcacc gtgtataacg agctgaccaa agtgaaatac   4260
gtgaccgagg gaatgagaaa gcccgccttc ctgagcggcg agcagaaaaa ggccatcgtg   4320
```

```
gacctgctgt tcaagaccaa ccggaaagtg accgtgaagc agctgaaaga ggactacttc    4380
aagaaaatcg agtgcttcga ctccgtggaa atctccggcg tggaagatcg gttcaacgcc    4440
tccctgggca cataccacga tctgctgaaa attatcaagg acaaggactt cctggacaat    4500
gaggaaaacg aggacattct ggaagatatc gtgctgaccc tgacactgtt tgaggacaga    4560
gagatgatcg aggaacggct gaaaacctat gcccacctgt tcgacgacaa agtgatgaag    4620
cagctgaagc ggcggagata caccggctgg ggcaggctga ccggaagct gatcaacggc     4680 atccgggaca agcagtccgg caagacaatc ctggatttcc tgaagtccga cggcttcgcc    4740
aacagaaact tcatgcagct gatccacgac gacagcctga cctttaaaga ggacatccag    4800
aaagcccagg tgtccggcca gggcgatagc ctgcacgagc acattgccaa tctggccggc    4860
agccccgcca ttaagaaggg catcctgcag acagtgaagg tggtggacga gctcgtgaaa    4920
gtgatgggcc ggcacaagcc cgagaacatc gtgatcgaaa tggccagaga gaaccagacc    4980
acccagaagg acagaagaa cagccgcgag agaatgaagc ggatcgaaga gggcatcaaa    5040
gagctgggca gccagatcct gaaagaacac cccgtggaaa cacccagct gcagaacgag   5100 aagctgtacc tgtactacct gcagaatggg cgggatatgt acgtggacca ggaactggac   5160
atcaaccggc tgtccgacta cgatgtggac catatcgtgc ctcagagctt tctgaaggac   5220
gactccatcg acaacaaggt gctgaccaga agcgacaaga accggggcaa gagcgacaac   5280 gtgcccctccg aagaggtcgt gaagaagatg aagaactact ggcggcagct gctgaacgcc   5340
aagctgatta cccagagaaa gttcgacaat ctgaccaagg ccgagagagg cggcctgagc   5400
gaactggata aggccggctt catcaagaga cagctggtgg aaacccggca gatcacaaag   5460
cacgtggcac agatcctgga ctcccggatg aacactaagt acgacgagaa tgacaagctg   5520
atccgggaag tgaaagtgat caccctgaag tccaagctgg tgtccgattt ccggaaggat   5580
ttccagtttt acaaagtgcg cgagatcaac aactaccacc acgcccacga cgcctacctg   5640
aacgccgtcg tgggaaccgc cctgatcaaa aagtacccta gctggaaag cgagttcgtg   5700 tacggcgact acaaggtgta cgacgtgcgg aagatgatcg ccaagagcga gcaggaaatc   5760
ggcaaggcta ccgccaagta cttcttctac agcaacatca tgaactttt caagaccgag   5820 attaccctgg ccaacggcga gatccggaag cggcctctga tcgagacaaa cggcgaaacc   5880
ggggagatcg tgtgggataa gggccgggat tttgccaccg tgcggaaagt gctgagcatg   5940
ccccaagtga atatcgtgaa aaagaccgag gtgcagacag cggcttcag caaagagtct   6000 atcctgccca gaggaacag cgataagctg atcgccagaa agaaggactg ggaccctaag   6060
aagtacggcg gcttcgacag ccccaccgtg gcctattctg tgctggtggt ggccaaagtg   6120
gaaaagggca gtccaagaa actgaagagt gtgaaagagc tgctggggat caccatcatg   6180
gaaagaagca gcttcgagaa gaatcccatc gactttctgg aagccaaggg ctacaaagaa   6240
gtgaaaaagg acctgatcat caagctgcct aagtactccc tgttcgagct ggaaaacggc   6300
cggaagagaa tgctggcctc tgccggcgaa ctgcagaagg gaaacgaact ggccctgccc   6360
tccaaatatg tgaacttcct gtacctggcc agccactatg agaagctgaa gggctccccc   6420
gaggataatg agcagaaaca gctgtttgtg aacagcaca agcactacct ggacgagatc   6480
atcgagcaga tcagcgagtt ctccaagaga gtgatcctgg ccgacgctaa tctggacaaa   6540
gtgctgtccg cctacaacaa gcaccggat aagcccatca gagagcaggc cgagaatatc   6600
atccacctgt ttaccctgac caatctggga gcccctgccg ccttcaagta ctttgacacc   6660
```

-continued

```
accatcgacc ggaagaggta caccagcacc aaagaggtgc tggacgccac cctgatccac    6720
cagagcatca ccggcctgta cgagacacgg atcgacctgt ctcagctggg aggcgacagc    6780
cccaagaaga agagaaaggt ggaggccagc taacatatga ttcgaatgtc tttcttgcgc    6840
tatgacactt ccagcaaaag gtagggcggg ctgcgagacg gcttcccggc gctgcatgca    6900
acaccgatga tgcttcgacc ccccgaagct ccttcggggc tgcatgggcg ctccgatgcc    6960
gctccagggc gagcgctgtt taaatagcca ggccccgat tgcaaagaca ttatagcgag     7020
ctaccaaagc catattcaaa cacctagatc actaccactt ctacacaggc cactcgagct    7080
tgtgatcgca ctccgctaag ggggcgcctc ttcctcttcg tttcagtcac aacccgcaaa    7140
catgacacaa gaatccctgt tacttctcga ccgtattgat tcggatgatt cctacgcgag    7200
cctgcggaac gaccaggaat ctgggaggt gagtcgacga gcaagcccgg cggatcaggc     7260
agcgtgcttg cagatttgac ttgcaacgcc cgcattgtgt cgacgaaggc ttttggctcc    7320
tctgtcgctg tctcaagcag catctaaccc tgcgtcgccg tttccatttg cagccgctgg    7380
cccgccgagc cctggaggag ctcgggctgc cggtgccgcc ggtgctgcgg gtgcccggcg    7440
agagcaccaa ccccgtactg gtcggcgagc ccggcccggt gatcaagctg ttcggcgagc    7500
actggtgcgt tccggagagc ctcgcgtcgg agtcggaggc gtacgcggtc ctggcggacg    7560
ccccggtgcc ggtgccccgc ctcctcggcc gcggcgagct gcggcccggc accggagcct    7620
ggccgtggcc ctacctggtg atgagccgga tgaccggcac cacctggcgg tccgcgatgg    7680
acggcacgac cgaccggaac gcgctgctcg ccctggcccg cgaactcggc cgggtgctcg    7740
gccggctgca cagggtgccg ctgaccggga acaccgtgct caccccccat tccgaggtct    7800
tcccggaact gctgcgggaa cgccgcgcgg cgaccgtcga ggaccaccgc gggtggggct    7860
acctctcgcc ccggctgctg gaccgcctgg aggactggct gccggacgtg acacgctgc     7920 tggccggccg cgaaccccgg ttcgtccacg gcgacctgca cgggaccaac atcttcgtgg    7980
acctggccgc gaccgaggtc accgggatcg tcgacttcac cgacgtctat gcgggagact    8040
cccgctacag cctggtgcaa ctgcatctca acgccttccg gggcgaccgc gagatcctgg    8100
ccgcgctgct cgacggggcg cagtggaagc ggaccgagga cttcgcccgc gaactgctcg    8160
ccttcacctt cctgcacgac ttcgaggtgt tcgaggagac cccgctggat ctctccggct    8220
tcaccgatcc ggaggaactg gcgcagttcc tctgggggcc gccggacacc gccccggcg     8280 cctgataagg atccggcaag actggccccg cttggcaacg caacagtgag cccctcccta    8340
gtgtgtttgg ggatgtgact atgtattcgt gtgttggcca acgggtcaac ccgaacagat    8400
tgatacccgc cttggcattt cctgtcagaa tgtaacgtca gttgatggta ct            8452
```

<210> SEQ ID NO 281
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281

```
gttttagagc tatgctgttt tgaatggtcc caaaacggaa gggcctgagt ccgagcagaa     60
gaagaagttt tagagctatg ctgttttgaa tggtcccaaa ac                       102
```

<210> SEQ ID NO 282
<211> LENGTH: 100
<212> TYPE: DNA

```
<213> ORGANISM: Homo sapiens

<400> SEQUENCE: 282
cggaggacaa agtacaaacg gcagaagctg gaggaggaag ggcctgagtc cgagcagaag      60
aagaagggct cccatcacat caaccggtgg cgcattgcca                          100

<210> SEQ ID NO 283
<211> LENGTH: 50
<212> TYPE: DNA
<213> ORGANISM: Homo sapiens

<400> SEQUENCE: 283
agctggagga ggaagggcct gagtccgagc agaagaagaa gggctcccac                50

<210> SEQ ID NO 284
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gaguccgagc agaagaagaa guuuuagagc                                      30

<210> SEQ ID NO 285
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
agctggagga ggaagggcct gagtccgagc agaagagaag ggctcccat                 49

<210> SEQ ID NO 286
<211> LENGTH: 53
<212> TYPE: DNA
<213> ORGANISM: Homo sapiens

<400> SEQUENCE: 286
ctggaggagg aagggcctga gtccgagcag aagaagaagg gctcccatca cat            53

<210> SEQ ID NO 287
<211> LENGTH: 52
<212> TYPE: DNA
<213> ORGANISM: Homo sapiens

<400> SEQUENCE: 287
ctggaggagg aagggcctga gtccgagcag aagagaaggg ctcccatcac at             52

<210> SEQ ID NO 288
<211> LENGTH: 54
<212> TYPE: DNA
<213> ORGANISM: Homo sapiens

<400> SEQUENCE: 288
ctggaggagg aagggcctga gtccgagcag aagaaagaag gctcccatc acat            54

<210> SEQ ID NO 289
<211> LENGTH: 50
<212> TYPE: DNA
<213> ORGANISM: Homo sapiens
```

-continued

```
<400> SEQUENCE: 289
ctggaggagg aagggcctga gtccgagcag aagaagggct cccatcacat            50

<210> SEQ ID NO 290
<211> LENGTH: 47
<212> TYPE: DNA
<213> ORGANISM: Homo sapiens

<400> SEQUENCE: 290
ctggaggagg aagggcctga gcccgagcag aagggctccc atcacat               47

<210> SEQ ID NO 291
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 291
nnnnnnnnnn nnnnnnnnnn guuuuagagc uagaaauagc aaguuaaaau aaggcuagtc  60
cguuuu                                                            66

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
gaguccgagc agaagaagaa                                             20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
gacaucgaug uccuccccau                                             20

<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
gucaccucca augacuaggg                                             20

<210> SEQ ID NO 295
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295 auugggguguu cagggcagag                                              20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
guggcgagag gggccgagau                                               20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ggggccgaga uuggguguuc                                               20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
gugccauuag cuaaaugcau                                               20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
guaccaccca caggugccag                                               20

<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
gaaagccucu gggccaggaa                                               20

<210> SEQ ID NO 301
<211> LENGTH: 48
<212> TYPE: DNA
```

<213> ORGANISM: Homo sapiens

<400> SEQUENCE: 301
ctggaggagg aagggcctga gtccgagcag aagaagaagg gctcccat                48

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gaguccgagc agaagaagau                                               20

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
gaguccgagc agaagaagua                                               20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gaguccgagc agaagaacaa                                               20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
gaguccgagc agaagaugaa                                               20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gaguccgagc agaaguagaa                                               20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gaguccgagc agaugaagaa                                              20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gaguccgagc acaagaagaa                                              20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gaguccgagg agaagaagaa                                              20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
gaguccgugc agaagaagaa                                              20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gagucggagc agaagaagaa                                              20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
gagaccgagc agaagaagaa                                              20

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
aatgacaagc ttgctagcgg tggg                                    24

<210> SEQ ID NO 314
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
aaaacggaag ggcctgagtc cgagcagaag aagaagttt                    39

<210> SEQ ID NO 315
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
aaacaggggc cgagattggg tgttcagggc agaggtttt                    39

<210> SEQ ID NO 316
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
aaaacggaag ggcctgagtc cgagcagaag aagaagtt                     38

<210> SEQ ID NO 317
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
aacggaggga ggggcacaga tgagaaactc agggttttag                   40

<210> SEQ ID NO 318
<211> LENGTH: 38
<212> TYPE: DNA
<213> ORGANISM: Homo sapiens

<400> SEQUENCE: 318
agcccttctt cttctgctcg gactcaggcc cttcctcc                     38

<210> SEQ ID NO 319
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
cagggaggga ggggcacaga tgagaaactc aggaggcccc                   40

```
<210> SEQ ID NO 320
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ggcaatgcgc caccggttga tgtgatggga gcccttctag gaggccccca gagcagccac      60
tggggcctca acactcaggc                                                  80

<210> SEQ ID NO 321
<211> LENGTH: 23
<212> TYPE: DNA
<213> ORGANISM: Homo sapiens

<400> SEQUENCE: 321
gtcacctcca atgactaggg tgg                                              23

<210> SEQ ID NO 322
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(25)
<223> OTHER INFORMATION: a, c, t, g, unknown or other

<400> SEQUENCE: 322
caccgnnnnn nnnnnnnnnn nnnnn                                            25

<210> SEQ ID NO 323
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, t, g, unknown or other

<400> SEQUENCE: 323
aaacnnnnnn nnnnnnnnnn nnnnc                                            25

<210> SEQ ID NO 324
<211> LENGTH: 33
<212> TYPE: DNA
<213> ORGANISM: Homo sapiens

<400> SEQUENCE: 324
catcgatgtc ctcccattg gcctgcttcg tgg                                    33

<210> SEQ ID NO 325
<211> LENGTH: 33
<212> TYPE: DNA
<213> ORGANISM: Homo sapiens

<400> SEQUENCE: 325
ttcgtggcaa tgcgccaccg gttgatgtga tgg                                   33
```

```
<210> SEQ ID NO 326
<211> LENGTH: 33
<212> TYPE: DNA
<213> ORGANISM: Homo sapiens

<400> SEQUENCE: 326
tcgtggcaat gcgccaccgg ttgatgtgat ggg                              33

<210> SEQ ID NO 327
<211> LENGTH: 33
<212> TYPE: DNA
<213> ORGANISM: Homo sapiens

<400> SEQUENCE: 327
tccagcttct gccgtttgta ctttgtcctc cgg                              33

<210> SEQ ID NO 328
<211> LENGTH: 33
<212> TYPE: DNA
<213> ORGANISM: Homo sapiens

<400> SEQUENCE: 328
ggagggaggg gcacagatga gaaactcagg agg                              33

<210> SEQ ID NO 329
<211> LENGTH: 33
<212> TYPE: DNA
<213> ORGANISM: Homo sapiens

<400> SEQUENCE: 329
aggggccgag attgggtgtt cagggcagag agg                              33

<210> SEQ ID NO 330
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
aacaccgggt cttcgagaag acctgtttta gagctagaaa tagcaagtta aaat       54

<210> SEQ ID NO 331
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
caaaacgggt cttcgagaag acgttttaga gctatgctgt tttgaatggt ccca       54

<210> SEQ ID NO 332
<211> LENGTH: 33
<212> TYPE: DNA
<213> ORGANISM: Mus musculus

<400> SEQUENCE: 332
caagcactga gtgccattag ctaaatgcat agg                              33

<210> SEQ ID NO 333
<211> LENGTH: 33
```

```
<212> TYPE: DNA
<213> ORGANISM: Mus musculus

<400> SEQUENCE: 333
aatgcatagg gtaccaccca caggtgccag ggg                               33

<210> SEQ ID NO 334
<211> LENGTH: 33
<212> TYPE: DNA
<213> ORGANISM: Mus musculus

<400> SEQUENCE: 334
acacacatgg gaaagcctct gggccaggaa agg                               33

<210> SEQ ID NO 335
<211> LENGTH: 37
<212> TYPE: DNA
<213> ORGANISM: Homo sapiens

<400> SEQUENCE: 335
ggaggaggta gtatacagaa acacagagaa gtagaat                           37

<210> SEQ ID NO 336
<211> LENGTH: 37
<212> TYPE: DNA
<213> ORGANISM: Homo sapiens

<400> SEQUENCE: 336
agaatgtaga ggagtcacag aaactcagca ctagaaa                           37

<210> SEQ ID NO 337
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ggacgaaaca ccggaaccat tcaaaacagc atagcaagtt aaaataaggc tagtccgtta   60
tcaacttgaa aaagtggcac cgagtcggtg cttttttt                           98

<210> SEQ ID NO 338
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338
ggacgaaaca ccgtagtat taagtattgt tttatggctg ataaatttct ttgaatttct    60
ccttgattat ttgttataaa agttataaaa taatcttgtt ggaaccattc aaaacagcat  120
agcaagttaa aataaggcta gtccgttatc aacttgaaaa agtggcaccg agtcggtgct  180
tttttt                                                            186

<210> SEQ ID NO 339
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 339
gggttttaga gctatgctgt tttgaatggt cccaaaacgg gtcttcgaga agacgtttta    60
gagctatgct gttttgaatg gtcccaaaac ttttt    95

<210> SEQ ID NO 340
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(34)
<223> OTHER INFORMATION: a, c, t, g, unknown or other

<400> SEQUENCE: 340
aaacnnnnnn nnnnnnnnnn nnnnnnnnnn nnnngt    36

<210> SEQ ID NO 341
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(36)
<223> OTHER INFORMATION: a, c, t, g, unknown or other

<400> SEQUENCE: 341
taaaacnnnn nnnnnnnnnn nnnnnnnnnn nnnnn    36

<210> SEQ ID NO 342
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gtggaaagga cgaaacaccg ggtcttcgag aagacctgtt ttagagctag aaatagcaag    60
ttaaaataag gctagtccgt tttt    84

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 343
caccgnnnnn nnnnnnnnnn nnnn    24

<210> SEQ ID NO 344
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 344
aaacnnnnnn nnnnnnnnnn nnnc                                          24

<210> SEQ ID NO 345
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gttttagagc tatgctgttt tgaatggtcc caaaactgag accaaaggtc tcgttttaga    60
gctatgctgt tttgaatggt cccaaaac                                      88

<210> SEQ ID NO 346
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
aaacggaagg gcctgagtcc gagcagaaga agaag                              35

<210> SEQ ID NO 347
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
aaaacttctt cttctgctcg gactcaggcc cttcc                              35

<210> SEQ ID NO 348
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other

<400> SEQUENCE: 348
nnnnnnnnnn nnnnnnnnng uuauuguacu cucaagauuu auuuuu                  46

<210> SEQ ID NO 349
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
```

```
guuacuuaaa ucuugcagaa gcuacaaaga uaaggcuuca ugccgaaauc aacacccugu    60
cauuuuaugg cagggugüuu ucguuauuua a                                  91
```

```
<210> SEQ ID NO 350
<211> LENGTH: 70
<212> TYPE: DNA
<213> ORGANISM: Homo sapiens

<400> SEQUENCE: 350
ttttctagtg ctgagtttct gtgactcctc tacattctac ttctctgtgt ttctgtatac    60
tacctcctcc                                                          70

<210> SEQ ID NO 351
<211> LENGTH: 122
<212> TYPE: DNA
<213> ORGANISM: Homo sapiens

<400> SEQUENCE: 351
ggaggaaggg cctgagtccg agcagaagaa gaagggctcc catcacatca accggtggcg    60
cattgccacg aagcaggcca atggggagga catcgatgtc acctccaatg actagggtgg   120
gc                                                                 122

<210> SEQ ID NO 352
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, u, g, unknown or other

<400> SEQUENCE: 352
acnnnnnnnn nnnnnnnnnn nnnnnnnnnn nnguuuuaga gcuaugcu                 48

<210> SEQ ID NO 353
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
agcauagcaa guuaaaauaa ggcuaguccg uuaucaacuu gaaaaagugg caccgagucg    60
gugcuuu                                                             67

<210> SEQ ID NO 354
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
```

<400> SEQUENCE: 354
nnnnnnnnnn nnnnnnnnnn guuuuagagc uagaaauagc aaguuaaaau aaggcuaguc    60
cg                                                                  62

<210> SEQ ID NO 355
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
tgaatggtcc caaaacggaa gggcctgagt ccgagcagaa gaagaagttt tagagctatg    60
ctgttttgaa tgg                                                      73

<210> SEQ ID NO 356
<211> LENGTH: 69
<212> TYPE: DNA
<213> ORGANISM: Homo sapiens

<400> SEQUENCE: 356
ctggtcttcc acctctctgc cctgaacacc caatctcggc ccctctcgcc accctcctgc    60
atttctgtt                                                           69

<210> SEQ ID NO 357
<211> LENGTH: 138
<212> TYPE: DNA
<213> ORGANISM: Mus musculus

<400> SEQUENCE: 357
acccaagcac tgagtgccat tagctaaatg catagggtac cacccacagg tgccaggggc    60
ctttcccaaa gttcccagcc ccttctccaa cctttcctgg cccagaggct ttcccatgtg   120
tgtggctgga ccctttga                                                138

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gtgctttgca gaggcctacc                                               20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
cctggagcgc atgcagtagt                                               20

<210> SEQ ID NO 360
<211> LENGTH: 22
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 360
accttctgtg tttccaccat tc                                           22

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
ttggggagtg cacagacttc                                              20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
ggctccctgg gttcaaagta                                              20

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363 agagggtct ggatgtcgta a                                             21

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
tagctctaaa acttcttctt ctgctcggac                                   30

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 365
ctagccttat tttaacttgc tatgctgttt                                   30

<210> SEQ ID NO 366
<211> LENGTH: 99
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 366
nnnnnnnnnn nnnnnnnnnn guuuuagagc uagaaauagc aaguuaaaau aaggcuaguc    60
cguuaucaac uugaaaaagu ggcaccgagu cggugcuuu                           99

<210> SEQ ID NO 367
<211> LENGTH: 12
<212> TYPE: DNA
<213> ORGANISM: Homo sapiens

<400> SEQUENCE: 367
tagcgggtaa gc                                                        12

<210> SEQ ID NO 368
<211> LENGTH: 12
<212> TYPE: DNA
<213> ORGANISM: Homo sapiens

<400> SEQUENCE: 368
tcggtgacat gt                                                        12

<210> SEQ ID NO 369
<211> LENGTH: 12
<212> TYPE: DNA
<213> ORGANISM: Homo sapiens

<400> SEQUENCE: 369
actccccgta gg                                                        12

<210> SEQ ID NO 370
<211> LENGTH: 12
<212> TYPE: DNA
<213> ORGANISM: Homo sapiens

<400> SEQUENCE: 370
actgcgtgtt aa                                                        12

<210> SEQ ID NO 371
<211> LENGTH: 12
<212> TYPE: DNA
<213> ORGANISM: Homo sapiens

<400> SEQUENCE: 371
acgtcgcctg at                                                        12

<210> SEQ ID NO 372
<211> LENGTH: 12
<212> TYPE: DNA
<213> ORGANISM: Homo sapiens

<400> SEQUENCE: 372
taggtcgacc ag                                                        12

<210> SEQ ID NO 373
<211> LENGTH: 12
<212> TYPE: DNA
<213> ORGANISM: Homo sapiens

<400> SEQUENCE: 373
```
ggcgttaatg at                    12

<210> SEQ ID NO 374
<211> LENGTH: 12
<212> TYPE: DNA
<213> ORGANISM: Homo sapiens

<400> SEQUENCE: 374
tgtcgcatgt ta                    12

<210> SEQ ID NO 375
<211> LENGTH: 12
<212> TYPE: DNA
<213> ORGANISM: Homo sapiens

<400> SEQUENCE: 375
atggaaacgc at                    12

<210> SEQ ID NO 376
<211> LENGTH: 12
<212> TYPE: DNA
<213> ORGANISM: Homo sapiens

<400> SEQUENCE: 376
gccgaattcc tc                    12

<210> SEQ ID NO 377
<211> LENGTH: 12
<212> TYPE: DNA
<213> ORGANISM: Homo sapiens

<400> SEQUENCE: 377
gcatggtacg ga                    12

<210> SEQ ID NO 378
<211> LENGTH: 12
<212> TYPE: DNA
<213> ORGANISM: Homo sapiens

<400> SEQUENCE: 378
cggtactctt ac                    12

<210> SEQ ID NO 379
<211> LENGTH: 12
<212> TYPE: DNA
<213> ORGANISM: Homo sapiens

<400> SEQUENCE: 379
gcctgtgccg ta                    12

<210> SEQ ID NO 380
<211> LENGTH: 12
<212> TYPE: DNA
<213> ORGANISM: Homo sapiens

<400> SEQUENCE: 380
tacggtaagt cg                    12

<210> SEQ ID NO 381
<211> LENGTH: 12
<212> TYPE: DNA
<213> ORGANISM: Homo sapiens

```
<400> SEQUENCE: 381
cacgaaatta cc                                                      12

<210> SEQ ID NO 382
<211> LENGTH: 12
<212> TYPE: DNA
<213> ORGANISM: Homo sapiens

<400> SEQUENCE: 382
aaccaagata cg                                                      12

<210> SEQ ID NO 383
<211> LENGTH: 12
<212> TYPE: DNA
<213> ORGANISM: Homo sapiens

<400> SEQUENCE: 383
gagtcgatac gc                                                      12

<210> SEQ ID NO 384
<211> LENGTH: 12
<212> TYPE: DNA
<213> ORGANISM: Homo sapiens

<400> SEQUENCE: 384
gtctcacgat cg                                                      12

<210> SEQ ID NO 385
<211> LENGTH: 12
<212> TYPE: DNA
<213> ORGANISM: Homo sapiens

<400> SEQUENCE: 385
tcgtcgggtg ca                                                      12

<210> SEQ ID NO 386
<211> LENGTH: 12
<212> TYPE: DNA
<213> ORGANISM: Homo sapiens

<400> SEQUENCE: 386
actccgtagt ga                                                      12

<210> SEQ ID NO 387
<211> LENGTH: 12
<212> TYPE: DNA
<213> ORGANISM: Homo sapiens

<400> SEQUENCE: 387
caggacgtcc gt                                                      12

<210> SEQ ID NO 388
<211> LENGTH: 12
<212> TYPE: DNA
<213> ORGANISM: Homo sapiens

<400> SEQUENCE: 388
tcgtatccct ac                                                      12

<210> SEQ ID NO 389
<211> LENGTH: 12
<212> TYPE: DNA
<213> ORGANISM: Homo sapiens
```

```
<400> SEQUENCE: 389
tttcaaggcc gg                                                         12

<210> SEQ ID NO 390
<211> LENGTH: 12
<212> TYPE: DNA
<213> ORGANISM: Homo sapiens

<400> SEQUENCE: 390
cgccggtgga at                                                         12

<210> SEQ ID NO 391
<211> LENGTH: 12
<212> TYPE: DNA
<213> ORGANISM: Homo sapiens

<400> SEQUENCE: 391
gaacccgtcc ta                                                         12

<210> SEQ ID NO 392
<211> LENGTH: 12
<212> TYPE: DNA
<213> ORGANISM: Homo sapiens

<400> SEQUENCE: 392
gattcatcag cg                                                         12

<210> SEQ ID NO 393
<211> LENGTH: 12
<212> TYPE: DNA
<213> ORGANISM: Homo sapiens

<400> SEQUENCE: 393
acaccggtct tc                                                         12

<210> SEQ ID NO 394
<211> LENGTH: 12
<212> TYPE: DNA
<213> ORGANISM: Homo sapiens

<400> SEQUENCE: 394
atcgtgccct aa                                                         12

<210> SEQ ID NO 395
<211> LENGTH: 12
<212> TYPE: DNA
<213> ORGANISM: Homo sapiens

<400> SEQUENCE: 395
gcgtcaatgt tc                                                         12

<210> SEQ ID NO 396
<211> LENGTH: 12
<212> TYPE: DNA
<213> ORGANISM: Homo sapiens

<400> SEQUENCE: 396
ctccgtatct cg                                                         12

<210> SEQ ID NO 397
<211> LENGTH: 12
<212> TYPE: DNA
```

-continued

```
<213> ORGANISM: Homo sapiens

<400> SEQUENCE: 397
ccgattcctt cg                                                        12

<210> SEQ ID NO 398
<211> LENGTH: 12
<212> TYPE: DNA
<213> ORGANISM: Homo sapiens

<400> SEQUENCE: 398
tgcgcctcca gt                                                        12

<210> SEQ ID NO 399
<211> LENGTH: 12
<212> TYPE: DNA
<213> ORGANISM: Homo sapiens

<400> SEQUENCE: 399
taacgtcgga gc                                                        12

<210> SEQ ID NO 400
<211> LENGTH: 12
<212> TYPE: DNA
<213> ORGANISM: Homo sapiens

<400> SEQUENCE: 400
aaggtcgccc at                                                        12

<210> SEQ ID NO 401
<211> LENGTH: 12
<212> TYPE: DNA
<213> ORGANISM: Homo sapiens

<400> SEQUENCE: 401
gtcggggact at                                                        12

<210> SEQ ID NO 402
<211> LENGTH: 12
<212> TYPE: DNA
<213> ORGANISM: Homo sapiens

<400> SEQUENCE: 402
ttcgagcgat tt                                                        12

<210> SEQ ID NO 403
<211> LENGTH: 12
<212> TYPE: DNA
<213> ORGANISM: Homo sapiens

<400> SEQUENCE: 403
tgagtcgtcg ag                                                        12

<210> SEQ ID NO 404
<211> LENGTH: 12
<212> TYPE: DNA
<213> ORGANISM: Homo sapiens

<400> SEQUENCE: 404
tttacgcaga gg                                                        12

<210> SEQ ID NO 405
<211> LENGTH: 12
```

<212> TYPE: DNA
<213> ORGANISM: Homo sapiens

<400> SEQUENCE: 405
aggaagtatc gc                                                          12

<210> SEQ ID NO 406
<211> LENGTH: 12
<212> TYPE: DNA
<213> ORGANISM: Homo sapiens

<400> SEQUENCE: 406
actcgatacc at                                                          12

<210> SEQ ID NO 407
<211> LENGTH: 12
<212> TYPE: DNA
<213> ORGANISM: Homo sapiens

<400> SEQUENCE: 407
cgctacatag ca                                                          12

<210> SEQ ID NO 408
<211> LENGTH: 12
<212> TYPE: DNA
<213> ORGANISM: Homo sapiens

<400> SEQUENCE: 408
ttcataaccg gc                                                          12

<210> SEQ ID NO 409
<211> LENGTH: 12
<212> TYPE: DNA
<213> ORGANISM: Homo sapiens

<400> SEQUENCE: 409
ccaaacggtt aa                                                          12

<210> SEQ ID NO 410
<211> LENGTH: 12
<212> TYPE: DNA
<213> ORGANISM: Homo sapiens

<400> SEQUENCE: 410
cgattccttc gt                                                          12

<210> SEQ ID NO 411
<211> LENGTH: 12
<212> TYPE: DNA
<213> ORGANISM: Homo sapiens

<400> SEQUENCE: 411
cgtcatgaat aa                                                          12

<210> SEQ ID NO 412
<211> LENGTH: 12
<212> TYPE: DNA
<213> ORGANISM: Homo sapiens

<400> SEQUENCE: 412
agtggcgatg ac                                                          12

<210> SEQ ID NO 413

```
<211> LENGTH: 12
<212> TYPE: DNA
<213> ORGANISM: Homo sapiens

<400> SEQUENCE: 413
cccctacggc ac                                                             12

<210> SEQ ID NO 414
<211> LENGTH: 12
<212> TYPE: DNA
<213> ORGANISM: Homo sapiens

<400> SEQUENCE: 414
gccaacccgc ac                                                             12

<210> SEQ ID NO 415
<211> LENGTH: 12
<212> TYPE: DNA
<213> ORGANISM: Homo sapiens

<400> SEQUENCE: 415
tgggacaccg gt                                                             12

<210> SEQ ID NO 416
<211> LENGTH: 12
<212> TYPE: DNA
<213> ORGANISM: Homo sapiens

<400> SEQUENCE: 416
ttgactgcgg cg                                                             12

<210> SEQ ID NO 417
<211> LENGTH: 12
<212> TYPE: DNA
<213> ORGANISM: Homo sapiens

<400> SEQUENCE: 417
actatgcgta gg                                                             12

<210> SEQ ID NO 418
<211> LENGTH: 12
<212> TYPE: DNA
<213> ORGANISM: Homo sapiens

<400> SEQUENCE: 418
tcacccaaag cg                                                             12

<210> SEQ ID NO 419
<211> LENGTH: 12
<212> TYPE: DNA
<213> ORGANISM: Homo sapiens

<400> SEQUENCE: 419
gcaggacgtc cg                                                             12

<210> SEQ ID NO 420
<211> LENGTH: 12
<212> TYPE: DNA
<213> ORGANISM: Homo sapiens

<400> SEQUENCE: 420
acaccgaaaa cg                                                             12
```

```
<210> SEQ ID NO 421
<211> LENGTH: 12
<212> TYPE: DNA
<213> ORGANISM: Homo sapiens

<400> SEQUENCE: 421
cggtgtattg ag                                                         12

<210> SEQ ID NO 422
<211> LENGTH: 12
<212> TYPE: DNA
<213> ORGANISM: Homo sapiens

<400> SEQUENCE: 422
cacgaggtat gc                                                         12

<210> SEQ ID NO 423
<211> LENGTH: 12
<212> TYPE: DNA
<213> ORGANISM: Homo sapiens

<400> SEQUENCE: 423
taaagcgacc cg                                                         12

<210> SEQ ID NO 424
<211> LENGTH: 12
<212> TYPE: DNA
<213> ORGANISM: Homo sapiens

<400> SEQUENCE: 424
cttagtcggc ca                                                         12

<210> SEQ ID NO 425
<211> LENGTH: 12
<212> TYPE: DNA
<213> ORGANISM: Homo sapiens

<400> SEQUENCE: 425
cgaaaacgtg gc                                                         12

<210> SEQ ID NO 426
<211> LENGTH: 12
<212> TYPE: DNA
<213> ORGANISM: Homo sapiens

<400> SEQUENCE: 426
cgtgccctga ac                                                         12

<210> SEQ ID NO 427
<211> LENGTH: 12
<212> TYPE: DNA
<213> ORGANISM: Homo sapiens

<400> SEQUENCE: 427
tttaccatcg aa                                                         12

<210> SEQ ID NO 428
<211> LENGTH: 12
<212> TYPE: DNA
<213> ORGANISM: Homo sapiens

<400> SEQUENCE: 428
cgtagccatg tt                                                         12
```

```
<210> SEQ ID NO 429
<211> LENGTH: 12
<212> TYPE: DNA
<213> ORGANISM: Homo sapiens

<400> SEQUENCE: 429
cccaaacggt ta                                                          12

<210> SEQ ID NO 430
<211> LENGTH: 12
<212> TYPE: DNA
<213> ORGANISM: Homo sapiens

<400> SEQUENCE: 430
gcgttatcag aa                                                          12

<210> SEQ ID NO 431
<211> LENGTH: 12
<212> TYPE: DNA
<213> ORGANISM: Homo sapiens

<400> SEQUENCE: 431
tcgatggtaa ac                                                          12

<210> SEQ ID NO 432
<211> LENGTH: 12
<212> TYPE: DNA
<213> ORGANISM: Homo sapiens

<400> SEQUENCE: 432
cgactttttg ca                                                          12

<210> SEQ ID NO 433
<211> LENGTH: 12
<212> TYPE: DNA
<213> ORGANISM: Homo sapiens

<400> SEQUENCE: 433
tcgacgactc ac                                                          12

<210> SEQ ID NO 434
<211> LENGTH: 12
<212> TYPE: DNA
<213> ORGANISM: Homo sapiens

<400> SEQUENCE: 434
acgcgtcaga ta                                                          12

<210> SEQ ID NO 435
<211> LENGTH: 12
<212> TYPE: DNA
<213> ORGANISM: Homo sapiens

<400> SEQUENCE: 435
cgtacggcac ag                                                          12

<210> SEQ ID NO 436
<211> LENGTH: 12
<212> TYPE: DNA
<213> ORGANISM: Homo sapiens

<400> SEQUENCE: 436
ctatgccgtg ca                                                          12
```

<210> SEQ ID NO 437
<211> LENGTH: 12
<212> TYPE: DNA
<213> ORGANISM: Homo sapiens

<400> SEQUENCE: 437
cgcgtcagat at                                                           12

<210> SEQ ID NO 438
<211> LENGTH: 12
<212> TYPE: DNA
<213> ORGANISM: Homo sapiens

<400> SEQUENCE: 438
aagatcggta gc                                                           12

<210> SEQ ID NO 439
<211> LENGTH: 12
<212> TYPE: DNA
<213> ORGANISM: Homo sapiens

<400> SEQUENCE: 439
cttcgcaagg ag                                                           12

<210> SEQ ID NO 440
<211> LENGTH: 12
<212> TYPE: DNA
<213> ORGANISM: Homo sapiens

<400> SEQUENCE: 440
gtcgtggact ac                                                           12

<210> SEQ ID NO 441
<211> LENGTH: 12
<212> TYPE: DNA
<213> ORGANISM: Homo sapiens

<400> SEQUENCE: 441
ggtcgtcatc aa                                                           12

<210> SEQ ID NO 442
<211> LENGTH: 12
<212> TYPE: DNA
<213> ORGANISM: Homo sapiens

<400> SEQUENCE: 442
gttaacagcg tg                                                           12

<210> SEQ ID NO 443
<211> LENGTH: 12
<212> TYPE: DNA
<213> ORGANISM: Homo sapiens

<400> SEQUENCE: 443
tagctaaccg tt                                                           12

<210> SEQ ID NO 444
<211> LENGTH: 12
<212> TYPE: DNA
<213> ORGANISM: Homo sapiens

<400> SEQUENCE: 444

-continued

```
agtaaaggcg ct                                                          12

<210> SEQ ID NO 445
<211> LENGTH: 12
<212> TYPE: DNA
<213> ORGANISM: Homo sapiens

<400> SEQUENCE: 445
ggtaatttcg tg                                                          12

<210> SEQ ID NO 446
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
gucaccucca augacuaggg guuuuagagc uagaaauagc aaguuaaaau aaggcuaguc       60
cguuuuuuu                                                              69

<210> SEQ ID NO 447
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
gacaucgaug uccuccccau guuuuagagc uagaaauagc aaguuaaaau aaggcuaguc       60
cguuuuuuu                                                              69

<210> SEQ ID NO 448
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
gaguccgagc agaagaagaa guuuuagagc uagaaauagc aaguuaaaau aaggcuaguc       60
cguuuuuuu                                                              69

<210> SEQ ID NO 449
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ggggccgaga uuggguguuc guuuuagagc uagaaauagc aaguuaaaau aaggcuaguc       60
cguuuuuuu                                                              69

<210> SEQ ID NO 450
<211> LENGTH: 69
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 450
guggcgagag gggccgagau guuuuagagc uagaaauagc aaguuaaaau aaggcuaguc    60
cguuuuuuu    69

<210> SEQ ID NO 451
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
gucaccucca augacuaggg guuuuagagc uagaaauagc aaguuaaaau aaggcuaguc    60
cguuaucauu uuuuuu    76

<210> SEQ ID NO 452
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
gacaucgaug uccuccccau guuuuagagc uagaaauagc aaguuaaaau aaggcuaguc    60
cguuaucauu uuuuuu    76

<210> SEQ ID NO 453
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
gaguccgagc agaagaagaa guuuuagagc uagaaauagc aaguuaaaau aaggcuaguc    60
cguuaucauu uuuuuu    76

<210> SEQ ID NO 454
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ggggccgaga uugggguguuc guuuuagagc uagaaauagc aaguuaaaau aaggcuaguc    60
cguuaucauu uuuuuu    76

<210> SEQ ID NO 455
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455

```
guggcgagag gggccgagau guuuuagagc uagaaauagc aaguuaaaau aaggcuaguc    60
cguuaucauu uuuuuu                                                    76

<210> SEQ ID NO 456
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
gucaccucca augacuaggg guuuuagagc uagaaauagc aaguuaaaau aaggcuaguc    60
cguuaucaac uugaaaaagu guuuuuuu                                       88

<210> SEQ ID NO 457
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
gacaucgaug uccuccccau guuuuagagc uagaaauagc aaguuaaaau aaggcuaguc    60
cguuaucaac uugaaaaagu guuuuuuu                                       88

<210> SEQ ID NO 458
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
gaguccgagc agaagaagaa guuuuagagc uagaaauagc aaguuaaaau aaggcuaguc    60
cguuaucaac uugaaaaagu guuuuuuu                                       88

<210> SEQ ID NO 459
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
ggggccgaga uugguguuc guuuuagagc uagaaauagc aaguuaaaau aaggcuaguc     60
cguuaucaac uugaaaaagu guuuuuuu                                       88

<210> SEQ ID NO 460
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
guggcgagag gggccgagau guuuuagagc uagaaauagc aaguuaaaau aaggcuaguc    60
cguuaucaac uugaaaaagu guuuuuuu                                       88
```

<210> SEQ ID NO 461
<211> LENGTH: 103
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gucaccucca augacuaggg guuuuagagc uagaaauagc aaguuaaaau aaggcuaguc    60
cguuaucaac uugaaaaagu ggcaccgagu cggugcuuuu uuu                     103

<210> SEQ ID NO 462
<211> LENGTH: 103
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gacaucgaug uccucoccau guuuuagagc uagaaauagc aaguuaaaau aaggcuaguc    60
cguuaucaac uugaaaaagu ggcaccgagu cggugcuuuu uuu                     103

<210> SEQ ID NO 463
<211> LENGTH: 103
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
gaguccgagc agaagaagaa guuuuagagc uagaaauagc aaguuaaaau aaggcuaguc    60
cguuaucaac uugaaaaagu ggcaccgagu cggugcuuuu uuu                     103

<210> SEQ ID NO 464
<211> LENGTH: 103
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ggggccgaga uugggguguuc guuuuagagc uagaaauagc aaguuaaaau aaggcuaguc   60
cguuaucaac uugaaaaagu ggcaccgagu cggugcuuuu uuu                     103

<210> SEQ ID NO 465
<211> LENGTH: 103
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
guggcgagag gggccgagau guuuuagagc uagaaauagc aaguuaaaau aaggcuaguc    60
cguuaucaac uugaaaaagu ggcaccgagu cggugcuuuu uuu                     103

<210> SEQ ID NO 466
<211> LENGTH: 120
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 466
gtggaaagga cgaaacaccg ggtcttcgag aagacctgtt ttagagctag aaatagcaag    60
ttaaaataag gctagtccgt tatcaacttg aaaaagtggc accgagtcgg tgcttttttt   120

<210> SEQ ID NO 467
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tcggtgcgct ggttgatttc ttcttgcgct tttttggctt                          40

<210> SEQ ID NO 468
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
gauuucuucu ugcgcuuuuu guuuua                                         26

<210> SEQ ID NO 469
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(26)
<223> OTHER INFORMATION: a, c, t, g, unknown or other

<400> SEQUENCE: 469
tgatttcttc ttgcgctttt tnnnnn                                         26

<210> SEQ ID NO 470
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 470
tgatttcttc ttgcgctttt ntggct                                         26

<210> SEQ ID NO 471
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (2)..(2)
<223> OTHER INFORMATION: a, c, t, g, unknown or other

<400> SEQUENCE: 471
tnatttcttc ttgcgctttt ttggct                                            26

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gatttcttct tgcgcttttt tgg                                               23

<210> SEQ ID NO 473
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 473 tcc atc cgt aca acc cac aac cct gct agt gag c                           34
Ser Ile Arg Thr Thr His Asn Pro Ala Ser Glu
1               5                   10

<210> SEQ ID NO 474
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ser Ile Arg Thr Thr His Asn Pro Ala Ser Glu
1               5                   10

<210> SEQ ID NO 475
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 475 tcc atc gca aca acc cac aac cct gct agt gag c                           34
Ser Ile Ala Thr Thr His Asn Pro Ala Ser Glu
1               5                   10

<210> SEQ ID NO 476
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 476

Ser Ile Ala Thr Thr His Asn Pro Ala Ser Glu
1               5                   10

<210> SEQ ID NO 477
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 477 tca atc cgt aca acc cac aac cct gct agt gag c                         34
Ser Ile Arg Thr Thr His Asn Pro Ala Ser Glu
1               5                   10

<210> SEQ ID NO 478
<211> LENGTH: 42
<212> TYPE: DNA
<213> ORGANISM: Homo sapiens
<220> FEATURE:
<221> NAME/KEY: CDS
<222> LOCATION: (1)..(36)

<400> SEQUENCE: 478 caa ttg aat tta aaa gaa acc gat acc gtt ttg gtt taagga               42
Gln Leu Asn Leu Lys Glu Thr Asp Thr Val Leu Val
1               5                   10

<210> SEQ ID NO 479
<211> LENGTH: 12
<212> TYPE: PRT
<213> ORGANISM: Homo sapiens

<400> SEQUENCE: 479

Gln Leu Asn Leu Lys Glu Thr Asp Thr Val Leu Val
1               5                   10

<210> SEQ ID NO 480
<211> LENGTH: 42
<212> TYPE: DNA
<213> ORGANISM: Homo sapiens
<220> FEATURE:
<221> NAME/KEY: CDS
<222> LOCATION: (1)..(42)

<400> SEQUENCE: 480 caa ttg aat tta aaa gaa acc gat acc gtt tac gaa att gga              42
Gln Leu Asn Leu Lys Glu Thr Asp Thr Val Tyr Glu Ile Gly
1               5                   10

<210> SEQ ID NO 481
<211> LENGTH: 14
<212> TYPE: PRT
<213> ORGANISM: Homo sapiens

<400> SEQUENCE: 481

Gln Leu Asn Leu Lys Glu Thr Asp Thr Val Tyr Glu Ile Gly
1               5                   10

<210> SEQ ID NO 482

```
<211> LENGTH: 34
<212> TYPE: DNA
<213> ORGANISM: Homo sapiens
<220> FEATURE:
<221> NAME/KEY: CDS
<222> LOCATION: (2)..(34)

<400> SEQUENCE: 482 t cct aaa aaa ccg aac tcc gcg ctg cgt aaa gta            34
  Pro Lys Lys Pro Asn Ser Ala Leu Arg Lys Val
  1               5                   10

<210> SEQ ID NO 483
<211> LENGTH: 11
<212> TYPE: PRT
<213> ORGANISM: Homo sapiens

<400> SEQUENCE: 483

Pro Lys Lys Pro Asn Ser Ala Leu Arg Lys Val
1               5                   10

<210> SEQ ID NO 484
<211> LENGTH: 34
<212> TYPE: DNA
<213> ORGANISM: Homo sapiens
<220> FEATURE:
<221> NAME/KEY: CDS
<222> LOCATION: (2)..(34)

<400> SEQUENCE: 484 t cct aca aaa ccg aac tcc gcg ctg cgt aaa gta            34
  Pro Thr Lys Pro Asn Ser Ala Leu Arg Lys Val
  1               5                   10

<210> SEQ ID NO 485
<211> LENGTH: 11
<212> TYPE: PRT
<213> ORGANISM: Homo sapiens

<400> SEQUENCE: 485

Pro Thr Lys Pro Asn Ser Ala Leu Arg Lys Val
1               5                   10

<210> SEQ ID NO 486
<211> LENGTH: 33
<212> TYPE: DNA
<213> ORGANISM: Homo sapiens

<400> SEQUENCE: 486
tgcgctggtt gatttcttct tgcgcttttt tgg              33

<210> SEQ ID NO 487
<211> LENGTH: 33
<212> TYPE: DNA
<213> ORGANISM: Homo sapiens

<400> SEQUENCE: 487
tacgctggtt gatttcttct tgcgcttttt ttg              33

<210> SEQ ID NO 488
<211> LENGTH: 27
<212> TYPE: DNA
<213> ORGANISM: Homo sapiens

<400> SEQUENCE: 488
ggagggtttt atgggaaag gccattg                     27
```

<210> SEQ ID NO 489
<211> LENGTH: 29
<212> TYPE: DNA
<213> ORGANISM: Homo sapiens

<400> SEQUENCE: 489
gtaaaaaaga agactagaaa ttttgatac                                     29

<210> SEQ ID NO 490
<211> LENGTH: 46
<212> TYPE: DNA
<213> ORGANISM: Homo sapiens

<400> SEQUENCE: 490
ggagggtttt atggggaaag gcaaagaaga ctagaaattt tgatac                  46

<210> SEQ ID NO 491
<211> LENGTH: 27
<212> TYPE: DNA
<213> ORGANISM: Homo sapiens

<400> SEQUENCE: 491
aggtgaagca taatgtctca aaaaata                                       27

<210> SEQ ID NO 492
<211> LENGTH: 29
<212> TYPE: DNA
<213> ORGANISM: Homo sapiens

<400> SEQUENCE: 492
attttattaa tacaaatcag tgaaatcat                                     29

<210> SEQ ID NO 493
<211> LENGTH: 46
<212> TYPE: DNA
<213> ORGANISM: Homo sapiens

<400> SEQUENCE: 493
aggtgaagca taatgtctca aaattaatac aaatcagtga aatcat                  46

<210> SEQ ID NO 494
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 494 aat tta aaa gaa acc gat acc gtt tac gaa att gga                     36
Asn Leu Lys Glu Thr Asp Thr Val Tyr Glu Ile Gly
1               5                   10

<210> SEQ ID NO 495
<211> LENGTH: 12
<212> TYPE: PRT
<213> ORGANISM: Homo sapiens

<400> SEQUENCE: 495

Asn Leu Lys Glu Thr Asp Thr Val Tyr Glu Ile Gly
1               5                   10

<210> SEQ ID NO 496

```
<211> LENGTH: 36
<212> TYPE: DNA
<213> ORGANISM: Homo sapiens
<220> FEATURE:
<221> NAME/KEY: CDS
<222> LOCATION: (1)..(30)

<400> SEQUENCE: 496 aat tta aaa gaa acc gat acc gtt ttg gtt taagga                      36
Asn Leu Lys Glu Thr Asp Thr Val Leu Val
1               5                   10

<210> SEQ ID NO 497
<211> LENGTH: 10
<212> TYPE: PRT
<213> ORGANISM: Homo sapiens

<400> SEQUENCE: 497

Asn Leu Lys Glu Thr Asp Thr Val Leu Val
1               5                   10

<210> SEQ ID NO 498
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 498 tgg gat cca aaa aaa tat ggt ggt ttt gat agt cca                     36
Trp Asp Pro Lys Lys Tyr Gly Gly Phe Asp Ser Pro
1               5                   10

<210> SEQ ID NO 499
<211> LENGTH: 12
<212> TYPE: PRT
<213> ORGANISM: Homo sapiens

<400> SEQUENCE: 499

Trp Asp Pro Lys Lys Tyr Gly Gly Phe Asp Ser Pro
1               5                   10

<210> SEQ ID NO 500
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 500 tgg gat cca aaa aaa tat tgt ggt ttt gat agt cca                     36
Trp Asp Pro Lys Lys Tyr Cys Gly Phe Asp Ser Pro
1               5                   10

<210> SEQ ID NO 501
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501
```

```
<210> SEQ ID NO 502
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
aaactacttt acgcagcgcg gagttcggtt ttttg                              35

<210> SEQ ID NO 503
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 503
```

| | | | | | | | | | | | | | | | | |
|---|---|---|---|---|---|---|---|---|---|---|---|---|---|---|---|---|
| atg | gac | aag | aag | tac | agc | atc | ggc | ctg | gac | atc | ggc | acc | aac | tct | gtg | 48 |
| Met | Asp | Lys | Lys | Tyr | Ser | Ile | Gly | Leu | Asp | Ile | Gly | Thr | Asn | Ser | Val | |
| 1 | | | | 5 | | | | | 10 | | | | | 15 | | |
| ggc | tgg | gcc | gtg | atc | acc | gac | gag | tac | aag | gtg | ccc | agc | aag | aaa | ttc | 96 |
| Gly | Trp | Ala | Val | Ile | Thr | Asp | Glu | Tyr | Lys | Val | Pro | Ser | Lys | Lys | Phe | |
| | | | 20 | | | | | 25 | | | | | 30 | | | |
| aag | gtg | ctg | ggc | aac | acc | gac | cgg | cac | agc | atc | aag | aag | aac | ctg | atc | 144 |
| Lys | Val | Leu | Gly | Asn | Thr | Asp | Arg | His | Ser | Ile | Lys | Lys | Asn | Leu | Ile | |
| | | 35 | | | | | 40 | | | | | 45 | | | | |
| gga | gcc | ctg | ctg | ttc | gac | agc | ggc | gaa | aca | gcc | gag | gcc | acc | cgg | ctg | 192 |
| Gly | Ala | Leu | Leu | Phe | Asp | Ser | Gly | Glu | Thr | Ala | Glu | Ala | Thr | Arg | Leu | |
| | 50 | | | | | 55 | | | | | 60 | | | | | |
| aag | aga | acc | gcc | aga | aga | aga | tac | acc | aga | cgg | aag | aac | cgg | atc | tgc | 240 |
| Lys | Arg | Thr | Ala | Arg | Arg | Arg | Tyr | Thr | Arg | Arg | Lys | Asn | Arg | Ile | Cys | |
| 65 | | | | | 70 | | | | | 75 | | | | | 80 | |
| tat | ctg | caa | gag | atc | ttc | agc | aac | gag | atg | gcc | aag | gtg | gac | gac | agc | 288 |
| Tyr | Leu | Gln | Glu | Ile | Phe | Ser | Asn | Glu | Met | Ala | Lys | Val | Asp | Asp | Ser | |
| | | | | 85 | | | | | 90 | | | | | 95 | | |
| ttc | ttc | cac | aga | ctg | gaa | gag | tcc | ttc | ctg | gtg | gaa | gag | gat | aag | aag | 336 |
| Phe | Phe | His | Arg | Leu | Glu | Glu | Ser | Phe | Leu | Val | Glu | Glu | Asp | Lys | Lys | |
| | | | 100 | | | | | 105 | | | | | 110 | | | |
| cac | gag | cgg | cac | ccc | atc | ttc | ggc | aac | atc | gtg | gac | gag | gtg | gcc | tac | 384 |
| His | Glu | Arg | His | Pro | Ile | Phe | Gly | Asn | Ile | Val | Asp | Glu | Val | Ala | Tyr | |
| | | 115 | | | | | 120 | | | | | 125 | | | | |
| cac | gag | aag | tac | ccc | acc | atc | tac | cac | ctg | aga | aag | aaa | ctg | gtg | gac | 432 |
| His | Glu | Lys | Tyr | Pro | Thr | Ile | Tyr | His | Leu | Arg | Lys | Lys | Leu | Val | Asp | |
| | 130 | | | | | 135 | | | | | 140 | | | | | |
| agc | acc | gac | aag | gcc | gac | ctg | cgg | ctg | atc | tat | ctg | gcc | ctg | gcc | cac | 480 |
| Ser | Thr | Asp | Lys | Ala | Asp | Leu | Arg | Leu | Ile | Tyr | Leu | Ala | Leu | Ala | His | |
| 145 | | | | | 150 | | | | | 155 | | | | | 160 | |
| atg | atc | aag | ttc | cgg | ggc | cac | ttc | ctg | atc | gag | ggc | gac | ctg | aac | ccc | 528 |
| Met | Ile | Lys | Phe | Arg | Gly | His | Phe | Leu | Ile | Glu | Gly | Asp | Leu | Asn | Pro | |
| | | | | 165 | | | | | 170 | | | | | 175 | | |
| gac | aac | agc | gac | gtg | gac | aag | ctg | ttc | atc | cag | ctg | gtg | cag | acc | tac | 576 |
| Asp | Asn | Ser | Asp | Val | Asp | Lys | Leu | Phe | Ile | Gln | Leu | Val | Gln | Thr | Tyr | |
| | | | 180 | | | | | 185 | | | | | 190 | | | |
| aac | cag | ctg | ttc | gag | gaa | aac | ccc | atc | aac | gcc | agc | ggc | gtg | gac | gcc | 624 |
| Asn | Gln | Leu | Phe | Glu | Glu | Asn | Pro | Ile | Asn | Ala | Ser | Gly | Val | Asp | Ala | |
| | | 195 | | | | | 200 | | | | | 205 | | | | |

```
aag gcc atc ctg tct gcc aga ctg agc aag agc aga cgg ctg gaa aat       672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac       720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc       768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac       816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac       864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac       912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct       960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa      1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc      1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc      1104
Asp Gln Ser Lys Asn Gly Tyr Ala Gly Tyr Ile Asp Gly Gly Ala Ser
        355                 360                 365 cag gaa gag ttc tac aag ttc atc aag ccc atc ctg gaa aag atg gac      1152
Gln Glu Glu Phe Tyr Lys Phe Ile Lys Pro Ile Leu Glu Lys Met Asp
    370                 375                 380 ggc acc gag gaa ctg ctc gtg aag ctg aac aga gag gac ctg ctg cgg      1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg      1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc      1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc      1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc      1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa      1584
Leu Leu Tyr Glu Tyr Phe Thr Val Tyr Asn Glu Leu Thr Lys Val Lys
        515                 520                 525
```

```
tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
    530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
        595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
    610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
        675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
    690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc    2256
Ile Leu Gln Thr Val Lys Val Val Asp Glu Leu Val Lys Val Met Gly
            740                 745                 750 cgg cac aag ccc gag aac atc gtg atc gcc atg gcc aga gag aac cag    2304
Arg His Lys Pro Glu Asn Ile Val Ile Ala Met Ala Arg Glu Asn Gln
        755                 760                 765 acc acc cag aag gga cag aag aac agc cgc gag aga atg aag cgg atc    2352
Thr Thr Gln Lys Gly Gln Lys Asn Ser Arg Glu Arg Met Lys Arg Ile
    770                 775                 780 gaa gag ggc atc aaa gag ctg ggc agc cag atc ctg aaa gaa cac ccc    2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg    2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg    2496
Gln Asn Gly Arg Asp Met Tyr Val Asp Gln Glu Leu Asp Ile Asn Arg
            820                 825                 830 ctg tcc gac tac gat gtg gac gcc atc gtg cct cag agc ttt ctg aag    2544
Leu Ser Asp Tyr Asp Val Asp Ala Ile Val Pro Gln Ser Phe Leu Lys
```

-continued

|     |     |     | 835 |     |     |     | 840 |     |     |     | 845 |     |     |     |     |
|-----|-----|-----|-----|-----|-----|-----|-----|-----|-----|-----|-----|-----|-----|-----|-----|

```
gac gac tcc atc gac gcc aag gtg ctg acc aga agc gac aag gcc cgg      2592
Asp Asp Ser Ile Asp Ala Lys Val Leu Thr Arg Ser Asp Lys Ala Arg
    850                 855                 860 ggc aag agc gac aac gtg ccc tcc gaa gag gtc gtg aag aag atg aag      2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag      2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat      2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca      2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac      2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc      2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc      2928
Lys Leu Val Ser Asp Phe Arg Lys Asp Phe Gln Phe Tyr Lys Val Arg
                965                 970                 975 gag atc aac aac tac cac cac gcc cac gcc gcc tac ctg aac gcc gtc      2976
Glu Ile Asn Asn Tyr His His Ala His Ala Ala Tyr Leu Asn Ala Val
            980                 985                 990 gtg gga acc gcc ctg atc aaa aag tac cct aag ctg gaa agc gag ttc      3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
      1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
    1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
    1040                1045                1050 aac ggc gag atc cgg aag cgg cct ctg atc gag aca aac ggc gaa          3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg          3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc          3294
Arg Lys Val Leu Ser Met Pro Gln Val Asn Ile Val Lys Lys Thr
    1085                1090                1095 gag gtg cag aca ggc ggc ttc agc aaa gag tct atc ctg ccc aag          3339
Glu Val Gln Thr Gly Gly Phe Ser Lys Glu Ser Ile Leu Pro Lys
    1100                1105                1110 agg aac agc gat aag ctg atc gcc aga aag aag gac tgg gac cct          3384
Arg Asn Ser Asp Lys Leu Ile Ala Arg Lys Lys Asp Trp Asp Pro
    1115                1120                1125 aag aag tac ggc ggc ttc gac agc ccc acc gtg gcc tat tct gtg          3429
Lys Lys Tyr Gly Gly Phe Asp Ser Pro Thr Val Ala Tyr Ser Val
    1130                1135                1140 ctg gtg gtg gcc aaa gtg gaa aag ggc aag tcc aag aaa ctg aag          3474
Leu Val Val Ala Lys Val Glu Lys Gly Lys Ser Lys Lys Leu Lys
```

| | | | | | | | | | | | | |
|---|---|---|---|---|---|---|---|---|---|---|---|---|
| Leu | Val | Val | Ala | Lys | Val | Glu | Lys | Gly | Lys | Ser | Lys | Lys Leu Lys |
| 1145 | | | | | 1150 | | | | | 1155 | | |

| | | | | | | | | | | | | | |
|---|---|---|---|---|---|---|---|---|---|---|---|---|---|
| agt | gtg | aaa | gag | ctg | ctg | ggg | atc | acc | atc | atg | gaa | aga agc agc | 3519 |
| Ser | Val | Lys | Glu | Leu | Leu | Gly | Ile | Thr | Ile | Met | Glu | Arg Ser Ser | |
| 1160 | | | | | 1165 | | | | | 1170 | | | |

| | | | | | | | | | | | | | |
|---|---|---|---|---|---|---|---|---|---|---|---|---|---|
| ttc | gag | aag | aat | ccc | atc | gac | ttt | ctg | gaa | gcc | aag | ggc tac aaa | 3564 |
| Phe | Glu | Lys | Asn | Pro | Ile | Asp | Phe | Leu | Glu | Ala | Lys | Gly Tyr Lys | |
| 1175 | | | | | 1180 | | | | | 1185 | | | |

| | | | | | | | | | | | | | |
|---|---|---|---|---|---|---|---|---|---|---|---|---|---|
| gaa | gtg | aaa | aag | gac | ctg | atc | atc | aag | ctg | cct | aag | tac tcc ctg | 3609 |
| Glu | Val | Lys | Lys | Asp | Leu | Ile | Ile | Lys | Leu | Pro | Lys | Tyr Ser Leu | |
| 1190 | | | | | 1195 | | | | | 1200 | | | |

| | | | | | | | | | | | | | |
|---|---|---|---|---|---|---|---|---|---|---|---|---|---|
| ttc | gag | ctg | gaa | aac | ggc | cgg | aag | aga | atg | ctg | gcc | tct gcc ggc | 3654 |
| Phe | Glu | Leu | Glu | Asn | Gly | Arg | Lys | Arg | Met | Leu | Ala | Ser Ala Gly | |
| 1205 | | | | | 1210 | | | | | 1215 | | | |

| | | | | | | | | | | | | | |
|---|---|---|---|---|---|---|---|---|---|---|---|---|---|
| gaa | ctg | cag | aag | gga | aac | gaa | ctg | gcc | ctg | ccc | tcc | aaa tat gtg | 3699 |
| Glu | Leu | Gln | Lys | Gly | Asn | Glu | Leu | Ala | Leu | Pro | Ser | Lys Tyr Val | |
| 1220 | | | | | 1225 | | | | | 1230 | | | |

| | | | | | | | | | | | | | |
|---|---|---|---|---|---|---|---|---|---|---|---|---|---|
| aac | ttc | ctg | tac | ctg | gcc | agc | cac | tat | gag | aag | ctg | aag ggc tcc | 3744 |
| Asn | Phe | Leu | Tyr | Leu | Ala | Ser | His | Tyr | Glu | Lys | Leu | Lys Gly Ser | |
| 1235 | | | | | 1240 | | | | | 1245 | | | |

| | | | | | | | | | | | | | |
|---|---|---|---|---|---|---|---|---|---|---|---|---|---|
| ccc | gag | gat | aat | gag | cag | aaa | cag | ctg | ttt | gtg | gaa | cag cac aag | 3789 |
| Pro | Glu | Asp | Asn | Glu | Gln | Lys | Gln | Leu | Phe | Val | Glu | Gln His Lys | |
| 1250 | | | | | 1255 | | | | | 1260 | | | |

| | | | | | | | | | | | | | |
|---|---|---|---|---|---|---|---|---|---|---|---|---|---|
| cac | tac | ctg | gac | gag | atc | atc | gag | cag | atc | agc | gag | ttc tcc aag | 3834 |
| His | Tyr | Leu | Asp | Glu | Ile | Ile | Glu | Gln | Ile | Ser | Glu | Phe Ser Lys | |
| 1265 | | | | | 1270 | | | | | 1275 | | | |

| | | | | | | | | | | | | | |
|---|---|---|---|---|---|---|---|---|---|---|---|---|---|
| aga | gtg | atc | ctg | gcc | gac | gct | aat | ctg | gac | aaa | gtg | ctg tcc gcc | 3879 |
| Arg | Val | Ile | Leu | Ala | Asp | Ala | Asn | Leu | Asp | Lys | Val | Leu Ser Ala | |
| 1280 | | | | | 1285 | | | | | 1290 | | | |

| | | | | | | | | | | | | | |
|---|---|---|---|---|---|---|---|---|---|---|---|---|---|
| tac | aac | aag | cac | cgg | gat | aag | ccc | atc | aga | gag | cag | gcc gag aat | 3924 |
| Tyr | Asn | Lys | His | Arg | Asp | Lys | Pro | Ile | Arg | Glu | Gln | Ala Glu Asn | |
| 1295 | | | | | 1300 | | | | | 1305 | | | |

| | | | | | | | | | | | | | |
|---|---|---|---|---|---|---|---|---|---|---|---|---|---|
| atc | atc | cac | ctg | ttt | acc | ctg | acc | aat | ctg | gga | gcc | cct gcc gcc | 3969 |
| Ile | Ile | His | Leu | Phe | Thr | Leu | Thr | Asn | Leu | Gly | Ala | Pro Ala Ala | |
| 1310 | | | | | 1315 | | | | | 1320 | | | |

| | | | | | | | | | | | | | |
|---|---|---|---|---|---|---|---|---|---|---|---|---|---|
| ttc | aag | tac | ttt | gac | acc | acc | atc | gac | cgg | aag | agg | tac acc agc | 4014 |
| Phe | Lys | Tyr | Phe | Asp | Thr | Thr | Ile | Asp | Arg | Lys | Arg | Tyr Thr Ser | |
| 1325 | | | | | 1330 | | | | | 1335 | | | |

| | | | | | | | | | | | | | |
|---|---|---|---|---|---|---|---|---|---|---|---|---|---|
| acc | aaa | gag | gtg | ctg | gac | gcc | acc | ctg | atc | cac | cag | agc atc acc | 4059 |
| Thr | Lys | Glu | Val | Leu | Asp | Ala | Thr | Leu | Ile | His | Gln | Ser Ile Thr | |
| 1340 | | | | | 1345 | | | | | 1350 | | | |

| | | | | | | | | | | | | | |
|---|---|---|---|---|---|---|---|---|---|---|---|---|---|
| ggc | ctg | tac | gag | aca | cgg | atc | gac | ctg | tct | cag | ctg | gga ggc gac | 4104 |
| Gly | Leu | Tyr | Glu | Thr | Arg | Ile | Asp | Leu | Ser | Gln | Leu | Gly Gly Asp | |
| 1355 | | | | | 1360 | | | | | 1365 | | | |

<210> SEQ ID NO 504
<211> LENGTH: 1368
<212> TYPE: PRT
<213> ORGANISM: Homo sapiens

<400> SEQUENCE: 504

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
```

```
                485                 490                 495
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Ala Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Ala Lys Val Leu Thr Arg Ser Asp Lys Ala Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910
```

-continued

Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Ala Ala Tyr Leu Asn Ala Val
                    980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305

```
Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365
```

<210> SEQ ID NO 505
<211> LENGTH: 15
<212> TYPE: DNA
<213> ORGANISM: Homo sapiens

<400> SEQUENCE: 505
cagaagaaga agggc                                              15

<210> SEQ ID NO 506
<211> LENGTH: 51
<212> TYPE: DNA
<213> ORGANISM: Homo sapiens

<400> SEQUENCE: 506
ccaatgggga ggacatcgat gtcacctcca atgactaggg tggtgggcaa c       51

<210> SEQ ID NO 507
<211> LENGTH: 15
<212> TYPE: DNA
<213> ORGANISM: Homo sapiens

<400> SEQUENCE: 507
ctctggccac tccct                                              15

<210> SEQ ID NO 508
<211> LENGTH: 52
<212> TYPE: DNA
<213> ORGANISM: Homo sapiens

<400> SEQUENCE: 508
acatcgatgt cacctccaat gacaagcttg ctagcggtgg gcaaccacaa ac      52

<210> SEQ ID NO 509
<211> LENGTH: 1733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 509
ccgtttaaac aattctgcag gaatctagtt attaatagta atcaattacg gggtcattag    60
ttcatagccc atatatggag ttccgcgtta cataacttac ggtaaatggc ccgcctggct   120
gaccgcccaa cgacccccgc ccattgacgt caataatgac gtatgttccc atagtaacgc   180
caatagggac tttccattga cgtcaatggg tggagtattt acggtaaact gcccacttgg   240
cagtacatca agtgtatcat atgccaagta cgccccctat tgacgtcaat gacgtaaat    300 ggcccgcctg gcattatgcc cagtacatga ccttatggga ctttcctact tggcagtaca   360
tctacgtatt agtcatcgct attaccatgg tcgaggtgag ccccacgttc tgcttcactc   420
tccccatctc cccccctcc ccaccccaa ttttgtattt atttattttt taattatttt    480

| | | | | |
|---|---|---|---|---|
| gtgcagcgat | ggggcgggg | ggggggggg | ggcgcgcgcc | aggcggggcg ggcggggcg | 540 |
| aggggcgggg | cggggcgagg | cggagaggtg | cggcggcagc | caatcagagc ggcgcgctcc | 600 |
| gaaagtttcc | ttttatggcg | aggcggcggc | ggcggcggcc | ctataaaaag cgaagcgcgc | 660 |
| ggcgggcgga | agtcgctgcg | cgctgccttc | gccccgtgcc | ccgctccgcc gccgcctcgc | 720 |
| gccgcccgcc | ccggctctga | ctgaccgcgt | tactcccaca | ggtgagcggg cgggacggcc | 780 |
| cttctcctcc | gggctgtaat | tagcgcttgg | tttaatgacg | gcttgtttct tttctgtggc | 840 |
| tgcgtgaaag | ccttgagggg | ctccggggag | gcccttttgtg | cgggggagc ggctcggggg | 900 |
| gtgcgtgcgt | gtgtgtgtgc | gtggggagcg | ccgcgtgcgg | ctccgcgctg cccggcggct | 960 |
| gtgagcgctg | cgggcgcggc | gcgggcttt | gtgcgctccg | cagtgtgcgc gaggggagcg | 1020 |
| cggccggggg | cggtgccccg | cggtgcgggg | ggggctgcga | ggggaacaaa ggctgcgtgc | 1080 |
| ggggtgtgtg | cgtgggggg | tgagcagggg | gtgtgggcgc | gtcggtcggg ctgcaacccc | 1140 |
| ccctgcaccc | ccctccccga | gttgctgagc | acggcccggc | ttcgggtgcg gggctccgta | 1200 |
| cggggcgtgg | cgcggggctc | gccgtgccgg | gcggggggtg | gcgcaggtg ggggtgccgg | 1260 |
| gcggggcggg | gccgcctcgg | gccggggagg | gctcggggga | ggggcgcggc ggccccgga | 1320 |
| gcgccggcgg | ctgtcgaggc | gcggcgagcc | gcagccattg | cctttatgg taatcgtgcg | 1380 |
| agagggcgca | gggacttcct | ttgtcccaaa | tctgtgcgga | ccgaaatct gggaggcgcc | 1440 |
| gccgcaccc | ctctagcggg | cgcggggcga | agcggtgcgg | cgccggcagg aaggaaatgg | 1500 |
| gcggggaggg | ccttcgtgcg | tcgccgcgcc | gccgtcccct | tctccctctc cagcctcggg | 1560 |
| gctgtccgcg | ggggacggc | tgccttcggg | ggggacgggg | cagggcgggg ttcggcttct | 1620 |
| ggcgtgtgac | cggcggctct | agagcctctg | ctaaccatgt | tcatgccttc ttctttttcc | 1680 |
| tacagctcct | gggcaacgtg | ctggttattg | tgctgtctca | tcattttggc aaa | 1733 |

<210> SEQ ID NO 510
<211> LENGTH: 4269
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 510

| | | | | |
|---|---|---|---|---|
| atggactata | aggaccacga | cggagactac | aaggatcatg | atattgatta caaagacgat | 60 |
| gacgataaga | tggcccccaaa | gaagaagcgg | aaggtcggta | tccacggagt cccagcagcc | 120 |
| gacaagaagt | acagcatcgg | cctggacatc | ggcaccaact | ctgtgggctg gccgtgatc | 180 |
| accgacgagt | acaaggtgcc | cagcaagaaa | ttcaaggtgc | tgggcaacac cgaccggcac | 240 |
| agcatcaaga | agaacctgat | cggagccctg | ctgttcgaca | gcggcgaaac agccgaggcc | 300 |
| acccggctga | agagaaccgc | cagaagaaga | tacaccagac | ggaagaaccg gatctgctat | 360 |
| ctgcaagaga | tcttcagcaa | cgagatggcc | aaggtggacg | acagcttctt ccacagactg | 420 |
| gaagagtcct | tcctggtgga | agaggataag | aagcacgagc | ggcaccccat cttcggcaac | 480 |
| atcgtggacg | aggtggccta | ccacgagaag | tacccaccca | tctaccacct gagaaagaaa | 540 |
| ctggtggaca | gcaccgacaa | ggccgacctg | cggctgatct | atctggccct ggcccacatg | 600 |
| atcaagttcc | ggggccactt | cctgatcgag | ggcgacctga | accccgacaa cagcgacgtg | 660 |
| gacaagctgt | tcatccagct | ggtgcagacc | tacaaccagc | tgttcgagga aaaccccatc | 720 |
| aacgccagcg | gcgtggacgc | caaggccatc | ctgtctgcca | gactgagcaa gagcagacgg | 780 |

```
ctggaaaatc tgatcgccca gctgccggc  gagaagaaga atggcctgtt cggaaacctg    840
attgccctga gcctgggcct gacccccaac ttcaagagca acttcgacct ggccgaggat    900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag  cgcctctatg   1080 atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc accagatcc  acctgggaga gctgcacgcc   1380
attctgcggc ggcaggaaga ttttacccca ttcctgaagg acaaccggga aaagatcgag   1440
aagatcctga ccttccgcat cccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aggaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgcacc tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220 ctgacctttta agaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa  catcgtgatc   2400 gaaatggcca gagaaaacca gaccacccag aagggacaga gaacagccg  cgagagaatg   2460 aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga aggcggcct  gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
```

```
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga acagcgataa gctgatcgcc    3480
agaaagaagg actgggaccc taagaagtac ggcggcttcg acagcccac cgtgcctat     3540 tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggcggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaag                                                            4269

<210> SEQ ID NO 511
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 511
ggaagcggag ccactaactt ctccctgttg aaacaagcag gggatgtcga agagaatccc     60
gggccagtga gcaagggcga ggagctgttc accggggtgg tgcccatcct ggtcgagctg    120
gacggcgacg taaacggcca agttcagc gtgtccggcg agggcgaggg cgatgccacc     180
tacggcaagc tgaccctgaa gttcatctgc accaccggca agctgcccgt gccctggccc    240
accctcgtga ccaccctgac ctacggcgtg cagtgcttca gccgctaccc cgaccacatg    300
aagcagcacg acttcttcaa gtccgccatg cccgaaggct acgtccagga gcgcaccatc    360
ttcttcaagg acgacggcaa ctacaagacc cgcgccgagg tgaagttcga gggcgacacc    420
ctggtgaacc gcatcgagct gaagggcatc gacttcaagg aggacggcaa catcctgggg    480
cacaagctgg agtacaacta caacagccac aacgtctata tcatggccga caagcagaag    540
aacggcatca aggtgaactt caagatccgc cacaacatcg aggacggcag cgtgcagctc    600
gccgaccact accagcagaa cacccccatc ggcgacggcc ccgtgctgct gcccgacaac    660
cactacctga gcacccagtc cgccctgagc aaagacccca acgagaagcg cgatcacatg    720
gtcctgctgg agttcgtgac cgccgccggg atcactctcg gcatggacga gctgtacaag    780

<210> SEQ ID NO 512
<211> LENGTH: 597
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 512
cgataatcaa cctctggatt acaaaatttg tgaaagattg actggtattc ttaactatgt     60
tgctcctttt acgctatgtg gatacgctgc tttaatgcct ttgtatcatg ctattgcttc    120
ccgtatggct ttcattttct cctccttgta taaatcctgg ttgctgtctc tttatgagga    180
gttgtggccc gttgtcaggc aacgtggcgt ggtgtgcact gtgtttgctg acgcaacccc    240
cactggttgg ggcattgcca ccacctgtca gctccttttcc gggactttcg ctttccccct    300
ccctattgcc acggcggaac tcatcgccgc ctgccttgcc cgctgctgga caggggctcg    360
gctgttgggc actgacaatt ccgtggtgtt gtcgggaaaa tcatcgtcct ttccttggct    420
gctcgcctgt gttgccacct ggattctgcg cgggacgtcc ttctgctacg tcccttcggc    480
cctcaatcca gcggaccttc cttcccgcgg cctgctgccg gctctgcggc ctcttccgcg    540
tcttcgcctt cgccctcaga cgagtcggat ctcccttgg gccgcctccc cgcatcg       597

<210> SEQ ID NO 513
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 513
cgacctcgac tgtgccttct agttgccagc catctgttgt ttgcccctcc cccgtgcctt     60
ccttgaccct ggaaggtgcc actcccactg tcctttccta ataaaatgag gaaattgcat    120
cgcattgtct gagtaggtgt cattctattc tggggggtgg ggtggggcag gacagcaagg    180
gggaggattg ggaagacaat ggcaggcatg                                     210

<210> SEQ ID NO 514
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other

<400> SEQUENCE: 514
ataacttcgt ataatgtatg ctatacgaag ttattcgcga tgaataaatg aaagcttgca     60
gatctgcgac tctagaggat ctgcgactct agaggatcat aatcagccnt accacatttt    120
gtagaggttt tactngcttt aaaaaacctc ccacacctcc ccctgaacct gaaacataaa    180
atgaatgcaa ttgttgttgt taacttgttt attgcagctt ataatggtta caaataaagc    240
aatagcatca caaatttcac aaataaagca ttttttcac tgcattctag ttgtggttg    300
tccaaactca tcaatgtatc ttatcatgtc tggatctgcg actctagagg atcataatca    360
gccataccac atttgtagag gttttacttg ctttaaaaaa cctcccacac ctcccctga    420
```

```
acctgaaaca taaaatgaat gcaattgttg ttgttaactt gtttattgca gcttataatg    480
gttacaaata aagcaatagc atcacaaatt tcacaaataa agcattttt tcactgcatt     540 ctagttgtgg tttgtccaaa ctcatcaatg tatcttatca tgtctggatc tgcgactcta    600
gaggatcata atcagccata ccacatttgt agaggtttta cttgctttaa aaaacctccc    660
acacctcccc ctgaacctga aacataaaat gaatgcaatt gttgttgtta acttgtttat    720
tgcagcttat aatggttaca aataaagcaa tagcatcaca aatttcacaa ataaagcatt    780 ttttcactg cattctagtt gtggtttgtc caaactcatc aatgtatctt atcatgtctg     840
gatccccatc aagctgatcc ggaacccta atataacttc gtataatgta tgctatacga    900
agttat                                                              906
```

<210> SEQ ID NO 515
<211> LENGTH: 1079
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 515

```
caggccctcc gagcgtggtg gagccgttct gtgagacagc cgggtacgag tcgtgacgct    60
ggaaggggca gcgggtggt gggcaggaat gcggtccgcc ctgcagcaac cggagggga     120 gggagaaggg agcggaaaag tctccaccgg acgcggccat ggctcggggg ggggggggca   180
gcggaggagc gcttccggcc gacgtctcgt cgctgattgg cttcttttcc tcccgccgtg    240
tgtgaaaaca caaatggcgt gttttggttg gcgtaaggcg cctgtcagtt aacggcagcc    300
ggagtgcgca gccgccggca gcctcgctct gcccactggg tggggcggga ggtaggtggg    360
gtgaggcgag ctggacgtgc gggcgcggtc ggcctctggc ggggcggggg aggggaggga    420
gggtcagcga aagtagctcg cgcgcgagcg ccgcccacc ctccccttcc tctggggag     480 tcgtttacc cgccgccggc cgggcctcgt cgtctgattg gctctcgggg cccagaaaac    540
tggcccttgc cattggctcg tgttcgtgca agttgagtcc atccgccggc cagcgggggc    600
ggcgaggagg cgctcccagg ttccggccct cccctcggcc ccgcgccgca gagtctggcc    660
gcgcgcccct gcgcaacgtg gcaggaagcg cgcgctgggg gcggggacgg gcagtagggc    720
tgagcggctg cggggcgggt gcaagcacgt ttccgacttg agttgcctca agagggcgt    780 gctgagccag acctccatcg cgcactccgg ggagtggagg gaaggagcga gggctcagtt    840
gggctgtttt ggaggcagga agcacttgct ctcccaaagt cgctctgagt tgttatcagt    900
aagggagctg cagtggagta ggcggggaga aggccgcacc cttctccgga gggggaggg    960 gagtgttgca ataccttct gggagttctc tgctgcctcc tggcttctga ggaccgccct   1020
gggcctggga gaatccttc ccctcttcc ctcgtgatct gcaactccag tctttctag     1079
```

<210> SEQ ID NO 516
<211> LENGTH: 4336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 516

```
agatgggcgg gagtcttctg ggcaggctta aaggctaacc tggtgtgtgg gcgttgtcct    60
```

```
gcagggggaat tgaacaggtg taaaattgga gggacaagac ttcccacaga tttcggttt      120 tgtcgggaag ttttttaata ggggcaaata aggaaaatgg gaggataggt agtcatctgg      180
ggttttatgc agcaaaacta caggttatta ttgcttgtga tccgcctcgg agtattttcc      240
atcgaggtag attaaagaca tgctcacccg agttttatac tctcctgctt gagatcctta      300
ctacagtatg aaattacagt gtcgcgagtt agactatgta agcagaattt taatcatttt      360
taaagagccc agtacttcat atccatttct cccgctcctt ctgcagcctt atcaaaaggt      420
attttagaac actcattta gccccatttt catttattat actggcttat ccaacccta       480 gacagagcat tggcattttc cctttcctga tcttagaagt ctgatgactc atgaaaccag      540
acagattagt tacatacacc acaaatcgag gctgtagctg gggcctcaac actgcagttc      600
ttttataact ccttagtaca cttttttgttg atcctttgcc ttgatcctta attttcagtg     660
tctatcacct ctcccgtcag gtggtgttcc acatttgggc ctattctcag tccagggagt      720
tttacaacaa tagatgtatt gagaatccaa cctaaagctt aactttccac tcccatgaat      780
gcctctctcc tttttctcca tttataaact gagctattaa ccattaatgg tttccaggtg      840
gatgtctcct cccccaatat tacctgatgt atcttacata ttgccaggct gatattttaa      900
gacattaaaa ggtatatttc attattgagc cacatgtgtat tgattactgc ttactaaaat    960
tttgtcattg tacacatctg taaaaggtgg ttcctttttgg aatgcaaagt tcaggtgttt     1020
gttgtctttc ctgacctaag gtcttgtgag cttgtatttt ttctattta gcagtgcttt      1080 ctcttggact ggcttgactc atggcattct acacgttatt gctggtctaa atgtgatttt      1140
gccaagcttc ttcaggacct ataattttgc ttgacttgta gccaaacaca agtaaaatga     1200
ttaagcaaca aatgtatttg tgaagcttgg ttttaggtt gttgtgttgt gtgtgcttgt      1260
gctctataat aatactatcc aggggctgga gaggtggctc ggagttcaag agcacagact      1320
gctcttccag aagtcctgag ttcaattccc agcaaccaca tggtggctca caaccatctg     1380
taatgggatc tgatgccctc ttctggtgtg tctgaagacc acaagtgtat tcacattaaa     1440
taaataaatc ctccttcttc ttctttttttt tttttttaaa gagaatactg tctccagtag    1500
aatttactga agtaatgaaa cttttgtgt ttgttccaat atggtagcca ataatcaaat      1560
tactctttaa gcactggaaa tgttaccaag gaactaattt ttatttgaag tgtaactgtg     1620
gacagaggag ccataactgc agacttgtgg gatacagaag accaatgcag actttaatgt    1680
cttttctctt acactaagca ataaagaaat aaaaattgaa cttctagtat cctatttgtt     1740
taaactgcta gctttactta acttttgtgc ttcatctata caaagctgaa agctaagtct    1800
gcagccatta ctaaacatga aagcaagtaa tgataatttt ggatttcaaa aatgtagggc    1860
cagagtttag ccagccagtg gtggtgcttg cctttatgcc tttaatccca gcactctgga    1920
ggcagagaca ggcagatctc tgagtttgag cccagcctgg tctacacatc aagttctatc    1980
taggatagcc aggaatacac acagaaaccc tgttggggag gggggctctg agatttcata    2040
aaattataat tgaagcattc cctaatgagc cactatggat gtggctaaat ccgtctacct    2100
ttctgatgag atttgggtat tattttttct gtctctgctg ttggttgggt cttttgacac    2160
tgtgggcttt ctttaaagcc tccttcctgc catgtggtct cttgtttgct actaacttcc    2220
catggcttaa atggcatggc ttttgccctt ctaagggcag ctgctgagat ttgcagcctg    2280
atttccaggg tgggggttggg aaatctttca aacactaaaa ttgtccttta atttttttt     2340 taaaaaatgg gttatataat aaacctcata aaatagttat gaggagtgag gtggactaat    2400
attaaatgag tccctcccct ataaaagagc tattaaggct ttttgtctta tacttaactt    2460
```

```
ttttttttaaa tgtggtatct ttagaaccaa gggtcttaga gttttagtat acagaaactg    2520
ttgcatcgct taatcagatt ttctagtttc aaatccagag aatccaaatt cttcacagcc    2580
aaagtcaaat taagaatttc tgacttttaa tgttaatttg cttactgtga atataaaaat    2640
gatagctttt cctgaggcag ggtctcacta tgtatctctg cctgatctgc aacaagatat    2700
gtagactaaa gttctgcctg cttttgtctc ctgaatacta aggttaaaat gtagtaatac    2760
ttttggaact tgcaggtcag attctttat aggggacaca ctaagggagc ttgggtgata     2820
gttggtaaat gtgtttaagt gatgaaaact tgaattatta tcaccgcaac ctactttta    2880 aaaaaaaaag ccaggcctgt tagagcatgc ttaagggatc cctaggactt gctgagcaca    2940
caagagtagt tacttggcag gctcctggtg agagcatatt tcaaaaaaca aggcagacaa    3000
ccaagaaact acagttaagg ttacctgtct ttaaaccatc tgcatataca cagggatatt    3060
aaaatattcc aaataatatt tcattcaagt tttcccccat caaattggga catggatttc    3120
tccggtgaat aggcagagtt ggaaactaaa caaatgttgg ttttgtgatt tgtgaaattg    3180
ttttcaagtg atagttaaag cccatgagat acagaacaaa gctgctattt cgaggtctct    3240
tggtttatac tcagaagcac ttcttgggt ttccctgcac tatcctgatc atgtgctagg     3300
cctaccttag gctgattgtt gttcaaataa acttaagttt cctgtcaggt gatgtcatat    3360
gatttcatat atcaaggcaa acatgttat atatgttaaa catttgtact taatgtgaaa     3420
gttaggtctt tgtgggtttg attttttaatt ttcaaaacct gagctaaata agtcattttt    3480
acatgtctta catttggtgg aattgtataa ttgtggtttg caggcaagac tctctgacct    3540 agtaaccta cctatagagc actttgctgg gtcacaagtc taggagtcaa gcatttcacc     3600
ttgaagttga acgttttgt tagtgtatac tagtttatat gttggaggac atgtttatcc     3660
agaagatatt caggactatt tttgactggg ctaaggaatt gattctgatt agcactgtta    3720
gtgagcattg agtggccttt aggcttgaat tggagtcact tgtatatctc aaataatgct    3780 ggccttttt aaaagcccctt gttctttatc accctgtttt ctacataatt tttgttcaaa    3840
gaaatacttg tttggatctc cttttgacaa caatagcatg ttttcaagcc atatttttt     3900 tccttttttt tttttttttt ggttttttcga gacagggttt ctctgtatag ccctggctgt    3960
cctggaactc actttgtaga ccaggctggc ctcgaactca gaaatccgcc tgcctctgcc    4020
tcctgagtgc cgggattaaa ggcgtgcacc accacgcctg gctaagttgg atattttgtt    4080
atataactat aaccaatact aactccactg ggtggatttt taattcagtc agtagtctta    4140
agtggtcttt attggccctt cattaaaatc tactgttcac tctaacagag gctgttggta    4200
ctagtggcac ttaagcaact tcctacggat atactagcag attaagggtc agggatagaa    4260
actagtctag cgtttgtat acctaccagc tttatactac cttgttctga tagaaatatt     4320
tcaggacatc tagctt                                                    4336
```

<210> SEQ ID NO 517
<211> LENGTH: 1846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 517

```
aattctaccg ggtaggggag gcgcttttcc caaggcagtc tggagcatgc gctttagcag     60
ccccgctggg cacttggcgc tacacaagtg gcctctggcc tcgcacacat tccacatcca    120
```

-continued

```
ccggtaggcg ccaaccggct ccgttctttg gtggcccctt cgcgccacct tctactcctc    180
ccctagtcag gaagttcccc cccgccccgc agctcgcgtc gtgcaggacg tgacaaatgg    240
aagtagcacg tctcactagt ctcgtgcaga tggacagcac cgctgagcaa tggaagcggg    300
taggcctttg gggcagcggc caatagcagc tttgctcctt cgctttctgg gctcagaggc    360
tgggaagggg tgggtccggg ggcgggctca ggggcgggct caggggcggg gcgggcgccc    420
gaaggtcctc cggaggcccg gcattctgca cgcttcaaaa gcgcacgtct gccgcgctgt    480
tctcctcttc ctcatctccg ggcctttcga cctgcaatcg ccgctagcga agttcctatt    540
ctctagaaag tataggaact tcgccaccat gggatcggcc attgaacaag atggattgca    600
cgcaggttct ccggccgctt gggtggagag gctattcggc tatgactggg cacaacagac    660
aatcggctgc tctgatgccg ccgtgttccg gctgtcagcg caggggcgcc cggttctttt    720
tgtcaagacc gacctgtccg gtgccctgaa tgaactgcag gacgaggcag cgcggctatc    780
gtggctggcc acgacgggcg ttccttgcgc agctgtgctc gacgttgtca ctgaagcggg    840
aagggactgg ctgctattgg gcgaagtgcc ggggcaggat ctcctgtcat ctcaccttgc    900
tcctgccgag aaagtatcca tcatggctga tgcaatgcgg cggctgcata cgcttgatcc    960
ggctacctgc ccattcgacc accaagcgaa acatcgcatc gagcgagcac gtactcggat   1020
ggaagccggt cttgtcgatc aggatgatct ggacgaagag catcagggc tcgcgccagc   1080 cgaactgttc gccaggctca aggcgcgcat gcccgacggc gatgatctcg tcgtgaccca   1140
tggcgatgcc tgcttgccga atatcatggt ggaaaatggc cgcttttctg gattcatcga   1200
ctgtggccgg ctgggtgtgg cggaccgcta tcaggacata gcgttggcta cccgtgatat   1260
tgctgaagag cttggcggcg aatgggctga ccgcttcctc gtgctttacg gtatcgccgc   1320
tcccgattcg cagcgcatcg ccttctatcg ccttcttgac gagttcttct gagggatcc   1380 gctgtaagtc tgcagaaatt gatgatctat aaacaataa agatgtccac taaaatggaa   1440 gttttttcctg tcatactttg ttaagaaggg tgagaacaga gtacctacat tttgaatgga   1500
aggattggag ctacggggt ggggtgggg tgggattaga taaatgcctg ctctttactg   1560
aaggctcttt actattgctt tatgataatg tttcatagtt ggatatcata atttaaacaa   1620
gcaaaaccaa attaagggcc agctcattcc tcccactcat gatctataga tctatagatc   1680
tctcgtggga tcattgtttt tctcttgatt cccactttgt ggttctaagt actgtggttt   1740
ccaaatgtgt cagtttcata gcctgaagaa cgagatcagc agcctctgtt ccacatacac   1800
ttcattctca gtattgtttt gccaagttct aattccatca gaaagc              1846
```

<210> SEQ ID NO 518
<211> LENGTH: 1519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 518

```
taccgggtag gggaggcgct tttcccaagg cagtctggag catgcgcttt agcagccccg     60
ctgggcactt ggcgctacac aagtggcctc tggcctcgca cacattccac atccaccggt    120
aggcgccaac cggctccgtt ctttggtggc cccttcgcgc caccttctac tcctccccta    180
gtcaggaagt tcccccccgc cccgcagctc gcgtcgtgca ggacgtgaca aatgaagta    240 gcacgtctca ctagtctcgt gcagatggac agcaccgctg agcaatggaa gcgggtaggc    300
```

```
ctttggggca gcggccaata gcagctttgc tccttcgctt tctgggctca gaggctggga    360 agggtgggt ccggggcgg gctcagggc gggctcaggg gcgggcggg cgcccgaagg        420 tcctccggag gcccggcatt ctgcacgctt caaaagcgca cgtctgccgc gctgttctcc    480
tcttcctcat ctccgggcct ttcgacctgc aggtcctcgc catggatcct gatgatgttg    540
ttgattcttc taaatctttt gtgatggaaa acttttcttc gtaccacggg actaaacctg    600
gttatgtaga ttccattcaa aaagtatac aaaagccaaa atctggtaca caaggaaatt     660
atgacgatga ttggaaaggg ttttatagta ccgacaataa atacgacgct gcgggatact    720
ctgtagataa tgaaacccg ctctctggaa aagctggagg cgtggtcaaa gtgacgtatc     780
caggactgac gaaggttctc gcactaaaag tggataatgc cgaaactatt aagaaagagt    840
taggtttaag tctcactgaa ccgttgatgg agcaagtcgg aacggaagag tttatcaaaa    900
ggttcggtga tggtgcttcg cgtgtagtgc tcagccttcc cttcgctgag gggagttcta    960
gcgttgaata tattaataac tgggaacagg cgaaagcgtt aagcgtagaa cttgagatta    1020
attttgaaac ccgtggaaaa cgtggccaag atgcgatgta tgagtatatg gctcaagcct    1080
gtgcaggaaa tcgtgtcagg cgatctcttt gtgaaggaac cttacttctg tggtgtgaca    1140
taattggaca aactacctac agagatttaa agctctaagg taaatataaa attttaagt    1200 gtataatgtg ttaaactact gattctaatt gtttgtgtat tttagattcc aacctatgga    1260
actgatgaat gggagcagtg gtggaatgca gatcctagag ctcgctgatc agcctcgact    1320
gtgccttcta gttgccagcc atctgttgtt tgccctccc ccgtgccttc cttgaccctg     1380
gaaggtgcca ctcccactgt cctttcctaa taaatgagg aaattgcatc gcattgtctg     1440
agtaggtgtc attctattct gggggtggg gtgggcagg acagcaaggg ggaggattgg      1500
gaagacaata gcaggcatg                                                  1519

<210> SEQ ID NO 519
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
gagggcctat ttcccatgat tcc                                              23

<210> SEQ ID NO 520
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
cttgtggaaa ggacgaaaca cc                                               22

<210> SEQ ID NO 521
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (4)..(23)
<223> OTHER INFORMATION: a, c, t, g, unknown or other

<400> SEQUENCE: 521
aacnnnnnnn nnnnnnnnnn nnnggtgttt cgtcctttcc acaag                45

<210> SEQ ID NO 522
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
cctgagtgtt gaggccccag tggctgct                                   28

<210> SEQ ID NO 523
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
acgagggcag agtgctgctt gctgctggcc aggcccc                         37

<210> SEQ ID NO 524
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
catcaggctc tcagctcagc ctgagtgttg aggccctgct ggccaggccc ctgcgtgggc  60
ccaagctg                                                         68

<210> SEQ ID NO 525
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
gagggcctat ttcccatgat tccttca                                    27

<210> SEQ ID NO 526
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (84)..(103)
<223> OTHER INFORMATION: a, c, t, g, unknown or other

<400> SEQUENCE: 526
aaaaaaagca ccgactcggt gccactttt caagttgata acggactagc cttatttaa   60 cttgctattt ctagctctaa aacnnnnnnn nnnnnnnnnn nnnggtgttt cgtcctttcc 120

```
acaag                                                                    125

<210> SEQ ID NO 527
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(28)
<223> OTHER INFORMATION: a, c, t, g, unknown or other

<400> SEQUENCE: 527
gaaacaccnn nnnnnnnnnn nnnnnnnngt tttagagcta gaaatagcaa gttaaaataa          60
ggctagtccg ttatcaactt gaaaaagtgg caccgagtcg gtgcttttt t                  111

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
agctgtttta ctggtcggct                                                     20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
aatggataca cctggtcgaa                                                     20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
caatggatac acctggtcga                                                     20

<210> SEQ ID NO 531
<211> LENGTH: 68
<212> TYPE: DNA
<213> ORGANISM: Homo sapiens

<400> SEQUENCE: 531
accatgtata ccacttgggc tttggcagta gctaactgca ctaaatataa tataaggagg         60
gttttatg                                                                  68
```

CRISPR-CAS NICKASE SYSTEMS, METHODS AND COMPOSITIONS FOR SEQUENCE MANIPULATION IN EUKARYOTES

RELATED APPLICATIONS AND INCORPORATION BY REFERENCE

This application is a continuation of U.S. application Ser. No. 14/105,031 filed Dec. 12, 2013, which claims priority to U.S. provisional patent applications 61/736,527, 61/748,427, 61/791,409 and 61/835,931 all entitled SYSTEMS METHODS AND COMPOSITIONS FOR SEQUENCE MANIPULATION filed on Dec. 12, 2012, Jan. 2, 2013, Mar. 15, 2013 and Jun. 17, 2013, respectively. This application also claims priority to U.S. provisional patent application 61/802,174 entitled ENGINEERING AND OPTIMIZATION OF SYSTEMS, METHODS AND COMPOSITIONS FOR SEQUENCE MANIPULATION, filed on Mar. 15, 2013.

Reference is made to U.S. provisional patent applications 61/758,468; 61/769,046; 61/802,174; 61/806,375; 61/814,263; 61/819,803 and 61/828,130, each entitled ENGINEERING AND OPTIMIZATION OF SYSTEMS, METHODS AND COMPOSITIONS FOR SEQUENCE MANIPULATION, filed on Jan. 30, 2013; Feb. 25, 2013; Mar. 15, 2013; Mar. 28, 2013; Apr. 20, 2013; May 6, 2013 and May 28, 2013 respectively. Reference is also made to U.S. provisional patent applications 61/835,936, 61/836,127, 61/836,101, 61/836,080 and 61/835,973 each filed Jun. 17, 2013. Reference is also made to U.S. provisional patent application 61/842,322 and U.S. patent application Ser. No. 14/054,414, entitled CRISPR-CAS SYSTEMS AND METHODS FOR ALTERING EXPRESSION OF GENE PRODUCTS filed on Jul. 2, 2013 and Oct. 15, 2013 respectively.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under the NIH Pioneer Award DP1MH 100706, awarded by the National Institutes of Health. The government has certain rights in the invention.

FIELD OF THE INVENTION

The present invention generally relates to systems, methods and compositions used for the control of gene expression involving sequence targeting, such as genome perturbation or gene-editing, that may use vector systems related to Clustered Regularly Interspaced Short Palindromic Repeats (CRISPR) and components thereof.

SEQUENCE LISTING

The instant application contains a Sequence Listing which has been submitted electronically in ASCII format and is hereby incorporated by reference in its entirety. Said ASCII copy, created on Feb. 13, 2014, is named 44790.06.2003_SL.txt and is 316,352 bytes in size.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit 3-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a vector comprising a regulatory element operably linked to an enzyme-coding sequence encoding a CRISPR enzyme comprising one or more nuclear localization sequences. In some embodiments, said regulatory element drives transcription of the CRISPR enzyme in a eukaryotic cell such that said CRISPR enzyme accumulates in a detectable amount in the nucleus of the eukaryotic cell. In some embodiments, the regulatory element is a polymerase II promoter. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes* or *S. thermophilus* Cas9, and may include mutated Cas9 derived from these organisms. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity.

In one aspect, the invention provides a CRISPR enzyme comprising one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumnoniae, S. pyogenes* or *S. thermophilus* Cas9, and may include mutated Cas9 derived from these organisms. The enzyme may be a Cas9 homolog or ortholog. In some embodiments, the CRISPR enzyme lacks the ability to cleave one or more strands of a target sequence to which it binds.

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumnoniae, S. pyogenes* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25 or between 15-20 nucleotides in length.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more prokaryotic cell(s) by introducing one or more mutations in a gene in the one or more prokaryotic cell (s), the method comprising: introducing one or more vectors into the prokaryotic cell (s), wherein the one or more vectors drive expression of one or more of: a CRISPR enzyme, a guide sequence linked to a tracr mate sequence, a tracr sequence, and a editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more prokaryotic cell(s) in which one or more mutations have been introduced to be selected. In a preferred embodiment, the CRISPR enzyme is Cas9. In another aspect of the invention the cell to be selected may be a eukaryotic cell. Aspects of the invention allow for selection of specific cells without requiring a selection marker or a two-step process that may include a counter-selection system.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-F show an exemplary CRISPR system, a possible mechanism of action, an example adaptation for expression in eukaryotic cells, and results of tests assessing nuclear localization and CRISPR activity. FIG. 2C discloses SEQ ID NOS 281-282, respectively, in order of appearance. FIG. 2E discloses SEQ ID NOS 283-285, respectively, in order of appearance. FIG. 2F discloses SEQ ID NOS 286-290, respectively, in order of appearance.

FIGS. 4A-D show results of an evaluation of SpCas9 specificity for an example target. FIG. 4A discloses SEQ ID NOS 301, 284 and 302-312, respectively, in order of appearance. FIG. 4C discloses SEQ ID NO: 301.

FIGS. 5A-G show an exemplary vector system and results for its use in directing homologous recombination in eukaryotic cells. FIG. 5E discloses SEQ ID NO: 313. FIG. 5F discloses SEQ ID NOS 314-315, respectively, in order of appearance. FIG. 5G discloses SEQ ID NOS 316-320, respectively, in order of appearance.

FIG. 6 provides a table of protospacer sequences (SEQ ID NOS 33, 32, 31, 324-329, 35, 34 and 332-336, respectively, in order of appearance) and summarizes modification efficiency results for protospacer targets designed based on exemplary *S. pyogenes* and *S. thermophilus* CRISPR systems with corresponding PAMs against loci in human and mouse genomes. Cells were transfected with Cas9 and either pre-crRNA/tracrRNA or chimeric RNA, and analyzed 72 hours after transfection. Percent indels are calculated based on Surveyor assay results from indicated cell lines (N=3 for all protospacer targets, errors are S.E.M., N.D. indicates not detectable using the Surveyor assay, and N.T. indicates not tested in this study).

FIGS. 7A-C show a comparison of different tracrRNA transcripts for Cas9-mediated gene targeting. FIG. 7A discloses SEQ ID NOS 337-338, respectively, in order of appearance.

FIGS. 9A-B show exemplary bicistronic expression vectors for expression of CRISPR system elements in eukaryotic cells. FIG. 9A discloses SEQ ID NOS 339-341, respectively, in order of appearance. FIG. 9B discloses SEQ ID NOS 342-344, respectively, in order of appearance.

FIG. 10A-D shows a bacterial plasmid transformation interference assay, expression cassettes and plasmids used therein, and transformation efficiencies of cells used therein. FIG. 10A discloses SEQ ID NOS 345-347, respectively, in order of appearance. FIG. 10B shows expression cassettes and plasmids. FIG. 10C shows transformation of *E. coli* with expression cassettes and plasmids. FIG. 10D shows transformation efficiencies of cells used therein.

FIGS. 11A-C show histograms of distances between adjacent *S. pyogenes* SF370 locus 1 PAM (NGG) (FIG. 10A) and *S. thermophilus* LMD9 locus 2 PAM (NNAGAAW) (FIG. 10B) in the human genome; and distances for each PAM by chromosome (Chr) (FIG. 10C).

FIGS. 12A-C show an exemplary CRISPR system, an example adaptation for expression in eukaryotic cells, and results of tests assessing CRISPR activity. FIG. 12B discloses SEQ ID NOS 348-349, respectively, in order of appearance. FIG. 12C discloses SEQ ID NO: 350.

FIGS. 13A-C show exemplary manipulations of a CRISPR system for targeting of genomic loci in mammalian cells. FIG. 13A discloses SEQ ID NO: 351. FIG. 13B discloses SEQ ID NOS 352-354, respectively, in order of appearance.

FIGS. 14A-B show the results of a Northern blot analysis of crRNA processing in mammalian cells. FIG. 14A discloses SEQ ID NO: 355.

FIG. 15A-B shows an exemplary selection of protospacers in the human PVALB and mouse Th loci. FIG. 15A discloses SEQ ID NO: 356. FIG. 15B discloses SEQ ID NO: 357.

FIG. 17 provides a table of sequences for primers and probes (SEQ ID NOS 36-39 and 358-365, respectively, in order of appearance) used for Surveyor, RFLP, genomic sequencing, and Northern blot assays.

FIG. 18A discloses SEQ ID NO: 366, respectively, in order of appearance.

FIGS. 19A-B show a graphical representation of the results of SURVEYOR assays for CRISPR system activity in eukaryotic cells.

FIG. 23A-B shows that Cas9 nuclease activity against endogenous targets may be exploited for genome editing. (a) Concept of genome editing using the CRISPR system. The CRISPR targeting construct directed cleavage of a chromosomal locus and was co-transformed with an editing template that recombined with the target to prevent cleavage. Kanamycin-resistant transformants that survived CRISPR attack contained modifications introduced by the editing template. tracr, trans-activating CRISPR RNA; aphA-3, kanamycin resistance gene. (b) Transformation of crR6M DNA in $R6^{8232.5}$ cells with no editing template, the R6 wild-type srtA or the R6370.1 editing templates. Recombination of either R6 srtA or $R6^{370.1}$ prevented cleavage by Cas9. Transformation efficiency was calculated as colony forming units (cfu) per µg of crR6M DNA; the mean values with standard deviations from at least three independent experiments are shown. PCR analysis was performed on 8 clones in each transformation. "Un." indicates the unedited srtA locus of strain $R6^{8232.5}$; "Ed." shows the editing template. $R6^{8232.5}$ and $R6^{370.1}$ targets are distinguished by restriction with EaeI.

FIG. 24A-C shows analysis of PAM and seed sequences that eliminate Cas9 cleavage. (a) PCR products with randomized PAM sequences or randomized seed sequences were transformed in crR6 cells (SEQ ID NOS 467-471, respectively, in order of appearance). These cells expressed Cas9 loaded with a crRNA that targeted a chromosomal region of $R6^{8232.5}$ cells (highlighted in pink) that is absent from the R6 genome. More than 2×105 chloramphenicol-resistant transformants, carrying inactive PAM or seed sequences, were combined for amplification and deep sequencing of the target region. (b) Relative proportion of number of reads after transformation of the random PAM constructs in crR6 cells (compared to number of reads in R6 transformants). The relative abundance for each 3-nucleotide PAM sequence is shown. Severely underrepresented sequences (NGG) are shown in red; partially underrepresented one in orange (NAG) (c) Relative proportion of number of reads after transformation of the random seed sequence constructs in crR6 cells (compared to number of reads in R6 transformants). The relative abundance of each nucleotide for each position of the first 20 nucleotides of the protospacer sequence is shown (SEQ ID NO: 472). High abundance indicates lack of cleavage by Cas9, i.e. a CRISPR inactivating mutation. The grey line shows the level of the WT sequence. The dotted line represents the level above which a mutation significantly disrupts cleavage (See section "Analysis of deep sequencing data" in Example 5)

FIG. 25A-F shows introduction of single and multiple mutations using the CRISPR system in S. pneumoniae. (a) Nucleotide and amino acid sequences of the wild-type and edited (green nucleotides; underlined amino acid residues) bgaA. The protospacer, PAM and restriction sites are shown (SEQ ID NOS 473-477 and 474, respectively, in order of appearance). (b) Transformation efficiency of cells transformed with targeting constructs in the presence of an editing template or control. (c) PCR analysis for 8 transformants of each editing experiment followed by digestion with BtgZI (R→A) and TseI (NE→AA). Deletion of bgaA was revealed as a smaller PCR product. (d) Miller assay to measure the β-galactosidase activity of WT and edited strains. (e) For a single-step, double deletion the targeting construct contained two spacers (in this case matching srtA and bgaA) and was co-transformed with two different editing templates (f) PCR analysis for 8 transformants to detect deletions in srtA and bgaA loci. 6/8 transformants contained deletions of both genes.

FIG. 26A-D provides mechanisms underlying editing using the CRISPR system. (a) A stop codon was introduced in the erythromycin resistance gene ennAM to generate strain JEN53. The wild-type sequence can be restored by targeting the stop codon with the CRISPR::ermAM(stop) construct, and using the ermAM wild-type sequence as an editing template. (b) Mutant and wild-type ernmAM sequences (SEQ ID NOS 478-481, respectively, in order of appearance). (c) Fraction of erythromicyn-resistant ($erm^R$) cfu calculated from total or kanamycin-resistant ($kan^R$) cfu. (d) Fraction of total cells that acquire both the CRISPR construct and the editing template. Co-transformation of the CRISPR targeting construct produced more transformants (t-test, p=0.011). In all cases the values show the mean±s.d. for three independent experiments.

FIG. 27A-D illustrates genome editing with the CRISPR system in E. coli. (a) A kanamycin-resistant plasmid carrying the CRISPR array (pCRISPR) targeting the gene to edit may be transformed in the HME63 recombineering strain containing a chloramphenicol-resistant plasmid harboring cas9 and tracr (pCas9), together with an oligonucleotide specifying the mutation. (b) A K42T mutation conferring streptomycin resistance was introduced in the rpsL gene (SEQ ID NOS 482-485, respectively, in order of appearance) (c) Fraction of streptomicyn-resistant ($strep^R$) cfu calculated from total or kanamycin-resistant ($kan^R$) cfu. (d) Fraction of total cells that acquire both the pCRISPR plasmid and the editing oligonucleotide. Co-transformation of the pCRISPR targeting plasmid produced more transformants (t-test, p=0.004). In all cases the values showed the mean±s.d. for three independent experiments.

FIG. 28A-B illustrates the transformation of crR6 genomic DNA leads to editing of the targeted locus (a) The IS1167 element of S. pneumoniae R6 was replaced by the CRISPR01 locus of S. pyogenes SF370 to generate crR6 strain. This locus encodes for the Cas9 nuclease, a CRISPR array with six spacers, the tracrRNA that is required for crRNA biogenesis and Cas1, Cas2 and Csn2, proteins not necessary for targeting. Strain crR6M contains a minimal functional CRISPR system without cas1, cas2 and csn2. The aphA-3 gene encodes kanamycin resistance. Protospacers from the streptococcal bacteriophages φ8232.5 and φ370.1 were fused to a chloramphenicol resistance gene (cat) and integrated in the srtA gene of strain R6 to generate strains R68232.5 and R6370.1. (b) Left panel: Transformation of crR6 and crR6M genomic DNA in $R6^{8232.5}$ and $R^{6370.1}$. As a control of cell competence a streptomycin resistant gene was also transformed. Right panel: PCR analysis of 8 $R6^{8232.5}$ transformants with crR6 genomic DNA. Primers that amplify the srtA locus were used for PCR. 7/8 genotyped colonies replaced the R68232.5 srtA locus by the WT locus from the crR6 genomic DNA.

FIG. 29A-F provides chromatograms of DNA sequences of edited cells obtained in this study. In all cases the wild-type and mutant protospacer and PAM sequences (or their reverse complement) are indicated. When relevant, the amino acid sequence encoded by the protospacer is provided. For each editing experiment, all strains for which PCR and restriction analysis corroborated the introduction of the desired modification were sequenced. A representative chromatogram is shown. (a) Chromatogram for the introduction of a PAM mutation into the $R6^{8232.5}$ target (FIG. 23d) (SEQ ID NOS 486-487, respectively, in order of appearance). (b) Chromatograms for the introduction of the R>A and NE>AA mutations into β-galactosidase (bgaA) (FIG. 25c) (SEQ ID NOS 473-477 and 474, respectively, in order of appearance). (c) Chromatogram for the introduction of a 6664 bp deletion within bgaA ORF (FIGS. 25c and 25f). The dotted line indicates the limits of the deletion (SEQ ID NOS 488-490, respectively, in order of appearance). (d) Chromatogram for the introduction of a 729 bp deletion within srtA ORF (FIG. 25f). The dotted line indicates the limits of the deletion (SEQ ID NOS 491-493, respectively, in order of appearance). (e) Chromatograms for the generation of a premature stop codon within ermAM (FIG. 33) (SEQ ID NOS 494-497, respectively, in order of appearance). (f) rpsL editing in E. coli (FIG. 27) (SEQ ID NOS 482-485, respectively, in order of appearance).

FIG. 30A-C illustrates CRISPR immunity against random S. pneumoniae targets containing different PAMs. (a) Position of the 10 random targets on the S. pneumoniae R6 genome. The chosen targets have different PAMs and are on both strands. (b) Spacers corresponding to the targets were cloned in a minimal CRISPR array on plasmid pLZ12 and transformed into strain crR6Rc, which supplies the processing and targeting machinery in trans. (c) Transformation efficiency of the different plasmids in strain R6 and crR6Rc. No colonies were recovered for the transformation of pDB99-108 (T1-T10) in crR6Rc. The dashed line represents limit of detection of the assay.

FIG. 38A-B illustrates the background mutation frequency of CRISPR in E. coli HME63. (a) Transformation of the pCRISPR::Ø or pCRISPR::rpsL plasmids into HME63 competent cells. Mutants that escape CRISPR interference were observed at a frequency of $2.6 \times 10^{-4}$. (b) Amplification of the CRISPR array of escapers showed that 8/8 have deleted the spacer.

FIG. 41A-M shows sequences where the mutation points are located within the SpCas9 gene (SEQ ID NOS 503-504, respectively, in order of appearance).

FIG. 44A discloses SEQ ID NOS 322-323 and 330, respectively, in order of appearance. FIG. 44B discloses SEQ ID NO: 331.

FIG. 47 shows a gel demonstrating that SpCas9 with nickase mutations (individually) do not induce double strand breaks.

FIG. 48A-B shows a design of the oligo DNA used as Homologous Recombination (HR) template in this experiment and a comparison of HR efficiency induced by different combinations of Cas9 protein and HR template. FIG. 48A shows a design of the oligo DNA used as Homologous Recombination (HR) template in this experiment. FIG. 48B shows a comparison of HR efficiency induced by different combinations of Cas9 protein and HR template.

FIG. 49B shows the Constitutive Cas9. Rosa26 targeting vector map.

FIG. 50A-H show the sequences of each element present in the vector maps of FIGS. 49A-B (SEQ ID NOS 509-518, respectively, in order of appearance).

FIG. 54 shows the quantification of Cas9 nuclease activity.

FIG. 63B discloses SEQ ID NOS 505-507, 505, 508 and 507, respectively, in order of appearance.

FIG. 69A shows a design of the CRISPR-TF (Transcription Factor) with transcriptional activation activity. The chimeric RNA is expressed by U6 promoter, while a human-codon-optimized, double-mutant version of the Cas9 protein (hSpCas9m), operably linked to triple NLS and a VP64 functional domain is expressed by a EF1a promoter. The double mutations, D10A and H840A, renders the cas9 protein unable to introduce any cleavage but maintained its capacity to bind to target DNA when guided by the chimeric RNA.

FIG. 69B shows transcriptional activation of the human SOX2 gene with CRISPR-TF system (Chimeric RNA and the Cas9-NLS-VP64 fusion protein). 293FT cells were transfected with plasmids bearing two components: (1) U6-driven different chimeric RNAs targeting 20-bp sequences within or around the human SOX2 genomic locus, and (2) EF1a-driven hSpCas9m (double mutant)-NLS-VP64 fusion protein. 96 hours post transfection, 293FT cells were harvested and the level of activation is measured by the induction of mRNA expression using a qRT-PCR assay. All expression levels are normalized against the control group (grey bar), which represents results from cells transfected with the CRISPR-TF backbone plasmid without chimeric RNA. The qRT-PCR probes used for detecting the SOX2 mRNA is Taqman Human Gene Expression Assay (Life Technologies). All experiments represents data from 3 biological replicates, n=3, error bars show s.e.m.

FIG. 73A-C shows RNA-guided repression of bgaA expression by dgRNA::cas9. a. The Cas9 protein binds to the tracrRNA, and to the precursor CRISPR RNA which is processed by RNAseIII to form the crRNA. The crRNA directs binding of Cas9 to the bgaA promoter and represses transcription. b. The targets used to direct Cas9 to the bgaA promoter are represented (SEQ ID NO: 531). Putative −35, −10 as well as the bgaA start codon are in bold. c. Betagalactosidase activity as measure by Miller assay in the absence of targeting and for the four different targets.

FIG. 74A-E shows characterization of Cas9** mediated repression. a. The gfpmut2 gene and its promoter, including the −35 and −10 signals are represented together with the position of the different target sites used the study. b. Relative fluorescence upon targeting of the coding strand. c. Relative fluorescence upon targeting of the non-coding strand. d. Northern blot with probes B477 and B478 on RNA extracted from T5, T10, B10 or a control strain without a target. e. Effect of an increased number of mutations in the 5' end of the crRNA of B1, T5 and B10.

Figure 1:
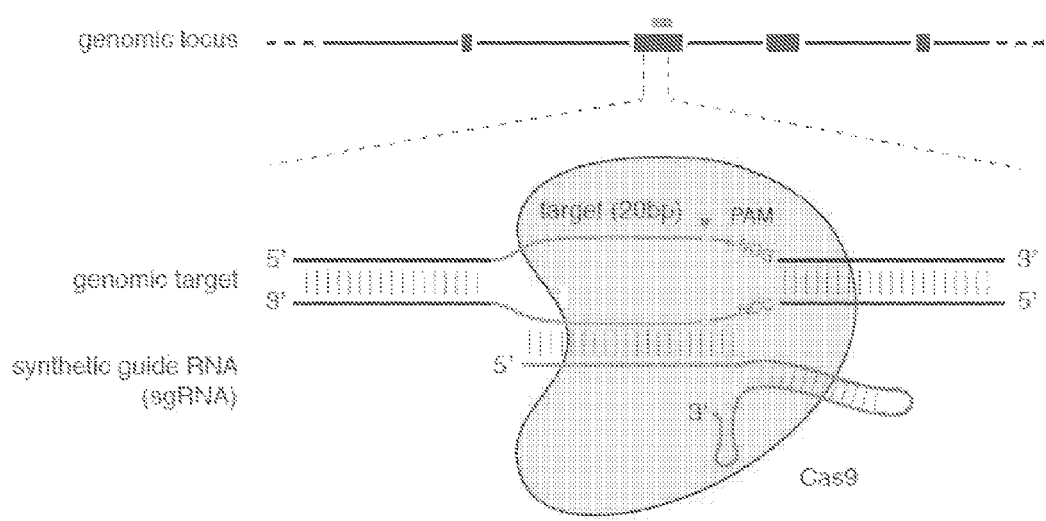
FIG. 1 shows a schematic model of the CRISPR system. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

The figures herein are for illustrative purposes only and are not necessarily drawn to scale.

DETAILED DESCRIPTION OF THE INVENTION

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing. Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as Escherichia coli, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in Escherichia coli with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast Saccharomyces cerivisae include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Themoplasma, Corynebacterium, Mycobacterium, Streptomyces, Aquifex, Porphvromonas, Chlorobium, Thermus, Bacillus, Listeria, Staphylococcus, Clostridium, Thenrmoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2. Cas3, Cas4, Cas5, Cas6. Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from S. pyogenes or S. pneumoniae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequenc(es), e.g., two guide sequences, which target respectively sense and antisense strands of the DNA target. This combination allows both strands to be nicked and used to induce NHEJ. Applicants have demonstrated (data not shown) the efficacy of two nickase targets (i.e., sgRNAs targeted at the same location but to different strands of DNA) in inducing mutagenic NHEJ. A single nickase (Cas9-D10A with a single sgRNA) is unable to induce NHEJ and create indels but Applicants have shown that double nickase (Cas9-D10A and two sgRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than S. pyogenes, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK (SEQ ID NO: 2)); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKG-GNFGGRSSGPYGGGGQYFAKPRNQGGY (SEQ ID NO: 5); the sequence RMRIZFKNKGKDTAELRRRRVEVS-VELRKAKKDEQILKRRNV (SEQ ID NO: 6) of the IBB domain from importin-alpha; the sequences VSRKRPRP (SEQ ID NO: 7) and PPKKARED (SEQ ID NO: 8) of the myoma T protein; the sequence PQPKKKPL (SEQ ID NO: 9) of human p53; the sequence SALIKKKKKMAP (SEQ ID NO: 10) of mouse c-abl IV; the sequences DRLRR (SEQ ID NO: 11) and PKQKKRK (SEQ ID NO: 12) of the influenza virus NS1: the sequence RKLKKKIKKL (SEQ ID NO: 13) of the Hepatitis virus delta antigen; the sequence REKKKFLKRR (SEQ ID NO: 14) of the mouse Mxl protein; the sequence KRKGDEVDGVDEVAKKKSKK (SEQ ID NO: 15) of the human poly(ADP-ribose) polymerase; and the sequence RKCLQAGMNLEARKTKK (SEQ ID NO: 16) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Examples of detectable markers include fluorescent proteins (such as Green fluorescent proteins, or GFP; RFP; CFP), and epitope tags (HA tag, flag tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome.

For example, for the *S. pyogenes* Cas9, a unique target sequence in a genome may include a Cas9 target site of the form MMMMMMMMMNNNNNNNNNNNXGG where NNNNNNNNNNNNXGG (N is A, G, T, or C; and X can be anything) has a single occurrence in the genome. A unique target sequence in a genome may include an *S. pyogenes* Cas9 target site of the form MMMMMMMMMNNNNNNNNNNNXGG where NNNNNNNNNNNXGG (N is A, G, T, or C; and X can be anything) has a single occurrence in the genome. For the *S. thermophilus* CRISPR1 Cas9, a unique target sequence in a genome may include a Cas9 target site of the form MMMMMMMMMNNNNNNNNNNNXXAGAAW (SEQ ID NO: 17) where NNNNNNNNNNNNXXAGAAW (SEQ ID NO: 18) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 19) where NNNNNNNNNNNXXAGAAW (SEQ ID NO: 20) (N is A, G, T, or C; X can be anything; and W is A or T) has a single occurrence in the genome. For the *S. pyogenes* Cas9, a unique target sequence in a genome may include a Cas9 target site of the form MMMMMMMMMNNNNNNNNNNNXGGXG where NNNNNNNNNNNNXGGXG (N is A, G, T, or C; and X can be anything) has a single occurrence in the genome. A unique target sequence in a genome may include an *S. pyogenes* Cas9 target site of the form MMMMMMMMMNNNNNNNNNNNXGGXG where NNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62). Further algorithms may be found in U.S. application Ser. No. 61/836,080; Broad Reference BI-2013/004A); incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. Example illustrations of optimal alignment between a tracr sequence and a tracr mate sequence are provided in FIGS. 12B and 13B. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. An example illustration of such a hairpin structure is provided in the lower portion of FIG. 13B, where the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents (SEQ ID NO: 21)
(1) NNNNNNNNNNNNNNNNNNNNgttttgtactctcaagatttaGAAAtaaa tcttgcagaagctacaaagataaggcttcatgccgaaatcaacaccctgt cattttatggcagggtgttttcgttatttaaTTTTTT;

(SEQ ID NO: 22)
(2) NNNNNNNNNNNNNNNNNNNNgttttgtactctcaGAAAtgcagaagcta caaagataaggcttcatgccgaaatcaacaccctgtcattttatggcaggg tgttttcgttatttaaTTTTTT;

(SEQ ID NO: 23)
(3) NNNNNNNNNNNNNNNNNNNNgttttgtactctcaGAAAtgcagaagcta caaagataaggcttcatgccgaaatcaacaccctgtcattttatggcagg gtgtTTTTTT;

(SEQ ID NO: 24)
(4) NNNNNNNNNNNNNNNNNNNNgttttagagctaGAAAtagcaagttaaaat aaggctagtccgttatcaacttgaaaaagtggcaccgagtcggtgcTTTT

TT;

(SEQ ID NO: 25)
(5) NNNNNNNNNNNNNNNNNNNNgttttagagctaGAAATAGcaagttaaaat aaggctagtccgttatcaacttgaaaaagtgTTTTTT;
and (6) NNNNNNNNNNNNNNNNNNNNNgttttagagctagAAATAGcaagttaaaat aaggctagtccgttatcaTTTTTTTT. (SEQ ID NO: 26)

In some embodiments, sequences (1) to (3) are used in combination with Cas9 lrom S. thermophilus CRISPR1. In some embodiments, sequences (4) to (6) are used in combination with Cas9 from S. pyogenes. In some embodiments, the tracr sequence is a separate transcript from a transcript comprising the tracr mate sequence (such as illustrated in the top portion of FIG. 13B).

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CR ISPR enzyme are described in US20110059502, incorporated herein by reference. In some embodiments, a tagged CRISPR enzyme is used to identify the location of a target sequence.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Böhm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4. EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassus, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence.

With recent advances in crop genomics, the ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety. In an advantageous embodiment of the invention, the CRISPR/Cas9 system is used to engineer microalgae (Example 15). Accordingly, reference herein to animal cells may also apply, mutatis mutandis, to plant cells unless otherwise apparent.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae), and modifying the cell or cells. Culturing may occur at any stage ex vivo. The cell or cells may even be re-introduced into the non-human animal or plant (including micro-algae).

In plants, pathogens are often host-specific. For example, *Fusariumn oxysporum* f. sp. *lycopersici* causes tomato wilt but attacks only tomato, and *F. oxysporum f. dianthii Puccinia graminis f.* sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provide individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR and BI-2011/008/WSGR respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 filed on Dec. 12, 2012 and 61/748,427 filed Jan. 2, 2013. Such genes, proteins and pathways may be the target polynucleotide of a CRISPR complex.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | API-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, |

TABLE B-continued

| | |
|---|---|
| Cell dysregulation and oncology diseases and disorders | LVWM, CACH, CLE, EIF2B4); Sickle cell anemia (HBB); Thalassemia (HBA2, HBB, HBD, LCRB, HBA1). B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228); HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSFS, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), IL-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/ Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A), Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5), Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuciein, DJ-1); Schizophrenia (Neuregulin1 (Nrg1), Erb4 (receptor for Neuregulin), Complexin1 (Cplx 1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYR1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGR7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; PIK3B; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; |

TABLE C-continued

| CELLULAR FUNCTION | GENES |
|---|---|
| Glucocorticoid Receptor Signaling | ESR1; ITGA2; MYC; TTK; CSNK1A1; CRKL; BRAF; ATF4; PRKCA; SRF; STAT1; SGK RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NEKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; |
| Leukocyte Extravasation Signaling | AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; MAPK9; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; |

TABLE C-continued

| CELLULAR FUNCTION | GENES |
|---|---|
| NF-KB Signaling | NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/ Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; |
| Fc Epsilon RI Signaling | RELB; MAP3K7; CREBBP; MAP2K2; CHUK; PDGFRA; MAP2K1; NFKB1; JUN; IL1R1; HSP90AA1 PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK3; KRAS; RELA; PIK3C2A; .BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and | PRKCE; IRAK1; PRKAA2; EIF2AK2; GRK6; MAPK1; PLK1; AKT2; CDK8; MAPK8; MAPK3; |

TABLE C-continued

| CELLULAR FUNCTION | GENES |
|---|---|
| Nicotinamide Metabolism | PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKC1; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NHKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NHKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEKI; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME1; SMARCA4; MYH9; RRM2; ADAR; EIF2AK4; PKM2; ENTPD1; RADS51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALD1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |

TABLE C-continued

| CELLULAR FUNCTION | GENES |
|---|---|
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMTI; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function Developmental Neurology | AIF; CytC; SMAC (Diablo); Aifm-1; Aifm-2 BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA.DNA hybrids. McIvor E I, Polak U, Napierala M. RNA Biol. 2010 Sep.-Oct.; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy. Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN and so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the (cr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53). PTGIS (prostaglandin I2 (prostacyclin) synthase), MB (myoglobin), IL4 (interleukin 4), ANGPT1 (angiopoietin 1). ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-crb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (C. elegans)), CTSB (cathepsin B), PSEN (presenilin 1), APP (amyloid beta (A4) precursor protein), APH1B (anterior pharynx defective 1 homolog B (C. elegans)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1). ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SODI (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRAI D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA 1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutieres Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARXx-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

CRISPR Complex Activity in the Nucleus of a Eukaryotic Cell

Figure 2A:
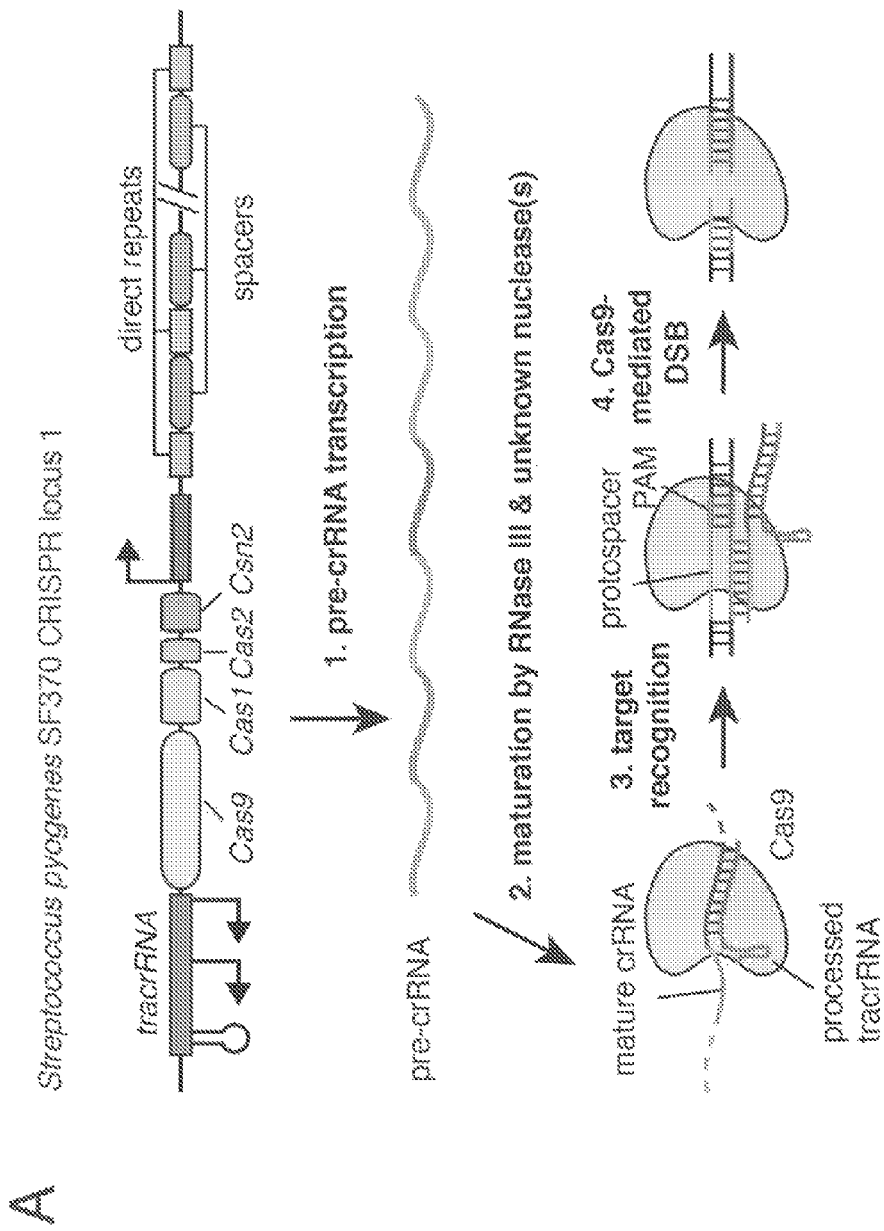

An example type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). This example describes an example process for adapting this RNA-programmable nuclease system to direct CRISPR complex activity in the nuclei of eukaryotic cells.

Cell Culture and Transfection

Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 µg/mL streptomycin at 37° C. with 5% $CO_2$ incubation. Mouse neuro2A (N2A) cell line (ATCC) was maintained with DMEM supplemented with 5% fetal bovine serum (HyClone), 2 mM GlutaMAX (Life Technologies), 100 U/mL penicillin, and 100 µg/mL streptomycin at 37° C. with 5% $CO_2$.

HEK 293FT or N2A cells were seeded into 24-well plates (Corning) one day prior to transfection at a density of 200,000 cells per well. Cells were transfected using Lipofectamine 2000 (Life Technologies) following the manufacturer's recommended protocol. For each well of a 24-well plate a total of 800 ng of plasmids were used.

Surveyor Assay and Sequencing Analysis for Genome Modification

HEK 293FT or N2A cells were transfected with plasmid DNA as described above. After transfection, the cells were incubated at 37° C. for 72 hours before genomic DNA extraction. Genomic DNA was extracted using the QuickExtract DNA extraction kit (Epicentre) following the manufacturer's protocol. Briefly, cells were resuspended in QuickExtract solution and incubated at 65° C. for 15 minutes and 98° C. for 10 minutes. Extracted genomic DNA was immediately processed or stored at −20° C.

Figure 8:
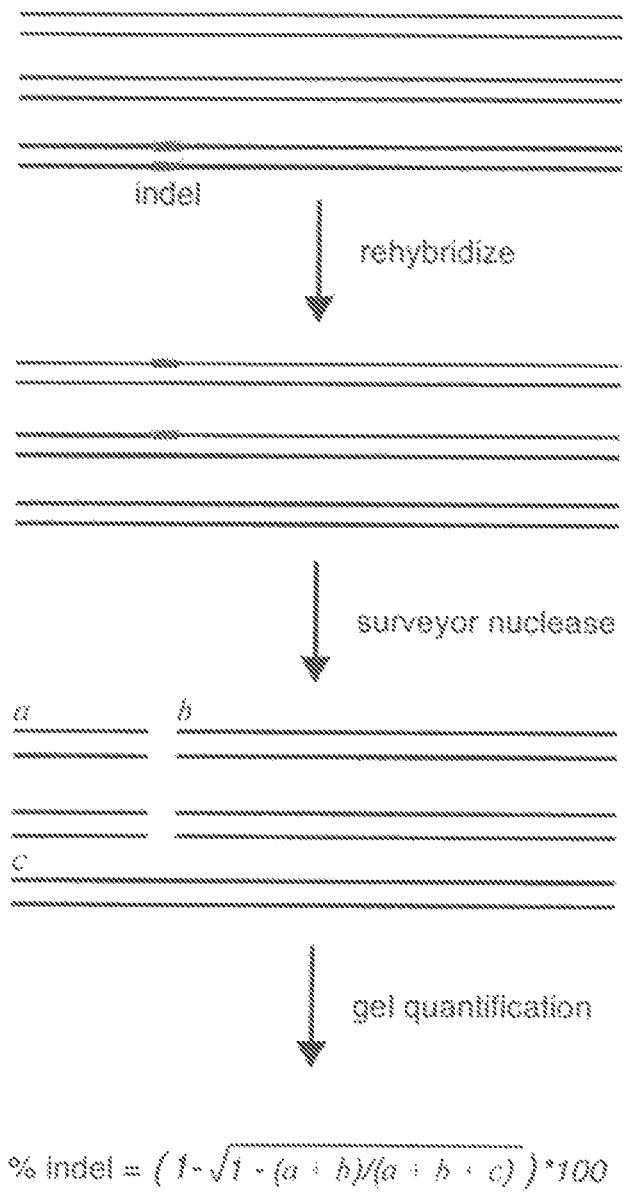
FIG. 8 shows a schematic of a surveyor nuclease assay for detection of double strand break-induced micro-insertions and -deletions.

The genomic region surrounding a CRISPR target site for each gene was PCR amplified, and products were purified using QiaQuick Spin Column (Qiagen) following manufacturer's protocol. A total of 400 ng of the purified PCR products were mixed with 2 µl 10× Taq polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with Surveyor nuclease and Surveyor enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities, as a measure of the fraction of cleaved DNA. FIG. 8 provides a schematic illustration of this Surveyor assay.

Restriction Fragment Length Polymorphism Assay for Detection of Homologous Recombination HEK 293FT and N2A cells were transfected with plasmid DNA, and incubated at 37° C. for 72 hours before genomic DNA extraction as described above. The target genomic region was PCR amplified using primers outside the homology arms of the homologous recombination (HR) template. PCR products were separated on a 1% agarose gel and extracted with MinElute GelExtraction Kit (Qiagen). Purified products were digested with HindIII (Fermentas) and analyzed on a 6% Novex TBE poly-acrylamide gel (Life Technologies).

RNA Secondary Structure Prediction and Analysis

RNA secondary structure prediction was performed using the online webserver RNAfold developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

Bacterial Plasmid Transformation Interference Assay

Elements of the S. pyogenes CRISPR locus I sufficient for CRISPR activity were reconstituted in E. coli using pCRISPR plasmid (schematically illustrated in FIG. 10A). pCRISPR contained tracrRNA, SpCas9, and a leader sequence driving the crRNA array. Spacers (also referred to as "guide sequences") were inserted into the crRNA array between BsaI sites using annealed oligonucleotides, as illustrated. Challenge plasmids used in the interference assay were constructed by inserting the protospacer (also referred to as a "target sequence") sequence along with an adjacent CRISPR motif sequence (PAM) into pUC19 (see FIG. 10B). The challenge plasmid contained ampicillin resistance. FIG. 10C provides a schematic representation of the interference assay. Chemically competent E. coli strains already carrying pCRISPR and the appropriate spacer were transformed with the challenge plasmid containing the corresponding protospacer-PAM sequence. pUC19 was used to assess the transformation efficiency of each pCRISPR-carrying competent strain. CRISPR activity resulted in cleavage of the pPSP plasmid carrying the protospacer, precluding ampicillin resistance otherwise conferred by pUC19 lacking the protospacer. FIG. 10D illustrates competence of each pCRISPR-carrying E. coli strain used in assays illustrated in FIG. 4C.

RNA Purification

HEK 293FT cells were maintained and transfected as stated above. Cells were harvested by trypsinization followed by washing in phosphate buffered saline (PBS). Total cell RNA was extracted with TRI reagent (Sigma) following manufacturer's protocol. Extracted total RNA was quantified using Naonodrop (Thermo Scientific) and normalized to same concentration.

Northern Blot Analysis of crRN4 and tracrRNA Expression in Mammalian Cells

RNAs were mixed with equal volumes of 2× loading buffer (Ambion), heated to 95° C. for 5 min, chilled on ice for 1 min, and then loaded onto 8% denaturing polyacrylamide gels (SequaGel, National Diagnostics) after pre-running the gel for at least 30 minutes. The samples were electrophoresed for 1.5 hours at 40 W limit. Afterwards, the RNA was transferred to Hybond N+ membrane (GE Healthcare) at 300 mA in a semi-dry transfer apparatus (Bio-rad) at room temperature for 1.5 hours. The RNA was crosslinked to the membrane using autocrosslink button on Stratagene UV Crosslinker the Stratalinker (Stratagene). The membrane was pre-hybridized in ULTRAhyb-Oligo Hybridization Buffer (Ambion) for 30 min with rotation at 42° C., and probes were then added and hybridized overnight. Probes were ordered from IDT and labeled with [gamma-$^{32}$P] ATP (Perkin Elmer) with T4 polynucleotide kinase (New England Biolabs). The membrane was washed once with pre-warmed (42° C.) 2×SSC, 0.5% SDS for 1 min followed by two 30 minute washes at 42° C. The membrane was exposed to a phosphor screen for one hour or overnight at room temperature and then scanned with a phosphorimager (Typhoon).

Bacterial CRISPR System Construction and Evaluation

CRISPR locus elements, including tracrRNA, Cas9, and leader were PCR amplified from Streptococcus pyogenes SF370 genomic DNA with flanking homology arms for Gibson Assembly. Two BsaI type IIS sites were introduced in between two direct repeats to facilitate easy insertion of spacers (FIG. 9). PCR products were cloned into EcoRV-digested pACYC184 downstream of the tet promoter using Gibson Assembly Master Mix (NEB). Other endogenous CRISPR system elements were omitted, with the exception of the last 50 bp of Csn2. Oligos (Integrated DNA Technology) encoding spacers with complimentary overhangs were cloned into the BsaI-digested vector pDC000 (NEB) and then ligated with T7 ligase (Enzymatics) to generate pCRISPR plasmids. Challenge plasmids containing spacers with PAM sequences (also referred to herein as "CRISPR motif sequences") were created by ligating hybridized oligos carrying compatible overhangs (Integrated DNA Technology) into BamH1-digested pUC19. Cloning for all constructs was performed in E. coli strain JM109 (Zymo Research).

pCRISPR-carrying cells were made competent using the Z-Competent E. coli Transformation Kit and Buffer Set (Zymo Research, T3001) according to manufacturer's instructions. In the transformation assay, 50 uL aliquots of competent cells carrying pCRISPR were thawed on ice and transformed with 1 ng of spacer plasmid or pUC19 on ice for 30 minutes, followed by 45 second heat shock at 42° C. and 2 minutes on ice. Subsequently, 250 ul SOC (Invitrogen) was added followed by shaking incubation at 37° C. for 1 hr, and 100 uL of the post-SOC outgrowth was plated onto double selection plates (12.5 ug/ml chloramphenicol, 100 ug/ml ampicillin). To obtain cfu/ng of DNA, total colony numbers were multiplied by 3.

Figure 2B:
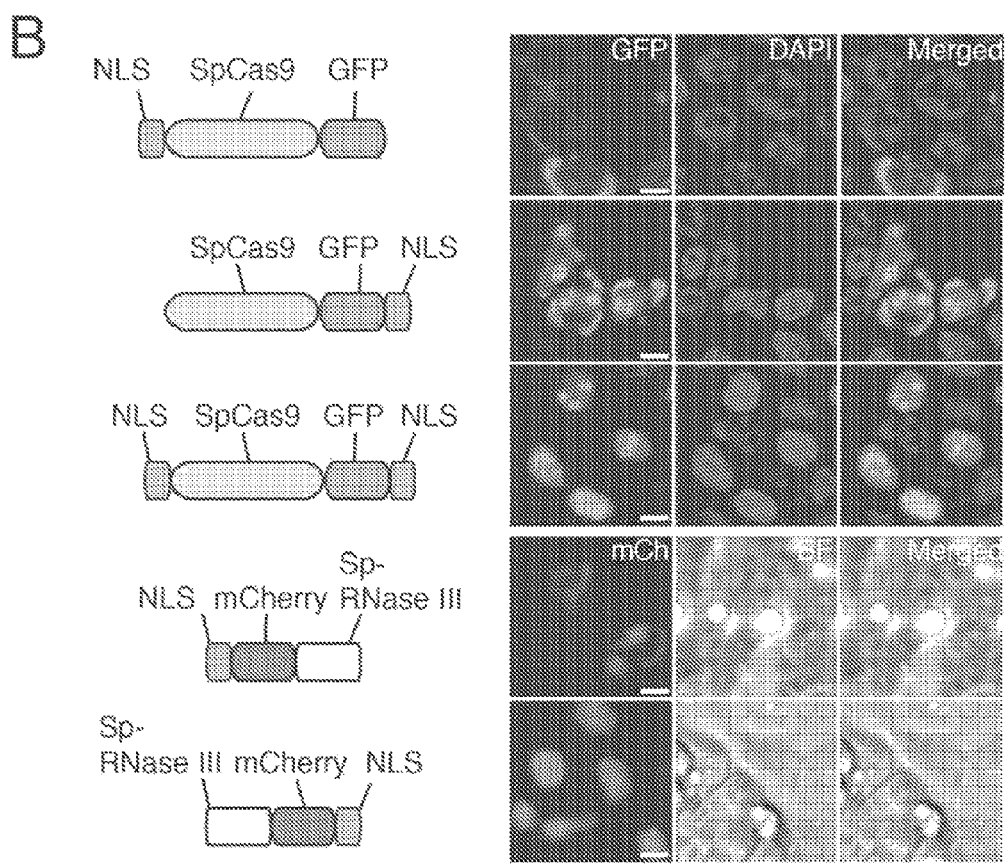

To improve expression of CRISPR components in mammalian cells, two genes from the SF370 locus 1 of Streptococcus pyogenes (S. pyogenes) were codon-optimized, Cas9 (SpCas9) and RNase III (SpRNase III). To facilitate nuclear localization, a nuclear localization signal (NLS) was included at the amino (N)- or carboxyl (C)-termini of both SpCas9 and SpRNase III (FIG. 2B). To facilitate visualization of protein expression, a fluorescent protein marker was also included at the N- or C-termini of both proteins (FIG. 2B). A version of SpCas9 with an NLS attached to both N- and C-termini (2×NLS-SpCas9) was also generated. Constructs containing NLS-fused SpCas9 and SpRNase III were transfected into 293FT human embryonic kidney (HEK) cells, and the relative positioning of the NLS to SpCas9 and SpRNase III was found to affect their nuclear localization efficiency. Whereas the C-terminal NLS was sufficient to target SpRNase III to the nucleus, attachment of a single copy of these particular NLS's to either the N- or C-terminus of SpCas9 was unable to achieve adequate nuclear localization in this system. In this example, the C-terminal NLS was that of nucleoplasmin (KRPAATKKAGQAKKKK (SEQ ID NO: 2)), and the C-terminal NLS was that of the SV40 large T-antigen (PKKKRKV (SEQ ID NO: 1)). Of the versions of SpCas9 tested, only 2×NLS-SpCas9 exhibited nuclear localization (FIG. 2B).

Figure 7C:
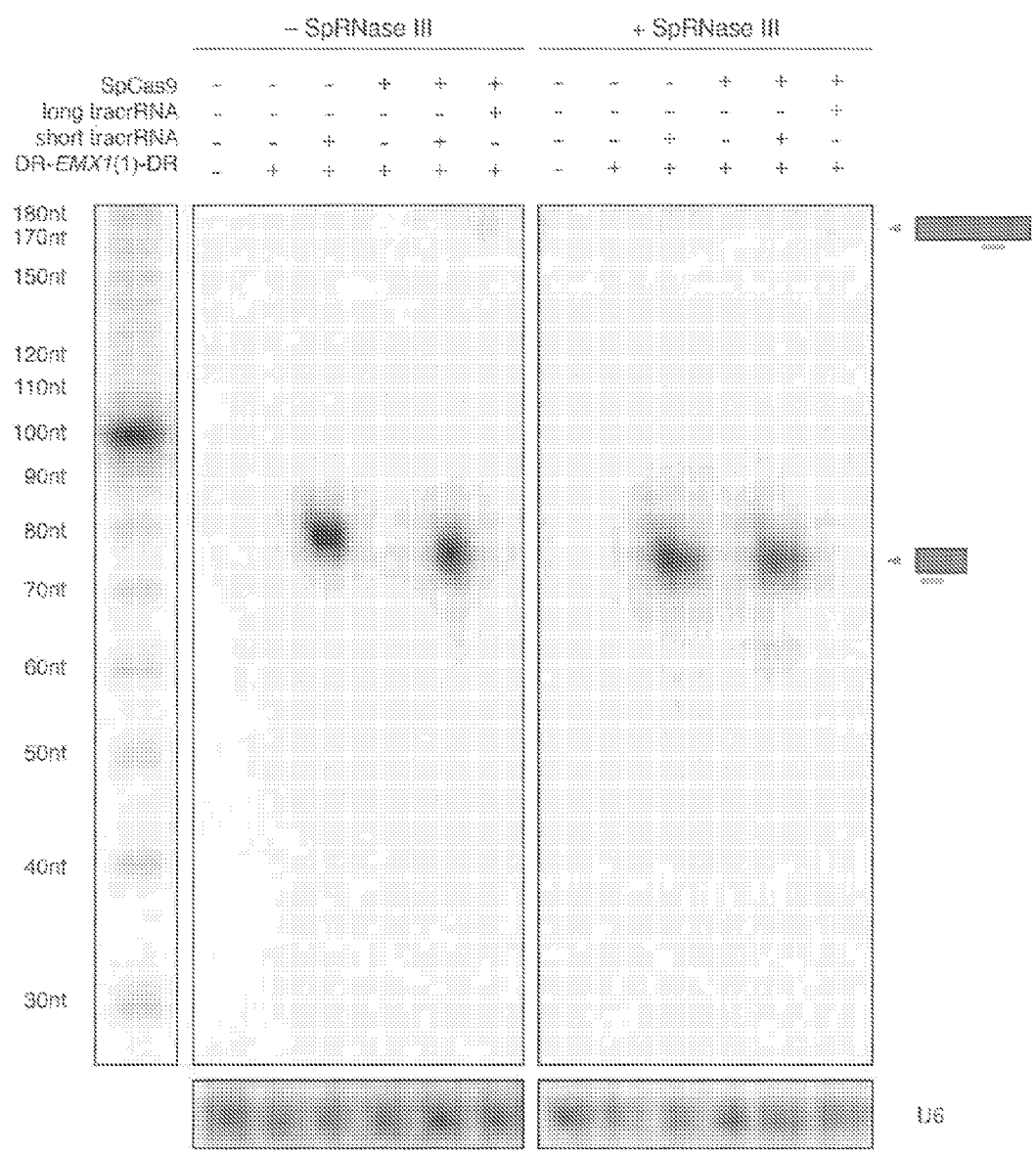

The tracrRNA from the CRISPR locus of *S. pyogenes* SF370 has two transcriptional start sites, giving rise to two transcripts of 89-nucleotides (nt) and 171 nt that are subsequently processed into identical 75 nt mature tracrRNAs. The shorter 89 nt tracrRNA was selected for expression in mammalian cells (expression constructs illustrated in FIG. 7A, with functionality as determined by results of the Surveyor assay shown in FIG. 7B). Transcription start sites are marked as +1, and transcription terminator and the sequence probed by northern blot are also indicated. Expression of processed tracrRNA was also confirmed by Northern blot. FIG. 7C shows results of a Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III, respectively. U6 indicate loading control blotted with a probe targeting human U6 snRNA. Transfection of the short tracrRNA expression construct led to abundant levels of the processed form of tracrRNA (~75 bp). Very low amounts of long tracrRNA are detected on the Northern blot.

Figure 2C:
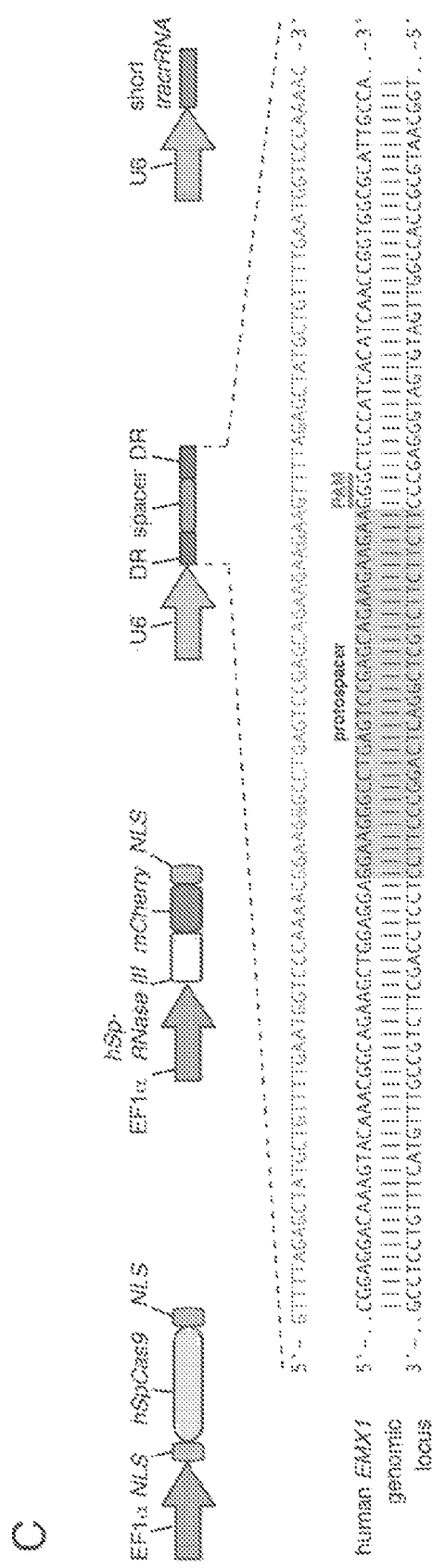

To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 2D:
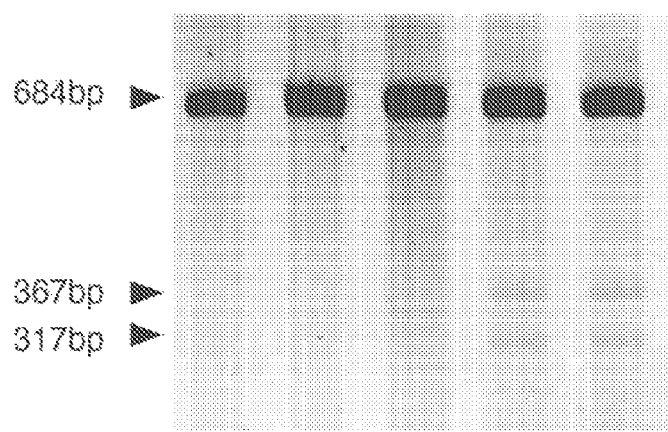

To test whether heterologous expression of the CRISPR system (SpCas9, SpRNase III, tracrRNA, and pre-crRNA) in mammalian cells can achieve targeted cleavage of mammalian chromosomes, HEK 293FT cells were transfected with combinations of CRISPR components. Since DSBs in mammalian nuclei are partially repaired by the non-homologous end joining (NHEJ) pathway, which leads to the formation of indels, the Surveyor assay was used to detect potential cleavage activity at the target EMX1 locus (FIG. 8) (see e.g. Guschin et al., 2010, *Methods Mol Biol* 649: 247). Co-transfection of all four CRISPR components was able to induce up to 5.0% cleavage in the protospacer (see FIG. 2D). Co-transfection of all CRISPR components minus SpRNase III also induced up to 4.7% indel in the protospacer, suggesting that there may be endogenous mammalian RNases that are capable of assisting with crRNA maturation, such as for example the related Dicer and Drosha enzymes. Removing any of the remaining three components abolished the genome cleavage activity of the CRISPR system (FIG. 2D). Sanger sequencing of amplicons containing the target locus verified the cleavage activity: in 43 sequenced clones, 5 mutated alleles (11.6%) were found. Similar experiments using a variety of guide sequences produced indel percentages as high as 29% (see FIGS. 4-7, 12, and 13). These results define a three-component system for efficient CRISPR-mediated genome modification in mammalian cells. To optimize the cleavage efficiency, Applicants also tested whether different isoforms of tracrRNA affected the cleavage efficiency and found that, in this example system, only the short (89-bp) transcript form was able to mediate cleavage of the human EMX1 genomic locus (FIG. 7B).

FIG. 14 provides an additional Northern blot analysis of crRNA processing in mammalian cells. FIG. 14A illustrates a schematic showing the expression vector for a single spacer flanked by two direct repeats (DR-EMX1(1)-DR). The 30 bp spacer targeting the human EMX1 locus protospacer 1 (see FIG. 6) and the direct repeat sequences are shown in the sequence beneath FIG. 14A. The line indicates the region whose reverse-complement sequence was used to generate Northern blot probes for EMX1(1) crRNA detection. FIG. 14B shows a Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA and was not dependent on the presence of SpRNase III. The mature crRNA detected from transfected 293FT total RNA is ~33 bp and is shorter than the 39-42 bp mature crRNA from *S. pyogenes*. These results demonstrate that a CRISPR system can be transplanted into eukaryotic cells and reprogrammed to facilitate cleavage of endogenous mammalian target polynucleotides.

FIG. 2 illustrates the bacterial CRISPR system described in this example. FIG. 2A illustrates a schematic showing the CRISPR locus 1 from *Streptococcus pyogenes* SF370 and a proposed mechanism of CRISPR-mediated DNA cleavage by this system. Mature crRNA processed from the direct repeat-spacer array directs Cas9 to genomic targets consisting of complimentary protospacers and a protospacer-adjacent motif (PAM). Upon target-spacer base pairing, Cas9 mediates a double-strand break in the target DNA. FIG. 2B illustrates engineering of *S. pyogenes* Cas9 (SpCas9) and RNase III (SpRNase III) with nuclear localization signals (NLSs) to enable import into the mammalian nucleus. FIG. 2C illustrates mammalian expression of SpCas9 and SpRNase III driven by the constitutive EF1a promoter and tracrRNA and pre-crRNA array (DR-Spacer-DR) driven by the RNA Pol3 promoter U6 to promote precise transcription initiation and termination. A protospacer from the human EMX1 locus with a satisfactory PAM sequence is used as the spacer in the pre-crRNA array. FIG. 2D illustrates surveyor nuclease assay for SpCas9-mediated minor insertions and deletions. SpCas9 was expressed with and without SpRNase III, tracrRNA, and a pre-crRNA array carrying the EMX1-target spacer. FIG. 2E illustrates a schematic representation of base pairing between target locus and EMX1-targeting crRNA, as well as an example chromatogram showing a micro deletion adjacent to the SpCas9 cleavage site. FIG. 2F illustrates mutated alleles identified from sequencing analysis of 43 clonal amplicons showing a variety of micro insertions and deletions. Dashes indicate deleted bases, and non-aligned or mismatched bases indicate insertions or mutations. Scale bar=10 μm.

To further simplify the three-component system, a chimeric crRNA-tracrRNA hybrid design was adapted, where a mature crRNA (comprising a guide sequence) is fused to a partial tracrRNA via a stem-loop to mimic the natural crRNA:tracrRNA duplex (FIG. 3A). To increase co-delivery efficiency, a bicistronic expression vector was created to drive co-expression of a chimeric RNA and SpCas9 in transfected cells (FIGS. 3A and 8). In parallel, the bicistronic vectors were used to express a pre-crRNA (DR-guide sequence-DR) with SpCas9, to induce processing into crRNA with a separately expressed tracrRNA (compare FIG. 13B top and bottom). FIG. 9 provides schematic illustrations of bicistronic expression vectors for pre-crRNA array (FIG. 9A) or chimeric crRNA (represented by the short line downstream of the guide sequence insertion site and upstream of the EF1α promoter in FIG. 9B) with hSpCas9, showing location of various elements and the point of guide sequence insertion. The expanded sequence around the location of the guide sequence insertion site in FIG. 9B also shows a partial DR sequence (GTTTTAGAGCTA (SEQ ID NO: 27)) and a partial tracrRNA sequence (TAGCAAGTTAAAATAAG-GCTAGTCCGTTTTT (SEQ ID NO: 28)). Guide sequences can be inserted between BbsI sites using annealed oligonucleotides. Sequence design for the oligonucleotides are shown below the schematic illustrations in FIG. 9, with appropriate ligation adapters indicated. WPRE represents the Woodchuck hepatitis virus post-transcriptional regulatory element. The efficiency of chimeric RNA-mediated cleavage was tested by targeting the same EMX1 locus described above. Using both Surveyor assay and Sanger sequencing of amplicons, Applicants confirmed that the chimeric RNA design facilitates cleavage of human EMX1 locus with approximately a 4.7% modification rate (FIG. 4).

Generalizability of CRISPR-mediated cleavage in eukaryotic cells was tested by targeting additional genomic loci in both human and mouse cells by designing chimeric RNA targeting multiple sites in the human EMX1 and PVALB, as well as the mouse Th loci. FIG. 15 illustrates the selection of some additional targeted protospacers in human PVALB (FIG. 15A) and mouse Th (FIG. 15B) loci. Schematics of the gene loci and the location of three protospacers within the last exon of each are provided. The underlined sequences include 30 bp of protospacer sequence and 3 bp at the 3' end corresponding to the PAM sequences. Protospacers on the sense and anti-sense strands are indicated above and below the DNA sequences, respectively. A modification rate of 6.3% and 0.75% was achieved for the human PVALB and mouse Th loci respectively, demonstrating the broad applicability of the CRISPR system in modifying different loci across multiple organisms (FIGS. 3B and 6). While cleavage was only detected with one out of three spacers for each locus using the chimeric constructs, all target sequences were cleaved with efficiency of indel production reaching 27% when using the co-expressed pre-crRNA arrangement (FIG. 6).

FIG. 13 provides a further illustration that SpCas9 can be reprogrammed to target multiple genomic loci in mammalian cells. FIG. 13A provides a schematic of the human EMX1 locus showing the location of five protospacers, indicated by the underlined sequences. FIG. 13B provides a schematic of the pre-crRNA/trcrRNA complex showing hybridization between the direct repeat region of the pre-crRNA and tracrRNA (top), and a schematic of a chimeric RNA design comprising a 20 bp guide sequence, and tracr mate and tracr sequences consisting of partial direct repeat and tracrRNA sequences hybridized in a hairpin structure (bottom). Results of a Surveyor assay comparing the efficacy of Cas9-mediated cleavage at five protospacers in the human EMX1 locus is illustrated in FIG. 13C. Each protospacer is targeted using either processed pre-crRNAitracrRNA complex (crRNA) or chimeric RNA (chiRNA).

Since the secondary structure of RNA can be crucial for intermolecular interactions, a structure prediction algorithm based on minimum free energy and Boltzmann-weighted structure ensemble was used to compare the putative secondary structure of all guide sequences used in our genome targeting experiment (FIG. 3B) (see e.g. Gruber et al., 2008, Nucleic Acids Research, 36: W70). Analysis revealed that in most cases, the effective guide sequences in the chimeric crRNA context were substantially free of secondary structure motifs, whereas the ineffective guide sequences were more likely to form internal secondary structures that could prevent base pairing with the target protospacer DNA. It is thus possible that variability in the spacer secondary structure might impact the efficiency of CRISPR-mediated interference when using a chimeric crRNA.

Figure 3:
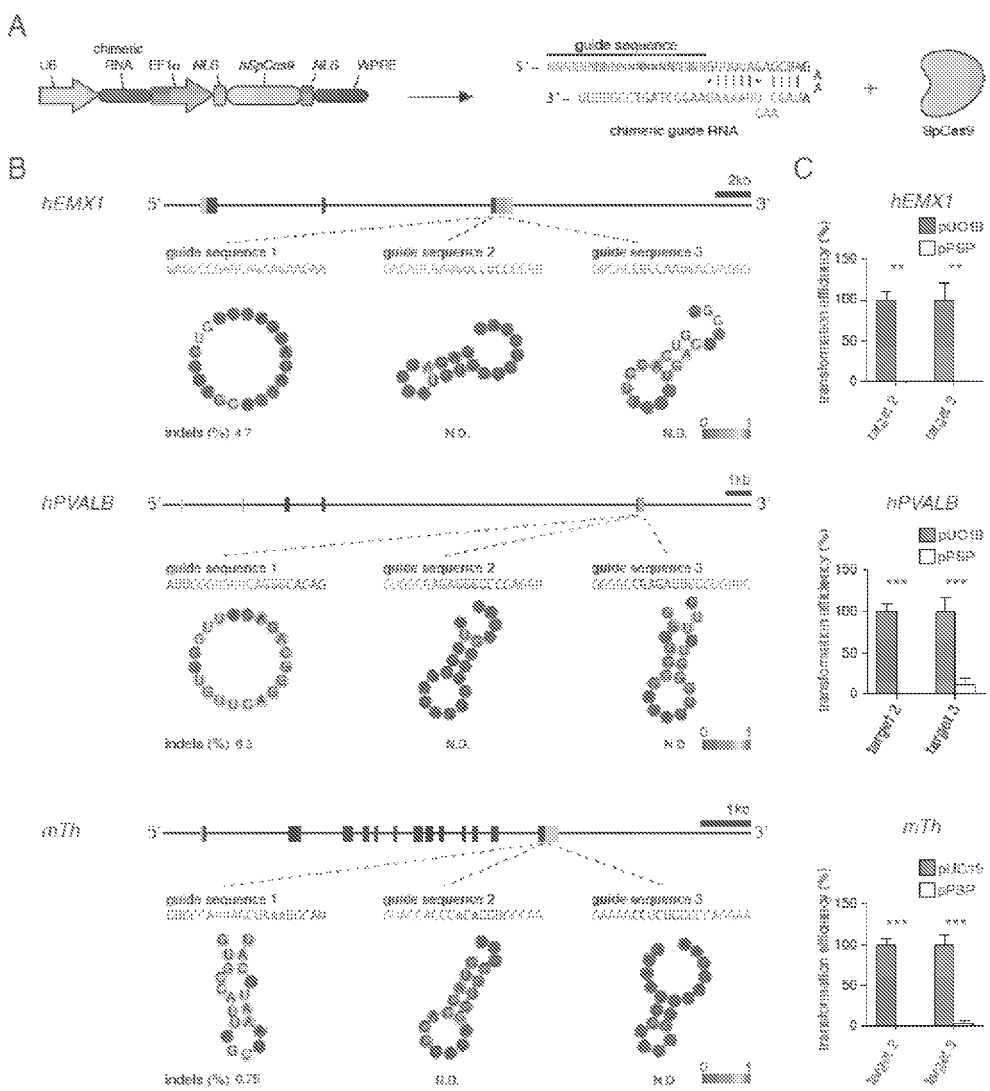
FIG. 3 shows an exemplary expression cassette for expression of CRISPR system elements in eukaryotic cells, predicted structures of example guide sequences, and CRISPR system activity as measured in eukaryotic and prokaryotic cells (SEQ ID NOS 291-300, respectively, in order of appearance).
Figure 44A:
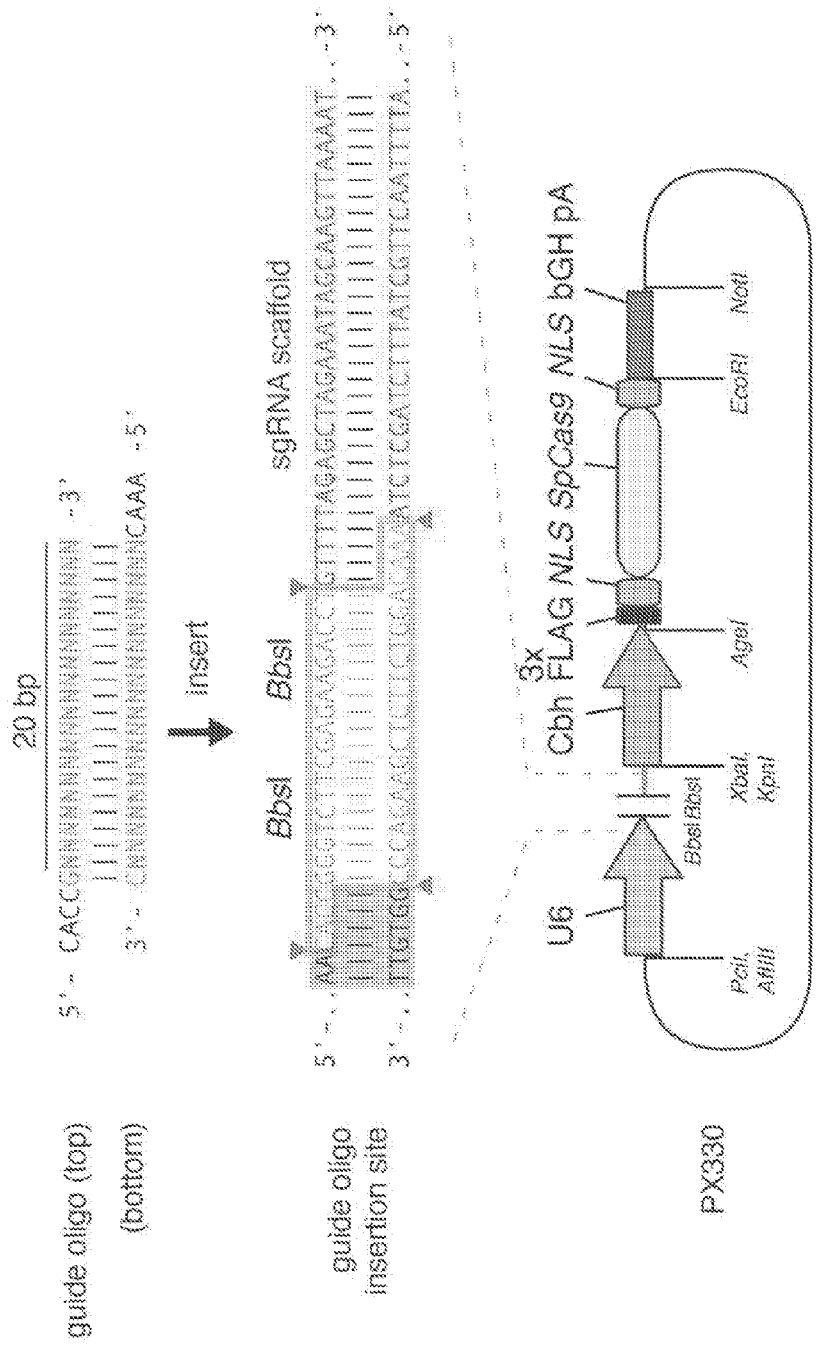
FIGS. 44A-B show single vector designs for SpCas9.
Figure 44B:
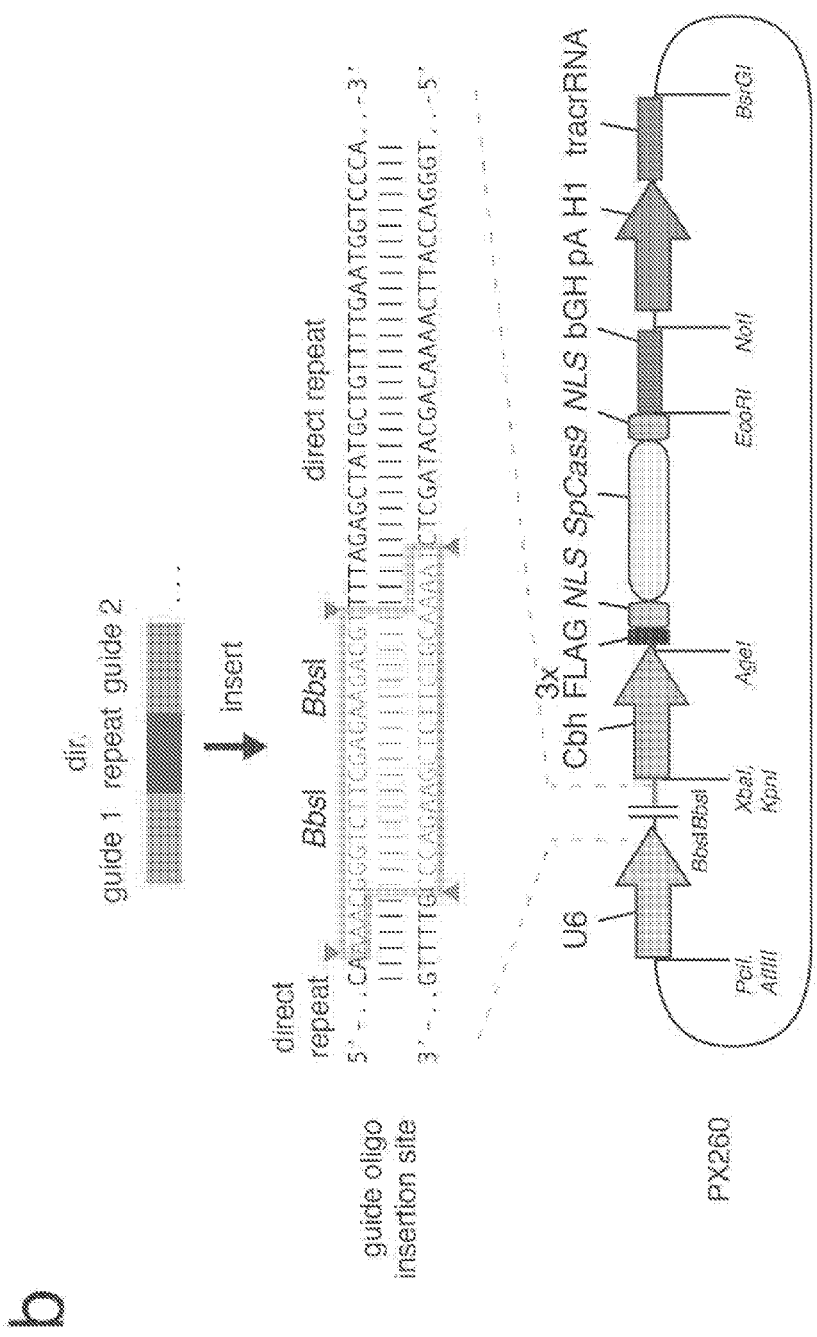

FIG. 3 illustrates example expression vectors. FIG. 3A provides a schematic of a bi-cistronic vector for driving the expression of a synthetic crRNA-tracrRNA chimera (chimeric RNA) as well as SpCas9. The chimeric guide RNA contains a 20-bp guide sequence corresponding to the protospacer in the genomic target site. FIG. 3B provides a schematic showing guide sequences targeting the human EMX1, PVALB, and mouse Th loci, as well as their predicted secondary structures. The modification efficiency at each target site is indicated below the RNA secondary structure drawing (EMX1, n=216 amplicon sequencing reads; PVALB, n=224 reads; Th, n=265 reads). The folding algorithm produced an output with each base colored according to its probability of assuming the predicted secondary structure, as indicated by a rainbow scale that is reproduced in FIG. 3B in gray scale. Further vector designs for SpCas9 are shown in FIG. 44, which illustrates single expression vectors incorporating a U6 promoter linked to an insertion site for a guide oligo, and a Cbh promoter linked to SpCas9 coding sequence. The vector shown in FIG. 44b includes a tracrRNA coding sequence linked to an H1 promoter.

To test whether spacers containing secondary structures are able to function in prokaryotic cells where CRISPRs naturally operate, transformation interference of protospacer-bearing plasmids were tested in an *E. coli* strain heterologously expressing the *S. pyogenes* SF370 CRISPR locus 1 (FIG. 10). The CRISPR locus was cloned into a low-copy *E. coli* expression vector and the crRNA array was replaced with a single spacer flanked by a pair of DRs (pCRISPR). *E. coli* strains harboring different pCRISPR plasmids were transformed with challenge plasmids containing the corresponding protospacer and PAM sequences (FIG. 10C). In the bacterial assay, all spacers facilitated efficient CRISPR interference (FIG. 4C). These results suggest that there may be additional factors affecting the efficiency of CRISPR activity in mammalian cells.

Figure 4D:
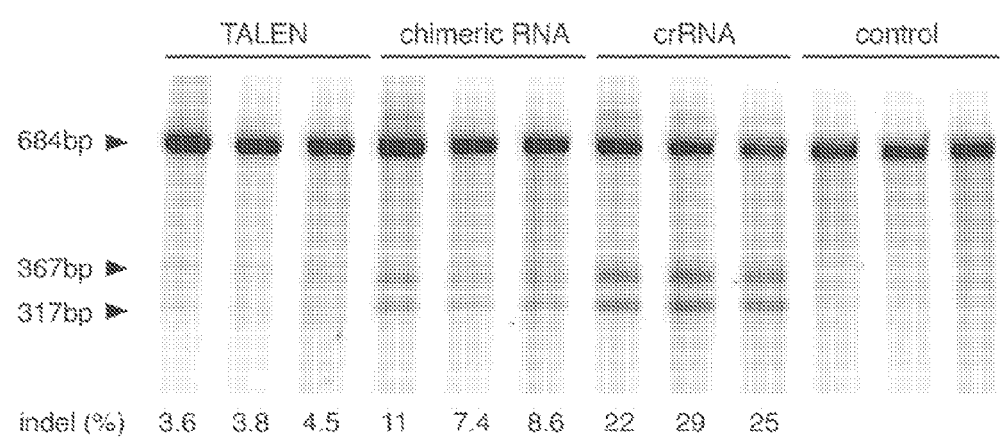

To investigate the specificity of CRISPR-mediated cleavage, the effect of single-nucleotide mutations in the guide sequence on protospacer cleavage in the mammalian genome was analyzed using a series of EMX1-targeting chimeric crRNAs with single point mutations (FIG. 4A). FIG. 4B illustrates results of a Surveyor nuclease assay comparing the cleavage efficiency of Cas9 when paired with different mutant chimeric RNAs. Single-base mismatch up to 12-bp 5' of the PAM substantially abrogated genomic cleavage by SpCas9, whereas spacers with mutations at farther upstream positions retained activity against the original protospacer target (FIG. 4B). In addition to the PAM, SpCas9 has single-base specificity within the last 12-bp of the spacer. Furthermore, CRISPR is able to mediate genomic cleavage as efficiently as a pair of TALE nucleases (TALEN) targeting the same EMX1 protospacer. FIG. 4C provides a schematic showing the design of TALENs targeting EMX1, and FIG. 4D shows a Surveyor gel comparing the efficiency of TALEN and Cas9 (n=3).

Figure 5F:
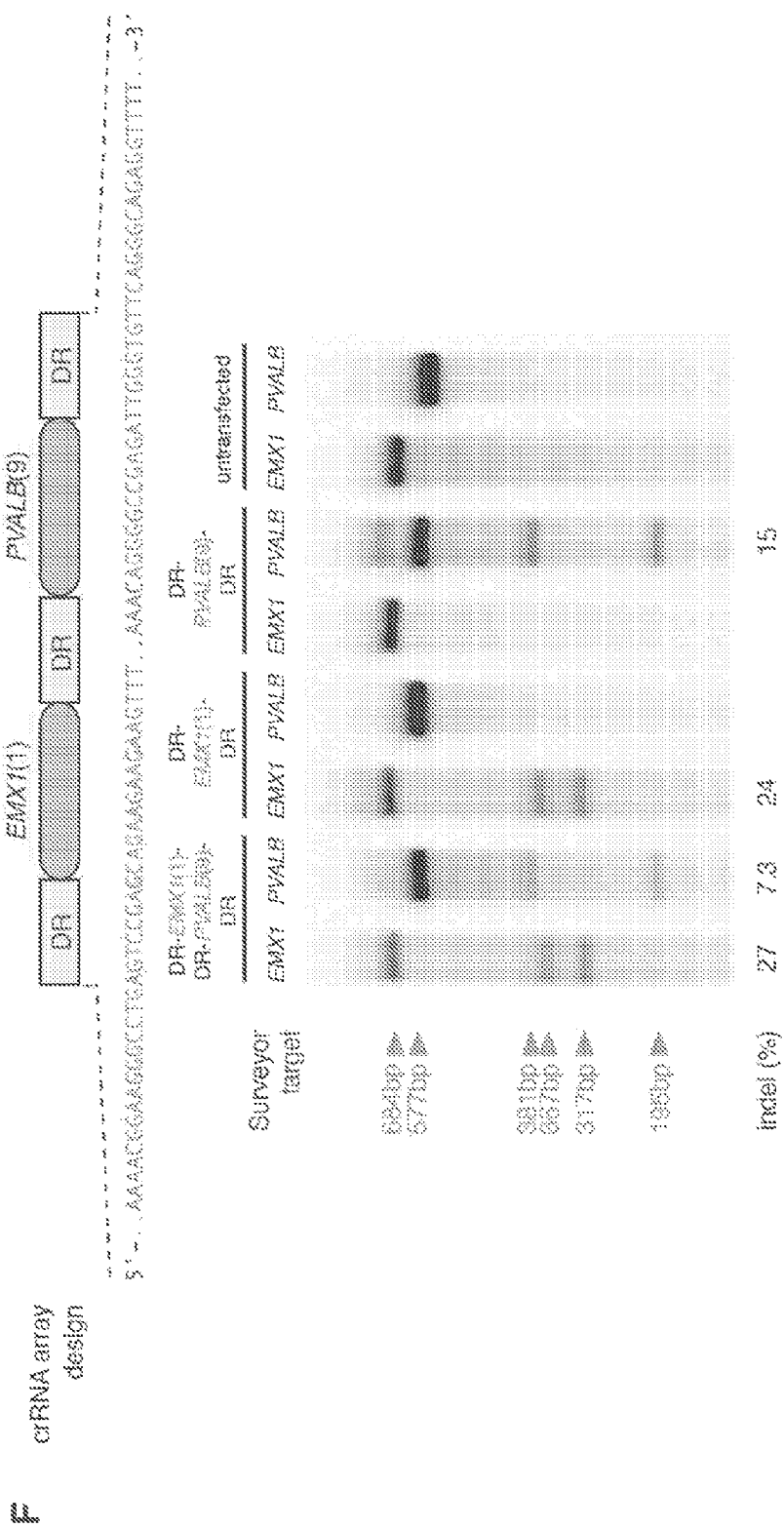
Figure 5G:
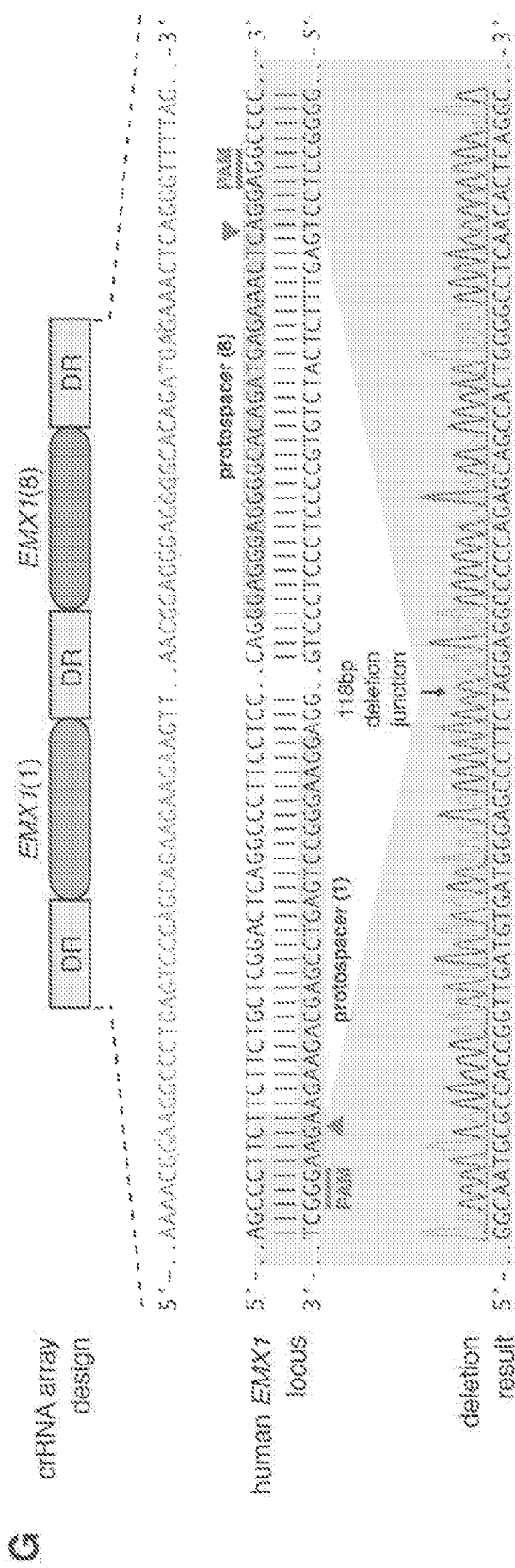

Having established a set of components for achieving CRISPR-mediated gene editing in mammalian cells through the error-prone NHEJ mechanism, the ability of CRISPR to stimulate homologous recombination (HR), a high fidelity gene repair pathway for making precise edits in the genome, was tested. The wild type SpCas9 is able to mediate site-specific DSBs, which can be repaired through both NHEJ and HR. In addition, an aspartate-to-alanine substitution (D10A) in the RuvC I catalytic domain of SpCas9 was engineered to convert the nuclease into a nickase (SpCas9n; illustrated in FIG. 5A) (see e.g. Sapranauskas et al., 2011, Nucleic Acids Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. As illustrated in FIG. 5B, co-expression of EMXA-targeting chimeric crRNA with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. FIG. 5C provides a schematic illustration of the HR strategy, with relative locations of recombination points and primer annealing sequences (arrows). SpCas9 and SpCas9n indeed catalyzed integration of the HR template into the EMX1 locus. PCR amplification of the target region followed by restriction digest with HindIII revealed cleavage products corresponding to expected fragment sizes (arrows in restriction fragment length polymorphism gel analysis shown in FIG. 5D), with SpCas9 and SpCas9n mediating similar levels of HR efficiencies. Applicants further verified HR using Sanger sequencing of genomic amplicons (FIG. 5E). These results demonstrate the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway.

Expression constructs mimicking the natural architecture of CRISPR loci with arrayed spacers (FIG. 2A) were constructed to test the possibility of multiplexed sequence targeting. Using a single CRISPR array encoding a pair of EMX1- and PVALB-targeting spacers, efficient cleavage at both loci was detected (FIG. 4F, showing both a schematic design of the crRNA array and a Surveyor blot showing efficient mediation of cleavage). Targeted deletion of larger genomic regions through concurrent DSBs using spacers against two targets within EMX1 spaced by 119 bp was also tested, and a 1.6% deletion efficacy (3 out of 182 amplicons; FIG. 4G) was detected. This demonstrates that the CRISPR system can mediate multiplexed editing within a single genome.

Example 2

CRISPR System Modifications and Alternatives

Figure 16:
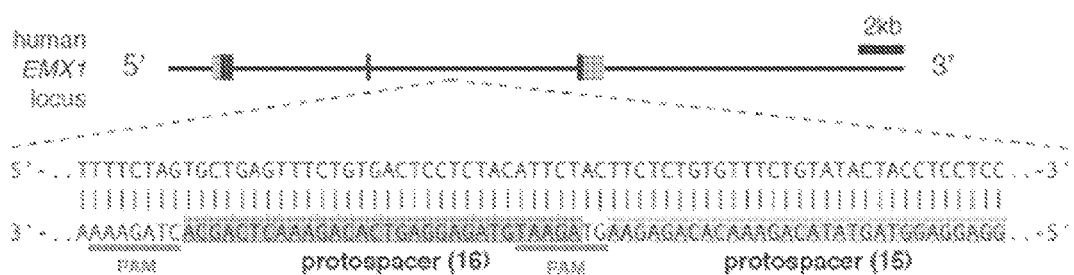
FIG. 16 shows example protospacer and corresponding PAM sequence targets of the *S. thermophilus* CRISPR system in the human EMX1 locus (SEQ ID NO: 350).

The ability to use RNA to program sequence-specific DNA cleavage defines a new class of genome engineering tools for a variety of research and industrial applications. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome (FIG. 11, evaluating both plus and minus strands of human chromosomal sequences). Some of these constraints can be overcome by exploring the diversity of CRISPR loci across the microbial metagenome (see e.g. Makarova et al., 2011, Nat Rev Microbiol, 9:467). Other CRISPR loci may be transplanted into the mammalian cellular milieu by a process similar to that described in Example 1. For example, FIG. 12 illustrates adaptation of the Type II CRISPR system from CRISPR 1 of Streptococcus thermophilus LMD-9 for heterologous expression in mammalian cells to achieve CRISPR-mediated genome editing. FIG. 12A provides a Schematic illustration of CRISPR 1 from S. thermophilus LMD-9. FIG. 12B illustrates the design of an expression system for the S. thermophilus CRISPR system. Human codon-optimized hStCas9 is expressed using a constitutive EF1α promoter. Mature versions of tracrRNA and crRNA are expressed using the U6 promoter to promote precise transcription initiation. Sequences from the mature crRNA and tracrRNA are illustrated. A single base indicated by the lower case "a" in the crRNA sequence is used to remove the polyU sequence, which serves as a RNA polIII transcriptional terminator. FIG. 12C provides a schematic showing guide sequences targeting the human EMX1 locus as well as their predicted secondary structures. The modification efficiency at each target site is indicated below the RNA secondary structures. The algorithm generating the structures colors each base according to its probability of assuming the predicted secondary structure, which is indicated by a rainbow scale reproduced in FIG. 12C in gray scale. FIG. 12D shows the results of hStCas9-mediated cleavage in the target locus using the Surveyor assay. RNA guide spacers 1 and 2 induced 14% and 6.4%, respectively. Statistical analysis of cleavage activity across biological replica at these two protospacer sites is also provided in FIG. 6. FIG. 16 provides a schematic of additional protospacer and corresponding PAM sequence targets of the S. thermophilus CRISPR system in the human EMX1 locus. Two protospacer sequences are highlighted and their corresponding PAM sequences satisfying NNAGAAW motif are indicated by underlining 3' with respect to the corresponding highlighted sequence. Both protospacers target the anti-sense strand.

Example 3

Sample Target Sequence Selection Algorithm

A software program is designed to identify candidate CRISPR target sequences on both strands of an input DNA sequence based on desired guide sequence length and a CRISPR motif sequence (PAM) for a specified CRISPR enzyme. For example, target sites for Cas9 from S. pyogenes, with PAM sequences NGG, may be identified by searching for 5'-$N_x$-NGG-3' both on the input sequence and on the reverse-complement of the input. Likewise, target sites for Cas9 of S. thermophilus CRISPR1, with PAM sequence NNAGAAW, may be identified by searching for 5'-$N_x$—NNAGAAW-3' (SEQ ID NO: 29) both on the input sequence and on the reverse-complement of the input. Likewise, target sites for Cas9 of S. thermophilus CRISPR3, with PAM sequence NGGNG, may be identified by searching for 5'-$N_x$—NGGNG-3' both on the input sequence and on the reverse-complement of the input. The value "x" in N, may be fixed by the program or specified by the user, such as 20.

Since multiple occurrences in the genome of the DNA target site may lead to nonspecific genome editing, after identifying all potential sites, the program filters out sequences based on the number of times they appear in the relevant reference genome. For those CRISPR enzymes for which sequence specificity is determined by a 'seed' sequence, such as the 11-12 bp 5' from the PAM sequence, including the PAM sequence itself, the filtering step may be based on the seed sequence. Thus, to avoid editing at additional genomic loci, results are filtered based on the number of occurrences of the seed:PAM sequence in the relevant genome. The user may be allowed to choose the length of the seed sequence. The user may also be allowed to specify the number of occurrences of the seed:PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s).

Further details of methods and algorithms to optimize sequence selection can be found in U.S. application Ser. No. 61/836,080; incorporated herein by reference.

Example 4

Evaluation of Multiple Chimeric crRNA-tracrRNA Hybrids

Figure 18A:
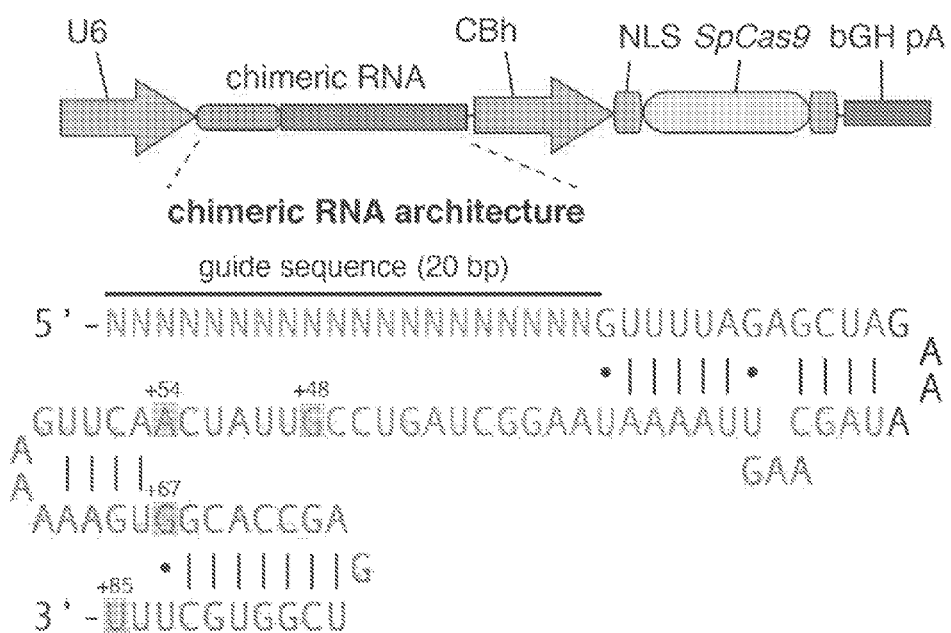
FIGS. 18A-C show exemplary manipulation of a CRISPR system with chimeric RNAs and results of SURVEYOR assays for system activity in eukaryotic cells.
Figure 18B:
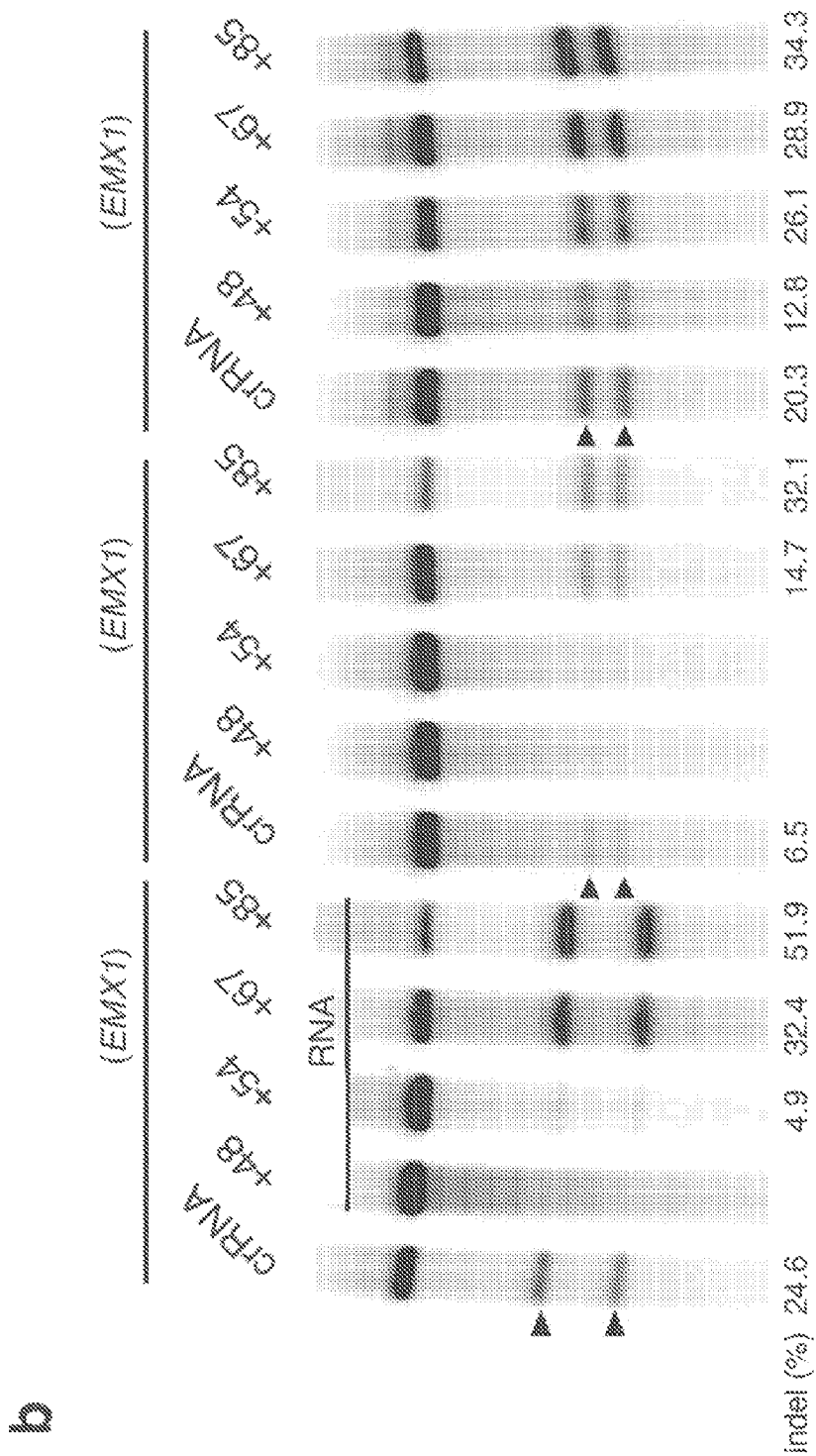
Figure 18C:
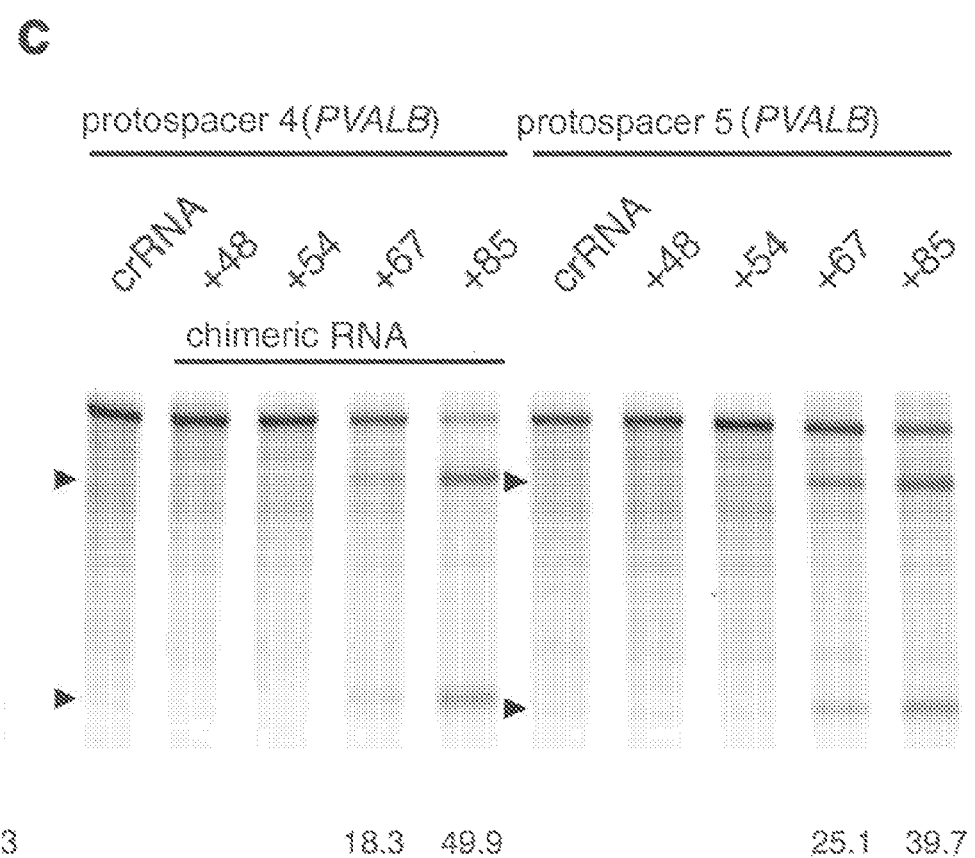
Figure 20:
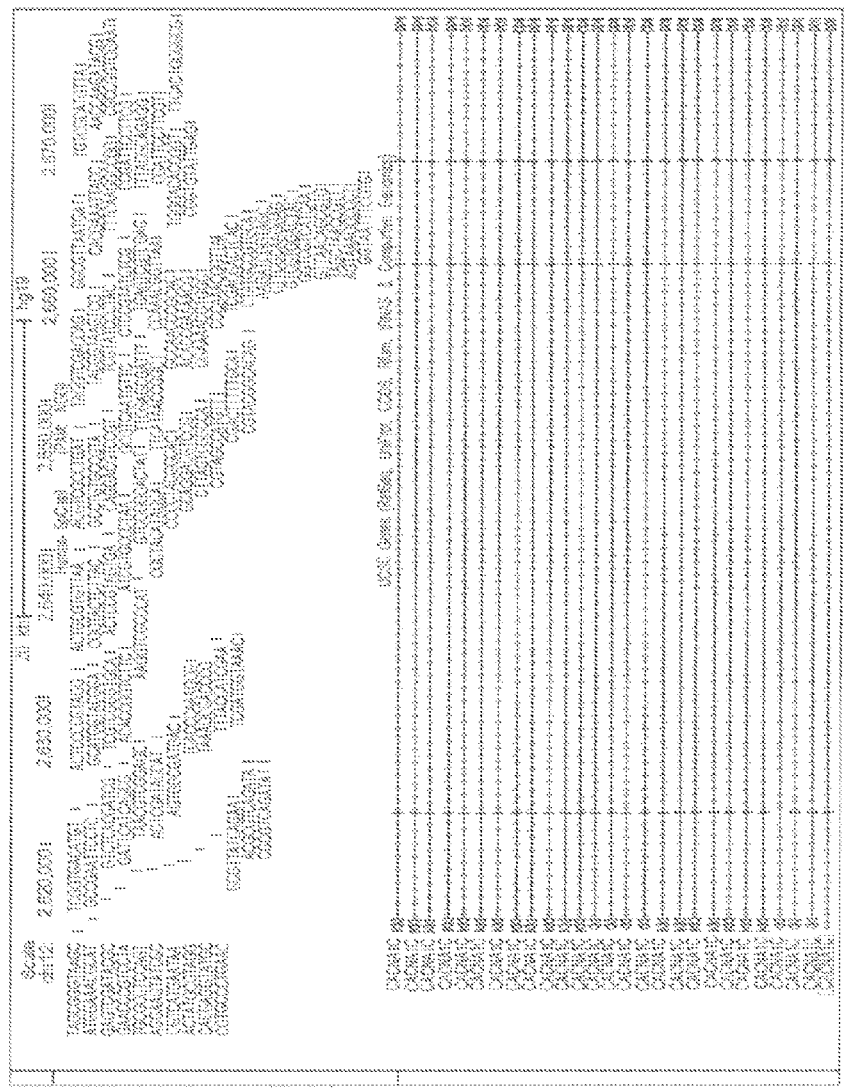
FIG. 20 shows an exemplary visualization of some S. pyogenes Cas9 target sites in the human genome using the UCSC genome browser (SEQ ID NOS 367-445, respectively, in order of appearance).

This example describes results obtained for chimeric RNAs (chiRNAs; comprising a guide sequence, a tracr mate sequence, and a tracr sequence in a single transcript) having tracr sequences that incorporate different lengths of wild-type tracrRNA sequence. FIG. 18a illustrates a schematic of a bicistronic expression vector for chimeric RNA and Cas9. Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA (SEQ ID NO: 30) followed by the loop sequence GAAA. Results of SURVEYOR assays for Cas9-mediated indels at the human EMX1 and PVALB loci are illustrated in FIGS. 18b and 18c, respectively. Arrows indicate the expected SURVEYOR fragments. ChiRNAs are indicated by their "+n" designation, and crRNA refers to a hybrid RNA where guide and tracr sequences are expressed as separate transcripts. Quantification of these results, performed in triplicate, are illustrated by histogram in FIGS. 19a and 19b, corresponding to FIGS. 18b and 18c, respectively ("N.D." indicates no indels detected). Protospacer IDs and their corresponding genomic target, protospacer sequence, PAM sequence, and strand location are provided in Table D. Guide sequences were designed to be complementary to the entire protospacer sequence in the case of separate transcripts in the hybrid system, or only to the underlined portion in the case of chimeric RNAs.

TABLE D

| proto-spacer ID | genomic target | protospacer sequence (5' to 3') | PAM | strand |
|---|---|---|---|---|
| 1 | EMX1 | GGACATCGAT<u>GTCACCTCCAATGAC</u>TGG TAGGG (SEQ ID NO: 31) | | + |

TABLE D-continued

| proto-spacer ID | genomic target | protospacer sequence (5' to 3') | PAM | strand |
|---|---|---|---|---|
| 2 | EMX1 | CATTGGAGGT<u>GACATCGATGTCCT</u>CTGG CCCAT (SEQ ID NO: 32) | | − |
| 3 | EMX1 | GGAAGGGCCT<u>GAGTCCGAGCAGAA</u>GGGG AAGAA (SEQ ID NO: 33) | | + |
| 4 | PVALB | GGTGGCGAGA<u>GGGGCCGAGATTGG</u>GAGG TGTTC (SEQ ID NO: 34) | | + |
| 5 | PVALB | ATGCAGGAGG<u>GTGGCGAGAGGGGC</u>CTGG GAGAT (SEQ ID NO: 35) | | + |

Cell Culture and Transfection

Human embryonic kidney (HEK) cell line 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 μg/mL streptomycin at 37° C. with 5% $CO_2$ incubation. 293FT cells were seeded onto 24-well plates (Corning) 24 hours prior to transfection at a density of 150,000 cells per well. Cells were transfected using Lipofectamine 2000 (Life Technologies) following the manufacturer's recommended protocol. For each well of a 24-well plate, a total of 500 ng plasmid was used.

SURVEYOR Assay for Genome Modification

293FT cells were transfected with plasmid DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes and 98° C. for 10 minutes. The genomic region flanking the CRISPR target site for each gene was PCR amplified (primers listed in Table E), and products were purified using QiaQuick Spin Column (Qiagen) following the manufacturer's protocol. 400 ng total of the purified PCR products were mixed with 2 μl 10× Taq DNA Polymerase PCR buffer (Enzymatics) and ultrapure water to a final volume of 20 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities.

TABLE E

| primer name | genomic target | primer sequence (5' to 3') |
|---|---|---|
| Sp-EMX1-F | EMX1 | AAAACCACCCTTCTCTCTGGC (SEQ ID NO: 36) |
| Sp-EMX1-R | EMX1 | GGAGATTGGAGACACGGAGAG (SEQ ID NO: 37) |

TABLE E-continued

| primer name | genomic target | primer sequence (5' to 3') |
|---|---|---|
| Sp-PVALB-F | PVALB | CTGGAAAGCCAATGCCTGAC (SEQ ID NO: 38) |
| Sp-PVALB-R | PVALB | GGCAGCAAACTCCTTGTCCT (SEQ ID NO: 39) |

Computational Identification of Unique CRISPR Target Sites

Figure 21:
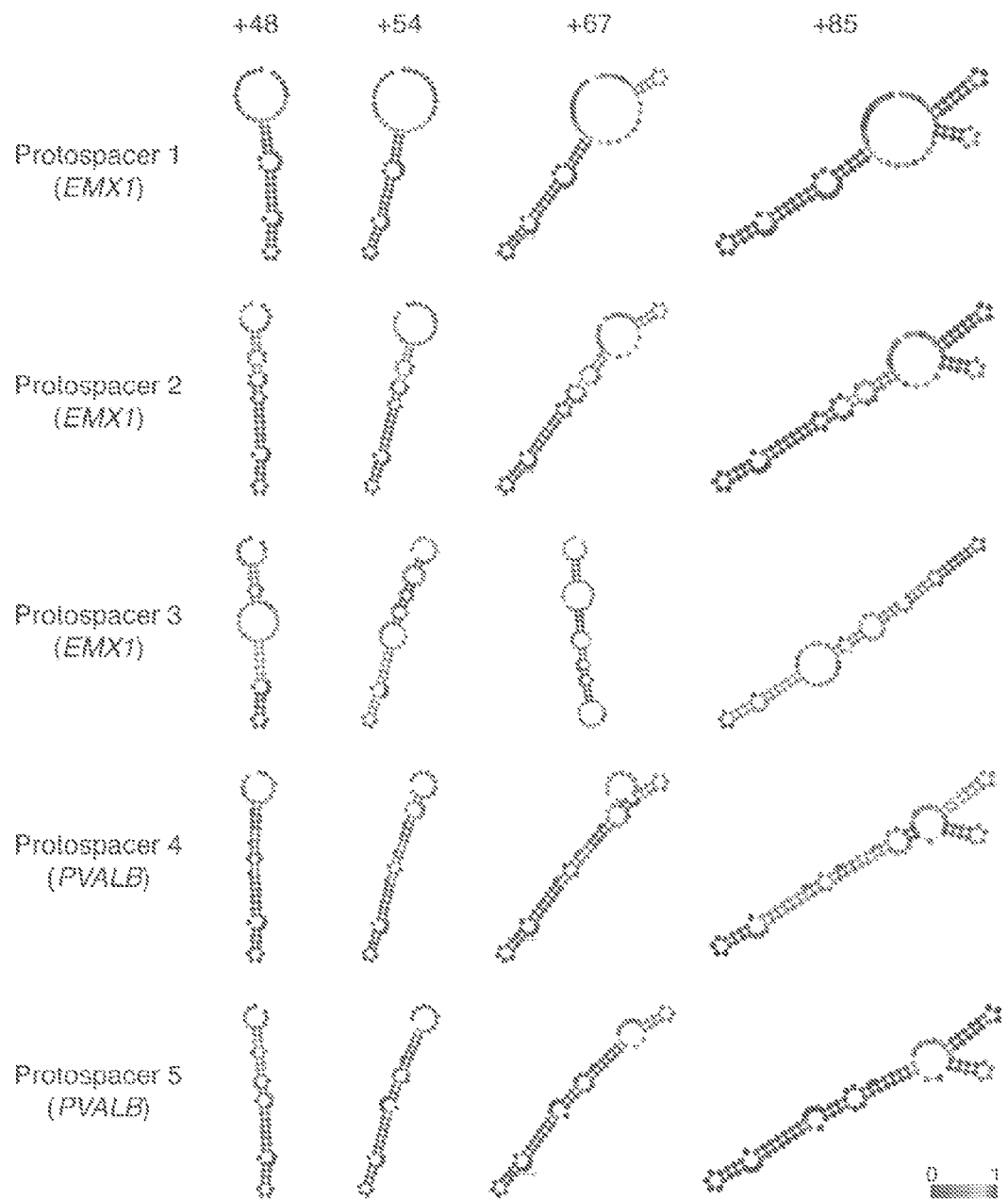
FIG. 21 shows predicted secondary structures for exemplary chimeric RNAs comprising a guide sequence, tracr mate sequence, and tracr sequence (SEQ ID NOS 446-465, respectively, in order of appearance).

To identify unique target sites for the S. pyogenes SF370 Cas9 (SpCas9) enzyme in the human, mouse, rat, zebrafish, fruit fly, and C. elegans genome, we developed a software package to scan both strands of a DNA sequence and identify all possible SpCas9 target sites. For this example, each SpCas9 target site was operationally defined as a 20 bp sequence followed by an NGG protospacer adjacent motif (PAM) sequence, and we identified all sequences satisfying this 5'-$N_{20}$—NGG-3' definition on all chromosomes. To prevent non-specific genome editing, after identifying all potential sites, all target sites were filtered based on the number of times they appear in the relevant reference genome. To take advantage of sequence specificity of Cas9 activity conferred by a 'seed' sequence, which can be, for example, approximately 11-12 bp sequence 5' from the PAM sequence, 5'-NNNNNNNNNN-NGG-3' sequences were selected to be unique in the relevant genome. All genomic sequences were downloaded from the UCSC Genome Browser (Human genome hg19, Mouse genome mm9, Rat genome rn5, Zebrafish genome danRer7, D. melanogaster genome dm4 and C. elegans genome ce10). The full search results are available to browse using UCSC Genome Browser information. An example visualization of some target sites in the human genome is provided in FIG. 21.

Initially, three sites within the EMX1 locus in human HEK 293FT cells were targeted. Genome modification efficiency of each chiRNA was assessed using the SURVEYOR nuclease assay, which detects mutations resulting from DNA double-strand breaks (DSBs) and their subsequent repair by the non-homologous end joining (NHEJ) DNA damage repair pathway. Constructs designated chiRNA(+n) indicate that up to the +n nucleotide of wild-type tracrRNA is included in the chimeric RNA construct, with values of 48, 54, 67, and 85 used for n. Chimeric RNAs containing longer fragments of wild-type tracrRNA (chiRNA(+67) and chiRNA(+85)) mediated DNA cleavage at all three EMX1 target sites, with chiRNA(+85) in particular demonstrating significantly higher levels of DNA cleavage than the corresponding crRNAtracrRNA hybrids that expressed guide and tracr sequences in separate transcripts (FIGS. 18b and 19a). Two sites in the PVALB locus that yielded no detectable cleavage using the hybrid system (guide sequence and tracr sequence expressed as separate transcripts) were also targeted using chiRNAs. chiRNA(+67) and chiRNA(+85) were able to mediate significant cleavage at the two PVALB protospacers (FIGS. 18c and 19b).

For all five targets in the EMX1 and PVALB loci, a consistent increase in genome modification efficiency with increasing tracr sequence length was observed. Without wishing to be bound by any theory, the secondary structure formed by the 3' end of the tracrRNA may play a role in enhancing the rate of CRISPR complex formation. An illustration of predicted secondary structures for each of the chimeric RNAs used in this example is provided in FIG. 21. The secondary structure was predicted using RNAfold (http://rna.tbi.univie.ac.at/cgi-bin/RNAfold.cgi) using minimum free energy and partition function algorithm. Pseudocolor for each based (reproduced in grayscale) indicates the probability of pairing. Because chiRNAs with longer tracr sequences were able to cleave targets that were not cleaved by native CRISPR crRNA/tracrRNA hybrids, it is possible that chimeric RNA may be loaded onto Cas9 more efficiently than its native hybrid counterpart. To facilitate the application of Cas9 for site-specific genome editing in eukaryotic cells and organisms, all predicted unique target sites for the S. pyogenes Cas9 were computationally identified in the human, mouse, rat, zebra fish, C. elegans, and D. melanogaster genomes. Chimeric RNAs can be designed for Cas9 enzymes from other microbes to expand the target space of CRISPR RNA-programmable nucleases.

Figure 22:
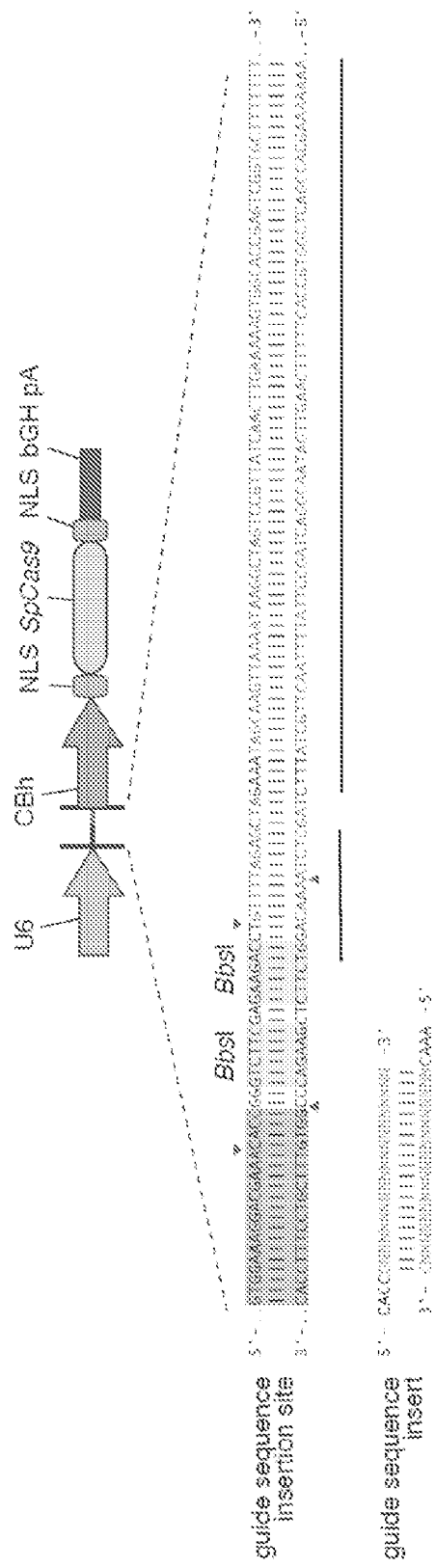
FIG. 22 shows exemplary bicistronic expression vectors for expression of CRISPR system elements in eukaryotic cells (SEQ ID NOS 466 and 343-344, respectively, in order of appearance).
Figure 31:
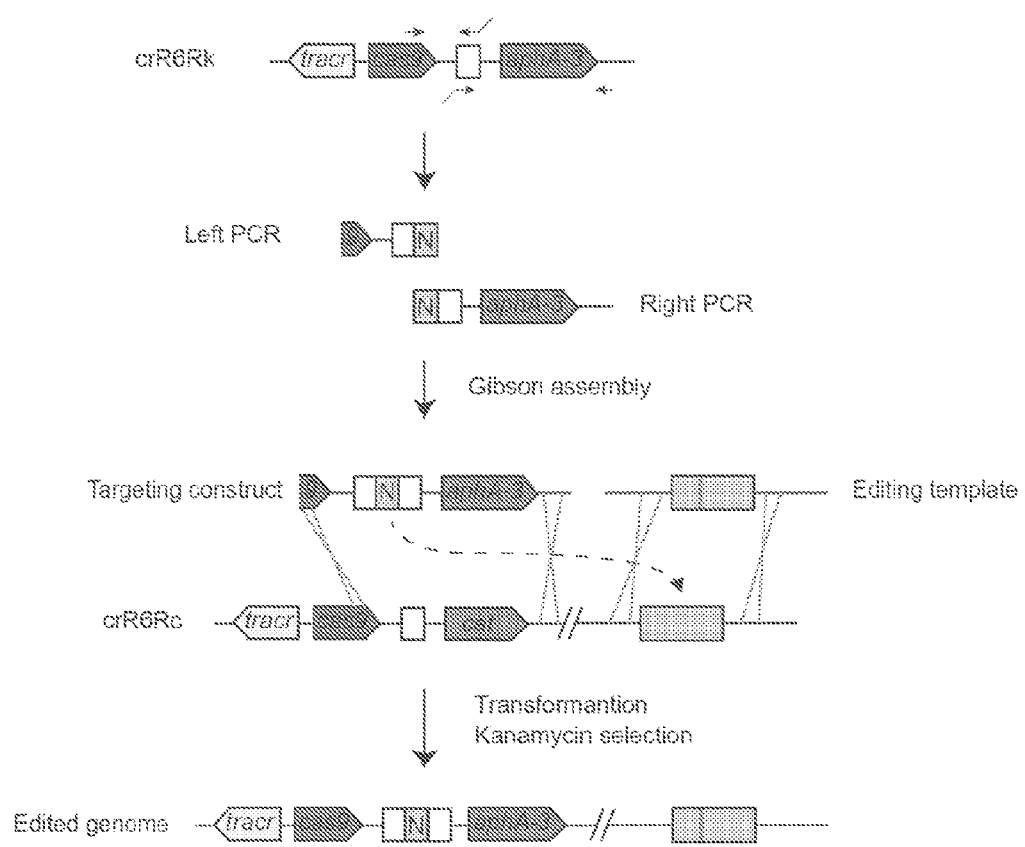
FIG. 31 provides a general scheme for targeted genome editing. To facilitate targeted genome editing, crR6M was further engineered to contain tracrRNA, Cas9 and only one repeat of the CRISPR array followed by kanamycin resistance marker (aphA-3), generating strain crR6Rk. DNA from this strain is used as a template for PCR with primers designed to introduce a new spacer (green box designated with N). The left and right PCRs are assembled using the Gibson method to create the targeting construct. Both the targeting and editing constructs are then transformed into strain crR6Rc, which is a strain equivalent to crR6Rk but has the kanamycin resistance marker replaced by a chloramphenicol resistance marker (cat). About 90% of the kanamycin-resistant transformants contain the desired mutation.
Figure 32:
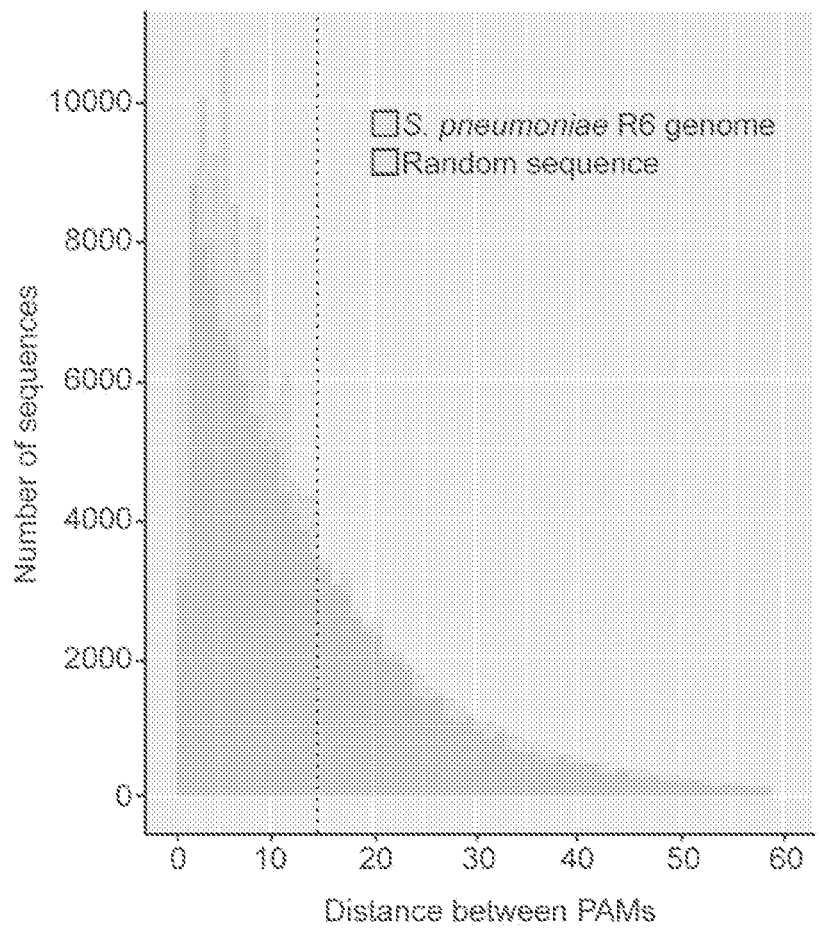
FIG. 32 illustrates the distribution of distances between PAMs. NGG and CCN that are considered to be valid PAMs. Data is shown for the S. pneumoniae R6 genome as well as for a random sequence of the same length and with the same GC-content (39.7%). The dotted line represents the average distance (12) between PAMs in the R6 genome.

FIG. 22 illustrates an exemplary bicistronic expression vector for expression of chimeric RNA including up to the +85 nucleotide of wild-type tracr RNA sequence, and SpCas9 with nuclear localization sequences. SpCas9 is expressed from a CBh promoter and terminated with the bGH polyA signal (bGH pA). The expanded sequence illustrated immediately below the schematic corresponds to the region surrounding the guide sequence insertion site, and includes, from 5' to 3',3'-portion of the U6 promoter (first shaded region), BbsI cleavage sites (arrows), partial direct repeat (tracr mate sequence GTTTTAGAGCTA (SEQ ID NO: 27), underlined), loop sequence GAAA, and +85 tracr sequence (underlined sequence following loop sequence). An exemplary guide sequence insert is illustrated below the guide sequence insertion site, with nucleotides of the guide sequence for a selected target represented by an "N".

Sequences described in the above examples are as follows (polynucleotide sequences are 5' to 3'):

U6-short tracrRNA (Streptococcus pyogenes SF370):

(SEQ ID NO: 40)
GAGGGCCTATTTCCCATGATTCCTTCATATTTGCATATACGATACAAG

GCTGTTAGAGAGATAATTGGAAT-
TAATTTGACTGTAAACACAAAGATA

TTAGTACAAAATACGTGACGTAGAAAG-
TAATAATTTCTTGGGTAGTTT

GCAGTTTTAAAATTATGTTTTAAAATGGACTATCATATGCTTACCGTA

ACTTGAAAGTATTTCGATTTCTTGGCTT-
TATATATCTTGTGGAAAGGA

CGAAACACC**GGAACCATTCAAAACAG-
CATAGCAAGTTAAAATAAGGCT**

AGTCCGTTATCAACTTGAAAAAGTGGCACCGAGTCGGTGC
TTTTTTT
(bold = tracrRNA sequence; underline = terminator sequence)

U6-long tracrRNA (Streptococcus pyogenes SF370):

(SEQ ID NO: 41)
GAGGGCCTATTTCCCATGATTCCTTCATATTTGCATATACGATACAAG

GCTGTTAGAGAGATAATTGGAATTAATTTGACTGTAAACACAAAGATA

TTAGTACAAAATACGTGACGTAGAAAGTAATAATTTCTTGGGTAGTTT

GCAGTTTTAAAATTATGTTTTAAAATGGACTATCATATGCTTACCGTA

ACTTGAAAGTATTTCGATTTCTTGGCTTTATATATCTTGTGGAAAGGA

CGAAACACCGGTAGTATTAAGTATTGTTTTATGGCTGATAAATTTCTT

-continued

TGAATTTCTCCTTGATTATTTGTTATAAAAGTTATAAAATAATCTTGT

TGGAACCATTCAAAACAGCATAGCAAGTTAAAATAAGGCTAGTCCGTT

ATCAACTTGAAAAAGTGGCACCGAGTCGGTGCTTTTTTT

U6-DR-BbsI backbone-DR (*Streptococcus pyogenes* SF370):

(SEQ ID NO: 42)
GAGGGCCTATTTCCCATGATTCCTTCATATTTGCATATACGATACAAG

GCTGTTAGAGAGATAATTGGAATTAATTTGACTGTAAACACAAAGATA

TTAGTACAAAATACGTGACGTAGAAAGTAATAATTTCTTGGGTAGTTT

GCAGTTTTAAAATTATGTTTTAAAATGGACTATCATATGCTTACCGTA

ACTTGAAAGTATTTCGATTTCTTGGCTTTATATATCTTGTGGAAAGGA

CGAAACACCGGGTTTTAGAGCTATGCTGTTTTGAATGGTCCCAAAACG

GGTCTTCGAGAAGACGTTTTAGAGCTATGCTATGCTGTTTTGAATGGT

CCCAAAAC

U6-chimeric RNA-BbsI backbone (*Streptococcus pyogenes* SF370)

(SEQ ID NO: 43)
GAGGGCCTATTTCCCATGATTCCTTCATATTTGCATATACGATACAAGGC

TGTTAGAGAGATAATTGGAATTAATTTGACTGTAAACACAAAGATATTAG

TACAAAATACGTGACGTAGAAAGTAATAATTTCTTGGGTAGTTTGCAGTT

TTAAAATTATGTTTTAAAATGGACTATCATATGCTTACCGTAACTTGAAA

GTATTTCGATTTCTTGGCTTTATATATCTTGTGGAAAGGACGAAACACCG

GGTCTTCGAGAAGACCTGTTTTAGAGCTAGAAATAGCAAGTTAAAATAAG

GCTAGTCCG

NLS-SpCas9-EGFP:

(SEQ ID NO: 44)
MDYKDHDGDYKDHDIDYKDDDDKMAPKKKRKVGIHGVPAADKKYSIGLDI

GTNSVGWAVITDEYKVPSKKFKVLGNTDRHSIKKNLIGALLFDSGETAEA

TRLKRTARRRYTRRKNRICYLQEIFSNEMAKVDDSFFHRLEESFLVEEDK

KHERHPIFGNIVDEVAYHEKYPTIYHLRKKLVDSTDKADLRLIYLALAHM

IKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAED

AKLQLSKDTYDDDLDNLLAQIGDQYADLFLAAKNLSDAILLSDILRVNTE

ITKAPLSASMIKRYDEHHQDLTLLKALVRQQLPEKYKEIFFDQSKNGYAG

YIDGGASQEEFYKFIKPILEKMDGTEELLVKLNREDLLRKQRTFDNGSIP

HQIHLGELHAILRRQEDFYPFLKDNREKIEKILTFRIPYYVGPLARGNSR

FAQNTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEE

NEDILEDIVLTLTLFEDREMIEERLKTYAHLFDDKVMKQLKRRRYTGWGR

LSRKLINGIRDKQSGKTILDFLKSDGFANRNFMQLIGDDSLTFKEDIQKA

QVSGQGDSLHEHIANLAGSPAIKKGILQTVKVVDELVKVMGRHKPENIVI

EMARENQTTQKGQKNSRERMKRIEEGIKELGSQILKEHPVENTQLQNEKL

YLYYLQNGREDMYVDQELDINRLSDYDVDHIVPQSFLKDDSIDNKVLTRS

DKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKS

KLVSDFRKDFQFYKVREINNYHHAHDAYLNAVVGTALIKKYPKLESEVYG

DYKVYDVRKMIAKSEQEIGKATAKYFFYSNIMNFFKTEITLANGEIRKRP

LIETNGETGEIVWDKGRDFATVRKVLSMPQVNIVKKTEVQTGGFSKESIL

PKRNSDKLIARKKDWDPKKYGGFDSPTVAYSVLVVAKVEKGKSKKLKSVK

ELLGITIMERSSFEKNPIDFLEAKGYKEVKKDLIIKLPKYSLFELENGRK

RMLASAGELQKGNELALPSKYVNFLYLASHYEKLKGSPEDNEQKQLFVEQ

HKHYLDEIIEQISEFSKRVILADANLDKVLSAYNKHRDKPIREQAENIIH

LFTLTNLGAPAAFKYFDTTIDRKRYTSKEVLDATLIHQSITGLYETRIDL

SQLGGDAAAVSKGEELFTGVVPILVELDGDVNGHKFSVSGEGEGDATYGK

LTLKFICTTGKLPVPWPTLVTTLTYGVQCFSRYPDHMKQHDFFKSAMPEG

YVQERTIFFKDDGNYKTRAEVKFEGDTLVNRIELKGIDFKEDGNILGHKL

EYNYNSHNVYIMADKQKNGIKVNFKIRHNIEDGSVQLADGYQQNTPIGDG

PVLLPDNHYLSTQSALSKDPNEKRDHMVLLEFVTAAGITLGMDELYK

SpCas9-EGFP-NLS:

(SEQ ID NO: 45)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

-continued

REVKVITLKSKLVSDFRKDFQFYKVREINNYHHAHDAYLNAVVGTALIKK
YPKLESEFVYGDYKVYDVRKMIAKSEQEIGKATAYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDDAAAVSKGEELFTGVVPILVELDGDVNGHKFSV
SGEGEGDATYGKLTLKFICTTGKLPVPWPTLVTTLTYGVQCFSRYPDHMK
QHDFFKSAMPEGYVQERTIFFKDDGNYKTRAEVKFEGDTLVNRIELKGID
FKEDGNILGHKLEYNYNSHNVYIMADKQKNGIKVNFKIRHNIDGSVQLAD
HYQQNTPIGDGPVLLPDNHYLSTQSALSKDPNEKRDHMVLLEFVTAAGIT
LGMDELYKKRPAATKKAGQAKKKK

NLS-SpCas9-EGFP-NLS:

(SEQ ID NO: 46)
MDYKDHDGDYKDHDIDYKDDDDKMAPKKKRKVGIHGVPAADKKYSIGLDI
GTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTE
ITKAPLSASMIKRYDEHHQDLTLLKALVRQQLPEKYKEIFFDQSKNGYAG
YIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTV
KQLKEDYFKKIECFDSVISGVEDRFNASLGTYHDLLKIIKDKDFLDNEEN
EDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQ
VSGQGDSLHEHIANLAGSPAIKKGILQTVKVVDELVKVMGRHKPENIVIE
MARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELD
KAGFIKRQLVETRQITKHVAQILDSRMNTKYDENDKLIREVKVITLKSKL
VSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPL
IETNGETGEIVWDKGRDFATVRKVLSMPQVNIVKKTEVQTGGFSKESILP
KRNSDKLIARKKDWDPKKYGGFDSPTVAYSVLVVAKVEKGKSKKLKSVKE

-continued

LLGITIMERSSFEKNPIDFLEAKGYKEVKKDLIIKLPKYSLFELENGRKR
MLASAGELQKGNELALPSKYVNFLYLASHYEKLKGSPEDNEQKQLFVEQH
KHYLDEIIEQISEFSKRVILADANLDKVLSAYNKHRDKPIREQAENIIHL
FTLTNLGAPAAFKYFDTTIDRKRYTSKEVLDATLIHQSITGLYETRIEDL
SQLGGDDAAAVSKGEELFTGVVPILVELDGDVNGHKFSVSGEGEGDATYG
KLTLKFICTTGKLPVPWPTLVTTLTYGVQCFSRYPDHMKQHDFFKSAMPE
GYVQERTIFFKDDGNYKTRAEVKFEGDTLVNRIELKGIDEFKEDGNILGH
KLEYNYNSHNVYIMADKQKNGIKVNFKIRHNIEDGSVQLADHYQQNTPIG
DGPVLLPDNHYLSTQSALSKDPNEKRDHMVLLEVTAAGITLGMDELYKKR
PAATKKAGQAKKKK

NLS-SpCas9-NLS:

(SEQ ID NO: 47)
MDYKDHDGDYKDHDIDYKDDDDKMAPKKKRKVGIHGVPAADKKYSIGLDI
GTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTE
ITKAPLSASMIKRYDEHHQDLTLLKALVRQQLPEKYKEIFFDQSKNGYAG
YIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEE
NEDILEDIVLTLTLFEDREMIEERLKTYAHLFDDKVMKQLKRRRYTGWGR
LSRKLINGIRDKQSGKTILDFLKSDGFANRNFMQLIHDDSLTFKEDIQKA
QVSGQGDSLHEHIANLAGSPAIKKGILQTVKVVDELVKVMGRHKPENIVI
EMARENQTTQKGQKNSRERMKRIEEGIKELGSQILKEHPVENTQLQNEKL
YLYYLQNGRDMYVDQELDINRLSDYDVDHIVPQSFLKDDSIDNKVLTRSD
KNRGKSDNVPSEEVVKKMKNYWRQLLNAKLITQRKFDNLTKAERGGLSEL
DKAGFIKRQLVETRQITKHVAQILDSRMNTKYDENDKLIREVKVITLKSK
LVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRP
LIETNGETGEIVWDKGRDFATVRKVLSMPQVNIVKKTEVQTGGFSKESIL
PKRNSDKLIARKKDWDPKKYGGFDSPTVAYSVLVVAKVEKGKSKKLKSVE
KELLGITIMERSSFEKNPIDFLEAKGYKEVKKDLIIKLPKYSLFELENGR
KRMLASAGELQKGNELALPSKYVNFLYLASHYEKLKGSPEDNEQKQLFVE
QHKHYLDEIIEQISEFSKRVILADANLDKVLSAYNKHRDKPIREQAENIIH

-continued

LFTLTNLGAPAAFKYFDTTIDRKRYTSTKEVLDATLIHQSITGLYETRID
LSQLGGDKRPAATKKAGQAKKKK

NLS-mCherry-SpRNa c3:

(SEQ ID NO: 48)
MFLFLSLTSFLSSSRTLVSKGEEDNMAIIKEFMRFKVHMEGSVNGHEFEI
EGEGEGRPYEGTQTAKLKVTKGGPLPGAWDILSPQFMYGSKAYVKHPADI
PDYLKLSFPEGFKWERVMNFEDGGVVTVTQDSSLQDGEFIYKVKLRGTNF
PSDGPVMQKKTMGWEASSERMYPEDGALKGEIKQRLKLKDGGHYDAEVKT
TYKAKKPVQLPGAYNVNIKLDITSHNEDYTIVEQYERAEGRHSTGGMDEL
YKGSKQLEELLSTSFDIQFNDLTLLETAFTHTSYANEHRLLNVSHNERLE
FLGDAVLQLIISEYLFAKYPKKTEGDMSKLRSMIVREESLAGFSRFCSFD
AYIKLGKGEEKSGGRRRDTILGDLFEAFLGALLLDKGIDAVRRFLKQVMI
PQVEKGNFERVKDYKTCLQEFLQTKGDVAIDYQVISEKGPAHAKQFEVSI
VVNGAVLSKGLGKSKKLAEQDAAKNALAQLSEV

SpRNase3-mCherry-NLS:

(SEQ ID NO: 49)
MKQLEELLSTSFDIQFNDLTLLETAFTHTSYANEHRLLNVSHNERLEFLG
DAVLQLIISEYLFAKYPKKTEGDMSKLRSMIVREESLAGFSRFCSFDAYI
KLGKGEEKSGGRRRDTILGDLFEAFLGALLLDKGIDAVRRFLKQVMIPQV
EKGNFERVKDYKTCLQEFLQTKGDVAIDYQVISEKGPAHAKQFEVSIVVN
GAVLSKGLGKSKKLAEQDAAKNALAQLSEVGSVSKGEEDNMAIIKEFMRF
KVHMEGSVNGHEFEIEGEGEGRPYEGTQTAKLKVTKGGPLPGAWDILSPQ
FMYGSKAYVKHPADIPDYLKLSFPEGFKWERVMNFEDGGVVTVTQDSSLQ
DGEFIYKVKLRGTNFPSDGPVMQKKTMGWEASSERMYPEDGALKGEIKQR
LKLKDGGHYDAEVKTTYKAKKPVQLPGAYNVNIKLDITSHNEDYTIVEQY
ERAEGRHSTGGMDELYKKRPAATKKAGQAKKKK

NLS-SpCas9n-NLS (the D10A nickase mutation is lowercase):

(SEQ ID NO: 50)
MDYKDHDGDYKDGDIDYKDDDDKMAPKKKRKVGIHGVPAADKKYSIGLaI
GTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTE
ITKAPLSASMIKRYDEHHQDLTLLKALVRQQLPEKYKEIFFDQSKNGYAG
YIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKH

SLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEE
NEDILEDIVLTLTLFEDREMIEERLKTYAHLFDDKVMKQLKRRRYTGWGR
LSRKLINGIRDKQSGKTILDFLKSDGFANRNFMQLIHDDSLTFKEDIQKA
QVSGQGDSLHEHIANLAGSPAIKKGILQTVKVVDELVKVMGRHPENIVIE
MARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELD
KAGFIKRQLVETRQITKHVAQILDSRMNTKYDENDKLIREVKVITLKSKL
VSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPL
IETNGETGEIVWDKGRDFATVRKVLSMPQVNIVKKTEVQTGGFSKESILP
KRNSDKLIARKKDWDPKKYGGFDSPTVAYSVLVVAKVEKGKSKKLKSVKE
LLGITIMERSSFEKNPIDFLEAKGYKEVKKDLIIKLPKYSLFELENGRKR
MLASAGELQKGNELALPSKYVNFLYLASHYEKLKGSPEDNEQKQLFVEQH
KHYLDEIIEQISEFSKRVILADANLDKVLSAYNKHRDKPIREQAENIIHL
FTLTNLGAPAAFKYFDTTIDRKRYTSTKEVLDATLIHQSITGLYETRIDL
SQLGGDKRPAATKKAGQAKKKK hEMX1-HR Template-HindIII-NheI:

(SEQ ID NO: 51)
GAATGCTGCCCTCAGACCGCTTCCTCCTGTCCTTGTCTGTCCAAGGAGAA
TGAGGTCTCACTGGTGGATTTCGGACTACCCTGAGGAGCTGGCACCTGAG
GGACAAGGCCCCCACCTGCCCAGCTCCAGCCTCTGATGAGGGGTGGGAG
AGAGCTACATGAGGTTGCTAAGAAAGCCTCCCCTGAAGGAGACCACACAG
TGTGTGAGGTTGGAGTCTCTAGCAGCGGGTTCTGTGCCCCCAGGGATAGT
CTGGCTGTCCAGGCACTGCTCTTGATATAAACACCACCTCCTAGTTATGA
AACCATGCCCATTCTGCCTCTCTGTATGGAAAAGAGCATGGGGCTGGCCC
GTGGGGTGGTGTCCACTTTAGGCCCTGTGGGAGATCATGGGAACCCACGC
AGTGGGTCATAGGCTCTCTCATTTACTACTCACATCCACTCTGTGAAGAA
GCGATTATGATCTCTCCTCTAGAAACTCGTAGAGTCCCATGTCTGCCGGC
TTCAGAGCCTGCACTCCTCCACCTTGGCTTGGCTTTGCTGGGGCTAGAGG
AGCTAGGATGCACAGCAGCTCTGTGACCCTTTGTTTGAGAGGAACAGGAA
AACCACCCTTCTCTCTGGCCCACTGTGTCCTCTTCCTGCCCTGCCATCCC
CTTCTGTGAATGTTAGACCCATGGGAGCAGCTGGTCAGAGGGGACCCCGG
CCTGGGCCCCTAACCCTATGTAGCCTCAGTCTTCCCATCAGGCTCTCAG
CTCAGCCTGAGTGTTGAGGCCCCAGTGGCTGCTCTGGGGGCCTCCTGAGT
TTCTCATCTGTGCCCCTCCCTCCCTGGCCCAGGTGAAGGTGTGGTTCCAG
AACCGGAGGACAAAGTACAAACGGCAGAAGCTGGAGGAGGAAGGGCCTGA
GTCCGAGCAGAAGAAGAAGGGCTCCCATCACATCAACCGGTGGCGCATTG
CCACGAAGCAGGCCAATGGGGAGGACATCGATGTCACCTCCAATGACaag

```
cttgctagcGGTGGGCAACCACAAACCCACGAGGGCAGAGTGCTGCTTGC
TGCTGGCCAGGCCCCTGCGTGGGCCCAAGCTGGACTCTGGCCACTCCCTG
GCCAGGCTTTGGGGAGGCCTGGAGTCATGGCCCCACAGGGCTTGAAGCCC
GGGGCCGCCATTGACAGAGGGACAAGCAATGGGCTGGCTGAGGCCTGGGA
CCACTTGGCCTTCTCCTCGGAGAGCCTGCCTGCCTGGGCGGGCCCGCCCG
CCACCGCAGCCTCCCAGCTGCTCTCCGTGTCTCCAATCTCCCTTTTGTTT
TGATGCATTTCTGTTTTAATTTATTTTCCAGGCACCACTGTAGTTTAGTG
ATCCCCAGTGTCCCCCTTCCCTATGGGAATAATAAAAGTCTCTCTCTTAA
TGACACGGGCATCCAGCTCCAGCCCCAGAGCCTGGGGTGGTAGATTCCGG
CTCTGAGGGCCAGTGGGGGCTGGTAGAGCAAACGCGTTCAGGGCCTGGGA
GCCTGGGTGGGGTACTGGTGGAGGGGGTCAAGGGTAATTCATTAACTCC
TCTCTTTTGTTGGGGGACCCTGGTCTCTACCTCCAGCTCCACAGCAGGAG
AAACAGGCTAGACATAGGGAAGGGCCATCCTGTATCTTGAGGGAGGACAG
GCCCAGGTCTTTCTTAACGTATTGAGAGGTGGGAATCAGGCCCAGGTAGT
TCAATGGGAGAGGGAGAGTGCTTCCCTCTGCTAGAGACTCTGGTGGCTTC
TCCAGTTGAGGAGAAACCAGAGGAAAGGGGAGGATTGGGGTCTGGGGAG
GGAACACCATTCACAAAGGCTGACGGTTCCAGTCCGAAGTCGTGGGCCCA
CCAGGATGCTCACCTGTCCTTGGAGAACCGCTGGGCAGGTTGAGACTGCA
GAGACAGGGCTTAAGGCTGAGCCTGCAACCAGTCCCCAGTGACTCAGGGC
CTCCTCAGCCCAAGAAAGAGCAACGTGCCAGGGCCCGCTGAGCTCTTGTG
TTCACCTG
```

NLS-StCsn1-NLS:

(SEQ ID NO: 52)
MKRPAATKKAGQAKKKKSDLVLGLDIGIGSVGVGILNKVTGEIIHKNSRI
FPAAQAENNLVRRTNRQGRRLARRKKHRRVRLNRLFEESGLITDFTKISI
NLNPYQLRVKGLTDELSNEELFIALKNMVKHRGISYLDDASDDGNSSVGD
YAQIVKENSKQLETKTPGQIQLERYQTYGQLRGDFTVEKDGKKHRLINVP
PTSAYRSEALRILQTQQEFNPQITDEFINRYLEILTGKRKYYHGPGNEKS
RTDYGRYRTSGETLDNIFGILIGKCTFYPDEFRAAKASYTAQEFNLLNDL
NNLTVPTETKKLSKEQKNQIINYVKNEKAMGPAKLFKYIAKLLSCDVADI
KGYRIDKSGKAEIHTFEAYRKMKTLETLDIEQMDRETLDKLAYVLTLNTE
REGIQEALEHEFADGSFSQKQVDELVQFRKANSSIFGKGWHNFSVKLMME
LIPELYETSEEQMTILTRLGKQKTTSSSNKTKYIDEKLLTEEIYNPVVAK
SVRQAIKIVNAAIKEYGDFDNIVIEMARETNEDDEKKAIQKIQKANKDEK
DAAMLKAANQYNGKAELPHSVFHGHKQLATKIRLWHQQGERCLYTGKTIS
IHDLINNSNQFEVDHILPLSITFDDSLANKVLVYATANQEKGQRTYPYQA
LDSMDDAWSFRELKAFVRESKTLSNKKKEYLLTEEDISKFDVRKKFIERN
LVDTRYASRVVLNALQEHFRAHKIDTKVSVVRGQFTSQLRRHWGIEKTRD
TYHHHAVDALIIAASSQLNLWKKQKNTLVSYSEDQLLDIETGELISDDEY
KESVFKAPYQHFVDTLKSKEFEDSILFSYQVDSKFNRKISDATIYATRQA
KVGKDKADETYVLGKIKDIYTQDGYDAFMKIYKKDKSKFLMYRHDPQTFE
KVIEPILENYPNKQINEKGKEVPCNPFLKYKEEHGYIRKYSKKGNGPEIK
SLKYYDSKLGNHIDITPKDSNNKVVLQSVSPWRADVYFNKTTGKYEILGL
KYADLQFEKGTGTYKISQEKYNDIKKKEGVDSDSEFKFTLYKNDLLLVKD
TETKEQQLFRFLSRTMPKQKHYVELKPYDKQKFEGGEALIKVLGNVANSG
QCKKGLGKSNISIYKVRTDVLGNQHIIKNEGDKPKLDFKRPAATKKAGQA
KKKK

U6-St_tracrRNA(7-97):

(SEQ ID NO: 53)
GAGGGCCTATTTCCCATGATTCCTTCATATTTGCATATACGATACAAGGC
TGTTAGAGAGATAATTGGAATTAATTTGACTGTAAACACAAAGATATTAG
TACAAAATACGTGACGTAGAAAGTAATAATTTCTTGGGTAGTTTGCAGTT
TTAAAATTATGTTTTAAAATGGACTATCATATGCTTACCGTAACTTGAAA
GTATTTCGATTTCTTGGCTTTATATATCTTGTGGAAAGGACGAAACACCG
TTACTTAAATCTTGCAGAAGCTACAAAGATAAGGCTTCATGCCGAAATCA
ACACCCTGTCATTTTATGGCAGGGTGTTTTCGTTATTTAA

U6-DR-spacer-DR (*S. pyogenes* SF370)

(SEQ ID NO: 54)
gagggcctatttcccatgattccttcatatttgcatatacgatacaaggc
tgttagagagataattggaattaatttgactgtaaacacaaagatattag
tacaaaatacgtgacgtagaaagtaataatttcttgggtagtttgcagtt
ttaaaattatgttttaaaatggactatcatatgcttaccgtaacttgaaa
gtatttcgatttcttggctttatatatcttgtggaaaggacgaaacaccg
ggttttagagctatgctgttttgaatggtcccaaaacNNNNNNNNNNNNNN
NNNNNNNNNNNNNNNNNNgttttagagctatgctgttttgaatggtccca
aacTTTTTTT
(lowercase underline = direct repeat; N = guide sequence; bold = terminator)

Chimeric RNA containing +48 tracr RNA (*S. pyogenes* SF370)

(SEQ ID NO: 55)
gagggcctattcccatgattccttcatatttgcatatacgatacaaggct
gttagagagataattggaattaatttgactgtaaacacaaagatattagt
acaaaatacgtgacgtagaaagtaataatttcttgggtagtttgcagttt
taaaattatgttttaaaatggactatcatatgcttaccgtaacttgaaag
tattcgatttcttggctttatatatcttgtggaaaggacgaaacaccNNN
NNNNNNNNNNNNNNNNNNgttttagagctagaaatagcaagttaaaataag
gctagtccgTTTTTTT
(N = guide sequence; first underline = tracr mate sequence; second underline = tracr sequence; bold = terminator)

Chimeric RNA containing +54 tracr RNA (*S. pyogenes* SF370)

(SEQ ID NO: 56)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatatcttgtggaaaggacgaaacaccN NNNNNNNNNNNNNNNNNNNgttttagagctagaaatagcaagttaaaata aggctagtccgttatcaTTTTTTTT
(N = guide sequence; first underline = tracr mate sequence; second underline = tracr sequence; bold = terminator)

Chimeric RNA containing +67 tracr RNA (*S. pyogenes* SF370)

(SEQ ID NO: 57)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatatcttgtggaaaggacgaaacacNN NNNNNNNNNNNNNNNNNNNgttttagagctagaaatagcaagttaaaataa ggctagtccgttatcaacttgaaaaagtgTTTTTTT
(N = guide sequence; first underline = tracr mate sequence; second underline = tracr sequence; bold = terminator)

Chimeric RNA containing +85 tracr RNA (*S. pyogenes* SF370)

(SEQ ID NO: 58)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatatcttgtggaaaggacgaaacaccN NNNNNNNNNNNNNNNNNNNgttttagagctagaaatagcaagttaaaa taaggctagtccatatcaacttgaaaaagtggcaccgagtcggtgcTTTT

TTT
(N = guide sequence; first underline = tracr mate sequence; second underline = tracr sequence; bold = terminator)

CBh-NLS-SpCas9-NLS (SEQ ID NO: 59)
CGTTACATAACTTACGGTAAATGGCCCGCCTGGCTGACCGCCCAACGACC

CCCGCCCATTGACGTCAATAATGACGTATGTTCCCATAGTAACGCCAATA

GGGACTTTCCATTGACGTCAATGGGTGGAGTATTTACGGTAAACTGCCCA

CTTGGCAGTACATCAAGTGTATCATATGCCAAGTACGCCCCCTATTGACG

TCAATGACGGTAAATGGCCCGCCTGGCATTATGCCCAGTACATGACCTTA

TGGGACTTTCCTACTTGGCAGTACATCTACGTATTAGTCATCGCTATTAC

CATGGTCGAGGTGAGCCCCACGTTCTGCTTCACTCTCCCCATCTCCCCCC

CCTCCCCACCCCCAATTTTGTATTTATTTATTTTTTAATTATTTTGTGCA

GCGATGGGGGCGGGGGGGGGGGGGGGCGCGCGCCAGGCGGGGCGGGGCG

GGGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGGCGG

CGGCCCTATAAAAAGCGAAGCGCGCGGCGGGCGGGAGTCGCTGCGACGCT

GCCTTCGCCCCGTGCCCCGCTCCGCCGCCGCCTCGCGCCGCCCGCCCCGG

CTCTGACTGACCGCGTTACTCCCACAGGTGAGCGGGCGGGACGGCCCTTC

TCCTCCGGGCTGTAATTAGCTGAGCAAGAGGTAAGGGYTTAAGGGATGGT

TGGTTGGTGGGGTATTAATGYTTAATTACCTGGAGCACCTGCCTGAAATC

ACTTTTTTTCAGGTTGGaccggtgccacc<u>ATGGACTATAAGGACCACGAC</u>

<u>GGAGACTACAAGGATCATGATATTGATTACAAAGACGATGACGATAAGAT</u>

<u>GGCCCCAAAGAAGAAGCGGAAGGTCGGTATCCACGGAGTCCCAGGAGCCG</u>

<u>ACAAGAAGTACAGCATCGGCCTGGACATCGGCACCAACTCTGTGGGCRTG</u>

<u>GCCGTGATCACCGACGAGTACAAGGTGCCCAGCAAGAAATTCAAGGTGCT</u>

<u>GGGCAACACCGACCGGCACAGCATCAAGAAGAACCTGATCGGAGCCCTGC</u>

<u>TGTTCGACAGCGGCGAAACAGCCGAGGCCACCCGGCTGAAGAGAACCGCC</u>

<u>AGAAGAAGATACACCAGACGGAAGAACCGGATCTGCTATCTGCAAGAGAT</u>

<u>CTTCAGCAACGAGATGGCCAAGGTGGACGACAGCTTCTTCCACAGACTGG</u>

<u>AAGAGTCCTTCCTGGTGGAAGAGGATAAGAAGCACGAGCGGCACCCCATC</u>

<u>TTCGGCAACATCGTGGACGAGGTGGCCTACCACGAGAAGTACCCCACCAT</u>

<u>CTACCACCTGAGAAAGAAACTGGTGGACAGCACCGACAAGGCCGACCTGC</u>

<u>GGCTGATCTATCTGGCCCTGGCCCACATGATCAAGTTCCGGGGCCACTTC</u>

<u>CTGATCGAGGGCGACCTGAACCCCGACAACAGCGACGTGGACAAGCTGTT</u>

<u>CATCCAGCTGGTGCAGACCTACAACCAGCTGTTCGAGGAAAACCCCATCA</u>

<u>ACGCCAGCGGCGTGGACGCCAAGGCCATCCTGTCTGCCAGACTGAGCAAG</u>

<u>AGCAGACGGCTGGAAAATCTGATCGCCCAGCTGCCCGGCGAGAAGAAGAA</u>

<u>TGGCCTGTTCGGCAACCTGATTGCCCTGAGCCTGGGCCTGACCCCCAACT</u>

<u>TCAAGAGCAACTTCGACCTGGCCGAGGATGCCAAACTGCAGCTGAGCAAG</u>

<u>GACACCTACGACGACGACCTGGACAACCTGCTGGCCCAGATCGGCGACCA</u>

<u>GTACGCCGACCTGTTTCTGGCCGCCAAGAACCTGTCCGACGCCATCCTGC</u>

<u>TGAGCGACATCCTGAGAGTGAACACCGAGATCACCAAGGCCCCCCTGAGC</u>

<u>GCCTCTATGATCAAGAGATACGACGAGCACCACCAGGACCTGACCCTGCT</u>

<u>GAAAGCTCTCGTGCGGCAGCAGCTGCCTGAGAAGTACAAAGAGATTTCTT</u>

<u>CGACCAGAGCAAGAACGGCTACGCCGGCTACATTGACGGCGGAGCCAGCC</u>

<u>AGGAAGAGTTCTACAAGTTCATCAAGCCCATCCTGGAAAAGATGGACGGC</u>

<u>ACCGAGGAACTGCTCGTGAAGCTGAACAGAGAGGACCTGCTGCGGAAGCA</u>

<u>GCGGACCTTCGACAACGGCAGCATCCCCCACCAGATCCACCTGGGAGAGC</u>

<u>TGCACGCCATTCTGCGGCGGCAGGAAGATTTTTACCCATTCCTGAAGGAC</u>

<u>AACCGGGAAAAGATCGAGAAGATCCTGACCTTCCGCATCCCCTACTACGT</u>

<u>GGGCCCTCTGGCCAGGGGAAACAGCAGATTCGCCTGGATGACCAGAAAGA</u>

-continued

GCGAGGAAACCATCACCCCCTGGAACTTCGAGGAAGTGGTGGACAAGGGC

GCTTCCGCCCAGAGCTTCATCGAGCGGATGACCAACTTCGATAAGAACCT

GCCCAACGAGAAGGTGCTGCCCAAGCACAGCCTGCTGTACGAGTACTTCA

CCGTGTATAACGAGCTGACCAAAGTGAAATACGTGACCGAGGGAATGAGA

AAGCCCGCCTTCCTGAGCGGCGAGCAGAAAAAGGCCATCGTGGACCTGCT

GTTCAAGACCAACCGGAAAGTGACCGTGAAGCAGCTGAAAGAGGACTACT

TCAAGAAAATCGAGTGCTTCGACTCCGTGGAAATCTCCGGCGTGGAAGAT

CGGTTCAACGCCTCCCTGGGCACATACCACGATCTGCTGAAAATTATCAA

GGACAAGGACTTCCTGGACAATGAGGAAAACGAGGACATTCTGGAAGATA

TCGTGCTGACCCTGACACTGTTTGAGGACAGAGAGATGATCGAGGAACGG

CTGAAAACCTATGCCCACCTGTTCGACGACAAAGTGATGAAGCAGCTGAA

GCGGCGGAGATACACCGGCTGGGGCAGGCTGAGCCGGAAGCTGATCAACG

GCATCCGGGACAAGCAGTCCGGCAAGACAATCGTGGATTTCCTGAAGTCC

GACGGCTTCGCCAACAGAAACTTCATGCAGCTGATCCACGACGACAGCCT

GACCTTTAAAGAGGACATCCAGAAAGCCCAGGTGTCCGGCCAGGGCGATA

GCCTGCACGAGCACATTGCCAATCTGGCCGGCAGCCCCGCCATTAAGAAG

GGCATCCTGCAGACAGTGAAGGTGGTGGACGAGCTCGTGAAAGTGATGGG

CCGGCACAAGCCCGAGAACATCGTGATCGAAATGGCCAGAGAGAACCAGA

CCACCCAGAAGGGACAGAAGAACAGCCGCGAGAGAATGAAGCGGATCGAA

GAGGGCATCAAAGAGCTGGGCAGCCAGATCCTGAAAGAACACCCCGTGGA

AAACACCCAGCTGCAGAACGAGAAGCTGTACCTGTACTACCTGCAGAATG

GGCGGGATATGTACGTGGACCAGGAACTGGACATCAACCGGCTGTCCGAC

TACGATGTGGACCATATCGTGCCTCAGAGCTTTCTGAAGGACGACTCCAT

CGACAACAAGGTGCTGACCAGAAGCGACAAGAACCGGGGCAAGAGCGACA

ACGTGCCCTCCGAAGAGGTCGTGAAGAAGATGAAGAACTACTGGCGGCAG

CTGCTGAACGCCAAGCTGATTACCCAGAGAAAGTTCGACAATCTGACCAA

GGCCGAGAGAGGCGGCCTGAGCGAACTGGATAAGGCCGGCTTCATCAAGA

GACAGCTGGTGGAAACCCGGCAGATCACAAAGCACGTGGCACAGATCCTG

GACTCCCGGATGAACACTAAGTACGACGAGAATGACAAGCTGATCCGGGA

AGTGAAAGTGATCACCCTGAAGTCCAAGCTGGTGTCCGATTTCCGGAAGG

ATTTCCAGTTTTACAAAGTGCGCGAGATCAACAACTACCACCACGCCCAC

GACGCCTACCTGAACGCCGTCGTGGGAACCGCCCTGATCAAAAAGTACCC

TAAGCTGGAAAGCGAGTTCGTGTACGGCGACTACAAGGTGTACGACGTGC

GGAAGATGATCGCCAAGAGCGAGCAGGAAATCGGCAAGGCTACCGCCAAG

TACTTCTTCTACAGCAACATCATGAACTTTTTCAAGACCGAGATTACCCT

GGCCAACGGCGAGATCCGGAAGCGGCCTCTGATCGAGACAAACGGCGAAA

CCGGGGAGATCGTGTGGGATAAGGGCCGGGATTTTGCCACCGTGCGGAAA

GTGCTGAGCATGCCCCAAGTGAATATCGTGAAAAAGACCGAGGTGCAGAC

AGGCGGCTTCAGCAAAGAGTCTATCCTGCCCAAGAGGAACAGCGATAAGC

TGATCGCCAGAAAGAAGGACTGGGACCCTAAGAAGTACGGCGGCTTCGAC

AGCCCCACCGTGGCCTATTCTGTGCTGGTGGTGGCCAAAGTGGAAAAGGG

CAAGTCCAAGAAACTGAAGAGTGTGAAAGAGCTGCTGGGGATCACCATCA

TGGAAAGAAGCAGCTTCGAGAAGAATCCCATCGACTTTCTGGAAGCCAAG

GGCTACAAAGAAGTGAAAAAGGACCTGATCATCAAGCTGCCTAAGTACTC

CCTGTTCGAGCFGGAAAACGGCCGGAAGAGAATGCTGGCCTCTGCCGGCG

AACTGCAGAAGGGAAACGAACTGGCCCTGCCCTCCAAATATGTGAACTTC

CTGTACCTGGCCAGCCACTATGAGAAGCTGAAGGGCTCCCCCGAGGATAA

TGAGCAGAAACAGCTGTTTGTGGAACAGCACAAGCACTACCTGGACGAGA

TCATCGAGCAGATCAGCGAGTTCTCCAAGAGAGTGATCCTGGCCGACGCT

AATCTGGACAAAGTGCTGTCCGCCTACAACAAGCACCGGGATAAGCCCAT

CAGAGAGCAGGCCGAGAATATCATCCACCTGTTTACCCTGACCAATCTGG

GAGCCCCTGCCGCCTTCAAGTACTTTGACACCACCATCGACCGGAAGAGC

TTACACCAGCACCAAAGAGGTGCTGGACGCCACCCTGATCCACCAGAGCA

TCACCGGCCTGTACGAGACACGGATCGACCTGTCTCAGCTGGGAGGCGAC

TTTCTTTTTCTTAGCTTGACCAGCTTTCTTAGTAGCAGCAGGACGCTTTA

A
(underline = NLS-hSpCas9-NLS)

Example chimeric RNA for *S. thermophilus* LMD-9 CRISPR1Cas9 (with PAM of NNAGAAW)

(SEQ ID NO: 21)
NNNNNNNNNNNNNNNNNNNNNgttttttgtactctcaagatttaGAAAtaaa tcttgcagaagctacaaagataaggcttcatgccgaaatcaacaccctgt catttatggcagggtgttttcgttatttaaTTTTTT
(N = guide sequence; first underline = tracr mate sequence; second underline = tracr sequence; bold = terminator)

Example chimeric RNA for *S. thermophilus* LMD-9 CRISPR1Cas9 (with PAM of NNAGAAW)

(SEQ ID NO: 22)
NNNNNNNNNNNNNNNNNNNNNgttttttgtactctcaGAAAtgcagaagcta caaagataaggcttcatgccgaaatcaacaccctgtcatttatggcagg gtgttttcgttatttaaTTTTT
(N = guide sequence; first underline = tracr mate sequence; second underline = tracr sequence; bold = terminator)

Example chimeric RNA for *S. thermophilus* LMD-9 CRISPR1Cas9 (with PAM of NNAGAAW)

(SEQ ID NO: 23)
NNNNNNNNNNNNNNNNNNNNNgttttttgtactctcaGAAAtgcagaagcta caaagataaggcttcatgccgaaatcaacaccctgtcatttatggcagg gtgtTTTTTT
(N = guide sequence; first underline = traer mate sequence; second underline = traer sequence; bold = terminator)

Example chimeric RNA for *S. thermophilus* LMD-9 CRISPR1Cas9 (with PAM of NNAGAAW)

(SEQ ID NO: 60)
NNNNNNNNNNNNNNNNNNNNNgttattgtactctcaagatttaGAAAtaaa tcttgcagaagctacaaagataaggcttcatgccgaaatcaacaccctgt catttatggcagggtgttttcgttatttaaTTTTTT
(N = guide sequence; first underline = tracr mate sequence; second underline = tracr sequence; bold = terminator)

Example chimeric RNA for *S. thermophilus* LMD-9 CRISPR1Cas9 (with PAM of NNAGAAW)

(SEQ ID NO: 61)
NNNNNNNNNNNNNNNNNNNNNgttattgtactctcaGAAAtgcagaagcta caaagataaggcttcatgccgaaatcaacaccctgtcattttatggcagg gtgttttcgttatttaaTTTTTT
(N = guide sequence; first underline = tracr mate sequence;
second underline = tracr sequence; bold = terminator)

Example chimeric RNA for *S. thermophilus* LMD-9 CRISPR1Cas9 (with PAM of NNAGAAW)

(SEQ ID NO: 62)
NNNNNNNNNNNNNNNNNNNNNgttattgtactctcaGAAAtgcagaagcta caaagataaggcttcatgccgaaatcaacaccctgtcattttatggcagg gtgtTTTTTT
(N = guide sequence; first underline = tracr mate sequence;
second underline = tracr sequence; bold = terminator)

Example chimeric RNA for *S. thermophilus* LMD-9 CRISPR1Cas9 (with PAM of NNAGAAW)

(SEQ ID NO: 63)
NNNNNNNNNNNNNNNNNNNNNgttattgtactctcaagatttaGAAAtaaa tcttgcagaagctacaatgataaggcttcatgccgaaatcaacaccctgt cattttatggcagggtgttttcgttatttaaTTTTTT
(N = guide sequence; first underline = tracr mate sequence;
second underline = tracr sequence; bold = terminator)

Example chimeric RNA for *S. thermophilus* LMD-9 CRISPR1Cas9 (with PAM of NNAGAAW)

(SEQ ID NO: 64)
NNNNNNNNNNNNNNNNNNNNNgttattgtactctcaGAAAtgcagaagcta caatgataaggcttatgccgaaatcaacaccctgtcattttatggcaggg tgttttcgttatttaaTTTTTT
(N = guide sequence; first underline = tracr mate sequence;
second underline = tracr sequence; bold = terminator)

Example chimeric RNA for *S. thermophilus* LMD-9 CRISPR1Cas9 (with PAM of NNAGAAW)

(SEQ ID NO: 65)
NNNNNNNNNNNNNNNNNNNNNgttattgtactctcaGAAAtgcagaagcta caatgataaggcttcatgccgaaatcaacaccctgtcattttatggcagg gtgtTTTTTT
(N = guide sequence; first underline = tracr mate sequence;
second underline = tracr sequence; bold = terminator)

Example chimeric RNA for *S. thermophilus* LMD-9 CRISPR3Cas9 (with PAM of NGGNG)

(SEQ ID NO: 66)
NNNNNNNNNNNNNNNNNNNNNgttttagagctgtgGAAAcacagcgagtta aaataaggcttagtccgtactcaacttgaaaaggcaccgattcggtgtTT TTTT
(N = guide sequence; first underline = trace mate sequence;
second underline = tracr sequence; bold = terminator)

Codon-optimized version of Cas9 from *S. thermophilus* LMD-9 CRISPR3 locus (with an NLS at both 5' and 3' ends)

(SEQ ID NO: 67)
ATGAAAAGGCCGGCGGCCACGAAAAAGGCCGGCCAGGCAAAAAAGAAAAA
GACCAAGCCCTACAGCATCGGCCTGGACATCGGCACCAATAGCGTGGGCT
GGGCCGTGACCACCGACAACTACAAGGTGCCCAGCAAGAAAATGAAGGTG
CTGGGCAACACCTCCAAGAAGTACATCAAGAAAAACCTGCTGGGCGTGCT
GCTGTTCGACAGCGGCATTACAGCCGAGGGCAGACGGCTGAAGAGPACCG
CCAGACGGCGGTACACCCGGCGGAGAAACAGAATCCTGTATCTGCAAGAG
ATCTTCAGCACCGAGATGGCTACCCTGGACGACGCCTTCTTCCAGCGGCT
GGACGACAGCTTCCTGGTGCCCGACGACAAGCGGGACAGCAAGTACCCCA
TCTTCGGCAACCTGGTGGAAGAGAAGGCCTACCACGACGAGTTCCCCACC
ATCTACCACCTGAGAAAGTACCTGGCCGACAGCACCAAGAAGGCCGACCT
GAGACTGGTGTATCTGGCCCTGGCCCACATGATCAAGTACCGGGGCCACT
TCCTGATCGAGGGCGAGTTCAACAGCAAGAACAACGACATCCAGAAGAAC
TTCCAGGACTTCCTGGACACCTACAACGCCATCTTCGAGAGCGACCTGTC
CCTGGAAAACAGCAAGCAGCTGGAAGAGATCGTGAAGGACAAGATCAGCA
AGCTGGAAAAGAAGGACCGCATCCTGAAGCTGTTCCCCGGCGAGAAGAAC
AGCGGAATCTTCAGCGAGTTTCTGAAGCTGATCGTGGGCAACCAGGCCGA
CTTCAGAAAGTGCTTCAACCTGGACGAGAAAGCCAGCCTGCACTTCAGCA
AAGAGAGCTACGACGAGGACCTGGAAACCCTGCTGGGATATATCGGCGAC
GACTACAGCGACGTGTTCCTGAAGGCCAAGAAGCTGTACGACGCTATCCT
GCTGAGCGGCTTCCTGACCGTGACCGACAACGAGACAGAGGCCCCACTGA
GGAGCGCCATGATTAAGCGGTACAACGAGCACAAAGAGGATCTGGCTCTG
CTGAAAGAGTACATCCGGAACATCAGCCTGAAAACCTACAATGAGGTGTT
CAAGGACGACACCAAGAACGGCTACGCCGGCTACATCGACGGCAAGACGA
ACCAGGAAGATTTCTATGTGTACCTGAAGAAGCTGCTGGCCGAGTTCGAG
GGGGCCGACTACTTTCTGGAAAAAATCGACCGCGAGGATTTCCTGCGGAA
GCAGCGGACCTTCGACAACGGCAGCATCCCCTACCAGATCCATCTGCAGG
AAATGCGGGCCATCCTGGACAAGCAGGCCAAGTTCTACCCATTCCTGGCC
AAGAACAAAGAGCGGATCGAGAAGATCCTGACCTTCCGCATCCCTTACTA
CGTGGGCCCCCTGGCCAGAGGCAACAGCGATTTTGCCTGGTCCATCCGGA
AGCGCAATGAGAAGATCACCCCCTGGAACTTCGAGGACGTGATCGACAAA
GAGTCCAGCGCCGAGGCCTTCATCAACCGGATGACCAGCTTCGACCTGTA
CCTGCCCGAGGAAAAGGTGCTGCCCAAGCACAGCCTGCTGTACGAGACAT
TCAATGTGTATAACGAGCTGACCAAAGTGCGGTTTATCGCCGAGTCTATG
CGGGACTACCAGTTCCTGGACTCCAAGCAGAAAAAGGACATCGTGCGGCT
GTACTTCAAGGACAAGCGGAAAGTGACCGATAAGGACATCATCGAGTACC
TGCACGCCATCTACGGCTACGATGGCATCGAGCTGAAGGGCATCGAGAAG
CAGTTCAACTCCAGCCTGAGCACATACCACGACCTGCTGAACATTATCAA
CGACAAAGAATTTCTGGACGACTCCAGCAACGAGGCCATCATCGAAGAGA
TCATCCACACCCTGACCATCTTTGAGGACCGCGAGATGATCAAGCAGCGG
CTGAGCAAGTTCGAGAACATCTTCGACAAGAGCGTGCTGAAAAAGCTGAG

```
CAGACGGCACTACACCGGCTGGGGCAAGCTGAGCGCCAAGCTGATCAACG

GCATCCGGGACGAGAAGTCCGGCAACACAATCCTGGACTACCTGATCGAC

GACGGCATCAGCAACCGGAACTTCATGCAGCTGATCCACGACGACGCCCT

GAGCTTCAAGAAGAAGATCCAGAAGGCCCAGATCATCGGGGACGAGGACA

AGGGCAACATCAAAGAAGTCGTGAAGTCCCTGCCCGGCAGCCCCGCCATC

AAGAAGGGAATCCTGCAGAGCATCAAGATCGTGGACGAGCTCGTGAAAGT

GATGGGCGGCAGAAAGCCCGAGAGCATCGTGGTGGAAATGGCTAGAGAGA

ACCAGTACACCAATCAGGGCAAGAGCAACAGCCAGCAGAGACTGAAGAGA

CTGGAAAAGTCCCTGAAAGAGCTGGGCAGCAAGATTCTGAAAGAGAATAT

CCCTGCCAAGCTGTCCAAGATCGACAACAACGCCCTGCAGAACGACCGGC

TGTACCTGTACTACCTGCAGAATGGCAAGGACATGTATAGAGGCGACGAC

CTGGATATCGACCGCCTGAGCAACTACGACATCGACCATATTATCCCCCA

GGCCTTCCTGAAAGACAACAGCATTGACAACAAAGTGCTGGTGTCCTCCG

CCAGCAACCGCGGCAAGTCCGATGATGTGCCCAGCCTGGAAGTCGTGAAA

AAGAGAAAGACCTTCTGGTATCAGCTGCTGAAAAGCAAGCTGATTAGCCA

GAGGAAGTTCGACAACCTGACCAAGGCCGAGAGAGGCGGCCTGAGCCCTG

AAGATAAGGCCGGCTTCATCCAGAGACAGCTGGTGGAAACCCGGCAGATC

ACCAAGCACGTGGCCAGACTGCTGGATGAGAAGTTTAACAACAAGAAGGA

CGAGAACAACCGGGCCCTTGCGGACCGTGAAGATCATCACCCTGAAGTCC

ACCCTGGTGTCCCAGTTCCGGAAGGACTTCGAGCTGTATAAAGTGCGCGA

GATCAATGACTTTCACCACGCCCACGACGTCCTACCTGAATGCCCTTGGT

GGGTTCCGCCCTGCTGAAGAAGTACCCTAAGCTGGAACCCGAGTTCGTGT

ACGGCGACTACCCCAAGTACAACTCCTTCAGAGAGCGGAAGTCCGCCACC

GAGAAGGTGTACTTCTACTCCAACATCATGAATATCTTTAAGAAGTCCAT

CTCCCTGGCCGATGGCAGAGTGATCGAGCGGCCCCTGATCGAAGTGAACG

AAGAGACAGGCGAGAGCGTGTGGAACAAAGAAAGCGACCTGGCCACCGTG

CGGCGGGTGCTGAGTTATCCTCAAGTGAATGTCGTGAAGAAGGTGGAAGA

ACAGAACCACGGCCTGGATCGGGGCAAGCCCAAGGGCCTGTTCAACGCCA

ACCTGTCCAGCAAGCCTAAGCCCAACTCCAACGAGAATCTCGTGGGGCC

AAAGAGTACTTGGACCCTAAGAAGTACGGCGGATACGCCGGCATCTCCAA

TAGCTTCACCGTGCTCGTGAAGGGCACAATCGAGAAGGGCGCTAAGAAAA

AGATCACAAACCTTGCTGGAATTTCAGGGGATCTCTATCCTGGACCGGAT

CAACTACCGGAAGGATAAGCTGAACTTTCTGCTGGAAAAAGGCTACAAGG

ACATTGAGCTGATTATCGAGCTGCCTAAGTACTCCCTGTTCGAACTGAGC

GACGGCTCCAGACGGATGCTGGCCTCCATCCTGTCCACCAACAACAAGCG

GGGCGAGATCCACAAGGGAAACCAGATCTTCCTGAGCCAGAAATTTGTGA

AACTGCTGTACCACGCCAAGCGGATCTCCAACACCATCAATGAGAACCAC

CGGAAATACGTGGAAAACCACAAGAAGAGTTTGAGGAACTGTTCTACTA

CATCCTGGAGTTCAACGAGAACTATGTGGGAGCCAAGAAGAACGGCAAAC

TGCTGAACTCCGCCTTCCAGAGCTGGCAGAACCACAGCATCGACGAGCTG

TGCAGCTCCTTCATCGGCCCTACCGGCAGCGAGCGGAAGGGACTGTTTGA

GCTGACCTCCAGAGGCTCTGCCGCCGACTTTGAGTTCCTGGGAGTGAAGA

TCCCCCGGTACAGAGACTACACCCCCTCTAGTCTGCTGAAGGACGCCACC

CTGATCCACCAGAGCGTGACCGGCCTGTACGAAACCCGGATCGACCTGGC

TAAGCTGGGCGAGGGAAAGCGTCCTGCTGCTACTAAGAAAGCTGGTCAAG

CTAAGAAAAGAAATAA
```

Example 5

RNA-Guided Editing of Bacterial Genomes Using CRISPR-Cas Systems

Applicants used the CRISPR-associated endonuclease Cas9 to introduce precise mutations in the genomes of *Streptococcus pneumoniae* and *Escherichia coli*. The approach relied on Cas9-directed cleavage at the targeted site to kill unmutated cells and circumvented the need for selectable markers or counter-selection systems. Cas9 specificity was reprogrammed by changing the sequence of short CRISPR RNA (crRNA) to make single- and multi-nucleotide changes carried on editing templates. Simultaneous use of two crRNAs enabled multiplex mutagenesis. In *S. pneumoniae*, nearly 100% of cells that survived Cas9 cleavage contained the desired mutation, and 65% when used in combination with recombineering in *E. coli*. Applicants exhaustively analyzed Cas9 target requirements to define the range of targetable sequences and showed strategies for editing sites that do not meet these requirements, suggesting the versatility of this technique for bacterial genome engineering.

The understanding of gene function depends on the possibility of altering DNA sequences within the cell in a controlled fashion. Site-specific mutagenesis in eukaryotes is achieved by the use of sequence-specific nucleases that promote homologous recombination of a template DNA containing the mutation of interest. Zinc finger nucleases (ZFNs), transcription activator-like effector nucleases (TALENs) and homing meganucleases can be programmed to cleave genomes in specific locations, but these approaches require engineering of new enzymes for each target sequence. In prokaryotic organisms, mutagenesis methods either introduce a selection marker in the edited locus or require a two-step process that includes a counter-selection system. More recently, phage recombination proteins have been used for recombineering, a technique that promotes homologuous recombination of linear DNA or oligonucleotides. However, because there is no selection of mutations, recombineering efficiency can be relatively low (0.1-10% for point mutations down to $10^{-5}$-$10^{-6}$ for larger modifications), in many cases requiring the screening of a large number of colonies. Therefore new technologies that are affordable, easy to use and efficient are still in need for the genetic engineering of both eukaryotic and prokaryotic organisms.

Recent work on the CRISPR (clustered, regularly interspaced, short palindromic repeats) adaptive immune system of prokaryotes has led to the identification of nucleases whose sequence specificity is programmed by small RNAs. CRISPR loci are composed of a series of repeats separated by 'spacer' sequences that match the genomes of bacteriophages and other mobile genetic elements. The repeat-spacer array is transcribed as a long precursor and processed within repeat sequences to generate small crRNA that specify the target sequences (also known as protospacers) cleaved by CRISPR systems. Essential for cleavage is the presence of a sequence motif immediately downstream of the target region, known as the protospacer-adjacent motif (PAM). CRISPR-associated (cas) genes usually flank the repeat-spacer array and encode the enzymatic machinery responsible for crRNA biogenesis and targeting. Cas9 is a dsDNA endonuclease that uses a crRNA guide to specify the site of cleavage. Loading of the crRNA guide onto Cas9 occurs during the processing of the crRNA precursor and requires a small RNA antisense to the precursor, the tracrRNA, and RNAse III. In contrast to genome editing with ZFNs or TALENs, changing Cas9 target specificity does not require protein engineering but only the design of the short crRNA guide.

Applicants recently showed in S. pneumoniae that the introduction of a CRISPR system targeting a chromosomal locus leads to the killing of the transformed cells. It was observed that occasional survivors contained mutations in the target region, suggesting that Cas9 dsDNA endonuclease activity against endogenous targets could be used for genome editing. Applicants showed that marker-less mutations can be introduced through the transformation of a template DNA fragment that will recombine in the genome and eliminate Cas9 target recognition. Directing the specificity of Cas9 with several different crRNAs allows for the introduction of multiple mutations at the same time. Applicants also characterized in detail the sequence requirements for Cas9 targeting and show that the approach can be combined with recombineering for genome editing in E. coli.

RESULTS: Genome Editing by Cas9 Cleavage of a Chromosomal Target

S. pneunmoniae strain crR6 contains a Cas9-based CRISPR system that cleaves a target sequence present in the bacteriophage φ8232.5. This target was integrated into the srL4 chromosomal locus of a second strain $R6^{8232.5}$. An altered target sequence containing a mutation in the PAM region was integrated into the srtA locus of a third strain $R6^{370.1}$, rendering this strain 'immune' to CRISPR cleavage (FIG. 28a). Applicants transformed $R6^{8232.5}$ and $R6^{370.1}$ cells with genomic DNA from crR6 cells, expecting that successful transformation of $R6^{8232.5}$ cells should lead to cleavage of the target locus and cell death. Contrary to this expectation, Applicants isolated $R6^{8232.5}$ transformants, albeit with approximately 10-fold less efficiency than $R6^{370.1}$ transformants (FIG. 28b). Genetic analysis of eight $R6^{8232.5}$ transformants (FIG. 28) revealed that the great majority are the product of a double recombination event that eliminates the toxicity of Cas9 targeting by replacing the φ8232.5 target with the crR6 genome's wild-type srtA locus, which does not contain the protospacer required for Cas9 recognition. These results were proof that the concurrent introduction of a CRISPR system targeting a genomic locus (the targeting construct) together with a template for recombination into the targeted locus (the editing template) led to targeted genome editing (FIG. 23a).

To create a simplified system for genome editing, Applicants modified the CRISPR locus in strain crR6 by deleting cas1, cas2 and csn2, genes which have been shown to be dispensable for CRISPR targeting, yielding strain crR6M (FIG. 28a). This strain retained the same properties of crR6 (FIG. 28b). To increase the efficiency of Cas9-based editing and demonstrate that a template DNA of choice can be used to control the mutation introduced, Applicants co-transformed $R6^{8232.5}$ cells with PCR products of the wild-type srtA gene or the mutant $R6^{370.1}$ target, either of which should be resistant to cleavage by Cas9. This resulted in a 5- to 10-fold increase of the frequency of transformation compared with genomic crR6 DNA alone (FIG. 23b). The efficiency of editing was also substantially increased, with 8/8 transformants tested containing a wild-type srtA copy and 7/8 containing the PAM mutation present in the $R6^{370.1}$ target (FIG. 23b and FIG. 29a). Taken together, these results showed the potential of genome editing assisted by Cas9.

Analysis of Cas9 Target Requirements:

To introduce specific changes in the genome, one must use an editing template carrying mutations that abolish Cas9-mediated cleavage, thereby preventing cell death. This is easy to achieve when the deletion of the target or its replacement by another sequence (gene insertion) is sought. When the goal is to produce gene fusions or to generate single-nucleotide mutations, the abolishment of Cas9 nuclease activity will only be possible by introducing mutations in the editing template that alter either the PAM or the protospacer sequences. To determine the constraints of CRISPR-mediated editing, Applicants performed an exhaustive analysis of PAM and protospacer mutations that abrogate CRISPR targeting.

Previous studies proposed that S. pyogenes Cas9 requires an NGG PAM immediately downstream of the protospacer. However, because only a very limited number of PAM-inactivating mutations have been described so far, Applicants conducted a systematic analysis to find all 5-nucleotide sequences following the protospacer that eliminate CRISPR cleavage. Applicants used randomized oligonucleotides to generate all possible 1,024 PAM sequences in a heterogeneous PCR product that was transformed into crR6 or R6 cells. Constructs carrying functional PAMs were expected to be recognized and destroyed by Cas9 in crR6 but not R6 cells (FIG. 24a). More than $2 \times 10^5$ colonies were pooled together to extract DNA for use as template for the co-amplification of all targets. PCR products were deep sequenced and found to contain all 1,024 sequences, with coverage ranging from 5 to 42,472 reads (See section "Analysis of deep sequencing data"). The functionality of each PAM was estimated by the relative proportion of its reads in the crR6 sample over the R6 sample. Analysis of the first three bases of the PAM, averaging over the two last bases, clearly showed that the NGG pattern was under-represented in crR6 transformants (FIG. 24b). Furthermore, the next two bases had no detectable effect on the NGG PAM (See section "Analysis of deep sequencing data"), demonstrating that the NGGNN sequence was sufficient to license Cas9 activity. Partial targeting was observed for NAG PAM sequences (FIG. 24b). Also the NNGGN pattern partially inactivated CRISPR targeting (Table G), indicating that the NGG motif can still be recognized by Cas9 with reduced efficiency when shifted by 1 bp. These data shed light onto the molecular mechanism of Cas9 target recognition, and they revealed that NGG (or CCN on the complementary strand) sequences are sufficient for Cas9 targeting and that NGG to NAG or NNGGN mutations in the editing template should be avoided. Owing to the high frequency of these tri-nucleotide sequences (once every 8 bp), this means that almost any position of the genome can be edited. Indeed, Applicants tested ten randomly chosen targets carrying various PAMs and all were found to be functional (FIG. 30).

Another way to disrupt Cas9-mediated cleavage is to introduce mutations in the protospacer region of the editing template. It is known that point mutations within the 'seed sequence' (the 8 to 10 protospacer nucleotides immediately adjacent to the PAM) can abolish cleavage by CRISPR nucleases. However, the exact length of this region is not known, and it is unclear whether mutations to any nucleotide in the seed can disrupt Cas9 target recognition. Applicants followed the same deep sequencing approach described above to randomize the entire protospacer sequence involved in base pair contacts with the crRNA and to determine all sequences that disrupt targeting. Each position of the 20 matching nucleotides (14) in the spc1 target present in R6$^{8232.5}$ cells (FIG. 23a) was randomized and transformed into crR6 and R6 cells (FIG. 24a). Consistent with the presence of a seed sequence, only mutations in the 12 nucleotides immediately upstream of the PAM abrogated cleavage by Cas9 (FIG. 24c). However, different mutations displayed markedly different effects. The distal (from the PAM) positions of the seed (12 to 7) tolerated most mutations and only one particular base substitution abrogated targeting. In contrast, mutations to any nucleotide in the proximal positions (6 to 1, except 3) eliminated Cas9 activity, although at different levels for each particular substitution. At position 3, only two substitutions affected CRISPR activity and with different strength. Applicants concluded that, although seed sequence mutations can prevent CRISPR targeting, there are restrictions regarding the nucleotide changes that can be made in each position of the seed. Moreover, these restrictions can most likely vary for different spacer sequences. Therefore Applicants believe that mutations in the PAM sequence, if possible, should be the preferred editing strategy. Alternatively, multiple mutations in the seed sequence may be introduced to prevent Cas9 nuclease activity.

Figure 33:
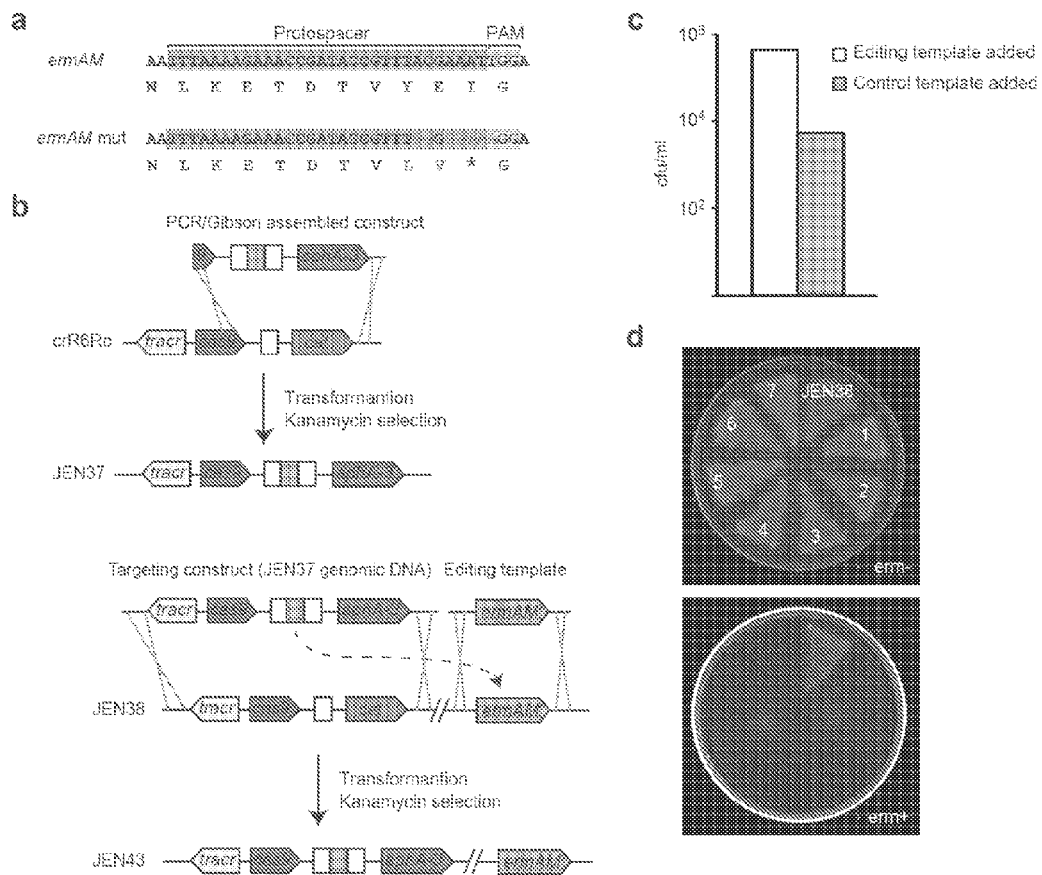
FIG. 33A-D illustrates CRISPR-mediated editing of the ermAM locus using genomic DNA as targeting construct. To use genomic DNA as targeting construct it is necessary to avoid CRISPR autoimmunity, and therefore a spacer against a sequence not present in the chromosome must be used (in this case the ermAM erythromycin resistance gene). (a) Nucleotide and amino acid sequences of the wild-type and mutated (red letters) ermAM gene. The protospacer and PAM sequences are shown (SEQ ID NOS 494-497, respectively, in order of appearance). (b) A schematic for CRISPR-mediated editing of the ermAM locus using genomic DNA. A construct carrying an ermAM-targeting spacer (blue box) is made by PCR and Gibson assembly, and transformed into strain crR6Rc, generating strain JEN37. The genomic DNA of JEN37 was then used as a targeting construct, and was co-transformed with the editing template into JEN38, a strain in which the srtA gene was replaced by a wild-type copy of ermAM. Kanamycin-resistant transformants contain the edited genotype (JEN43). (c) Number of kanamycin-resistant cells obtained after co-transformation of targeting and editing or control templates. In the presence of the control template $5.4 \times 10^3$ cfu/ml were obtained, and $4.3 \times 10^5$ cfu/ml when the editing template was used. This difference indicates an editing efficiency of about 99% [$(4.3 \times 10^5 - 5.4 \times 10^3)/4.3 \times 10^5$]. (d) To check for the presence of edited cells seven kanamycin-resistant clones and JEN38 were streaked on agar plates with (erm+) or without (erm−) erythromycin. Only the positive control displayed resistance to erythromycin. The ermAM mut genotype of one of these transformants was also verified by DNA sequencing (FIG. 29e).

Cas9-Mediated Genome Editing in *S. pneumonia*:

To develop a rapid and efficient method for targeted genome editing, Applicants engineered strain crR6Rk, a strain in which spacers can be easily introduced by PCR (FIG. 33). Applicants decided to edit the β-galactosidase (bgaA) gene of *S. pneumoniae*, whose activity can be easily measured. Applicants introduced alanine substitutions of amino acids in the active site of this enzyme: R481A (R→A) and N563A,E564A (NE→AA) mutations. To illustrate different editing strategies, Applicants designed mutations of both the PAM sequence and the protospacer seed. In both cases the same targeting construct with a crRNA complementary to a region of the β-galactosidase gene that is adjacent to a TGG PAM sequence (CCA in the complementary strand, FIG. 26) was used. The R→A editing template created a three-nucleotide mismatch on the protospacer seed sequence (CGT to GCA, also introducing a BtgZI restriction site). In the NE→AA editing template Applicants simultaneously introduced a synonymous mutation that created an inactive PAM (TGG to TTG) along with mutations that are 218 nt downstream of the protospacer region (AAT GAA to GCT GCA, also generating a TseI restriction site). This last editing strategy demonstrated the possibility of using a remote PAM to make mutations in places where a proper target may be hard to choose. For example, although the *S. pneunmoniae* R6 genome, which has a 39.7% GC content, contains on average one PAM motif every 12 bp, some PAM motifs are separated by up to 194 bp (FIG. 33). In addition Applicants designed a ΔbgaA in-frame deletion of 6,664 bp. In all three cases, co-transformation of the targeting and editing templates produced 10-times more kanamycin-resistant cells than co-transformation with a control editing template containing wild-type bgaA sequences (FIG. 25b). Applicants genotyped 24 transformants (8 for each editing experiment) and found that all but one incorporated the desired change (FIG. 25c). DNA sequencing also confirmed not only the presence of the introduced mutations but also the absence of secondary mutations in the target region (FIG. 29b,c). Finally, Applicants measured β-galactosidase activity to confirm that all edited cells displayed the expected phenotype (FIG. 25d).

Figure 34:
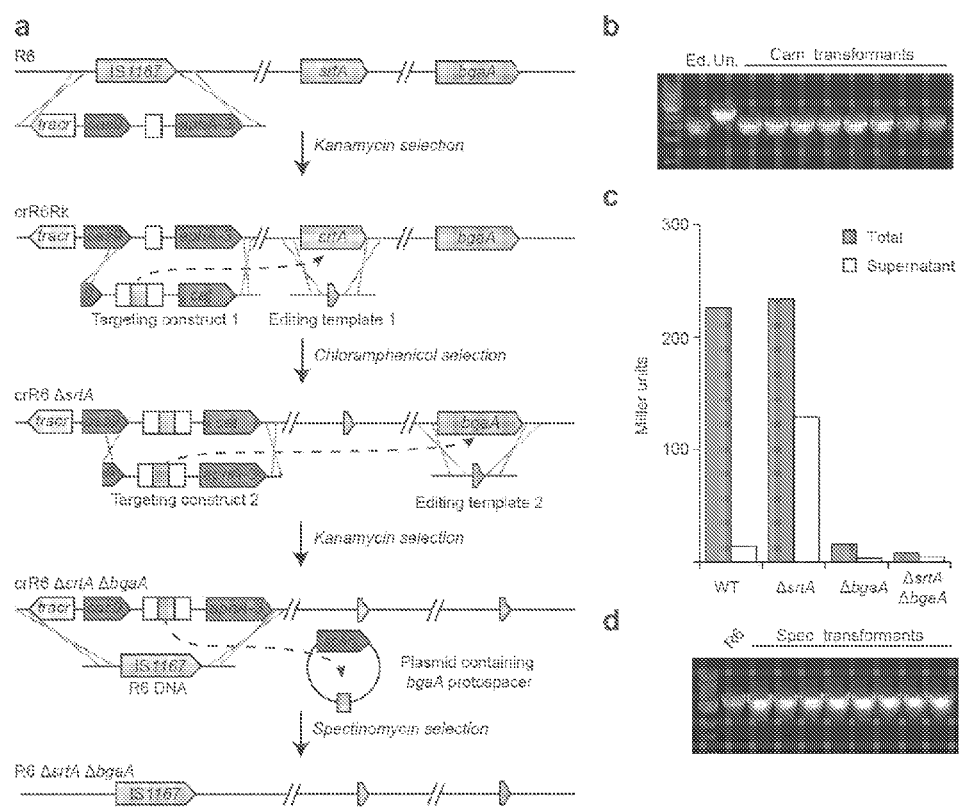
FIG. 34A-D illustrates sequential introduction of mutations by CRISPR-mediated genome editing. (a) A schematic for sequential introduction of mutations by CRISPR-mediated genome editing. First, R6 is engineered to generate crR6Rk. crR6Rk is co-transformed with a srtA-targeting construct fused to cat for chloramphenicol selection of edited cells, along with an editing construct for a ΔsrtA in-frame deletion. Strain crR6ΔsrtA is generated by selection on chloramphenicol. Subsequently, the ΔsrtA strain is co-transformed with a bgaA-targeting construct fused to aphA-3 for kanamycin selection of edited cells, and an editing construct containing a ΔbgaA4 in-frame deletion. Finally, the engineered CRISPR locus can be erased from the chromosome by first co-transforming R6 DNA containing the wild-type IS1167 locus and a plasmid carrying a bgaA protospacer (pDB97), and selection on spectinomycin. (b) PCR analysis for 8 chloramphenicol (Cam)-resistant transformants to detect the deletion in the srtA locus. (c) β-galactosidase activity as measured by Miller assay. In S. pneumoniae, this enzyme is anchored to the cell wall by sortase A. Deletion of the srtA gene results in the release of β-galactosidase into the supernatant. ΔbgaA mutants show no activity. (d) PCR analysis for 8 spectinomycin (Spec)-resistant transformants to detect the replacement of the CRISPR locus by wild-type IS1167.

Cas9-mediated editing can also be used to generate multiple mutations for the study of biological pathways. Applicants decided to illustrate this for the sortase-dependent pathway that anchors surface proteins to the envelope of Gram-positive bacteria. Applicants introduced a sortase deletion by co-transformation of a chloramphenicol-resistant targeting construct and a ΔsrtA editing template (FIG. 33a,b), followed by a ΔbgaA deletion using a kanamycin-resistant targeting construct that replaced the previous one. In *S. pneumoniae*, β-galactosidase is covalently linked to the cell wall by sortase. Therefore, deletion of srtA results in the release of the surface protein into the supernatant, whereas the double deletion has no detectable β-galactosidase activity (FIG. 34c). Such a sequential selection can be iterated as many times as required to generate multiple mutations.

These two mutations may also be introduced at the same time. Applicants designed a targeting construct containing two spacers, one matching srtA and the other matching bgaA, and co-transformed it with both editing templates at the same time (FIG. 25e). Genetic analysis of transformants showed that editing occurred in 6/8 cases (FIG. 25f). Notably, the remaining two clones each contained either a ΔsrtA or a ΔbgaA deletion, suggesting the possibility of performing combinatorial mutagenesis using Cas9. Finally, to eliminate the CRISPR sequences, Applicants introduced a plasmid containing the bgaA target and a spectinomycin resistance gene along with genomic DNA from the wild-type strain R6. Spectinomycin-resistant transformants that retain the plasmid eliminated the CRISPR sequences (FIG. 34a,d).

Mechanism and Efficiency of Editing:

To understand the mechanisms underlying genome editing with Cas9, Applicants designed an experiment in which the editing efficiency was measured independently of Cas9 cleavage. Applicants integrated the ermAM erythromycin resistance gene in the srtA locus, and introduced a premature stop codon using Cas9-mediated editing (FIG. 33). The resulting strain (JEN53) contains an ermAMf(stop) allele and is sensitive to erythromycin. This strain may be used to assess the efficiency at which the ermAM gene is repaired by measuring the fraction of cells that restore antibiotic resistance with or without the use of Cas9 cleavage. JEN53 was transformed with an editing template that restores the wild-type allele, together with either a kanamycin-resistant CRISPR construct targeting the ermAM(stop) allele (CRISPR::ermAM(stop)) or a control construct without a spacer (CRISPR::Ø) (FIG. 26a,b). In the absence of kanamycin selection, the fraction of edited colonies was on the order of $10^{-2}$ (erythromycin-resistant cfu/total cfu) (FIG. 26c), representing the baseline frequency of recombination without Cas9-mediated selection against unedited cells. However, if kanamycin selection was applied and the control CRISPR construct was co-transformed, the fraction of edited colonies increased to about $10^{-1}$ (kanamycin- and erythromycin-resistant cfu/kanamycin-resistant cfu) (FIG. 26c). This result shows that selection for the recombination of the CRISPR locus co-selected for recombination in the ermAM locus independently of Cas9 cleavage of the genome, suggesting that a subpopulation of cells is more prone to transformation and/or recombination. Transformation of the CRISPR::ermAM(stop) construct followed by kanamycin selection resulted in an increase of the fraction of erythromycin-resistant, edited cells to 99% (FIG. 26c). To determine if this increase is caused by the killing of non-edited cells, Applicants compared the kanamycin-resistant colony forming units (cfu) obtained after co-transformation of JEN53 cells with the CRISPR::ermAM(stop) or CRISPR::Ø constructs.

Applicants counted 5.3 times less kanamycin-resistant colonies after transformation of the ermAM(stop) construct ($2.5 \times 10^4/4.7 \times 10^3$, FIG. 35a), a result that suggests that indeed targeting of a chromosomal locus by Cas9 leads to the killing of non-edited cells. Finally, because the introduction of dsDNA breaks in the bacterial chromosome is known to trigger repair mechanisms that increase the rate of recombination of the damaged DNA, Applicants investigated whether cleavage by Cas9 induces recombination of the editing template. Applicants counted 2.2 times more colonies after co-transformation with the CRISPR::erm(stop) construct than with the CRISPR::Ø construct (FIG. 26d), indicating that there was a modest induction of recombination. Taken together, these results showed that co-selection of transformable cells, induction of recombination by Cas9-mediated cleavage and selection against non-edited cells, each contributed to the high efficiency of genome editing in *S. pneumoniae*.

Figure 35:
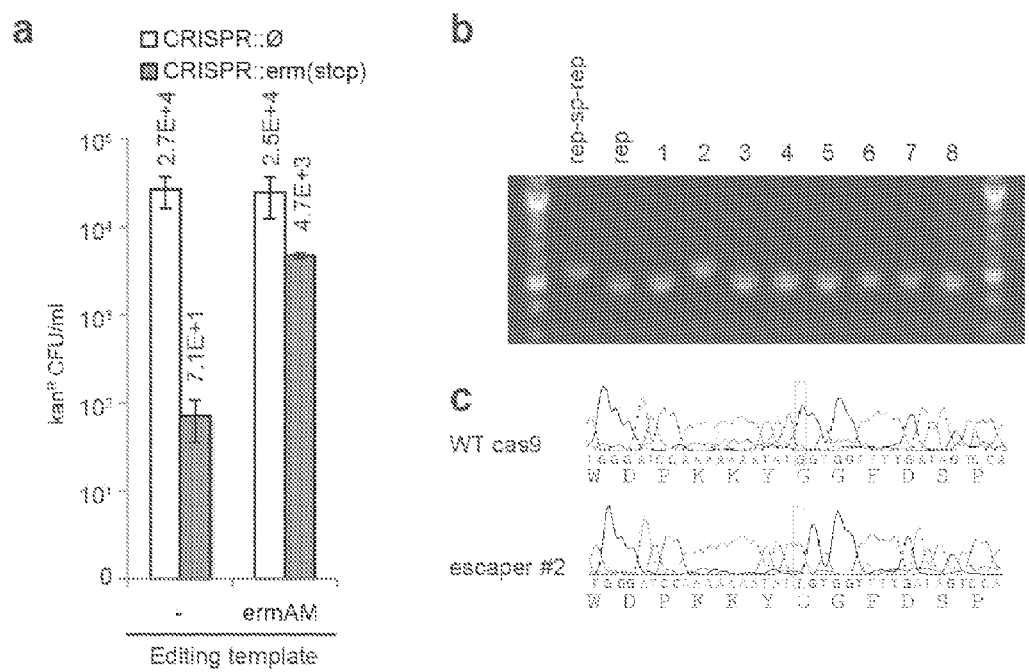
FIG. 35A-C illustrates the background mutation frequency of CRISPR in S. pneumoniae. (a) Transformation of the CRISPR::Ø or CRISPR::erm(stop) targeting constructs in JEN53, with or without the ermAM editing template. The difference in $kan^R$ CFU between CRISPR::Ø and CRISPR::erm(stop) indicates that Cas9 cleavage kills non-edited cells. Mutants that escape CRISPR interference in the absence of editing template are observed at a frequency of $3 \times 10^{-3}$. (b) PCR analysis of the CRISPR locus of escapers shows that 7/8 have a spacer deletion. (c) Escaper #2 carries a point mutation in cas9 (SEQ ID NOS 498-501, respectively, in order of appearance).

As cleavage of the genome by Cas9 should kill non-edited cells, one would not expect to recover any cells that received the kanamycin resistance-containing Cas9 cassette but not the editing template. However, in the absence of the editing template Applicants recovered many kanamycin-resistant colonies after transformation of the CRISPR::ermAM(stop) construct (FIG. 35a). These cells that 'escape' CRISPR-induced death produced a background that determined a limit of the method. This background frequency may be calculated as the ratio of CRISPR::ermAM(stop)/CRISPR::Ø cfu, $2.6 \times 10^{-3}$ ($7.1 \times 10^{1}/2.7 \times 10^{4}$) in this experiment, meaning that if the recombination frequency of the editing template is less than this value, CRISPR selection may not efficiently recover the desired mutants above the background. To understand the origin of these cells, Applicants genotyped 8 background colonies and found that 7 contained deletions of the targeting spacer (FIG. 35b) and one harbored a presumably inactivating mutation in Cas9 (FIG. 35c).

Figure 36:
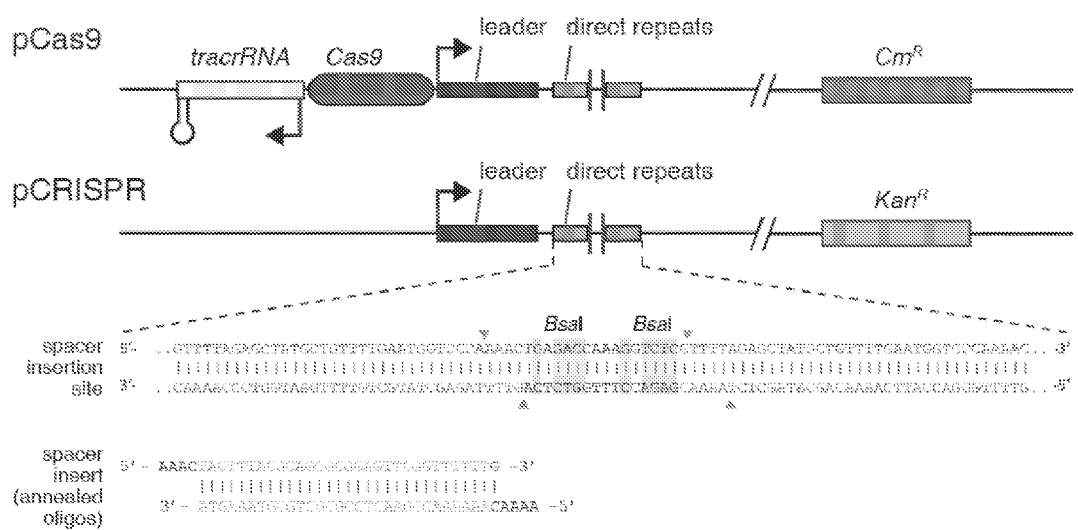
FIG. 36 illustrates that the essential elements of the S. pyogenes CRISPR locus 1 are reconstituted in E. coli using pCas9. The plasmid contained tracrRNA, Cas9, as well as a leader sequence driving the crRNA array. The pCRISPR plasmids contained the leader and the array only. Spacers may be inserted into the crRNA array between BsaI sites using annealed oligonucleotides (SEQ ID NOS 345, 502 and 127, respectively, in order of appearance). Oligonucleotide design is shown at bottom. pCas9 carried chloramphenicol resistance (CmR) and is based on the low-copy pACYC184 plasmid backbone. pCRISPR is based on the high-copy number pZE21 plasmid. Two plasmids were required because a pCRISPR plasmid containing a spacer targeting the E. coli chromosome may not be constructed using this organism as a cloning host if Cas9 is also present (it will kill the host).
Figure 37:
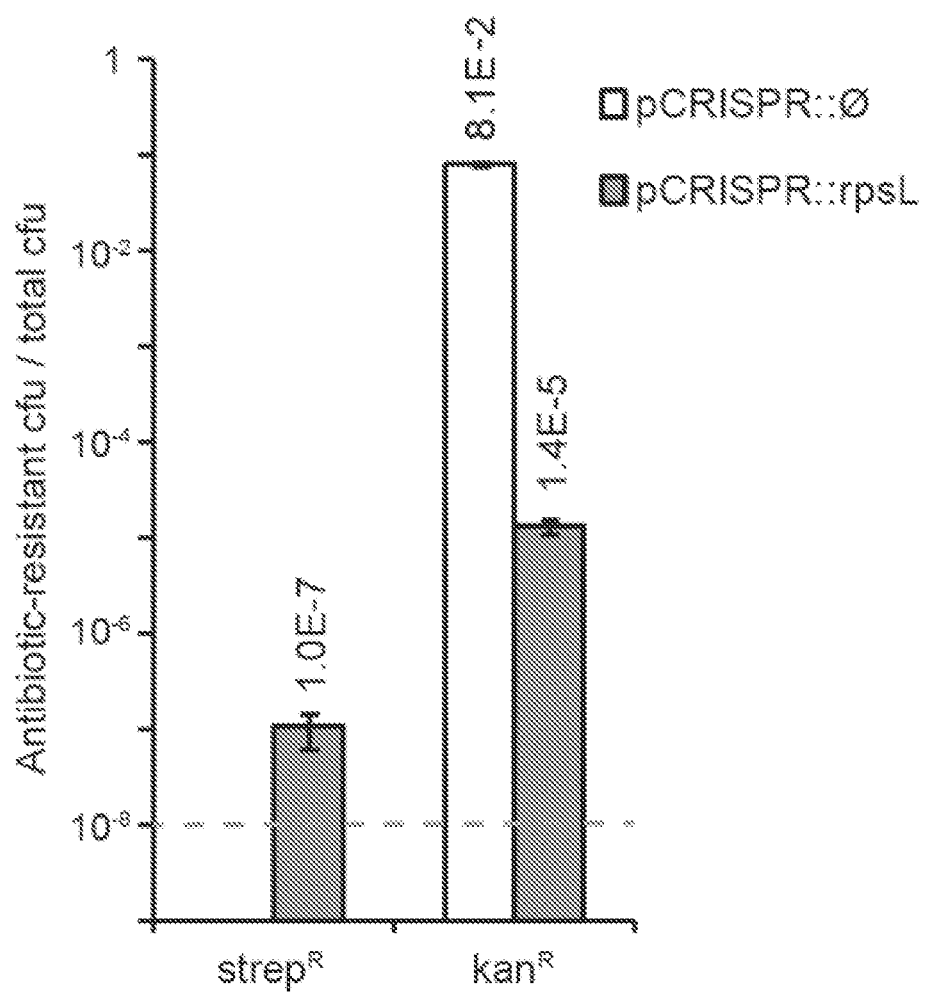
FIG. 37 illustrates CRISPR-directed editing in E. coli MG1655. An oligonucleotide (W542) carrying a point mutation that both confers streptomycin resistance and abolishes CRISPR immunity, together with a plasmid targeting rpsL (pCRISPR::rpsL) or a control plasmid (pCRISPR::Ø) were co-transformed into wild-type E. coli strain MG1655 containing pCas9. Transformants were selected on media containing either streptomycin or kanamycin. Dashed line indicates limit of detection of the transformation assay.
Figure 39A:
FIGS. 39A-D show a circular depiction of the phylogenetic analysis revealing five families of Cas9s, including three groups of large Cas9s (~1400 amino acids) and two of small Cas9s (~1100 amino acids).
Figure 39B:
Figure 39C:
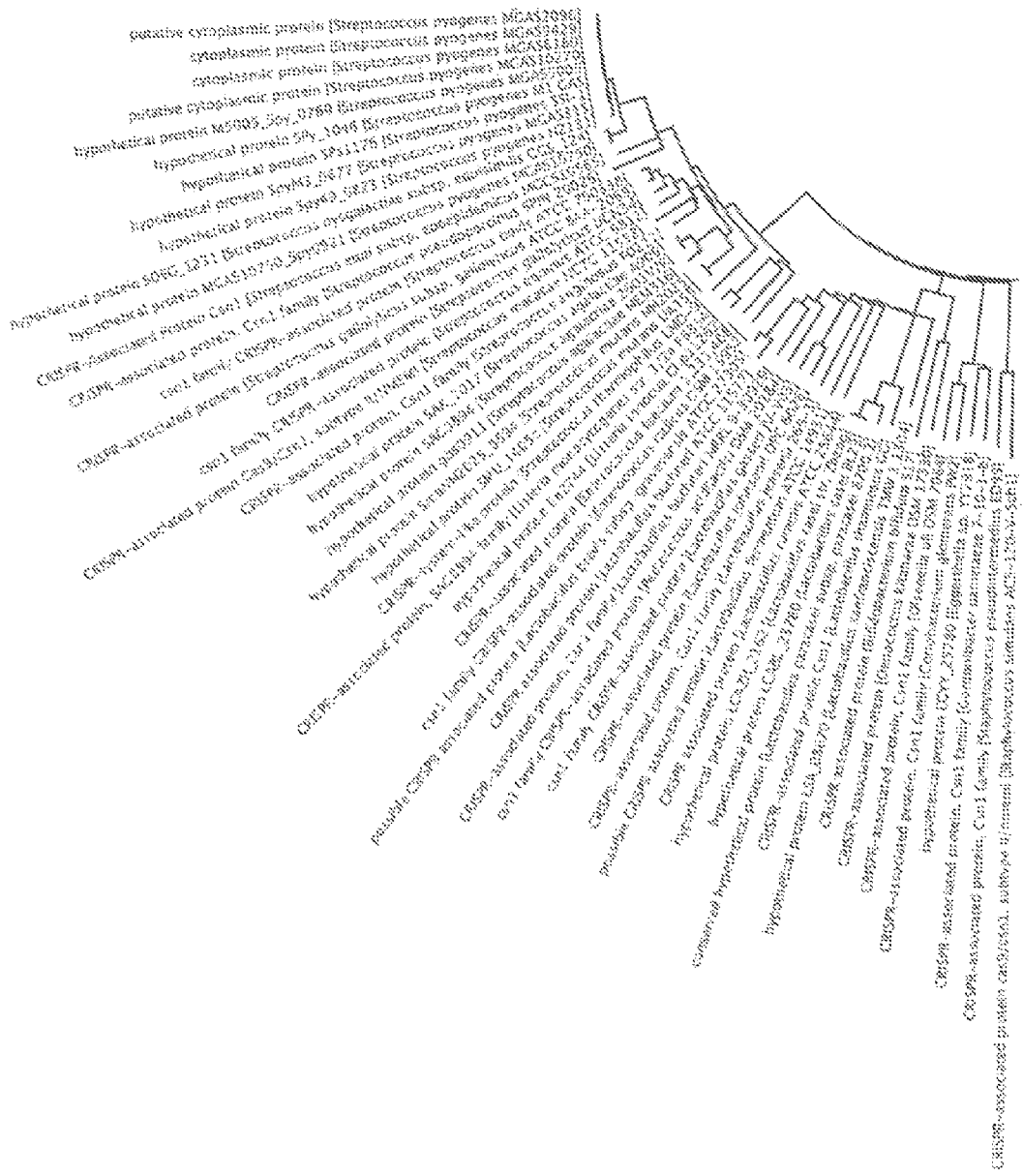
Figure 39D:
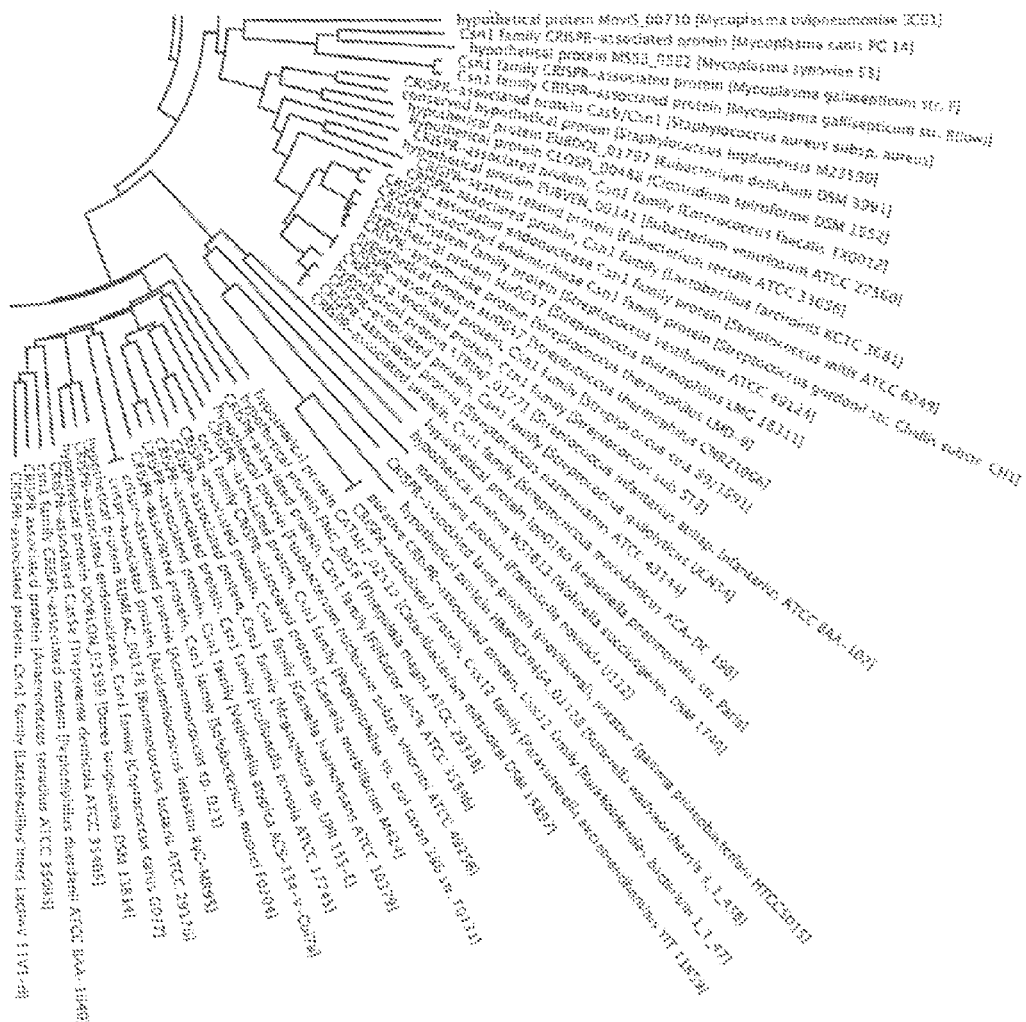
Figure 40A:
FIGS. 40A-F show the linear depiction of the phylogenetic analysis revealing five families of Cas9s, including three groups of large Cas9s (~1400 amino acids) and two of small Cas9s (~1100 amino acids).
Figure 40B:
Figure 40C:
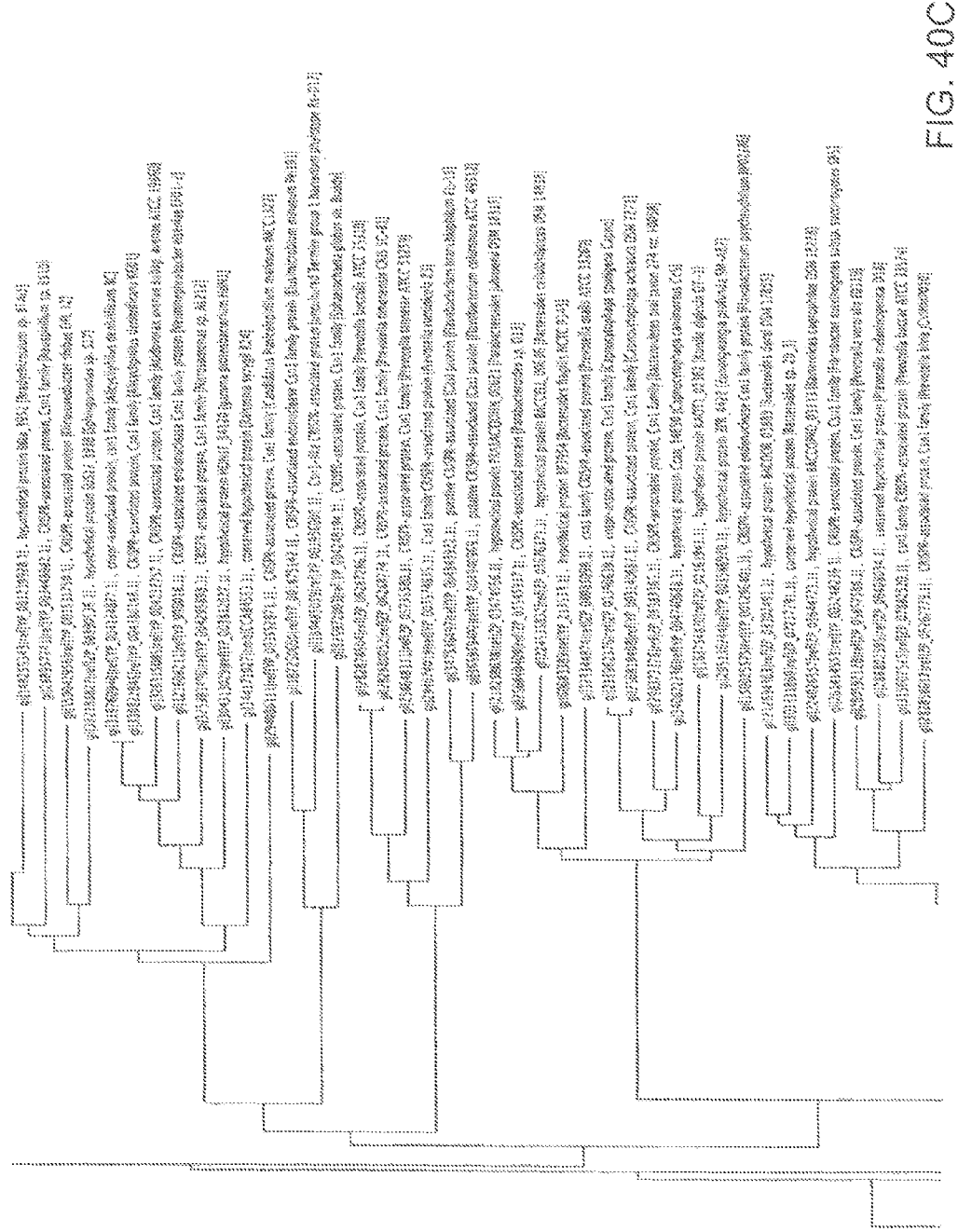
Figure 40D:
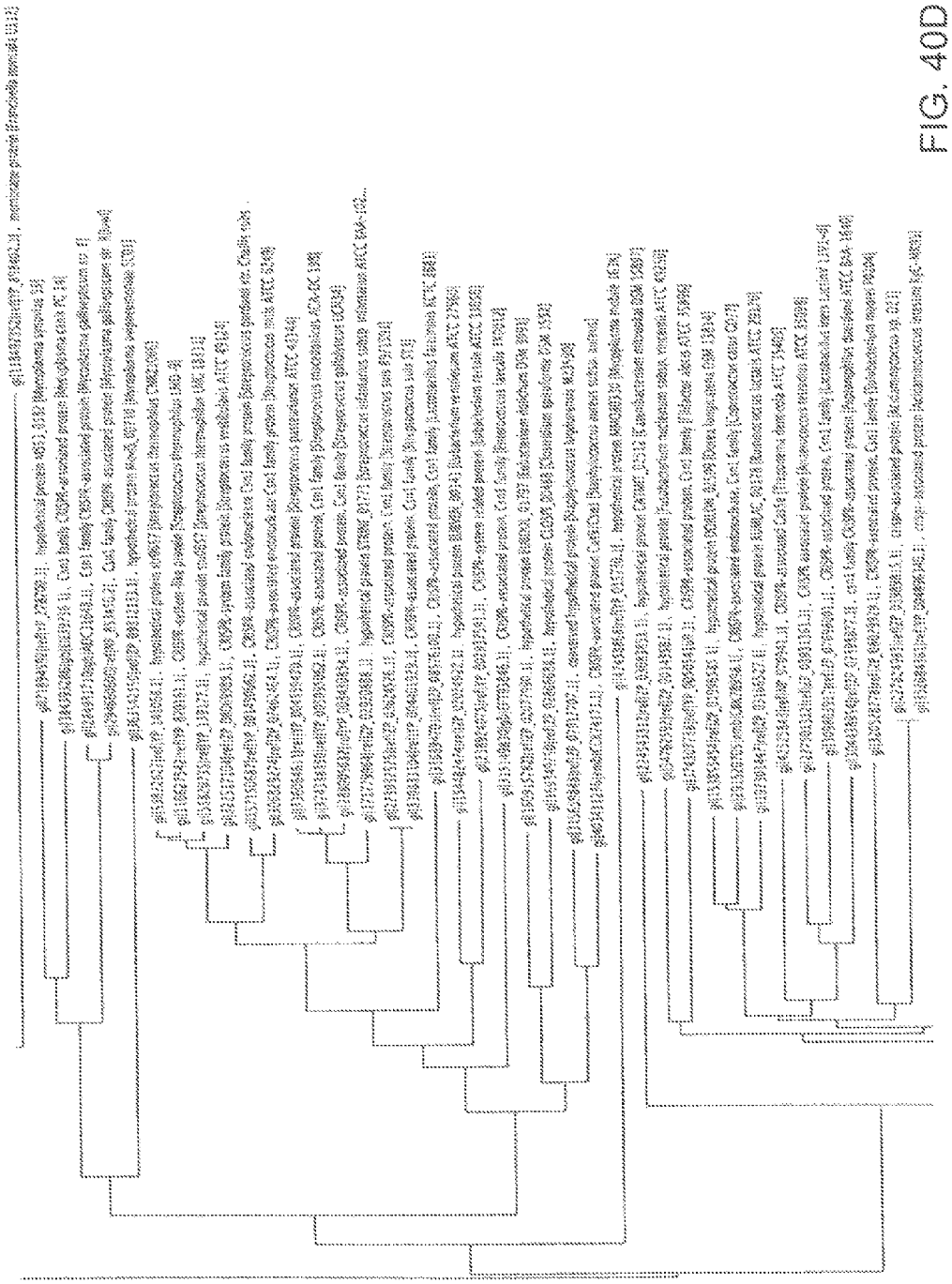
Figure 40E:
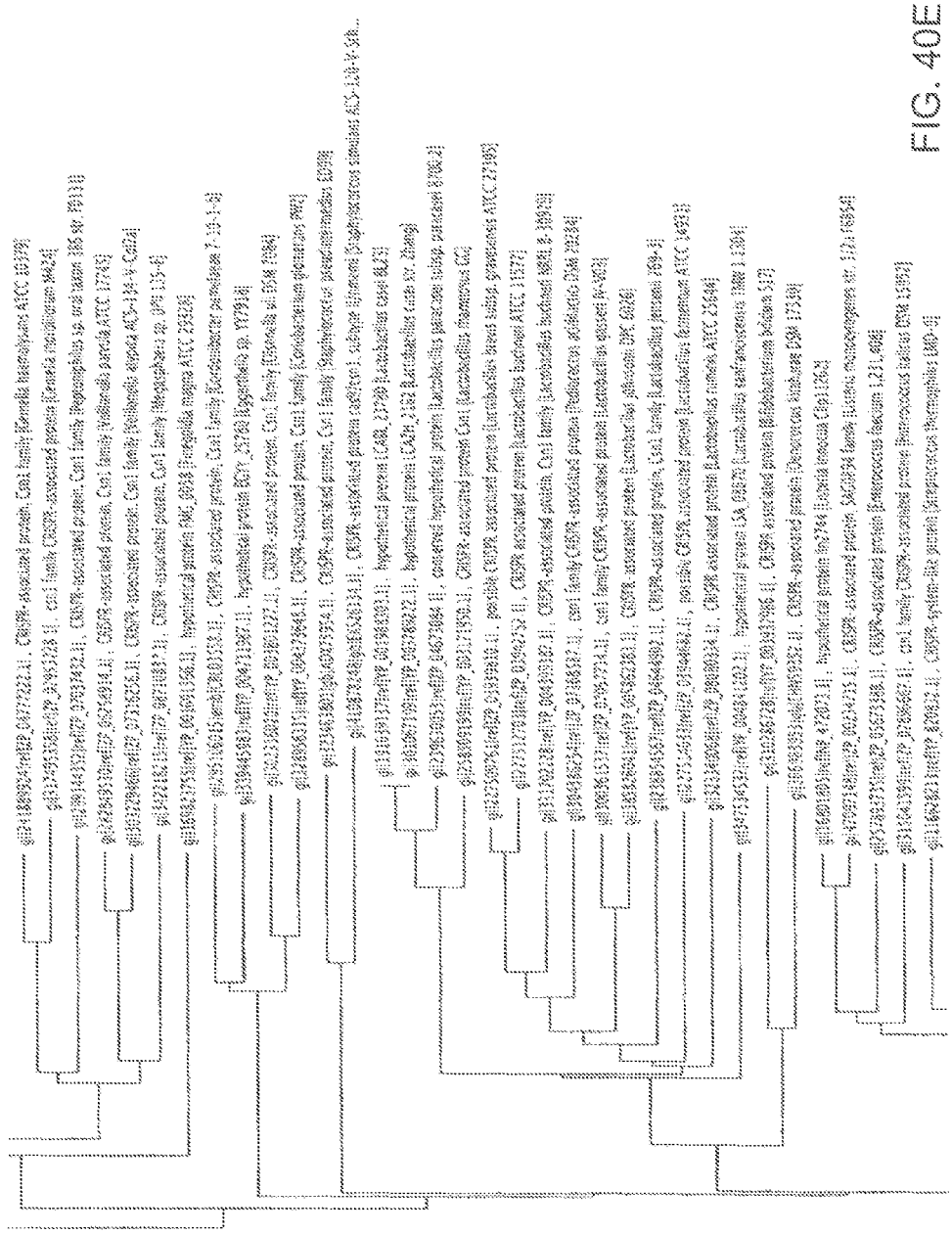
Figure 40F:

Genome Editing with Cas9 in *E. coli*:

The activation of Cas9 targeting through the chromosomal integration of a CRISPR-Cas system is only possible in organisms that are highly recombinogenic. To develop a more general method that is applicable to other microbes, Applicants decided to perform genome editing in *E. coli* using a plasmid-based CRISPR-Cas system. Two plasmids were constructed: a pCas9 plasmid carrying the tracrRNA, Cas9 and a chloramphenicol resistance cassette (FIG. 36), and a pCRISPR kanamycin-resistant plasmid carrying the array of CRISPR spacers. To measure the efficiency of editing independently of CRISPR selection, Applicants sought to introduce an A to C transversion in the rpsL gene that confers streptomycin resistance. Applicants constructed a pCRISPR::rpsL plasmid harboring a spacer that would guide Cas9 cleavage of the wild-type, but not the mutant rpsL allele (FIG. 27b). The pCas9 plasmid was first introduced into *E. coli* MG1655 and the resulting strain was co-transformed with the pCRISPR::rpsL plasmid and W542, an editing oligonucleotide containing the A to C mutation. streptomycin-resistant colonies after transformation of the pCRISPR::rpsL plasmid were only recovered, suggesting that Cas9 cleavage induces recombination of the oligonucleotide (FIG. 37). However, the number of streptomycin-resistant colonies was two orders of magnitude lower than the number of kanamycin-resistant colonies, which are presumably cells that escape cleavage by Cas9. Therefore, in these conditions, cleavage by Cas9 facilitated the introduction of the mutation, but with an efficiency that was not enough to select the mutant cells above the background of 'escapers'.

To improve the efficiency of genome editing in *E. coli*, Applicants applied their CRISPR system with recombineering, using Cas9-induced cell death to select for the desired mutations. The pCas9 plasmid was introduced into the recombineering strain HME63 (31), which contains the Gam, Exo and Beta functions of the □-red phage. The resulting strain was co-transformed with the pCRISPR::rpsL plasmid (or a pCRISPR::Ø control) and the W542 oligonucleotide (FIG. 27a). The recombineering efficiency was $5.3 \times 10^{-5}$, calculated as the fraction of total cells that become streptomycin-resistant when the control plasmid was used (FIG. 27c). In contrast, transformation with the pCRISPR::rpsL plasmid increased the percentage of mutant cells to 65±14% (FIGS. 27c and 29f). Applicants observed that the number of cfu was reduced by about three orders of magnitude after transformation of the pCRISPR::rpsL plasmid than the control plasmid ($4.8 \times 10^{5}/5.3 \times 10^{2}$, FIG. 38a), suggesting that selection results from CRISPR-induced death of non-edited cells. To measure the rate at which Cas9 cleavage was inactivated, an important parameter of Applicants' method, Applicants transformed cells with either pCRISPR::rpsL or the control plasmid without the W542 editing oligonucleotide (FIG. 38a). This background of CRISPR 'escapers', measured as the ratio of pCRISPR::rpsL/pCRISPR::Ø cfu, was $2.5 \times 10^{-4}$ ($1.2 \times 10^{2}/4.8 \times 10^{5}$). Genotyping eight of these escapers revealed that in all cases there was a deletion of the targeting spacer (FIG. 38b). This background was higher than the recombineering efficiency of the rpsL mutation, $5.3 \times 10^{-5}$, which suggested that to obtain 65% of edited cells, Cas9 cleavage must induce oligonucleotide recombination. To confirm this, Applicants compared the number of kanamycin- and streptomycin-resistant cfu after transformation of pCRISPR::rpsL or pCRISPR::Ø (FIG. 27d). As in the case for *S. pneumroniae*, Applicants observed a modest induction of recombination, about 6.7 fold ($2.0 \times 10^{-4}/3.0 \times 10^{-5}$). Taken together, these results indicated that the CRISPR system provided a method for selecting mutations introduced by recombineering.

Applicants showed that CRISPR-Cas systems may be used for targeted genome editing in bacteria by the co-introduction of a targeting construct that killed wild-type cells and an editing template that both eliminated CRISPR cleavage and introduced the desired mutations. Different types of mutations (insertions, deletions or scar-less single-nucleotide substitutions) may be generated. Multiple mutations may be introduced at the same time. The specificity and versatility of editing using the CRISPR system relied on several unique properties of the Cas9 endonuclease: (i) its target specificity may be programmed with a small RNA, without the need for enzyme engineering, (ii) target specificity was very high, determined by a 20 bp RNA-DNA interaction with low probability of non-target recognition, (iii) almost any sequence may be targeted, the only requirement being the presence of an adjacent NGG sequence, (iv) almost any mutation in the NGG sequence, as well as mutations in the seed sequence of the protospacer, eliminates targeting.

Applicants showed that genome engineering using the CRISPR system worked not only in highly recombinogenic bacteria such as *S. pneumoniae*, but also in *E. coli*. Results in *E. coli* suggested that the method may be applicable to other microorganisms for which plasmids may be introduced. In *E. coli*, the approach complements recombineering of mutagenic oligonucleotides. To use this methodology in microbes where recombineering is not a possible, the host homologous recombination machinery may be used by providing the editing template on a plasmid. In addition, because accumulated evidence indicates that CRISPR-mediated cleavage of the chromosome leads to cell death in many bacteria and archaea, it is possible to envision the use of endogenous CRISPR-Cas systems for editing purposes.

In both *S. pneunoniae* and *E. coli*, Applicants observed that although editing was facilitated by a co-selection of transformable cells and a small induction of recombination at the target site by Cas9 cleavage, the mechanism that contributed the most to editing was the selection against non-edited cells. Therefore the major limitation of the method was the presence of a background of cells that escape CRISPR-induced cell death and lack the desired mutation. Applicants showed that these 'escapers' arose primarily through the deletion of the targeting spacer, presumably after the recombination of the repeat sequences that flank the targeting spacer. Future improvements may focus on the engineering of flanking sequences that can still support the biogenesis of functional crRNAs but that are sufficiently different from one another to eliminate recombination. Alternatively, the direct transformation of chimeric crRNAs may be explored. In the particular case of E. coli, the construction of the CRISPR-Cas system was not possible if this organism was also used as a cloning host. Applicants solved this issue by placing Cas9 and the tracrRNA on a different plasmid than the CRISPR array. The engineering of an inducible system may also circumvent this limitation.

Although new DNA synthesis technologies provide the ability to cost-effectively create any sequence with a high throughput, it remains a challenge to integrate synthetic DNA in living cells to create functional genomes. Recently, the co-selection MAGE strategy was shown to improve the mutation efficiency of recombineering by selecting a subpopulation of cells that has an increased probability to achieve recombination at or around a given locus. In this method, the introduction of selectable mutations is used to increase the chances of generating nearby non-selectable mutations. As opposed to the indirect selection provided by this strategy, the use of the CRISPR system makes it possible to directly select for the desired mutation and to recover it with a high efficiency. These technologies add to the toolbox of genetic engineers, and together with DNA synthesis, they may substantially advance both the ability to decipher gene function and to manipulate organisms for biotechnological purposes. Two other studies also relate to CRISPR-assisted engineering of mammalian genomes. It is expected that these crRNA-directed genome editing technologies may be broadly useful in the basic and medical sciences.

Strains and Culture Conditions.

S. pneumoniae strain R6 was provided by Dr. Alexander Tomasz. Strain crR6 was generated in a previous study. Liquid cultures of S. pneumoniae were grown in THYE medium (30 g/l Todd-Hewitt agar, 5 g/l yeast extract). Cells were plated on tryptic soy agar (TSA) supplemented with 5% defibrinated sheep blood. When appropriate, antibiotics were added as followings: kanamycin (400 jpg/ml), chloramphenicol (5 µg/ml), erythromycin (1 µg/ml) streptomycin (100 µg/ml) or spectinomycin (100 µg/ml). Measurements of β-galactosidase activity were made using the Miller assay as previously described.

E. coli strains MG1655 and HME63 (derived from MG1655, Δ(argF-lac) U169λ cI857 Δcro-bioA galK tyr 145 UAG mutS< >amp) (31) were provided by Jeff Roberts and Donald Court, respectively. Liquid cultures of E. coli were grown in LB medium (Difco). When appropriate, antibiotics were added as followings: chloramphenicol (25 µg/ml), kanamycin (25 µg/ml) and streptomycin (50 µg/ml).

S. pneumoniae Transformation.

Competent cells were prepared as described previously (23). For all genome editing transformations, cells were gently thawed on ice and resuspended in 10 volumes of M2 medium supplemented with 100 ngiml of competence-stimulating peptide CSP1(40), and followed by addition of editing constructs (editing constructs were added to cells at a final concentration between 0.7 ng/µl to 2.5 µg/ul). Cells were incubated 20 min at 37° C. before the addition of 2 µl of targeting constructs and then incubated 40 min at 37° C. Serial dilutions of cells were plated on the appropriate medium to determine the colony forming units (cfu) count.

E. coli Lambda-Red Recombineering.

Strain HME63 was used for all recombineering experiments. Recombineering cells were prepared and handled according to a previously published protocol (6). Briefly, a 2 ml overnight culture (LB medium) inoculated from a single colony obtained from a plate was grown at 30° C. The overnight culture was diluted 100-fold and grown at 30° C. with shaking (200 rpm) until the $OD_{600}$ is from 0.4-0.5 (approximately 3 hrs). For Lambda-red induction, the culture was transferred to a 42° C. water bath to shake at 200 rpm for 15 min. Immediately after induction, the culture was swirled in an ice-water slurry and chilled on ice for 5-10 min. Cells were then washed and aliquoted according to the protocol. For electro-transformation, 50 µl of cells were mixed with 1 mM of salt-free oligos (IDT) or 100-150 ng of plasmid DNA (prepared by QIAprep Spin Miniprep Kit, Qiagen). Cells were electroporated using 1 mm Gene Pulser cuvette (Biorad) at 1.8 kV and were immediately resuspended in 1 ml of room temperature LB medium. Cells were recovered at 30° C. for 1-2 hrs before being plated on LB agar with appropriate antibiotic resistance and incubated at 32° C. overnight.

Preparation of S. pneumoniae Genomic DNA.

For transformation purposes, S. pneumoniae genomic DNA was extracted using the Wizard Genomic DNA Purification Kit, following instructions provided by the manufacturer (Promega). For genotyping purposes, 700 ul of overnight S. pneumoniae cultures were pelleted, resuspended in 60 ul of lysozyme solution (2 mg/ml) and incubated 30 min at 37° C. The genomic DNA was extracted using QIAprep Spin Miniprep Kit (Qiagen).

Strain Construction.

All primers used in this study are provided in Table G. To generate S. pneumoniae crR6M, an intermediate strain, LAM226, was made. In this strain the aphA-3 gene (providing kanamycin resistance) adjacent to the CRISPR array of S. pneumoniae crR6 strain was replaced by a cat gene (providing chloramphenicol resistance). Briefly, crR6 genomic DNA was amplified using primers L448/L444 and L447/L481, respectively. The cat gene was amplified from plasmid pC194 using primers L445/L446. Each PCR product was gel-purified and all three were fused by SOEing PCR with primers L448/L481. The resulting PCR product was transformed into competent S. pneumoniae crR6 cells and chloramphenicol-resistant transformants were selected. To generate S. pneumoniae crR6M, S. pneumoniae crR6 genomic DNA was amplified by PCR using primers L409/L488 and L448/L481, respectively. Each PCR product was gel-purified and they were fused by SOEing PCR with primers L409/L481. The resulting PCR product was transformed into competent S. pneumoniae LAM226 cells and kanamycin-resistant transformants were selected.

To generate S. pneumoniae crR6Rc, S. pneumoniae crR6M genomic DNA was amplified by PCR using primers L430/W286, and S. pneumoniae LAM226 genomic DNA was amplified by PCR using primers W288/L481. Each PCR product was gel-purified and they were fused by SOEing PCR with primers L430/L481. The resulting PCR product was transformed into competent S. pneumoniae crR6M cells and chloramphenicol-resistant transformants were selected.

To generate S. pneumoniae crR6Rk, S. pneumoniae crR6M genomic DNA was amplified by PCR using primers L430/W286 and W287/L481, respectively. Each PCR product was gel-purified and they were fused by SOEing PCR with primers L430/L481. The resulting PCR product was transformed into competent *S. pneumoniae* crR6Rc cells and kanamycin-resistant transformants were selected.

To generate JEN37, *S. pneumoniae* crR6Rk genomic DNA was amplified by PCR using primers L430/W356 and W357/L481, respectively. Each PCR product was gel-purified and they were fused by SOEing PCR with primers L430/L481. The resulting PCR product was transformed into competent *S. pneumoniae* crR6Rc cells and kanamycin-resistant transformants were selected.

To generate JEN38, R6 genomic DNA was amplified using primers L422/L461 and L459/L426, respectively. The ermAM gene (specifying erythromycin resistance) was amplified from plasmid pFW15[43] using primers L457/L458. Each PCR product was gel-purified and all three were fused by SOEing PCR with primers L422/L426. The resulting PCR product was transformed into competent *S. pneumoniae* crR6Rc cells and erythromycin-resistant transformants were selected.

*S. pneumoniae* JEN53 was generated in two steps. First JEN43 was constructed as illustrated in FIG. 33. JEN53 was generated by transforming genomic DNA of JEN25 into competent JEN43 cells and selecting on both chloramphenicol and erythromycin.

To generate *S. pneumoniae* JEN62, *S. pneumoniae* crR6Rk genomic DNA was amplified by PCR using primers W256/W365 and W366/L403, respectively. Each PCR product was purified and ligated by Gibson assembly. The assembly product was transformed into competent *S. pneumoniae* crR6Rc cells and kanamycin-resistant transformants were selected.

Plasmid construction. pDB97 was constructed through phosphorylation and annealing of oligonucleotides B296/B297, followed by ligation in pLZ12spec digested by EcoRI/BamHI. Applicants fully sequenced pLZ12spec and deposited its sequence in genebank (accession: KC112384).

pDB98 was obtained after cloning the CRISPR leader sequence was cloned together with a repeat-spacer-repeat unit into pLZ12spec. This was achieved through amplification of crR6Rc DNA with primers B298/B320 and B299/B321, followed by SOEing PCR of both products and cloning in pLZ12spcc with restriction sites BamHI/EcoRI. In this way the spacer sequence in pDB98 was engineered to contain two BsaI restriction sites in opposite directions that allow for the scar-less cloning of new spacers.

pDB99 to pDB108 were constructed by annealing of oligonucleotides B300/B301 (pDB99), B302/B303 (pDB100), B304/B305 (pDB101), B306/B307 (pDB102), B308/B309 (pDB103), B310/B311 (pDB104), B312/B313 (pDB105), B314/B315 (pDB106), B315/B317 (pDB107), B318/B319 (pDB108), followed by ligation in pDB98 cut by BsaI.

The pCas9 plasmid was constructed as follow. Essential CRISPR elements were amplified from Streptococos pyogenes SF370 genomic DNA with flanking homology arms for Gibson Assembly. The tracrRNA and Cas9 were amplified with oligos HC008 and HC010. The leader and CRISPR sequences were amplified HC011/HC014 and HC015/HC009, so that two BsaI type HS sites were introduced in between two direct repeats to facilitate easy insertion of spacers.

pCRISPR was constructed by subcloning the pCas9 CRISPR array in pZE21-MCS1 through amplification with oligos B298+B299 and restriction with EcoRI and BamHI. The rpsL targeting spacer was cloned by annealing of oligos B352+B353 and cloning in the BsaI cut pCRISPR giving pCRISPR::rpsL.

Generation of Targeting and Editing Constructs.

Targeting constructs used for genome editing were made by Gibson assembly of Left PCRs and Right PCRs (Table G). Editing constructs were made by SOEing PCR fusing PCR products A (PCR A), PCR products B (PCR B) and PCR products C (PCR C) when applicable (Table G). The CRISPR::Ø and CRISPR::ermAM(stop) targeting constructs were generated by PCR amplification of JEN62 and crR6 genomic DNA respectively, with oligos L409 and L481.

Generation of Targets with Randomized PAM or Protospacer Sequences.

The 5 nucleotides following the spacer 1 target were randomized through amplification of $R6^{8232.5}$ genomic DNA with primers W377/L426. This PCR product was then assembled with the cat gene and the srtA upstream region that were amplified from the same template with primers L422/W376. 80 ng of the assembled DNA was used to transform strains R6 and crR6. Samples for the randomized targets were prepared using the following primers: B280-B290/L426 to randomize bases 1-10 of the target and B269-B278/L426 to randomize bases 10-20. Primers L422/B268 and L422/B279 were used to amplify the cat gene and srtA upstream region to be assembled with the first and last 10 PCR products respectively. The assembled constructs were pooled together and 30 ng was transformed in R6 and crR6. After transformation, cells were plated on chloramphenicol selection. For each sample more than $2 \times 10^5$ cells were pooled together in 1 ml of THYE and genomic DNA was extracted with the Promega Wizard kit. Primers B250/B251 were used to amplify the target region. PCR products were tagged and run on one Illumina MiSeq paired-end lane using 300 cycles.

Analysis of Deep Sequencing Data.

Randomized PAM: For the randomized PAM experiment 3,429,406 reads were obtained for crR6 and 3,253,998 for R6. It is expected that only half of them will correspond to the PAM-target while the other half will sequence the other end of the PCR product. 1,623,008 of the crR6 reads and 1,537,131 of the R6 reads carried an error-free target sequence. The occurrence of each possible PAM among these reads is shown in supplementary file. To estimate the functionality of a PAM, its relative proportion in the crR6 sample over the R6 sample was computed and is denoted $r_{ijklm}$ where I,j,k,l,m are one of the 4 possible bases. The following statistical model was constructed:

$$\log(r_{ijklm}) = \mu + b2_i + b3_j + b4_k + b2b3_{i,j} + b3b4_{j,k} + \epsilon_{ijklm},$$

where $\epsilon$ is the residual error, b2 is the effect of the $2^{nd}$ base of the PAM, b3 of the third, b4 of the fourth, b2b3 is the interaction between the second and third bases, b3b4 between the third and fourth bases. An analysis of variance was performed:

Anova Table

|  | Df | Sum Sq | Mean Sq | F value | Pr (>F) |
|---|---|---|---|---|---|
| b3 | 3 | 151.693 | 50.564 | 601.8450 | <2.2e−16 *** |
| b2 | 3 | 90.521 | 30.174 | 359.1454 | <2.2e−16 *** |
| b4 | 3 | 1.881 | 0.627 | 7.4623 | 6.070e−05 *** |
| b3:b2 | 9 | 228.940 | 25.438 | 302.7738 | <2.2e−16 *** |
| b3:b4 | 9 | 3.010 | 0.334 | 3.9809 | 5.227e−05 *** |
| Residuals | 996 | 83.680 | 0.084 |  |  |

When added to this model, b1 or b5 do not appear to be significant and other interactions than the ones included can also be discarded. The model choice was made through successive comparisons of more or less complete models using the anova method in R. Tukey's honest significance test was used to determine if pairwise differences between effects are significant.

NGGNN patterns are significantly different from all other patterns and carry the strongest effect (see table below).

Figure 71:
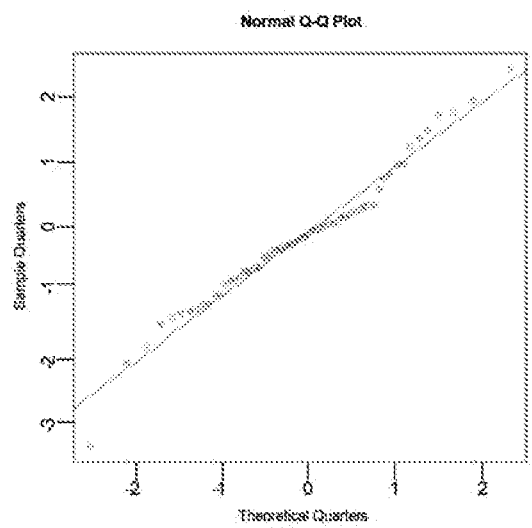
FIG. 71 shows a QQ plot for NGGNN sequences.

In order to show that positions 1, 4 or 5 do not affect the NGGNN pattern Applicants looked at theses sequences only. Their effect appears to be normally distributed (see QQ plot in FIG. 71), and model comparisons using the anova method in R shows that the null model is the best one, i.e. there is no significant role of b1, b4 and b5.

Model Comparison Using the Anova Method in R for the NGGNN Sequences

| | | Model 1: ratio.log ~1 Model 2: ratio.log ~b1 + b4 + b5 | | | | |
|---|---|---|---|---|---|---|
| Res. | Df | RSS | Df | Sum of Sq | F | Pr(>F) |
| | 1 | 63 | 14.579 | | | |
| | 2 | 54 | 11.295 | 9 | 3.2836 1.744 | 0.1013 |

Partial Interference of NAGNN and NNGGN Patterns

NAGNN patterns are significantly different from all other patterns but carry a much smaller effect than NGGNN (see Tukey's honest significance test below).

Finally, NTGGN and NCGGN patterns are similar and show significantly more CRISPR interference than NTGHN and NCGHN patterns (where H is A, T or C), as shown by a bonferroni adjusted pairwise student-test.

Pairwise Comparisons of the Effect of b4 on NYGNN Sequences Using t Tests with Pooled SD

| | Data: b4 | | |
|---|---|---|---|
| | A | C | G |
| C | 1.00 | — | — |
| G | 9.2e−05 | 2.4e−06 | — |
| T | 0.31 | 1.00 | 1.2e−08 |

Taken together, these results allow concluding that NNGGN patterns in general produce either a complete interference in the case of NGGGN, or a partial interference in the case of NAGGN, NTGGN or NCGGN.

Tukey multiple comparisons of means: 95% family-wise confidence level

| | diff | lwr | upr | p adj |
|---|---|---|---|---|
| | $b2:b3 | | | |
| G:G-A:A | −2.76475 | −2.94075 | −2.58875 | <1E−07 |
| G:G-C:A | −2.79911 | −2.97511 | −2.62311 | <1E−07 |
| G:G-T:A | −2.7809 | −2.9569 | −2.6049 | <1E−07 |
| G:G-A:C | −2.81643 | −2.99244 | −2.64043 | <1E−07 |
| G:G-C:C | −2.77903 | −2.95504 | −2.60303 | <1E−07 |
| G:G-G:C | −2.64867 | −2.82468 | −2.47267 | <1E−07 |
| G:G-T:C | −2.79718 | −2.97319 | −2.62118 | <1E−07 |
| G:G-A:G | −2.67068 | −2.84668 | −2.49468 | <1E−07 |
| G:G-C:G | −2.73525 | −2.91125 | −2.55925 | <1E−07 |
| G:G-T:G | −2.7976 | −2.62159 | −2.9736 | <1E−07 |
| G:G-A:T | −2.76727 | −2.59127 | −2.94328 | <1E−07 |
| G:G-C:T | −2.84114 | −2.66513 | −3.01714 | <1E−07 |
| G:G-G:T | −2.76409 | −2.58809 | −2.94009 | <1E−07 |
| G:G-T:T | −2.76781 | −2.59181 | −2.94381 | <1E−07 |
| G:G-G:A | −2.13964 | −2.31565 | −1.96364 | <1E−07 |
| G:A-A:A | −0.62511 | −0.80111 | −0.4491 | <1E−07 |
| G:A-C:A | −0.65947 | −0.83547 | −0.48346 | <1E−07 |

-continued

| | diff | lwr | upr | p adj |
|---|---|---|---|---|
| G:A-T:A | −0.64126 | −0.46525 | −0.81726 | <1E−07 |
| G:A-A:C | −0.67679 | −0.50078 | −0.85279 | <1E−07 |
| G:A-C:C | −0.63939 | −0.46339 | −0.81539 | <1E−07 |
| G:A-G:C | −0.50903 | −0.33303 | −0.68503 | <1E−07 |
| G:A-T:C | −0.65754 | −0.48154 | −0.83354 | <1E−07 |
| G:A-A:G | −0.53104 | −0.35503 | −0.70704 | <1E−07 |
| G:A-C:G | −0.59561 | −0.4196 | −0.77161 | <1E−07 |
| G:A-T:G | −0.65795 | −0.48195 | −0.83396 | <1E−07 |
| G:A-A:T | −0.62763 | −0.45163 | −0.80363 | <1E−07 |
| G:A-C:T | −0.70149 | −0.52549 | −0.8775 | <1E−07 |
| G:A-G:T | −0.62445 | −0.44844 | −0.80045 | <1E−07 |
| G:A-T:T | −0.62817 | −0.45216 | −0.80417 | <1E−07 |
| | $b3:b4 | | | |
| G:G-G:A | −0.33532 | −0.51133 | −0.15932 | <1E−07 |
| G:G-G:C | −0.18113 | −0.35719 | −0.00518 | 0.036087 |
| G:G-G:T | −0.31626 | −0.14026 | −0.49226 | <1E−07 |

Randomized Target

Figure 72:
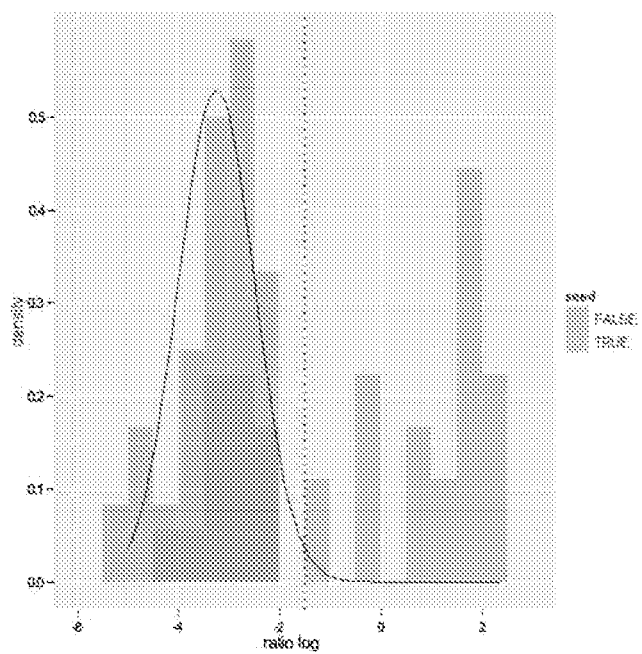
FIG. 72 shows a histogram of the data density with fitted normal distribution (black line) and 0.99 quantile (dotted line).

For the randomized target experiment 540,726 reads were obtained for crR6 and 753,570 for R6. As before, only half of the reads are expected to sequence the interesting end of the PCR product. After filtering for reads that carry a target that is error-free or with a single point mutation, 217,656 and 353, 141 reads remained for crR6 and R6 respectively. The relative proportion of each mutant in the crR6 sample over the R6 sample was computed (FIG. 24c). All mutations outside of the seed sequence (13-20 bases away from the PAM) show full interference. Those sequences were used as a reference to determine if other mutations inside the seed sequence can be said to significantly disrupt interference. A normal distribution was fitted to theses sequences using the fitdistr function of the MASS R package. The 0.99 quantile of the fitted distribution is shown as a dotted line in FIG. 24c. FIG. 72 shows a histogram of the data density with fitted normal distribution (black line) and 0.99 quantile (dotted line).

TABLE F

Relative abdundance of PAM sequences in the crR6/R6 samples averaged over bases 1 and 5.

| 2nd position | 3rd position | | | | | | | | 4th position |
|---|---|---|---|---|---|---|---|---|---|
| | A | | C | | G | | T | | |
| A | AAA | 1.04 | ACA | 1.12 | AGA | 0.73 | ATA | 1.10 | A |
| | AAC | 1.07 | ACC | 1.04 | AGC | 0.64 | ATC | 0.97 | C |
| | AAG | 1.00 | ACG | 1.09 | AGG | 0.61 | ATG | 1.07 | G |
| | AAT | 0.98 | ACT | 1.02 | AGT | 0.65 | ATT | 1.01 | T |
| C | CAA | 1.05 | CCA | 1.05 | CGA | 0.99 | CTA | 1.07 | A |
| | CAC | 1.04 | CCC | 1.02 | CGC | 1.08 | CTC | 1.04 | C |
| | CAG | 1.08 | CCG | 1.08 | CGG | 0.81 | CTG | 1.05 | G |
| | CAT | 1.13 | CCT | 1.05 | CGT | 1.07 | CTT | 1.08 | T |
| G | GAA | 0.97 | GCA | 1.05 | GGA | 0.08 | GTA | 0.99 | A |
| | GAC | 0.92 | GCC | 1.00 | GGC | 0.05 | GTC | 1.15 | C |
| | GAG | 0.96 | GCG | 0.98 | GGG | 0.07 | GTG | 0.98 | G |
| | GAT | 0.98 | GCT | 0.99 | GGT | 0.06 | GTT | 1.05 | T |
| | TAA | 1.08 | TCA | 1.16 | TGA | 1.05 | TTA | 1.14 | A |
| | TAC | 1.00 | TCC | 1.08 | TGC | 1.08 | TTC | 1.05 | C |
| T | TAG | 1.02 | TCG | 1.11 | TGG | 0.77 | TTG | 1.01 | G |
| | TAT | 1.01 | TCT | 1.12 | TGT | 1.21 | TTT | 1.02 | T |

TABLE G

Primers used in this study (SEQ ID NOS 68-183, respectively, in order of appearance).

| Primer | Sequence 5'-3' |
|---|---|
| B217 | TCCTAGCAGGATTTCTGATATTACTGTCACGTTTTAGAGCTATGCTGTTTTGA |
| B218 | GTGACAGTAATATCAGAAATCCTGCTAGGAGTTTTGGGACCATTCAAAACAGC |
| B229 | GGGTTTCAAGTCTTTGTAGCAAGAG |
| B230 | GCCAATGAACGGGAACCCTTGGTC |
| B250 | NNNNGACGAGGCAATGGCTGAAATC |
| B251 | NNNNTTATTTGGCTCATATTTGCTG |
| B255 | CTTTACACCAATCGCTGCAACAGAC |
| B256 | CAAAATTTCTAGTCTTCTTTGCCTTTCCCCATAAAACCCTCCTTA |
| B257 | AGGGTTTTATGGGGAAAGGCAAAGAAGACTAGAAATTTTGATACC |
| B258 | CTTACGGTGCATAAAGTCAATTTCC |
| B269 | TGGCTCGATTTCAGCCATTGC |
| B270 | CTTTGACGAGGCAATGGCTGAAATCGAGCCAANAAAGCGCAAG |
| B271 | CTTTGACGAGGCAATGGCTGAAATCGAGCCAAANAAGCGCAAG |
| B272 | CTTTGACGAGGCAATGGCTGAAATCGAGCCAAAANAGCGCAAG |
| B273 | CTTTGACGAGGCAATGGCTGAAATCGAGCCAAAAANGCGCAAG |
| B274 | CTTTGACGAGGCAATGGCTGAAATCGAGCCAAAAAANCGCAAG |
| B275 | CTTTGACGAGGCAATGGCTGAAATCGAGCCAAAAAAGNGCAAG |
| B276 | CTTTGACGAGGCAATGGCTGAAATCGAGCCAAAAAAGCNCAAGAAG |
| B277 | CTTTGACGAGGCAATGGCTGAAATCGAGCCAAAAAAGCGNAAGAAG |
| B278 | CTTTGACGAGGCAATGGCTGAAATCGAGCCAAAAAAGCGCNAGAAG |
| B279 | GCGCTTTTTGGCTCGATTTCAG |
| B280 | CAATGGCTGAAATCGAGCCAAAAAAGCGCANGAAGAAATC |
| B281 | CAATGGCTGAAATCGAGCCAAAAAAGCGCAANAAGAAATC |
| B282 | CAATGGCTGAAATCGAGCCAAAAAAGCGCAAGNAGAAATC |
| B283 | CAATGGCTGAAATCGAGCCAAAAAAGCGCAAGANGAAATC |
| B284 | CAATGGCTGAAATCGAGCCAAAAAAGCGCAAGAANAAATC |
| B285 | CAATGGCTGAAATCGAGCCAAAAAAGCGCAAGAAGNAATCAACC |
| B286 | CAATGGCTGAAATCGAGCCAAAAAAGCGCAAGAAGANATCAACC |
| B287 | CAATGGCTGAAATCGAGCCAAAAAAGCGCAAGAAGAANTCAACC |
| B288 | CAATGGCTGAAATCGAGCCAAAAAAGCGCAAGAAGAAANCAACC |
| B289 | CAATGGCTGAAATCGAGCCAAAAAAGCGCAAGAAGAAATNAACCAGC |
| B290 | CAATGGCTGAAATCGAGCCAAAAAAGCGCAAGAAGAAATCNACCAGC |
| B296 | gatccTCCATCCGTACAACCCACAACCCTGg |
| B297 | aattcCAGGGTTGTGGGTTGTACGGATGGAg |
| B298 | CATGGATCCTATTTCTTAATAACTAAAAATATGG |
| B299 | CATGAATTCAACTCAACAAGTCTCAGTGTGCTG |
| B300 | AAACATTTTTTCTCCATTTAGGAAAAAGGATGCTG |
| B301 | AAAACAGCATCCTTTTTCCTAAATGGAGAAAAAAT |
| B302 | AAACCTTAAATCAGTCACAAATAGCAGCAAATTG |
| B303 | AAAACAATTTGCTGCTATTTGTGACTGATTTAAG |
| B304 | AAACTTTTCATCATACGACCAATCTGCTTTATTTG |
| B305 | AAAACAAATAAAGCAGATTGGTCGTATGATGAAAA |
| B306 | AAACTCGTCAGAAGTTATCGTAAAGAAATCGAG |
| B307 | AAAACTCGATTTCTTTTACGATAACTTCTGGACGA |
| B308 | AAACAATCTCTCCAAGGTTTCCTTAAAAATCTCTG |
| B309 | AAAACAGAGATTTTTAAGGAAACCTTGGAGAGATT |
| B310 | AAACGCCATCGTCAGGAAGAAGCTATGCTTGAGTG |
| B311 | AAAACACTCAAGCATAGCTTCTTCCTGACGATGGC |
| B312 | AAACATCTCTATACTTATTGAAATTTCTTTGTATG |
| B313 | AAAACATACAAAGAAATTTCAATAAGTATAGAGAT |
| B314 | AAACTAGCTGTGATAGTCCGCAAAACCAGCCTTCG |
| B315 | AAAACGAAGGCTGGTTTTGCGGACTATCACAGCTA |
| B316 | AAACATCGGAAGGTCGAGCAAGTAATTATCTTTTG |
| B317 | AAAACAAAGATAATTACTTGCTCGACCTTCCGAT |
| B318 | AAACAAGATGGTATCGCAAAGTAAGTGACAATAAG |
| B319 | AAAACTTATTGTCACTTACTTTGCGATACCATCTT |
| B320 | GAGACCTTTGAGCTTCCGAGACTGGTCTCAGTTTTGGGACCATTCAAAACAG |
| B321 | TGAGACCAGTCTCGGAAGCTCAAAGGTCTCGTTTTAGAGCTATGCTGTTTTG |
| B352 | aaacTACTTTACGCAGCGCGGAGTTCGGTTTTTTg |
| B353 | aaaacAAAAAACCGAACTCCGCGCTGCGTAAAGTA |
| HC008_SP | ATGCCGGTACTGCCGGGCCTCTTGCGGGATTACGAAATCATCCTG |
| HC009_SP | GTGACTGGCGATGCTGTCGGAATGGACGATCACACTACTCTTCTT |

TABLE G-continued

Primers used in this study (SEQ ID NOS 68-183, respectively, in order of appearance).

| Primer | Sequence 5'-3' |
|---|---|
| HC010_SP | TTAAGAAATAATCTTCATCTAAAATATACTTCAGTCACCTCCTAGCTGAC |
| HC011_SP | ATTGATTTGAGTCAGCTAGGAGGTGACTGAAGTATATTTTAGATGAAG |
| HC014_SP | GAGACCTTTGAGCTTCCGAGACTGGTCTCAGTTTTGGGACCATTCAAAACAGCATAGCTCTAAAACCTCGTAGACTATTTTTGTC |
| HC-015_SP | GAGACCAGTCTCGGAAGCTCAAAGGTCTCGTTTTAGAGCTATGCTGTTTGAATGGTCCCAAAACTTCAGCACACTGAGACTTG |
| L403 | AGTCATCCCAGCAACAAATGG |
| L409 | CGTGGTAAATCGGATAACGTTCCAAGTGAA |
| L422 | Tgctcttcttcacaaacaaggg |
| L426 | AAGCCAAAGTTTGGCACCACC |
| L430 | GTAGCTTATTCAGTCCTAGTGG |
| L444 | CGTTTGTTGAACTAATGGGTGCAAATTACGAATCTTCTCCTGACG |
| L445 | CGTCAGGAGAAGATTCGTAATTTGCACCCATTAGTTCAACAAACG |
| L446 | GATATTATGGAGCCTATTTTTGTGGGTTTTTAGGCATAAAACTATATG |
| L447 | CATATAGTTTTATGCCTAAAAACCCACAAAAATAGGCTCCATAATATC |
| L448 | ATTATTTCTTAATAACTAAAAATATGG |
| L457 | CGTgtacaattgctagcgtacggc |
| L458 | GCACCGGTGATCACTAGTCCTAGG |
| L459 | cctaggactagtgatcaccggtGCAAATATGAGCCAAATAAATATAT |
| L461 | GCCGTACGCTAGCAATTGTACACGTTTGTTGAACTAATGGGTGC |
| L481 | TTCAAATTTTCCCATTTGATTCTCC |
| L488 | CCATATTTTTAGTTATTAAGAAATAATACCAGCCATCAGTCACCTCC |
| W256 | AGACGATTCAATAGACAATAAGG |
| W286 | GTTTTGGGACCATTCAAAACAGCATAGCTCTAAAACCTCGTAGAC |
| W287 | GCTATGCTGTTTTGAATGGTCCCAAAACcattattttaacacacgaggtg |
| W288 | GCTATGCTGTTTTGAATGGTCCCAAAACGCACCCATTAGTTCAACAAACG |
| W326 | AATTCTTTTCTTCATCATCGGTC |
| W327 | AAGAAAGAATGAAGATTGTTCATG |
| W341 | GGTACTAATCAAAATAGTGAGGAGG |
| W354 | GTTTTTCAAAATCTGCGGTTGCG |
| W355 | AAAAATTGAAAAAATGGTGGAAACAC |
| W356 | ATTTCGTAAACGGTATCGGTTTCTTTTAAAGTTTTGGGACCATTCAAAACAGC |
| W357 | TTTAAAAGAAACCGATACCGTTTACGAAATGTTTTAGAGCTATGCTGTTTTGA |
| W365 | AAACGGTATCGGTTTCTTTTAAATTCAATTGTTTTGGGACCATTCAAAACAGC |
| W366 | AATTGAATTTAAAAGAAACCGATACCGTTTGTTTTAGAGCTATGCTGTTTTGA |
| W370 | GTTCCTTAAACCAAAACGGTATCGGTTTCTTTTAAATTC |
| W371 | GAAACCGATACCGTTTTGGTTTAAGGAAACAGGTAAAGGGCATTTAAC |
| W376 | CGATTTCAGCCATTGCCTCGTC |
| W377 | GCCTTTGACGAGGCAATGGCTGAAATCGNNNNNAAAAAGCGCAAGAAGAAATCAAC |
| W391 | TCCGTACAACCCACAACCCTGCTAGTGAGCGTTTTGGGACCATTCAAAACAGC |
| W392 | GCTCACTAGCAGGGTTGTGGGTTGTACGGAGTTTTAGAGCTATGCTGTTTTGA |
| W393 | TTGTTGCCACTCTTCCTTCTTTC |
| W397 | CAGGGTTGTGGGTTGTTGCGATGGAGTTAACTCCCATCTCC |
| W398 | GGGAGTTAACTCCATCGCAACAACCCACAACCCTGCTAGTG |
| W403 | GTGGTATCTATCGTGATGTGAC |
| W404 | TTACCGAAACGGAATTTATCTGC |
| W405 | AAAGCTAGAGTTCCGCAATTGG |
| W431 | GTGGGTTGTACGGATTGAGTTAACTCCCATCTCCTTC |
| W432 | GATGGGAGTTAACTCAATCCGTACAACCCACAACCCTG |
| W433 | GCTTCACCTATTGCAGCACCAATTGACCACATGAAGATAG |
| W434 | GTGGTCAATTGGTGCTGCAATAGGTGAAGCTAATGGTGATG |
| W463 | CTGATTTGTATTAATTTTGAGACATTATGCTTCACCTTC |
| W464 | GCATAATGTCTCAAAATTAATACAAATCAGTGAAATCATG |
| W465 | GTTTTGGGACCATTCAAAACAGCATAGCTCTAAAACGTGACAGTAATATCAG |
| W466 | GTTTTAGAGCTATGCTGTTTTGAATGGTCCCAAAACGCTCACTAGCAGGGTTG |
| W542 | ATACTTTACGCAGCGCGGAGTTCGGTTTTgTAGGAGTGGTAGTATATACACGAGTACAT |

TABLE H

Design of targeting and editing constructs used in this study
(SEQ ID NOS 184, 184, 184, 185 and 186, respectively, in order of appearance).

| Edition | Targeting Constructs Template DNA | Left PCR | Right PCR | Spacer sequence | PAM |
|---|---|---|---|---|---|
| bgaA R > A | crR6Rk | W256/W391 | W392/L403 | GCTCACTAGCAGGGTTGTGGGTTGTACGGA | TGG |
| bgaA NE > AA | crR6Rk | W256/W391 | W392/L403 | GCTCACTAGCAGGGTTGTGGGTTGTACGGA | TGG |
| Δ bgaA | crR6Rk | W256/W391 | W392/L403 | GCTCACTAGCAGGGTTGTGGGTTGTACGGA | TGG |
| Δ srtA | crR6Rc | W256/B218 | B217/L403 | TCCTAGCAGGATTTCTGATATTACTGTCAC | TGG |
| ermB Stop | crR6Rk | W256/W356 | W357/L403 | TTTAAAAGAAACCGATACCGTTTACGAAAT | TGG |
| Δ srtA Δ bgaA | JEN51 (for Left PCR) and JEN52 (for Right PCR) | W256/W465 | W466/W403 | same as the ones used for Δ srtA and Δ bgaA | TGG |

| Edition | Editing Constructs Template DNA | PCR A | PCR B | PCR C | SOEing PCR | Name of resulting strains | Primers used to verify edited genotype |
|---|---|---|---|---|---|---|---|
| bgaA R > A | R6 | W403/W397 | W398/W404 | N/A | W403/W404 | JEN56 | W403/W404 |
| bgaA NE > AA | R6 | W403/W431 | W432/W433 | W434/W404 | W403/W404 | JEN60 | W403/W404 |
| Δ bgaA | R6 | B255/B256 | B257/B258 | N/A | B255/B258 | JEN52 | W393/W405 |
| Δ srtA | R6 | B230/W463 | W464/B229 | N/A | B230/B229 | JEN51 | W422/W426 |
| ermB Stop | JEN38 | L422/W370 | W371/L426 | N/A | L422/L426 | JEN43 | L457/L458 |
| Δ srtA Δ bgaA | same as the ones used for Δ srtA and Δ bgaA | | | | | JEN64 | same as the ones used for Δ srtA and Δ bgaA |

Example 6

Optimization of the Guide RNA for *Streptococcus pyogenes* Cas9 (Referred to as SpCas9)

Applicants mutated the tracrRNA and direct repeat sequences, or mutated the chimeric guide RNA to enhance the RNAs in cells.

The optimization is based on the observation that there were stretches of thymines (Ts) in the tracrRNA and guide RNA, which might lead to early transcription termination by the pol 3 promoter. Therefore Applicants generated the following optimized sequences. Optimized tracrRNA and corresponding optimized direct repeat are presented in pairs.

Optimized tracrRNA 1 (mutation underlined):

(SEQ ID NO: 18)
GGAACCATTCAtAACAGCATAGCAAGTTAtAATAAGGCTAGTCCGTTATC

AACTTGAAAAAGTGGCACCGAGTCGGTGCTTTTT

Optimized direct repeat 1 (mutation underlined):

(SEQ ID NO: 188)
GTTaTAGAGCTATGCTGTTaTGAATGGTCCCAAAAC

Optimized tracrRNA 2 (mutation underlined):

(SEQ ID NO: 189)
GGAACCATTCAtACAGCATAGCAAGTTAAtATAAGGCTAGTCCGTTATC

AACTTGAAAAAGTGGCACCGAGTCGGTGCTTTTT

Optimized direct repeat 2 (mutation underlined):

(SEQ ID NO: 190)
GTaTTAGAGCTATGCTGTaTTGAATGGTCCCAAAAC

Applicants also optimized the chimeric guideRNA for optimal activity in eukaryotic cells.

Original guide RNA:

(SEQ ID NO: 191)
NNNNNNNNNNNNNNNNNNNNNNNGTTTTAGAGCTAGAAATAGCAAGTTAAAAT

AAGGCTAGTCCGTTATCAACTTGAAAAAGTGGCACCGAGTCGGTGCTTTT

TTT

Optimized chimeric guide RNA sequence 1:

(SEQ ID NO: 192)
NNNNNNNNNNNNNNNNNNNNNNNGTATTAGAGCTAGAAATAGCAAGTTAATAT

AAGGCTAGTCCGTTATCAACTTGAAAAAGTGGCACCGAGTCGGTGCTTTT

TTT

Optimized chimeric guide RNA sequence 2:

(SEQ ID NO: 193)
NNNNNNNNNNNNNNNNNNNNNNNGTTTTAGAGCTATGCTGTTTTGGAAACAAA

ACAGCATAGCAAGTTAAAATAAGGCTAGTCCGTTATCAACTTGAAAAAGT

GGCACCGAGTCGGTGCTTTTTTT

Optimized chimeric guide RNA sequence 3:

(SEQ ID NO: 194)
NNNNNNNNNNNNNNNNNNNNNNNGTATTAGAGCTATGCTGTATTGGAAACAAT

ACAGCATAGCAAGTTAATATAAGGCTAGTCCGTTATCAACTTGAAAAAGT

GGCACCGAGTCGGTGCTTTTTTT

Applicants showed that optimized chimeric guide RNA works better as indicated in FIG. 3. The experiment was conducted by co-transfecting 293FT cells with Cas9 and a U6-guide RNA DNA cassette to express one of the four RNA forms shown above. The target of the guide RNA is the same target site in the human Emx1 locus: "GTCACCTCCAAT-GACTAGGG (SEQ ID NO: 195)"

Example 7

Optimization of *Streptococcus thermophiles* LMD-9 CRISPR1 Cas9 (Referred to as St1Cas9)

Applicants designed guide chimeric RNAs as shown in FIG. 4.

The St1Cas9 guide RNAs can undergo the same type of optimization as for SpCas9 guide RNAs, by breaking the stretches of poly thymines (Ts)

Example 8

Cas9 Diversity, and Mutations

The CRISPR-Cas system is an adaptive immune mechanism against invading exogenous DNA employed by diverse species across bacteria and archaea. The type II CRISPR-Cas9 system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (FIGS. 39 and 40A-F).

In this example, Applicants show that the following mutations can convert SpCas9 into a nicking enzyme: D10A, E762A, H840A, N854A, N863A, D986A.

Figure 41A:
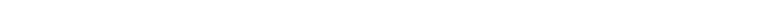
Figure 41D:
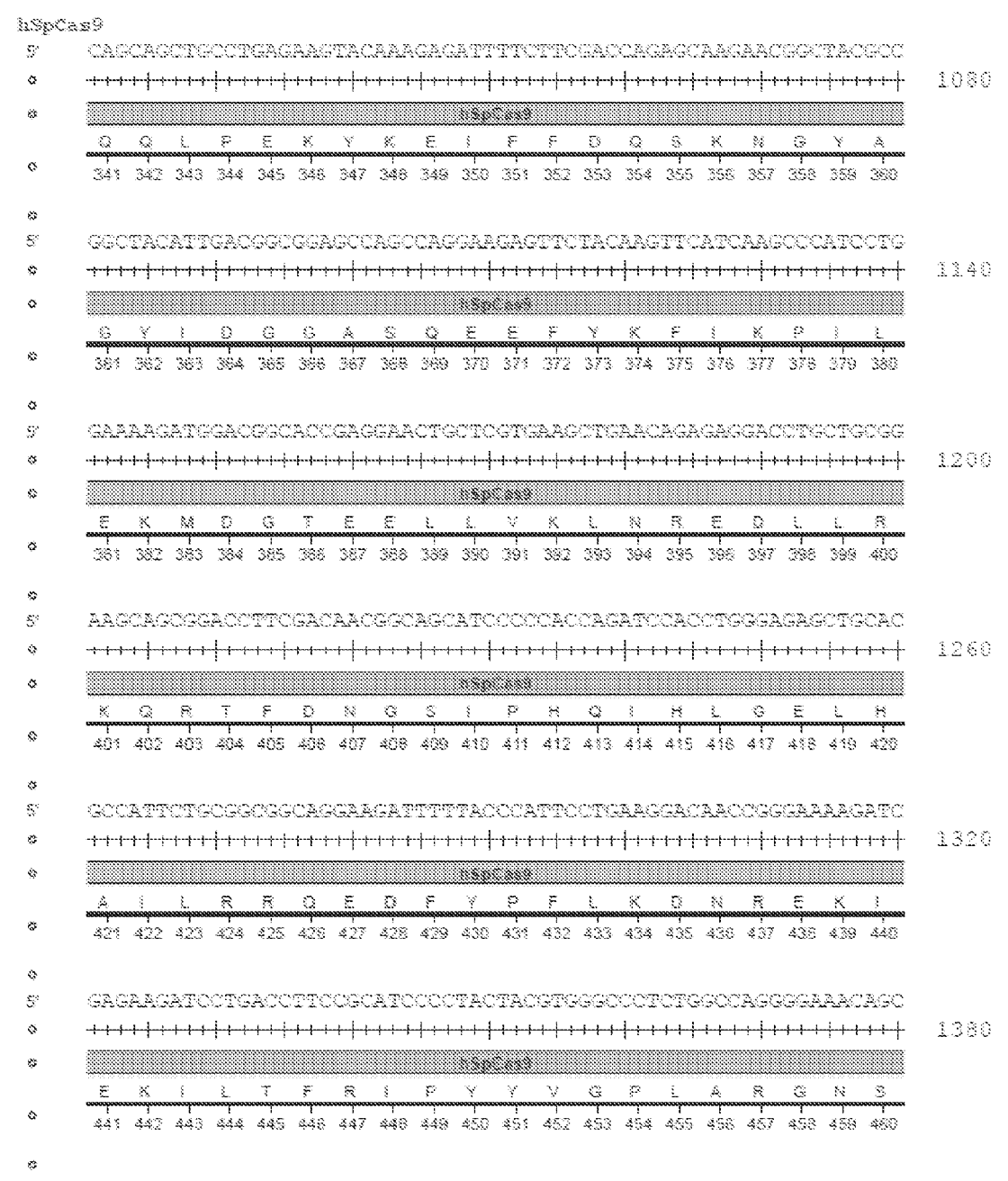
Figure 41F:
Figure 41G:
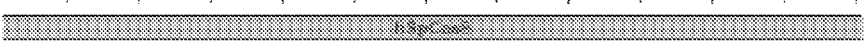
Figure 41J:
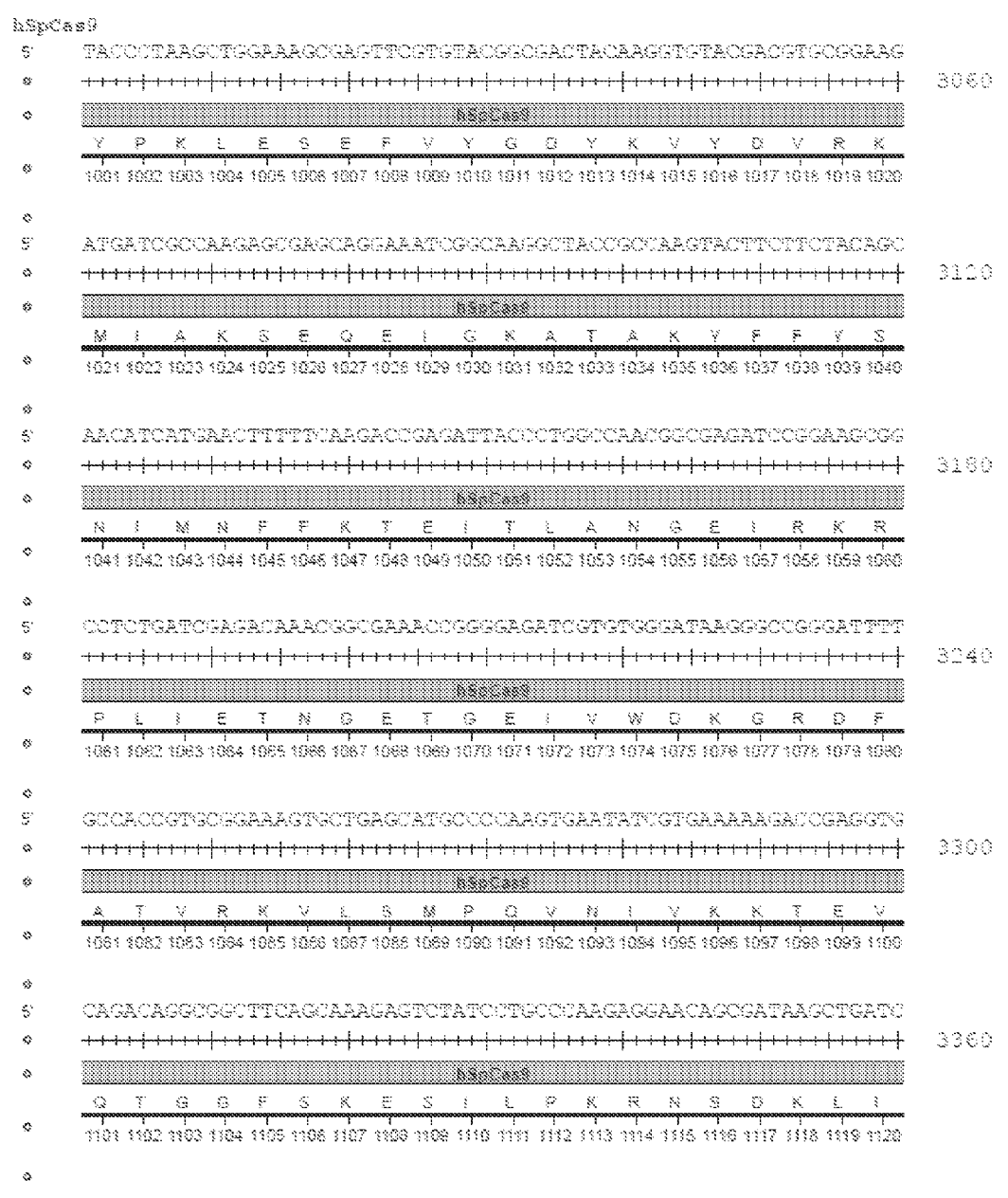
Figure 42:
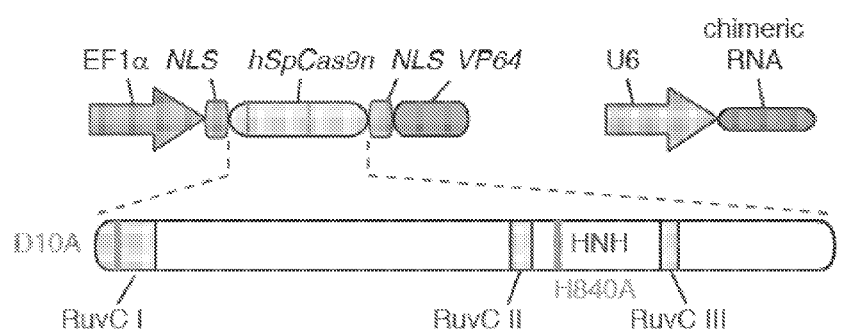
FIG. 42 shows a schematic construct in which the transcriptional activation domain (VP64) is fused to Cas9 with two mutations in the catalytic domains (D10 and H840).
Figure 43A:
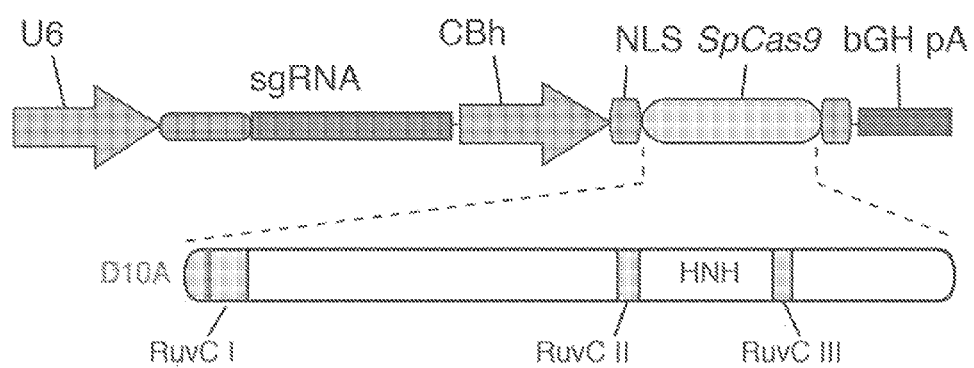
FIG. 43A-D shows genome editing via homologous recombination. (a) Schematic of SpCas9 nickase, with D10A mutation in the RuvC I catalytic domain. (b) Schematic representing homologous recombination (HR) at the human EMX1 locus using either sense or antisense single stranded oligonucleotides as repair templates. Red arrow above indicates sgRNA cleavage site; PCR primers for genotyping (Tables J and K) are indicated as arrows in right panel. (c) Sequence of region modified by HR. d, SURVEYOR assay for wildtype (wt) and nickase (D10A) SpCas9-mediated indels at the EMX1 target 1 locus (n=3) (SEQ ID NOS 505-507, 505, 508 and 507, respectively, in order of appearance). Arrows indicate positions of expected fragment sizes.
Figure 43B:
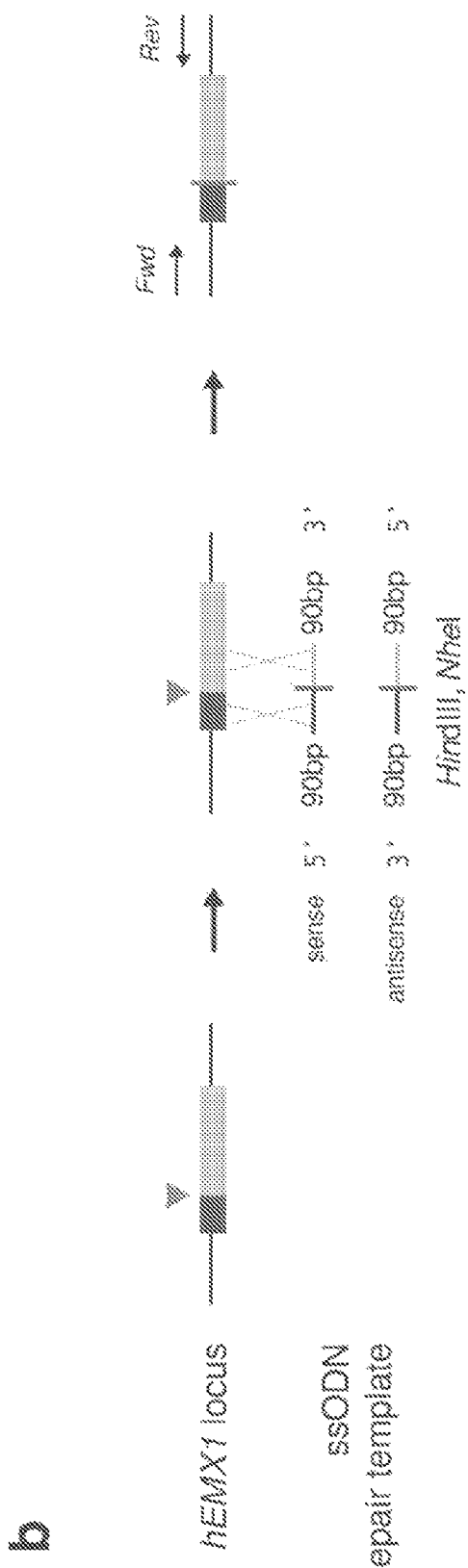
Figure 43C:
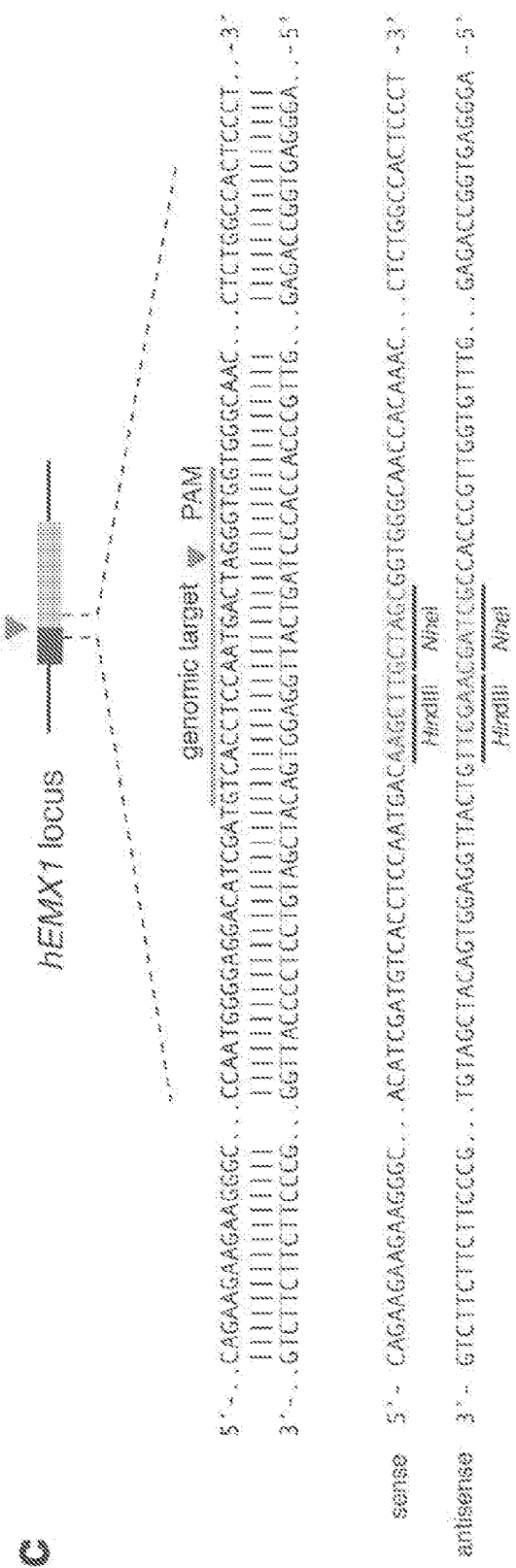
Figure 43D:
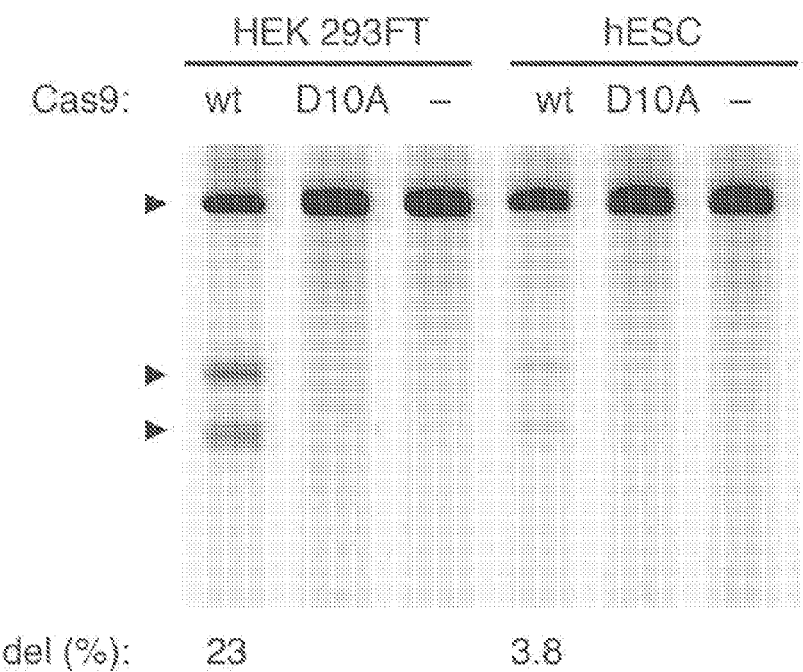

Applicants provide sequences showing where the mutation points are located within the SpCas9 gene (FIG. 41). Applicants also show that the nickases are still able to mediate homologous recombination (Assay indicated in FIG. 2). Furthermore, Applicants show that SpCas9 with these mutations (individually) do not induce double strand break (FIG. 47).

Furthermore, potential nicking mutation sites were chosen based on sequence homology between Cas9 orthologs (named original set below). The nickase mutant Cas9s were re-cloned to incorporate both N' and C'-NLS sequences as in Cong, L et al., Multiplex genome engineering using CRISPR/Cas systems, Science. 2013 Feb. 15; 339(6121):819-23. (sequences for NLS-E762A-NLS and >NLS-D986A-NLS listed below).

Nuclease and double-nicking activities for these potential nickases were tested in HEK 293FT cells as follows: co-transfection of 400 ng of nickase and 100 ng of U6-driven sgRNA (100 ng for one guide, or 50 ng each for a pair of sgRNAs) by Lipofectamine 2000 into ~200,000 cells. DNAs from transfected cells were collected for SURVEYOR analysis. Nickases do not result in indel mutations when co-transfected with a single sgRNA, but do when co-transfected with a pair of appropriately off-set sgRNAs. Based on data from the original D10A SpCas9 nickase, the pair of sgRNA chosen (A1/C1) for RuvC domain mutants have 0-bp offset and 5'-overhang for maximal cleavage.

| Original set: | Mutant domain | Functional? |
|---|---|---|
| Cbh-hSpCas9(D10A)-NLS | RuvCI | nickase activity |
| Cbh-hSpCas9(E762A)-NLS | RuvCII | |
| Cbh-hSpCas9(H840A)-NLS | HNH | no activity |
| Cbh-hSpCas9(N854A)-NLS | HNH | wt nuclease activity |
| Cbh-hSpCas9(N863A)-NLS | HNH | nickase activity |
| Cbh-hSpCas9(D986A)-NLS | RuvCIII | |

(SEQ ID NO: 196)
>NLS-E762A-NLS
ATGGCCCCAAAGAAGAAGCGGAAGGTCGGTATCCACGGAGTCCCAGCAG

CCGACAAGAAGTACAGCATCGGCCTGGACATCGGCACCAACTCTGTGGGC

TGGGCCGTGATCACCGACGAGTACAAGGTGCCCAGGAAGAAATTCAAGGT

GCTGGGCAACACCGACCGGCACAGCATCAAGAAGAACCTGATCGGAGCCC

TGCTGTTCGACAGCGGCGAAACAGCCGAGGCCACCCGGCTGAAGAGAACC

GCCAGAAGAAGATACACCAGACGGAAGAACCGGATCTGCTATCTGCAAGA

GATCTTCAGCAACGAGATGGCCAAGGTGGACGACAGCTTCTTCCACAGAC

TGGAAGAGTCCTTCCTGGTGGAAGAGGATAAGAAGCACGAGCGGCACCCC

ATCTTCGGCAACATCGTGGACGAGGTGGCCTACCACGAGAAGTACCCCAC

CATCTACCACCTGAGAAAGAAACTGGTGGACAGCACCGACAAGGCCGACC

TGCGGCTGATCTATCTGGCCCTGGCCCACATGATCAAGTTCCGGGGCCAT

TCCTGATCGAGGGCGACCTGAACCCCGACAACAGCGACGTGGACAAGCTG

TTCATCCAGCTGGTGCAGACCTACAACCAGCTGTTCGAGGAAAACCCCAT

CAACGCCAGCGGCGTGGACGCCAAGGCCATCCTGTCTGCCAGACTGAGCA

AGAGCAGACGGCTGGAAAATCTGATCGCCCAGCTGCCCGGCGAGAAGAAG

AATGGCCTGTTCGGAAACCTGATTGCCCTGAGCCTGGGCCTGACCCCCAA

CTTCAAGAGCAACTTCGACCTGGCCGAGGATGCCAAACTGCAGCTGAGCA

-continued

AGGACACCTACGACGACGACCTGGACAACCTGCTGGCCCAGATCGGCGAC
CAGTACGCCGACCTGTTTCTGGCCGCCAAGAACCTGTCCGACGCCATCCT
GCTGAGCGACATCCTGAGAGTGAACACCGAGATCACCAAGGCCCCCCTGA
GCGCCTCTATGATCAAGAGATACGACGAGCACCACCAGGACCTGACCCTG
CTGAAAGCTCTCGTGCGGCAGCAGCTGCCTGAGAAGTACAAAGAGATTTT
CTTCGACCAGAGCAAGAACGGCTACGCCGGCTACATTGACGGCGGAGCCA
GCCAGGAAGAGTTCTACAAGTTCATCAAGCCCATCCTGGAAAAGATGGAC
GGCACCGAGGAACTGCTCGTGAAGCTGAACAGAGAGGACCTGCTGCGGAA
GCAGCGGACCTTCGACAACGGCAGCATCCCCCACCAGATCCACCTGGGAG
AGCTGCACGCCATTCTGCGGCGGCAGGAAGATTTTTACCCATTCCTGAAG
GACAACCGGGAAAAGATCGAGAAGATCCTGACCTTCCGCATCCCCTACTA
CGTGGGCCCTCTGGCCAGGGGAAACAGCAGATTCGCCTGGATGACCAGAA
AGAGCGAGGAAACCATCACCCCCTGGAACTTCGAGGAAGTGGTGGACAAG
GGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACT
TCACCGTGTATAACGAGCTGACCAAAGTGAAATACGTGACCGAGGGAATG
AGAAAGCCCGCCTTCCTGAGCGGCGAGCAGAAAAAGGCCATCGTGGACCT
GCTGTTCAAGACCAACCGGAAAGTGACCGTGAAGCAGCTGAAAGAGGACT
ACTTCAAGAAAATCGAGTGCTTCGACTCCGTGGAAATCTCCGGCGTGGAA
GATCGGTTCAACGCCTCCCTGGGCACATACCACGATCTGCTGAAAATTAT
CAAGGACAAGGACTTCCTGGACAATGAGGAAAACGAGGACATTCTGGAAG
ATATCGTGCTGACCCTGACACTGTTTGAGGACAGAGAGATGATCGAGGAA
CGGCTGAAAACCTATGCCCACCTGTTCGACGACAAAGTGATGAAGGAGCT
GAAGCGGCGGAGATACACCGGCTGGGGCAGGCTGAGCCGGAAGCTGATCA
ACGGCATCCGGGACAAGCAGTCCGGCAAGACAATCCTGGATTTCCTGAAG
TCCGACGGCTTCGCCAACAGAAACTTCATGCAGCTGATCCACGACGACAG
CCTGACCTTTAAAGAGGACATCCAGAAAGCCCAGGTGTCCGGCCAGGGCG
ATAGCCTGCACGAGCACATTGCCAATCTGGCCGGCAGCCCCGCCATTAAG
AAGGGCATCCTGCAGACAGTGAAGGTGGTGGACGAGGTCGTGAAAGTGAT
GGGCCGGCACAAGCCCGAGAACATCGTGATCGccATGGCCAGAGAGAACC
AGACCACCCAGAAGGGACAGAAGAACAGCCGCGAGAGAATGAAGCGGATC
GAAGAGGGCATCAAAGAGCTGGGCAGCCAGATCCTGAAAGAACACCCCGT
GGAAAACACCCAGCTGCAGAACGAGAAGCTGTACCTGTACTACCTGCAGA
ATGGGCGGGATATGTACGTGGACCAGGAACTGGACATCAACCGGCTGTCC
GACTACGATGTGGACCATATCGTGCCTCAGAGCTTTCTGAAGGACGACTC
CATCGACAACAAGGTGCTGACCAGAAGCGACAAGAACCGGGGCAAGAGCG
ACAACGTGCCCTCCGAAGAGGTCGTGAAGAAGATGAAGAACTACTGGCGG
CAGCTGCTGAACGCCAAGCTGATTACCCAGAGAAAGTTCGACAATCTGAC
CAAGGCCGAGAGAGGCGGCCTGAGCGAACTGGATAAGGCCGGCTTCATCA
AGAGACAGCTGGTGGAAACCCGGCAGATCACAAAGCACGTGGCACAGATC

-continued

CTGGACTCCCGGATGAACACTAAGTACGACGAGAATGACAAGCTGATCCG
GGAAGTGAAAGTGATCACCCTGAAGTCCAAGCTGGTGTCCGATTTCCGGA
AGGATTTCCAGTTTTACAAAGTGCGCGAGATCAACAACTACCACCACGCC
CACGACGCCTACCTGAACGCCGTCGTGGGAACCGCCCTGATCAAAAAGTA
CCCTAAGCTGGAAAGCGAGTTCGTGTACGGCGACTACAAGGTGTACGACG
TGCGGAAGATGATCGCCAAGAGCGAGCAGGAAATCGGCAAGGCTACCGCC
AAGTACTTCTTCTACAGCAACATCATGAACTTTTTCAAGACCGAGATTAC
CCTGGCCAACGGCGAGATCCGGAAGCGGCCTCTGATCGAGACAAACGGCG
AAACCGGGGAGATCGTGTGGGATAAGGGCCGGGATTTTGCCACCGTGCGG
AAAGTGCTGAGCATGCCCCAAGTGAATATCGTGAAAAAGACCGAGGTGCA
GACAGGCGGCTTCAGCAAAGAGTCTATCCTGCCCAAGAGGAACAGCGATA
AGCTGATCGCCAGAAAGAAGGACTGGGACCCTAAGAAGTACGGCGGCTTC
GACAGCCCCACCGTGGCCTATTCTGTGCTGGTGGTGGCCAAAGTGGAAAA
GGGCAAGTCCAAGAAACTGAAGAGTGTGAAAGAGCTGCTGGGGATCACCA
TCATGGAAAGAAGCAGCTTCGAGAAGAATCCCATCGACTTTCTGGAAGCC
AAGGGCTACAAAGAAGTGAAAAAGGACCTGATCATCAAGCTGCCTAAGTA
CTCCCTGTTCGAGCTGGAAAACGGCCGGAAGAGAATGCTGGCCTCTGCCG
GCGAACTGCAGAAGGGAAACGAACTGGCCCTGCCCTCCAAATATGTGAAC
TTCCTGTACCTGGCCAGCCACTATGAGAAGCTGAAGGGCTCCCCCGAGGA
TAATGAGCAGAAACAGCTGTTTGTGGAACAGCACAAGGACTACCTGGACG
AGATCATCGAGCAGATCAGCGAGTTCTCCAAGAGAGTGATCCTGGCCGAC
GCTAATCTGGACAAAGTGCTGTCCGCCTAGAACAAGCACCGGGATAAGCC
CATCAGAGAGCAGGCCGAGAATATCATCCACCTGTTTACCCTGACCAATC
TGGGAGCCCCTGCCGCCTTCAAGTACTTTGACACCACCATCGACCGGAAG
AGGTACACCAGCACCAAAGAGGTGCTGGACGCCACCCTGATCCACCAGAG
CATCACCGGCCTGTACGAGACACGGATCGACCTGTCTCAGCTGGGAGGCG
ACAAAAGGCCGGCGGCCACGAAAAGGCCGGCCAGGCAAAAAAGAAAAAG
taa (SEQ ID NO: 197)
>NLS-D986A-NLS
ATGGCCCCAAAGAAGAAGCGGAAGGTCGGTATCCACGGAGTCCCAGCAG
CCGACAAGAAGTACAGCATCGGCCTGGACATCGGCACCAACTCTGTGGGC
TGGGCCGTGATCACCGACGAGTACAAGGTGCCCAGCAAGAAATTCAAGGT
GCTGGGCAACACCGACCGGCACAGCATCAAGAAGAACCTGATCGGAGCCC
TGCTGTTCGACAGCGGCGAAACAGCCGAGGCCACCCGGCTGAAGAGAACC
GCCAGAAGAAGATACACCAGACGGAAGAACCGGATCTGCTATCTGCAAGA
GATCTTCAGCAACGAGATGGCCAAGGTGGACGACAGCTTCTTCCACAGAC
TGGAAGAGTCCTTCCTGGTGGAAGAGGATAAGAAGCACGAGCGGCACCCC
ATCTTCGGCAACATCGTGGACGAGGTGGCCTACCACGAGAAGTACCCCAC
CATCTACCACCTGAGAAAGAAACTGGTGGACAGCACCGACAAGGCCGACC
TGCGGCTGATCTATCTGGCCCTGGCCCACATGATCAAGTTCCGGGGCCAC
TTCCTGATCGAGGGCGACCTGAACCCCGACAACAGCGACGTGGACAAGCT -continued

GTTCATCCAGCTGGTGCAGACCTACAACCAGCTGTTCGAGGAAAACCCCA

TCAACGCCAGCGGCGTGGACGCCAAGGCCATCCTGTCTGCCAGACTGAGC

AAGAGCAGACGGCTGGAAAATCTGATCGCCCAGCTGCCCGGCGAGAAGAA

GAATGGCCTGTTCGGAAACCTGATTGCCCTGAGCCTGGGCCTGACCCCCA

ACTTCAAGAGGAACTTCGACCTGGCCGAGGATGCCAAACTGCAGCTGAGC

AAGGACACCTACGACGACGACCTGGACAACCTGCTGGCCCAGATCGGCGA

CCAGTACGCCGACCTGTTTCTGGCCGCCAAGAACCTGTCCGACGCCATCC

TGCTGAGCGACATCCTGAGAGTGAACACCGAGATCACCAAGGCCCCCCTG

AGCGCCTCTATGATCAAGAGATACGACGAGCACCACCAGGACCTGACCCT

GCTGAAAGCTCTCGTGCGGCAGCAGCTGCCTGAGAAGTACAAAGAGATTT

TCTTCGACCAGAGCAAGAACGGCTACGCCGGCTACATTGACGGCGGAGCC

AGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGA

AGCAGCGGACCTTCGACAACGGCAGCATCCCCCACCAGATCCACCTGGGA

GAGCTGCACGCCATTCTGCGGCGGCAGGAAGATTTTTACCCATTCCTGAA

GGACAACCGGGAAAAGATCGAGAAGATCCTGACCTTCCGCATCCCCTACT

ACGTGGGCCCTCTGGCCAGGGGAAACAGCAGATTCGCCTGGATGACCAGA

AAGAGCGAGGAAACCATCACCCCCTGGAACTTCGAGGAAGTGGTGGACAA

GGGCGCTTCCGCCCAGAGCTTCATCGAGCGGATGACCAACTTCGATAAGA

ACCTGCCCAACGAGAAGGTGCTGCCCAAGCACAGCCTGCTGTACGAGTAC

TTCACCGTGTATAACGAGCTGACCAAAGTGAAATACGTGACCGAGGGAAT

GAGAAAGCCCGCCTTCCTGAGCGGCGAGCAGAAAAAGGCCATCGTGGACC

TGCTGTTCAAGACCAACCGGAAAGTGACCGTGAAGCACCTGAAAGAGGAC

TACTTCAAGAAAATCGAGTGCTTCGACTCCGTGGAAATCTCCGGCGTGGA

AGATCGGTTCAACGCCTCCCTGGGCACATACCACGATCTGCTGAAAATTA

TCAAGGACAAGGACTTCCTGGACAATGAGGAAAACGAGGACATTCTGGAA

GATATCGTGCTGACCCTGACACTGTTTGAGGACAGAGAGATGATCGAGGA

ACGGCTGAAAACCTATGCCCACCTGTTCGACGACAAAGTGATGAAGCAGC

TGAAGCGGCGGAGATACACCGGCTGGGGCAGGCTGAGCCGGAAGCTGATC

AACGGCATCCGGGACAAGCAGTCCGGCAAGACAATCCTGGATTTCCTGAA

GTCCGACGGCTTCGCCAACAGAAACTTCATGCAGCTGATCCACGACGACA

GCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAA

GAAGGGCATCCTGCAGACAGTGAAGGTGGTGGACGAGCTCGTGAAAGTGA

TGGGCCGGCACAAGCCCGAGAACATCGTGATCGAAATGGCCAGAGAGAAC

CAGACCACCCAGAAGGGACAGAAGAACAGCCGCGAGAGAATGAAGCGGAT

CGAAGAGGGCATCAAAGAGCTGGGCAGCCAGATCCTGAAAGAACACCCCG

TGGAAAACACCCAGCTGCAGAACGAGAAGCTGTACCTGTACTACCTGCAG

AATGGGCGGGATATGTACGTGGACCAGGAACTGGACATCAACCGGCTGTC

CGACTACGATGTGGACCATATCGTGCCTCAGAGCTTTCTGAAGGACGACT

CCATCGACAACAAGGTGCTGACCAGAAGCGACAAGAACCGGGGCAAGAGC

GACAACGTGCCCTCCGAAGAGGTCGTGAAGAAGATGAAGAACTACTGGCG

GCAGCTGCTGAACGCCAAGCTGATTACCCAGAGAAAGTTCGACAATCTGA

CCAAGGCCGAGAGAGGCGGCCTGAGCGAACTGGATAAGGCCGGCTTCATC

AAGAGACAGCTGGTGGAAACCCGGCAGATCACAAAGCACGTGGCACAGAT

CCTGGACTCCCGGATGAACACTAAGTACGACGAGAATGACAAGCTGATCC

GGGAAGGTGAAAGTGATCACCCTGAAGTCCAAGCTGGTGTCCGATTTCCG

GAAGGATTTCCAGTTTTACAAAGTGCGCGAGATCAACAACTACCACCACG

CCCACGcCGCCTACCTGAACGCCGTCGTGGGAACCGCCCTGATCAAAAAG

TACCCTAAGCTGGAAAGCGAGTTCGTGTACGGCGACTACAAGGTGTACGA

CGTGCGGAAGATGATCGCCAAGAGCGAGCAGGAAATCGGCAAGGCTACCG

CCAAGTACTTCTTCTACAGCAACATCATGAACTTTTTCAAGACCGAGATT

ACCCTGGCCAACGGCGAGATCCGGAAGCGGCCTCTGATCGAGACAAACGG

CGAAACCGGGGAGATCGTGTGGGATAAGGGCCGGGATTTTGCCACCGTGC

GGAAAGTGCTGAGCATGCCCCAAGTGAATATCGTGAAAAAGACCGAGGTG

CAGACAGGCGGCTTCAGCAAAGAGTCTATCCTGCCCAAGAGGAACAGCGA

TAAGCTGATCGCCAGAAAGAAGGACTGGGACCCTAAGAAGTACGGCGGCT

TCGACAGCCCCACCGTGGCCTATTCTGTGCTGGTGGTGGCCAAAGTGGAA

AAGGGCAAGTCCAAGAAACTGAAGAGTGTGAAAGAGCTGCTGGGGATCAC

CATCATGGAAAGAAGCAGCTTCGAGAAGAATCCCATCGACTTTCTGGAAG

CCAAGGGCTACAAAGAAGTGAAAAAGGACCTGATCATCAAGCTGCCTAAG

TACTCCCTGTTCGAGCTGGAAAACGGCCGGAAGAGAATGCTGGCCTCTGC

CGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAG

GATAATGAGCAGAAACAGCTGTTTGTGGAACAGCACAAGCACTACCTGGA

CGAGATCATCGAGCAGATCAGCGAGTTCTCCAAGAGAGTGATCCTGGCCG

ACGCTAATCTGGACAAAGTGCTGTCCGCCTACAACAAGCACCGGGATAAG

CCCATCAGAGAGCAGGCCGAGAATATCATCCACCTGTTTACCCTGACCAA

TCTGGGAGCCCCTGCCGCCTTCAAGTACTTTGACACCACCATCGACCGGA

AGAGGTACACCAGCACCAAAGAGGTGCTGGACGCGACCCTGATCCACCAG

AGCATCACCGGCCTGTACGAGACACGGATCGACCTGTCTCAGCTGGGAGG

CGACAAAAGGCCGGCGGCCACGAAAAAGGCCGGCCAGGCAAAAAAGAAAA

AG

Example 9

Supplement to DNA Targeting Specificity of the RNA-Guided Cas9 Nuclease

Cell Culture and Transfection

Human embryonic kidney (HEK) cell line 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 µg/mL streptomycin at 37° C. with 5% CO2 incubation.

293FT cells were seeded either onto 6-well plates, 24-well plates, or 96-well plates (Corning) 24 hours prior to transfection. Cells were transfected using Lipofectamine 2000 (Life Technologies) at 80-90% confluence following the manufacturer's recommended protocol. For each well of a 6-well plate, a total of 1 ug of Cas9+sgRNA plasmid was used. For each well of a 24-well plate, a total of 500 ng Cas9+sgRNA plasmid was used unless otherwise indicated. For each well of a 96-well plate, 65 ng of Cas9 plasmid was used at a 1:1 molar ratio to the U6-sgRNA PCR product.

Human embryonic stem cell line HUES9 (Harvard Stem Cell Institute core) was maintained in feeder-free conditions on GelTrex (Life Technologies) in mTesR medium (Stemcell Technologies) supplemented with 100 ug/ml Normocin (InvivoGen). HUES9 cells were transfected with Amaxa P3 Primary Cell 4-D Nucleofector Kit (Lonza) following the manufacturer's protocol.

SURVEYOR Nuclease Assay for Genome Modification

293FT cells were transfected with plasmid DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes and 98° C. for 10 minutes.

The genomic region flanking the CRISPR target site for each gene was PCR amplified (primers listed in Tables J and K), and products were purified using QiaQuick Spin Column (Qiagen) following the manufacturer's protocol. 400 ng total of the purified PCR products were mixed with 2 μl 10× Taq DNA Polymerase PCR buffer (Enzymatics) and ultrapure water to a final volume of 20 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities.

Northern Blot Analysis of tracrRNA Expression in Human Cells

Northern blots were performed as previously described 1. Briefly, RNAs were heated to 95° C. for 5 min before loading on 8% denaturing polyacrylamide gels (SequaGel, National Diagnostics). Afterwards, RNA was transferred to a pre-hybridized Hybond N+ membrane (GE Healthcare) and crosslinked with Stratagene UV Crosslinker (Stratagene). Probes were labeled with [gamma-32P] ATP (Perkin Elmer) with T4 polynucleotide kinase (New England Biolabs). After washing, membrane was exposed to phosphor screen for one hour and scanned with phosphorimager (Typhoon).

Bisulfite Sequencing to Assess DNA Methylation Status

HEK 293FT cells were transfected with Cas9 as described above. Genomic DNA was isolated with the DNeasy Blood & Tissue Kit (Qiagen) and bisulfite converted with EZ DNA Methylation-Lightning Kit (Zymo Research). Bisulfite PCR was conducted using KAPA2G Robust HotStart DNA Polymerase (KAPA Biosystems) with primers designed using the Bisulfite Primer Seeker (Zymo Research, Tables J and K). Resulting PCR amplicons were gel-purified, digested with EcoRI and HindIII, and ligated into a pUC19 backbone prior to transformation. Individual clones were then Sanger sequenced to assess DNA methylation status.

In Vitro Transcription and Cleavage Assay

HEK 293FT cells were transfected with Cas9 as described above. Whole cell lysates were then prepared with a lysis buffer (20 mM HEPES, 100 mM KCl, 5 mM MgCl2, 1 mM DTT, 5% glycerol, 0.1% Triton X-100) supplemented with Protease Inhibitor Cocktail (Roche). T7-driven sgRNA was in vitro transcribed using custom oligos (Example 10) and HiScribe T7 In Vitro Transcription Kit (NEB), following the manufacturer's recommended protocol. To prepare methylated target sites, pUC19 plasmid was methylated by M.SssI and then linearized by NheI. The in vitro cleavage assay was performed as follows: for a 20 uL cleavage reaction, 10 uL of cell lysate with incubated with 2 uL cleavage buffer (100 mM HEPES, 500 mM KCl, 25 mM MgCl2, 5 mM DTT, 25% glycerol), the in vitro transcribed RNA, and 300 ng pUC19 plasmid DNA.

Deep Sequencing to Assess Targeting Specificity

HEK 293FT cells plated in 96-well plates were transfected with Cas9 plasmid DNA and single guide RNA (sgRNA) PCR cassette 72 hours prior to genomic DNA extraction (FIG. 72). The genomic region flanking the CRISPR target site for each gene was amplified (FIG. 74, (Example 10) by a fusion PCR method to attach the Illumina P5 adapters as well as unique sample-specific barcodes to the target amplicons (schematic described in FIG. 73). PCR products were purified using EconoSpin 96-well Filter Plates (Epoch Life Sciences) following the manufacturer's recommended protocol.

Barcoded and purified DNA samples were quantified by Quant-iT PicoGreen dsDNA Assay Kit or Qubit 2.0 Fluorometer (Life Technologies) and pooled in an equimolar ratio. Sequencing libraries were then deep sequenced with the Illumina MiSeq Personal Sequencer (Life Technologies).

Sequencing Data Analysis and Indel Detection

MiSeq reads were filtered by requiring an average Phred quality (Q score) of at least 23, as well as perfect sequence matches to barcodes and amplicon forward primers. Reads from on- and off-target loci were analyzed by first performing Smith-Waterman alignments against amplicon sequences that included 50 nucleotides upstream and downstream of the target site (a total of 120 bp). Alignments, meanwhile, were analyzed for indels from 5 nucleotides upstream to 5 nucleotides downstream of the target site (a total of 30 bp). Analyzed target regions were discarded if part of their alignment fell outside the MiSeq read itself, or if matched base-pairs comprised less than 85% of their total length.

Negative controls for each sample provided a gauge for the inclusion or exclusion of indels as putative cutting events. For each sample, an indel was counted only if its quality score exceeded $\mu-\sigma$, where $\mu$ was the mean quality-score of the negative control corresponding to that sample and $\sigma$ was the standard deviation of same. This yielded whole target-region indel rates for both negative controls and their corresponding samples. Using the negative control's per-target-region-per-read error rate, q, the sample's observed indel count n, and its read-count R, a maximum-likelihood estimate for the fraction of reads having target-regions with true-indels, p, was derived by applying a binomial error model, as follows.

Letting the (unknown) number of reads in a sample having target regions incorrectly counted as having at least 1 indel be E, we can write (without making any assumptions about the number of true indels)

$$\text{Prob}(E \mid p) = \binom{R(1-p)}{E} q^E (1-q)^{R(1-p)-E}$$

since R(1−p) is the number of reads having target-regions with no true indels. Meanwhile, because the number of reads observed to have indels is n, n=E+Rp, in other words the number of reads having target-regions with errors but no true indels plus the number of reads whose target-regions correctly have indels. We can then re-write the above $$\text{Prob}(E \mid p) = \text{Prob}(n = E + Rp \mid p) = \binom{R(1-p)}{n-Rp} q^{n-Rp} (1-q)^{R-n}$$

Taking all values of the frequency of target-regions with true-indels p to be equally probable a priori, $\text{Prob}(n/p) \propto \text{Prob}(p/n)$. The maximum-likelihood estimate (MLE) for the frequency of target regions with true-indels was therefore set as the value of p that maximized Prob(n/p). This was evaluated numerically.

In order to place error bounds on the true-indel read frequencies in the sequencing libraries themselves, Wilson score intervals (2) were calculated for each sample, given the MLE-estimate for true-indel target-regions, Rp, and the number of reads R. Explicitly, the lower bound l and upper bound u were calculated as $$l = \left(Rp + \frac{z^2}{2} - z\sqrt{Rp(1-p) + z^2/4}\right) \Big/ (R + z^2)$$

$$u = \left(Rp + \frac{z^2}{2} + z\sqrt{Rp(1-p) + z^2/4}\right) \Big/ (R + z^2)$$

where z, the standard score for the confidence required in normal distribution of variance 1, was set to 1.96, meaning a confidence of 95%.

qRT-PCR Analysis of Relative Cas9 and sgRNA Expression

FT cells plated in 24-well plates were transfected as described above. 72 hours post-transfection, total RNA was harvested with miRNeasy Micro Kit (Qiagen). Reverse-strand synthesis for sgRNAs was performed with qScript Flex cDNA kit (VWR) and custom first-strand synthesis primers (Tables J and K). qPCR analysis was performed with Fast SYBR Green Master Mix (Life Technologies) and custom primers (Tables J and K), using GAPDH as an endogenous control. Relative quantification was calculated by the ΔΔCT method.

TABLE I

Target site sequences.

| Target site ID | genomic target | Target site sequence (5' to 3') | PAM | strand |
|---|---|---|---|---|
| 1 | EMXI | GTCACCTCCAATGACTAGGG (SEQ ID NO: 321) | TGG | + |
| 2 | EMXI | GACATCGATGTCCTCCCCAT (SEQ ID NO: 198) | TGG | − |
| 3 | EMXI | GAGTCCGAGCAGAAGAAGAA (SEQ ID NO: 199) | GGG | + |
| 6 | EMXI | GCGCCACCGGTTGATGTGAT (SEQ ID NO: 200) | GGG | − |

TABLE I-continued

Target site sequences.

| Target site ID | genomic target | Target site sequence (5' to 3') | PAM | strand |
|---|---|---|---|---|
| 10 | EMXI | GGGGCACAGATGAGAAACTC (SEQ ID NO: 201) | AGG | − |
| 11 | EMXI | GTACAAACGGCAGAAGCTGG (SEQ ID NO: 202) | AGG | + |
| 12 | EMXI | GGCAGAAGCTGGAGGAGGAA (SEQ ID NO: 203) | GGG | + |
| 13 | EMXI | GGAGCCCTTCTTCTTCTGCT (SEQ ID NO: 204) | CGG | − |
| 14 | EMXI | GGGCAACCACAAACCCACGA (SEQ ID NO: 205) | GGG | + |
| 15 | EMXI | GCTCCCATCACATCAACCGG (SEQ ID NO: 206) | TGG | + |
| 16 | EMXI | GTGGCGCATTGCCACGAAGC (SEQ ID NO: 207) | AGG | + |
| 17 | EMXI | GGCAGAGTGCTGCTTGCTGC (SEQ ID NO: 208) | TGG | + |
| 18 | EMXI | GCCCCTGCGTGGGCCCAAGC (SEQ ID NO: 209) | TGG | + |
| 19 | EMXI | GAGTGGCCAGAGTCCAGCTT (SEQ ID NO: 210) | GGG | − |
| 20 | EMXI | GGCCTCCCCAAAGCCTGGCC (SEQ ID NO: 211) | AGG | − |
| 4 | PVALB | GGGGCCGAGATTGGGTGTTC (SEQ ID NO: 212) | AGG | + |
| 5 | PVALB | GTGGCGAGAGGGGCCGAGAT (SEQ ID NO: 213) | TGG | + |
| 1 | SERPINB5 | GAGTGCCGCCGAGGCGGGGC (SEQ ID NO: 214) | GGG | + |
| 2 | SERPINB5 | GGAGTGCCGCCGAGGCGGGG (SEQ ID NO: 215) | CGG | + |
| 3 | SERPINB5 | GGAGAGGGAGTGCCGCCGAGG (SEQ ID NO: 216) | CGG | + |

Tested target sites for *S. pyogenes* type II CRISPR system with the requisite PAM.
Cells were transfected with Cas9 and either crRNA-tracrRNA or chimeric sgRNA for each target.

Table J|Primer sequences
SURVEYOR Assay

TABLE J

Primer sequences

SURVEYOR assay

| primer name | genomic target | primer sequence (5' to 3') |
|---|---|---|
| Sp-EMX1-F1 | EMX1 | AAAACCACCCTTCTCTCTGGC (SEQ ID NO: 36) |
| Sp-EMX1-R1 | EMX1 | GGAGATTGGAGACACGGAGAG (SEQ ID NO: 37) |
| Sp-EMX1-F2 | EMX1 | CCATCCCCTTCTGTGAATGT (SEQ ID NO: 217) |
| Sp-EMX1-R2 | EMX1 | GGAGATTGGAGACACGGAGA (SEQ ID NO: 218) |
| Sp-PVALB-F | PVALB | CTGGAAAGCCAATGCCTGAC (SEQ ID NO: 38) |
| Sp-PVALB-R | PVALB | GGCAGCAAACTCCTTGTCCT (SEQ ID NO: 39) |

| primer name | primer sequence (5' to 3') | |
|---|---|---|
| qRT-PCR for Cas9 and sgRNA expression | | |
| sgRNA reverse- | AAGCACCGACTCGGTGCCAC (SEQ ID NO: 219) | |

TABLE J-continued

Primer sequences

| strand synthesis | |
|---|---|
| EMX1.1 sgRNA qPCR F | TCACCTCCAATGACTAGGGG (SEQ ID NO: 220) |
| EMX1.1 sgRNA qPCR R | CAAGTTGATAACGGACTAGCCT (SEQ ID NO: 221) |
| EMX1.3 sgRNA qPCR F | AGTCCGAGCAGAAGAAGAAGTTT (SEQ ID NO: 222) |
| EMX1.3 sgRNA qPCR R | TTTCAAGTTGATAACGGACTAGCCT (SEQ ID NO: 223) |
| Cas9 qPCR F | AAACAGCAGATTCGCCTGGA (SEQ ID NO: 224) |
| Cas9 qPCR R | TCATCCGCTCGATGAAGCTC (SEQ ID NO: 225) |
| GAPDH qPCR F | TCCAAAATCAAGTGGGGCGA (SEQ ID NO: 226) |
| GAPDH qPCR R | TGATGACCCTTTTGGCTCCC (SEQ ID NO: 227) |

Bisulfite PCR and sequencing

| Bisulfite PCR F (SERPINB5 locus) | GAGGAATTCTTTTTTTGTTYGAATATGTTGGAGGTTT TTTGGAAG (SEQ ID NO: 228) |
|---|---|
| Bisulfite PCR R (SERPINB5 locus) | GAGAAGCTTAAATAAAAAACRACAATACTCAACCCAA CAACC (SEQ ID NO: 229) |
| pUC19 sequencing | CAGGAAACAGCTATGAC (SEQ ID NO: 230) |

TABLE L

Target sites with alternate PAMs for testing PAM specificity of Cas9. All target sites for PAM specificity testing are found within the human EMX1 locus.

| Target site sequence (5' to 3') | PAM |
|---|---|
| AGGCCCCAGTGGCTGCTCT (SEQ ID NO: 236) | NAA |
| ACATCAACCGGTGGCGCAT (SEQ ID NO: 237) | NAT |
| AAGGTGTGGTTCCAGAACC (SEQ ID NO: 238) | NAC |
| CCATCACATCAACCGGTGG (SEQ ID NO: 239) | NAG |
| AAACGGCAGAAGCTGGAGG (SEQ ID NO: 240) | NTA |
| GGCAGAAGCTGGAGGAGGA (SEQ ID NO: 241) | NTT |
| GGTGTGGTTCCAGAACCGG (SEQ ID NO: 242) | NTC |
| AACCGGAGGACAAAGTACA (SEQ ID NO: 243) | NTG |
| TTCCAGAACCGGAGGACAA (SEQ ID NO: 244) | NCA |
| GTGTGGTTCCAGAACCGGA (SEQ ID NO: 245) | NCT |
| TCCAGAACCGGAGGACAAA (SEQ ID NO: 246) | NCC |
| CAGAAGCTGGAGGAGGAAG (SEQ ID NO: 247) | NCG |
| CATCAACCGGTGGCGCATT (SEQ ID NO: 248) | NGA |
| GCAGAAGCTGGAGGAGGAA (SEQ ID NO: 249) | NGT |
| CCTCCCTCCCTGGCCCAGG (SEQ ID NO: 250) | NGC |
| TCATCTGTGCCCCTCCCTC (SEQ ID NO: 251) | NAA |
| GGGAGGACATCGATGTCAC (SEQ ID NO: 252) | NAT |

TABLE K

Sequences for primers to test sgRNA architecture. Primers hybridize to the reverse strand of the U6 promoter unless otherwise indicated. The U6 priming site is in italics, the guide sequence is indicated as a stretch of Ns, the direct repeat sequence is highlighted in bold, and the tracrRNA sequence underlined. The secondary structure of each sgRNA architecture is shown in FIG. 43.

| primer name | primer sequence (5' to 3') |
|---|---|
| U6-Forward | GCCTCTAGA*GGGTACCTGAGGGCCTATTTCCCATGATTCC* (SEQ ID NO: 231) |
| I: sgRNA(DR + 12, tracrRNA + 85) | ACCTCTAGAAAAAAAGCACCGACTCGGTGCCACTTTTTCAAGT TGATAACGGACTAGCCTTATTTTAACTTGCTATTTCTAGCTCT AAAACNNNNNNNNNNNNNNNNNNNN*GGTGTTTCGTCCTTTCC ACAAG* (SEQ ID NO: 232) |
| II: sgRNA(DR + 12, tracrRNA + 85) mut2 | ACCTCTAGAAAAAAAGCACCGACTCGGTGCCACTTTTTCAAGT TGATAACGGACTAGCCTTATATTAACTTGCTATTTCTAGCTCT AATACNNNNNNNNNNNNNNNNNNNN*GGTGTTTCGTCCTTTCCA CAAG* (SEQ ID NO: 233) |
| III: sgRNA(DR + 22, tracrRNA + 85) | ACCTCTAGAAAAAAAGCACCGACTCGGTGCCACTTTTTCAAGT TGATAACGGACTAGCCTTATTTTAACTTGCTATGCTGTTTTGTT TCCAAAACAGCATAGCTCTAAAACNNNNNNNNNNNNNNNNN NNN*GGTGTTTCGTCCTTTCCACAAG* (SEQ ID NO: 234) |
| IV: sgRNA(DR + 22, tracrRNA + 85) mut4 | ACCTCTAGAAAAAAAGCACCGACTCGGTGCCACTTTTTCAAGT TGATAACGGACTAGCCTTATATTAACTTGCTATGCTGTATTGT TCCAATACAGCATAGCTCTAATACNNNNNNNNNNNNNNNNN NNN*GGTGTTTCGTCCTTTCCACAAG* (SEQ ID NO: 235) |

TABLE L-continued

Target sites with alternate PAMs for testing PAM specificity of Cas9. All target sites for PAM specificity testing are found within the human EMX1 locus.

| Target site sequence (5' to 3') | PAM |
|---|---|
| CAAACGGCAGAAGCTGGAG (SEQ ID NO: 253) | NAC |
| GGGTGGGCAACCACAAACC (SEQ ID NO: 254) | NAG |
| GGTGGGCAACCACAAACCC (SEQ ID NO: 255) | NTA |
| GGCTCCCATCACATCAACC (SEQ ID NO: 256) | NTT |
| GAAGGGCCTGAGTCCGAGC (SEQ ID NO: 257) | NTC |
| CAACCGGTGGCGCATTGCC (SEQ ID NO: 258) | NTG |
| AGGAGGAAGGGCCTGAGTC (SEQ ID NO: 259) | NCA |
| AGCTGGAGGAGGAAGGGCC (SEQ ID NO: 260) | NCT |
| GCATTGCCACGAAGCAGGC (SEQ ID NO: 261) | NCC |
| ATTGCCACGAAGCAGGCCA (SEQ ID NO: 262) | NCG |
| AGAACCGGAGGACAAAGTA (SEQ ID NO: 263) | NGA |
| TCAACCGGTGGCGCATTGC (SEQ ID NO: 264) | NGT |
| GAAGCTGGAGGAGGAAGGG (SEQ ID NO: 265) | NGC |

Example 10

Supplementary Sequences

All sequences are in the 5' to 3' direction. For U6 transcription, the string of underlined Ts serve as the transcriptional terminator.

>U6-short tracrRNA (*Streptococcus pyogenes* SF370)

(SEQ. ID NO: 40)
gagggcctatttcccatgattccttcatatttgcatatacgatacaagge
tgttagagagataattggaattaatttgactgtaaacacaaagatattag
tacaaaatacgtgacgtagaaagtaataatttcttgggtagtttgcagtt
ttaaaattatgttttaaaatggactatcatatgcttaccgtaacttgaaa
gtatttcgatttcttggctttatatatcttgtggaaaggacgaaacaccG
GAACCATTCAAAACAGCATAGCAAGTTAAAATAAGGCTAGTCCGTTATCA
ACTTGAAAAAGTGGCACCGAGTCGGTGC<u>TTTTTTT</u>
(tracrRNA sequence in bold)

>U6-DR-guide sequence-DR (*Streptococcus pyogenes* SF370)

(SEQ ID NO: 54)
gagggcctatttcccatgattccttcatatttgcatatacgatacaaggc
tgttagagagataattggaataatttgactgtaaacacaaagatattagt
acaaaatacgtgacgtagaaagtaataatttcttgggtagtttgcagttt
taaaattatgttttaaaatggactatcatatgcttaccgtaacttgaaag
tatttcgatttcttggctttatatatcttgtggaaaggacgaaacaccgg
gttttagagctatgctgttttgaatggtcccaaaacNNNNNNNNNNNNNNN
NNNNNNNNNNNNNNNNNgttttagagctatgctgttttgaatggtcccaaa
ac<u>TTTTTTT</u>

(direct repeat sequence is highlighted in gray and the guide sequence is in bold Ns)

>sgRNA containing +48 tracrRNA (*Streptococcus pyogenes* SF370)

(SEQ ID NO: 55)
gagggcctatttcccatgattccttcatatttgcatatacgatacaaggc
tgttagagagataattggaattaatttgactgtaaacacaaagatattag
tacaaaatacgtgacgtagaaagtaataatttcttgggtagtttgcagtt
ttaaaattatgttttaaaatggactatcatatgcttacccgtaacttgaa
agtatttcgatttcttggctttatatatcttgtggaaaggacgaaacacc
NNNNNNNNNNNNNNNNNNNNgttttagagctagaaatagcaagttaaaata
aggctagtccg<u>TTTTTTT</u>

(guide sequence is in bold Ns and the tracrRNA fragment is in bold)

>sgRNA containing +54 tracrRNA (*Streptococcus pyogenes* SF370)

(SEQ ID NO: 56)
gagggcctatttcccatgattccttcatatttgcatatacgatacaaggc
tgttagagagataattggaattaatttgactgtaaacacaaagatattag
tacaaaatacgtgacgtagaaagtaataatttcttgggtagtttgcagtt
ttaaaattatgttttaaaatggactatcatatgcttaccgtaacttgaaa
gtatttcgatttcttggctttatatatcttgtggaaaggacgaaacaccN
NNNNNNNNNNNNNNNNNNNgttttagagctagaaatagcaagttaaaataa
taaggctagtccgttatca<u>TTTTTTTT</u>

(guide sequence is in bold Ns and the tracrRNA fragment is in bold)

>sgRNA containing +67 tracrRNA (Streptococcus pyogenes SF370)

(SEQ ID NO: 57)

gagggcctatttcccatgattccttcatatttgcatatacgatacaaggc
tgttagagagataattggaattaatttgactgtaaacacaaagatattag
tacaaaatacgtgacgtagaaagtaataatttcttgggtagtttgcagtt
ttaaaattatgttttaaaatggactatcatatgcttaccgtaacttgaaa
gtatttcgatttcttggctttatatatcttgtggaaaggacgaaacacc**N
NNNNNNNNNNNNNNNNNNNgttttagagctagaaatagcaagttaaaata
aggctagtccgttatcaacttgaaaaagtgTTTTTTT (guide sequence is in bold Ns and the tracrRNA fragment is in bold**)

(guide sequence is in bold Ns and the tracrRNA fragment is in bold)

>sgRNA containing +85 tracrRNA (Streptococcus pyogenes SF370)

(SEQ ID NO: 58)

gagggcctatttcccatgattccttcatatttgcatatacgatacaaggc
tgttagagagataatggaattaatttgactgtaaacacaaagatattagt
acaaaatacgtgacgtagaaagtaataatttcttgggtagtttgcagttt
taaaattatgttttaaaatggacctatcatatgcttaccgtaacttgaaa
gtatttcgatttcttggctttatatatcttgtggaaaggacgaaacacc**N
NNNNNNNNNNNNNNNNNNNgttttagagctagaaatagcaagttaaaat
aaggctagtccgttatcaacttgaaaaagtggcaccgagtcggtgc**TTTT
TTT (guide sequence is in bold Ns and the tracrRNA fragment is in bold)

(guide sequence is in bold Ns and the tracrRNA fragment is in bold)

>CBh-NLS-SpCas9-NLS (SEQ ID NO: 59)
CGTTACATAACTTACGGTAAATGGCCCGCCTGGCTGACCGCCCAACGACC
CCCGCCCATTGACGTCAATAATGACGTATGTTCCCATAGTAACGCCAATAG
GGACTTTCCATTGACGTCAATGGGTGGAGTATTTACGGTAAACTGCCCACT
TGGCAGTACATCAAGTGTATCATATGCCAAGTACGCCCCCTATTGACGTCA
ATGACGGTAAATGGCCCGCCTGGCATTATGCCCAGTACATGACCTTATGGG
ACTTTCCTACTTGGCAGTACATCTACGTATTAGTCATCGCTATTACCATGG
TCGAGGTGAGCCCCACGTTCTGCTTCACTCTCCCCATCTCCCCCCCCTCCC
CACCCCCAATTTTGTATTTATTTATTTTTTAATTATTTTGTGCAGCGATGG
GGGCGGGGGGGGGGGGGGCGCGCGCCAGGCGGGGCGGGGCGGGGCGAGG
GGCGGGGCGGGGCGAGGCGGAGAGGTGCGGCGGCAGCCAATCAGAGCGGCG
CGCTCCGAAAGTTTCCTTTTATGGCGAGGCGGCGGCGGCGGCGGCCCTATA
AAAAGCGAAGCGCGCGGCGGGCGGGAGTCGCTGCGACGCTGCCTTCGCCCC
GTGCCCCGCTCCGCCGCCGCCTCGCGCCGCCCGCCCCGGCTCTGACTGACC
GCGTTACTCCCACAGGTGAGCGGGCGGGACGGCCCTTCTCCTCCGGGCTGT
AATTAGCTGAGCAAGAGGTAAGGGTTTAAGGGATGGTTGGTTGGTGGGGTA
TTAATGTTTAATTACCTGGAGCACCTGCCTGAAATCACTTTTTTTCAGGTT
GGaccggtgccaccATGGACTATAAGGACCACGACGGAGACTACAAGGATC
ATGATATTGATTACAAAGACGATGACGATAAGATGGCCCCAAAGAAGAAGC
GGAAGGTCGGTATCCACGGAGTCCCAGCAGCCGACAAGAAGTACAGCATCG
GCCTGGACATCGGCACCAACTCTGTGGGCTGGGCCGTGATCACCGACGAGT
ACAAGGTGCCCAGCAAGAAATIVAAGGTGCTGGGCAACACCGACCGGCACA
GCATCAAGAAGAACCTGATCGGAGCCCTGCTGTTCCACAGCCGCGAAACAG
CCGAGGCCACCCGGCTGAAGAGAACCGCCAGAAGAAGATACACCAGACGGA
AGAACCGGATCTGCTATCTGCAAGAGATCTTCAGCAACGAGATGCCCAAGG
TGGACGACAGCTTCTTCCACAGACTGGAAGAGTCCTTCCTGGTGGAAGAGG
ATAAGAAGCACGAGCGGCACCCCATCTTCGGCAACATCGTGGACGAGGTGG
CCTACCACGAGAAGTACCCCACCATCTACCACCTGAGAAAGAAACTGGTGG
ACAGCACCGACAAGGCCGACCTGCGGCTGATCTATCTGGCCCTGGCCCACA
TGATCAAGTTCCGGGGCCACTTCCTGATCGAGGGCGACCTGAACCCCGACA
ACAGCGACGTGGACAAGCTGTTCATCCAGCTGGTGCAGACCTACAACCAGC
TGTTCGAGGAAAACCCCATCAACGCCAGCGGCGTGGACGCCAAGGCCATCC
TGTCTGCCAGACTGAGCAAGAGCAGACGGCTGGAAAATCTGATCGCCCAGC
TGCCCGGCGAGAAGAAGAATGGCCTGTTCGGCAACCTGATTGCCCTGAGCC
TGGGCCTGACCCCCAACTTCAAGAGCAACTTCGACCTGGCCGAGGATGCCA
AACTGCAGCTGAGCAAGGACACCTACGACGACGACCTGGACAACCTGCTGG
CCCAGATCGGCGACCAGTACGCCGACCTGTTTCTGGCCGCCAAGAACCTGT
CCGACGCCATCCTGCTGAGCGACATCCTGAGAGTGAACACCGAGATCACCA
AGGCCCCCCTGAGCGCCTCTATGATCAAGAGATACGACGAGCACCACCAGG
ACCTGACCCTGCTGAAAGCTCTCGTGCGGCAGCAGCTGCCTGAGAAGTACA
AAGAGATTTTCTTCGACCAGAGCAAGAACGGCTACGCCGGCTACATTGACG
CCGGAGCCACCCAGGAAGAGTTCTACAAGTTCATCAAGCCCATCCTGGAAA
AGATGGACGGCACCGAGGAACTGCTCGTGAAGCTGAACAGAGAGGACCTGC
TGCGGAAGCAGCGGACCTTCGACAACGGCAGCATCCCCCACCAGATCCACC
TGGGAGAGCTGCACGCCATTCTGCGGCGGCAGGAAGATTTTTACCCATTCC
TGAAGGACAACCGGGAAAAGATCGAGAAGATCCTGACCTTCCGCATCCCCT
ACTACGTGGGCCCTCTGGCCAGGGGAAACAGCAGATTCGCCTGGATGACCA
GAAAGAGCGAGGAAACCATCACCCCCTGGAACTTCGAGGAAGTGGTGGACA
AGGCCGCTTCCGCCCAGAGCTTCATCGAGCGGATCACCAACTTCGATAAGA
ACCTGCCCAACGAGAAGGTGCTGCCCAAGCACAGCCTGCTGTACGAGTACT
TCACCGTGTATAACGAGCTGACCAAAGTGAAATACGTGACCGAGGGAATGA
GAAAGCCCGCCTTCCTGAGCGGCGAGCAGAAAAAGGCCATCGTGGACCTGC -continued
```
TGTTCAAGACCAACCGGAAAGTGACCGTGAAGCAGCTGAAAGAGGACTACT
TCAAGAAAATCGAGTGCTTCGACTCCGTGGAAATCTCCGGCGTGGAAGATC
GGTTCAACGCCTCCCTGGGCACATACCACGATCTGCTGAAAATTATCAAGG
ACAAGGACTTCCTGGACAATGAGGAAAACGAGGACATTCTGGAAGATATCG
TGCTGACCCTGACACTGTTTGAGGACAGAGAGATGATCGAGGAACGGCTGA
AAACCTATGCCCACCTGTTCGACGACAAAGTGATGAAGCAGCTGAAGCGGC
GGAGATACACCGGCTGGGGCAGGCTGAGCCGGAAGCTGATCAACGGCATCC
GGGACAAGCAGTCCGGCAAGACAATCCTGGATTTCCTGAAGTCCGACGGCT
TCGCCAACAGAAACTTCATGCAGCTGATCCACGACGACAGCCTGACCTTTA
AGAGGACATCCAGAAAGCCCAGGTGTCCGGCCAGGGCGATAGCCTGCACG
AGCACATTGCCAATCTGGCCGGCAGCCCCGCCATTAAGAAGGGCATCCTGC
AGACAGTGAAGGTGGTGGACGAGCTCGTGAAAGTGATGGGCCGGCACAAGC
CCGACAACATCCTCATCCAAATGGCCAGAGAGAACCAGACCACCCAGAAGG
GACAGAAGAACAGCCGCGAGAGAATGAAGCGGATCGAAGAGGGCATCAAAG
AGCTGGGCAGCCAGATCCTGAAAGAACACCCCGTGGAAAACACCCAGCTGC
AGAACGAGAAGCTGTACCTGTACTACCTGCAGAATGGGCGGGATATGTACG
TGGACCAGGAACTGGACATCAACCGGCTGTCCGACTACGATGTGGACCATA
TCCAGCCTCAGAGCTTTCTGAAGGACGACTCCATCGACAACAAGGTGCTGA
CCAGAAGCGACAAGAACCGGGGCAAGAGCGACAACGTGCCCTCCGAAGAGG
TCGTGAAGAAGATGAAGAACTACTGGCGGCAGCTGCTGAACGCCAAGCTGA
TTACCCAGAGAAAGTTCGACAATCTGACCAAGGCCGAGAGAGGCGGCCTGA
GCGAACTGGATAAGGCCGGCTTCATCAAGAGACAGCTGGTGGAAACCCGGC
AGATCACAAAGCACGTGGCACAGATCCTGGACTCCCGGATGAACACTAAGT
ACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCG
AGATCAACAACTACCACCACGCCCACCACGCCTACCTGAACGCCGTCGTGG
GAACCGCCCTGATCAAAAAGTACCCTAAGCTGGAAAGCGAGTTCGTGTACG
GCGACTACAAGGTGTACGACGTGCGGAAGATGATCGCCAAGAGCGAGCAGG
AAATCGGCAAGGCTACCGCCAAGTACTTCTTCTACAGCAACATCATGAACT
TTTTCAAGACCGAGATTACCCTGGCCAACGGCGAGATCCGGAAGCGGCCTC
TGATCGAGACAAACGGCGAAACCGGGGAGATCGTGTGGGATAAGGGCCGGG
ATTTTGCCACCGTGCGGAAAGTGCTGAGCATGCCCCAAGTGAATATCGTGA
AAAGACCGAGGTGCAGACAGGCGGCTTCAGCAAAGAGTCTATCCTGCCCAA
GAGGAACAGCGATAAGCTGATCGCCAGAAAGAAGGACTGGGACCCTAAGAA
GTACGGCGGCTTCGACAGCCCCACCGTGGCCTATTCTGTGCTGGTGGTGGC
CAAAGTGGAAAAGGGCAAGTCCAAGAAACTGAAGAGTGTGAAAGAGCTGCT
GGGGATCACCATCATGGAAAGAAGCAGCTTCGAGAAGAATCCCATCGACTT
TCTGGAAGCCAAGGGCTACAAAGAAGTGAAAAAGGACCTGATCATCAAGCT
GCCTAAGTACTCCCTGTTCGAGCTGGAAAACGGCCGGAAGAGAATGCTGGC
CTCTGCCGGCGAACTGCAGAAGGGAAACGAACTGGCCCTGCCCTCCAAATA
TGTGAACTTCCTGTACCTGGCCAGCCACTATGAGAAGCTGAAGGGCTCCCC
CGAGGATAATGAGCAGAAACAGCTGTTTGTGGAACAGCACAAGCACTACCT
GGACGAGATCATCGAGCAGATCAGCGAGTTCTCCAAGAGAGTGATCCTGGC
CGACGCTAATCTGGACAAAGTGCTGTCCGCCTACAACAAGCACCGGGATAA
GCCCATCAGAGAGCAGGCCGAGAATATCATCCACCTGTTTACCCTGACCAA
TCTGGGAGCCCCTGCCGCCTTCAAGTACTTTGACACCACCATCGACCGGAA
GAGGTACACCAGCACCAAAGAGGTGCTGGACGCCACCCTGATCCACCAGAG
CATCACCGGCCTGTACGAGACACGGATCGACCTGTCTCAGCTGGGAGGCGA
CTTTCTTTTTCTTAGCTTGACCAGCTTTCTTAGTAGCAGCAGGACGCTTTA
A
```
(NLS-hSpCas9-NLS is highlighted in bold)

>Sequencing amplicon for EMX1 guides 1.1, 1.14, 1.17

(SEQ ID NO: 266)
```
CCAATGGGGAGGACATCGATGTCACCTCCAATGACTAGGGTGGGCAACCA
CAAACCCACGAGGGCAGAGTGCTGCTTGCTGCTGGCCAGGCCCCTGCGTG
GGCCCAAGCTGGACTCTGGCCAC
```

>Sequencing amplicon for EMX1 guides 1.2, 1.16

(SEQ ID NO: 267)
```
CGAGCAGAAGAAGAAGGGCTCCCATCACATCAACCGGTGGCGCATTGCCA
CGAAGCAGGCCAATGGGGAGGACATCGATGTCACCTCCAATGACTAGGGT
GGGCAACCACAAACCCACGAG
```

>Sequencing amplicon for EMX1 guides 1.3, 1.13, 1.15

(SEQ ID NO: 268)
```
GGAGGACAAAGTACAAACGGCAGAAGCTGGAGGAGGAAGGGCCTGAGTCC
GAGCAGAAGAAGAAGGGCTCCCATCACATCAACCGGTGGCGCATTGCCAC
GAAGCAGGCCAATGGGGAGGACATCGAT
```

>Sequencing amplicon for EMX1 guides 1.6

(SEQ ID NO: 269)
```
AGAAGCTGGAGGAGGAAGGGCCTGAGTCCGAGCAGAAGAAGAAGGGCTCC
CATCACATCAACCGGTGGCGCATTGCCACGAAGCAGGCCAATGGGGAGGA
CATCGATGTCACCTCCAATGACTAGGGTGG
```

>Sequencing amplicon for EMX1 guides 1.10

(SEQ ID NO: 270)
```
CCTCAGTCTTCCCATCAGGCTCTCAGCTCAGCCTGAGTGTTGAGGCCCCA
GTGGCTGCTCTGGGGGCCTCCTGAGTTTCTCATCTGTGCCCCTCCCTCCC
TGGCCCAGGTGAAGGTGTGGTTCCA
```

>Sequencing amplicon for EMX1 guides 1.11, 1.12

(SEQ ID NO: 271)
```
TCATCTGTGCCCCTCCCTCCCTGGCCCAGGTGAAGGTGTGGTTCCAGAAC
CGGAGGACAAAGTACAAACGGCAGAAGCTGGAGGAGGAAGGGCCTGAGTC
CGAGCAGAAGAAGAAGGGCTCCCATCACA
```

\>Sequencing amplicon for EMX1 guides 1.18, 1.19

```
                                       (SEQ ID NO: 272)
CTCCAATGACTAGGGTGGGCAACCACAAACCCACGAGGGCAGAGTGCTGC

TTGCTGCTGGCCAGGCCCCTGCGTGGGCCCAAGCTGGACTCTGGCCACTC

CCTGGCCAGGCTTTGGGGAGGCCTGGAGT
```

\>Sequencing amplicon for EMX1 guides 1.20

```
                                       (SEQ ID NO: 273)
CTGCTTGCTGCTGGCCAGGCCCTGCGTGGGCCCAAGCTGGACTCTGGCC

ACTCCCTGGCCAGGCTTTGGGGAGGCCTGGAGTCATGGCCCCACAGGGCT

TGAAGCCCGGGGCCGCCATTGACAGAG
```

\>T7 promoter F primer for annealing with target strand

```
      GAAATTAATACGACTCACTATAGGG    (SEQ ID NO: 274)
```

\>oligo containing pUC19 target site 1 for methylation (T7 reverse)

```
                                       (SEQ ID NO: 275)
AAAAAAGCACCGACTCGGTGCCACTTTTTCAAGTTGATAACGGACTAGCC

TTATTTTAACTTGCTATTTCTAGCTCTAAAACAACGACGAGCGTGACACC

ACCCTATAGTGAGTCGTATTAATTTC
```

\>oligo containing pUC19 target site 2 for methylation (T7 reverse)

```
                                       (SEQ. ID NO: 276)
AAAAAAGCACCGACTCGGTGCCACTTTTTCAAGTTGATAACGGACTAGCC

TTATTTTAACTTGCTATTTCTAGCTCTAAAACGCAACAATTAATAGACTG

GACCTATAGTGAGTCGTATTAATTTC
```

Example 11

Oligo-Mediated Cas9-Induced Homologous Recombination

The oligo homologous recombination test is a comparison of efficiency across different Cas9 variants and different HR template (oligo vs. plasmid).

293FT cells were used. SpCas9=Wildtype Cas9 and SpCas9n=nickase Cas9 (D10A). The chimeric RNA target is the same EMX1 Protospacer Target 1 as in Examples 5, 9 and 10 and oligos synthesized by IDT using PAGE purification.

FIG. 44 depicts a design of the oligo DNA used as Homologous Recombination (HR) template in this experiment. Long oligos contain 100 bp homology to the EMX1 locus and a HindIII restriction site. 293FT cells were co-transfected with: first, a plasmid containing a chimeric RNA targeting human EMX1 locus and wild-type cas9 protein, and second, the oligo DNA as HR template. Samples are from 293FT cells collected 96 hours post transfection with Lipofectamine 2000. All products were amplified with an EMX1 HR Primer, gel purified, followed by digestion with HindIII to detect the efficiency of integration of HR template into the human genome.

Figure 45:
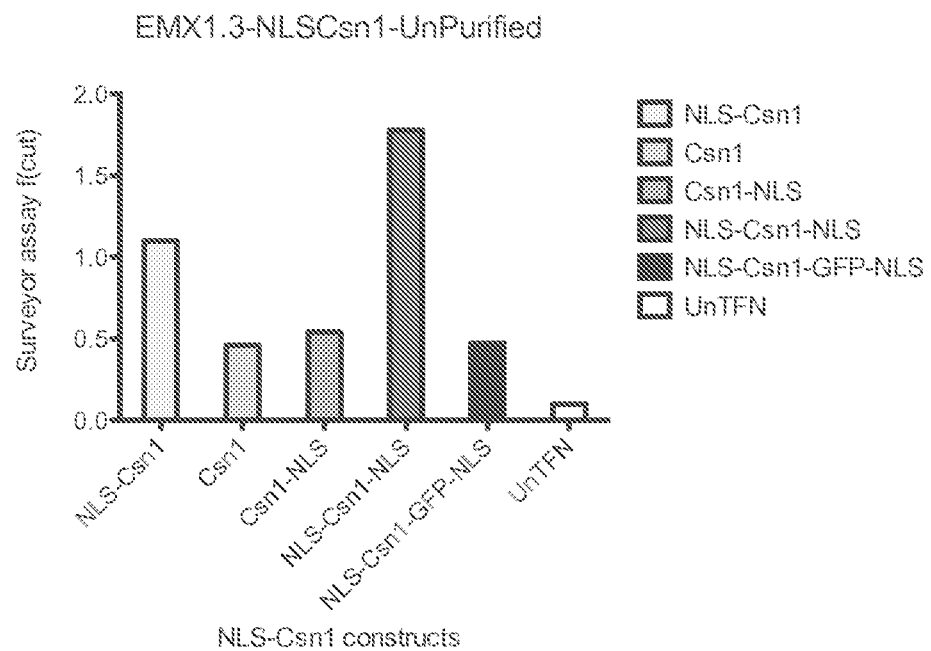
FIG. 45 shows quantification of cleavage of NLS-Csn1 constructs NLS-Csn1, Csn1, Csn1-NLS, NLS-Csn1-NLS, NLS-Csn1-GFP-NLS and UnTFN.
Figure 46:
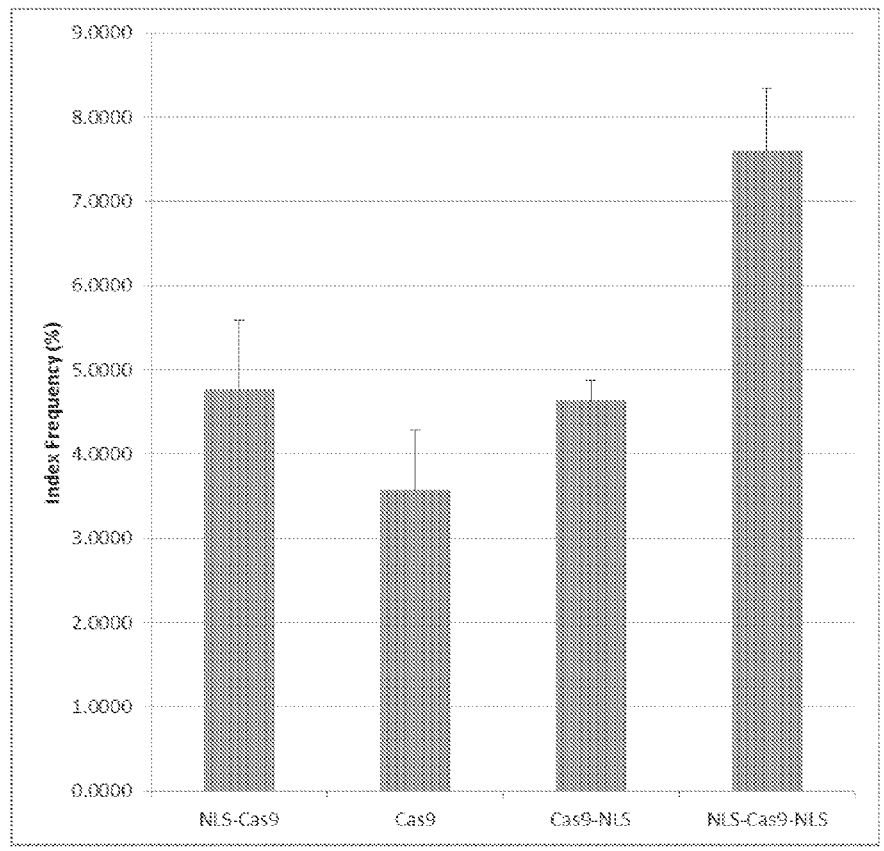
FIG. 46 shows index frequency of NLS-Cas9, Cas9, Cas9-NLS and NLS-Cas9-NLS.
Figure 49A:
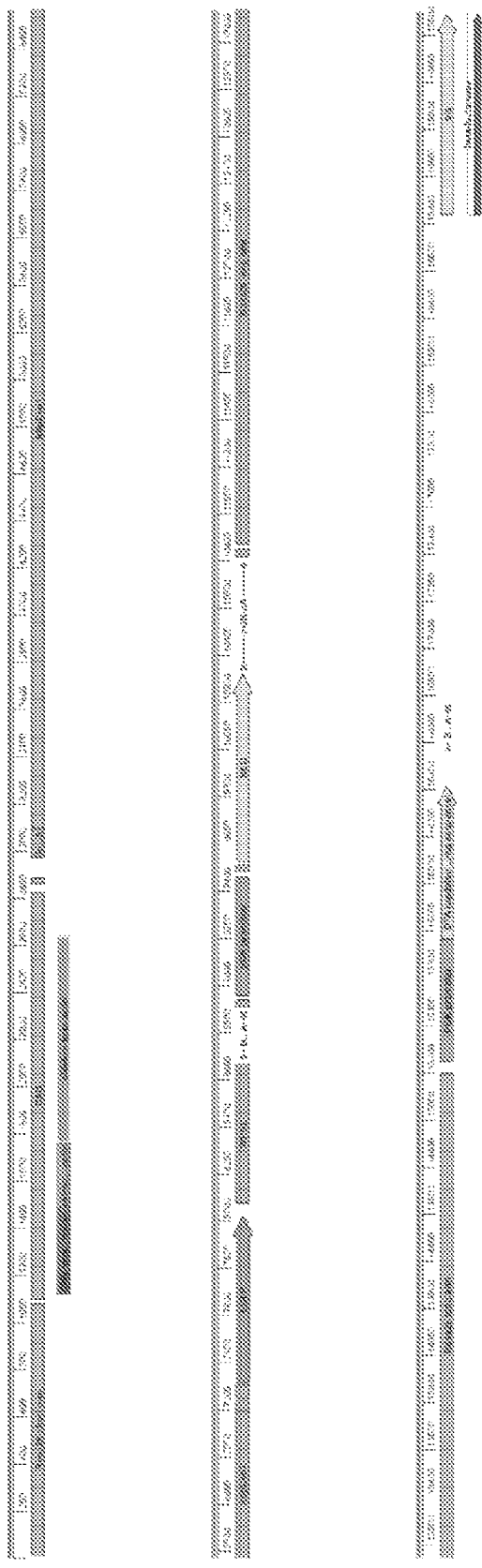
FIG. 49A shows the Conditional Cas9, Rosa26 targeting vector map.
Figure 51:
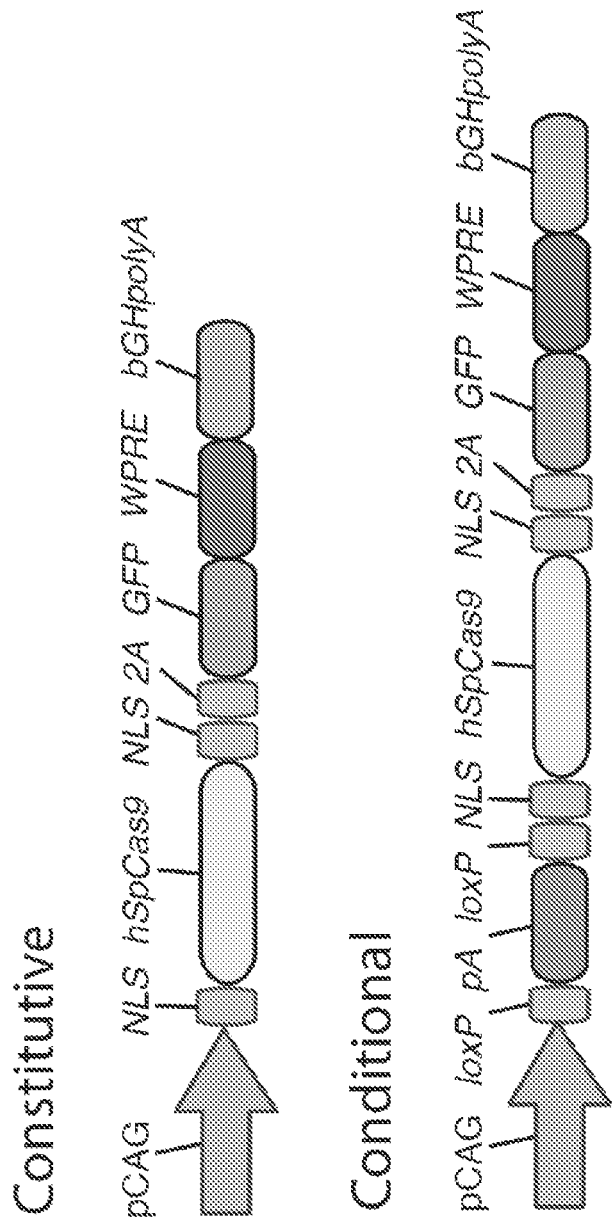
FIG. 51 shows a schematic of the important elements in the Constitutive and Conditional Cas9 constructs.
Figure 52:
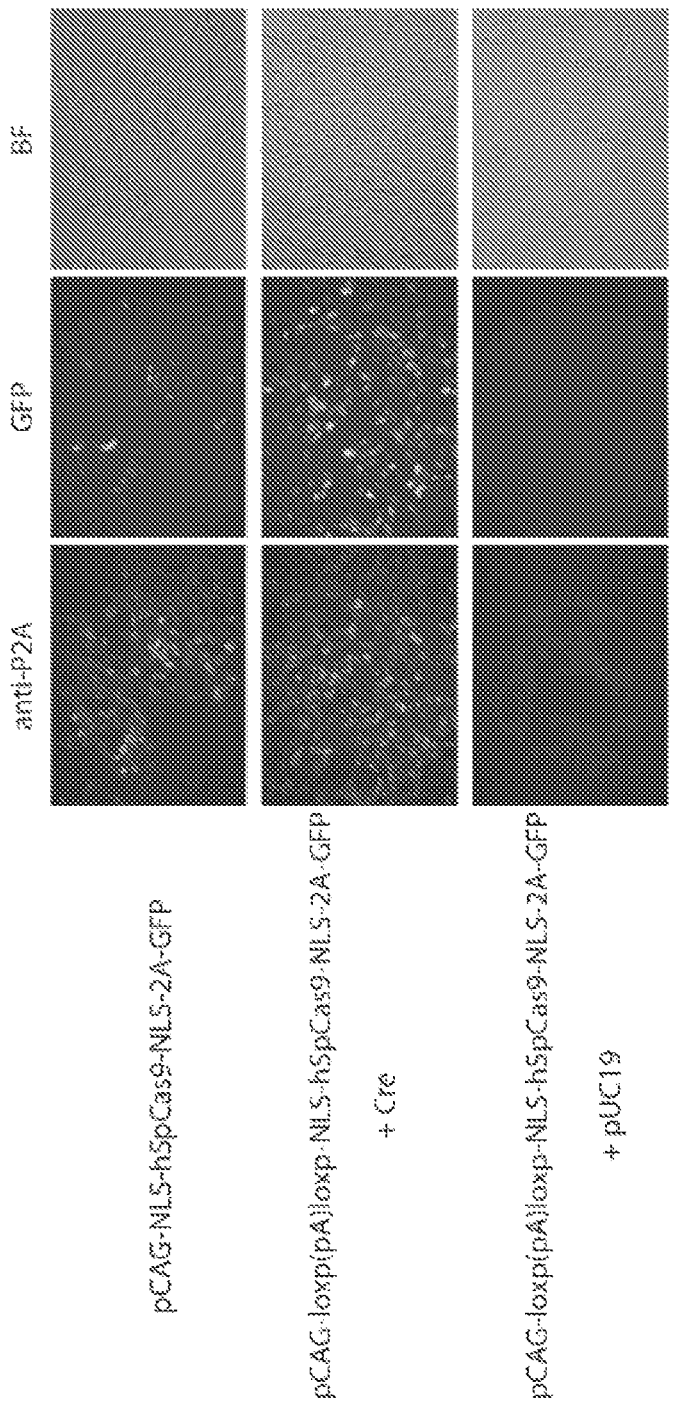
FIG. 52 shows the functional validation of the expression of Constitutive and Conditional Cas9 constructs.
Figure 53:
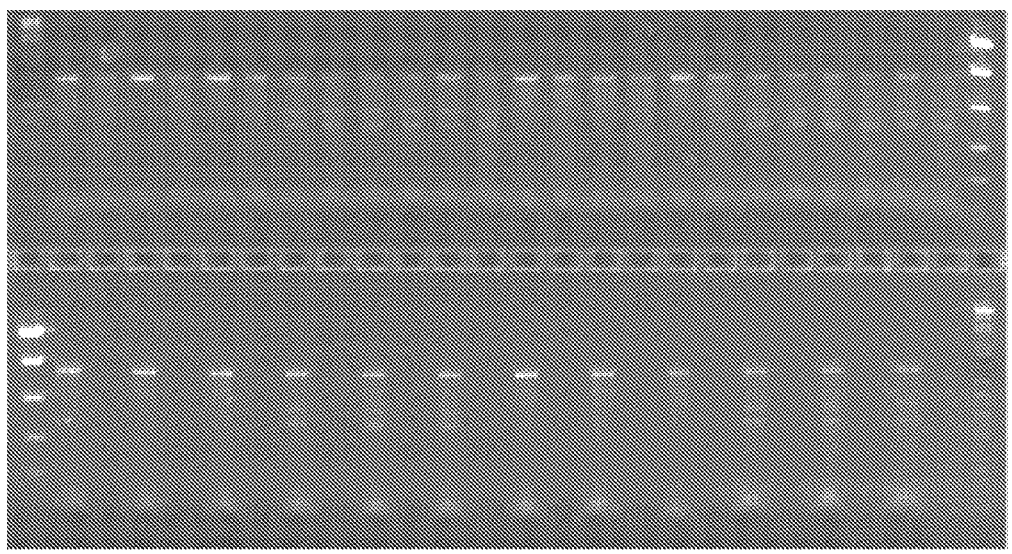
FIG. 53 shows the validation of Cas9 nuclease activity by Surveyor.
Figure 55:
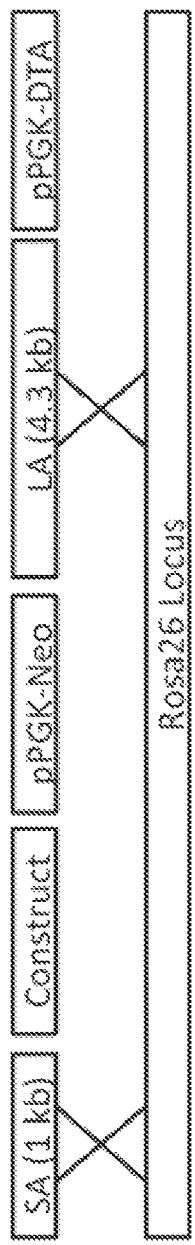
FIG. 55 shows construct design and homologous recombination (HR) strategy.
Figure 56:
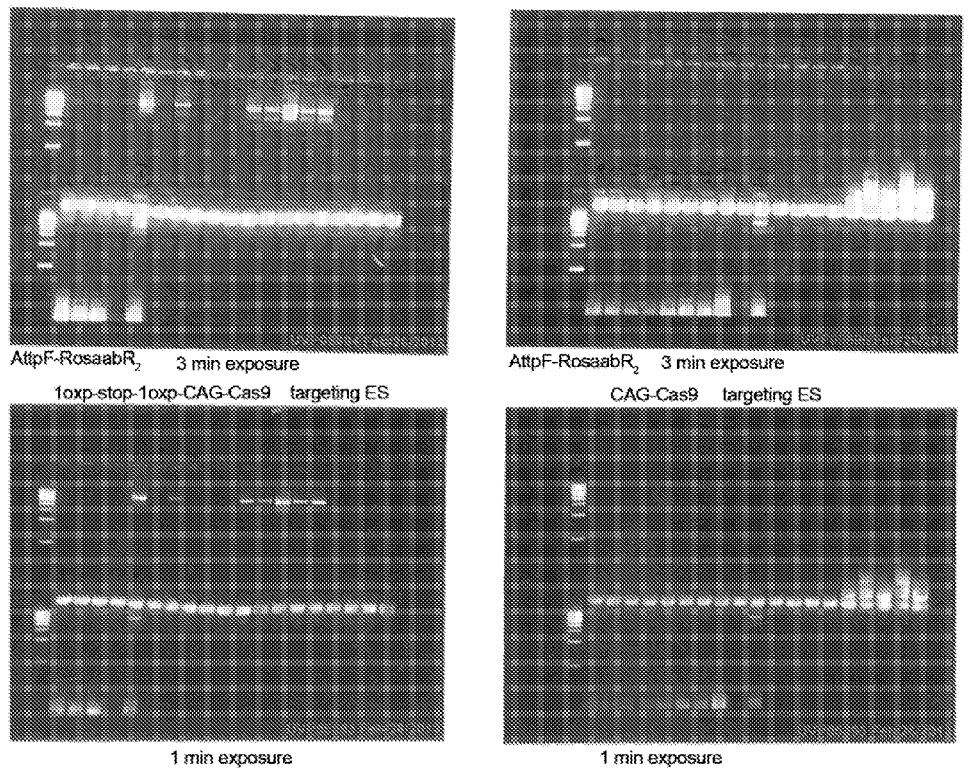
FIG. 56 shows the genomic PCR genotyping results for the constitutive (Right) and conditional (Left) constructs at two different gel exposure times (top row for 3 min and bottom row for 1 min).
Figure 57:
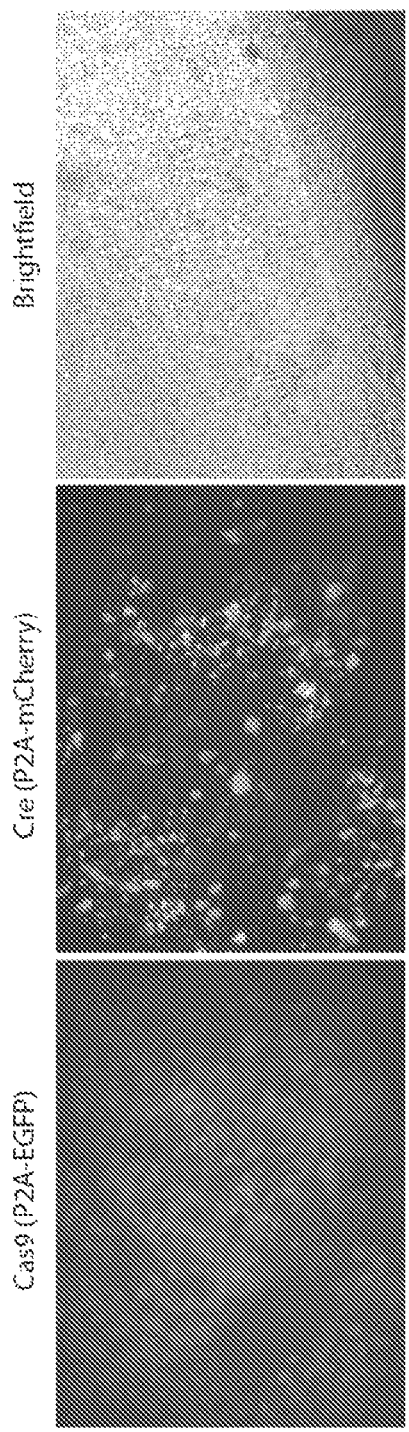
FIG. 57 shows Cas9 activation in mESCs.
Figure 58:
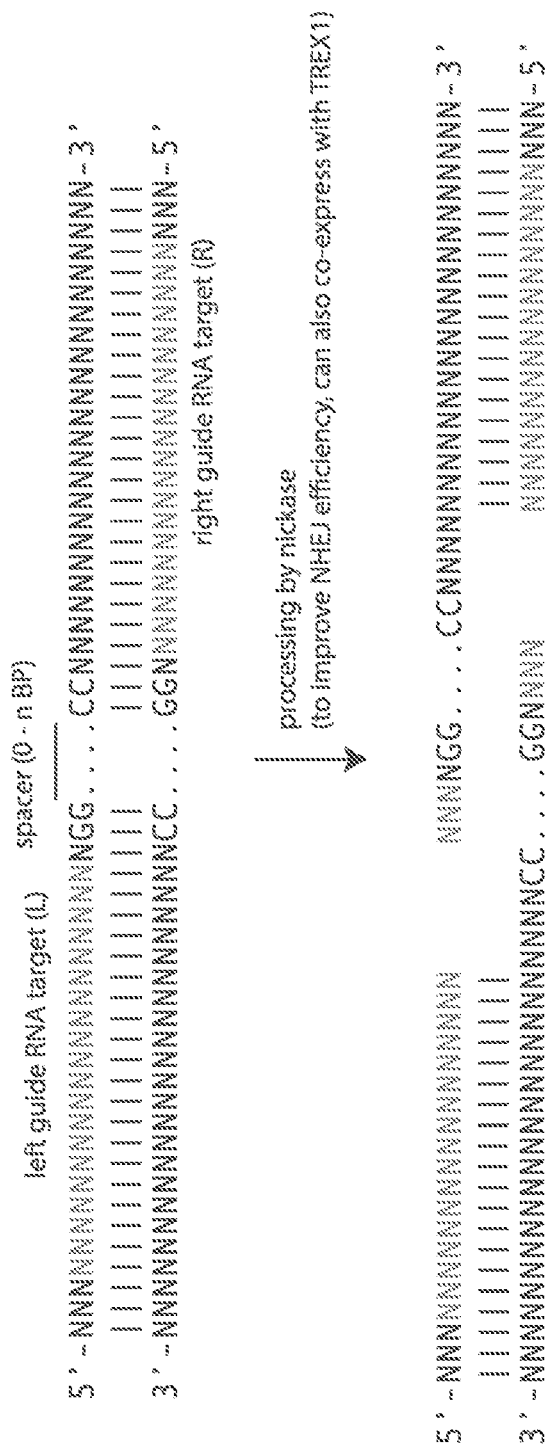
FIG. 58 shows a schematic of the strategy used to mediate gene knockout via NHEJ using a nickase version of Cas9 along with two guide RNAs.
Figure 59:
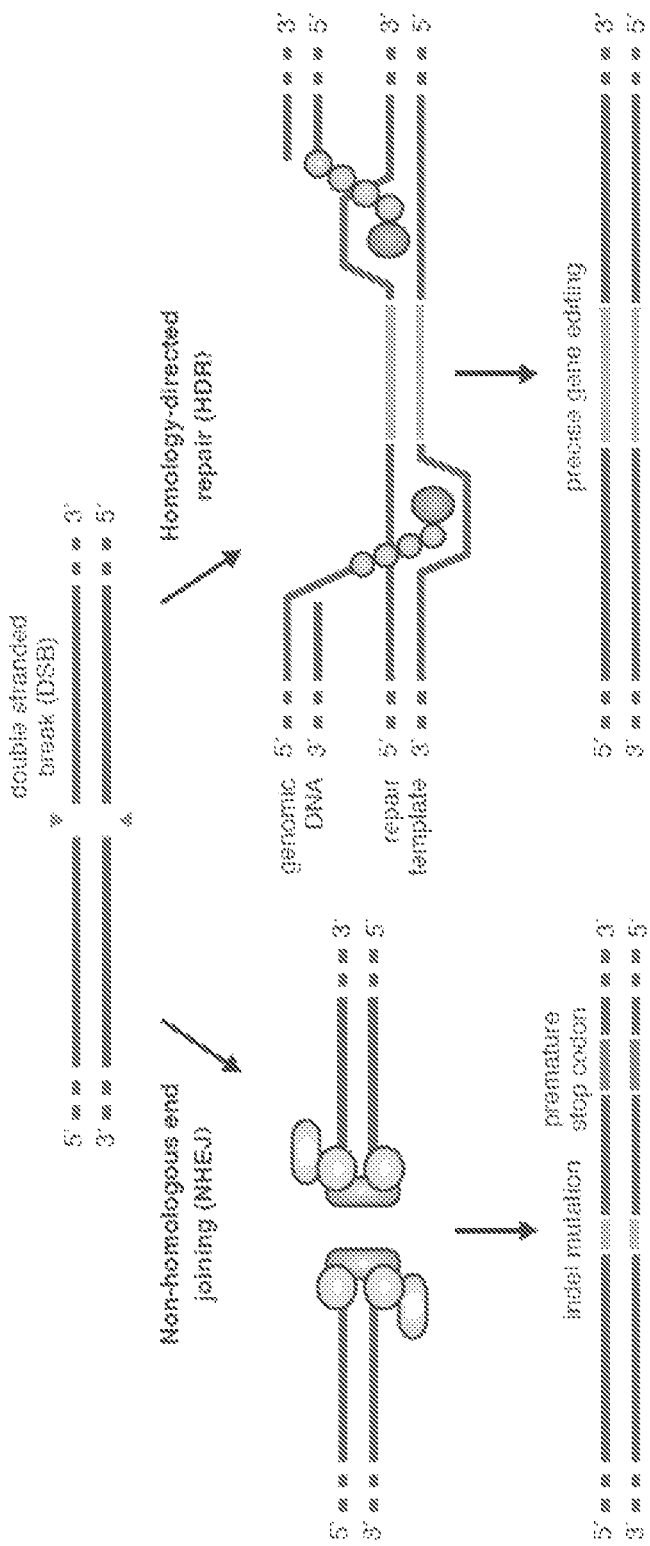
FIG. 59 shows how DNA double-strand break (DSB) repair promotes gene editing. In the error-prone non-homologous end joining (NHEJ) pathway, the ends of a DSB are processed by endogenous DNA repair machineries and rejoined together, which can result in random insertion/deletion (indel) mutations at the site of junction. Indel mutations occurring within the coding region of a gene can result in frame-shift and a premature stop codon, leading to gene knockout. Alternatively, a repair template in the form of a plasmid or single-stranded oligodeoxynucleotides (ssODN) can be supplied to leverage the homology-directed repair (HDR) pathway, which allows high fidelity and precise editing.
Figure 60:
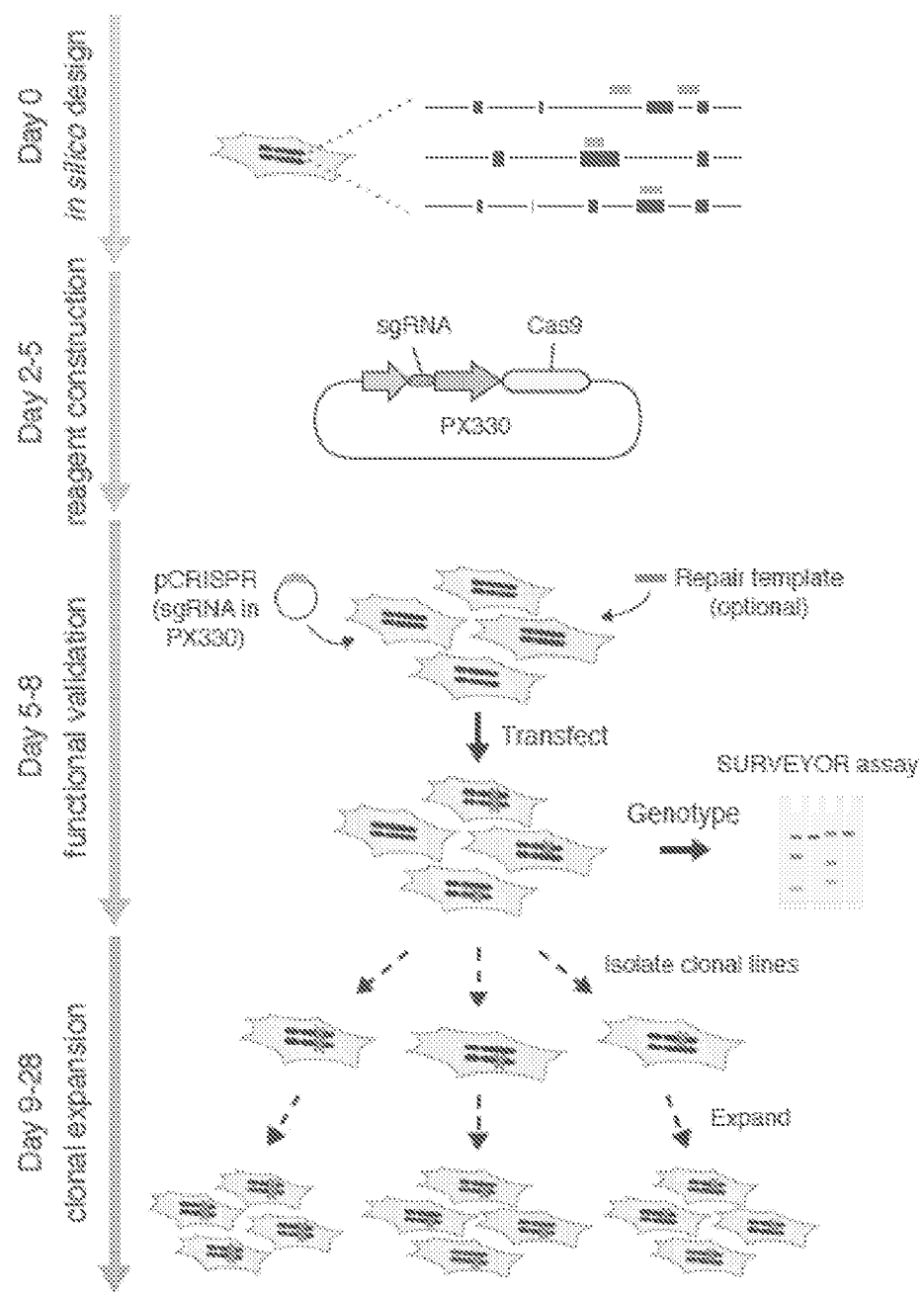
FIG. 60 shows the timeline and overview of experiments. Steps for reagent design, construction, validation, and cell line expansion. Custom sgRNAs (light blue bars) for each target, as well as genotyping primers, are designed in silico via our online design tool (available at the website genome-engineering.org/tools). sgRNA expression vectors are then cloned into a plasmid containing Cas9 (PX330) and verified via DNA sequencing. Completed plasmids (pCRISPRs), and optional repair templates for facilitating homology directed repair, are then transfected into cells and assayed for ability to mediate targeted cleavage. Finally, transfected cells can be clonally expanded to derive isogenic cell lines with defined mutations.
Figure 61:
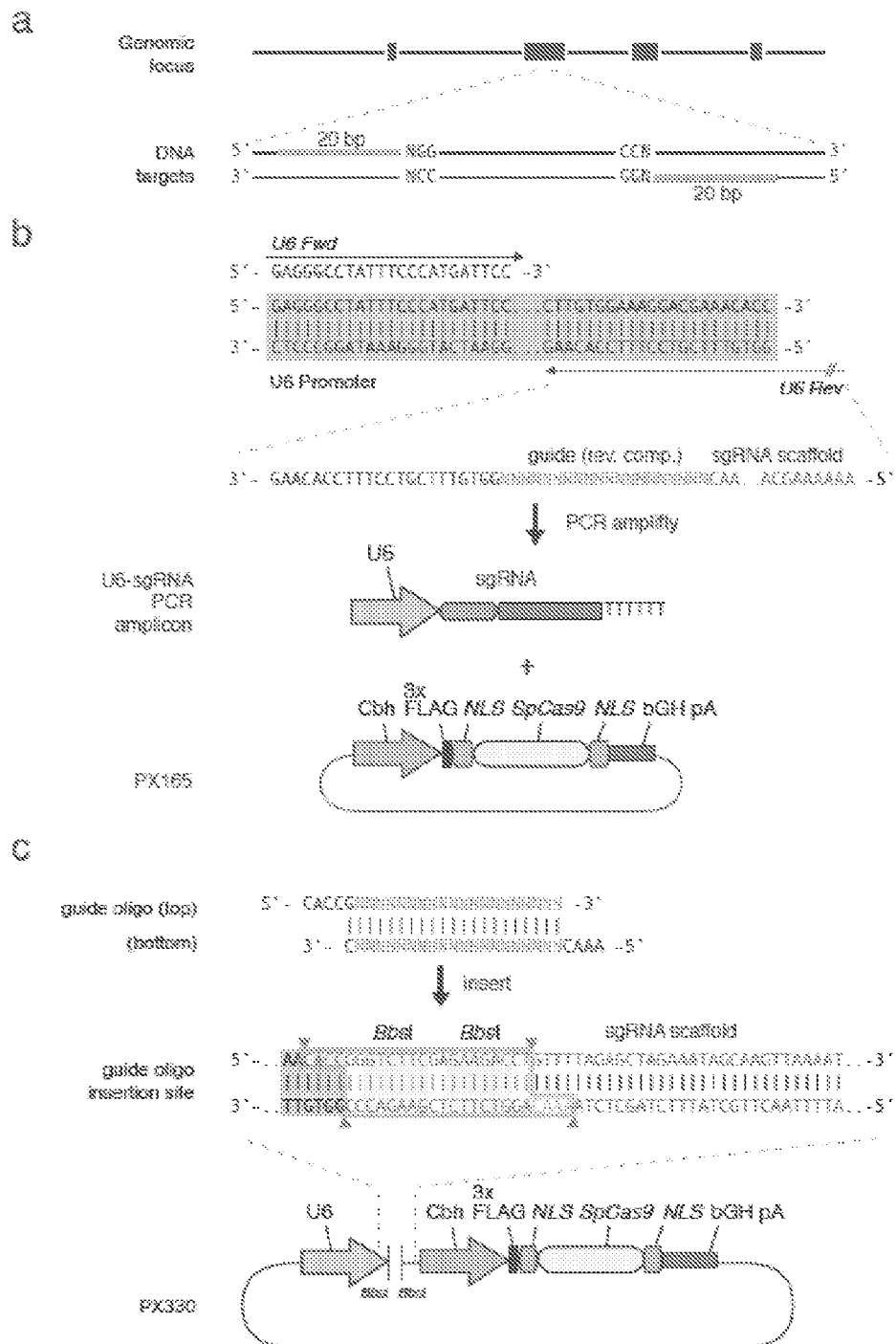
FIG. 61A-C shows Target selection and reagent preparation. (a) For S. pyogenes Cas9, 20-bp targets (highlighted in blue) must be followed by 5'-NGG, which can occur in either strand on genomic DNA. We recommend using the online tool described in this protocol in aiding target selection (www.genome-engineering.org/tools). (b) Schematic for co-transfection of Cas9 expression plasmid (PX165) and PCR-amplified U6-driven sgRNA expression cassette. Using a U6 promoter-containing PCR template and a fixed forward primer (U6 Fwd), sgRNA-encoding DNA can appended onto the U6 reverse primer (U6 Rev) and synthesized as an extended DNA oligo (Ultramer oligos from IDT). Note the guide sequence (blue N's) in U6 Rev is the reverse complement of the 5'-NGG flanking target sequence (SEQ ID NOS 519 and 519-521, respectively, in order of appearance). (c) Schematic for scarless cloning of the guide sequence oligos into a plasmid containing Cas9 and sgRNA scaffold (PX330). The guide oligos (blue N's) contain overhangs for ligation into the pair of BbsI sites on PS330, with the top and bottom strand orientations matching those of the genomic target (i.e. top oligo is the 20-bp sequence preceding 5'-NGG in genomic DNA). Digestion of PX330 with BbsI allows the replacement of the Type IIs restriction sites (blue outline) with direct insertion of annealed oligos. It is worth noting that an extra G was placed before the first base of the guide sequence. Applicants have found that an extra G in front of the guide sequence does not adversely affect targeting efficiency. In cases when the 20-nt guide sequence of choice does not begin with guanine, the extra guanine will ensure the sgRNA is efficiently transcribed by the U6 promoter, which prefers a guanine in the first base of the transcript (SEQ ID NOS 322-323 and 330, respectively, in order of appearance).
Figure 62:
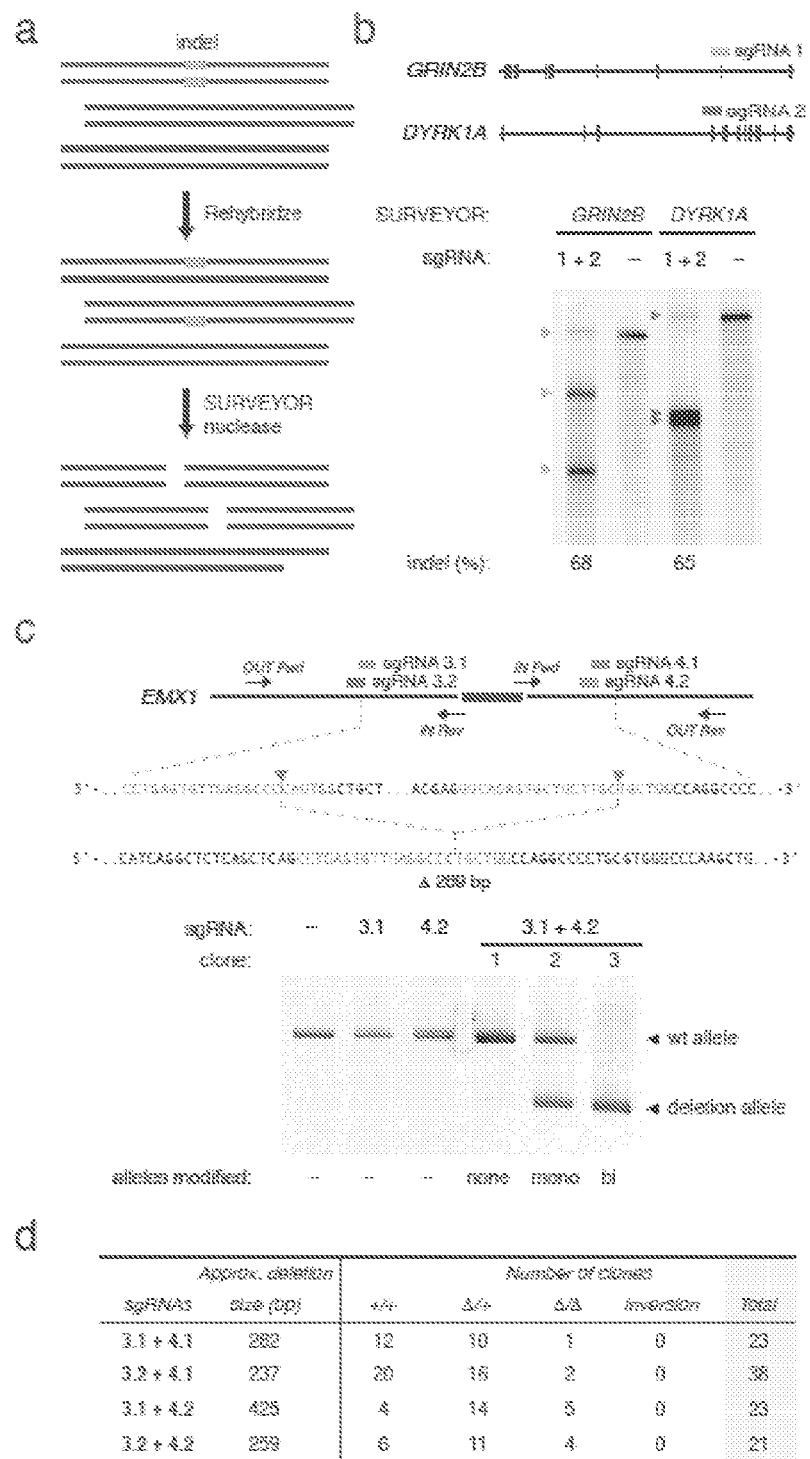
FIG. 62A-D shows the anticipated results for multiplex NHEJ. (a) Schematic of the SURVEYOR assay used to determine indel percentage. First, genomic DNA from the heterogeneous population of Cas9-targeted cells is amplified by PCR. Amplicons are then reannealed slowly to generate heteroduplexes. The reannealed heteroduplexes are cleaved by SURVEYOR nuclease, whereas homoduplexes are left intact. Cas9-mediated cleavage efficiency (% indel) is calculated based on the fraction of cleaved DNA, as determined by integrated intensity of gel bands. (b) Two sgRNAs (orange and blue bars) are designed to target the human GRIN2B and DYRK1A loci. SURVEYOR gel shows modification at both loci in transfected cells. Colored arrows indicated expected fragment sizes for each locus. (c) A pair of sgRNAs (light blue and green bars) are designed to excise an exon (dark blue) in the human EMX1 locus. Target sequences and PAMs (red) are shown in respective colors, and sites of cleavage indicated by red triangle. Predicted junction is shown below. Individual clones isolated from cell populations transfected with sgRNA 3, 4, or both are assayed by PCR(OUT Fwd, OUT Rev), reflecting a deletion of ~270-bp. Representative clones with no modification (12/23), mono-allelic (10/23), and bi-allelic (1/23) modifications are shown. IN Fwd and IN Rev primers are used to screen for inversion events (FIG. 6d) (SEQ ID NOS 522-524, respectively, in order of appearance). (d) Quantification of clonal lines with EMX1 exon deletions. Two pairs of sgRNAs (3.1, 3.2 left-flanking sgRNAs; 4.1, 4.2, right flanking sgRNAs) are used to mediate deletions of variable sizes around one EMX1 exon. Transfected cells are clonally isolated and expanded for genotyping analysis for deletions and inversion events. Of the 105 clones are screened, 51 (49%) and 11 (10%) carrying heterozygous and homozygous deletions, respectively. Approximate deletion sizes are given since junctions may be variable.
Figure 63:
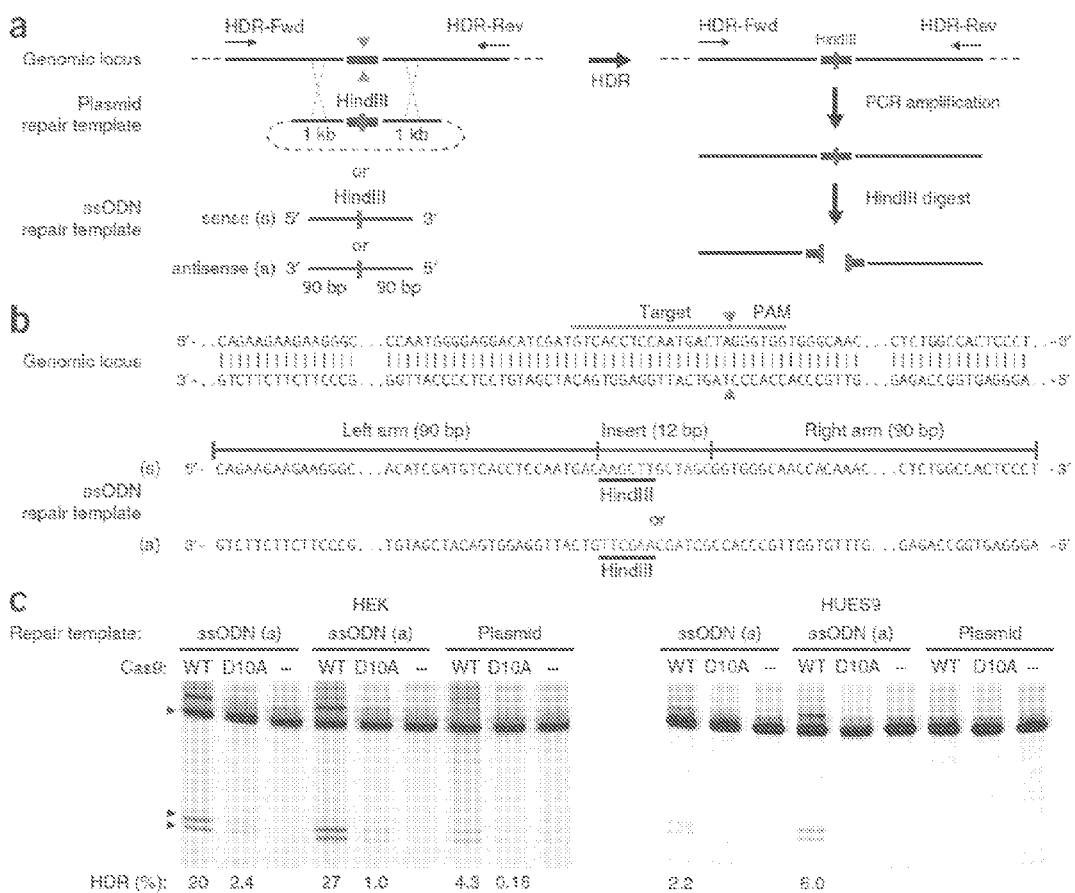
FIG. 63A-C shows the application of ssODNs and targeting vector to mediate HR with both wildtype and nickase mutant of Cas9 in HEK293FT and HUES9 cells with efficiencies ranging from 1.0-27%.
Figure 64:
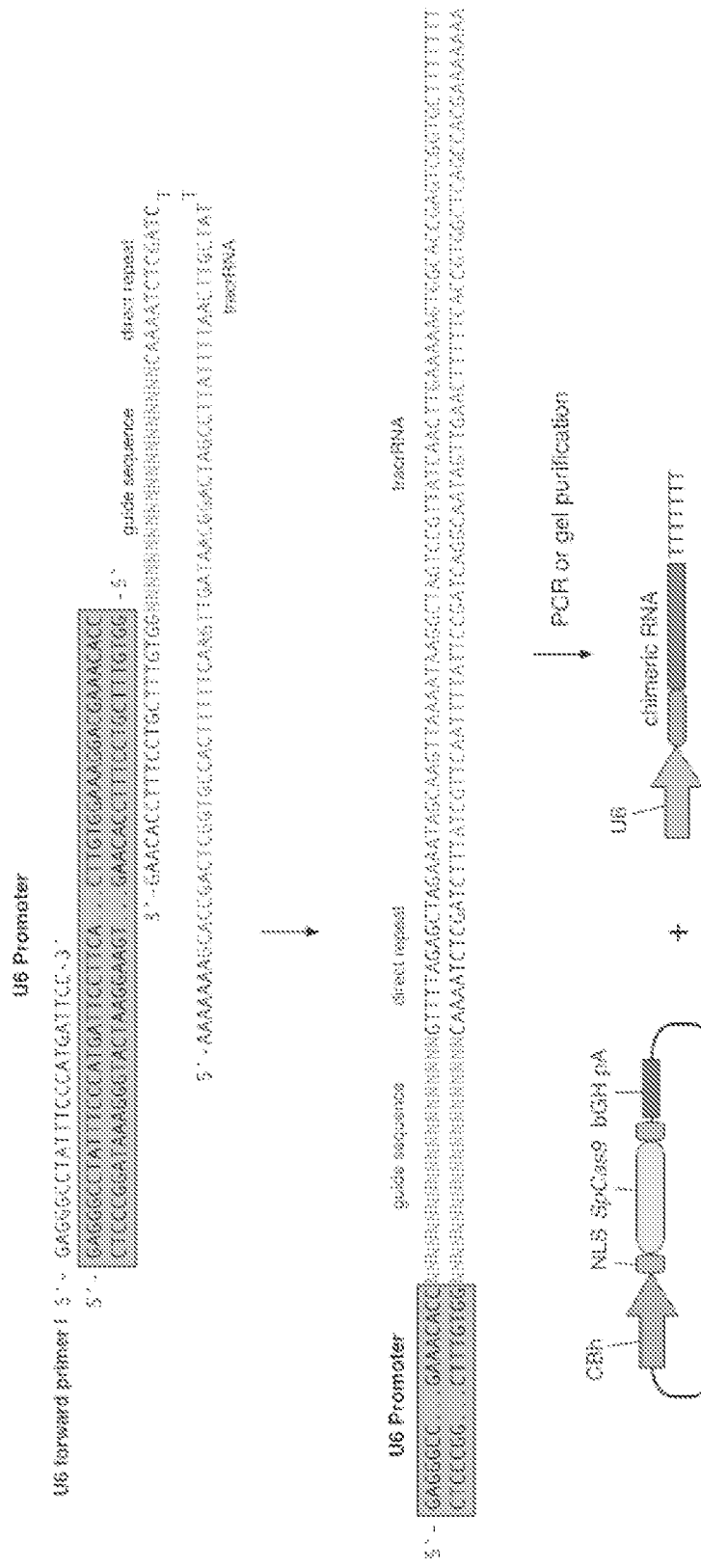
FIG. 64 shows a schematic of a PCR-based method for rapid and efficient CRISPR targeting in mammalian cells. A plasmid containing the human RNA polymerase III promoter U6 is PCR-amplified using a U6-specific forward primer and a reverse primer carrying the reverse complement of part of the U6 promoter, the sgRNA(+85) scaffold with guide sequence, and 7 T nucleotides for transcriptional termination. The resulting PCR product is purified and co-delivered with a plasmid carrying Cas9 driven by the CBh promoter (SEQ ID NOS 519, 525, 520 and 526-527, respectively, in order of appearance).
Figure 65:
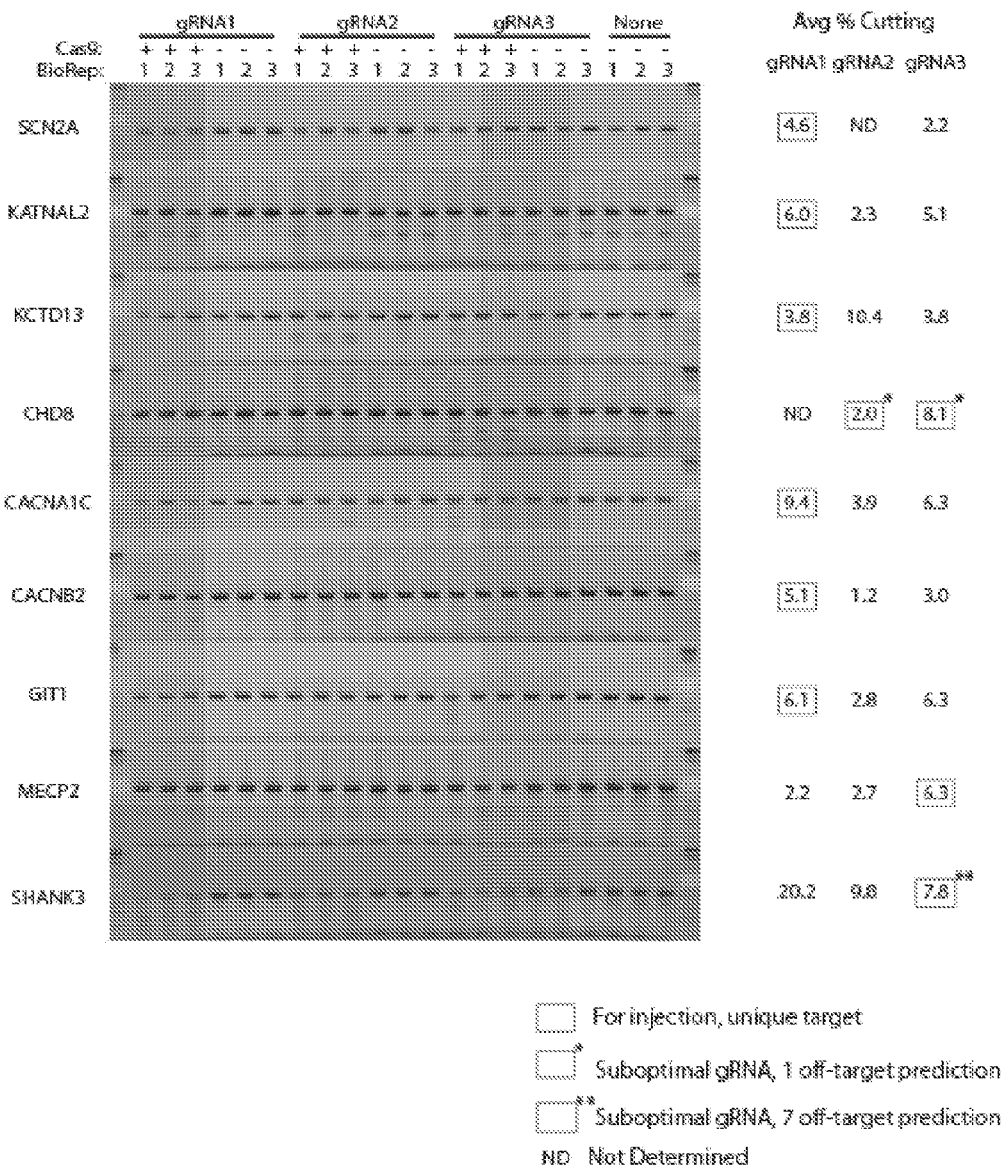
FIG. 65 shows SURVEYOR Mutation Detection Kit from Transgenomics results for each gRNA and respective controls. A positive SURVEYOR result is one large band corresponding to the genomic PCR and two smaller bands that are the product of the SURVEYOR nuclease making a double-strand break at the site of a mutation. Each gRNA was validated in the mouse cell line, Neuro-N2a, by liposomal transient co-transfection with hSpCas9. 72 hours post-transfection genomic DNA was purified using QuickExtract DNA from Epicentre. PCR was performed to amplify the locus of interest.
Figure 66:
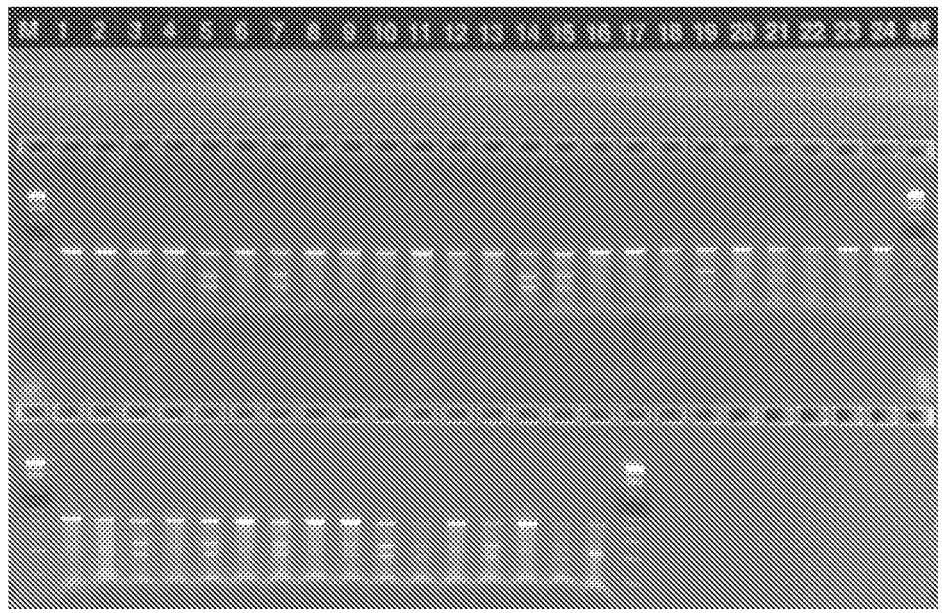
FIG. 66 shows Surveyor results for 38 live pups (lanes 1-38) 1 dead pup (lane 39) and 1 wild-type pup for comparison (lane 40). Pups 1-19 were injected with gRNA Chd8.2 and pups 20-38 were injected with gRNA Chd8.3. Of the 38 live pups, 13 were positive for a mutation. The one dead pup also had a mutation. There was no mutation detected in the wild-type sample. Genomic PCR sequencing was consistent with the SURVEYOR assay findings (SEQ ID NOS 528-530, respectively, in order of appearance).

FIGS. 45 and 46 depict a comparison of HR efficiency induced by different combination of Cas9 protein and HR template. The Cas9 construct used were either wild-type Cas9 or the nickase version of Cas9 (Cas9n). The HR template used were: antisense oligo DNA (Antisense-Oligo in above figure), or sense oligo DNA (Sense-Oligo in above figure), or plasmid HR template (HR template in above figure). The sense/anti-sense definition is that the actively-transcribed strand with sequence corresponding to the transcribed mRNA is defined as the sense strand of genome. HR Efficiency is shown as percentage of HindIII digestion band as against all genomic PCR amplified product (bottom numbers).

Example 12

Autistic Mouse

Recent large-scale sequencing initiatives have produced a large number of genes associated with disease. Discovering the genes is only the beginning in understanding what the gene does and how it leads to a diseased phenotype. Current technologies and approaches to study candidate genes are slow and laborious. The gold standards, gene targeting and genetic knockouts, require a significant investment in time and resources, both monetary and in terms of research personnel. Applicants set out to utilize the hSpCas9 nuclease to target many genes and do so with higher efficiency and lower turnaround compared to any other technology. Because of the high efficiency of hSpCas9 Applicants can do RNA injection into mouse zygotes and immediately get genome-modified animals without the need to do any preliminary gene targeting in mESCs.

Chromodomain helicase DNA binding protein 8 (CHD8) is a pivotal gene in involved in early vertebrate development and morphogenesis. Mice lacking CHD8 die during embryonic development. Mutations in the CHD8 gene have been associated with autism spectrum disorder in humans. This association was made in three different papers published simultaneously in Nature. The same three studies identified a plethora of genes associated with autism spectrum disorder. Applicants' aim was to create knockout mice for the four genes that were found in all papers, Chd8, Katna12, Kctd13, and Scn2a. In addition, Applicants chose two other genes associated with autism spectrum disorder, schizophrenia, and ADHD, GIT1, CACNA1C, and CACNB2. And finally, as a positive control Applicants decide to target MeCP2.

For each gene Applicants designed three gRNAs that would likely knockout the gene. A knockout would occur after the hSpCas9 nuclease makes a double strand break and the error prone DNA repair pathway, non-homologous end joining, corrects the break, creating a mutation. The most likely result is a frameshift mutation that would knockout the gene. The targeting strategy involved finding proto-spacers in the exons of the gene that had a PAM sequence, NGG, and was unique in the genome. Preference was given to proto-spacers in the first exon, which would be most deleterious to the gene.

Each gRNA was validated in the mouse cell line, Neuro-N2a, by liposomal transient co-transfection with hSpCas9. 72 hours post-transfection genomic DNA was purified using QuickExtract DNA from Epicentre. PCR was performed to amplify the locus of interest. Subsequently the SURVEYOR Mutation Detection Kit from Transgenomics was followed. The SURVEYOR results for each gRNA and respective controls are shown in Figure A1. A positive SURVEYOR result is one large band corresponding to the genomic PCR and two smaller bands that are the product of the SURVEYOR nuclease making a double-strand break at the site of a mutation. The average cutting efficiency of each gRNA was also determined for each gRNA. The gRNA that was chosen for injection was the highest efficiency gRNA that was the most unique within the genome.

RNA (hSpCas9+gRNA RNA) was injected into the pronucleus of a zygote and later transplanted into a foster mother. Mothers were allowed to go full term and pups were sampled by tail snip 10 days postnatal. DNA was extracted and used as a template for PCR, which was then processed by SURVEYOR. Additionally, PCR products were sent for sequencing. Animals that were detected as being positive in either the SURVEYOR assay or PCR sequencing would have their genomic PCR products cloned into a pUC19 vector and sequenced to determine putative mutations from each allele.

So far, mice pups from the Chd8 targeting experiment have been fully processed up to the point of allele sequencing. The Surveyor results for 38 live pups (lanes 1-38) 1 dead pup (lane 39) and 1 wild-type pup for comparison (lane 40) are shown in Figure A2. Pups 1-19 were injected with gRNA Chd8.2 and pups 20-38 were injected with gRNA Chd8.3. Of the 38 live pups, 13 were positive for a mutation. The one dead pup also had a mutation. There was no mutation detected in the wild-type sample. Genomic PCR sequencing was consistent with the SURVEYOR assay findings.

Example 13

CRISPR/Cas-Mediated Transcriptional Modulation

Figure 67:
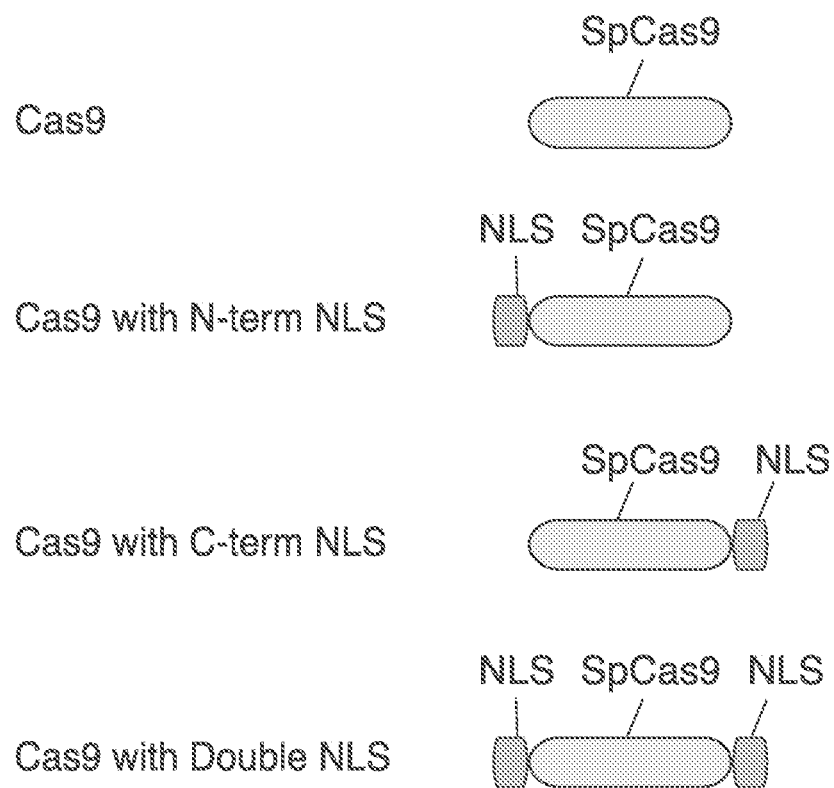
FIG. 67 shows a design of different Cas9 NLS constructs. All Cas9 were the human-codon-optimized version of the Sp Cas9. NLS sequences are linked to the cas9 gene at either N-terminus or C-terminus. All Cas9 variants with different NLS designs were cloned into a backbone vector containing so it is driven by EF1a promoter. On the same vector there is a chimeric RNA targeting human EMX1 locus driven by U6 promoter, together forming a two-component system.

FIG. 67 depicts a design of the CRISPR-TF (Transcription Factor) with transcriptional activation activity. The chimeric RNA is expressed by U6 promoter, while a human-codon-optimized, double-mutant version of the Cas9 protein (hSpCas9m), operably linked to triple NLS and a VP64 functional domain is expressed by a EF1a promoter. The double mutations, D10A and H840A, renders the cas9 protein unable to introduce any cleavage but maintained its capacity to bind to target DNA when guided by the chimeric RNA.

Figure 68:
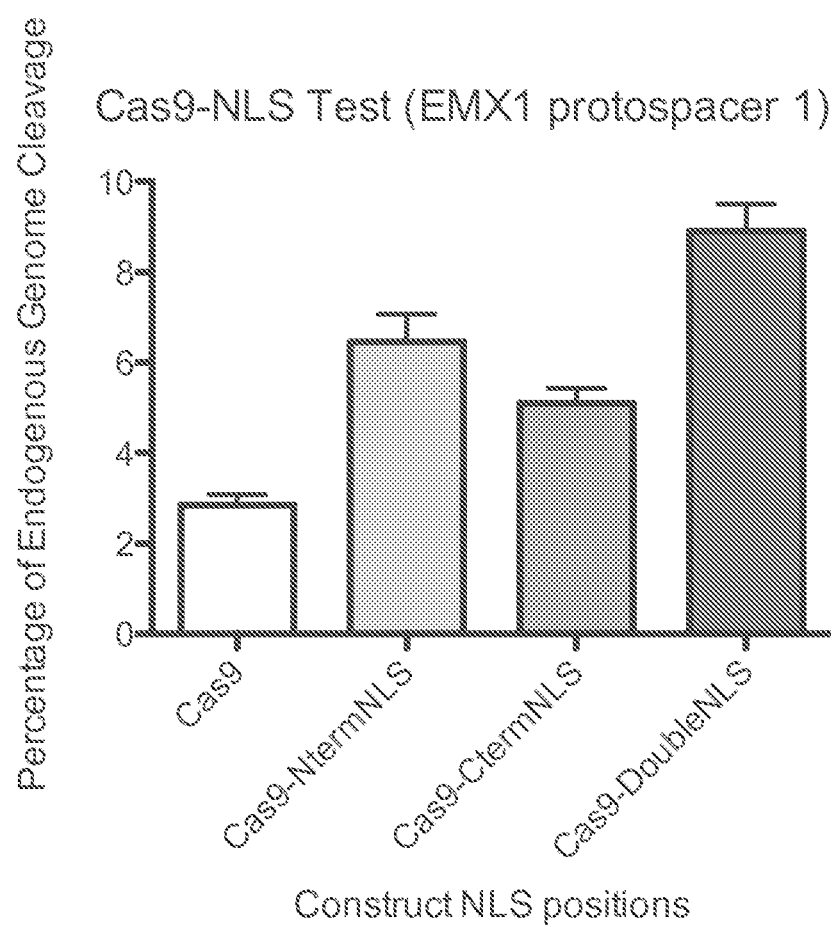
FIG. 68 shows the efficiency of genomic cleavage induced by Cas9 variants bearing different NLS designs. The percentage indicate the portion of human EMX1 genomic DNA that were cleaved by each construct. All experiments are from 3 biological replicates. n=3, error indicates S.E.M.

FIG. 68 depicts transcriptional activation of the human SOX2 gene with CRISPR-TF system (Chimeric RNA and the Cas9-NLS-VP64 fusion protein). 293FT cells were transfected with plasmids bearing two components: (1) U6-driven different chimeric RNAs targeting 20-bp sequences within or around the human SOX2 genomic locus, and (2) EF1a-driven hSpCas9m (double mutant)-NLS-VP64 fusion protein. 96 hours post transfection, 293FT cells were harvested and the level of activation is measured by the induction of mRNA expression using a qRT-PCR assay. All expression levels are normalized against the control group (grey bar), which represents results from cells transfected with the CRISPR-TF backbone plasmid without chimeric RNA. The qRT-PCR probes used for detecting the SOX2 mRNA is Taqman Human Gene Expression Assay (Life Technologies). All experiments represents data from 3 biological replicates, n=3, error bars show s.e.m.

Example 14

NLS: Cas9 NLS

293FT cells were transfected with plasmid containing two components: (1) EF1a promoter driving the expression of Cas9 (wild-type human-codon-optimized Sp Cas9) with different NLS designs (2) U6 promoter driving the same chimeric RNA targeting human EMX1 locus.

Cells were collect at 72 h time point post transfection, and then extracted with 50 µl of the QuickExtract genomic DNA extraction solution following manufacturer's protocol. Target EMX1 genomic DNA were PCR amplified and then Gel-purify with 1% agarose gel. Genomic PCR product were re-anneal and subjected to the Surveyor assay following manufacturer's protocol. The genomic cleavage efficiency of different constructs were measured using SDS-PAGE on a 4-12% TBE-PAGE gel (Life Technologies), analyzed and quantified with ImageLab (Bio-rad) software, all following manufacturer's protocol.

FIG. 69 depicts a design of different Cas9 NLS constructs. All Cas9 were the human-codon-optimized version of the Sp Cas9. NLS sequences are linked to the cas9 gene at either N-terminus or C-terminus. All Cas9 variants with different NLS designs were cloned into a backbone vector containing so it is driven by EF1a promoter. On the same vector there is a chimeric RNA targeting human EMX1 locus driven by U6 promoter, together forming a two-component system.

TABLE M

Cas9 NLS Design Test Results. Quantification of genomic cleavage of different cas9-nls constructs by surveyor assay.

| Percentage Genome Cleavage as measured by Surveyor assay | Biological Replicate 1 (%) | Biological Replicate 2 (%) | Biological Replicate 3 (%) | Average (%) | Error (S.E.M., standard error of the mean) |
|---|---|---|---|---|---|
| Cas9 (No NLS) | 2.50 | 3.30 | 2.73 | 2.84 | 0.24 |
| Cas9 with N-term NLS | 7.61 | 6.29 | 5.46 | 6.45 | 0.63 |
| Cas9 with C-term NLS | 5.75 | 4.86 | 4.70 | 5.10 | 0.33 |
| Cas9 with Double (N-term and C-term) NLS | 9.08 | 9.85 | 7.78 | 8.90 | 0.60 |

Figure 70:
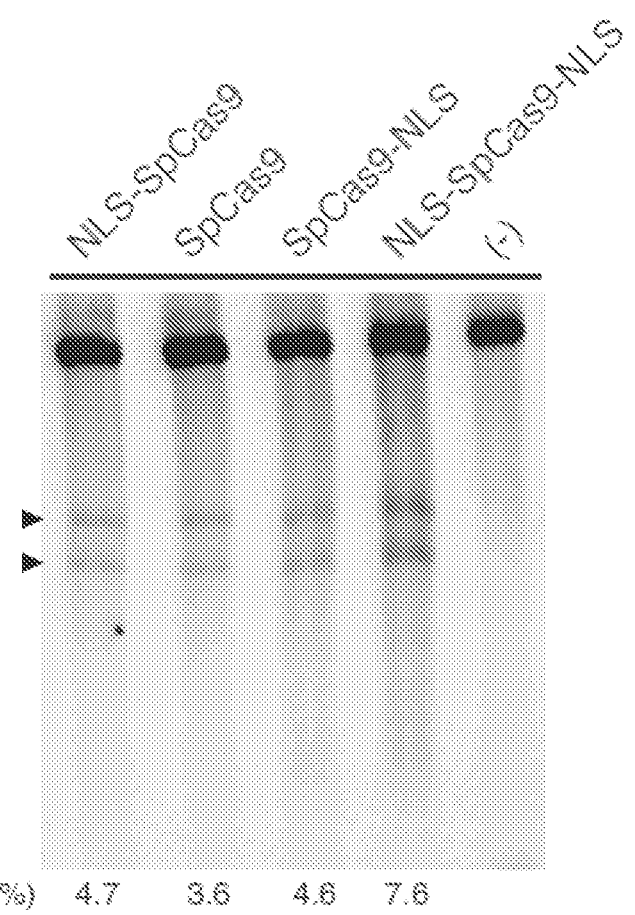
FIG. 70 depicts NLS architecture optimization for SpCas9.

FIG. 70 depicts the efficiency of genomic cleavage induced by Cas9 variants bearing different NLS designs. The percentage indicate the portion of human EMX1 genomic DNA that were cleaved by each construct. All experiments are from 3 biological replicates. n=3, error indicates S.E.M.

Example 15

Engineering of Microalgae Using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

(SEQ ID NO: 277)
TCTTTCTTGCGCTATGACACTTCCAGCAAAAGGTAGGGCGGGCTGCGAGA
CGGCTTCCCGGCGCTGCATGCAACACCGATGATGCTTCGACCCCCCGAAG
CTCCTTCGGGGCTGCATGGGCGCTCCGATGCCGCTCCAGGGCGAGCGCTG
TTTAAATAGCCAGGCCCCCGATTGCAAAGACATTATAGCGAGCTACCAAA
GCCATATTCAAACACCTAGATCACTACCACTTCTACACAGGCCACTCGAG
CTTGTGATCGCACTCCGCTAAGGGGGCGCCTCTTCCTCTTCGTTTCAGTC
ACAACCCGCAAACATGTACCCATACGATGTTCCAGATTACGCTTCGCCGA
AGAAAAAGCGCAAGGTCGAAGCGTCCGACAAGAAGTACAGCATCGGCCTG
GACATCGGCACCAACTCTGTGGGCTGGGCCGTGATCACCGACGAGTACAA
GGTGCCCAGCAAGAAATTCAAGGTGCTGGGCAACACCGACCGGCACAGCA
TCAAGAAGAACCTGATCGGAGCCCTGCTGTTCGACAGCGGCGAAACAGCC
GAGGCCACCCGGCTGAAGAGAACCGCCAGAAGAAGATACACCAGACGGAA
GAACCGGATCTGCTATCTGCAAGAGATCTTCAGCAACGAGATGGCCAAGG
TGGACGACAGCTTCTTCCACAGACTGGAAGAGTCCTTCCTGGTGGAAGAG
GATAAGAAGCACGAGCGGCACCCCATCTTCGGCAACATCGTGGACGAGGT
GGCCTACCACGAGAAGTACCCCACCATCTACCACCTGAGAAAGAAACTGG
TGGACAGCACCGACAAGGCCGACCTGCGGCTGATCTATCTGGCCCTGGCC
CACATGATCAAGTTCCGGGGCCACTTCCTGATCGAGGGCGACCTGAACCC
CGACAACAGCGACGTGGACAAGCTGTTCATCCAGCTGGTGCAGACCTACA
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
CGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC
AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGGAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGC
CGGAAGAGAATGCTGGCCTCTGCCGGCGAACTGCAGAAGGGAAACGAACT

```
GGCCCTGCCCTCCAAATATGTGAACTTCCTGTACCTGGCCAGCCACTATG
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAAGGATCCGGCAAGACTGGCCCCGCTTGGCAACGCAACA
GTGAGCCCCTCCCTAGTGTGTTTGGGGATGTGACTATGTATTCGTGTGTT
GGCCAACGGGTCAACCCGAACAGATTGATACCCGCCTTGGCATTTCCTGT
CAGAATGTAACGTCAGTTGATGGTACT
```

Sequence for a cassette driving the expression of T7 polymerase under the control of beta-2 tubulin promoter, followed by the 3' UTR of Cop1:

(SEQ ID NO: 278)
```
TCTTTCTTGCGCTATGACACTTCCAGCAAAAGGTAGGGCGGGCTGCGAGA
CGGCTTCCCGGCGCTGCATGCAACACCGATGATGCTTCGACCCCCCGAAG
CTCCTTCGGGGCTGCATGGGCGCTCCGATGCCGCTCCAGGGCGAGCGCTG
TTTAAATAGCCAGGCCCCCGATTGCAAAGACATTATAGCGAGCTACCAAA
GCCATATTCAAACACCTAGATCACTACCACTTCTACACAGGCCACTCGAG
CTTGTGATCGCACTCCGCTAAGGGGGCGCCTCTTCCTCTTCGTTTCAGTC
ACAACCCGCAAAatgcctaagaagaagaggaaggttaacacgattaaca
tcgctaagaacgacttctctgacatcgaactggctgctatcccgttcaac
actctggctgaccattacggtgagcgtttagctcgcgaacagttggccct
tgagcatgagtcttacgagatgggtgaagcacgcttccgcaagatgtttg
agcgtcaacttaaagctggtgaggttgcggataacgctgccgccaagcct
ctcatcactaccctactccctaagatgattgcacgcatcaacgactggtt
tgaggaagtgaaagctaagcgcggcaagcgccgacagccttccagttcc
tgcaagaaatcaagccggaagccgtagcgtacatcaccattaagaccact
ctggcttgcctaaccagtgctgacaatacaaccgttcaggctgtagcaag
cgcaatcggtcgggccattgaggacgaggctcgcttcggtcgtatccgtg
accttgaagctaagcacttcaagaaaaacgttgaggaacaactcaacaag
cgcgtagggcacgtctacaagaaagcatttatgcaagttgtcgaggctga
catgctctctaagggtctactcggtggcgaggcgtggtcttcgtggcata
aggaagactctattcatgtaggagtacgctgcatcgagatgctcattgag
tcaaccggaatggttagcttacaccgccaaaatgctggcgtagtaggtca
agactctgagactatcgaactcgcacctgaatacgctgaggctatcgcaa
cccgtgcaggtgcgctggctggcatctctccgatgttccaaccttgcgta
gttcctcctaagccgtggactggcattactggtggtggtggctattggctaa
```

```
cggtcgtcgtcctctggcgctggtgcgtactcacagtaagaaagcactga
tgcgctacgaagacgtttacatgcctgaggtgtacaaagcgattaacatt
gcgcaaaacaccgcatggaaaatcaacaagaaagtcctagcggtcgccaa
cgtaatcaccaagtggaagcattgtccggtcgaggacatccctgcgattg
agcgtgaagaactcccgatgaaaccggaagacatcgacatgaatcctgag
gctctcaccgcgtggaaacgtgctgccgctgctgtgtaccgcaaggacaa
ggctcgcaagtctcgccgtatcagccttgagttcatgcttgagcaagcca
ataagtttgctaaccataaggccatctggttccccttacaacatggactgg
cgcggtcgtgtttacgctgtgtcaatgttcaacccgcaaggtaacgatat
gaccaaaggactgcttacgctggcgaaaggtaaaccaatcggtaaggaag
gttactactggctgaaaatccacggtgcaaactgtgcgggtgtcgacaag
gttccgttccctgagcgcatcaagttcattgaggaaaaccacgagaacat
catggcttgcgctaagtctccactggagaacacttggtgggctgagcaag
attctccgttctgcttccttgcgttctgctttgagtacgctggggtacag
caccacggcctgagctataactgctcccttccgctggcgtttgacgggtc
ttgctctgcatccagcacttctccgcgatgctccgagatgaggtaggtg
gtcgcgcggttaacttgcttcctagtgaaaccgttcaggacatctacggg
attgttgctaagaaagtcaacgagattctacaagcagacgcaatcaatgg
gaccgataacgaagtagttaccgtgaccgatgagaacactggtgaaatct
ctgagaaagtcaagctgggcactaaggcactggctggtcaatggctggct
tacggtgttactcgcagtgtgactaagcgttcagtcatgacgctggctta
cgggtccaaagagttcggcttccgtcaacaagtgctggaagataccattc
agccagctattgattccggcaagggtctgatgttcactcagccgaatcag
gctgctggatacatggctaagctgatttgggaatctgtgagcgtgacggt
ggtagctgcggttgaagcaatgaactggcttaagtctgctgctaagctgc
tggctgctgaggtcaaagataagaagactggagagattcttcgcaagcgt
tgcgctgtgcattgggtaactcctgatggttccctgtgtggcaggaata
caagaagcctattcagacgcgcttgaacctgatgttcctcggtcagttcc
gcttacagcctaccattaacaccaacaaagatagcgagattgatgcacac
aaacaggagtctggtatcgctcctaactttgtacacagccaagacggtag
ccaccttcgtaagactgtagtgtgggcacacgagaagtacgaatcgaat
cattttgcactgattcacgactccttcggtacgattccggctgacgctgc
gaacctgttcaaagcagtgcgcgaaactatggttgacacatatgagtctt
gtgatgtactggctgatttctacgaccagttcgctgaccagttgcacgag
tctcaattggacaaaatgccagcacttccggctaaaggtaacttgaacct
ccgtgacatcttagagtcggacttcgcgttcgcgtaaGGATCCGGCAAGA
CTGGCCCCGCTTGGCAACGCAACAGTGAGCCCCTCCCTAGTGTGTTTGGG
GATGTGACTATGTATTCGTGTGTTGGCCAACGGGTCAACCCGAACAGATT
GATACCCGCCTTGGCATTTCCTGTCAGAATGTAACGTCAGTTGATGGTAC
T
```

Sequence of guide RNA driven by the T7 promoter (T7 promoter, Ns represent targeting sequence):

(SEQ ID NO: 279)
gaaatTAATACGACTCACTATANNNNNNNNNNNNNNNNNNNNgttttaga gctaGAAAtagcaagttaaaataaggctagtccgttatcaacttgaaaaa gtggcaccgagtcggtgcttttttt Gene delivery:
*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit.

Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 280)
TGCGGTATTTCACACCGCATCAGGTGGCACTTTTCGGGGAAATGTGCGCG

GAACCCCTATTTGTTTATTTTTCTAAATACATTCAAATATGTATCCGCTC

ATGAGATTATCAAAAAGGATCTTCACCTAGATCCTTTTAAATTAAAAATG

AAGTTTTAAATCAATCTAAAGTATATATGAGTAAACTTGGTCTGACAGTT

ACCAATGCTTAATCAGTGAGGCACCTATCTCAGCGATCTGTCTATTTCGT

TCATCCATAGTTGCCTGACTCCCCGTCGTGTAGATAACTACGATACGGGA

GGGCTTACCATCTGGCCCCAGTGCTGCAATGATACCGCGAGACCCACGCT

CACCGGCTCCAGATTTATCAGCAATAAACCAGCCAGCCGGAAGGGCCGAG

CGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATG

GCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCAT

AATTCTCTTACTGTCATGCCATCCGTAAGATGCTTTTCTGTGACTGGTGA

GTACTCAACCAAGTCATTCTGAGAATAGTGTATGCGGCGACCGAGTTGCT

CTTGCCCGGCGTCAATACGGGATAATACCGCGCCACATAGCAGAACTTTA

AAAGTGCTCATCATTGGAAAACGTTCTTCGGGGCGAAAACTCTCAAGGAT

CTTACCGCTGTTGAGATCCAGTTCGATGTAACCCACTCGTGCACCCAACT

GATCTTCAGCATCTTTTACTTTCACCAGCGTTTCTGGGTGAGCAAAAACA

GGAAGGCAAAATGCCGCAAAAAAGGGAATAAGGGCGACACGGAAATGTTG

AATACTCATACTCTTCCTTTTTCAATATTATTGAAGCATTTATCAGGGTT

ATTGTCTCATGACCAAAATCCCTTAACGTGAGTTTTCGTTCCACTGAGCG

TCAGACCCCGTAGAAAAGATCAAAGGATCTTCTTGAGATCCTTTTTTTCT

-continued
GCGCGTAATCTGCTGCTTGCAAACAAAAAAACCACCGCTACCAGCGGTGG

TTTGTTTGCCGGATCAAGAGCTACCAACTCTTTTTCCGAAGGTAACTGGC

TTCAGCAGAGCGCAGATACCAAATACTGTTCTTCTAGTGTAGCCGTAGTT

AGGCCACCACTTCAAGAACTCTGTAGCACCGCCTACATACCTCGCTCTGC

TAATCCTGTTACCAGTGGCTGTTGCCAGTGGCGATAAGTCGTGTCTTACC

GGGTTGGACTCAAGACGATAGTTACCGGATAAGGCGCAGCGGTCGGGCTG

AACGGGGGGTTCGTGCACACAGCCCAGCTTGGAGCGAACGACCTACACCG

AACTGAGATACCTACAGCGTGAGCTATGAGAAAGCGCCACGCTTCCCGAA

GGGAGAAAGGCGGACAGGTATCCGGTAAGCGGCAGGGTCGGAACAGGAGA

GCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCA

GGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCC

CTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGT

CGCTGAGGCTTGACATGATTGGTGCGTATGTTTGTATGAAGCTACAGGAC

TGATTTGGCGGGCTATGAGGGCGGGGGAAGCTCTGGAAGGGCCGCGATGG

GGCGCGCGGCGTCCAGAAGGCGCCATACGGCCCGCTGGCGGCACCCATCC

GGTATAAAAGCCCGCGACCCCGAACGGTGACCTCCACTTTCAGCGACAAA

CGAGCACTTATACATACGCGACTATTCTGCCGCTATACATAACCACTCAG

CTAGCTTAAGATCCCATCAAGCTTGCATGCCGGGCGCGCCAGAAGGAGCG

CAGCCAAACCAGGATGATGTTTGATGGGGTATTTGAGCACTTGCAACCCT

TATCCGGAAGCCCCCTGGCCCACAAAGGCTAGGCGCCAATGCAAGCAGTT

CGCATGCAGCCCCTGGAGCGGTGCCCTCCTGATAAACCGGCCAGGGGCC

TATGTTCTTTACTTTTTTACAAGAGAAGTCACTCAACATCTTAAAATGGC

CAGGTGAGTCGACGAGCAAGCCCGGCGGATCAGGCAGCGTGCTTGCAGAT

TTGACTTGCAACGCCCGCATTGTGTCGACGAAGGCTTTTGGCTCCTCTGT

CGCTGTCTCAAGCAGCATCTAACCCTGCGTCGCCGTTTCCATTTGCAGGA

GATTCGAGGTACCATGTACCCATACGATGTTCCAGATTACGCTTCGCCGA

AGAAAAAGCGCAAGGTCGAAGCGTCCGACAAGAAGTACAGCATCGGCCTG

GACATCGGCACCAACTCTGTGGGCTGGGCCGTGATCACCGACGAGTACAA

GGTGCCCAGCAAGAAATTCAAGGTGCTGGGCAACACCGACCGGCACAGCA

TCAAGAAGAACCTGATCGGAGCCCTGCTGTTCGACAGCGGCGAAACAGCC

GAGGCCACCCGGCTGAAGAGAACCGCCAGAAGAAGATACACCAGACGGAA

GAACCGGATCTGCTATCTGCAAGAGATCTTCAGCAACGAGATGGCCAAGG

TGGACGACAGCTTCTTCCACAGACTGGAAGAGTCCTTCCTGGTGGAAGAG

GATAAGAAGCACGAGCGGCACCCCATCTTCGGCAACATCGTGGACGAGGT

GGCCTACCACGAGAAGTACCCCACCATCTACCACCTGAGAAAGAAACTGG

TGGACAGCACCGACAAGGCCGACCTGCGGCTGATCTATCTGGCCCTGGCC

CACATGATCAAGTTCCGGGGCCACTTCCTGATCGAGGGCGACCTGAACCC

CGACAACAGCGACGTGGACAAGCTGTTCATCCAGCTGGTGCAGACCTACA

```
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
CGAGCACCACCAGGACCTGACCCTGCTGAAAGCTCTCGTGCGGCAGCAGC
TGCCTGAGAAGTACAAAGAGATTTTCTTCGACCAGACGCAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC
AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA

AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGGAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGC
CGGAAGAGAATGCTGGCCTCTGCCGGCGAACTGCAGAAGGGAAACGAACT
GGCCCTGCCCTCCAAATATGTGAACTTCCTGTACCTGGCCAGCCACTATG
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAACATATGATTCGAATGTCTTTCTTGCGCTATGACACTT
CCAGCAAAAGGTAGGGCGGGCTGCGAGACGGCTTCCCGGCGCTGCATGCA
ACACCGATGATGCTTCGACCCCCCGAAGCTCCTTCGGGGCTGCATGGGCG
CTCCGATGCCGCTCCAGGGCGAGCGCTGTTTAAATAGCCAGGCCCCCGAT
TGCAAAGACATTATAGCGAGCTACCAAAGCCATATTCAAACACCTAGATC
ACTACCACTTCTACACAGGCCACTCGAGCTTGTGATCGCACTCCGCTAAG
GGGGCGCCTCTTCCTCTTCGTTTCAGTCACAACCCGCAAACATGACACAA
GAATCCCTGTTACTTCTCGACCGTATTGATTCGGATGATTCCTACGCGAG
CCATGCGGAACGACCAGGAATTCTGGGAGGTGAGTCGACGAGCAAGCCCG
GCGGATCAGGCAGCGTGCTTGCAGATTTGACTTGCAACGCCCGCATTGTG
```

-continued

```
TCGACGAAGGCTTTTGGCTCCTCTGTCGCTGTCTCAAGCAGCATCTAACC
CTGCGTCGCCGTTTCCATTTGCAGCCGCTGGCCCGCCGAGCCCTGGAGGA
GCTCGGGCTGCCGGTGCCGCCGGTGCTGCGGGTGCCCGGCGAGAGCACCA
ACCCCGTACTGGTCGGCGAGCCCGGCCCGGTGATCAAGCTGTTCGGCGAG
CACTGGTGCGGTCCGGAGAGCCTCGCGTCGGAGTCGGAGGCGTACGCGGT
CCTGGCGGACGCCCGGTGCCGGTGCCCCGCCTCCTCGGCCGCGGCGAGC
TGCCGGCCCGGCACCGGAGCCTGGCCGTGGCCCTACCTGGTGATGAGCCGG
ATGACCGGCACCACCTGGCGGTCCGCGATGGACGGCACGACCGACCGGAA
CGCGCTGCTCGCCCTGGCCCGCGAACTCGGCCGGGTGCTCGGCCGGCTGC
ACAGGGTGCCGCTGACCGGGAACACCGTGCTCACCCCCCATTCCGAGGTC
TTCCCGGAACTGCTGCGGGAACGCCGCGCGGCGACCGTCGAGGACCACCG
CGGGTGGGGCTACCTCTCGCCCCGGCTGCTGGACCGCCTGGAGGACTGGC
TGCCGGACGTGGACACGCTGCTGGCCGGCCGCGAACCCCGGTTCGTCCAC
GGCGACCTGCACGGGACCAACATCTTCGTGGACCTGGCCGCGACCGAGGT
CACCGGGATCGTCGACTTCACCGACGTCTATGCGGGAGACTCCCGCTACA
GCCTGGTGCAACTGCATCTCAACGCCTTCCGGGGCGACCGCGAGATCCTG
GCCGCGCTGCTCGACGGGGCGCAGTGGAAGCGGACCGAGGACTTCGCCCG
CGAACTGCTCGCCTTCACCTTCCTGCACGACTTCGAGGTGTTCGAGGAGA
CCCCGCTGGATCTCTCCGGCTTCACCGATCCGGAGGAACTGGCGCAGTTC
CTCTGGGGGCCGCCGGACACCGCCCCCGGCGCCTGATAAGGATCCGGCAA
GACTGGCCCCGCTTGGCAACGCAACAGTGAGCCCCTCCCTAGTGTGTTTG
GGGATGTGACTATGTATTCGTGTGTTGGCCAACGGGTCAACCCGAACAGA
TTGATACCCGCCTTGGCATTTCCTGTCAGAATGTAACGTCAGTTGATGGT
ACT
```

For all modified *Chlamydomonas reinhardtii* cells, Applicants used PCR, SURVEYOR nuclease assay, and DNA sequencing to verify successful modification.

Example 16

Use of Cas9 as a Transcriptional Repressor in Bacteria

The ability to artificially control transcription is essential both to the study of gene function and to the construction of synthetic gene networks with desired properties. Applicants describe here the use of the RNA-guided Cas9 protein as a programmable transcriptional repressor.

Applicants have previously demonstrated how the Cas9 protein of *Streptococcus pyogenes* SF370 can be used to direct genome editing in *Streptococcus pneumoniae*. In this study Applicants engineered the crR6Rk strain containing a minimal CRISPR system, consisting of cas9, the tracrRNA and a repeat. The D10A-H840 mutations were introduced into cas9 in this strain, giving strain crR6Rk**. Four spacers targeting different positions of the bgaA β-galactosidase gene promoter were cloned in the CRISPR array carried by the previously described pDB98 plasmid. Applicants observed a X to Y fold reduction in β-galactosidase activity depending on the targeted position, demonstrating the potential of Cas9 as a programmable repressor (FIG. 73).

To achieve Cas9** repression in *Escherichia coli* a green fluorescence protein (GFP) reporter plasmid (pDB127) was constructed to express the gfpmut2 gene from a constituitive promoter. The promoter was designed to carry several NPP PAMs on both strands, to measure the effect of Cas9 binding at various positions. Applicants introduced the D10A-H840 mutations into pCas9, a plasmid described carrying the tracrRNA, cas9 and a minimal CRISPR array designed for the easy cloning of new spacers. Twenty-two different spacers were designed to target different regions of the gfpmut2 promoter and open reading frame. An approximately 20-fold reduction of fluorescence of was observed upon targeting regions overlapping or adjacent to the −35 and −10 promoter elements and to the Shine-Dalgarno sequence. Targets on both strands showed similar repression levels. These results suggest that the binding of Cas9 to any position of the promoter region prevents transcription initiation, presumably through steric inhibition of RNAP binding.

To determine whether Cas9 could prevent transcription elongation, Applicants directed it to the reading frame of gpfmut2. A reduction in fluorescence was observed both when the coding and non-coding strands where targeted, suggesting that Cas9 binding is actually strong enough to represent an obstacle to the running RNAP. However, while a 40% reduction in expression was observed when the coding strand was the target, a 20-fold reduction was observed for the non-coding strand (FIG. 21b, compare T9, T10 and T11 to B9, B10 and B11). To directly determine the effects of Cas9 binding on transcription, Applicants extracted RNA from strains carrying either the T5, T10, B10 or a control construct that does not target pDB127 and subjected it to Northern blot analysis using either a probe binding before (B477) or after (B510) the B10 and T10 target sites. Consistent with Applicants' fluorescence methods, no gfpmut2 transcription was detected when Cas9 was directed to the promoter region (T5 target) and a transcription was observed after the targeting of the T10 region. Interestingly, a smaller transcript was observed with the B477 probe. This band corresponds to the expected size of a transcript that would be interrupted by Cas9, and is a direct indication of a transcriptional termination caused by dgRNA::Cas9 binding to the coding strand. Surprisingly, Applicants detected no transcript when the non-coding strand was targeted (B10). Since Cas9 binding to the B10 region is unlikely to interfere with transcription initiation, this result suggests that the mRNA was degraded. DgRNA::Cas9 was shown to bind ssRNA in vitro. Applicants speculate that binding may trigger degradation of the mRNA by host nucleases. Indeed, ribosome stalling can induce cleavage on the translated mRNA in *E. coli*.

Some applications require a precise tuning gene expression rather than its complete repression. Applicants sought to achieve intermediate repression levels through the introduction of mismatches that will weaken the crRNA/target interactions. Applicants created a series of spacers based on the B1, T5 and B10 constructs with increasing numbers of mutations in the 5' end of the crRNA. Up to 8 mutations in B1 and T5 did not affect the repression level, and a progressive increased in fluorescence was observed for additional mutations.

The observed repression with only an 8 nt match between the crRNA and its target raises the question of off-targeting effects of the use of Cas9 as a transcriptional regulator. Since a good PAM (NGG) is also required for Cas9 binding, the number of nucleotides to match to obtain some level of respiration is 10. A 100 nt match occurs randomly once every ~1 Mbp, and such sites are thus likely to be found even in small bacterial genomes. However, to effectively repress transcription, such site needs to be in the promoter region of gene, which makes off-targeting much less likely. Applicants also showed that gene expression can be affected if the non-coding strand of a gene is targeted. For this to happen, a random target would have to be in the right orientation, but such events relatively more likely to happen. As a matter of fact, during the course of this study Applicants were unable to construct one of the designed spacer on pCas9. Applicants later found this spacer showed a 12 bp match next to a good PAM in the essential murC gene. Such off-targeting could easily be avoided by a systematic blast of the designed spacers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

1. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
2. Bogdanove, A. J. & Voytas, D. F. TAL effectors: customizable proteins for DNA targeting. *Science* 333, 1843-1846 (2011).
3. Stoddard, B. L. Homing endonuclease structure and function. *Q. Rev. Biophys.* 38, 49-95 (2005).
4. Bae, T. & Schneewind, O. Allelic replacement in *Staphylococcus aureus* with inducible counter-selection. *Plasmid* 55, 58-63 (2006).
5. Sung, C. K., L1, H., Clayerys, J. P. & Morrison, D. A. An rpsL cassette, janus, for gene replacement through negative selection in *Streptococcus pneumoniae. Appl. Environ. Microbiol.* 67, 5190-5196 (2001).
6. Sharan, S. K., Thomason, L. C., Kuznetsov, S. G. & Court, D. L. Recombineering: a homologous recombination-based method of genetic engineering. *Nat. Protoc.* 4, 206-223 (2009).
7. Jinek, M. et al. A programmable dual-RNA-guided DNA endonuclease in adaptive bacterial immunity. *Science* 337, 816-821 (2012).
8. Deveau, H., Garneau, J. E. & Moineau, S. CRISPR/Cas system and its role in phage-bacteria interactions. *Annu. Rev. Microbiol.* 64, 475-493 (2010).
9. Horvath, P. & Barrangou, R. CRISPR/Cas, the immune system of bacteria and archaea. *Science* 327, 167-170 (2010).
10. Terns, M. P. & Terns, R. M. CRISPR-based adaptive immune systems. *Curr. Opin. Microbiol.* 14, 321-327 (2011).
11. van der Oost, J., Jore, M. M., Westra, E. R., Lundgren, M. & Brouns, S. J. CRISPR-based adaptive and heritable immunity in prokaryotes. *Trends. Biochem. Sci.* 34, 401-407 (2009).
12. Brouns, S. J. et al. Small CRISPR RNAs guide antiviral defense in prokaryotes. *Science* 321, 960-964 (2008).
13. Carte, J., Wang, R., L1, H., Terns, R. M. & Terns, M. P. Cas6 is an endoribonuclease that generates guide RNAs for invader defense in prokaryotes. *Genes Dev.* 22, 3489-3496 (2008).
14. Deltcheva, E. et al. CRISPR RNA maturation by trans-encoded small RNA and host factor RNase III. *Nature* 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek. M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus. J. Bacteriol.* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli. Nucleic Acids Res.* (2011).
25. Semenova, E. et al. Interference by clustered regularly interspaced short palindromic repeat (CRISPR) RNA is governed by a seed sequence. *Proc. Natl. Acad. Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).
27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O, Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli. Mol. Genet. Genonics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).

32. Edgar, R. & Qimron. U. The *Escherichia coli* CRISPR system protects from lambda lysogenization, lysogens, and prophage induction. *J. Bacteriol.* 192, 6291-6294 (2010).
33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chemn.* 287, 33351-33363 (2012).
35. Gudbergsdottir, S. et al. Dynamic properties of the *Sulfolobus* CRISPR/Cas and CRISPR/cmr systems when challenged with vector-borne viral and plasmid genes and protospacers. *Mol. Microbiol.* 79, 35-49 (2011).
36. Wang, H. H. et al. Genome-scale promoter engineering by coselection MAGE. *Nat Methods* 9, 591-593 (2012).
37. Cong, L. et al. Multiplex Genome Engineering Using CRISPR/Cas Systems. *Science In press* (2013).
38. Mali, P. et al. RNA-Guided Human Genome Engineering via Cas9. *Science In press* (2013).
39. Hoskins, J. et al. Genome of the bacterium *Streptococcus pneumoniae* strain R6. *J. Bacteriol.* 183, 5709-5717 (2001).
40. Havarstein, L. S., Coomaraswamy, G. & Morrison, D. A. An unmodified heptadecapeptide pheromone induces competence for genetic transformation in *Streptococcus pneumoniae. Proc. Natl. Acad. Sci. U.S.A.* 92, 11140-11144 (1995).
41. Horinouchi, S. & Weisblum, B. Nucleotide sequence and functional map of pC194, a plasmid that specifies inducible chloramphenicol resistance. *J. Bacteriol.* 150, 815-825 (1982).
42. Horton, R. M. In Vitro Recombination and Mutagenesis of DNA: SOEing Together Tailor-Made Genes. *Methods Mol. Biol.* 15, 251-261 (1993).
43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).
44. Husmann, L. K., Scott, J. R., Lindahl, G. & Stenberg, L. Expression of the Arp protein, a member of the M protein family, is not sufficient to inhibit phagocytosis of *Streptococcus pyogenes. Infection and immunity* 63, 345-348 (1995).
45. Gibson, D. G. et al. Enzymatic assembly of DNA molecules up to several hundred kilobases. *Nat Methods* 6, 343-345 (2009).

---

What is claimed is:

1. A method of altering expression of at least one gene product comprising introducing into a eukaryotic cell containing and expressing a DNA molecule having a target sequence and encoding the gene product an engineered, non-naturally occurring Clustered Regularly Interspaced Short Palindromic Repeats (CRISPR)-CRISPR associated (Cas) system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, wherein components (a) and (b) are located on same or different vectors of the system, wherein the CRISPR-Cas system comprises two or more nuclear localization signals (NLSs), wherein the Cas9 protein comprises one or more mutations in a catalytic domain, whereby the guide RNA targets the target sequence and the Cas9 protein is a nickase that cleaves only one strand of the DNA molecule, whereby expression of the at least one gene product is altered; and, wherein the Cas9 protein and the guide RNA do not naturally occur together.

2. The method of claim 1, wherein the method further comprises the insertion of a homologous recombination (HR) template into the cleaved strand of the DNA molecule.

3. The method of claim 1, wherein the expression of two or more gene products is altered.

4. The method of claim 1, wherein the CRISPR-Cas system comprises a trans-activating cr (tracr) sequence.

5. The method of claim 1, wherein the Cas9 protein comprises a mutation, wherein the mutation comprises D10A, E762A, H840A, N854A, N863A or D986A with reference to the position numbering of a *Streptococcus pyogenes* Cas9 protein.

6. The method of claim 1, wherein the Cas9 protein is codon optimized for expression in the eukaryotic cell.

7. The method of claim 1, wherein the eukaryotic cell is a mammalian or human cell.

8. The method of claim 1, wherein the expression of one or more gene products is altered by genome editing.

9. The method of claim 1, wherein the expression of one or more gene products is increased.

10. The method of claim 1, wherein the expression of one or more gene products is decreased.

11. The method of claim 1, wherein the one or more vectors are viral vectors.

12. The method of claim 11, wherein the one or more viral vectors are selected from the group consisting of retroviral, lentiviral, adenoviral, adeno-associated and herpes simplex viral vectors.

13. A CRISPR-Cas system-mediated genome editing method comprising introducing into a eukaryotic cell containing a polynucleotide having a sequence wherein the polynucleotide sequence includes a target sequence, an engineered, non-naturally occurring CRISPR-Cas system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a Type-II Cas9 protein, wherein components (a) and (b) are located on same or different vectors of the system, wherein the Cas9 protein comprises one or more mutations in a catalytic domain whereby the Cas9 protein is a nickase that cleaves only one strand of the polynucleotide, wherein the CRISPR-Cas system comprises two or more NLSs, whereby the polynucleotide sequence is modified through the CRISPR-Cas system directing sequence-specific genome editing; and, wherein the Cas9 protein and the guide RNA do not naturally occur together.

14. The method of claim 13, wherein the sequence-specific genome editing comprises high-fidelity homology-directed repair (HDR).

15. The method of claim 13, wherein the sequence-specific genome editing comprises creation of a nick in the polynucleotide which is repaired by a homologous recombination (HR) cell repair mechanism incorporating a HR template into the polynucleotide thereby modifying the polynucleotide sequence.

16. The method of claim 13, wherein the expression of two or more gene products is altered.

17. The method of claim 13, wherein the CRISPR-Cas system comprises a tracr sequence.

18. The method of claim 13, wherein the Cas9 protein comprises a mutation, wherein the mutation comprises D10A, E762A, H840A, N854A, N863A or D986A with reference to the position numbering of a *Streptococcus pyogenes* Cas9 protein.

19. The method of claim 13, wherein the Cas9 protein is codon optimized for expression in the eukaryotic cell.

20. The method of claim 13, wherein the eukaryotic cell is a mammalian or human cell.

21. The method of claim 13, wherein the expression of one or more gene products is increased.

22. The method of claim 13, wherein the expression of one or more gene products is decreased.

23. The method of claim 13, wherein the one or more vectors are viral vectors.

24. The method of claim 23, wherein the one or more viral vectors are selected from the group consisting of retroviral, lentiviral, adenoviral, adeno-associated and herpes simplex viral vectors.

25. An engineered, programmable, non-naturally occurring Type II CRISPR-Cas system comprising a Cas9 protein and at least one guide RNA that targets and hybridizes to a target sequence of a DNA molecule in a eukaryotic cell, wherein the DNA molecule encodes and the eukaryotic cell expresses at least one gene product, wherein the Cas9 protein comprises one or more mutations in a catalytic domain whereby the Cas9 protein is a nickase that cleaves only one strand of the DNA molecule, wherein the CRISPR-Cas system comprises two or more NLSs, whereby expression of the at least one gene product is altered; and, wherein the Cas9 protein and the guide RNA do not naturally occur together.

26. The CRISPR-Cas system of claim 25, wherein the CRISPR-Cas system comprises a tracr sequence.

27. The method of claim 25, wherein the Cas9 protein comprises a mutation, wherein the mutation comprises D10A, E762A, H840A, N854A, N863A or D986A with reference to the position numbering of a *Streptococcus pyogenes* Cas9 protein.

28. The method of claim 27, wherein the Cas9 protein comprises the mutation D10A.

29. The method of claim 27, wherein the Cas9 protein comprises the mutation H840A.

30. The CRISPR-Cas system of claim 25, wherein the eukaryotic cell is a mammalian or human cell.

* * * * *

UNITED STATES PATENT AND TRADEMARK OFFICE
CERTIFICATE OF CORRECTION

| | | |
|---|---|---|
| PATENT NO. | : 8,932,814 B2 | Page 1 of 1 |
| APPLICATION NO. | : 14/258458 | |
| DATED | : January 13, 2015 | |
| INVENTOR(S) | : Cong et al. | |

It is certified that error appears in the above-identified patent and that said Letters Patent is hereby corrected as shown below:

In the Specification

Column 1, Line 47, (approx.), Before the "STATEMENT AS TO FEDERALLY SPONSORED RESEARCH" Please insert the following:
--PARTIES TO A JOINT RESEARCH AGREEMENT
The claimed invention was made by, on behalf of, and/or in connection with one or more of the following parties to a joint research agreement: The Broad Institute Inc., Massachusetts Institute of Technology and President and Fellows of Harvard College. The agreement was in effect on and before the date the claimed invention was made, and the claimed invention was made as a result of activities undertaken within the scope of the agreement.--

Signed and Sealed this
Twentieth Day of August, 2019

Andrei Iancu
*Director of the United States Patent and Trademark Office*